(12) United States Patent
Mizutani et al.

(10) Patent No.: US 9,209,406 B2
(45) Date of Patent: Dec. 8, 2015

(54) AROMATIC HETEROCYCLIC DERIVATIVE, MATERIAL FOR ORGANIC ELECTROLUMINESCENT ELEMENT, AND ORGANIC ELECTROLUMINESCENT ELEMENT

(71) Applicant: IDEMITSU KOSAN CO., LTD., Tokyo (JP)

(72) Inventors: Sayaka Mizutani, Sodegaura (JP); Takayasu Sado, Sodegaura (JP)

(73) Assignee: IDEMITSU KOSAN CO., LTD., Tokyo (JP)

( * ) Notice: Subject to any disclaimer, the term of this patent is extended or adjusted under 35 U.S.C. 154(b) by 0 days.

(21) Appl. No.: 13/989,698

(22) PCT Filed: Nov. 21, 2012

(86) PCT No.: PCT/JP2012/080156
§ 371 (c)(1),
(2) Date: May 24, 2013

(87) PCT Pub. No.: WO2013/077352
PCT Pub. Date: May 30, 2013

(65) Prior Publication Data
US 2014/0073784 A1    Mar. 13, 2014

(30) Foreign Application Priority Data

Nov. 22, 2011 (JP) .................. 2011-255472
Sep. 3, 2012 (JP) .................. 2012-193349

(51) Int. Cl.
*H01L 51/54* (2006.01)
*C09K 11/06* (2006.01)
(Continued)

(52) U.S. Cl.
CPC .......... *H01L 51/0052* (2013.01); *C07D 405/10* (2013.01); *C07D 405/14* (2013.01);
(Continued)

(58) Field of Classification Search
None
See application file for complete search history.

(56) References Cited

U.S. PATENT DOCUMENTS

2003/0072967 A1 *  4/2003  Kido et al. ............... 428/690
2006/0040131 A1 *  2/2006  Klubek et al. ............ 428/690
(Continued)

FOREIGN PATENT DOCUMENTS

EP          1 962 354 A1     8/2008
JP          2010 040830      2/2010
(Continued)

OTHER PUBLICATIONS

International Search Report Issued Jan. 29, 2013 in PCT/JP12/80156 Filed Nov. 21, 2012.
(Continued)

*Primary Examiner* — Andrew K Bohaty
(74) *Attorney, Agent, or Firm* — Oblon, McClelland, Maier & Neustadt, L.L.P.

(57) ABSTRACT

An organic EL device includes an anode, an emitting layer, an electron transporting zone and a cathode in this sequence, in which the electron transporting zone contains an aromatic heterocyclic derivative represented by a formula (1) below. In the formula (1), $X_1$ to $X_3$ are a nitrogen atom or $CR_1$, and A is represented by a formula (2) below. In the formula (2), $L_1$ is s single bond or a linking group, and HAr is represented by a formula (3) below. In the formula (3), $Y_1$ is an oxygen atom, a sulfur atom or the like, and one of $X_{11}$ to $X_{18}$ is a carbon atom bonded to $L_1$ by a single bond and the rest of $X_{11}$ to $X_{18}$ are a nitrogen atom or $CR_{13}$.

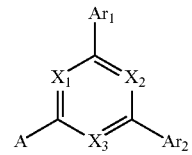

(1)

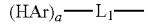

(2)

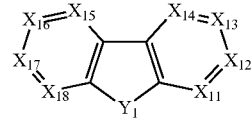

(3)

16 Claims, 14 Drawing Sheets

(51) Int. Cl.
*H01L 51/00* (2006.01)
*C07D 405/14* (2006.01)
*C07D 405/10* (2006.01)
*C07D 409/10* (2006.01)
*C07D 409/14* (2006.01)
*H01L 51/50* (2006.01)

(52) U.S. Cl.
CPC ............ *C07D409/10* (2013.01); *C07D 409/14* (2013.01); *H01L 51/0054* (2013.01); *H01L 51/0067* (2013.01); *H01L 51/0071* (2013.01); *H01L 51/0073* (2013.01); *H01L 51/0074* (2013.01); *H01L 51/5004* (2013.01); *H01L 51/5072* (2013.01)

(56) References Cited

U.S. PATENT DOCUMENTS

| | | | |
|---|---|---|---|
| 2006/0273714 A1* | 12/2006 | Forrest et al. | 313/504 |
| 2007/0132372 A1 | 6/2007 | Inoue et al. | |
| 2007/0141387 A1 | 6/2007 | Nakano et al. | |
| 2010/0084971 A1 | 4/2010 | Nakano et al. | |
| 2010/0295444 A1 | 11/2010 | Kuma et al. | |
| 2010/0301318 A1 | 12/2010 | Kuma et al. | |
| 2011/0114928 A1* | 5/2011 | Suzuki et al. | 257/40 |
| 2011/0272687 A1 | 11/2011 | Katakura et al. | |
| 2011/0309343 A1 | 12/2011 | Langer et al. | |
| 2012/0126205 A1 | 5/2012 | Kawamura et al. | |
| 2012/0126208 A1 | 5/2012 | Kawamura et al. | |
| 2013/0256645 A1 | 10/2013 | Min et al. | |
| 2014/0001456 A1 | 1/2014 | Mizutani et al. | |

FOREIGN PATENT DOCUMENTS

| | | |
|---|---|---|
| JP | 2012 97006 | 5/2012 |
| KR | 2011 0107680 | 10/2011 |
| KR | 2011 0107681 | 10/2011 |
| KR | 2012 0122812 | 11/2012 |
| WO | 2007 069569 | 6/2007 |
| WO | 2010 001817 | 1/2010 |
| WO | 2010 044342 | 4/2010 |
| WO | 2010 134350 | 11/2010 |
| WO | 2010 136109 | 12/2010 |
| WO | WO 2011019156 A1 * | 2/2011 |
| WO | WO 2011/071255 | 6/2011 |
| WO | WO 2011/136520 | 11/2011 |
| WO | WO 2011/136755 | 11/2011 |
| WO | WO 2011/139055 | 11/2011 |
| WO | WO 2011/157790 A1 | 12/2011 |

OTHER PUBLICATIONS

Office Action mailed Jan. 13, 2014, in co-pending U.S. Appl. No. 13/964,237.
Supplementary European Search Report issued Dec. 18, 2014 in EP Patent Application 12 85 1292.

* cited by examiner

AROMATIC HETEROCYCLIC DERIVATIVE, MATERIAL FOR ORGANIC ELECTROLUMINESCENT ELEMENT, AND ORGANIC ELECTROLUMINESCENT ELEMENT

FIELD

Embodiment(s) described herein relates to an organic electroluminescence device, an aromatic heterocyclic derivative applicable to the organic electroluminescence device, and an organic-electroluminescence-device material including the aromatic heterocyclic derivative.

BACKGROUND

An organic electroluminescence device (hereinafter, occasionally referred to as an organic EL device) can be classified by the emission principle into two types: a fluorescent organic EL device and a phosphorescent organic EL device. When a voltage is applied to the organic EL device, holes are injected from an anode and electrons are injected from a cathode. The holes and the electrons are recombined in an emitting layer to form excitons. According to the electron spin statistics theory, singlet excitons and triplet excitons are generated at a ratio of 25%:75%. In a fluorescent organic EL device which uses emission caused by singlet excitons, the limited value of an internal quantum efficiency is believed to be 25%. A technology for extending a lifetime of a fluorescent organic EL device using a fluorescent material has recently been improved and applied to a full-color display of a mobile phone, TV and the like. However, as compared with a phosphorescent organic EL device, a fluorescent organic EL device is required to be improved in efficiency.

In contrast, in relation to a technology of manufacturing a highly efficient fluorescent-organic-EL device, there has been disclosed a technology of extracting emissions derived from triplet excitons by a phenomenon (i.e., TTF (Triplet-Triplet Fusion) phenomenon) in which two triplet excitons collide and fuse with each other to generate singlet excitons. A blocking layer that effectively induces the TTF phenomenon requires to be made of a highly electron-resistant compound serving as a layer for transporting electrons as well as having a wide gap for increasing triplet energy. In view of this point, a compound formed of a hydrocarbon ring has been considered suitable.

Patent Literature 1 discloses an organic EL device having a pyrene skeleton or an anthracene skeleton and further a substituent selected from a carbazolyl group, dibenzofuranyl group or dibenzothiophenyl group in an electron transporting layer adjacent to a fluorescent emitting layer.

Patent Literature 2 discloses an organic-EL device using a fluoranthene derivative for a blocking layer in order to effectively induce The TTF phenomenon.

CITATION LIST

Patent Literatures

Patent Literature 1: International Publication No. WO2010/001817
Patent Literature 2: International Publication No. WO2010/134350

SUMMARY OF THE INVENTION

Problems to be Solved by the Invention

An object of the invention is to provide an organic EL device that emits at a high efficiency and is driven at a lower drive voltage, an aromatic heterocyclic derivative applicable to the organic EL device, and an organic-EL-device material including the aromatic heterocyclic derivative.

Means for Solving the Problems

[1] An organic electroluminescence device according to an aspect of the invention includes: an anode; an emitting layer; an electron transporting zone; and a cathode in this sequence, in which the electron transporting zone comprises an aromatic heterocyclic derivative represented by a formula (1) below.

[Formula 1]

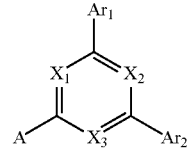

(1)

In the formula (1), $X_1$ to $X_3$ are a nitrogen atom or $CR_1$, with a proviso that at least one of $X_1$ to $X_3$ is a nitrogen atom;

$R_1$ independently represents a hydrogen atom, a halogen atom, a cyano group, a substituted or unsubstituted aryl group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted alkenyl group having 2 to 30 carbon atoms, a substituted or unsubstituted alkynyl group having 2 to 30 carbon atoms, a substituted or unsubstituted alkylsilyl group having 3 to 30 carbon atoms, a substituted or unsubstituted arylsilyl group having 6 to 30 ring carbon atoms, a substituted or unsubstituted alkoxy group having 1 to 30 carbon atoms, a substituted or unsubstituted aralkyl group having 6 to 30 ring carbon atoms, or a substituted or unsubstituted aryloxy group having 6 to 30 ring carbon atoms.

In the formula (1), A is represented by a formula (2) below.

[Formula 2]

$(HAr)_a$-$L_1$-    (2)

In the formula (2), HAr is represented by a formula (3) below.

In the formula (2), a is an integer of 1 to 5.

When a is 1, $L_1$ is a single bond or a divalent linking group.

When a is in a range of 2 to 5, $L_1$ is a trivalent to hexavalent linking group and HAr is the same or different.

The linking group is a substituted or unsubstituted aryl group having 6 to 30 ring carbon atoms, substituted or unsubstituted heterocyclic group having 5 to 30 ring atoms, or a residue having 2 to 6 valences induced from any one of a group formed by bonding two or three of the substituted or unsubstituted aryl group having 6 to 30 ring carbon atoms and the substituted or unsubstituted heterocyclic group having 5 to 30 ring atoms.

The mutually bonded groups are the same or different.

[Formula 3]

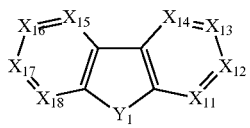

(3)

In the formula (3), $X_{11}$ to $X_{18}$ each are independently a nitrogen atom, $CR_{13}$ or a carbon atom bonded to $L_1$ by a single bond.

In the formula (3), $Y_1$ is a nitrogen atom, a sulfur atom, $SiR_{11}R_{12}$ or a silicon atom bonded to each of $R_{11}$ and $L_1$ by a single bond.

$L_1$ is bonded by one of a carbon atom at $X_{11}$ to $X_{18}$ and $R_{11}$ to $R_{12}$ and a silicon atom at $Y_1$.

$R_{11}$ and $R_{12}$ represent the same as $R_1$ in the formula (1). $R_{11}$ and $R_{12}$ are the same or different.

$R_{13}$ independently represents a hydrogen atom, a halogen atom, a cyano group, a substituted or unsubstituted aryl group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted alkenyl group having 2 to 30 carbon atoms, a substituted or unsubstituted alkynyl group having 2 to 30 carbon atoms, a substituted or unsubstituted alkylsilyl group having 3 to 30 carbon atoms, a substituted or unsubstituted arylsilyl group having 6 to 30 ring carbon atoms, a substituted or unsubstituted alkoxy group having 1 to 30 carbon atoms, a substituted or unsubstituted aralkyl group having 6 to 30 ring carbon atoms, or a substituted or unsubstituted aryloxy group having 6 to 30 ring carbon atoms. A plurality of $R_{13}$ are mutually the same or different. Adjacent $R_{13}$ may bond to each other to form a ring.

In the above formula (1), $Ar_1$ and $Ar_2$ each are independently represented by the formula (2), or represent a substituted or unsubstituted aryl group having 6 to 30 ring carbon atoms or a substituted or unsubstituted heterocyclic group having 5 to 30 ring atoms.

[2] In the organic electroluminescence device according to the above aspect of the invention, in the formula (3), $X_{13}$ or $X_{16}$ is a carbon atom bonded to $L_1$ by a single bond.

[3] In the organic electroluminescence device according to the above aspect of the invention, in the formula (3), $X_{11}$ or $X_{18}$ is a carbon atom bonded to $L_1$ by a single bond.

[4] In the organic electroluminescence device according to the above aspect of the invention, in the formula (2), a is an integer of 1 to 3.

[5] In the organic electroluminescence device according to the above aspect of the invention, in the formula (2), a is 1 or 2.

[6] In the organic electroluminescence device according to the above aspect of the invention, in the formula (2), a is 1, $L_1$ is a linking group, and the linking group is a divalent residue of a substituted or unsubstituted aryl group having 6 to 30 ring carbon atoms, or a divalent residue of a substituted or unsubstituted heterocyclic group having 5 to 30 ring atoms.

[7] In the organic electroluminescence device according to the above aspect of the invention, in the formula (2), a is 2 and $L_1$ is a linking group, and the linking group is a trivalent residue of a substituted or unsubstituted aryl group having 6 to 30 ring carbon atoms, or a trivalent residue of a substituted or unsubstituted heterocyclic group having 5 to 30 ring atoms.

[8] In the organic electroluminescence device according to the above aspect of the invention, in the formula (3), $Y_1$ is an oxygen atom or a sulfur atom.

In the organic electroluminescence device according to the above aspect of the invention, in the formula (3), $Y_1$ is an oxygen atom or a sulfur atom, and one of $X_{11}$ to $X_{18}$ is a carbon atom bonded to $L_1$ by a single bond and the rest of $X_{11}$ to $X_{18}$ are $CR_{13}$.

[10] In the organic electroluminescence device according to the above aspect of the invention, in the formula (1), two or three of $X_1$ to $X_3$ are a nitrogen atom.

[11] In the organic electroluminescence device according to the above aspect of the invention, in the formula (2), $L_1$ is a divalent or trivalent residue induced from any one of benzene, biphenyl, terphenyl, naphthalene and phenanthrene.

[12] In the organic electroluminescence device according to the above aspect of the invention, the electron transporting zone includes a blocking layer, the blocking layer including the aromatic heterocyclic derivative represented by the formula (1).

[13] The organic electroluminescence device according to the above aspect of the invention further includes at least one of an electron injecting layer and an electron transporting layer between the blocking layer and the cathode, in which the at least one of the electron injecting layer and the electron transporting layer includes at least one of an electron-donating dopant material and an organic metal complex.

[14] In the organic electroluminescence device according to the above aspect of the invention, the electron-donating dopant material is at least one material selected from the group consisting of an alkali metal, an alkaline-earth metal, a rare earth metal, an alkali metal oxide, an alkali metal halogenide, an alkaline-earth metal oxide, an alkaline-earth metal halogenide, a rare earth metal oxide and a rare earth metal halogenide, and the organic metal complex is at least one complex selected from the group consisting of an organic metal complex comprising an alkali metal, an organic metal complex comprising an alkaline-earth metal, and an organic metal complex comprising a rare-earth metal.

[15] In the organic electroluminescence device according to the above aspect of the invention, the emitting layer is in contact with the electron transporting zone comprising the aromatic heterocyclic derivative.

[16] In the organic electroluminescence device according to the above aspect of the invention, the emitting layer includes an anthracene derivative represented by a formula (20D) below.

[Formula 4]

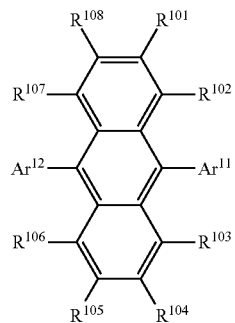

(20D)

In the formula (20D), $Ar^{11}$ and $Ar^{12}$ each independently represent a substituted or unsubstituted monocyclic group having 5 to 30 ring atoms, a substituted or unsubstituted fused cyclic group having 10 to 30 ring atoms or a group formed by combining the monocyclic group and the fused cyclic group.

In the formula (20D), $R^{101}$ to $R^{108}$ each independently represent a hydrogen atom, a halogen atom, a cyano group, a substituted or unsubstituted monocyclic group having 5 to 30 ring atoms, a substituted or unsubstituted fused cyclic group having 10 to 30 ring atoms, a group formed by combining the monocyclic group and the fused cyclic group, a substituted or unsubstituted alkyl group having 1 to 30 carbon atoms, a substituted or unsubstituted cycloalkyl group having 3 to 30 ring carbon atoms, a substituted or unsubstituted alkylsilyl group having 3 to 30 carbon atoms, a substituted or unsubstituted arylsilyl group having 8 to 30 ring carbon atoms, a substituted or unsubstituted alkoxy group having 1 to 30 carbon atoms, a substituted or unsubstituted aralkyl group having 7 to 30 carbon atoms, a substituted or unsubstituted aryloxy group having 6 to 30 ring carbon atoms, or a substituted or unsubstituted silyl group.

[17] In the organic electroluminescence device according to the above aspect of the invention, the emitting layer includes a fluorescent dopant material having a main peak wavelength of 500 nm or less.

An aromatic heterocyclic derivative according to another aspect of the invention is represented by a formula (4) below.

[Formula 5]

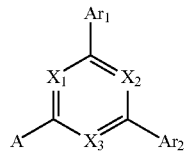

(4)

In the formula (4), $X_1$ to $X_3$ are a nitrogen atom or $CR_1$, with a proviso that at least one of $X_1$ to $X_3$ is a nitrogen atom.

$R_1$ independently represents a hydrogen atom, a halogen atom, a cyano group, a substituted or unsubstituted aryl group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted alkenyl group having 2 to 30 carbon atoms, a substituted or unsubstituted alkynyl group having 2 to 30 carbon atoms, a substituted or unsubstituted alkylsilyl group having 3 to 30 carbon atoms, a substituted or unsubstituted arylsilyl group having 6 to 30 ring carbon atoms, a substituted or unsubstituted alkoxy group having 1 to 30 carbon atoms, a substituted or unsubstituted aralkyl group having 6 to 30 ring carbon atoms, or a substituted or unsubstituted aryloxy group having 6 to 30 ring carbon atoms.

In the formula (4), A is represented by a formula (5) below.
[Formula 6]

$$(HAr)_a\text{-}L_1\text{-} \quad (5)$$

In the formula (5), HAr is represented by a formula (6) below.

In the formula (5), a is an integer of 1 to 5.

When a is 1, $L_1$ is a divalent linking group.

When a is in a range of 2 to 5, $L_1$ is a trivalent to hexavalent linking group and HAr is the same or different.

The linking group is a substituted or unsubstituted aryl group having 6 to 30 ring carbon atoms, substituted or unsubstituted heterocyclic group having 5 to 30 ring atoms, or a residue having 2 to 6 valences induced from any one of a group formed by bonding two or three of the substituted or unsubstituted aryl group having 6 to 30 ring carbon atoms and the substituted or unsubstituted heterocyclic group having 5 to 30 ring atoms.

The mutually bonded groups are the same or different.

[Formula 7]

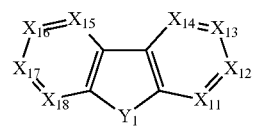

(6)

In the formula (6), $Y_1$ is an oxygen atom or a sulfur atom.
In the formula (6), $X_{11}$ and $X_{18}$ are a nitrogen atom or $CR_{13}$.
In the formula (6), one of $X_{12}$ to $X_{17}$ is a carbon atom bonded to $L_1$ by a single bond and the rest of $X_{12}$ to $X_{17}$ are a nitrogen atom or $CR_{13}$.

$R_{13}$ independently represents a hydrogen atom, a halogen atom, a cyano group, a substituted or unsubstituted aryl group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted alkenyl group having 2 to 30 carbon atoms, a substituted or unsubstituted alkynyl group having 2 to 30 carbon atoms, a substituted or unsubstituted alkylsilyl group having 3 to 30 carbon atoms, a substituted or unsubstituted arylsilyl group having 6 to 30 ring carbon atoms, a substituted or unsubstituted alkoxy group having 1 to 30 carbon atoms, a substituted or unsubstituted aralkyl group having 6 to 30 ring carbon atoms, or a substituted or unsubstituted aryloxy group having 6 to 30 ring carbon atoms.

A plurality of $R_{13}$ are mutually the same or different. Adjacent $R_{13}$ may bond to each other to form a ring.

In the above formula (4), $Ar_1$ and $Ar_2$ each are independently represented by the formula (5), or represent a substituted or unsubstituted aryl group having 6 to 30 ring carbon atoms or a substituted or unsubstituted heterocyclic group having 5 to 30 ring atoms.

[19] In the aromatic heterocyclic derivative according to the above aspect of the invention, in the formula (6), $X_{13}$ or $X_{16}$ is a carbon atom bonded to $L_1$ by a single bond.

[20] In the aromatic heterocyclic derivative according to the above aspect of the invention, in the formula (5), a is an integer of 1 to 3.

[21] In the aromatic heterocyclic derivative according to the above aspect of the invention, in the formula (5), a is 1 or 2.

[22] In the aromatic heterocyclic derivative according to the above aspect of the invention, in the formula (5), a is 1 and $L_1$ is a linking group, and the linking group is a divalent residue of a substituted or unsubstituted aryl group having 6 to 30 ring carbon atoms, or a divalent residue of a substituted or unsubstituted heterocyclic group having 5 to 30 ring atoms.

[23] In the aromatic heterocyclic derivative according to the above aspect of the invention, in the formula (5), a is 2 and $L_1$ is a linking group, and the linking group is a trivalent residue of a substituted or unsubstituted aryl group having 6 to 30 ring carbon atoms, or a trivalent residue of a substituted or unsubstituted heterocyclic group having 5 to 30 ring atoms.

[24] In the aromatic heterocyclic derivative according to the above aspect of the invention, in the formula (6), $Y_1$ is an oxygen atom.

[25] In the aromatic heterocyclic derivative according to the above aspect of the invention, in the formula (6), $Y_1$ is an oxygen atom, $X_{11}$ and $X_{18}$ are $CR_{13}$, and one of $X_{12}$ to $X_{17}$ is a carbon atom bonded to $L_1$ by a single bond and the rest of $X_{12}$ to $X_{17}$ are $CR_{13}$.

[26] In the aromatic heterocyclic derivative according to the above aspect of the invention, In the formula (4), two or three of $X_1$ to $X_3$ are a nitrogen atom.

[27] In the aromatic heterocyclic derivative according to the above aspect of the invention, In the formula (5), $L_1$ is a divalent or trivalent residue induced from any one of benzene, biphenyl, terphenyl, naphthalene and phenanthrene.

[28] An organic-electroluminescence-device material according to further aspect of the invention includes the aromatic heterocyclic derivative according to the above aspect of the invention.

According to the embodiment(s), an organic EL device that emits at a high efficiency and is driven at a lower drive voltage, an aromatic heterocyclic derivative applicable to the organic EL device, and an organic-EL-device material including the aromatic heterocyclic derivative can be provided.

DESCRIPTION OF EMBODIMENTS

Aromatic Heterocyclic Derivative

Figure 1:
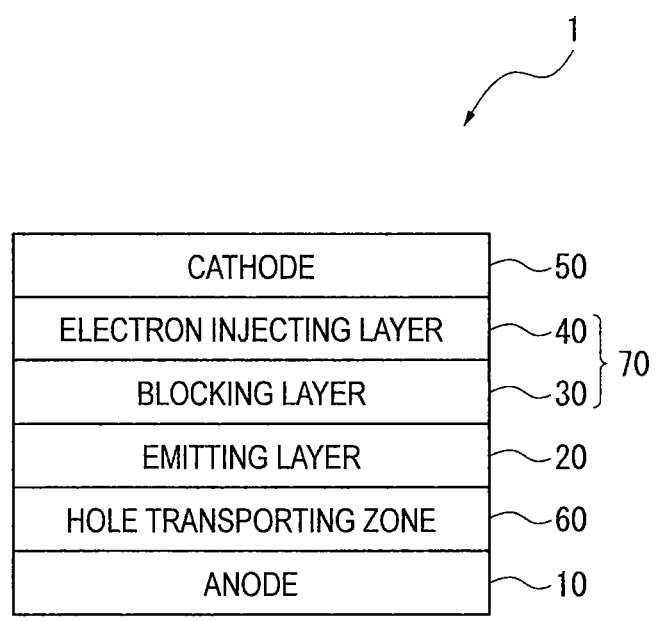
FIG. 1 is a view showing one example of an organic EL device according to a first exemplary embodiment of the invention.

An aromatic heterocyclic derivative according to an exemplary embodiment is represented by a formula (4) below.

[Formula 8]

In the formula (4), $X_1$ to $X_3$ are a nitrogen atom or $CR_1$.

However, at least one of $X_1$ to $X_3$ is a nitrogen atom.

$R_1$ independently represents a hydrogen atom, halogen atom, cyano group, substituted or unsubstituted aryl group having 6 to 30 ring carbon atoms, substituted or unsubstituted heterocyclic group having 5 to 30 ring atoms, substituted or unsubstituted alkyl group having 1 to 30 carbon atoms, substituted or unsubstituted alkenyl group having 2 to 30 carbon atoms, substituted or unsubstituted alkynyl group having 2 to 30 carbon atoms, substituted or unsubstituted alkylsilyl group having 3 to 30 carbon atoms, substituted or unsubstituted arylsilyl group having 6 to 30 ring carbon atoms, substituted or unsubstituted alkoxy group having 1 to 30 carbon atoms, substituted or unsubstituted aralkyl group having 6 to 30 ring carbon atoms, or substituted or unsubstituted aryloxy group having 6 to 30 ring carbon atoms.

In the formula (4), A is represented by a formula (5) below.

[Formula 9]

In the formula (5), HAr is represented by a formula (6) below.

In the formula (5), a is an integer of 1 to 5.

When a is 1, $L_1$ is a divalent linking group.

When a is in a range of 2 to 5, $L_1$ is a trivalent to hexavalent linking group and HAr is the same or different.

The linking group is a substituted or unsubstituted aryl group having 6 to 30 ring carbon atoms, substituted or unsubstituted heterocyclic group having 5 to 30 ring atoms, or a divalent to hexavalent residue induced from any one of a group formed by bonding two or three of the above groups.

The mutually bonded groups are the same or different.

[Formula 10]

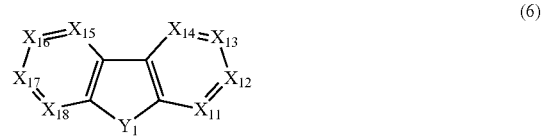

In the formula (6), $Y_1$ is an oxygen atom or a sulfur atom.

In the formula (6), $X_{11}$ and $X_{18}$ are a nitrogen atom or $CR_{13}$.

In the formula (6), one of $X_{12}$ to $X_{17}$ is a carbon atom bonded to $L_1$ by a single bond and the rest of $X_{12}$ to $X_{17}$ are a nitrogen atom or $CR_{13}$.

$R_{13}$ independently represents a hydrogen atom, halogen atom, cyano group, substituted or unsubstituted aryl group having 6 to 30 ring carbon atoms, substituted or unsubstituted heterocyclic group having 5 to 30 ring atoms, substituted or unsubstituted alkyl group having 1 to 30 carbon atoms, substituted or unsubstituted alkenyl group having 2 to 30 carbon atoms, substituted or unsubstituted alkynyl group having 2 to 30 carbon atoms, substituted or unsubstituted alkylsilyl group having 3 to 30 carbon atoms, substituted or unsubstituted arylsilyl group having 6 to 30 ring carbon atoms, substituted or unsubstituted alkoxy group having 1 to 30 carbon atoms, substituted or unsubstituted aralkyl group having 6 to 30 ring carbon atoms, or substituted or unsubstituted aryloxy group having 6 to 30 ring carbon atoms. A plurality of $R_{13}$ are mutually the same or different. Adjacent $R_{13}$ may bond to each other to form a ring.

In the above formula (4), $Ar_1$ and $Ar_2$ each are independently represented by the formula (5), or represent a substituted or unsubstituted aryl group having 6 to 30 ring carbon atoms or a substituted or unsubstituted heterocyclic group having 5 to 30 ring atoms.

In the formula (6), $X_{13}$ or $X_{16}$ is preferably a carbon atom bonded to $L_1$ by a single bond.

In the formula (5), a is an integer in a range of 1 to 5, more preferably of 1 to 3, particularly preferably 1 or 2.

When a is 1, $L_1$ is a divalent linking group and the formula (5) is represented by a formula (5-1).

When a is in a range of 2 to 5, $L_1$ is a trivalent to hexavalent linking group. When a is 2, $L_1$ is a trivalent linking group and the formula (5) is represented by a formula (5-2). At this time, HAr is the same or different.

[Formula 11]

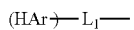   (5-1)

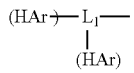   (5-2)

The linking group is a substituted or unsubstituted aryl group having 6 to 30 ring carbon atoms, substituted or unsubstituted heterocyclic group having 5 to 30 ring atoms, or a divalent or trivalent residue induced from any one of a group formed by bonding two or three of the above groups.

In $L_1$ of the formulae (5), (5-1) and (5-2), the group formed by bonding two or three of the above groups means a group formed by bonding, with a single bond, two or three of the divalent or trivalent residue induced from the aryl group having 6 to 30 ring carbon atoms and the heterocyclic group having 5 to 30 ring atoms. In the linking group, the mutually bonded groups are the same or different.

In the formulae (5), (5-1) and (5-2), $L_1$ is preferably a substituted or unsubstituted aryl group having 6 to 30 ring carbon atoms, or substituted or unsubstituted heterocyclic group having 5 to 30 ring atoms.

Moreover, in the formulae (5), (5-1) and (5-2), $L_1$ is more preferably a divalent or trivalent residue induced from any one of benzene, biphenyl, terphenyl, naphthalene and phenanthrene.

In the formula (5), it is more preferable that a is 1 and $L_1$ is a divalent residue of a substituted or unsubstituted aryl group having 6 to 30 ring carbon atoms, or a divalent residue of a substituted or unsubstituted heterocyclic group having 5 to 30 ring atoms.

In the formula (5), it is more preferable that a is 2 and $L_1$ is a linking group, specifically, a trivalent residue of a substituted or unsubstituted aryl group having 6 to 30 ring carbon atoms, or a trivalent residue of a substituted or unsubstituted heterocyclic group having 5 to 30 ring atoms.

In the formula (6), $X_{13}$ or $X_{16}$ is preferably a carbon atom bonded to $L_1$ by a single bond.

In the formula (6), $Y_1$ is preferably an oxygen atom.

Moreover, in the formula (6), it is more preferable that $Y_1$ is an oxygen atom, $X_{11}$ and $X_{18}$ are $CR_{13}$, one of $X_{12}$ to $X_{17}$ is a carbon atom bonded to $L_1$ by a single bond and the rest of $X_{12}$ to $X_{17}$ are $CR_{13}$.

In the formula (4), two or three of $X_1$ to $X_3$ are preferably a nitrogen atom.

$Ar_1$, $Ar_2$, $L_1$, $R_1$, $R_{11}$ to $R_{13}$ in the formulae (4) to (6) and (5-1) to (5-2) will be described below.

Examples of the aryl group having 6 to 30 ring carbon atoms in the formulae (4) to (6) and (5-1) to (5-2) are a phenyl group, 1-naphthyl group, 2-naphthyl group, 1-anthryl group, 2-anthryl group, 9-anthryl group, benzanthryl group, 1-phenanthryl group, 2-phenanthryl group, 3-phenanthryl group, 4-phenanthryl group, 9-phenanthryl group, naphthacenyl group, pyrenyl group, 1-chrysenyl group, 2-chrysenyl group, 3-chrysenyl group, 4-chrysenyl group, 5-chrysenyl group, 6-chrysenyl group, benzo[c]phenanthryl group, benzo[g]chrysenyl group, 1-triphenylenyl group, 2-triphenylenyl group, 3-triphenylenyl group, 4-triphenylenyl group, 1-fluorenyl group, 2-fluorenyl group, 3-fluorenyl group, 4-fluorenyl group, 9-fluorenyl group, benzofluorenyl group, dibenzofluorenyl group, 2-biphenylyl group, 3-biphenylyl group, 4-biphenylyl group, o-terphenyl group, m-terphenyl-4-yl group, m-terphenyl-3-yl group, m-terphenyl-2-yl group, p-terphenyl-4-yl group, p-terphenyl-3-yl group, p-terphenyl-2-yl group, m-quarter-phenyl group, 3-fluoranthenyl group, 4-fluoranthenyl group, 8-fluoranthenyl group, 9-fluoranthenyl group, benzofluoranthenyl group, o-tolyl group, m-tolyl group, p-tolyl group, 2,3-xylyl group, 3,4-xylyl group, 2,5-xylyl group, mesityl group, o-cumenyl group, m-cumenyl group, p-cumenyl group, p-t-butylphenyl group, p-(2-phenylpropyl)phenyl group, 4'-methylbiphenylyl group, 4"-t-butyl-p-terphenyl-4-yl group, 9,9-dimethyl-1-fluorenyl group, 9,9-dimethyl-2-fluorenyl group, 9,9-dimethyl-3-fluorenyl group, 9,9-dimethyl-4-fluorenyl group, 9,9-diphenyl-1-fluorenyl group, 9,9-diphenyl-2-fluorenyl group, 9,9-diphenyl-3-fluorenyl group, and 9,9-diphenyl-4-fluorenyl group.

The aryl group in the formulae (4) to (6) and (5-1) to (5-2) preferably has 6 to 20 ring carbon atoms, more preferably 6 to 12 ring carbon atoms. Among the aryl group, a phenyl group, biphenyl group, naphthyl group, phenanthryl group, terphenyl group, fluorenyl group and triphenylenyl group are particularly preferable. In 1-fluorenyl group, 2-fluorenyl group, 3-fluorenyl group and 4-fluorenyl group, a carbon atom at the ninth position is preferably substituted by the substituted or unsubstituted alkyl group having 1 to 30 carbon atoms in the formula (4).

Examples of the heterocyclic group having 5 to 30 ring atoms in the formulae (4) to (6) and (5-1) to (5-2) are a pyroryl group, pyrazinyl group, pyridinyl group, indolyl group, isoindolyl group, imidazolyl group, furyl group, benzofuranyl group, isobenzofuranyl group, dibenzofuranyl group, dibenzothiophenyl group, quinolyl group, isoquinolyl group, quinoxalinyl group, carbazolyl group, phenantridinyl group, acridinyl group, phenanthrolinyl group, phenazinyl group, phenothiazinyl group, phenoxazinyl group, oxazolyl group, oxadiazolyl group, furazanyl group, thienyl group, benzothiophenyl group and a group formed from a pyridine ring, pyrazine ring, pyrimidine ring, pyridazine ring, triazine ring, indole ring, quinoline ring, acridine ring, pyrrolidine ring, dioxane ring, piperidine ring, morpholine ring, piperadine ring, carbazole ring, furan ring, thiophene ring, oxazole ring, oxadiazole ring, benzooxazole ring, thiazole ring, thiadiazole ring, benzothiazole ring, triazole ring, imidazole ring, benzoimidazole ring, pyrane ring and dibenzofuran ring.

Specific examples of the heterocyclic group having 5 to 30 ring atoms in the formulae (4) to (6) and (5-1) to (5-2) are a 1-pyroryl group, 2-pyroryl group, 3-pyroryl group, pyrazinyl group, 2-pyridinyl group, 2-pyrimidinyl group, 4-pyrimidinyl group, 5-pyrimidinyl group, 6-pyrimidinyl group, 1,2,3-triazine-4-yl group, 1,2,4-triazine-3-yl group, 1,3,5-triazine-2-yl group, 1-imidazolyl group, 2-imidazolyl group, 1-pyrazolyl group, 1-indolidinyl group, 2-indolidinyl group, 3-indolidinyl group, 5-indolidinyl group, 6-indolidinyl group, 7-indolidinyl group, 8-indolidinyl group, 2-imidazopyridinyl group, 3-imidazopyridinyl group, 5-imidazopyridinyl group, 6-imidazopyridinyl group, 7-imidazopyridinyl group, 8-imidazopyridinyl group, 3-pyridinyl group, 4-pyridinyl group, 1-indolyl group, 2-indolyl group, 3-indolyl group, 4-indolyl group, 5-indolyl group, 6-indolyl group, 7-indolyl group, 1-isoindolyl group, 2-isoindolyl group, 3-isoindolyl group, 4-isoindolyl group, 5-isoindolyl group, 6-isoindolyl group, 7-isoindolyl group, 2-furyl group, 3-furyl group, 2-benzofuranyl group, 3-benzofuranyl group, 4-benzofuranyl group, 5-benzofuranyl group, 6-benzofuranyl group, 7-benzofuranyl group, 1-isobenzofuranyl group, 3-isobenzofuranyl group, 4-isobenzofuranyl group, 5-isobenzofuranyl group, 6-isobenzofuranyl group, 7-isobenzofuranyl group, 2-quinolyl group, 3-quinolyl group, 4-quinolyl group, 5-quinolyl group, 6-quinolyl group, 7-quinolyl group, 8-quinolyl group, 1-isoquinolyl group, 3-isoquinolyl group, 4-isoquinolyl group, 5-isoquinolyl group, 6-isoquinolyl group, 7-isoquinolyl group, 8-isoquinolyl group, 2-quinoxalinyl group, 5-quinoxalinyl group, 6-quinoxalinyl group, 1-carbazolyl group, 2-carbazolyl group, 3-carbazolyl group, 4-carbazolyl group, 9-carbazolyl group, azacarbazolyl-1-yl group, azacarbazolyl-2-yl group, azacarbazolyl-3-yl group, azacarbazolyl-4-yl group, azacarbazolyl-5-yl group, azacarbazolyl-6-yl group, azacarbazolyl-7-yl group, azacarbazolyl-8-yl group, azacarbazolyl-9-yl group, 1-phenanthrydinyl group, 2-phenanthrydinyl group, 3-phenanthrydinyl group, 4-phenanthrydinyl group, 6-phenanthrydinyl group, 7-phenanthrydinyl group, 8-phenanthrydinyl group, 9-phenanthrydinyl group, 10-phenanthrydinyl group, 1-acridinyl group, 2-acridinyl group, 3-acridinyl group, 4-acridinyl group, 9-acridinyl group, 1,7-phenanthroline-2-yl group, 1,7-phenanthroline-3-yl group, 1,7-phenanthroline-4-yl group, 1,7-phenanthroline-5-yl group, 1,7-phenanthroline-6-yl group, 1,7-phenanthroline-8-yl group, 1,7-phenanthroline-9-yl group, 1,7-phenanthroline-10-yl group, 1,8-phenanthroline-2-yl group, 1,8-phenanthroline-3-yl group, 1,8-phenanthroline-4-yl group, 1,8-phenanthroline-5-yl group, 1,8-phenanthroline-6-yl group, 1,8-phenanthroline-7-yl group, 1,8-phenanthroline-9-yl group, 1,8-phenanthroline-10-yl group, 1,9-phenanthroline-2-yl group, 1,9-phenanthroline-3-yl group, 1,9-phenanthroline-4-yl group, 1,9-phenanthroline-5-yl group, 1,9-phenanthroline-6-yl group, 1,9-phenanthroline-7-yl group, 1,9-phenanthroline-8-yl group, 1,9-phenanthroline-10-yl group, 1,10-phenanthroline-2-yl group, 1,10-phenanthroline-3-yl group, 1,10-phenanthroline-4-yl group, 1,10-phenanthroline-5-yl group, 2,9-phenanthroline-1-yl group, 2,9-phenanthroline-3-yl group, 2,9-phenanthroline-4-yl group, 2,9-phenanthroline-5-yl group, 2,9-phenanthroline-6-yl group, 2,9-phenanthroline-7-yl group, 2,9-phenanthroline-8-yl group, 2,9-phenanthroline-10-yl group, 2,8-phenanthroline-1-yl group, 2,8-phenanthroline-3-yl group, 2,8-phenanthroline-4-yl group, 2,8-phenanthroline-5-yl group, 2,8-phenanthroline-6-yl group, 2,8-phenanthroline-7-yl group, 2,8-phenanthroline-9-yl group, 2,8-phenanthroline-O-yl group, 2,7-phenanthroline-7-yl group, 2,7-phenanthroline-3-yl group, 2,7-phenanthroline-4-yl group, 2,7-phenanthroline-5-yl group, 2,7-phenanthroline-6-yl group, 2,7-phenanthroline-8-yl group, 2,7-phenanthroline-9-yl group, 2,7-phenanthroline-10-yl group, 1-phenazinyl group, 2-phenazinyl group, 1-phenothiazinyl group, 2-phenothiazinyl group, 3-phenothiazinyl group, 4-phenothiazinyl group, 10-phenothiazinyl group, 1-phenoxazinyl group, 2-phenoxazinyl group, 3-phenoxazinyl group, 4-phenoxazinyl group, 10-phenoxazinyl group, 2-oxazolyl group, 4-oxazolyl group, 5-oxazolyl group, 2-oxadiazolyl group, 5-oxadiazolyl group, 3-furazanyl group, 2-thienyl group, 3-thienyl group, 2-methylpyrrole-1-yl group, 2-methylpyrrole-3-yl group, 2-methylpyrrole-4-yl group, 2-methylpyrrole-5-yl group, 3-methylpyrrole-1-yl group, 3-methylpyrrole-2-yl group, 3-methylpyrrole-4-yl group, 3-methylpyrrole-5-yl group, 2-t-butylpyrrole-4-yl group, 3-(2-phenylpropyl)pyrrole-1-yl group, 2-methyl-1-indolyl group, 4-methyl-1-indolyl group, 2-methyl-3-indolyl group, 4-methyl-3-indolyl group, 2-t-butyl-1-indolyl group, 4-t-butyl-1-indolyl group, 2-t-butyl-3-indolyl group, 4-t-butyl-3-indolyl group, 1-dibenzofuranyl group, 2-dibenzofuranyl group, 3-dibenzofuranyl group, 4-dibenzofuranyl group, 1-dibenzothiophenyl group, 2-dibenzothiophenyl group, 3-dibenzothiophenyl group, 4-dibenzothiophenyl group, 1-silafluorenyl group, 2-silafluorenyl group, 3-silafluorenyl group, 4-silafluorenyl group, 1-germafluorenyl group, 2-germafluorenyl group, 3-germafluorenyl group and 4-germafluorenyl group.

The heterocyclic group in the formulae (4) to (6) and (5-1) to (5-2) preferably has 5 to 20 ring atoms, more preferably 5 to 14 ring atoms. Among the heterocyclic group, 1-dibenzofuranyl group, 2-dibenzofuranyl group, 3-dibenzofuranyl group, 4-dibenzofuranyl group, 1-dibenzothiophenyl group, 2-dibenzothiophenyl group, 3-dibenzothiophenyl group, 4-dibenzothiophenyl group, 2-pyridinyl group, 2-imidazopyridinyl group, 3-imidazopyridinyl group, 5-imidazopyridinyl group, 6-imidazopyridinyl group, 7-imidazopyridinyl group, 8-imidazopyridinyl group, 3-pyridinyl group, 4-pyridinyl group, 1-imidazolyl group, 2-imidazolyl group, 2-quinolyl group, 3-quinolyl group, 4-quinolyl group, 5-quinolyl group, 6-quinolyl group, 7-quinolyl group, 8-quinolyl group, phenanthrolinyl group, and a group formed from a triazine ring or a benzoimidazole ring are preferable.

The alkyl group having 1 to 30 carbon atoms in the formulae (4) and (6) may be linear, branched or cyclic. Examples of the linear or branched alkyl group are a methyl group, ethyl group, propyl group, isopropyl group, n-butyl group, s-butyl group, isobutyl group, t-butyl group, n-pentyl group, n-hexyl group, n-heptyl group, n-octyl group, n-nonyl group, n-decyl group, n-undecyl group, n-dodecyl group, n-tridecyl group, n-tetradecyl group, n-pentadecyl group, n-hexadecyl group, n-heptadecyl group, n-octadecyl group, neopentyl group, 1-methylpentyl group, 2-methylpentyl group, 1-pentylhexyl group, 1-butylpentyl group, 1-heptyloctyl group, 3-methylpentyl group, hydroxymethyl group, 1-hydroxyethyl group, 2-hydroxyethyl group, 2-hydroxyisobutyl group, 1,2-dihydroxyethyl group, 1,3-dihydroxyisopropyl group, 2,3-dihydroxy-t-butyl group, 1,2,3-trihydroxypropyl group, chloromethyl group, 1-chloroethyl group, 2-chloroethyl group, 2-chloroisobutyl group, 1,2-dichloroethyl group, 1,3-dichloroisopropyl group, 2,3-dichloro-t-butyl group, 1,2,3-trichloropropyl group, bromomethyl group, 1-bromoethyl group, 2-bromoethyl group, 2-bromoisobutyl group, 1,2-dibromoethyl group, 1,3-dibromoisopropyl group, 2,3-dibromo-t-butyl group, 1,2,3-tribromopropyl group, iodomethyl group, 1-iodoethyl group, 2-iodoethyl group, 2-iodoisobutyl group, 1,2-diiodoethyl group, 1,3-diiodoisopropyl group, 2,3-diiodo-t-butyl group, 1,2,3-triiodopropyl group, aminomethyl group, 1-aminoethyl group, 2-aminoethyl group, 2-aminoisobutyl group, 1,2-diaminoethyl group, 1,3-diaminoisopropyl group, 2,3-diamino-t-butyl group, 1,2,3-triaminopropyl group, cyanomethyl group, 1-cyanoethyl group, 2-cyanoethyl group, 2-cyanoisobutyl group, 1,2-dicyanoethyl group, 1,3-dicyanoisopropyl group, 2,3-dicyano-t-butyl group, 1,2,3-tricyanopropyl group, nitromethyl group, 1-nitroethyl group, 2-nitroethyl group, 1,2-dinitroethyl group, 2,3-dinitro-t-butyl group, and 1,2,3-trinitropropyl group.

Examples of the cyclic alkyl group (cycloalkyl group) are a cyclopropyl group, cyclobutyl group, cyclopentyl group, cyclohexyl group, 4-methylcyclohexyl group, 1-adamantyl group, 2-adamantyl group, 1-norbornyl group, and 2-norbornyl group.

The linear or branched alkyl group in the formulae (4) and (6) preferably has 1 to 10 carbon atoms, more preferably 1 to 6 carbon atoms. Among the linear or branched alkyl group, a methyl group, ethyl group, propyl group, isopropyl group, n-butyl group, s-butyl group, isobutyl group, t-butyl group, n-pentyl group and n-hexyl group are preferable.

The cycloalkyl group in the formulae (4) and (6) preferably has 3 to 10 ring carbon atoms, more preferably 5 to 8 ring carbon atoms. Among the cycloalkyl group, a cyclopentyl group and a cyclohexyl group are preferable.

A halogenated alkyl group provided by substituting the alkyl group with a halogen atom is exemplified by a halogenated alkyl group provided by substituting the alkyl group having 1 to 30 carbon atoms with one or more halogen groups. Specific examples of the halogenated alkyl group are a fluoromethyl group, difluoromethyl group, trifluoromethyl group, fluoroethyl group and trifluoromethylmethyl group.

The alkenyl group having 2 to 30 carbon atoms in the formulae (4) and (6) may be linear, branched or cyclic. Examples of the alkenyl group are vinyl, propenyl, butenyl, oleyl, eicosapentaenyl, docosahexaenyl, styryl, 2,2-diphenylvinyl, 1,2,2-triphenylvinyl, and 2-phenyl-2-propenyl. Among the alkenyl group, a vinyl group is preferable.

The alkynyl group having 2 to 30 carbon atoms in the formulae (4) and (6) may be linear, branched or cyclic. Examples of the alkynyl group are ethynyl, propynyl, and 2-phenylethynyl. Among the alkynyl group, an ethynyl group is preferable.

The alkylsilyl group having 3 to 30 carbon atoms in the formulae (4) and (6) is exemplified by a trialkylsilyl group having the examples of the alkyl group having 1 to 30 carbon atoms. Specific examples of the alkylsilyl group are a trimethylsilyl group, triethylsilyl group, tri-n-butylsilyl group, tri-n-octylsilyl group, triisobutylsilyl group, dimethylethylsilyl group, dimethylisopropylsilyl group, dimethyl-n-propylsilyl group, dimethyl-n-butylsilyl group, dimethyl-t-butylsilyl group, diethylisopropylsilyl group, vinyldimethylsilyl group, propyldimethylsilyl group and triisopropylsilyl group. Three alkyl groups may be the same or different.

The arylsilyl group having 6 to 30 ring carbon atoms in the formulae (4) and (6) may be a dialkylarylsilyl group, alkyldiarylsilyl group and triarylsilyl group.

The dialkylarylsilyl group is exemplified by a dialkylarylsilyl group having two of the examples of the alkyl group having 1 to 30 carbon atoms and one of the aryl group having 6 to 30 ring carbon atoms. The dialkylarylsilyl group preferably has 8 to 30 carbon atoms. Two alkyl groups may be the same or different.

The alkyldiarylsilyl group is exemplified by an alkyldiarylsilyl group having one of the examples of the alkyl group having 1 to 30 carbon atoms and two of the aryl group having 6 to 30 ring carbon atoms. The dialkylarylsilyl group preferably has 13 to 30 carbon atoms. Two aryl groups may be the same or different.

The triarylsilyl group is exemplified by a triarylsilyl group having three of the aryl group having 6 to 30 ring carbon atoms. The dialkylarylsilyl group preferably has 18 to 30 carbon atoms. Three aryl groups may be the same or different.

The alkoxy group having 1 to 30 carbon atoms in the formulae (4) and (6) is represented by —OY. Y is exemplified by the alkyl group having 1 to 30 carbon atoms. Examples of the alkoxy group are a methoxy group, ethoxy group, propoxy group, butoxy group, pentyloxy group and hexyloxy group.

A halogenated alkoxy group provided by substituting the alkoxy group with a halogen atom is exemplified by a halogenated alkoxy group provided by substituting the alkoxy group having 1 to 30 carbon atoms with one or more halogen groups.

The aralkyl group having 6 to 30 ring carbon atoms in the formulae (4) and (6) is represented by —Y—Z. Y is exemplified by an alkylene group corresponding to the alkyl group having 1 to 30 carbon atoms. Z is exemplified by the examples of the aryl group having 6 to 30 ring carbon atoms. This aralkyl group is preferably an aralkyl group having 7 to 30 carbon atoms, in which an aryl moiety has 6 to 30 carbon atoms, preferably 6 to 20 carbon atoms, more preferably 6 to 12 carbon atoms, and an alkyl moiety has 1 to 30 carbon atoms, preferably 1 to 20 carbon atoms, more preferably 1 to 10 carbon atoms, further preferably 1 to 6 carbon atoms. Examples of the aralkyl group are a benzyl group, 2-phenylpropane-2-yl group, 1-phenylethyl group, 2-phenylethyl group, 1-phenylisopropyl group, 2-phenylisopropyl group, phenyl-t-butyl group, á-naphthylmethyl group, 1-á-naphthylethyl group, 2-á-naphthylethyl group, 1-â-naphthylisopropyl group, 2-á-naphthylisopropyl group, â-naphthylmethyl group, 1-â-naphthylethyl group, 2-â-naphthylethyl group, 1-â-naphthylisopropyl group, 2-â-naphthylisopropyl group, 1-pyrorylmethyl group, 2-(1-pyroryl)ethyl group, p-methylbenzyl group, m-methylbenzyl group, o-methylbenzyl group, p-chlorobenzyl group, m-chlorobenzyl group, o-chlorobenzyl group, p-bromobenzyl group, m-bromobenzyl group, o-bromobenzyl group, p-iodobenzyl group, m-iodobenzyl group, o-iodobenzyl group, p-hydroxybenzyl group, m-hydroxybenzyl group, o-hydroxybenzyl group, p-aminobenzyl group, m-aminobenzyl group, o-aminobenzyl group, p-nitrobenzyl group, m-nitrobenzyl group, o-nitrobenzyl group, p-cyanobenzyl group, m-cyanobenzyl group, o-cyanobenzyl group, 1-hydroxy-2-phenylisopropyl group and 1-chloro-2-phenylisopropyl group.

The aryloxy group having 6 to 30 ring carbon atoms in the formulae (4) and (6) is represented by —OZ. Z is exemplified by the aryl group having 6 to 30 ring carbon atoms or the following monocyclic group and fused cyclic group. The aryloxy group is exemplified by a phenoxy group.

Examples of the halogen atom in the formulae (4) and (6) are fluorine, chlorine, bromine and iodine, among which fluorine is preferable.

In the invention, "carbon atoms forming a ring (ring carbon atoms)" mean carbon atoms forming a saturated ring, unsaturated ring, or aromatic ring. "Atoms forming a ring (ring atoms)" mean carbon atoms and hetero atoms forming a hetero ring including a saturated ring, unsaturated ring, or aromatic ring.

Examples of the substituent meant by "substituted or unsubstituted" are the above-described aryl group, heterocyclic group, alkyl group (linear or branched alkyl group, cycloalkyl group and halogenated alkyl group), alkenyl group, alkynyl group, alkylsilyl group, arylsilyl group, alkoxy group, halogenated alkoxy group, aralkyl group, aryloxy group, halogen atom, cyano group, hydroxyl group, nitro group and carboxy group. In the above-described substituents, the aryl group, heterocyclic group, alkyl group, halogen atom, alkylsilyl group, arylsilyl group and cyano group are preferable. The preferable ones of the specific examples of each substituent are further preferable. Moreover, these substituents may be further substituted by the above-described substituents.

"Unsubstituted" in "substituted or unsubstituted" means that a hydrogen atom is substituted.

In a later-described compound or a partial structure thereof, the same applies to the description of "substituted or unsubstituted."

In the invention, a "hydrogen atom" means isotopes having different neutron numbers and specifically encompasses protium, deuterium and tritium.

Examples of specific structures of the aromatic heterocyclic derivative according to this exemplary embodiment represented by the formula (4) are as follows. However, the invention is not limited to the aromatic derivative having these structures.

[Formula 12]

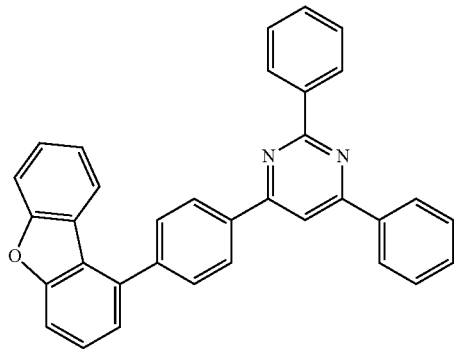
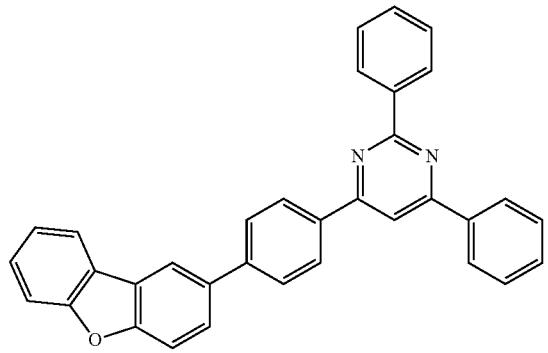
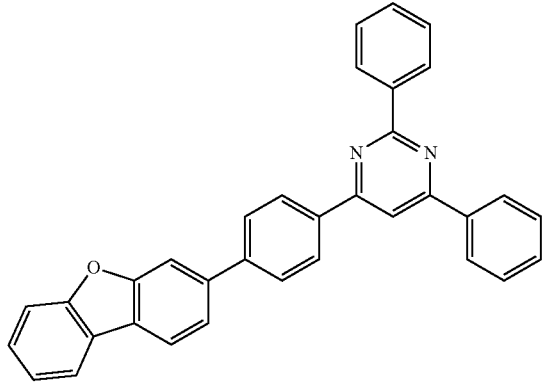
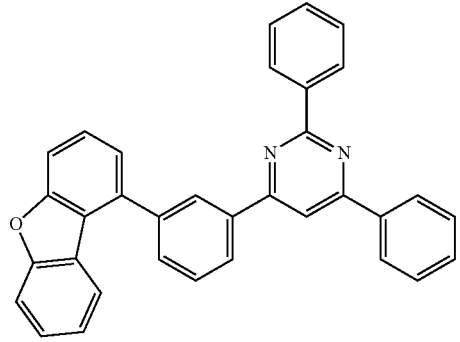
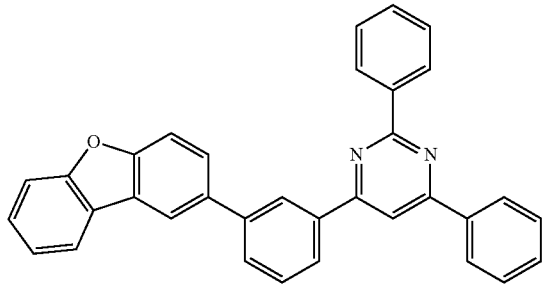
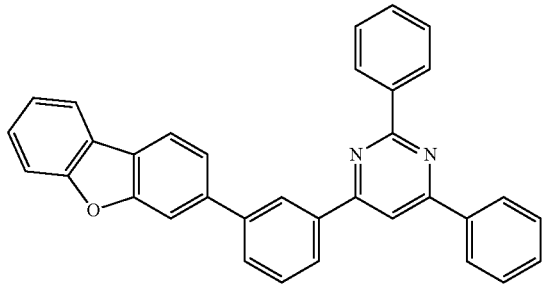

17 18
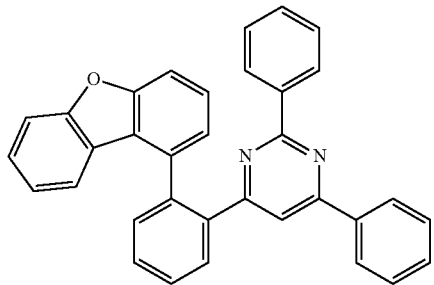 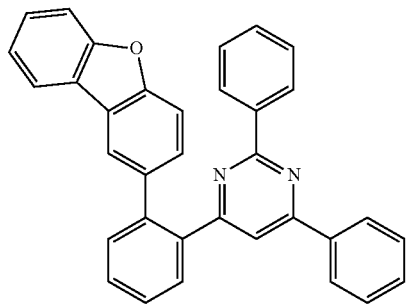
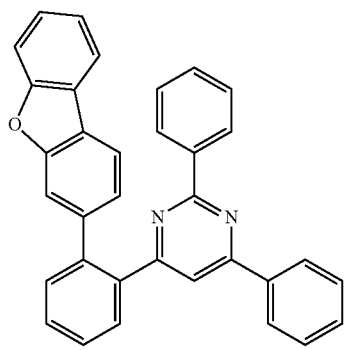
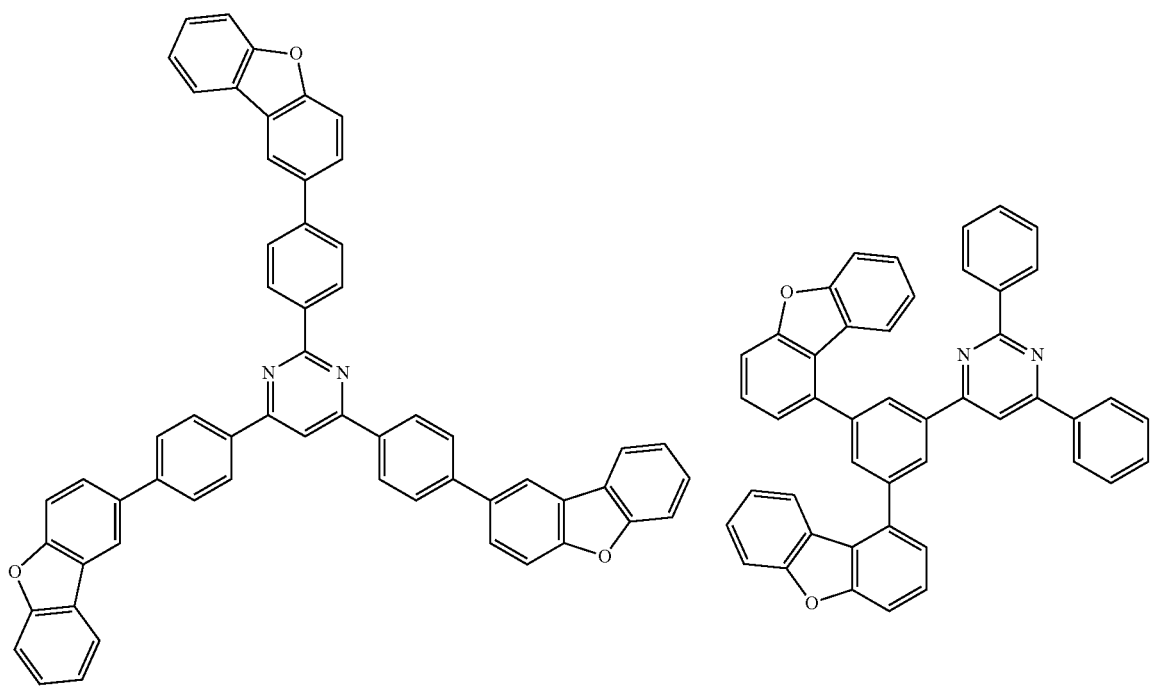

-continued
| 19 | 20 |
|---|---|
| 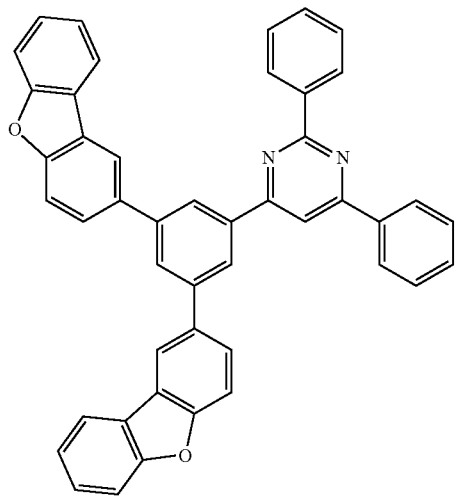 | 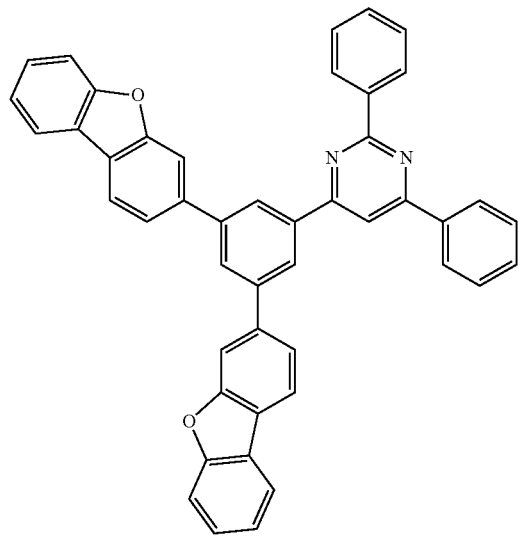 |
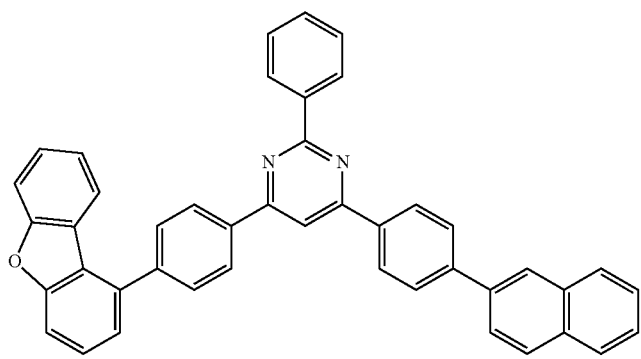
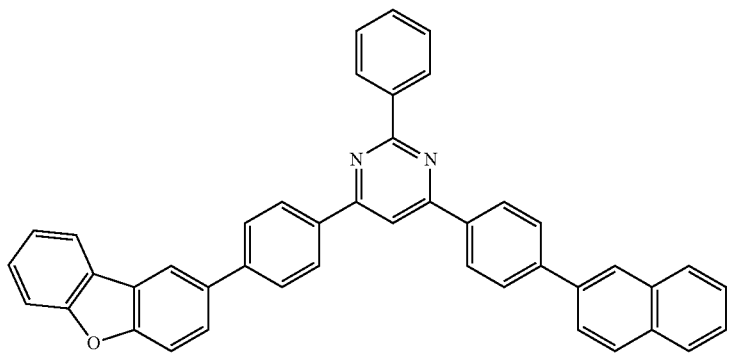
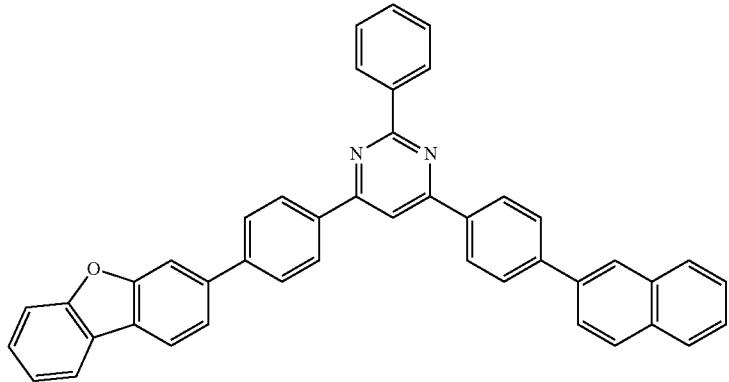

-continued
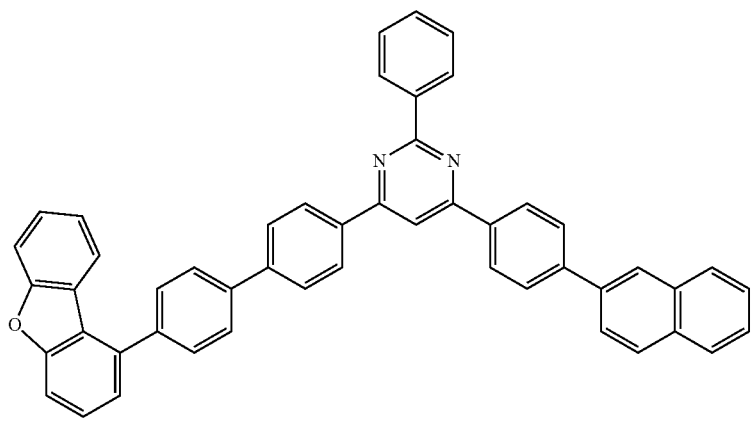
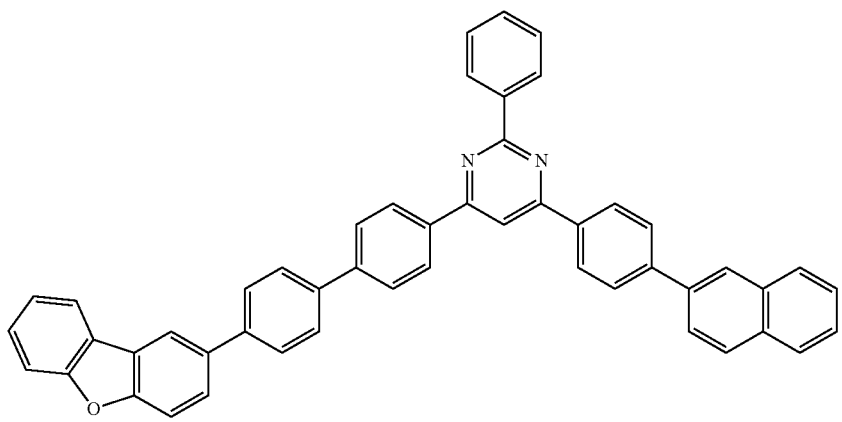
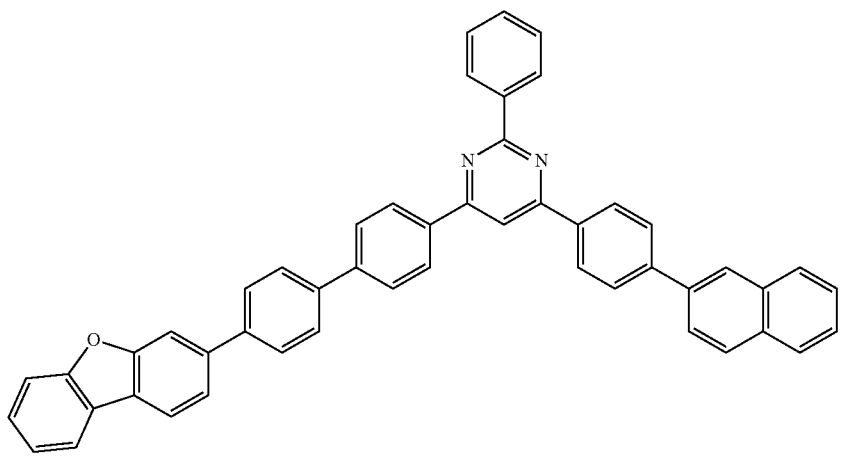
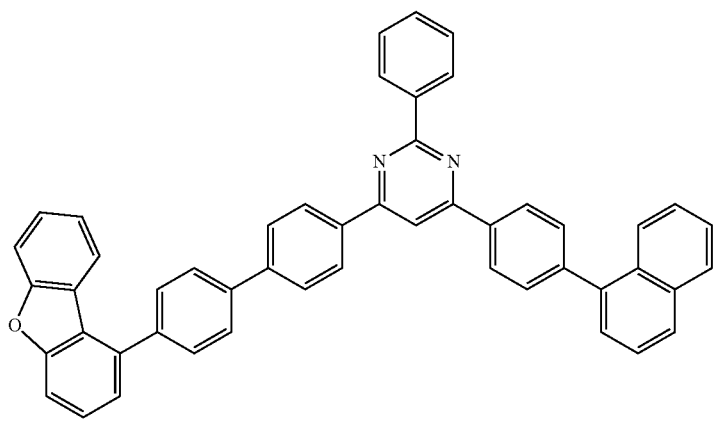

-continued
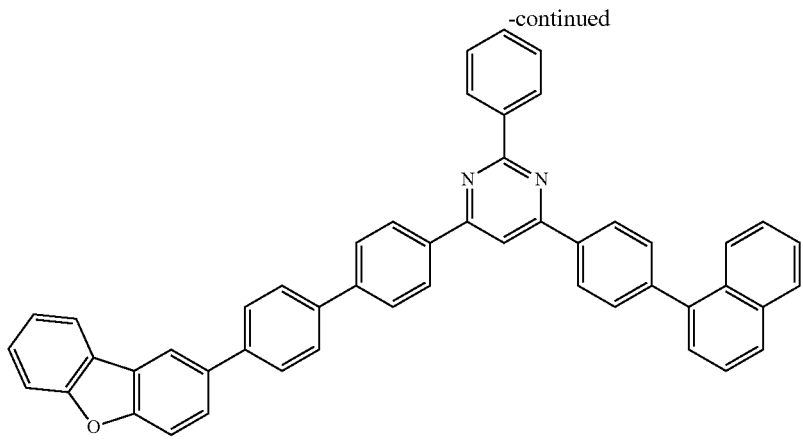
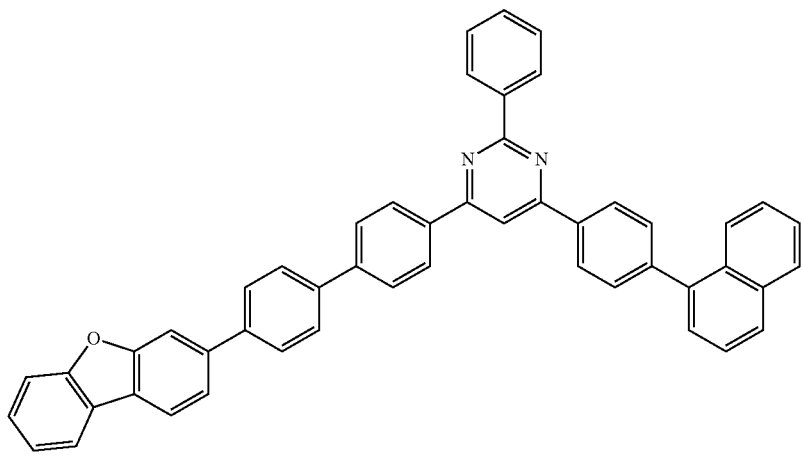
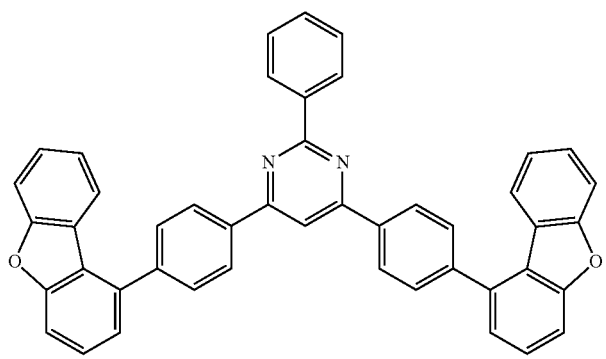
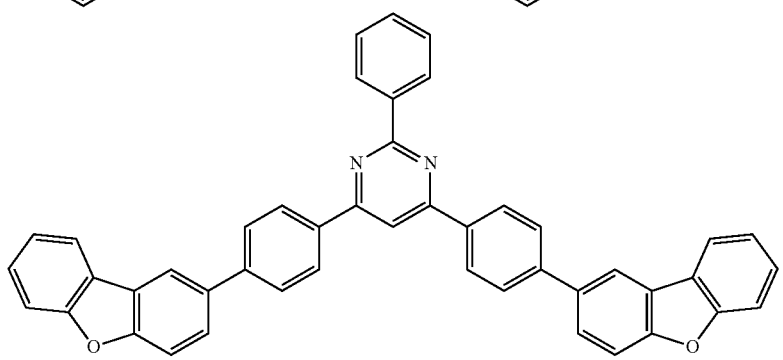

-continued
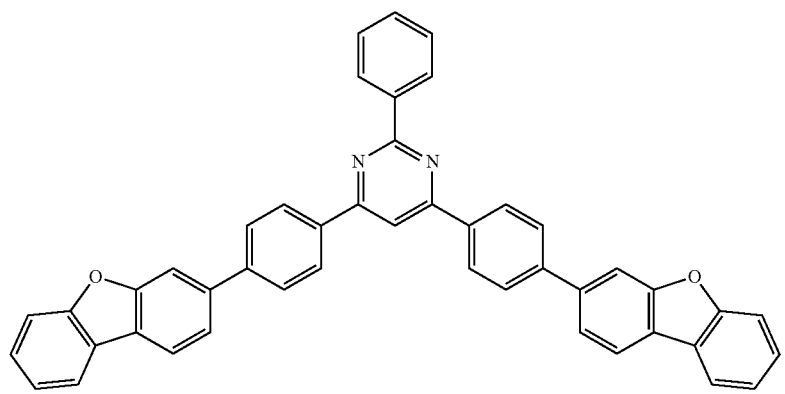
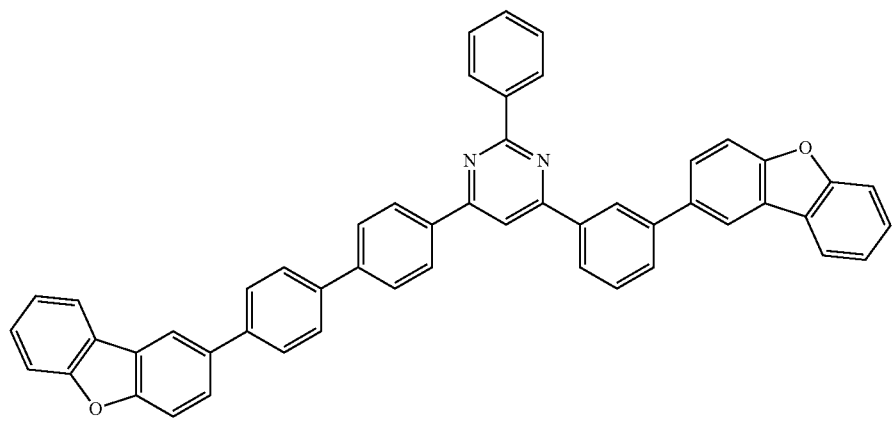
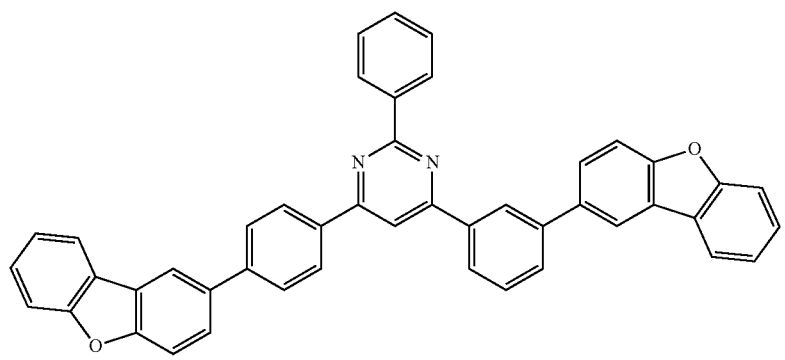
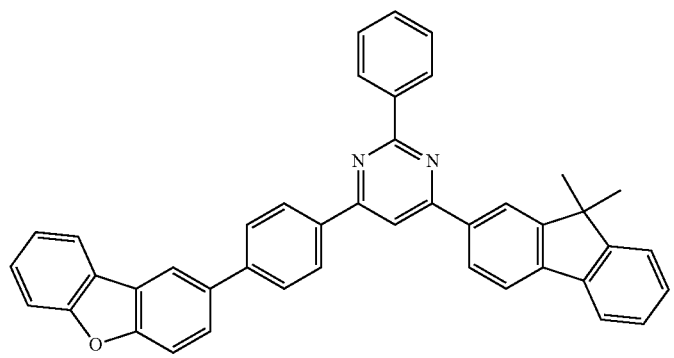

[Formula 13]
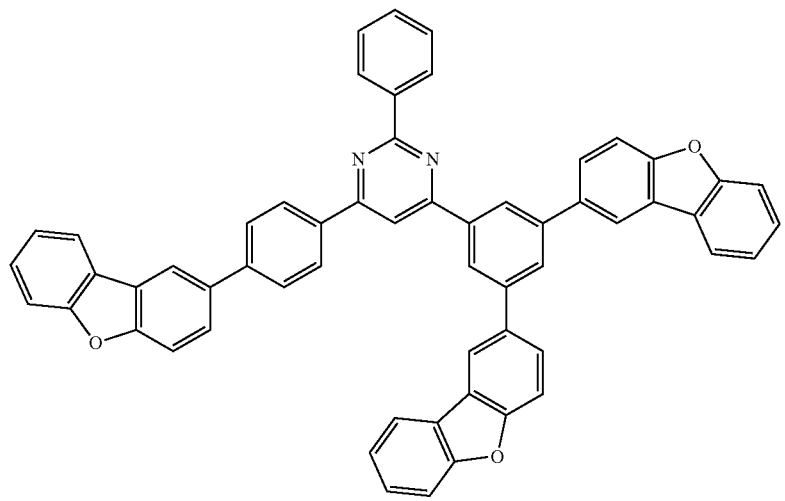
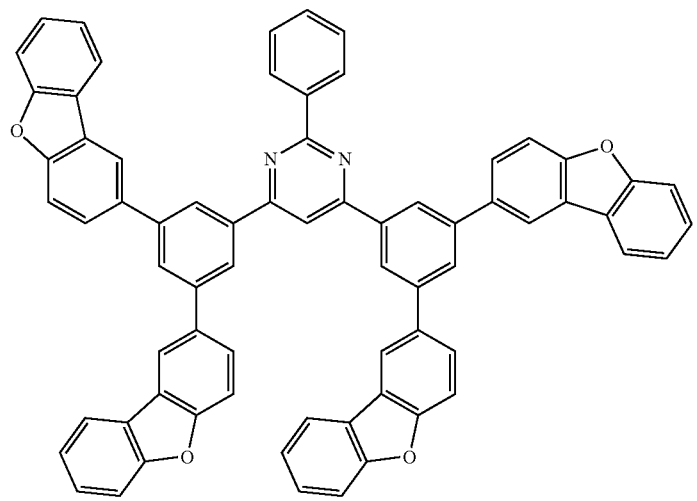
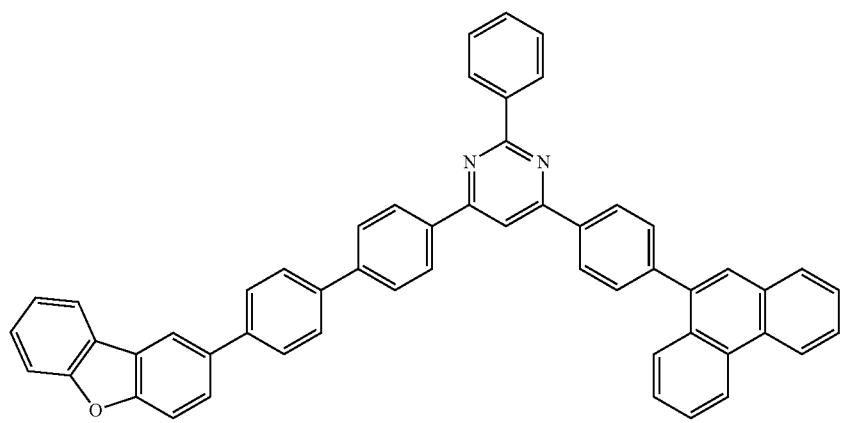

-continued
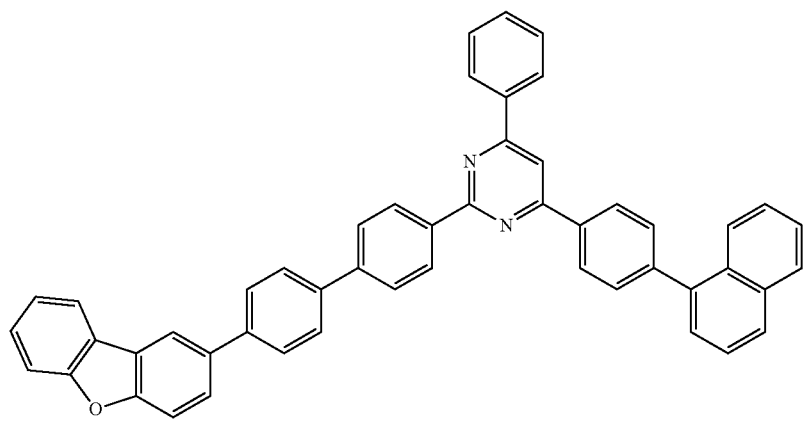
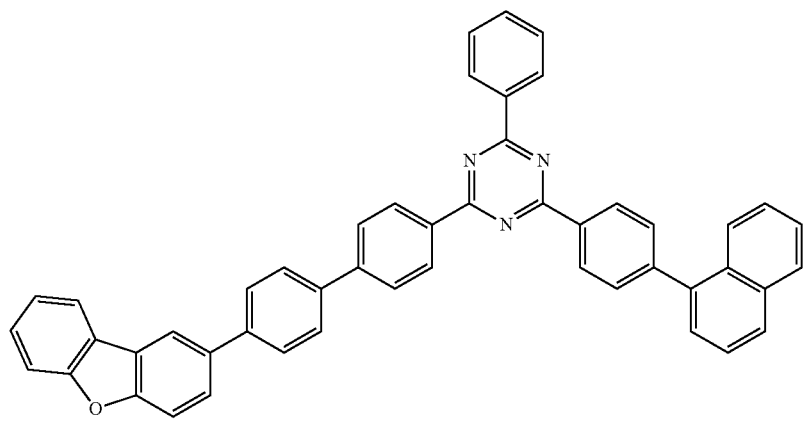
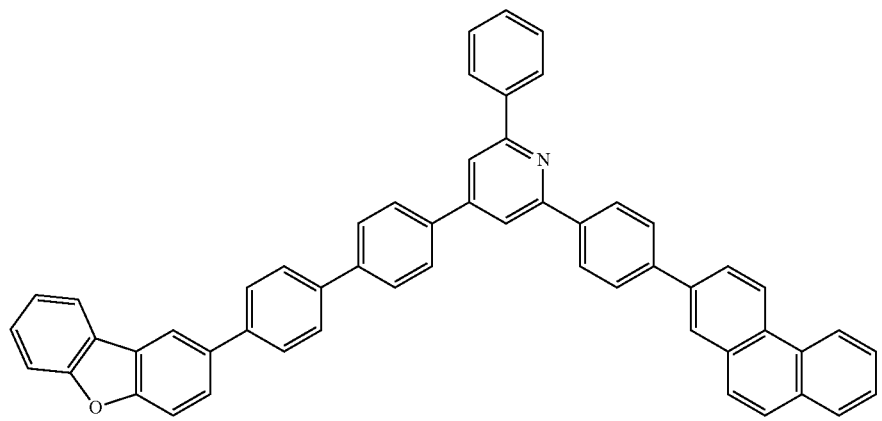
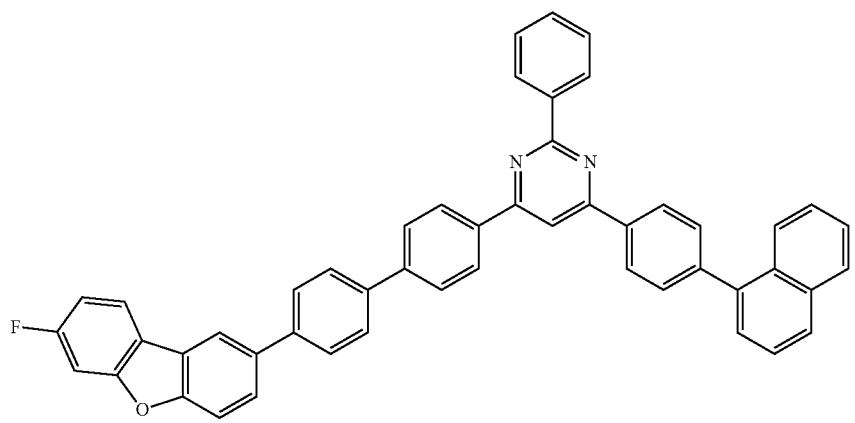

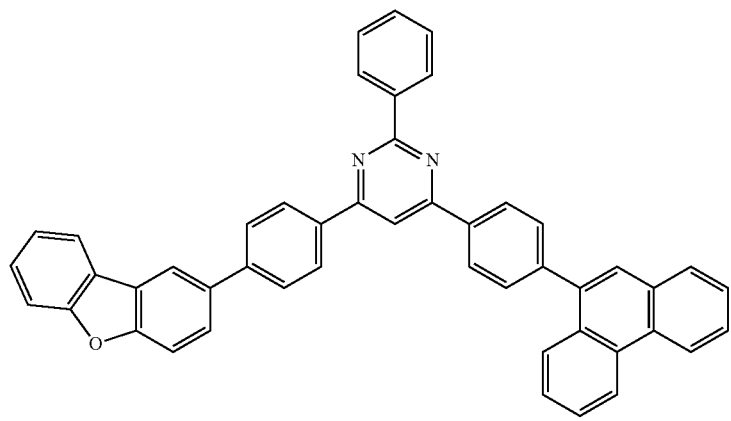
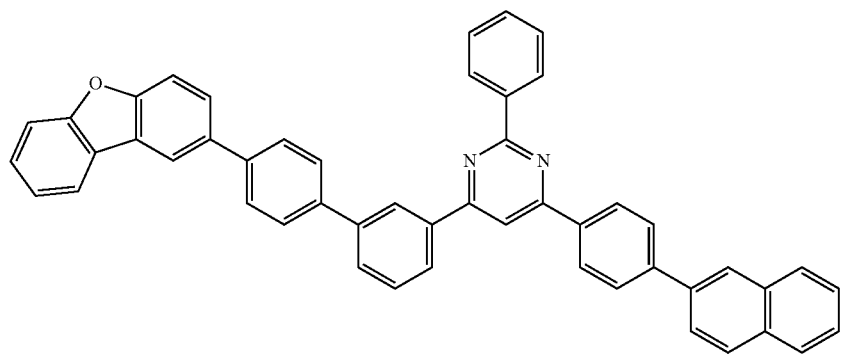
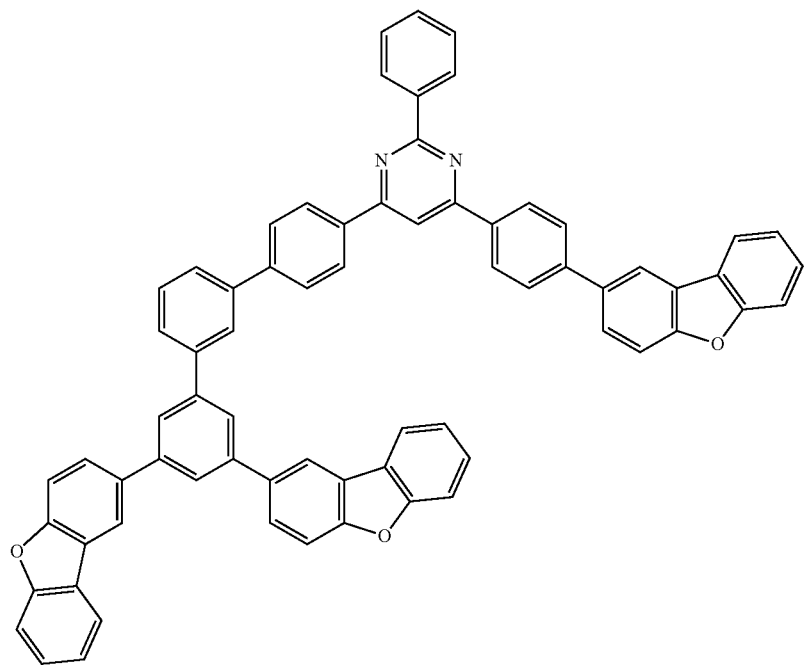

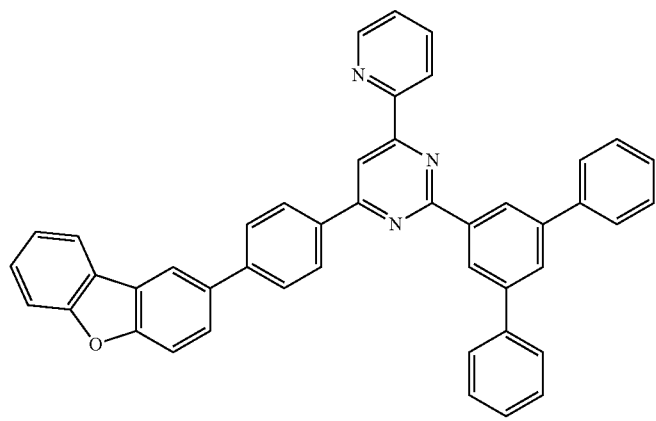
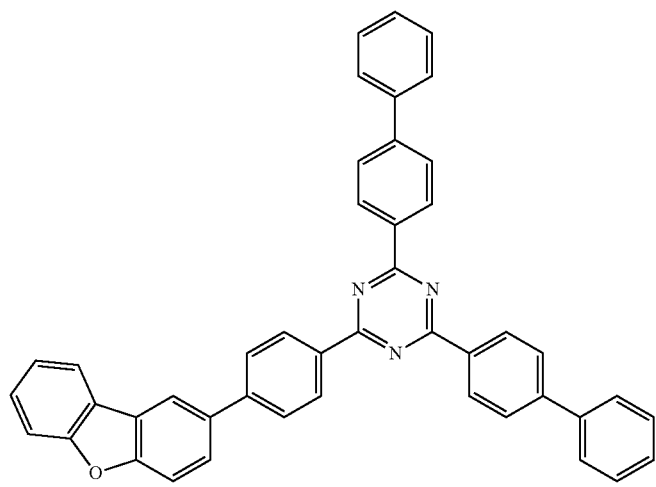
[Formula 14]
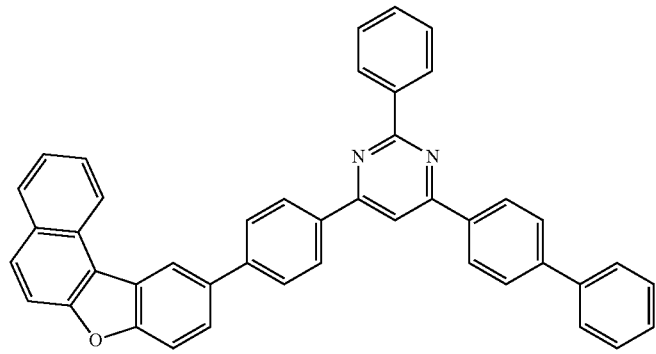
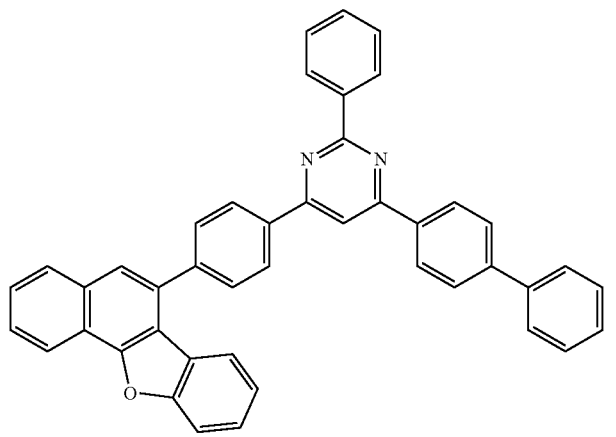

-continued
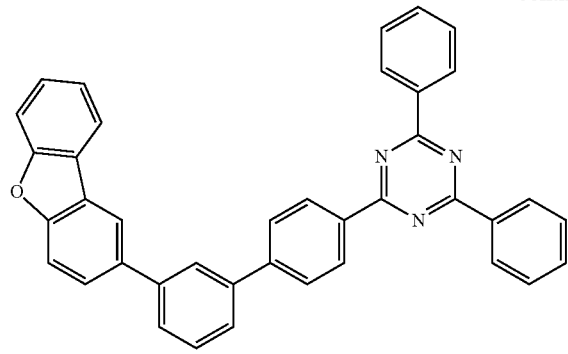
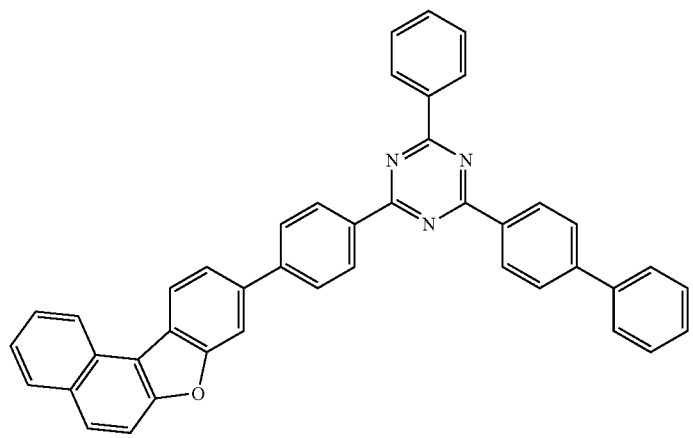
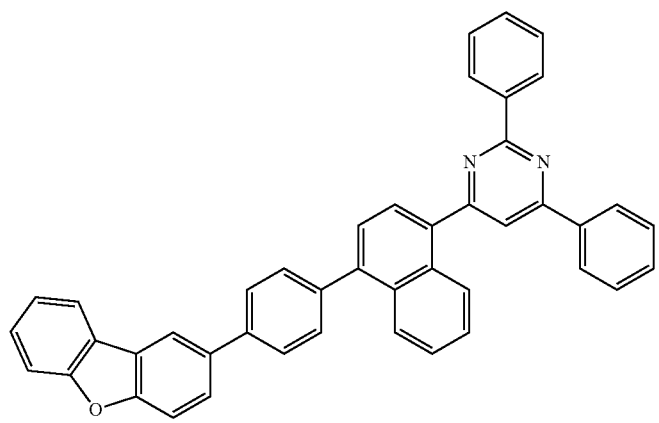
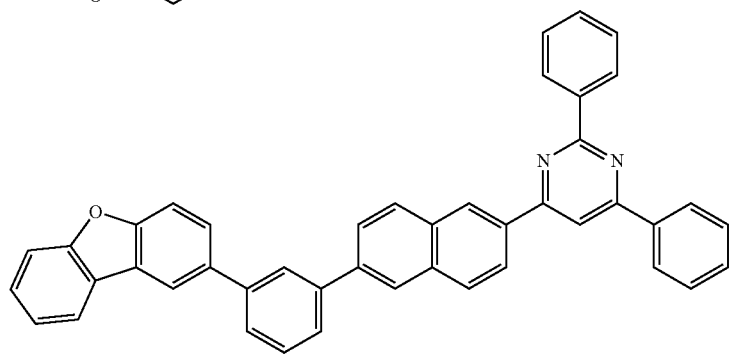

-continued
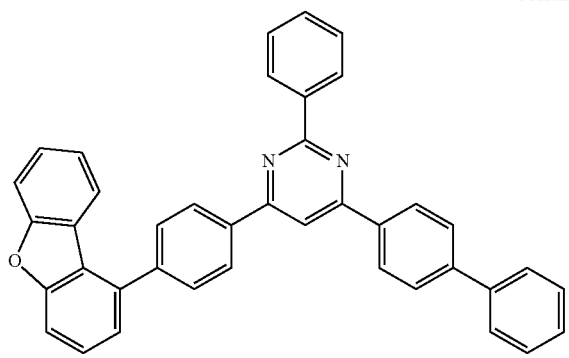
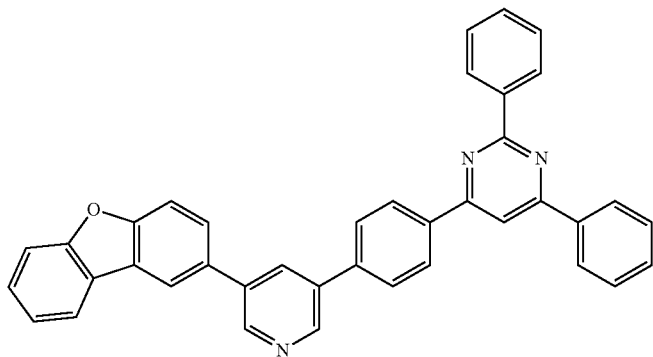
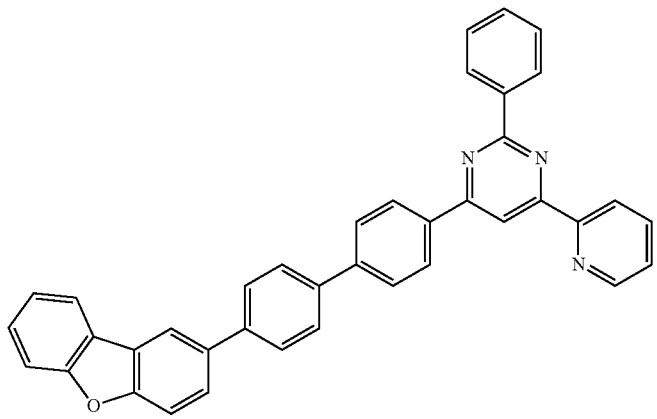
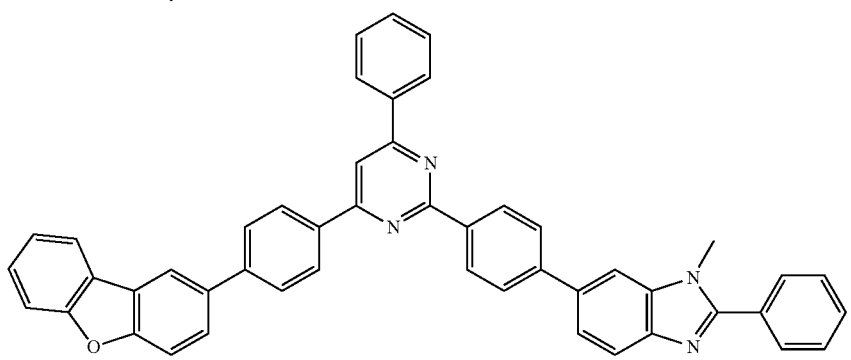

[Formula 15]
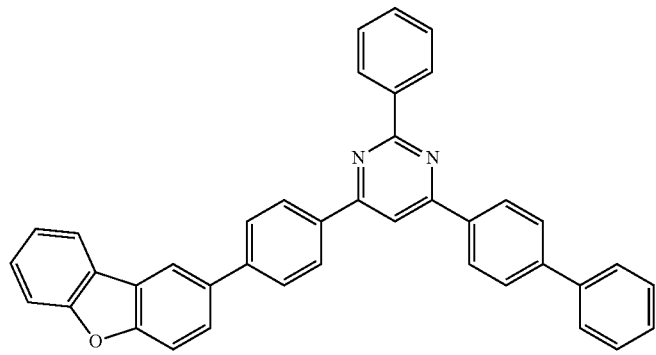
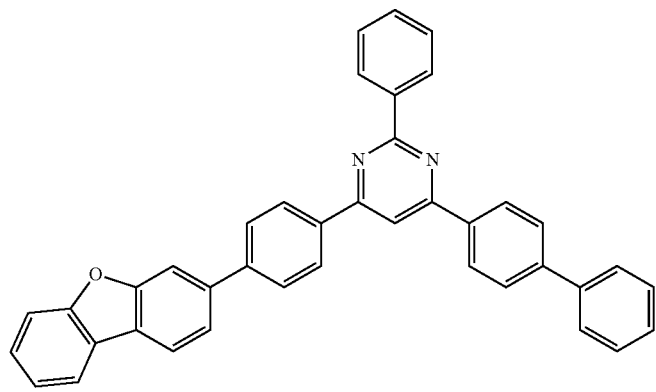
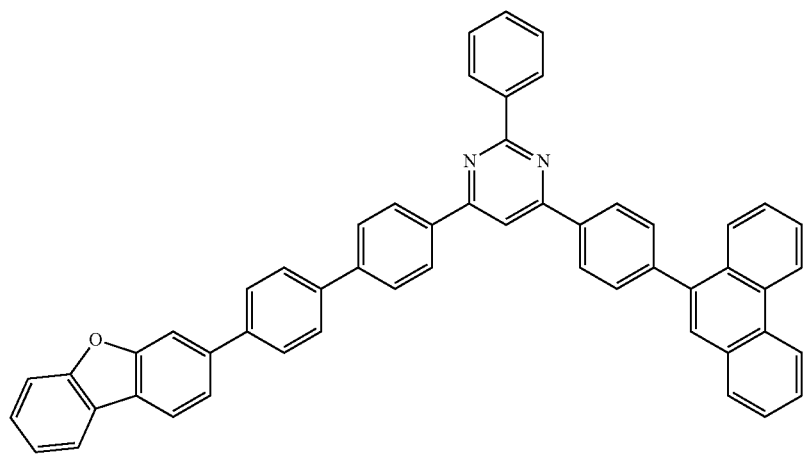
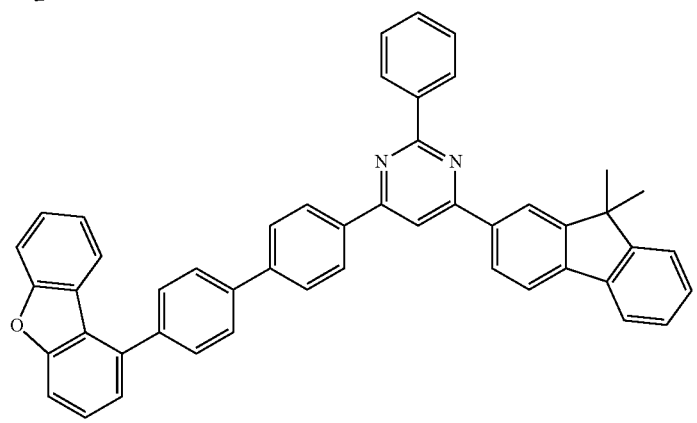

-continued
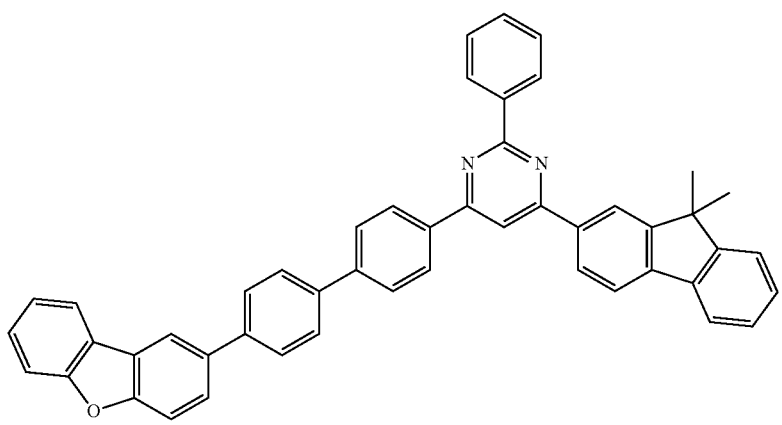
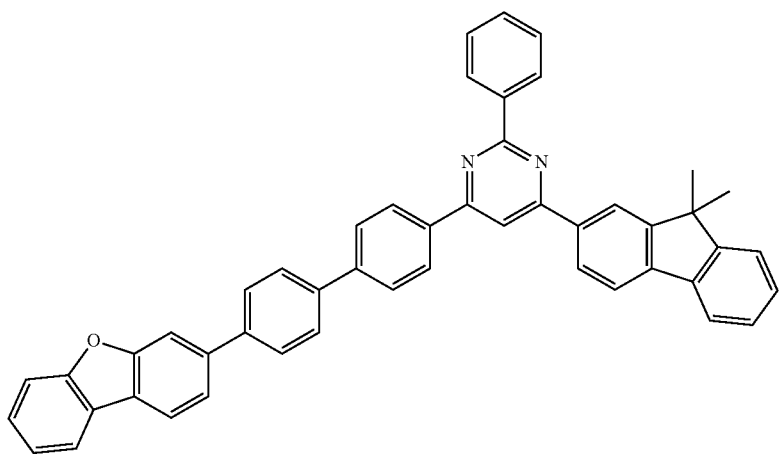
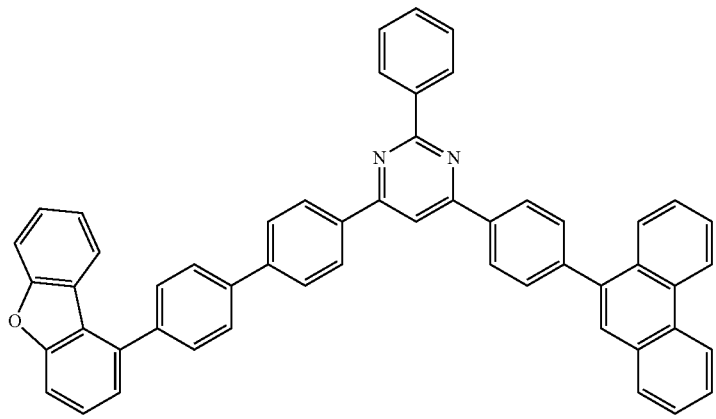
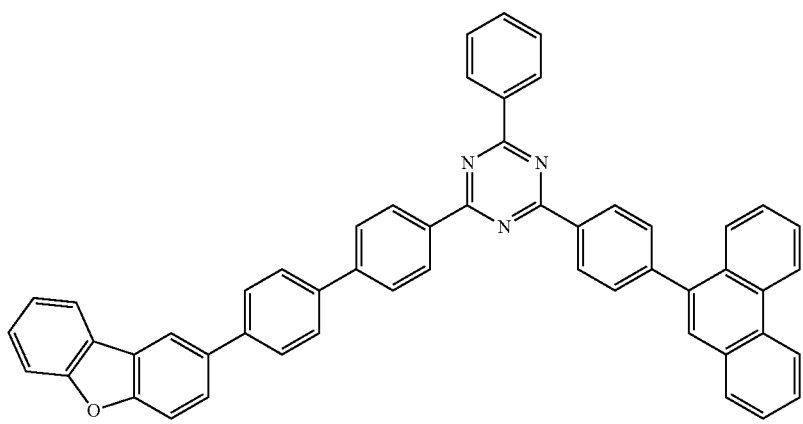

-continued
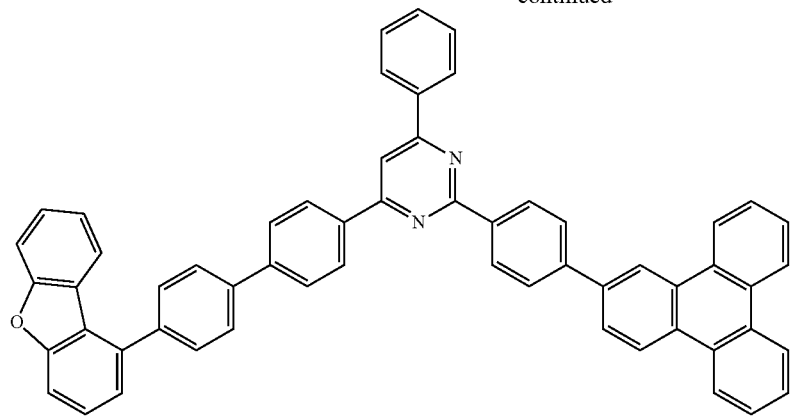
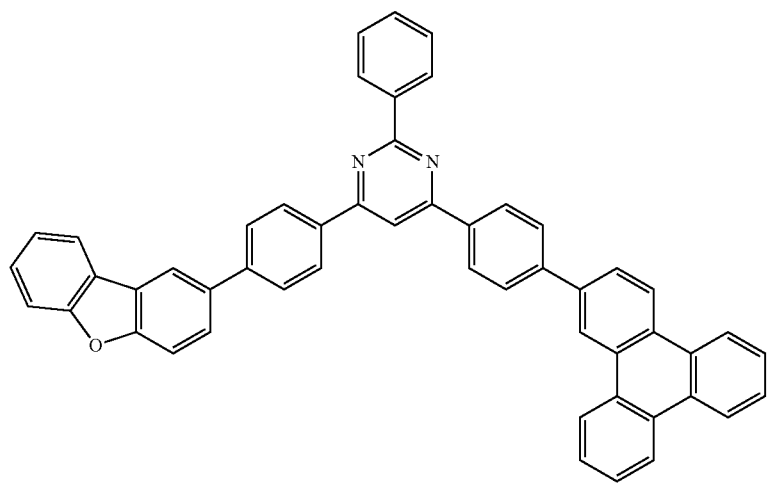
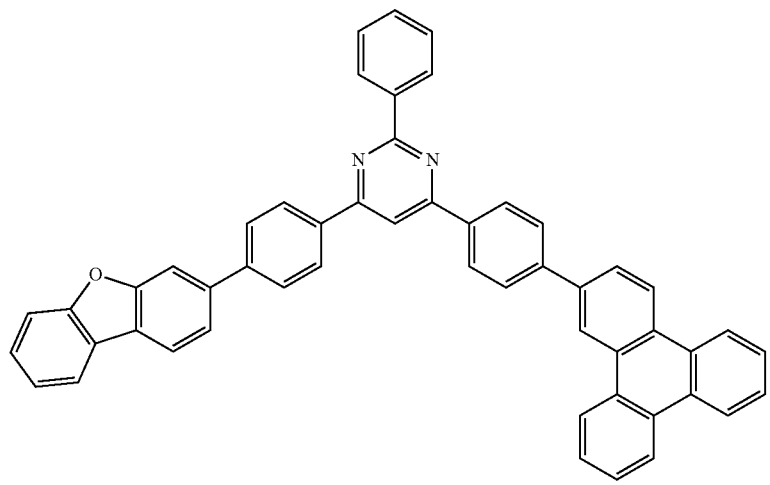

-continued
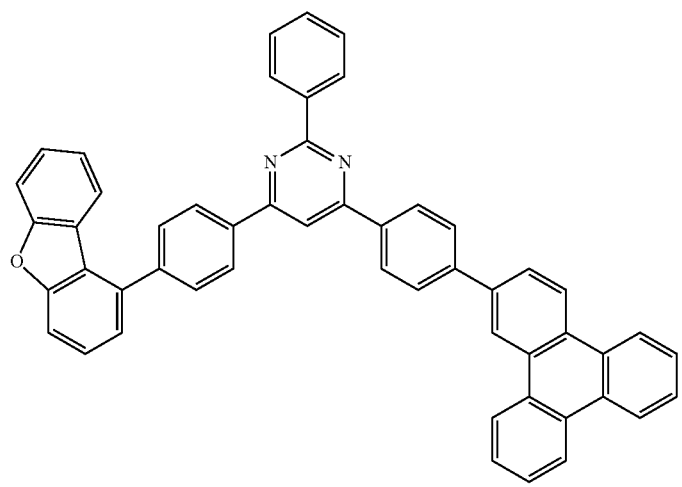
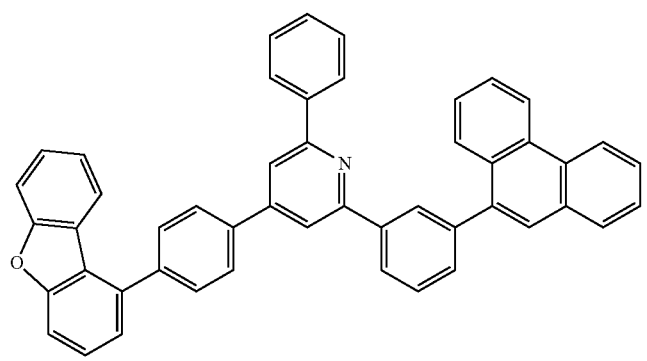
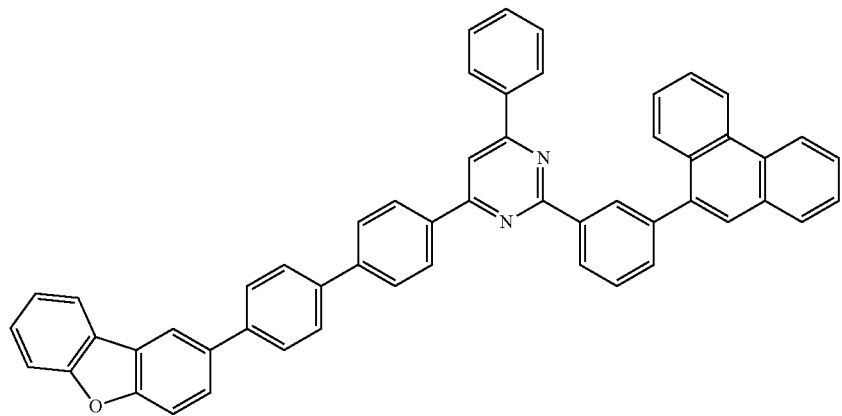
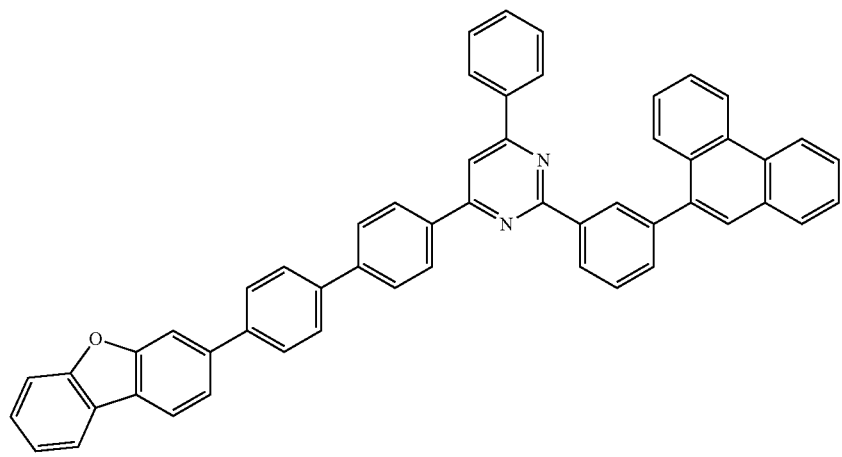

-continued
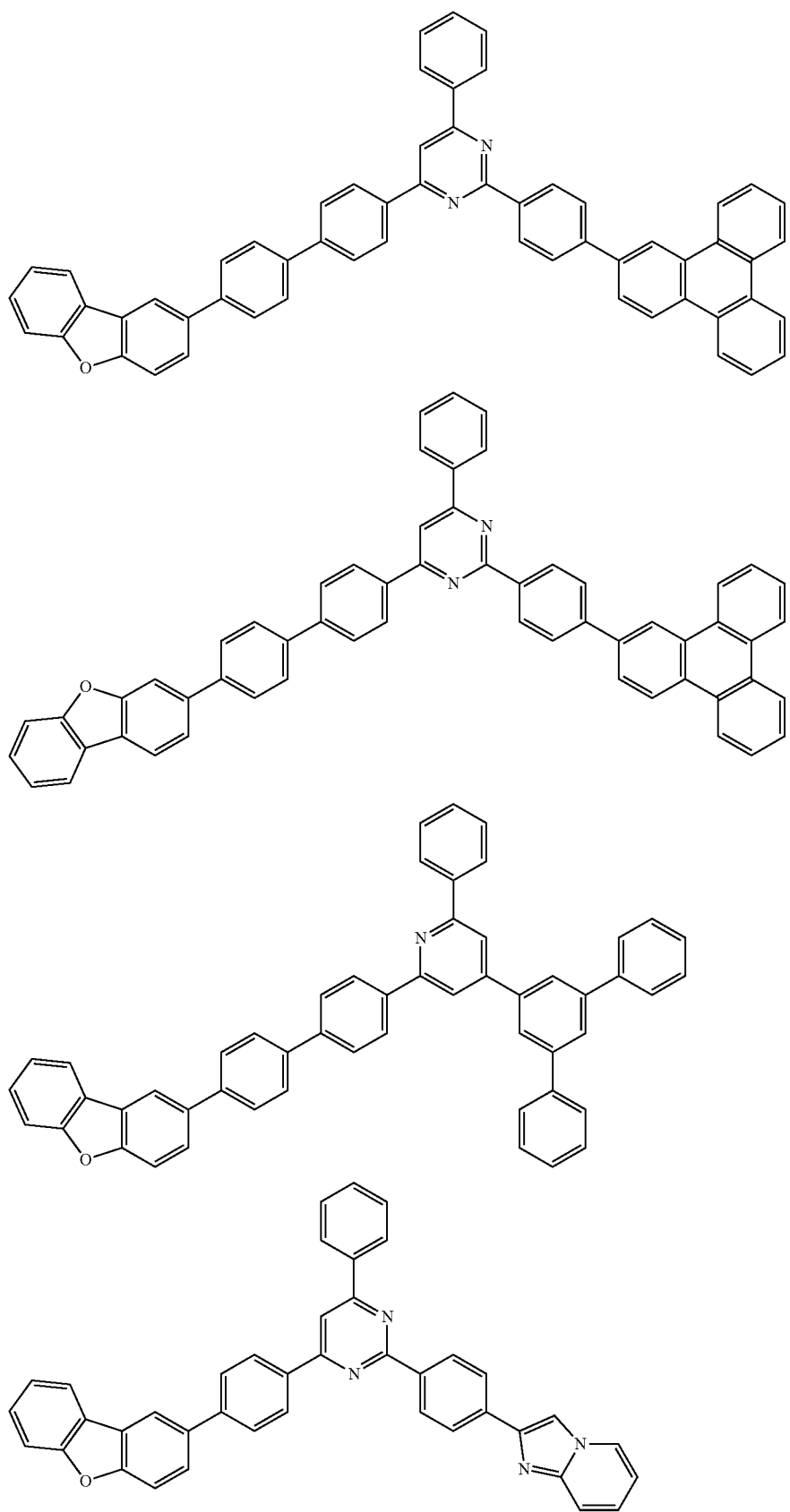

-continued
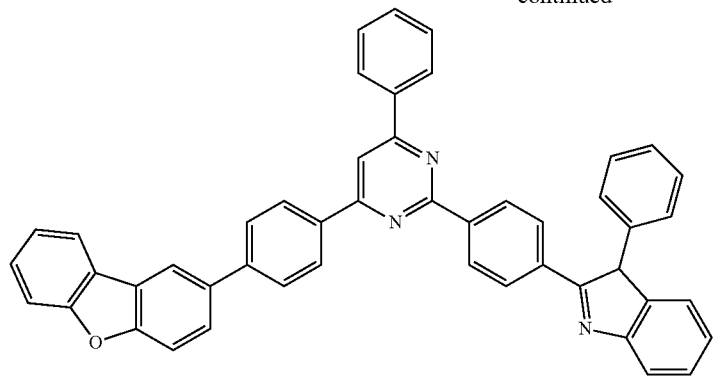
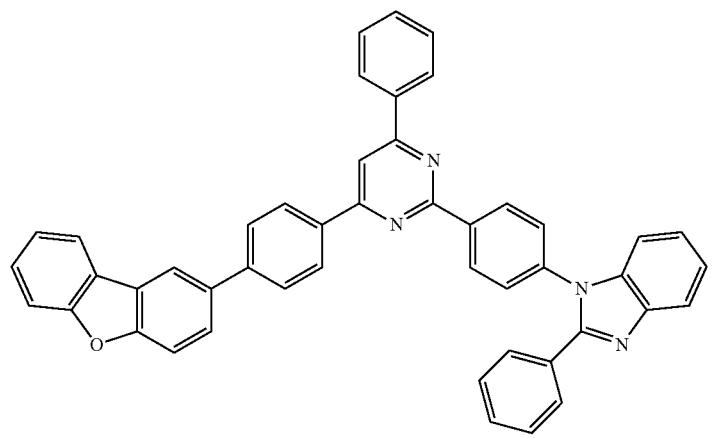
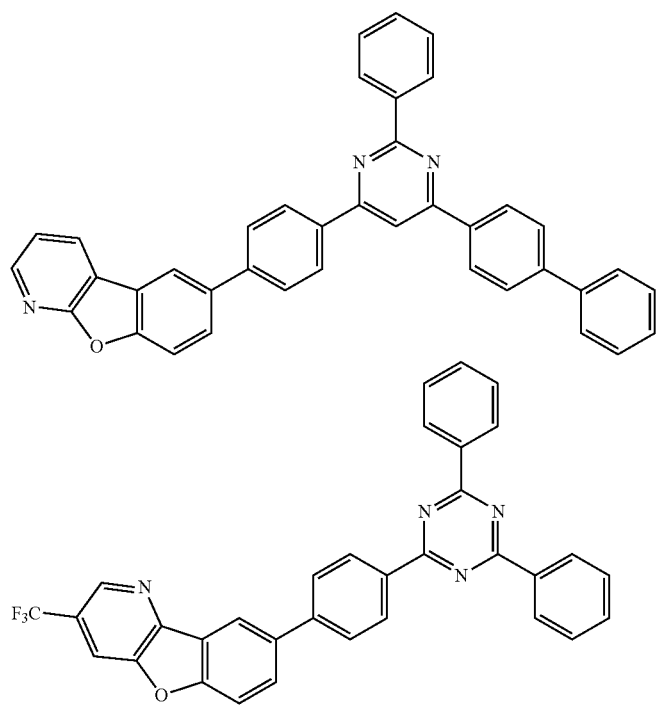

-continued
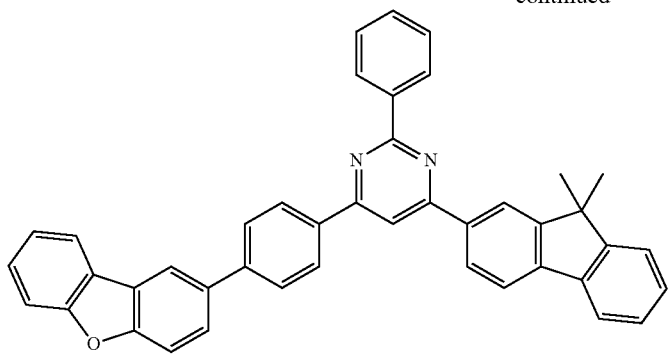
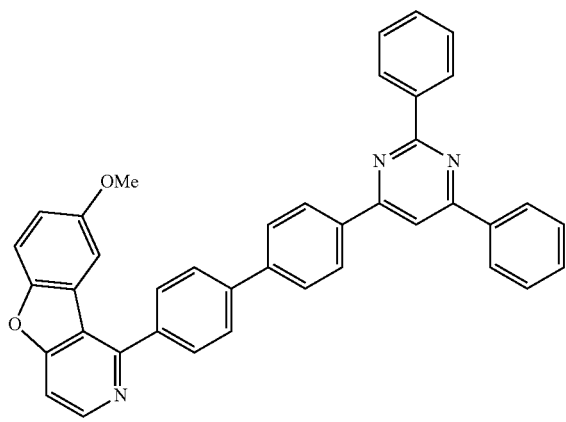
[Formula 16]
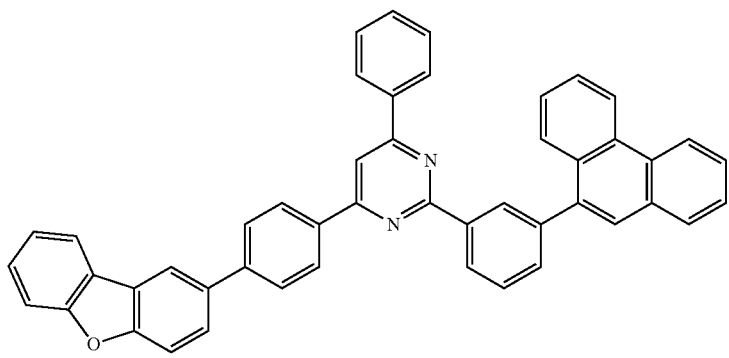
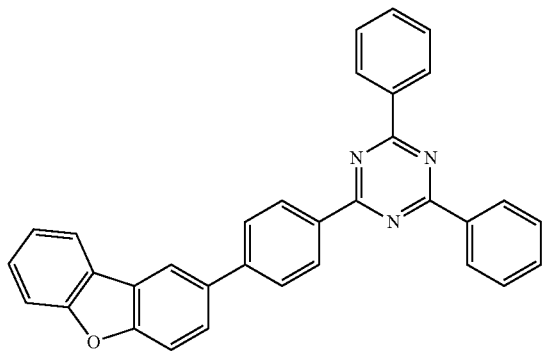

-continued
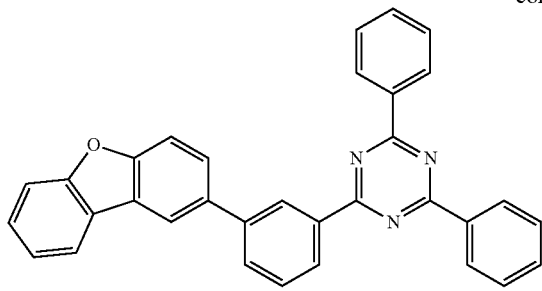
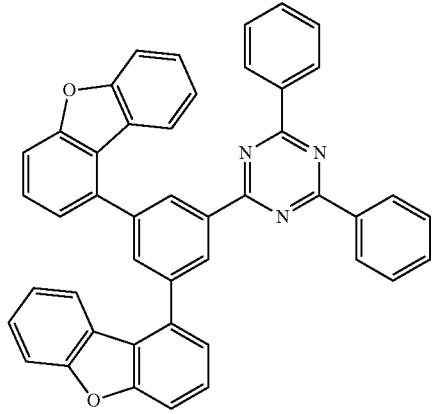
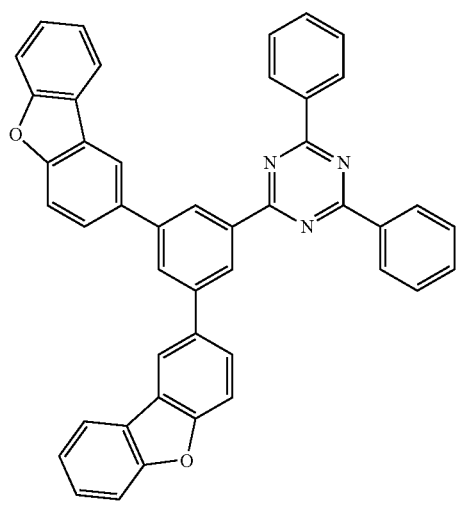
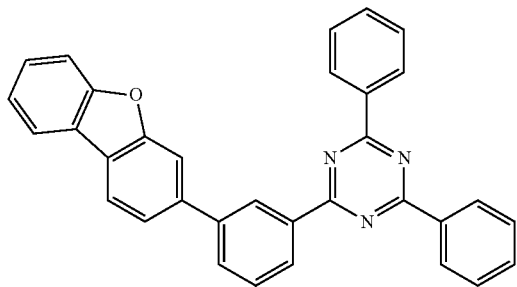
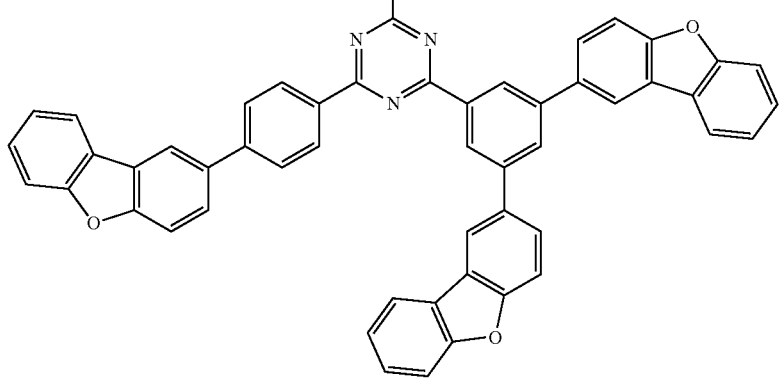

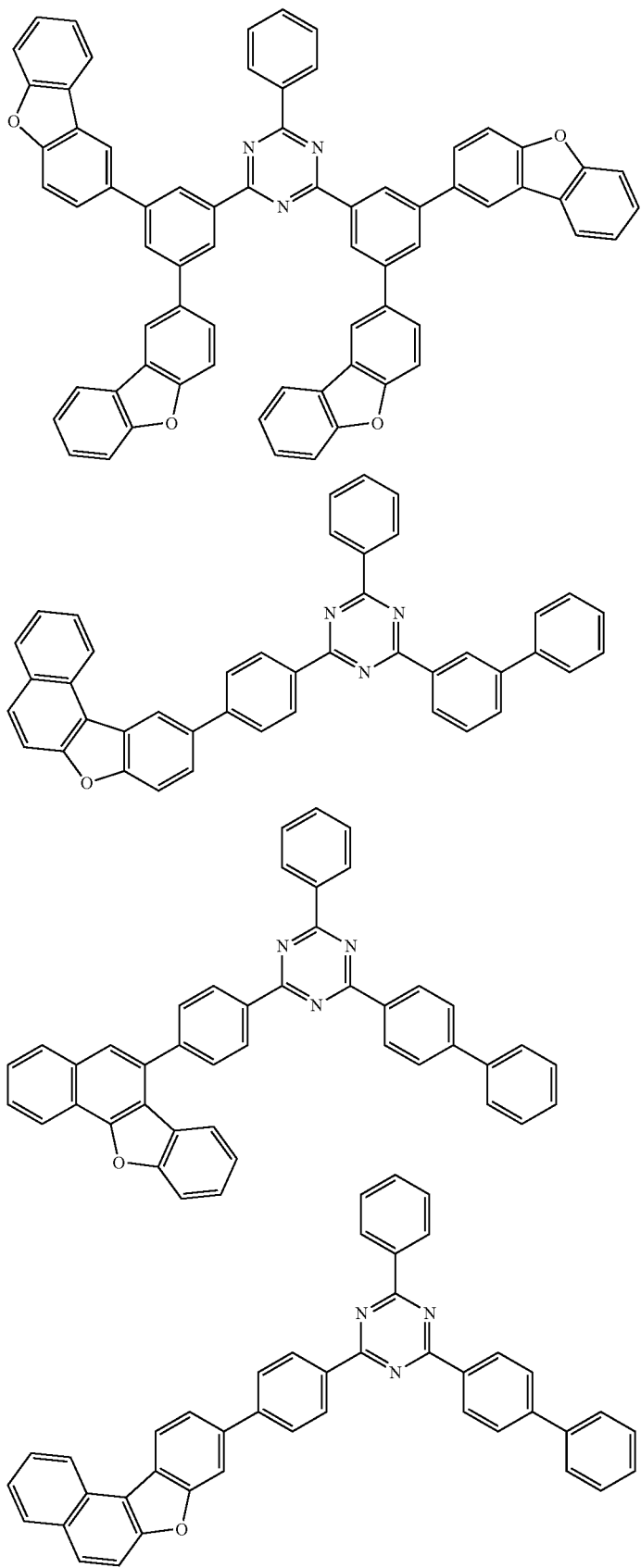

-continued
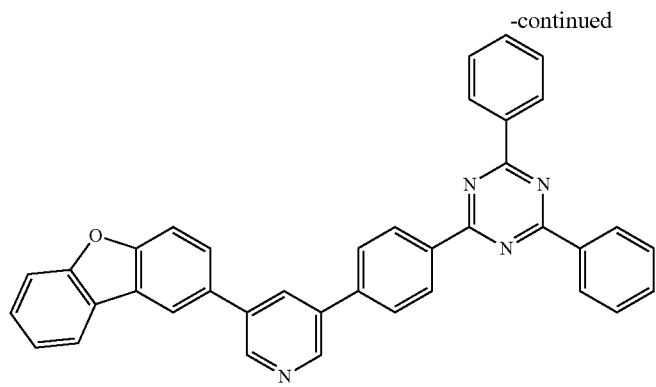
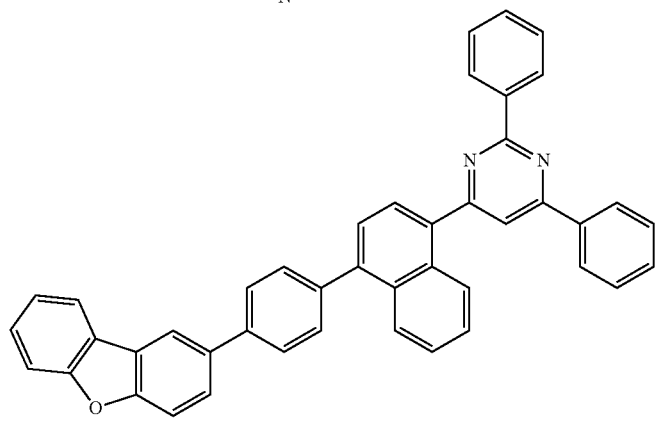
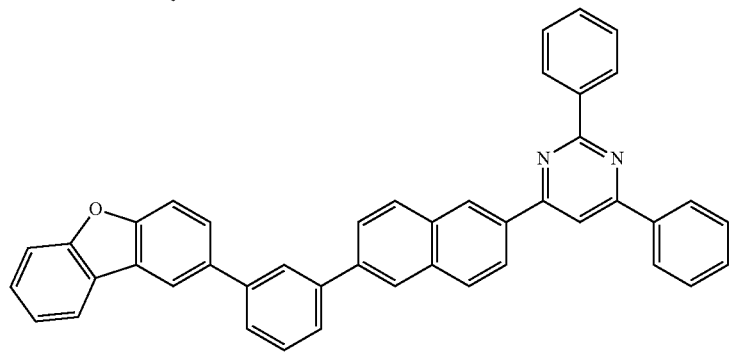
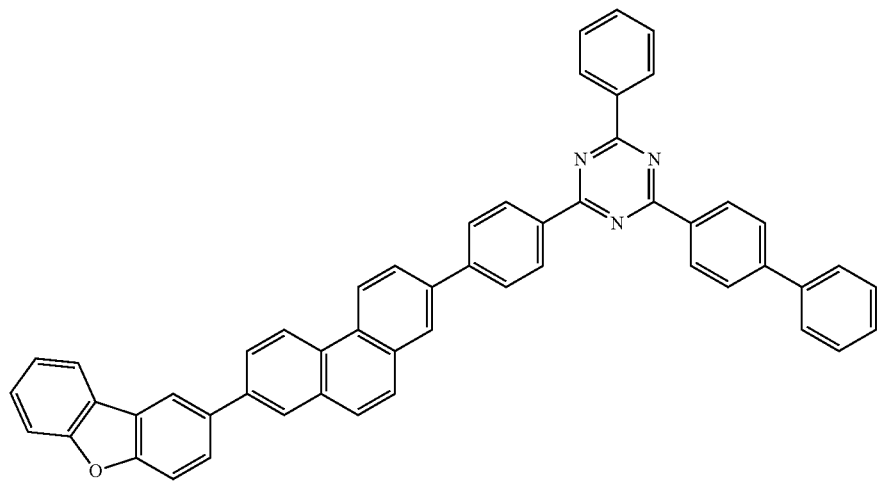

-continued
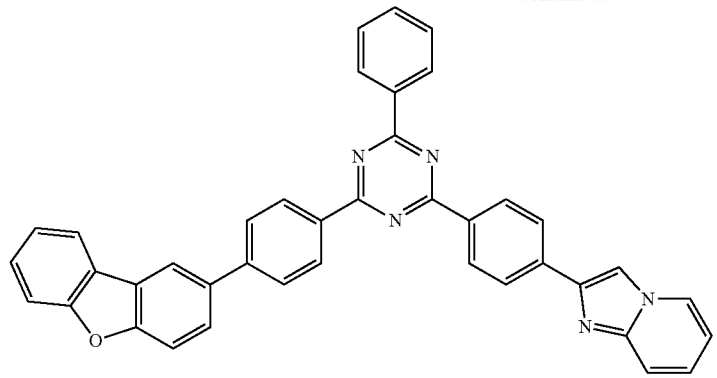
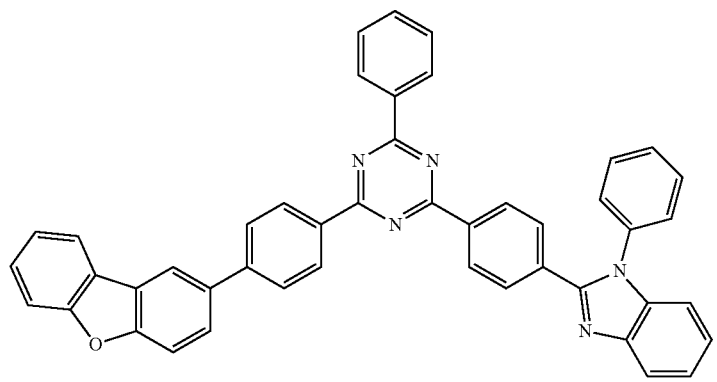
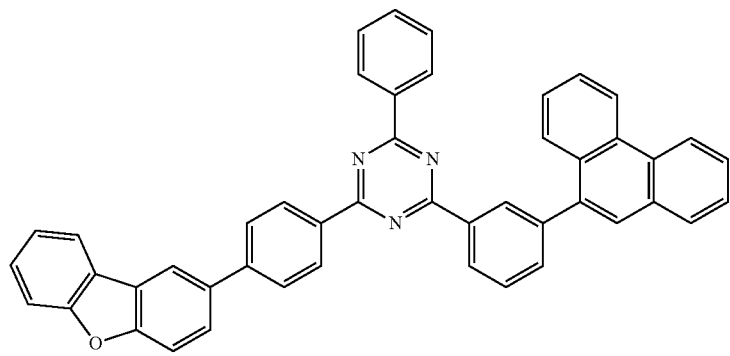
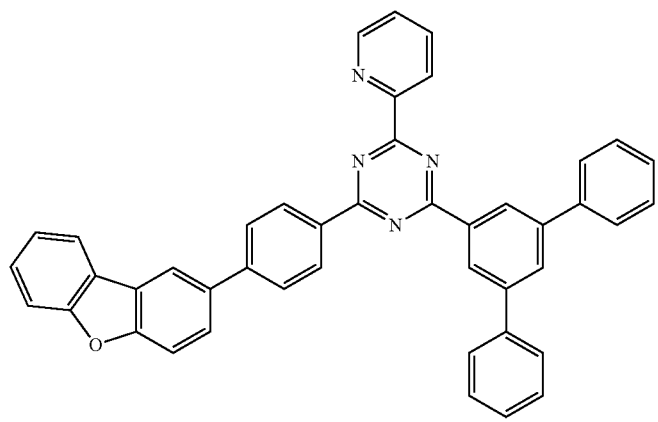

-continued
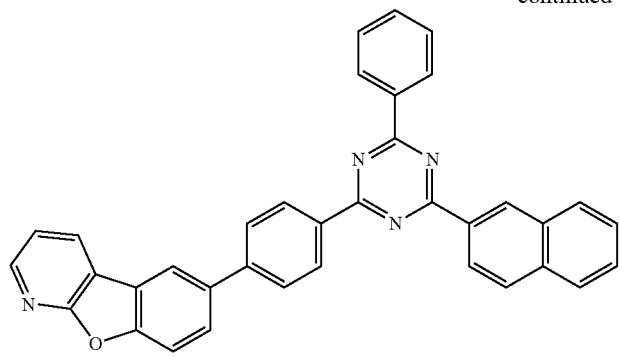
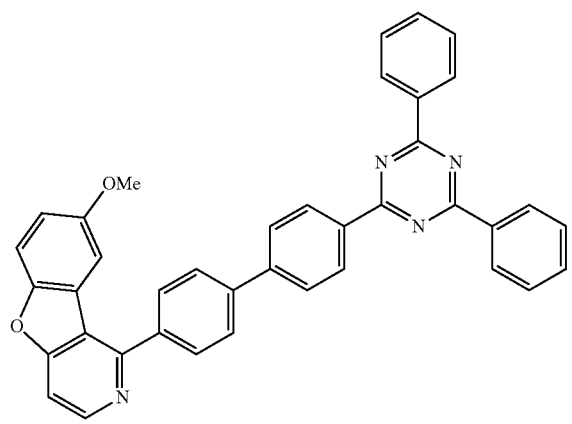
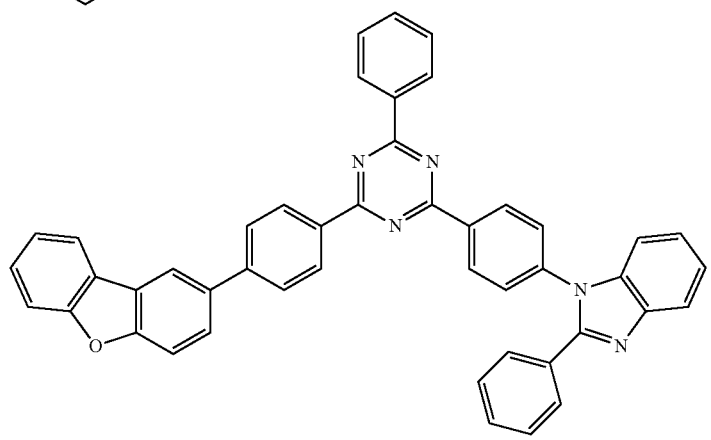
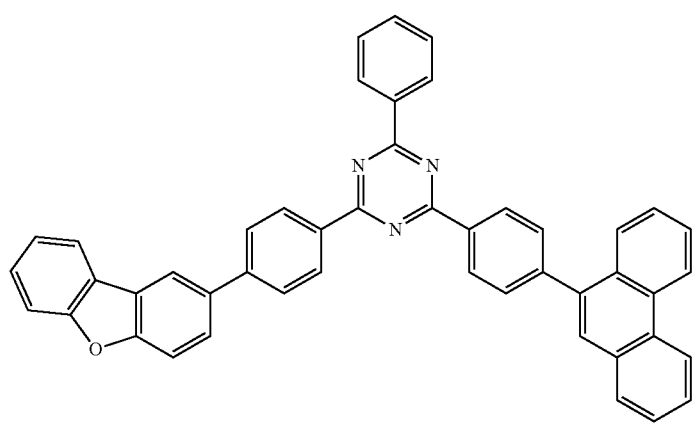

-continued
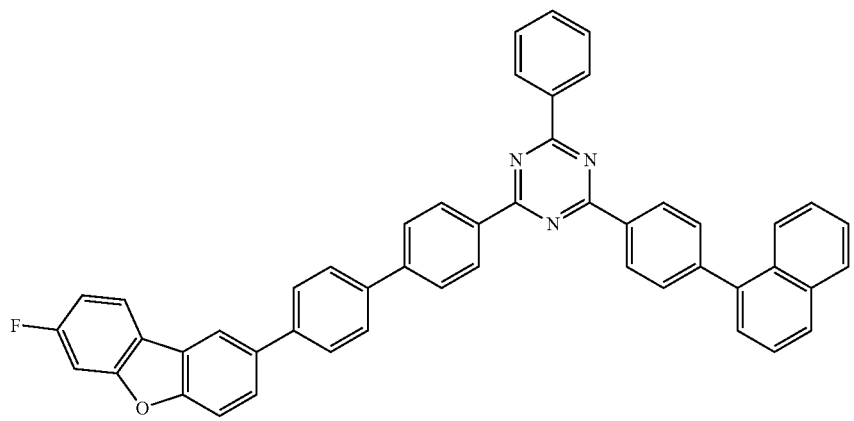
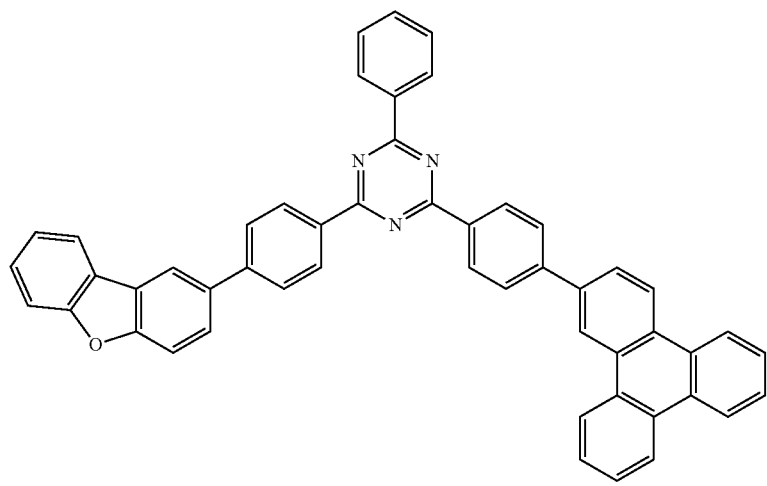
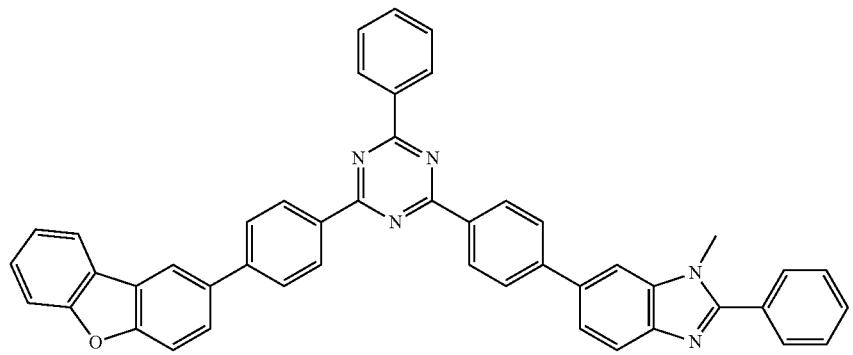

-continued
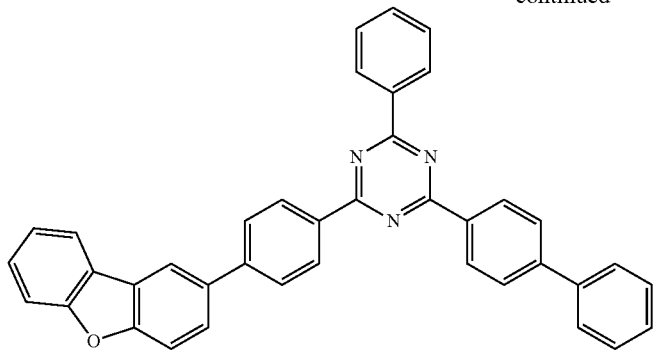
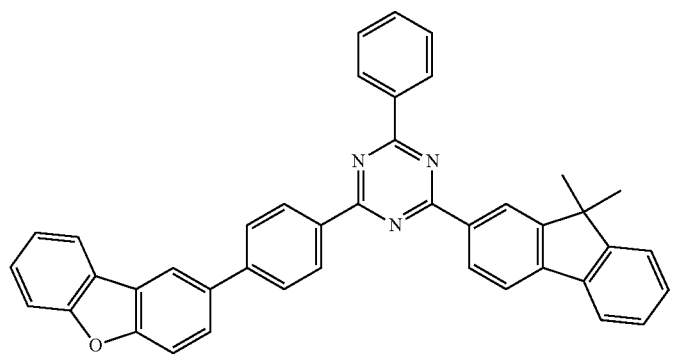
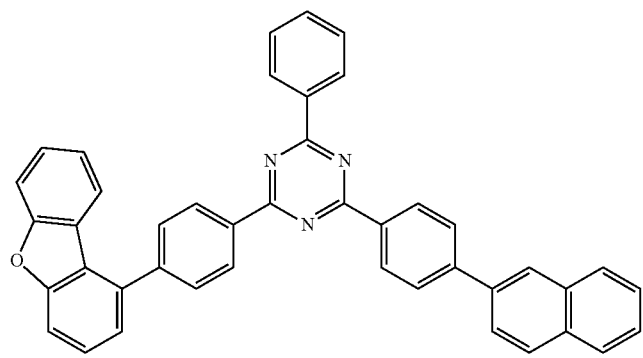
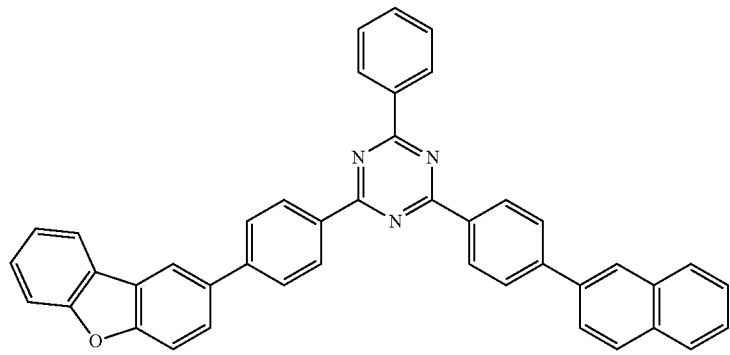

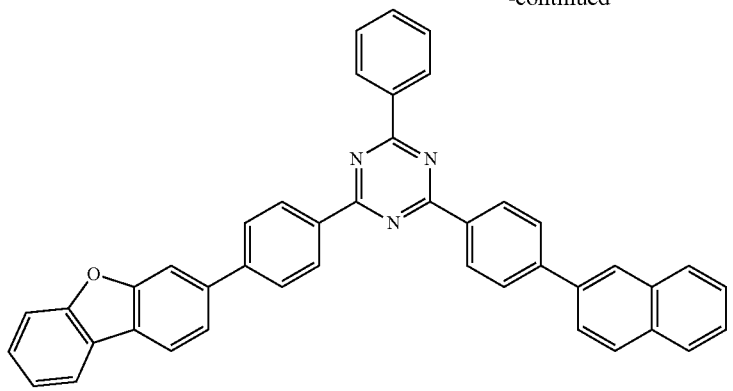
[Formula 17]
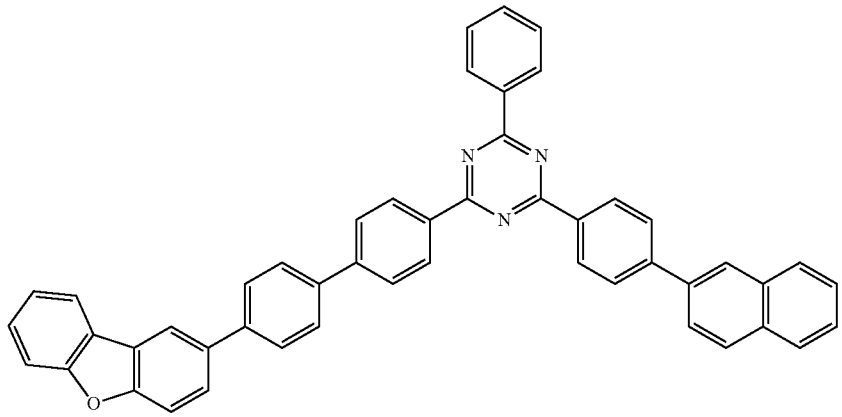
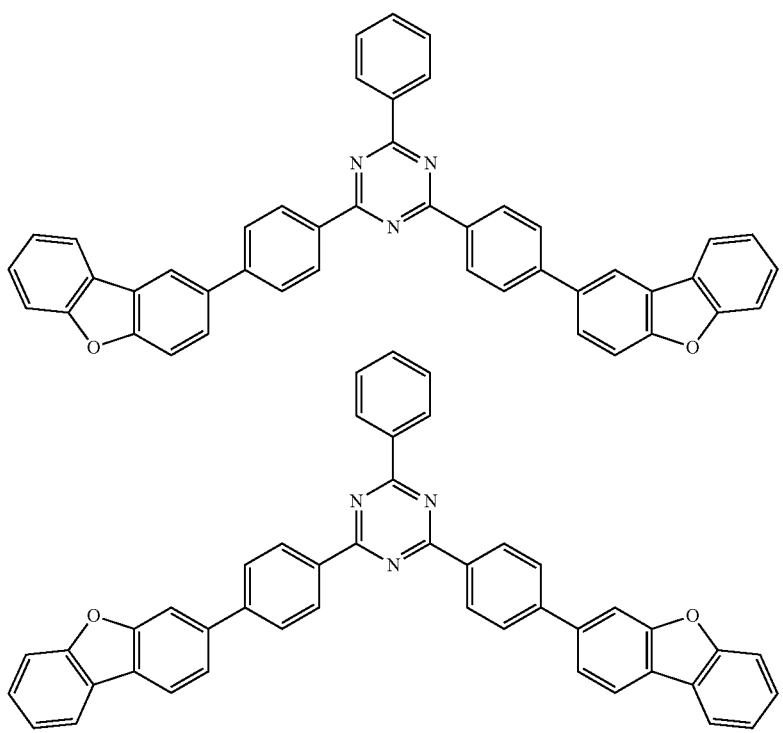

-continued
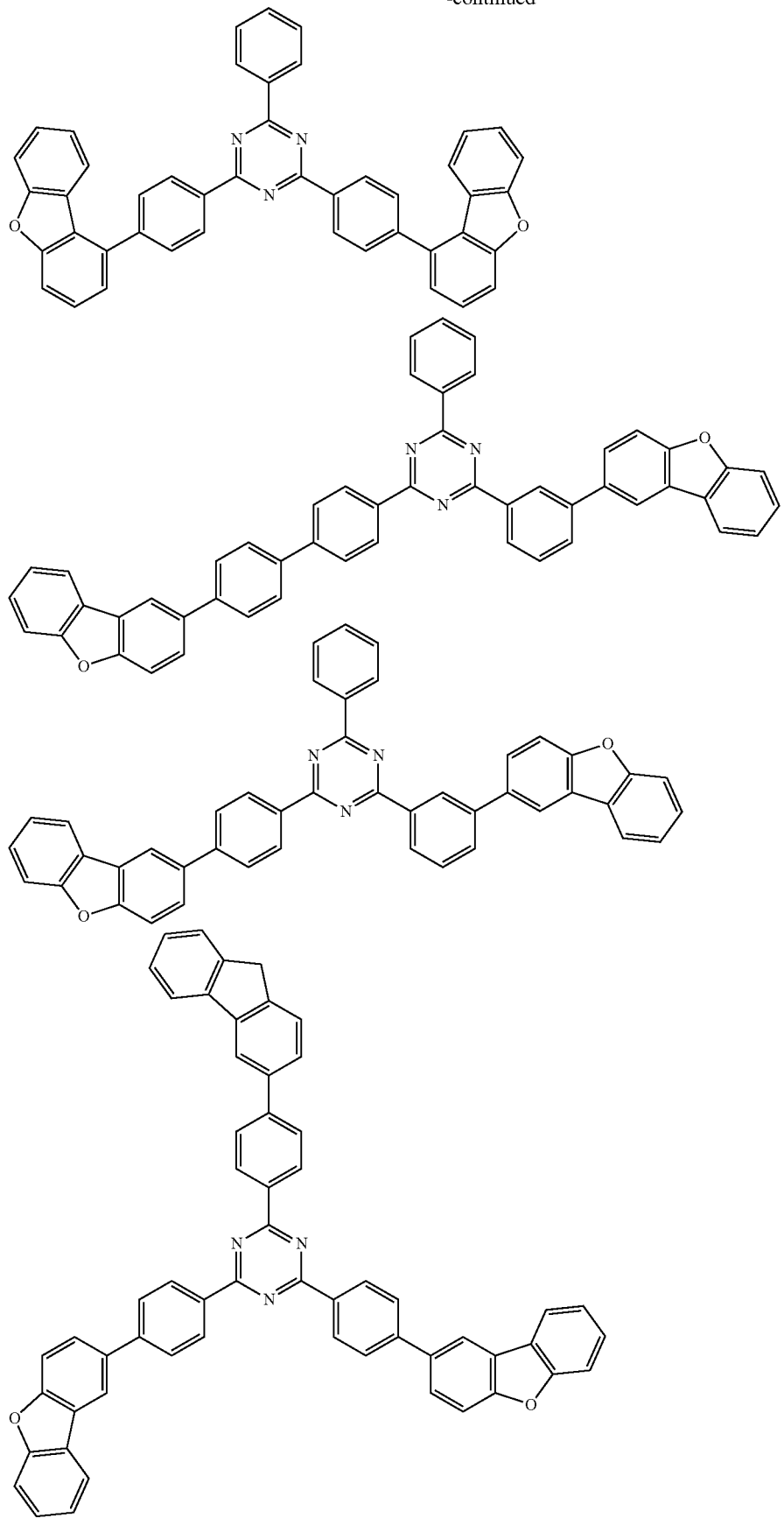

-continued
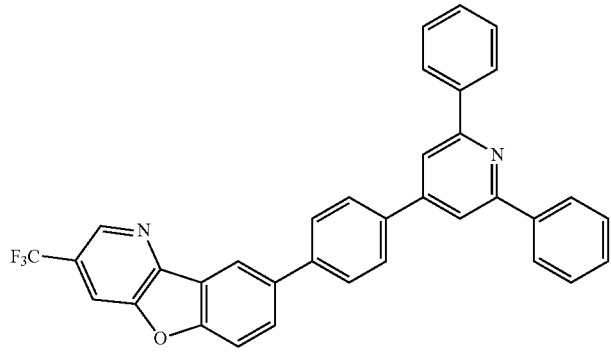
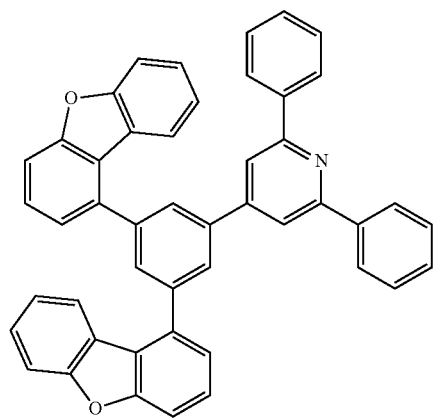
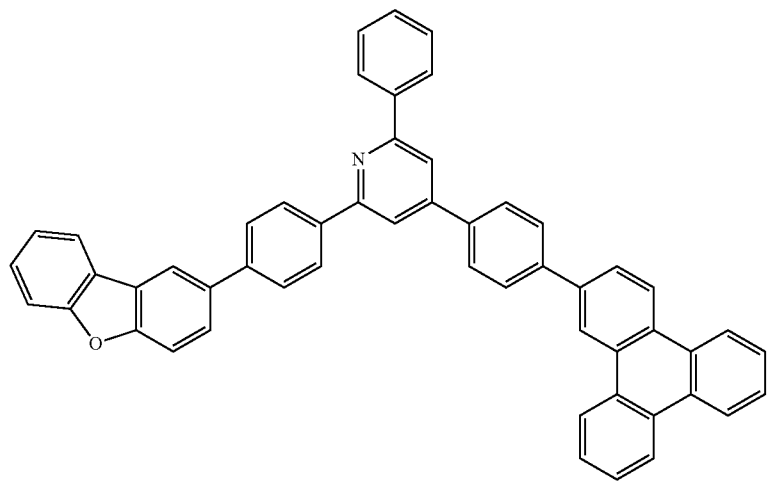
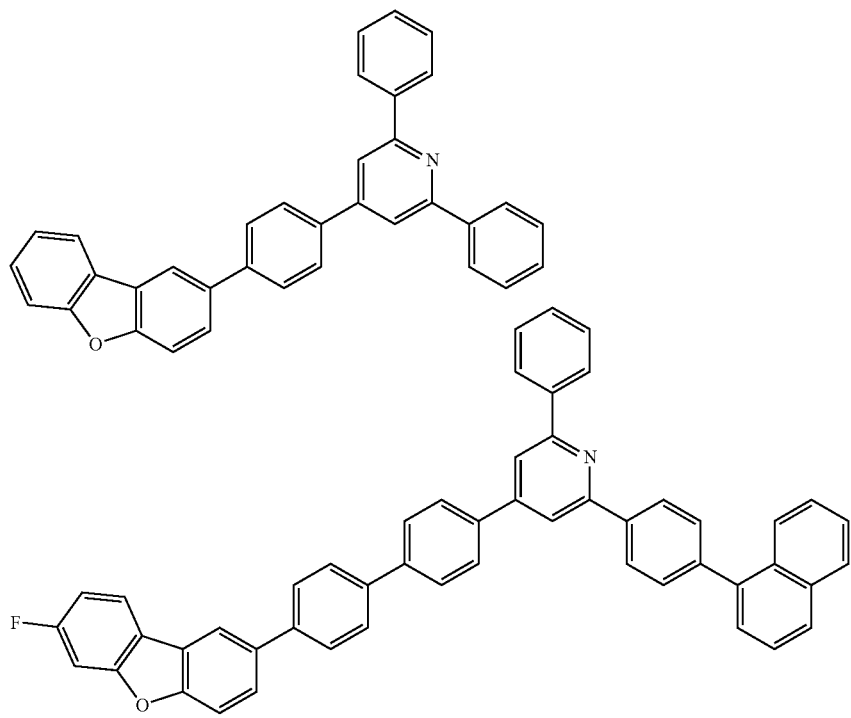

-continued
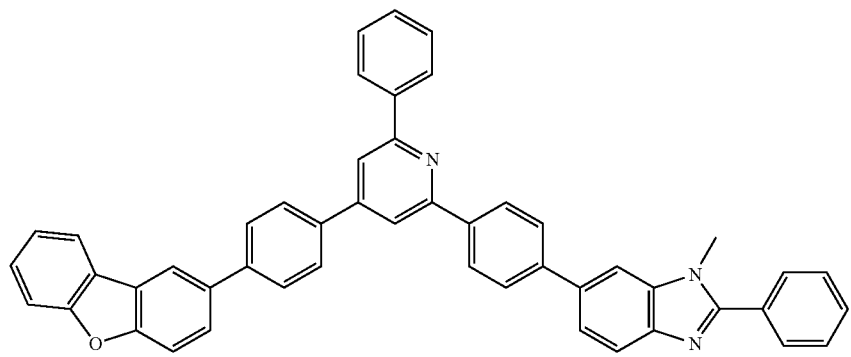
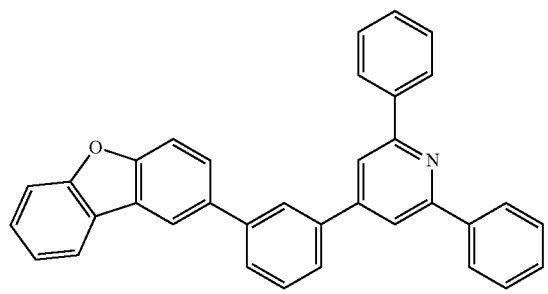
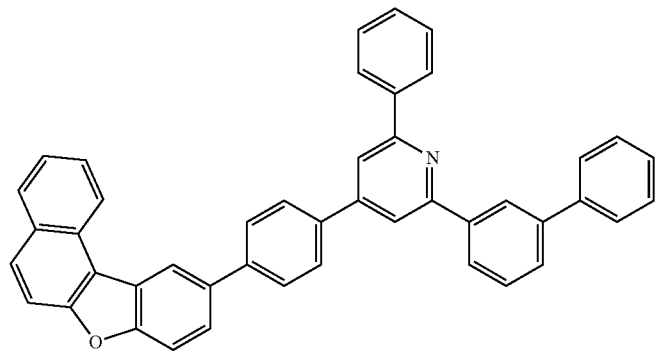
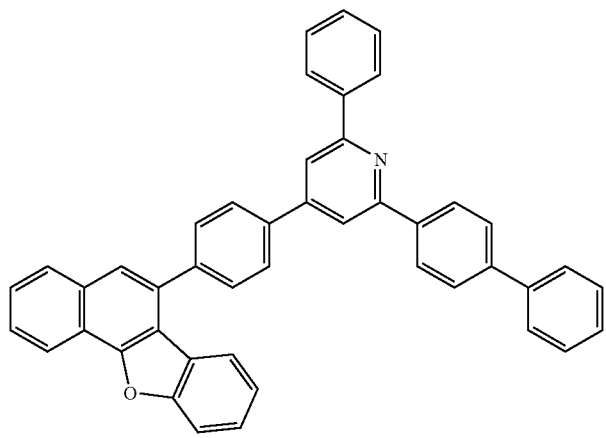

-continued
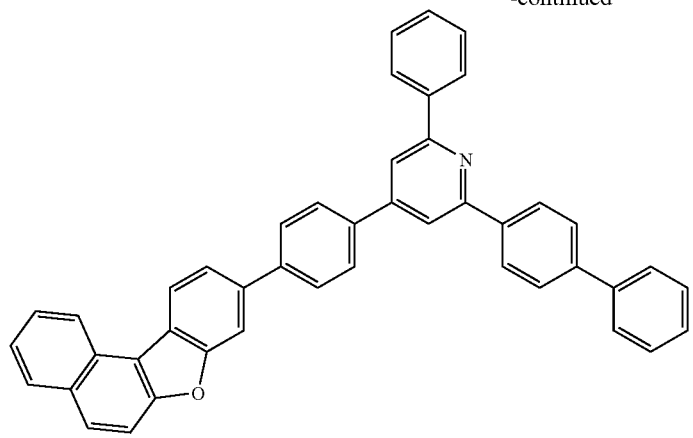
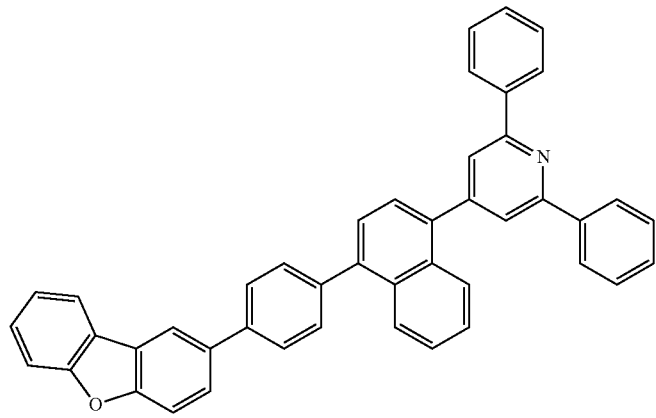
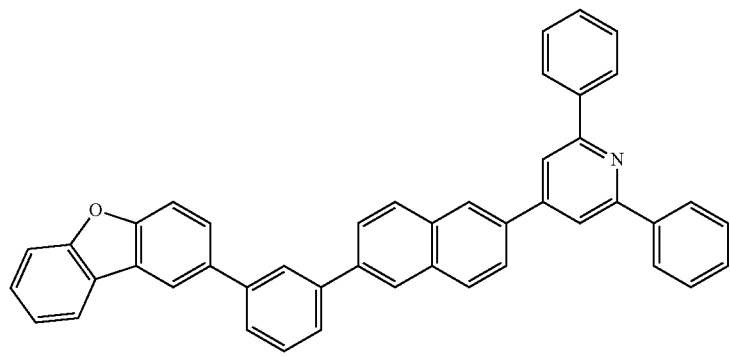

-continued
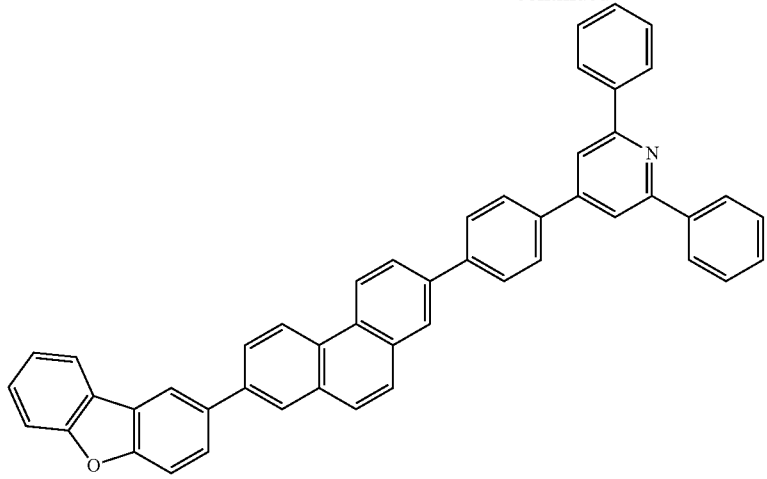
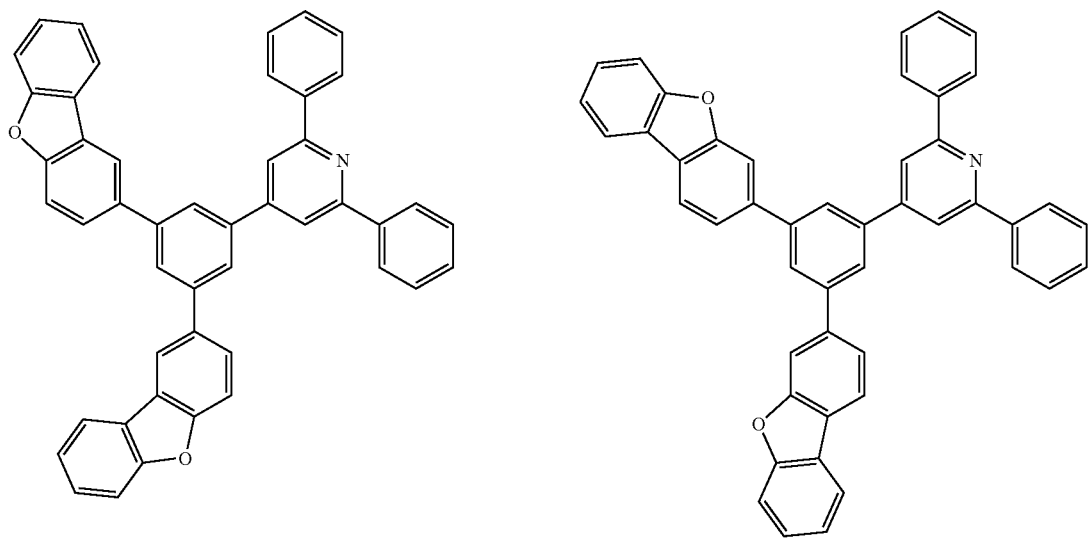
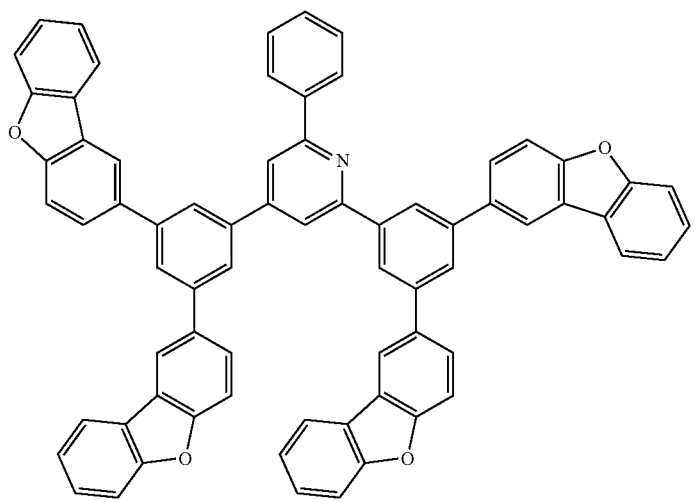

-continued
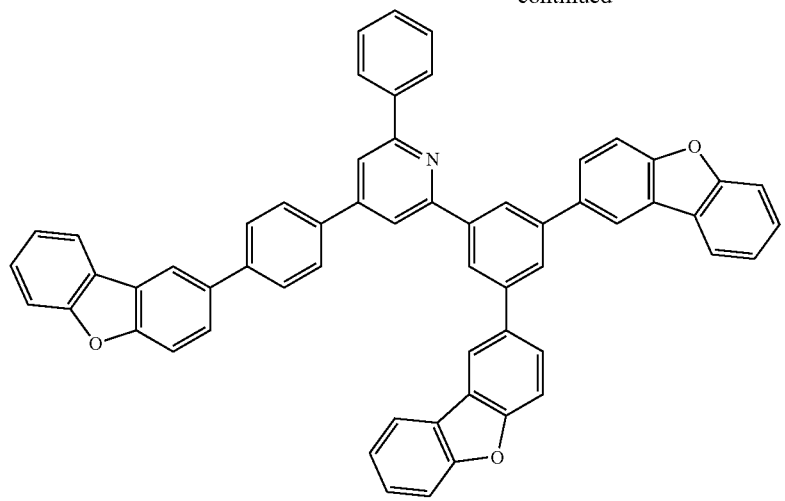
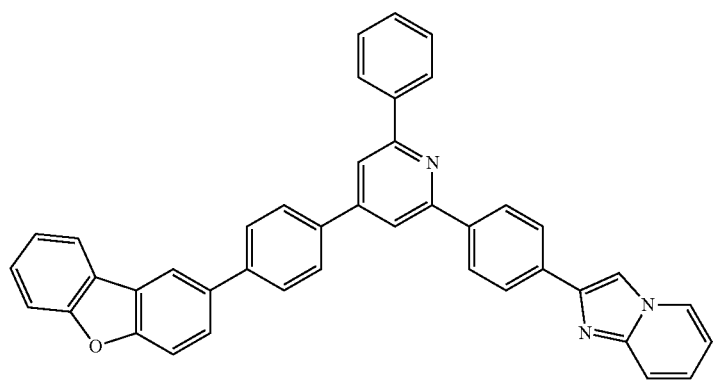
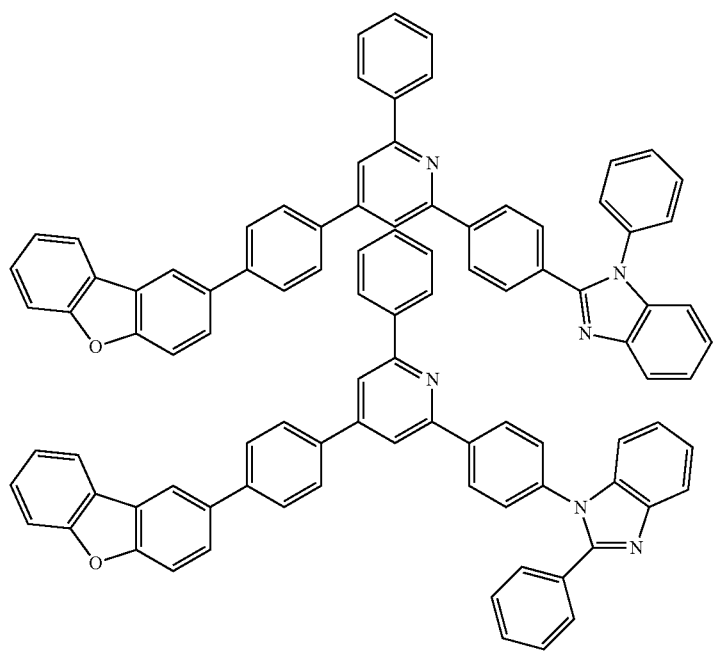

-continued
[Formula 18]
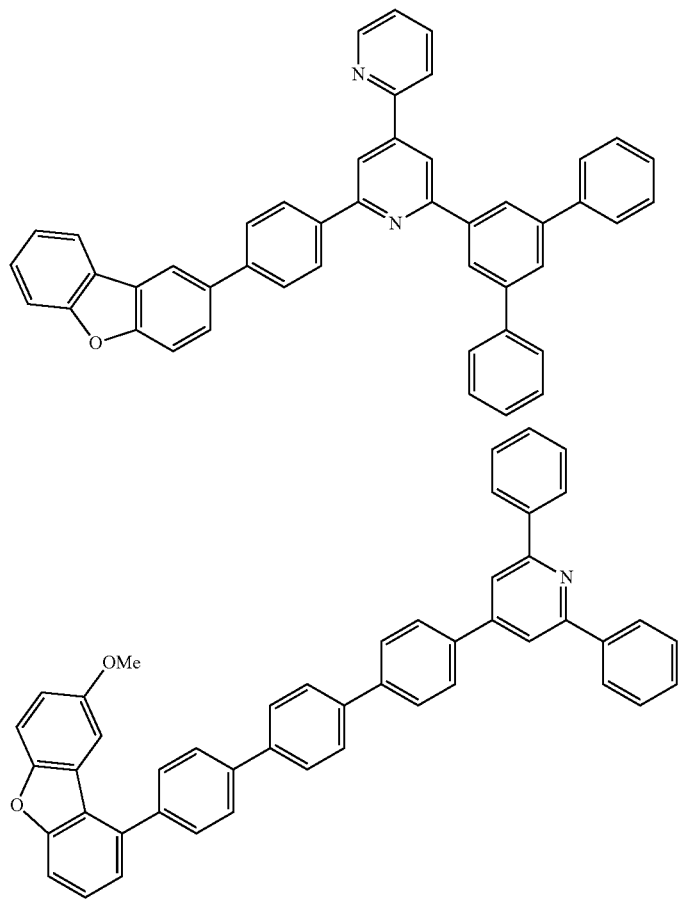
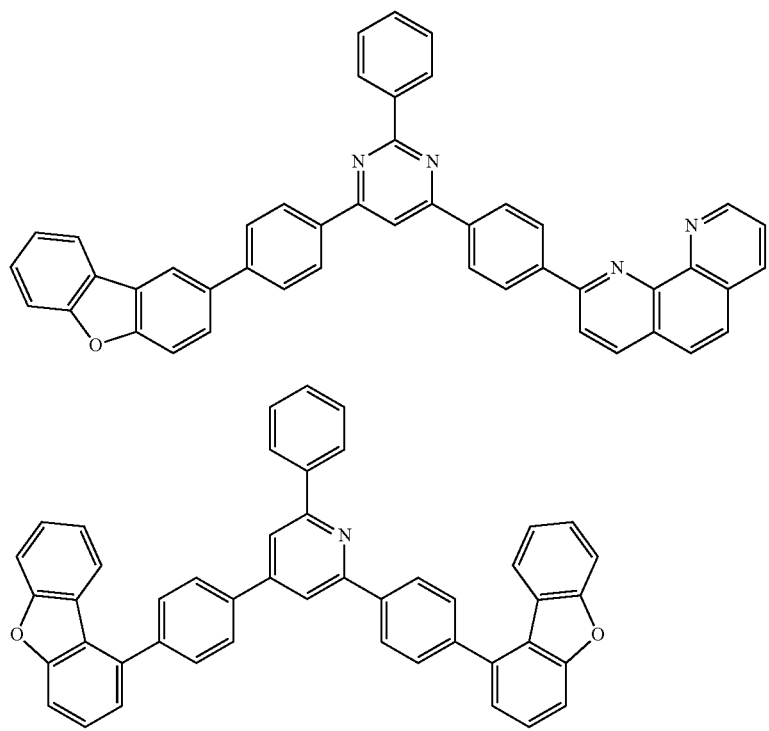

-continued
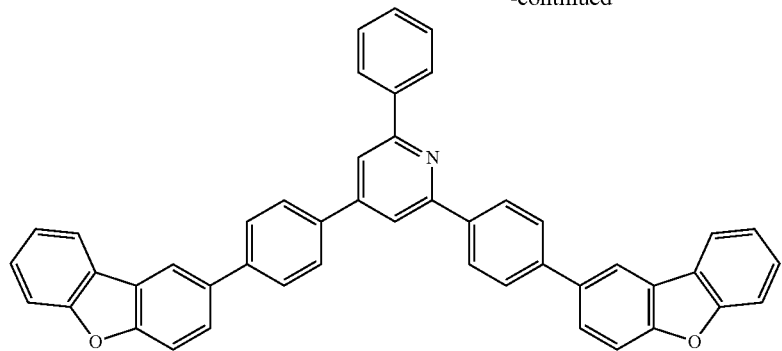
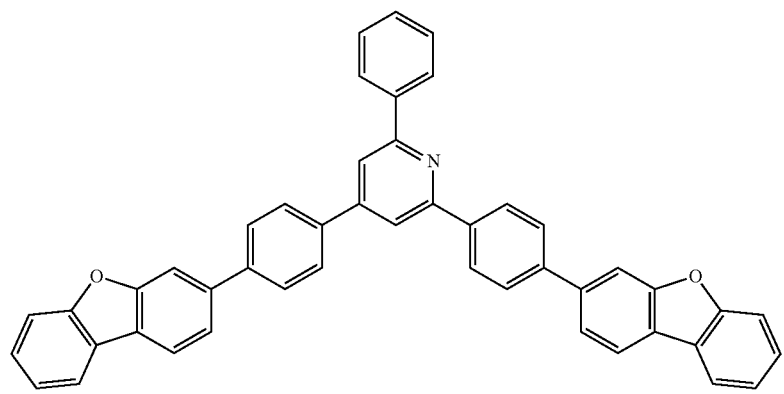
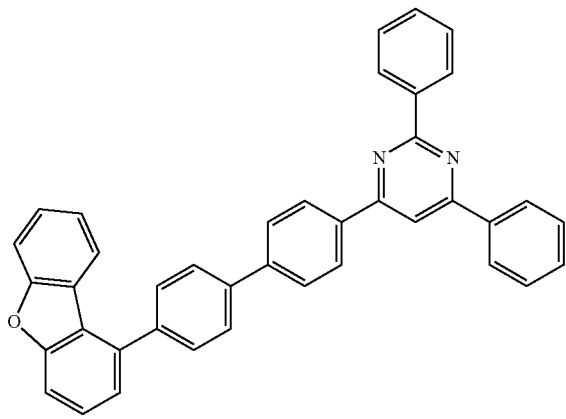
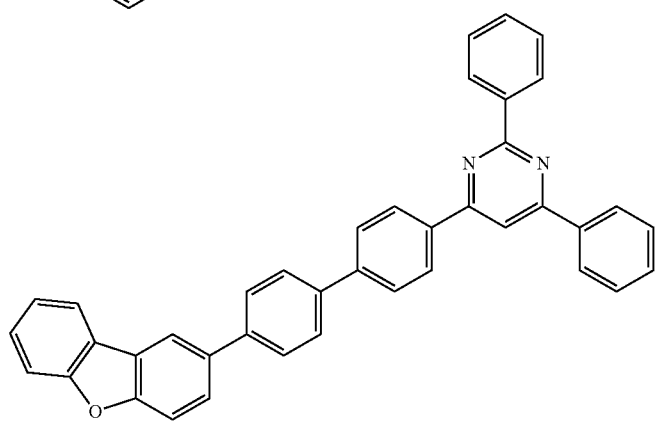

-continued
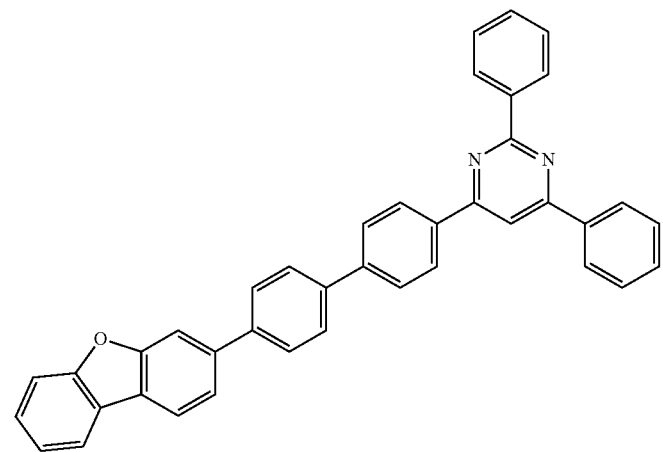
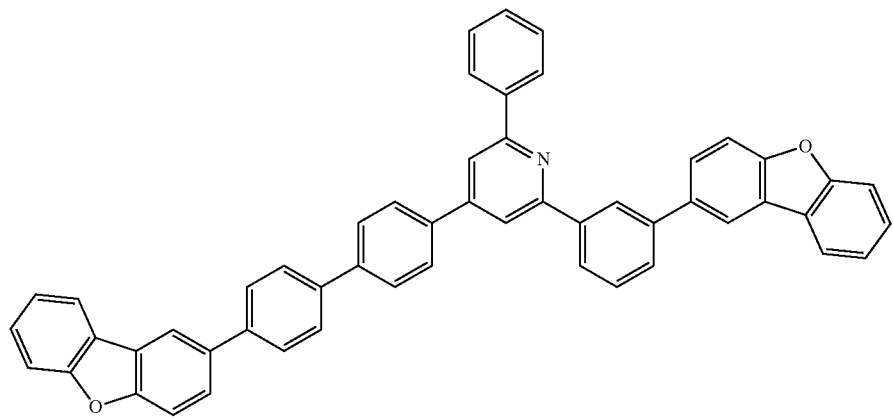
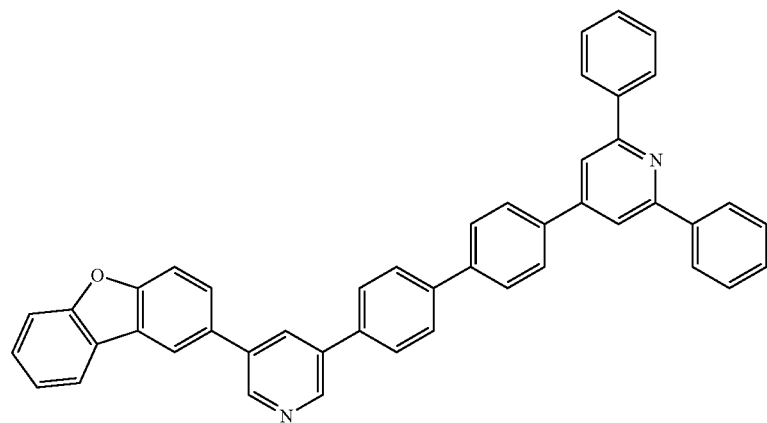
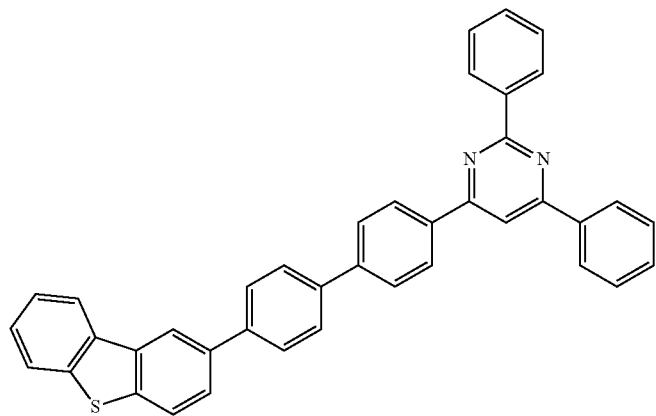

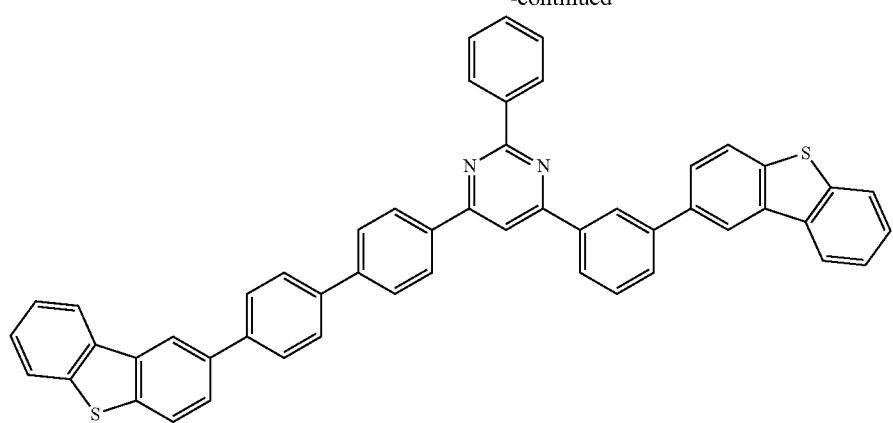
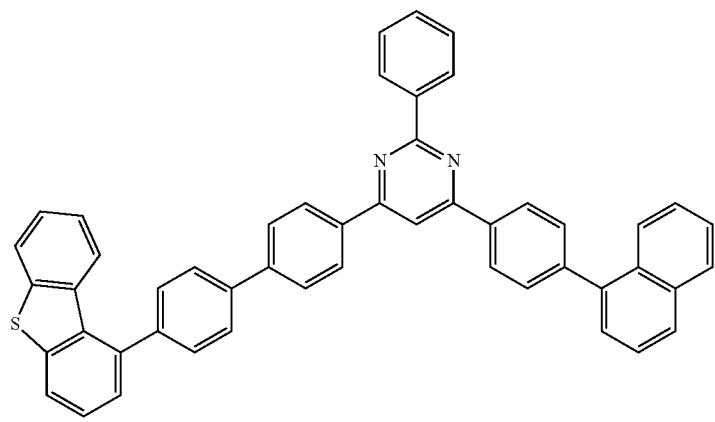
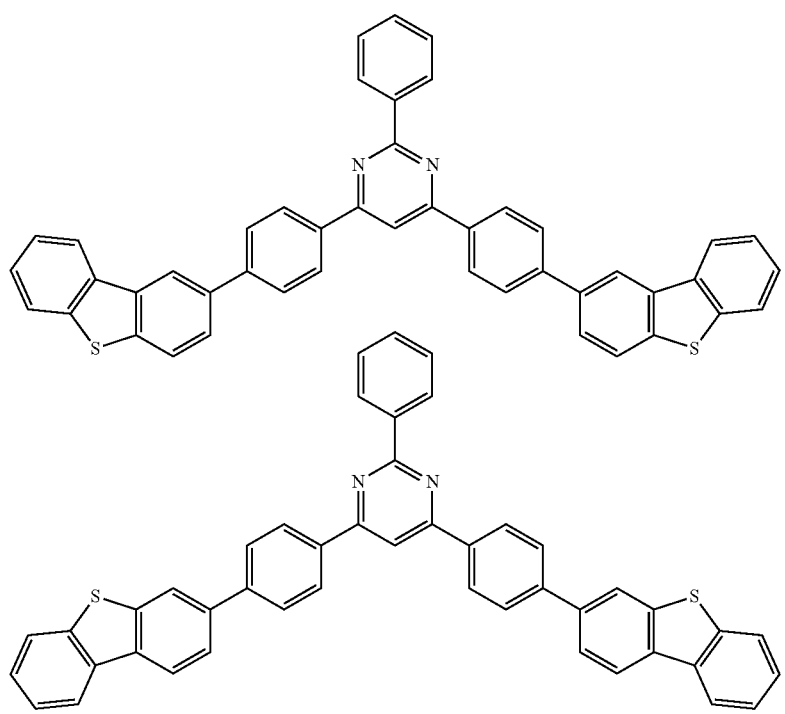

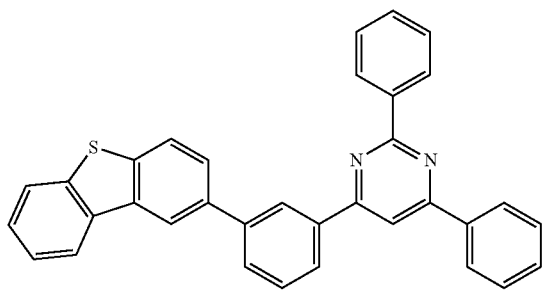
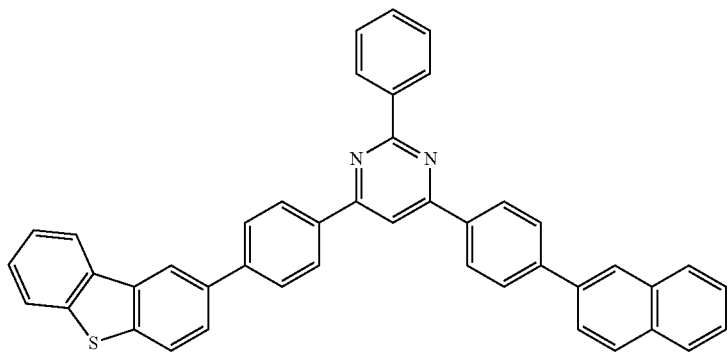
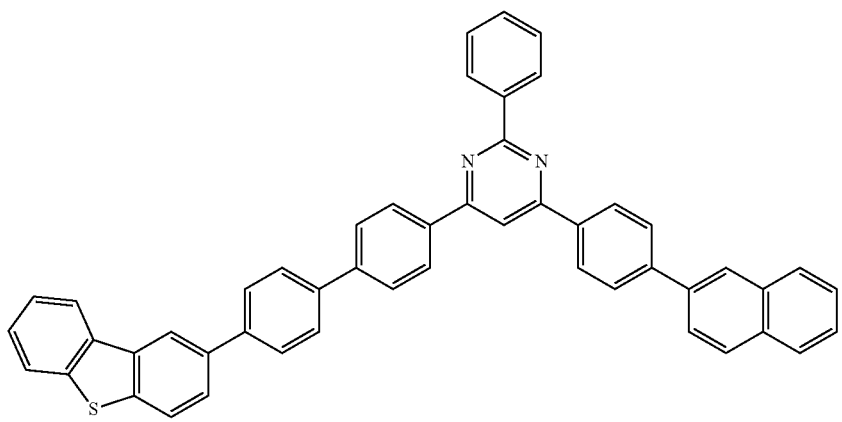
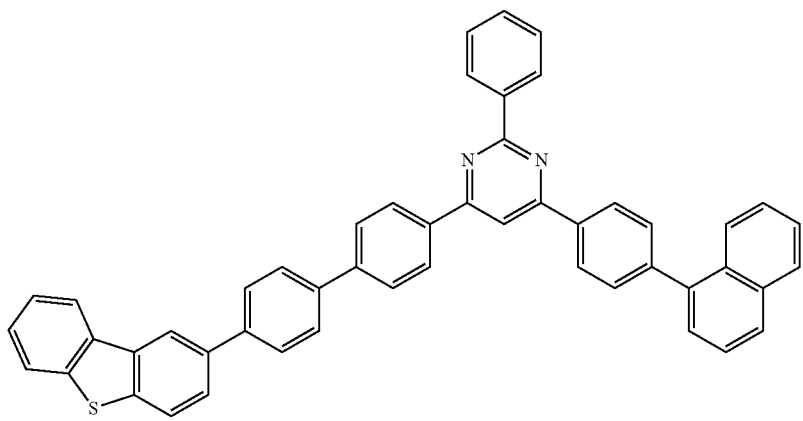

-continued
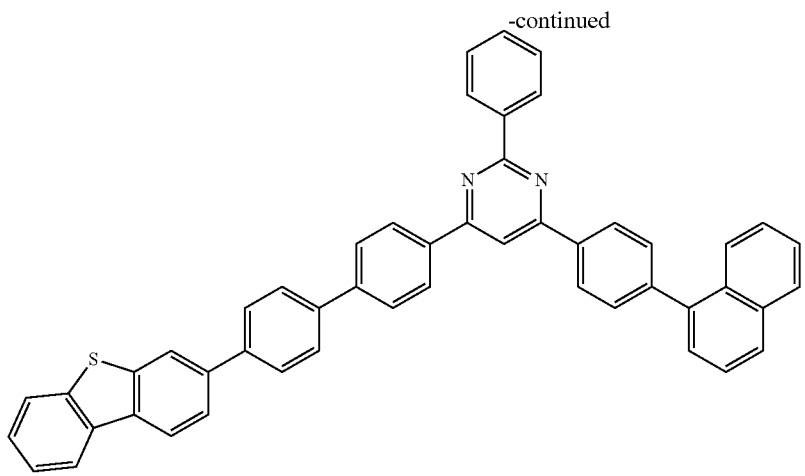
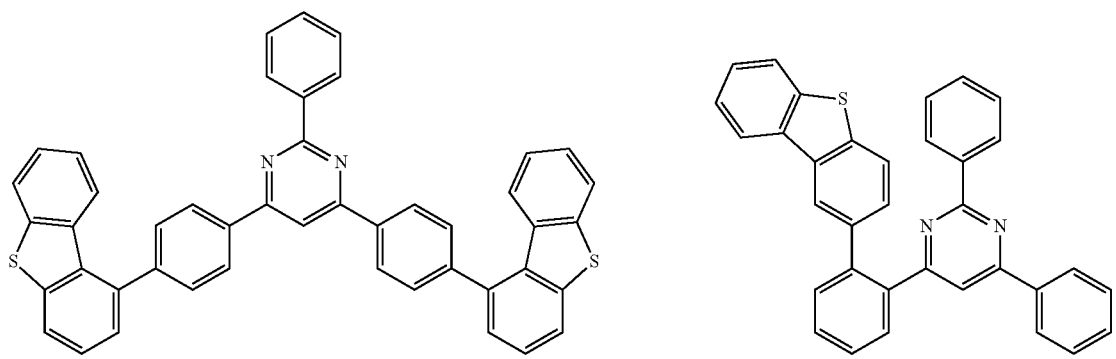
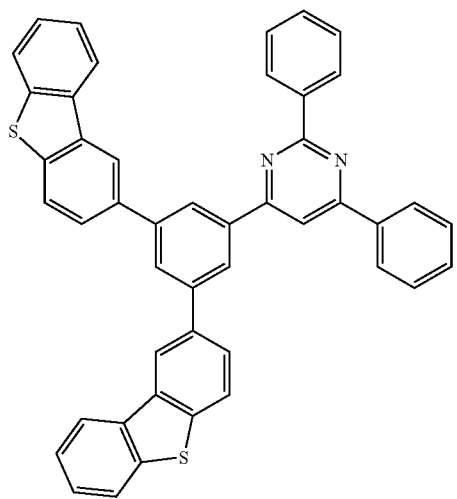

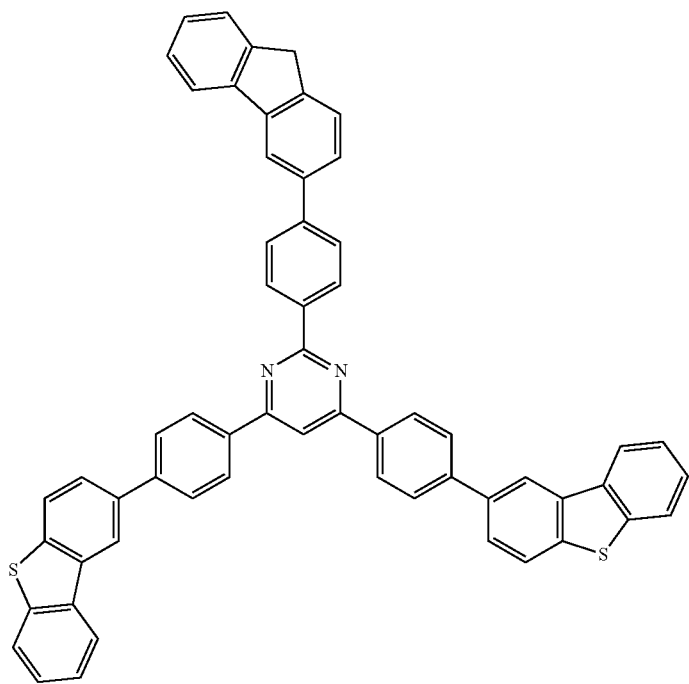
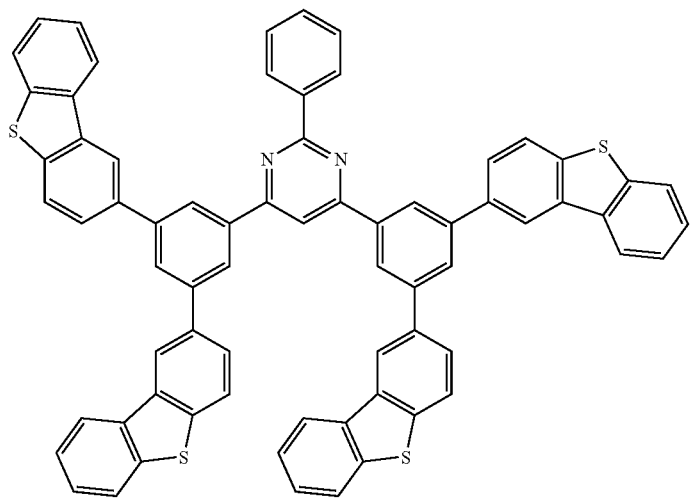
[Formula 19]
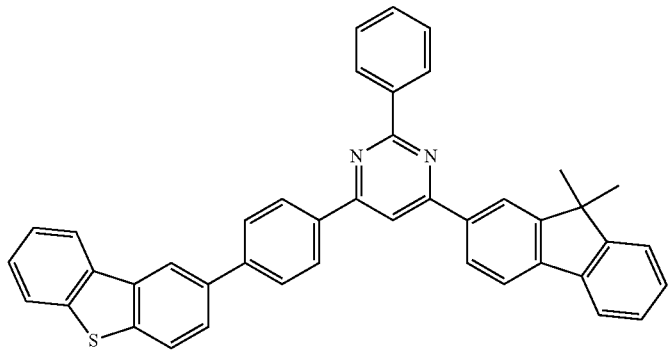

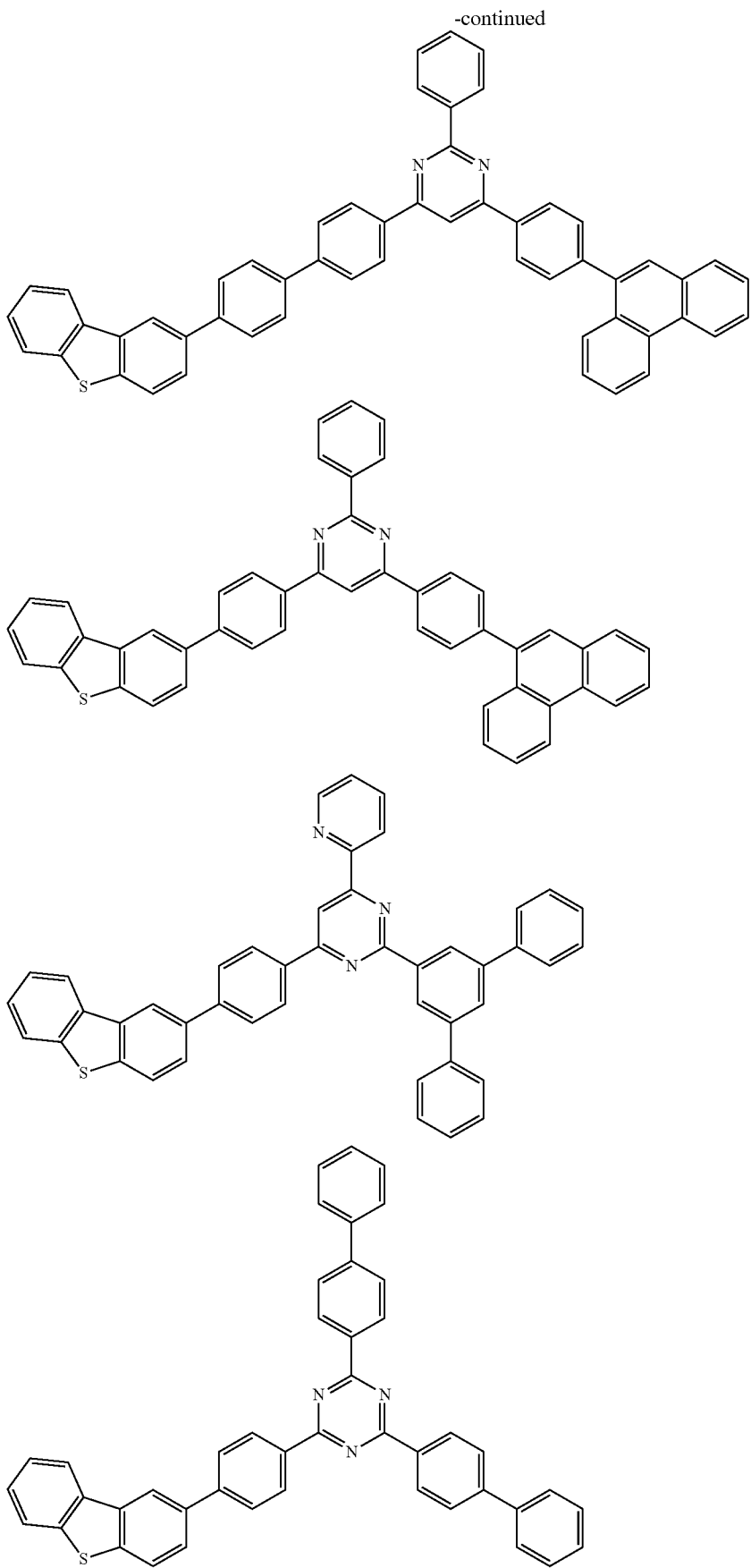

-continued
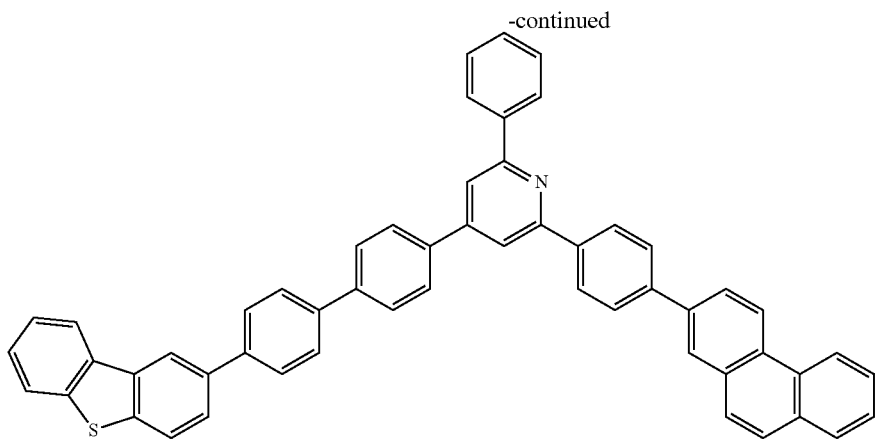

-continued
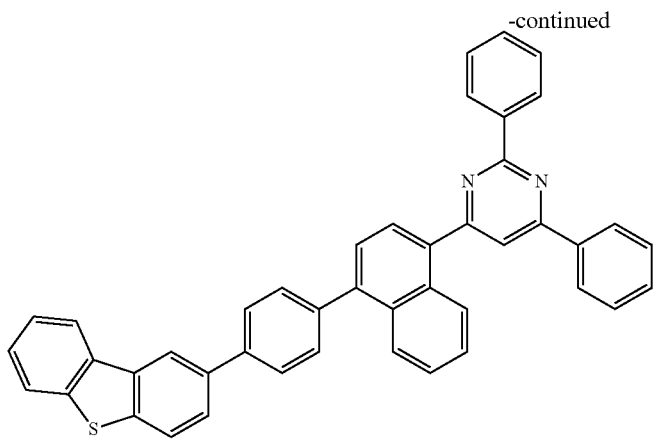
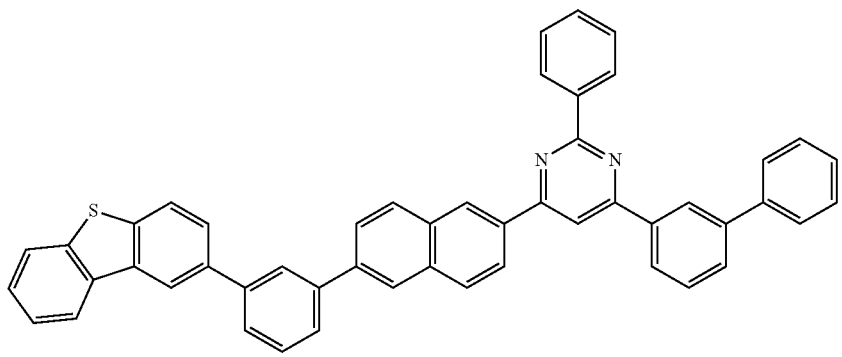
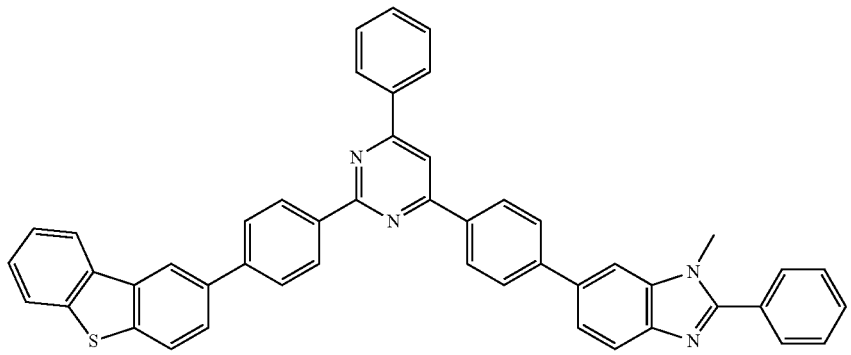
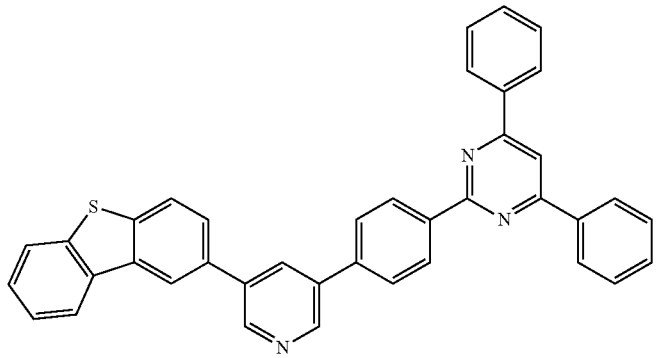

-continued
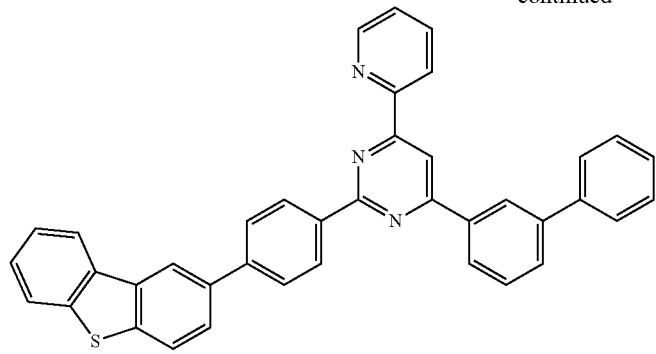
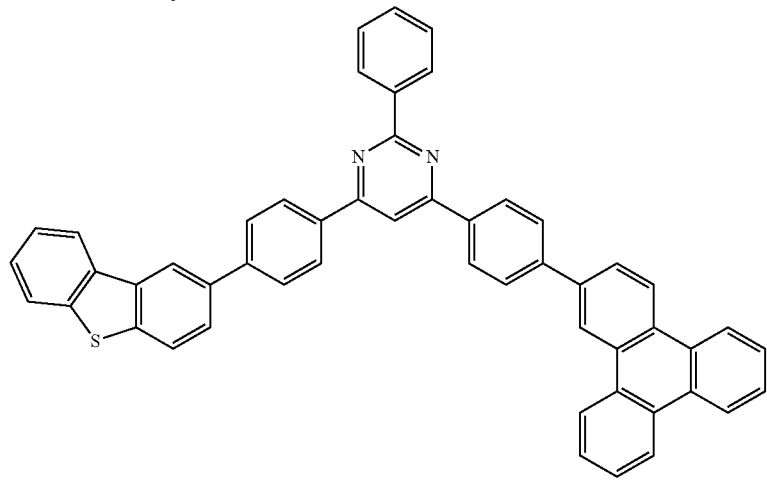
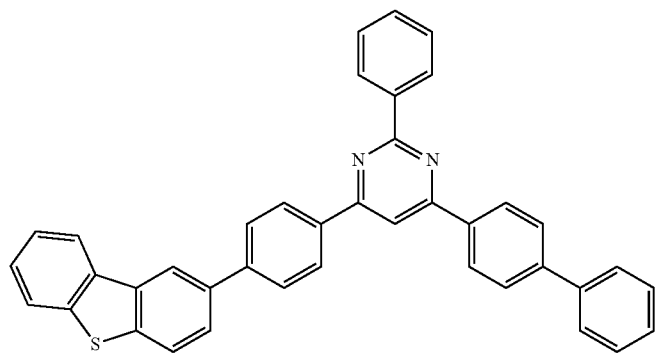
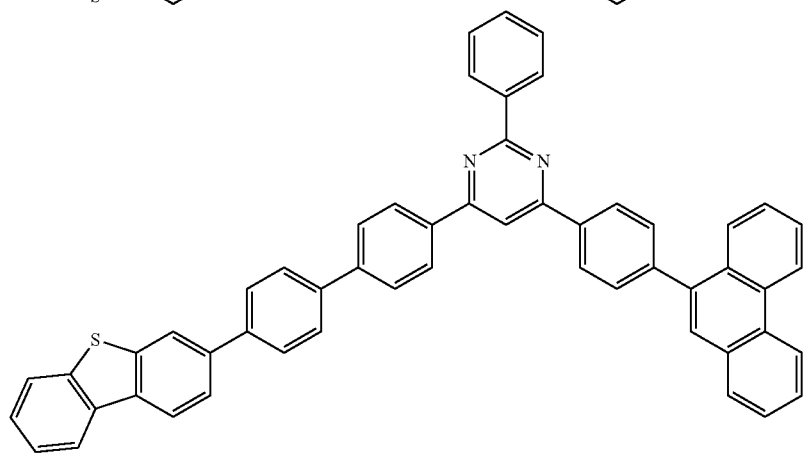

-continued
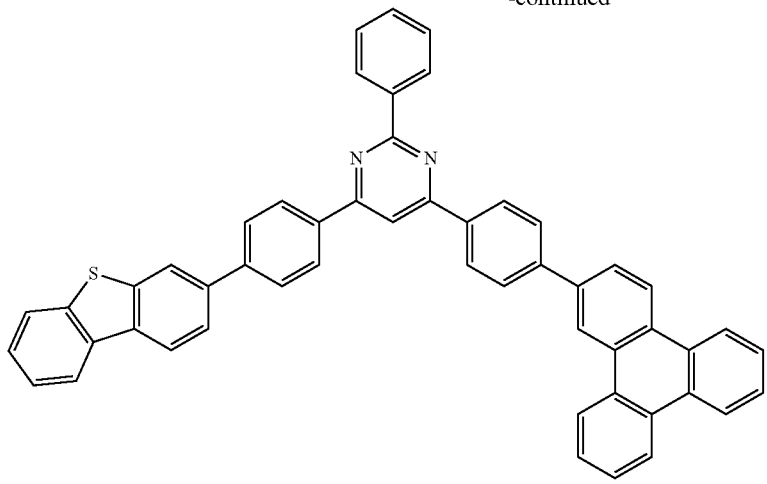
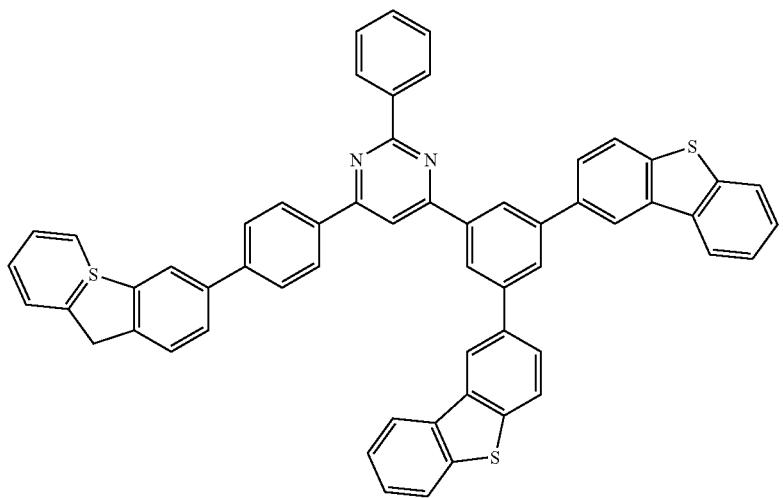
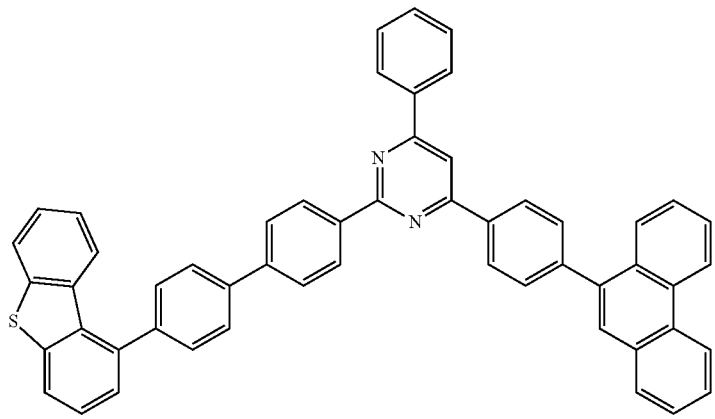

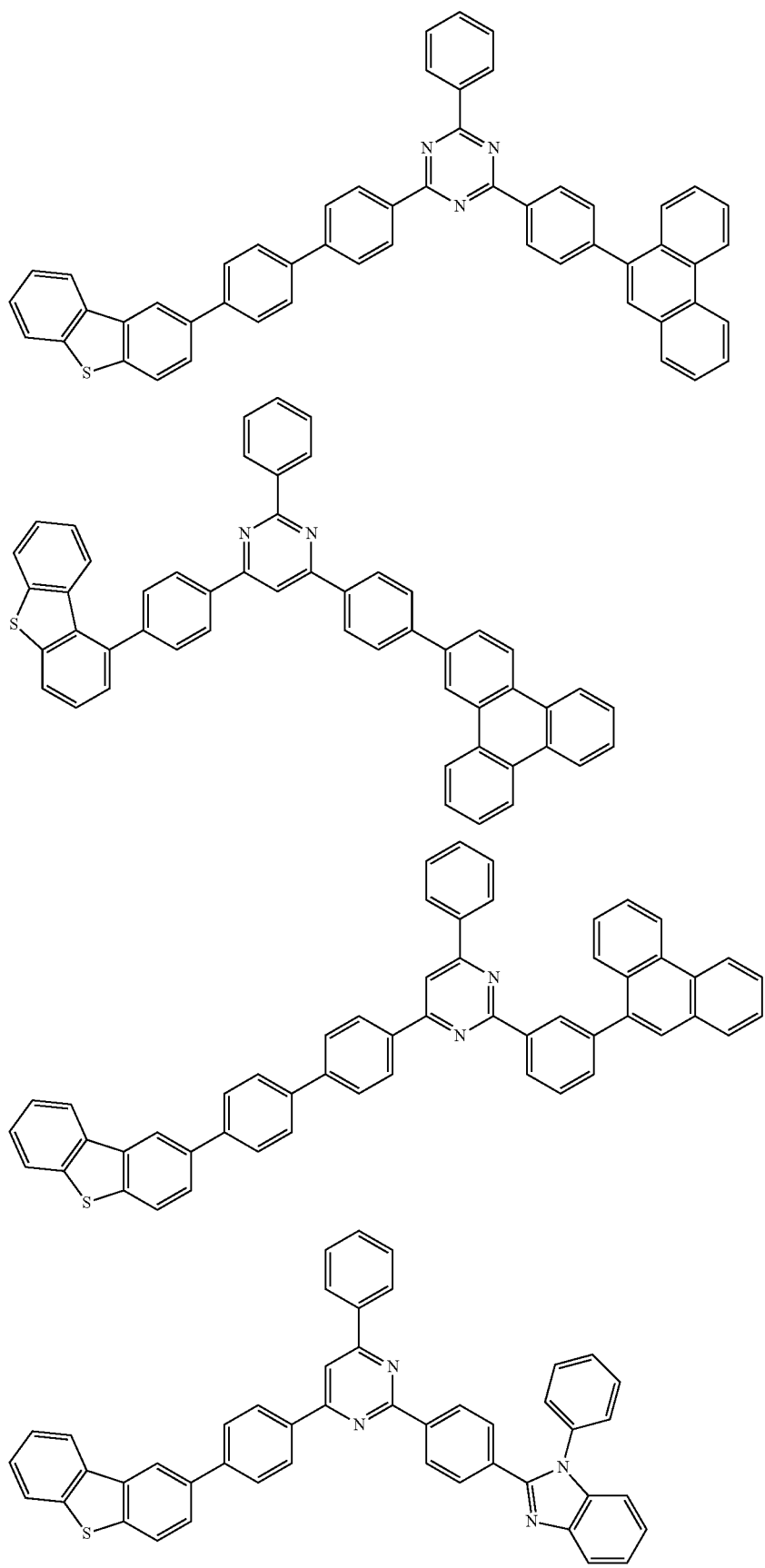

[Formula 20]
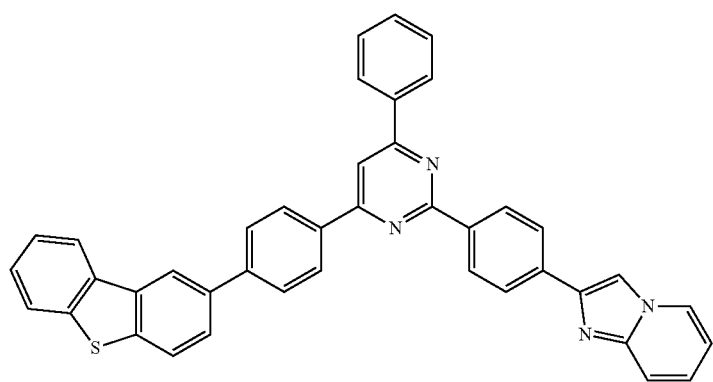
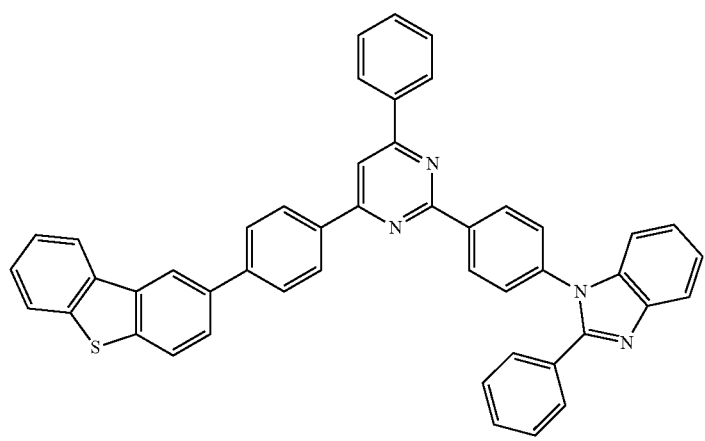
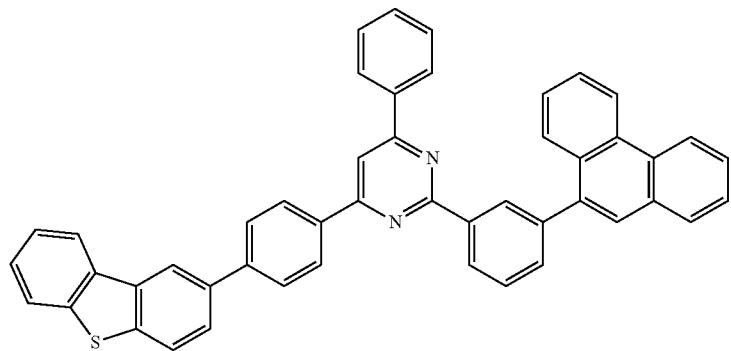

-continued
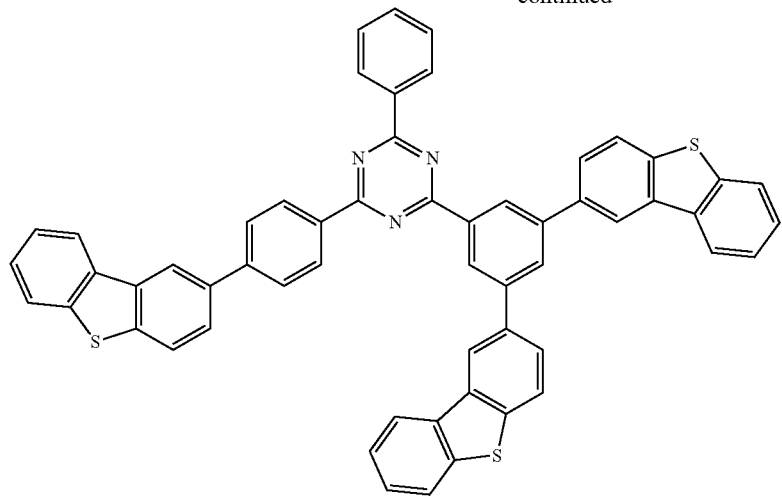
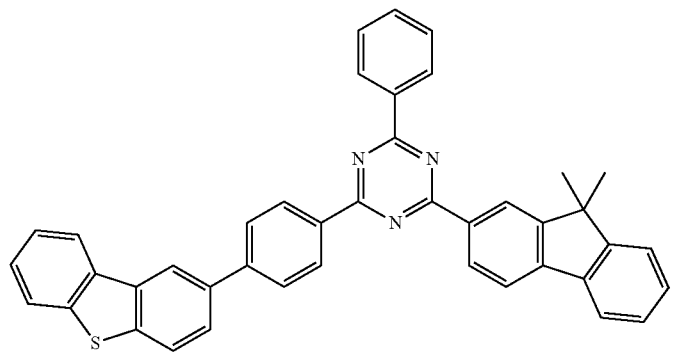
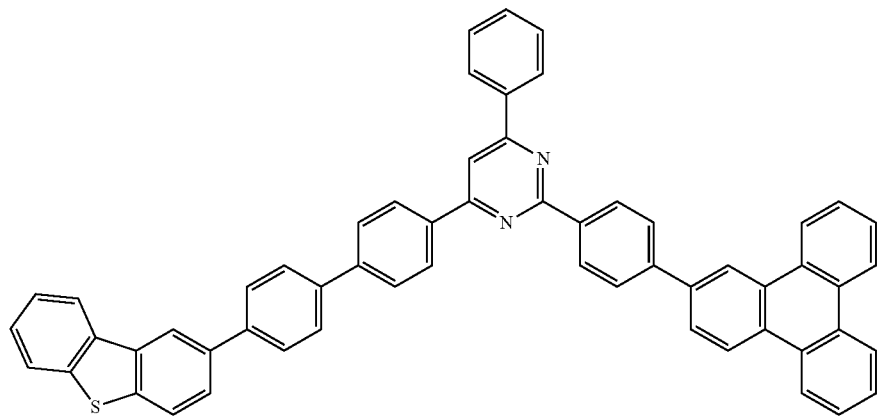

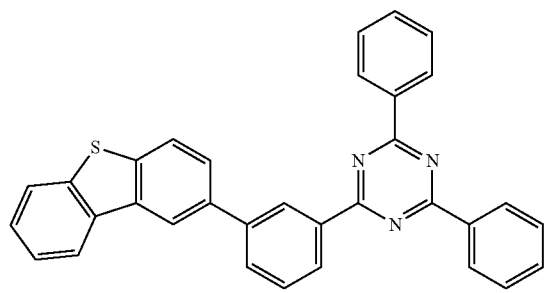
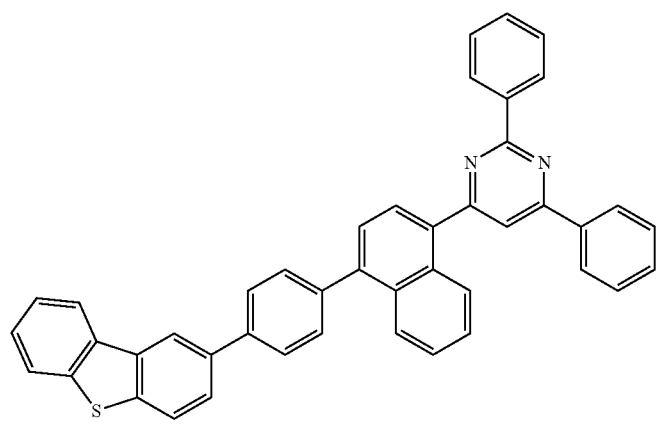
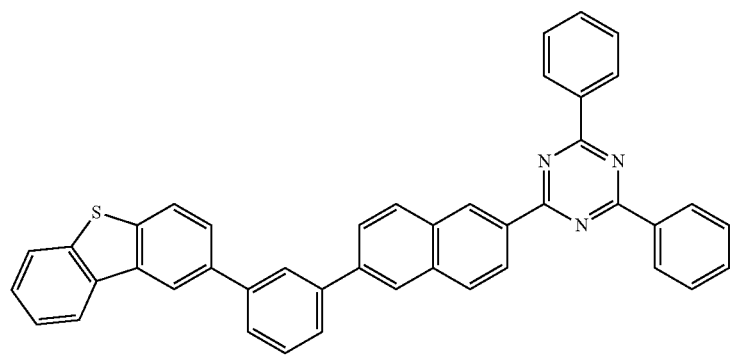
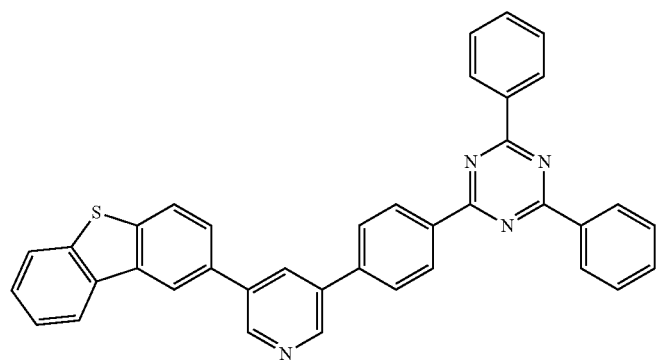

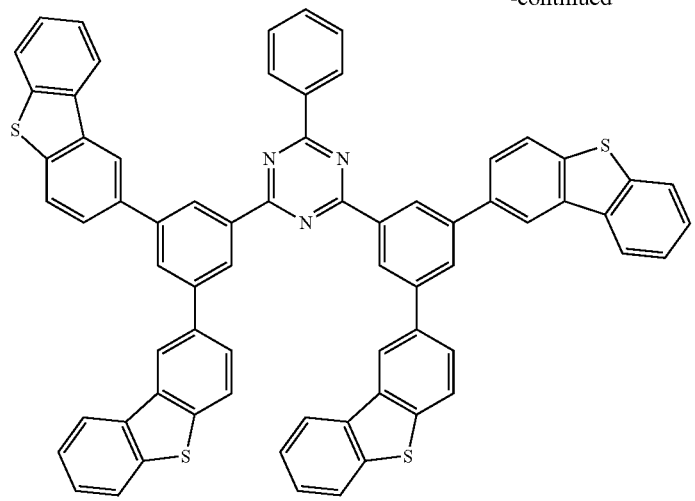
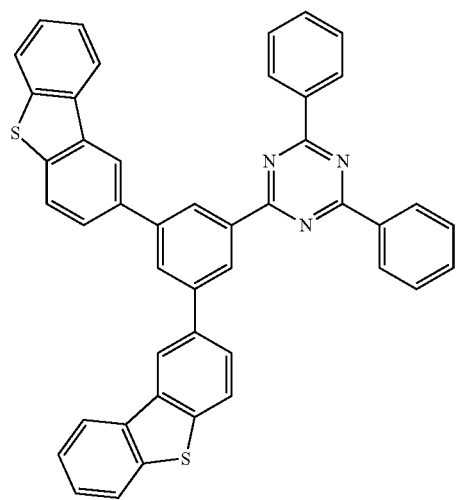
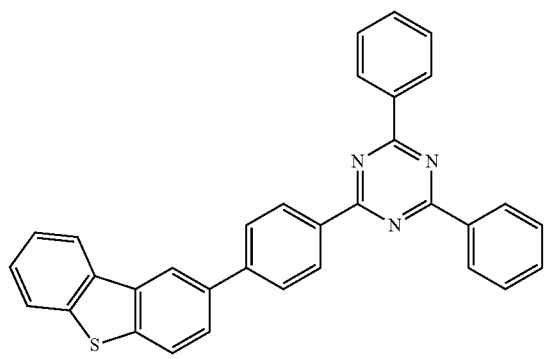
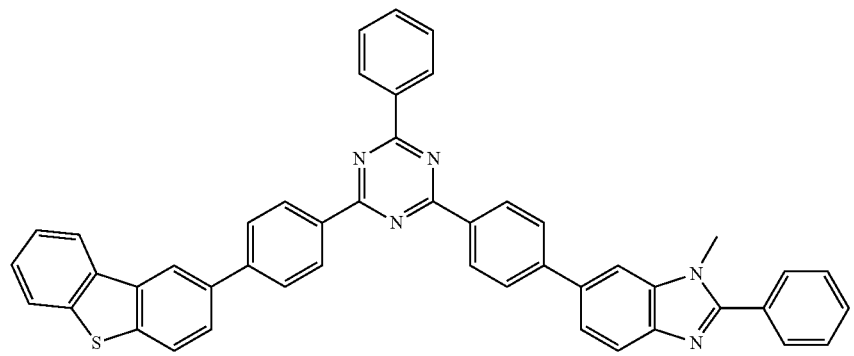

-continued
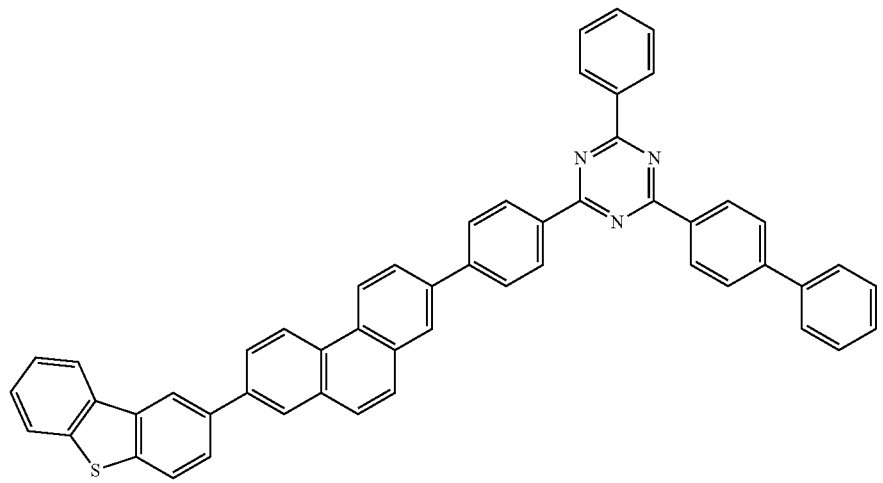
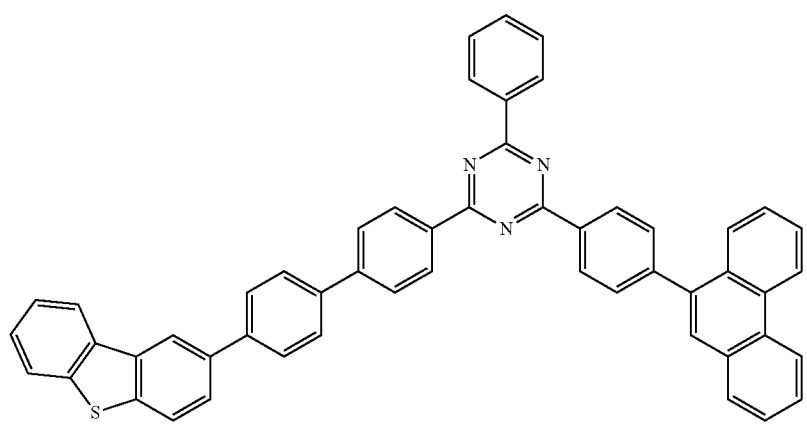
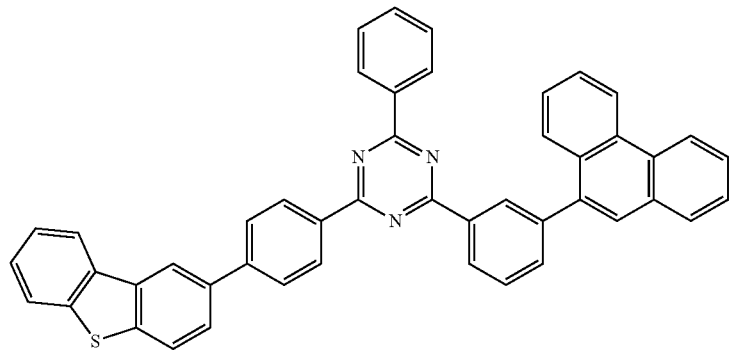
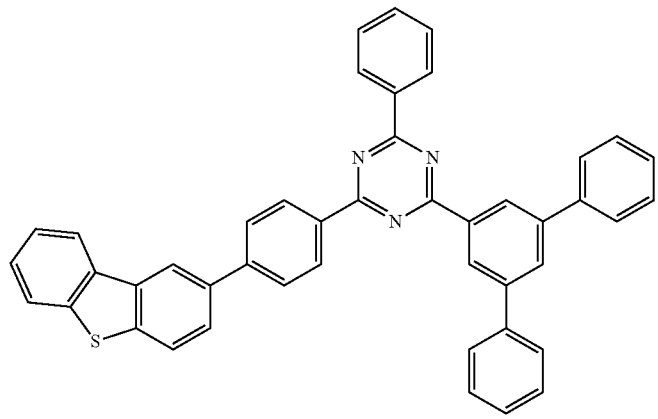

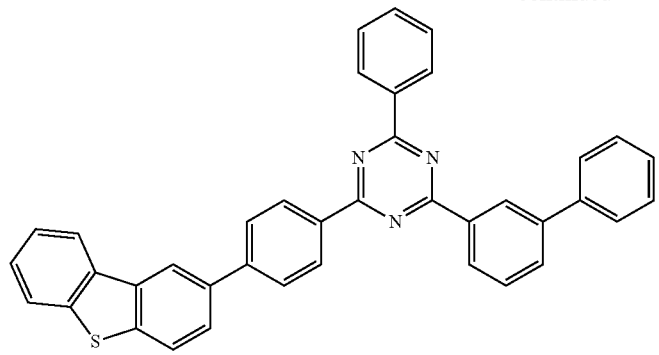
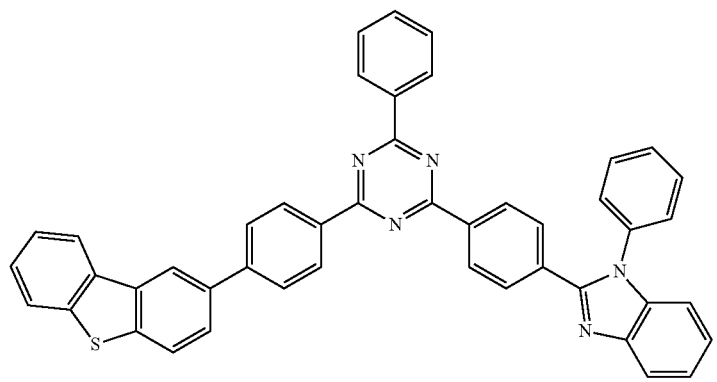
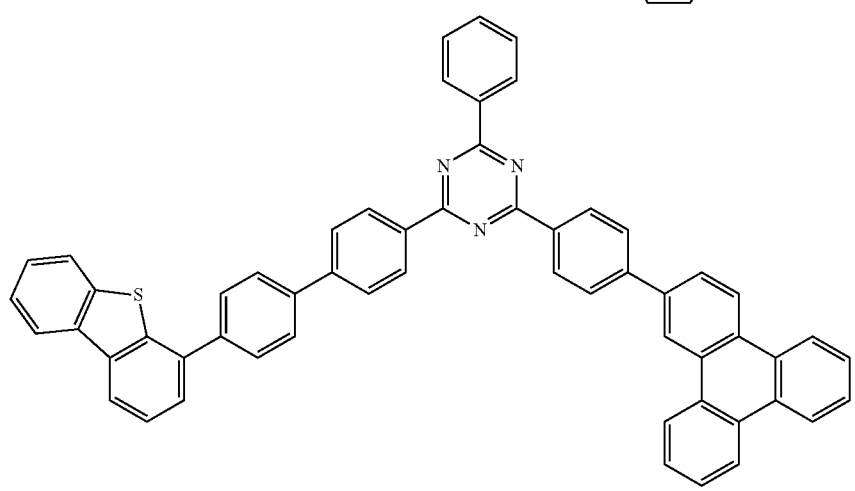
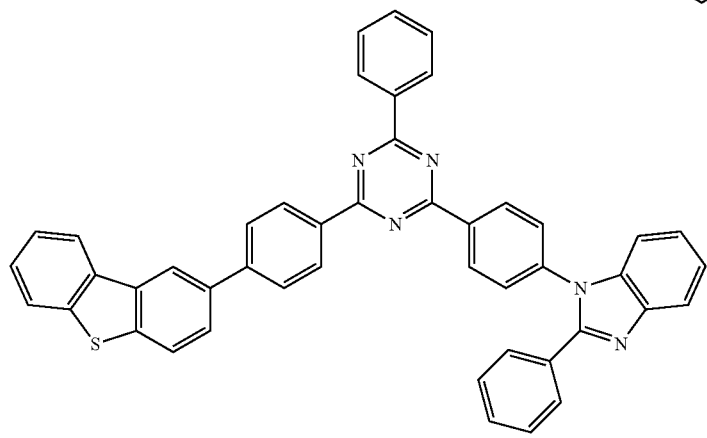

-continued
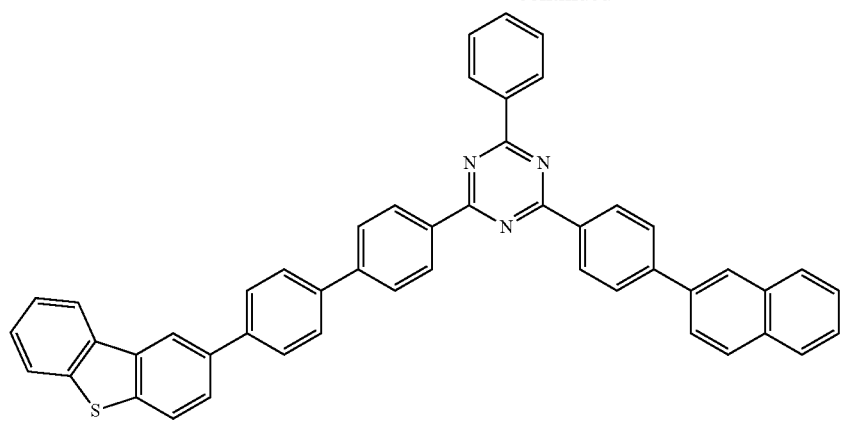
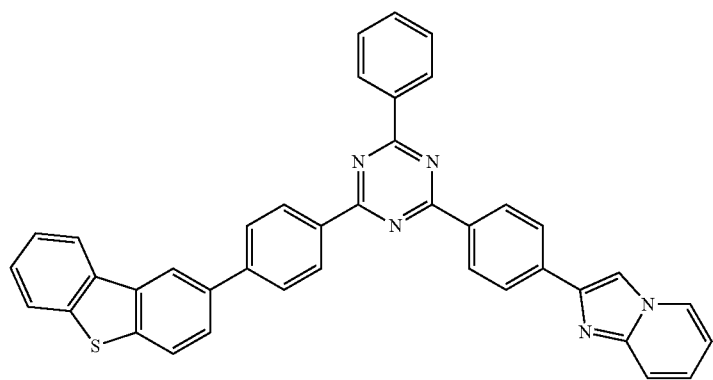
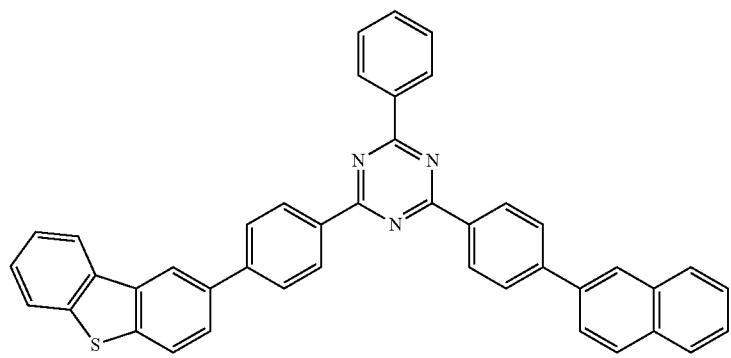
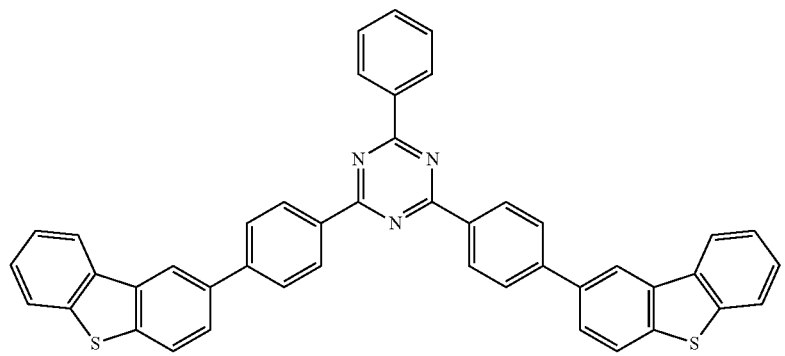

-continued
[Formula 21]
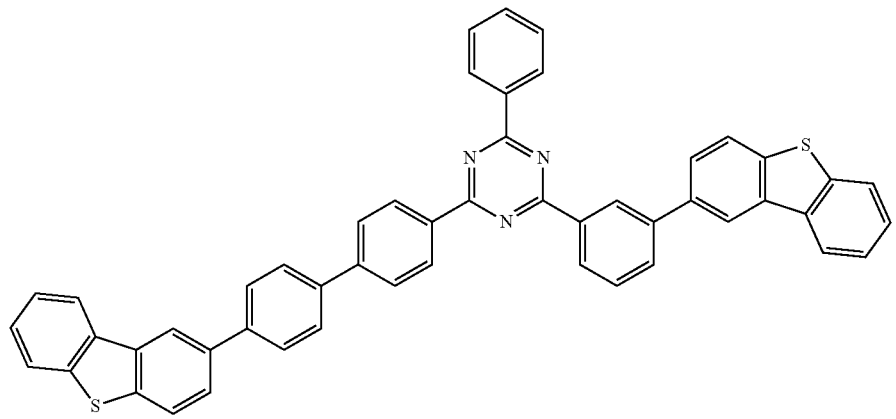
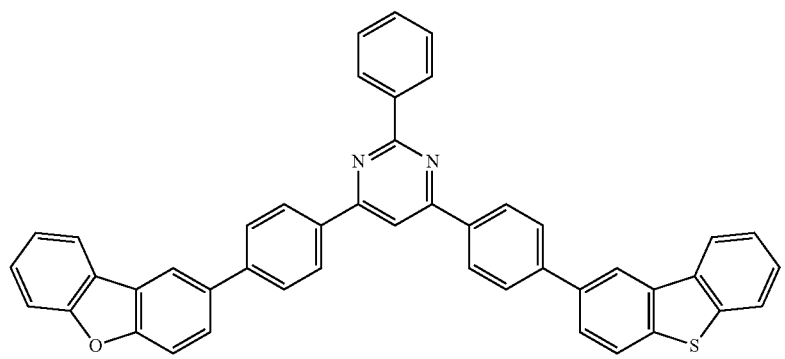
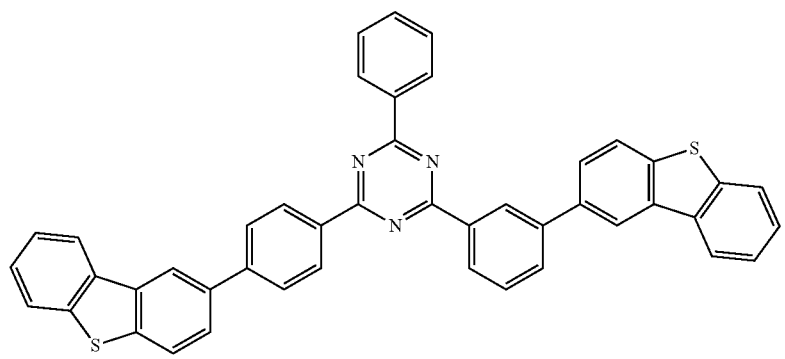
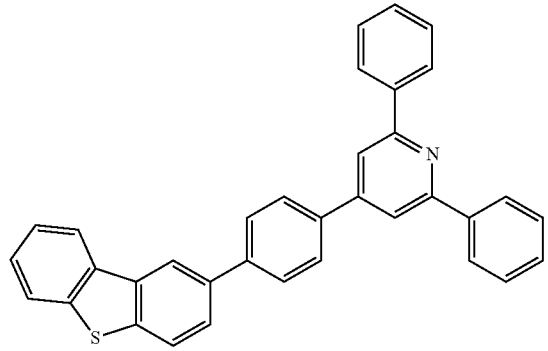

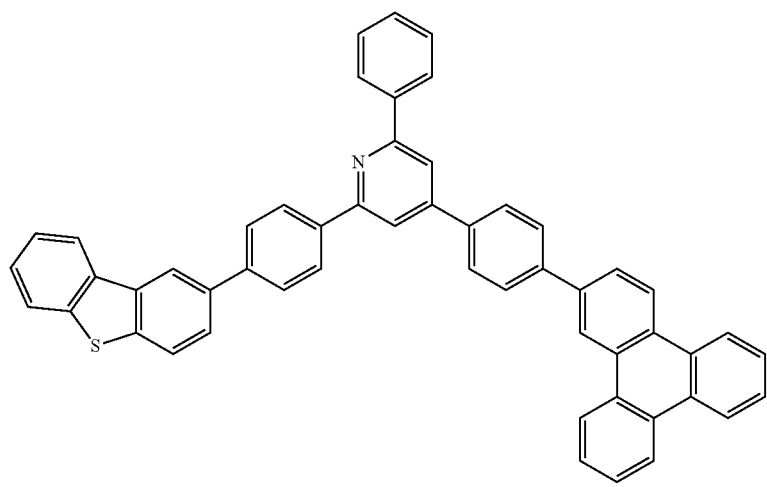
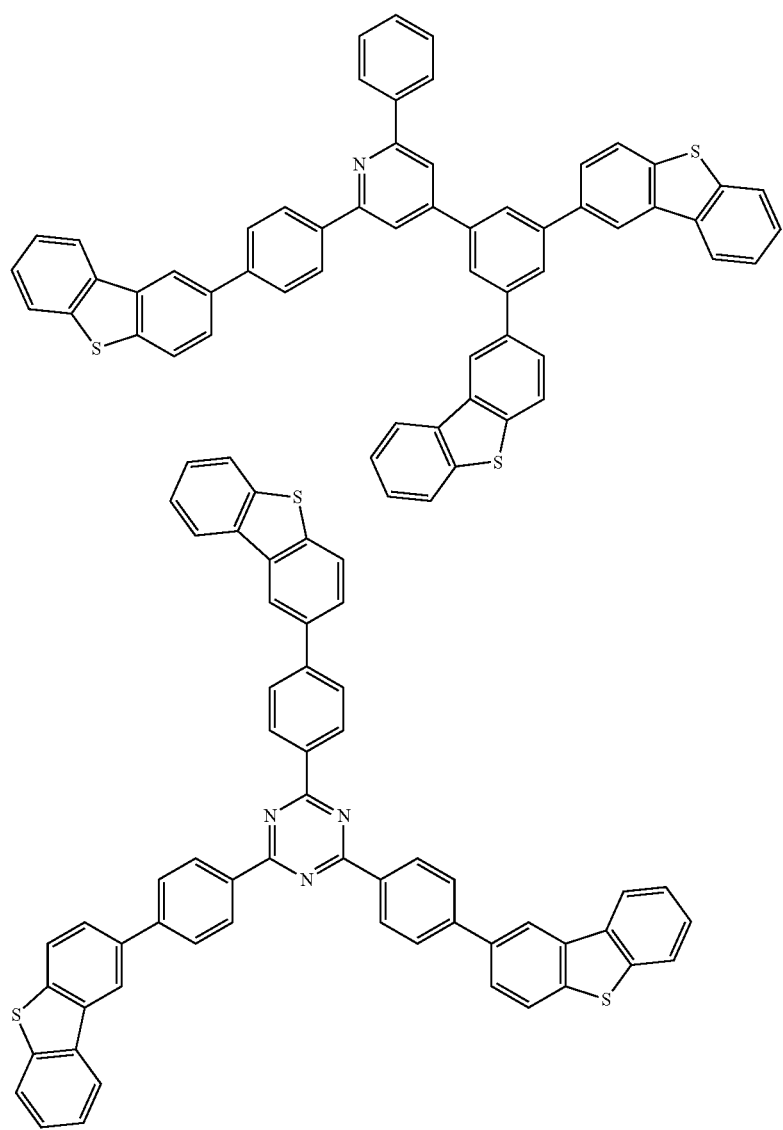

-continued
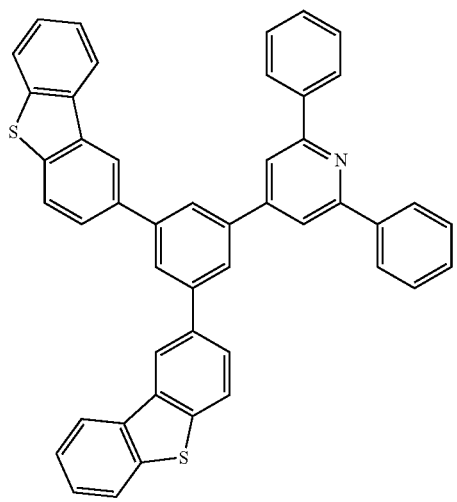
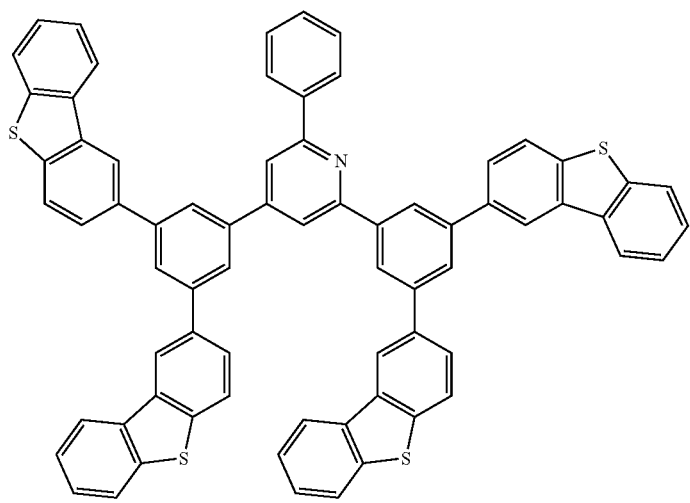
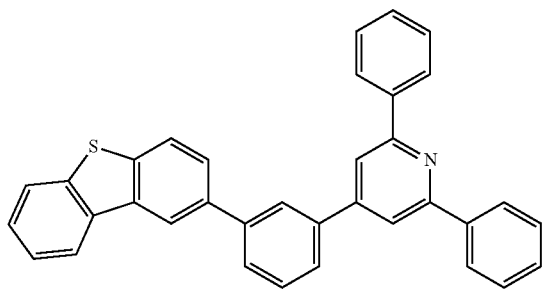

127
128
-continued
[Formula 22]
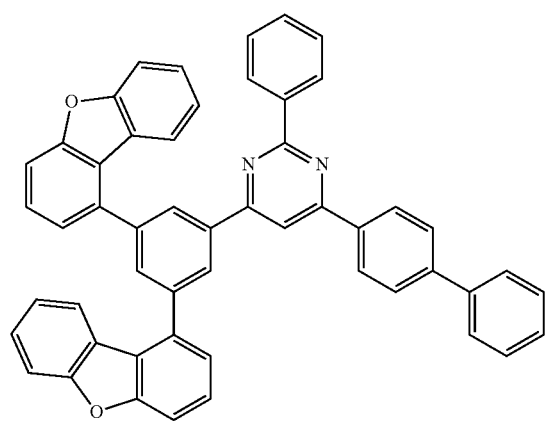
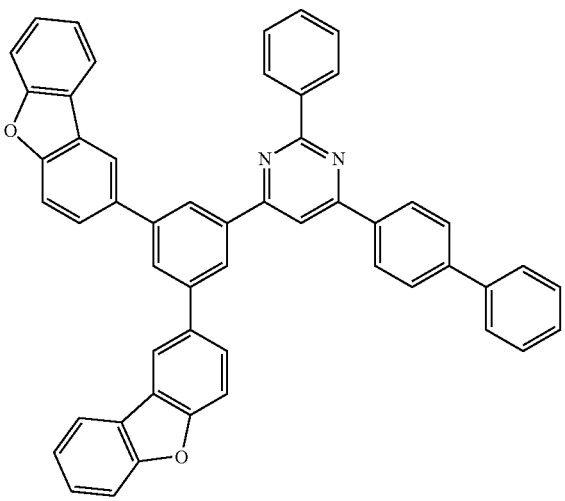
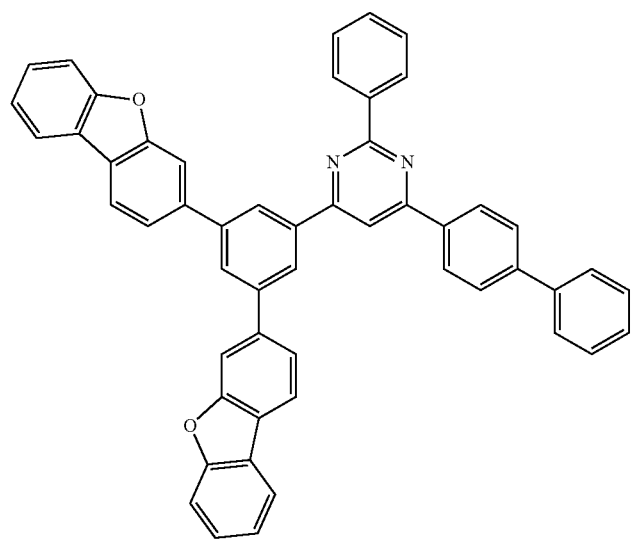
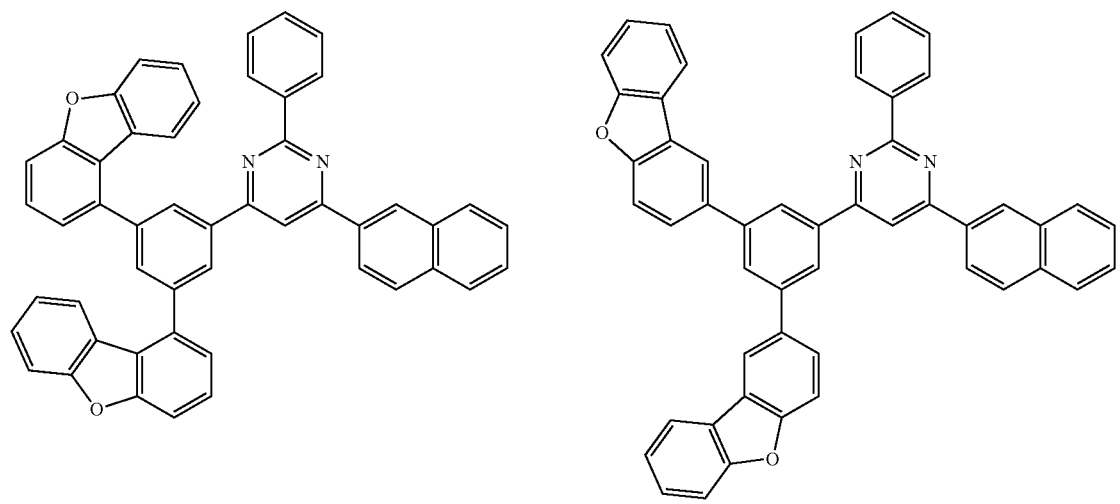

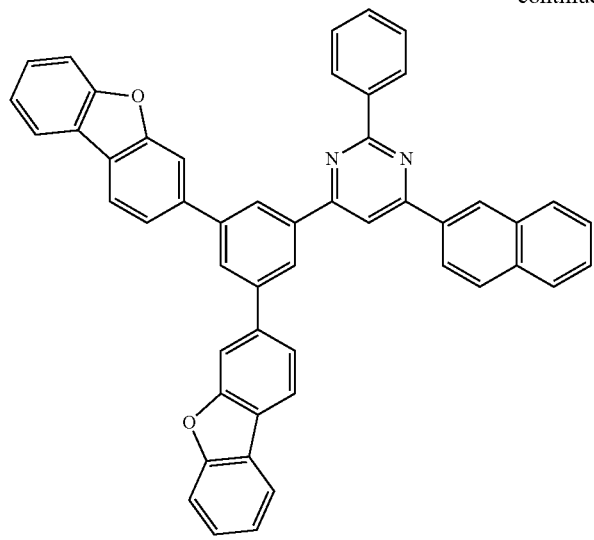
[Formula 23]
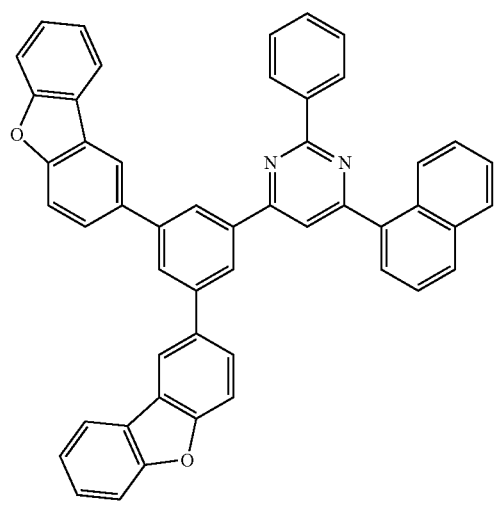
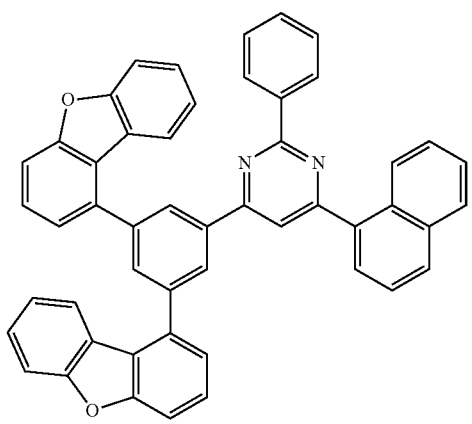
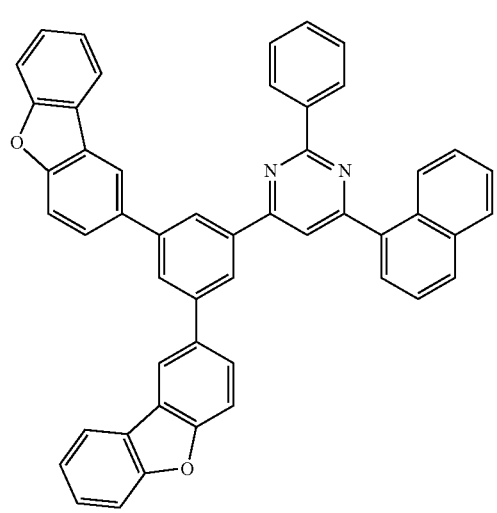
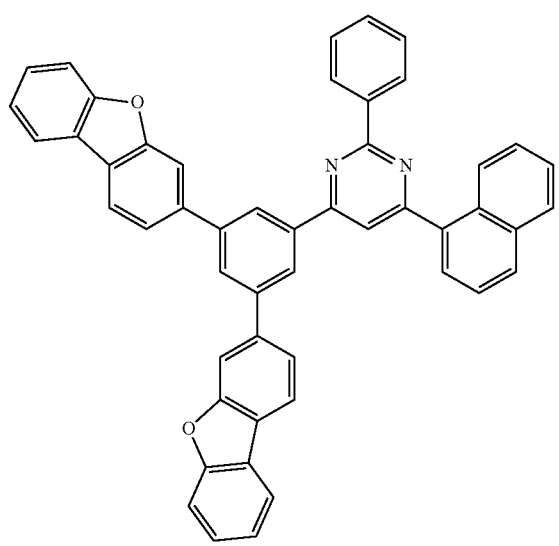

131
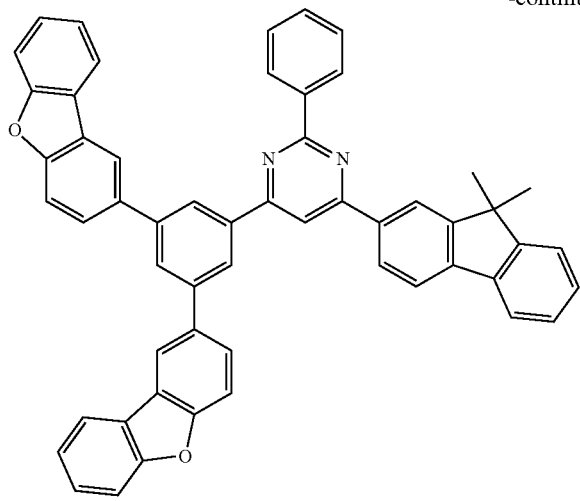
[Formula 24]
132
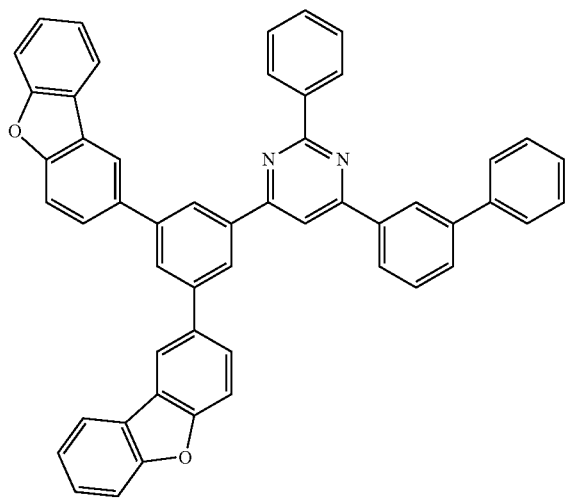
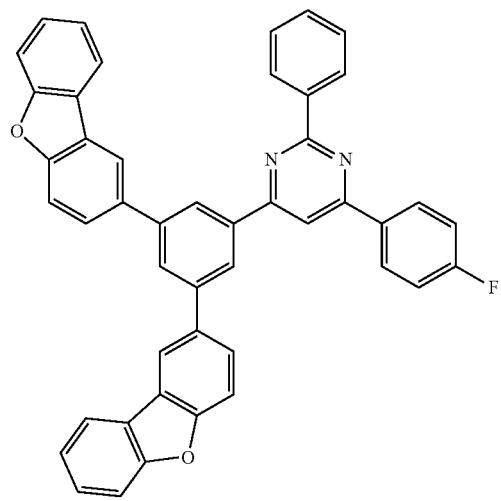
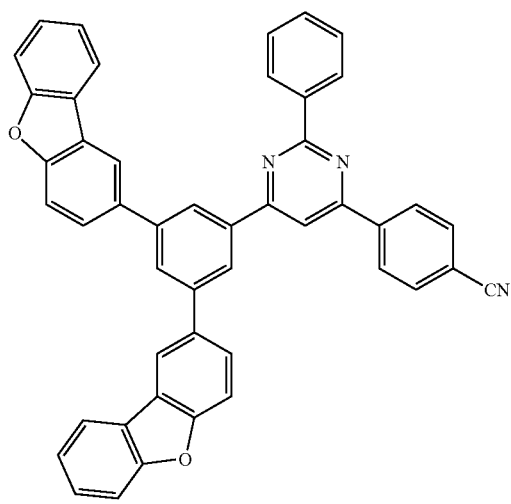
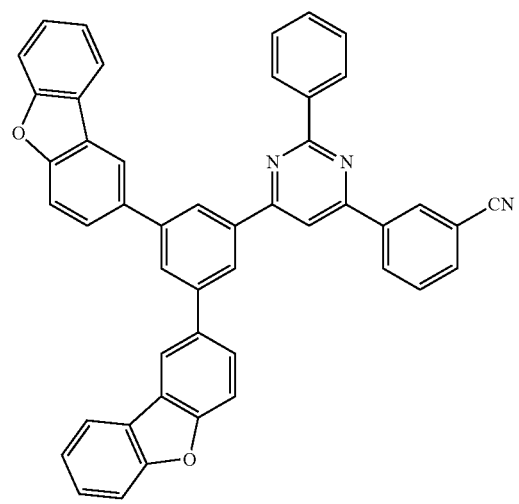

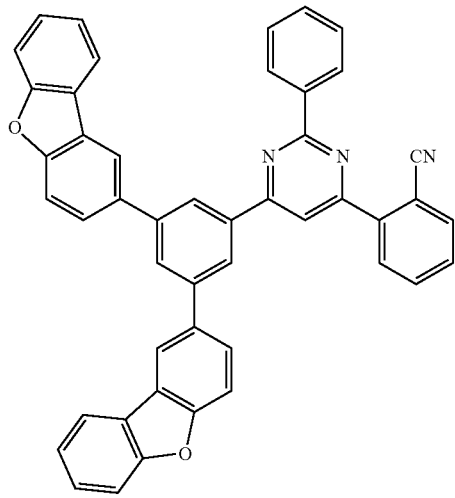
[Formula 25]
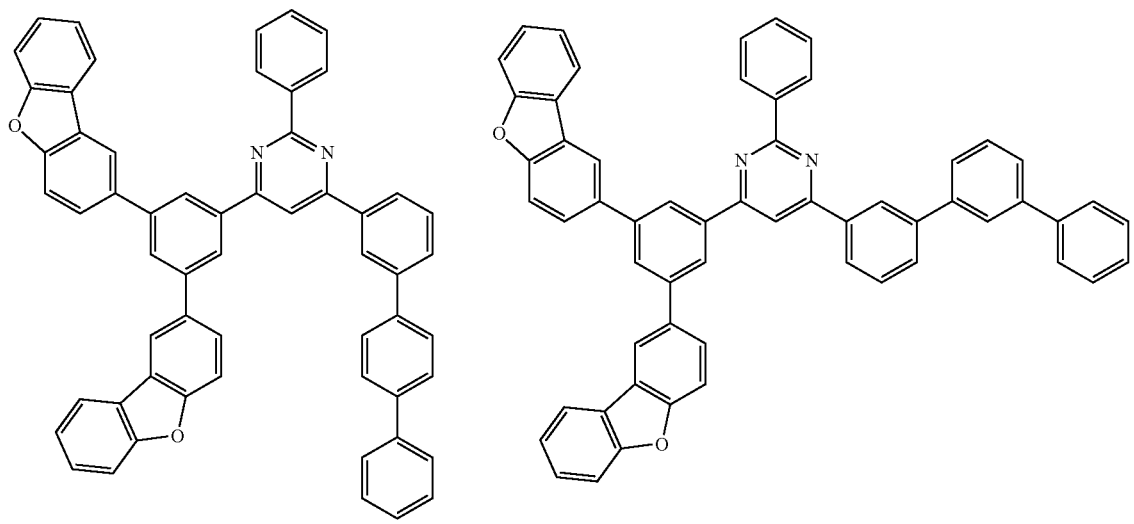
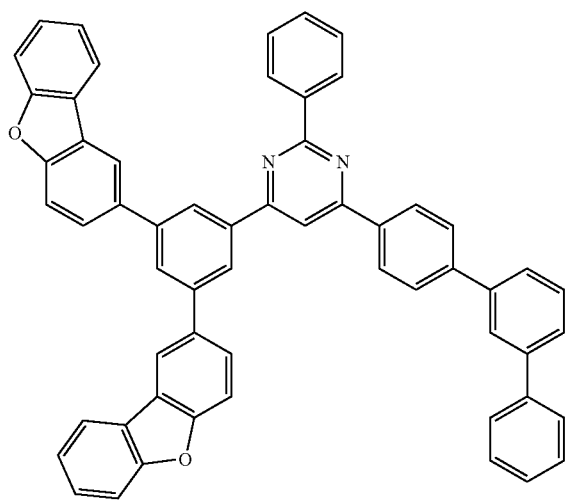

[Formula 26]
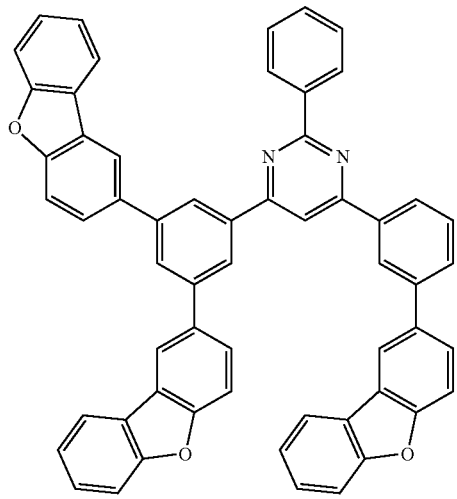
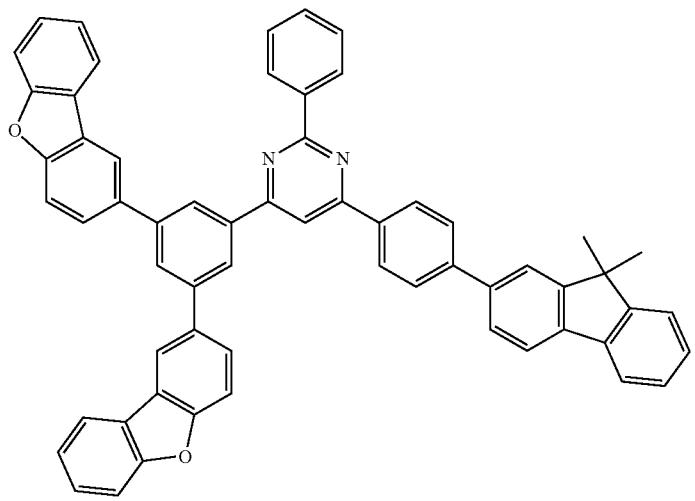
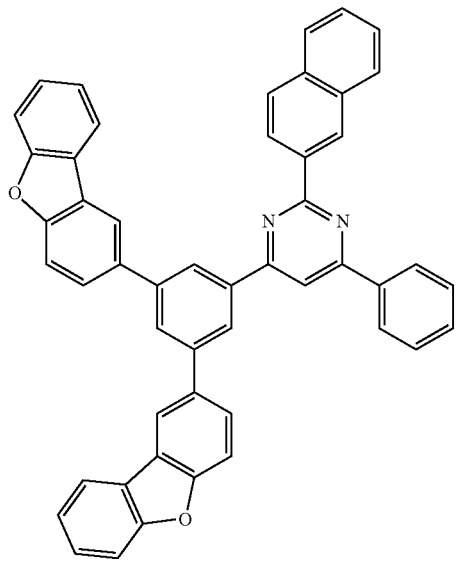
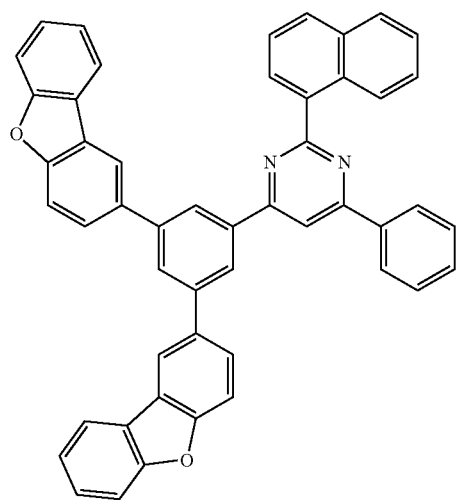

-continued
[Formula 27]
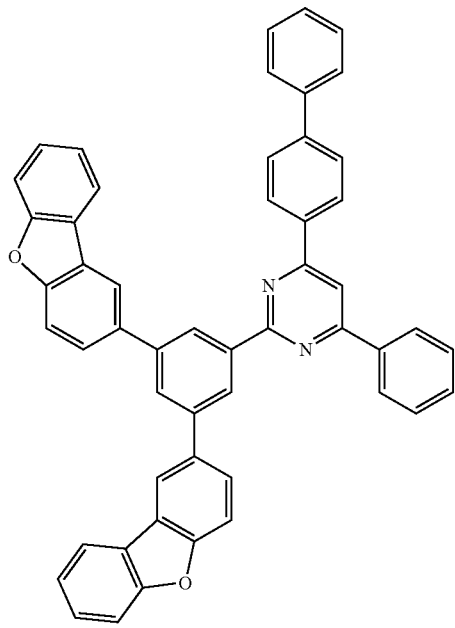
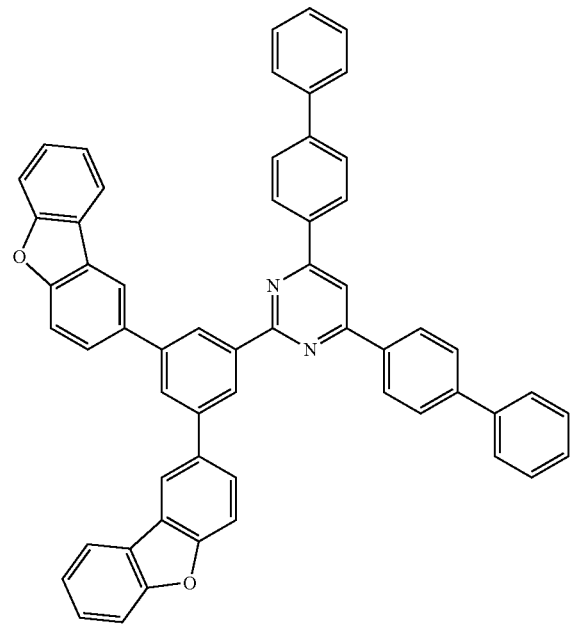
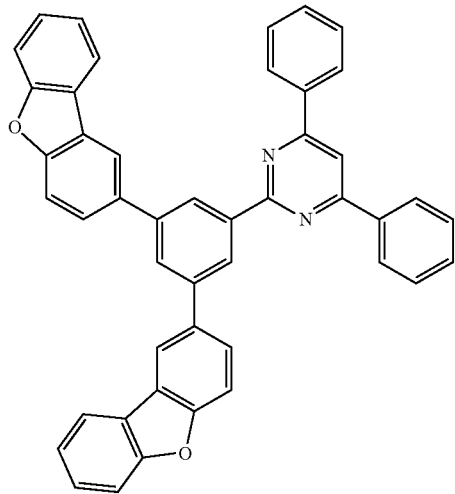
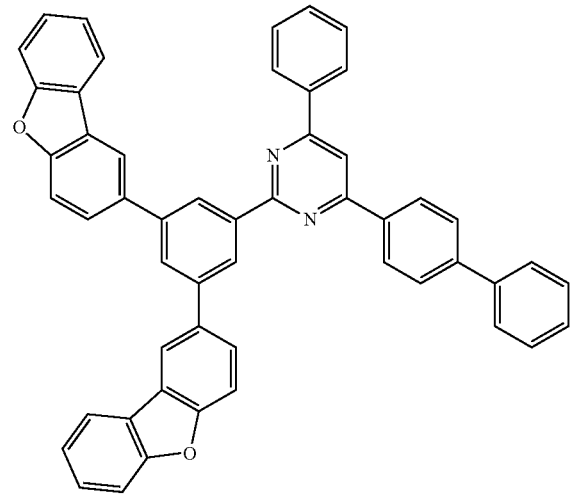
[Formula 28]
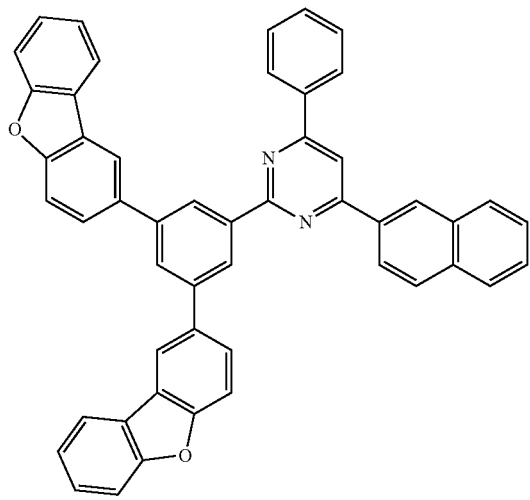
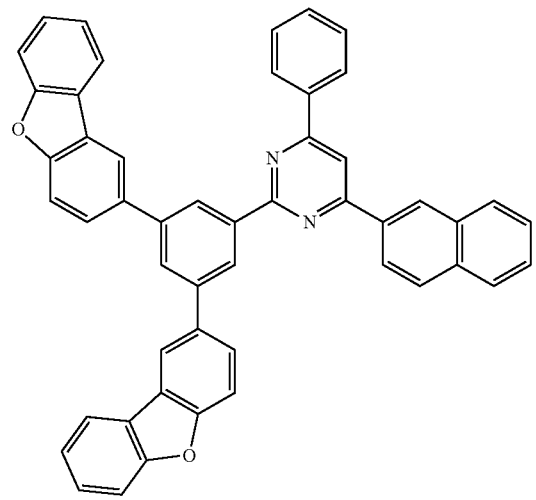

-continued
139
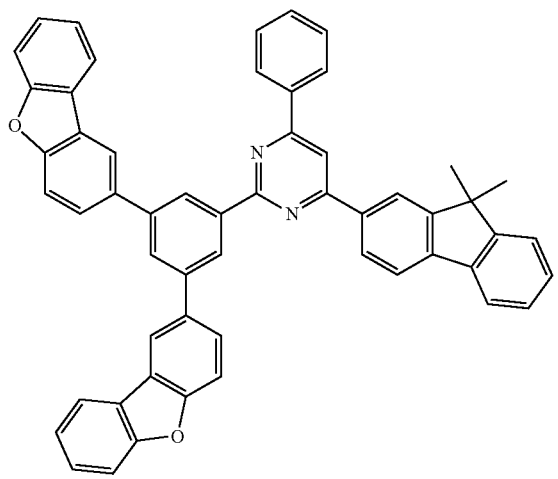
140
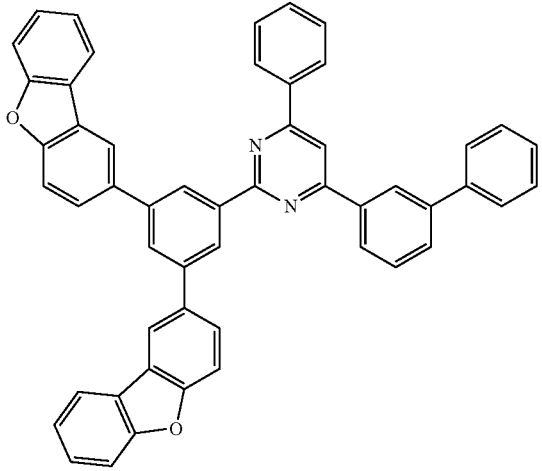
[Formula 29]
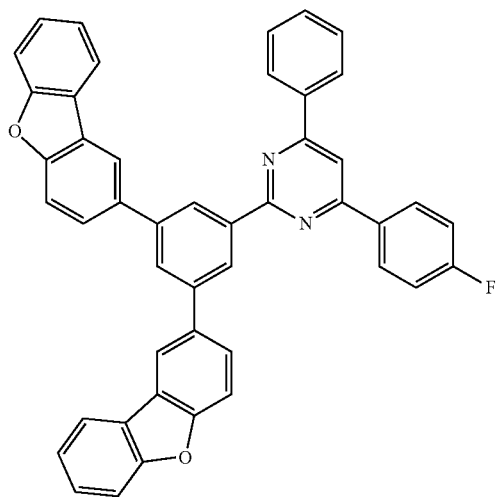
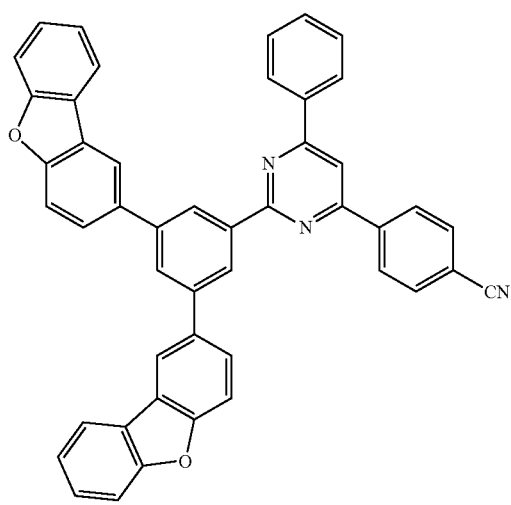
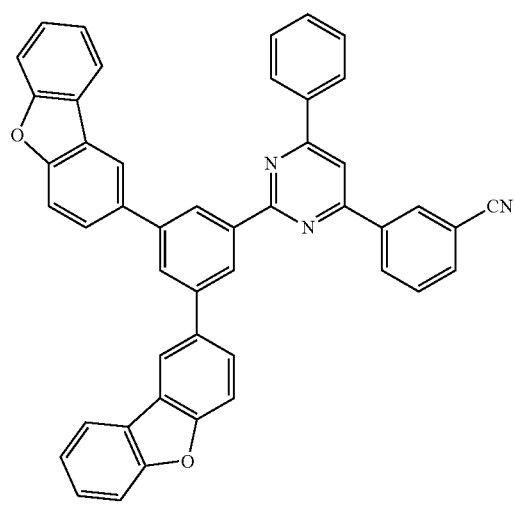

[Formula 30]
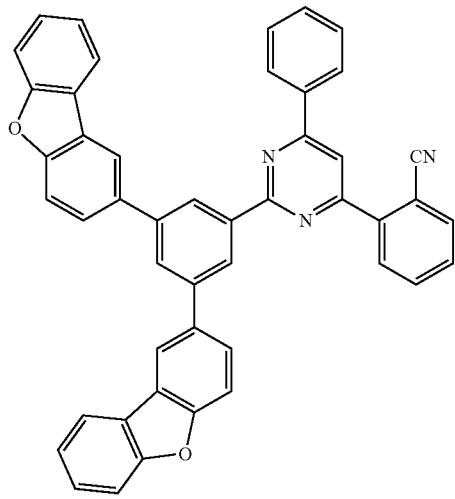
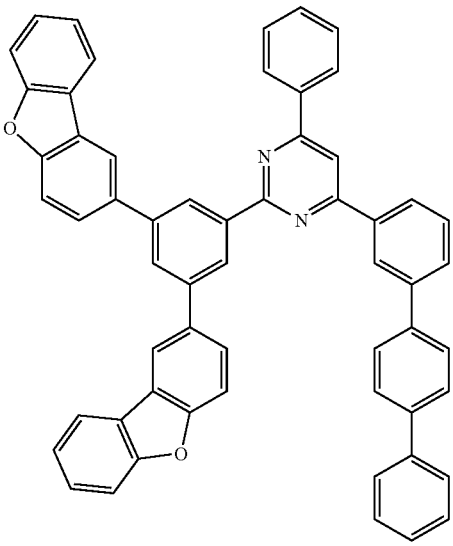
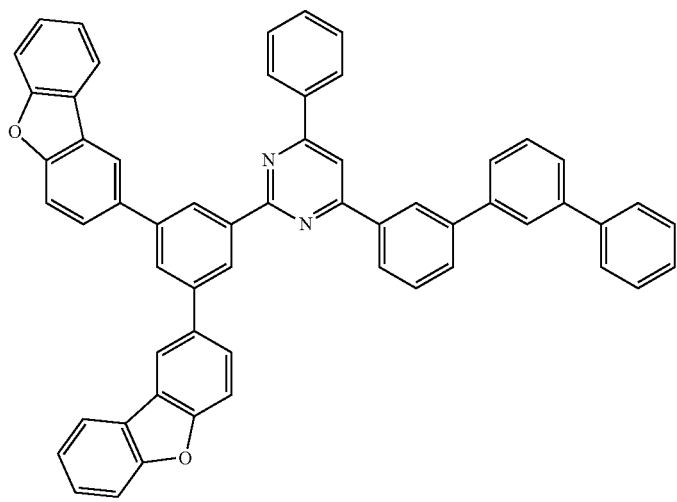
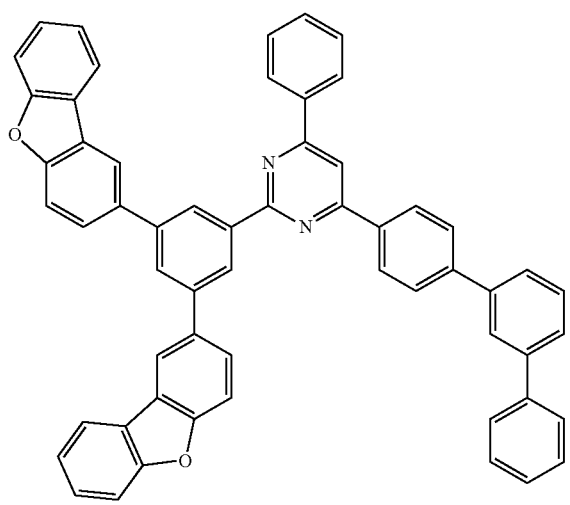

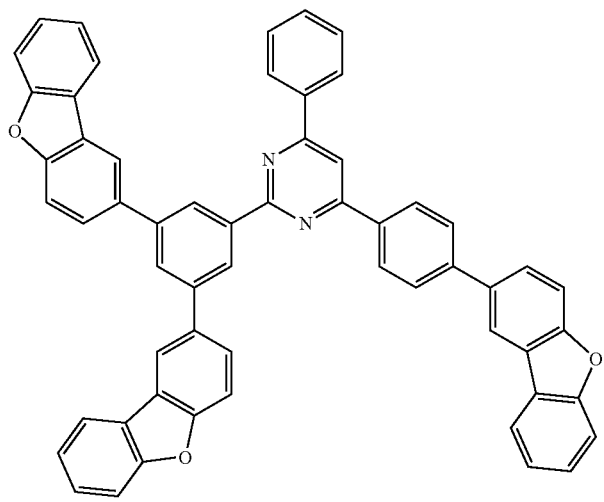
[Formula 31]
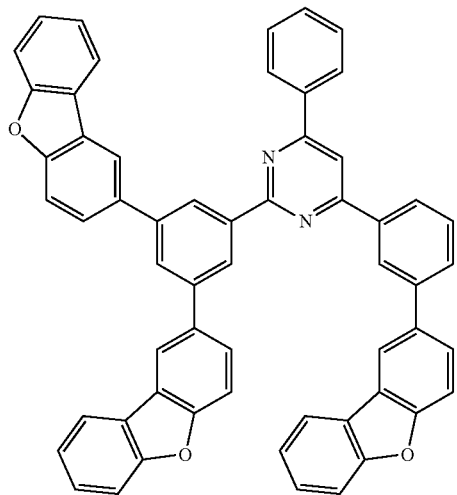
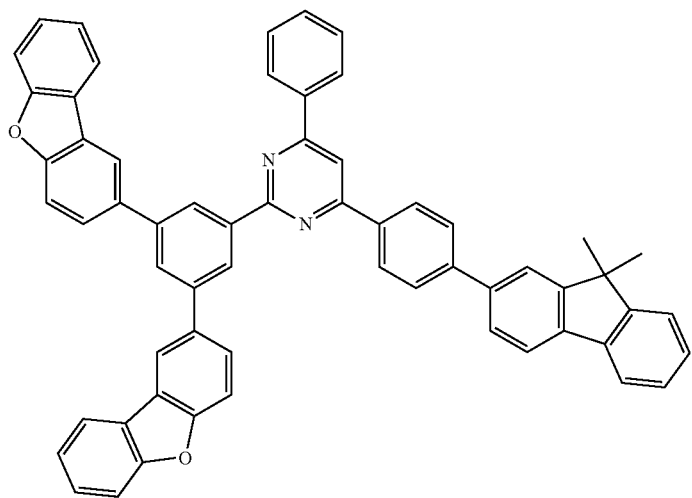

-continued
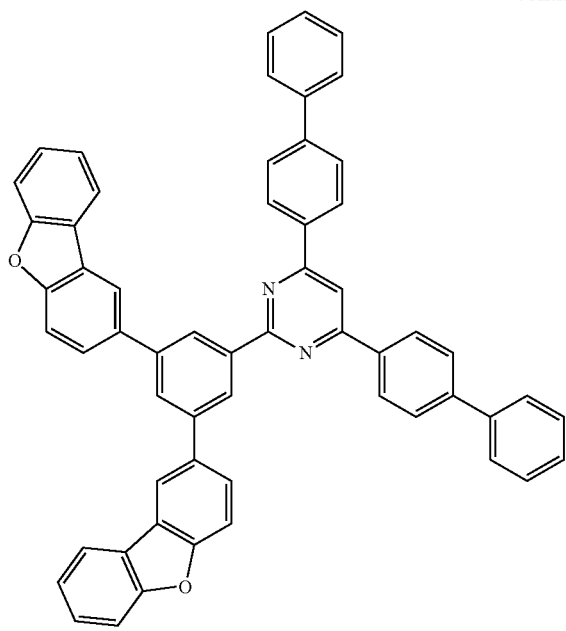
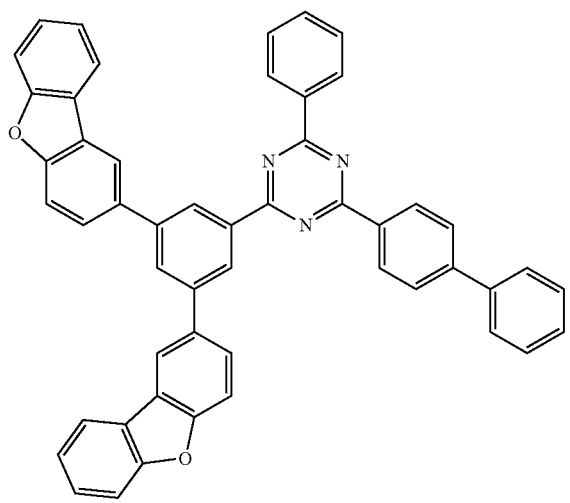
[Formula 32]
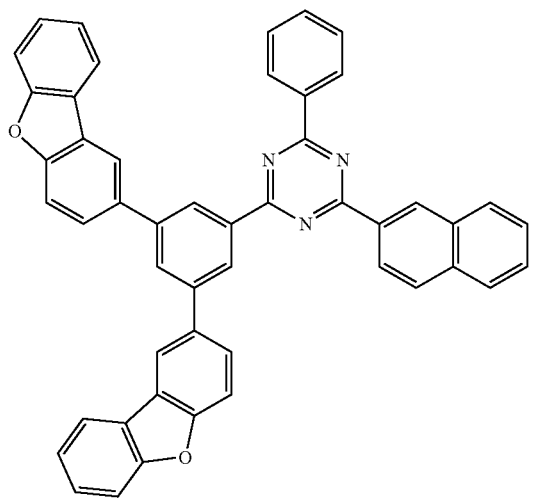 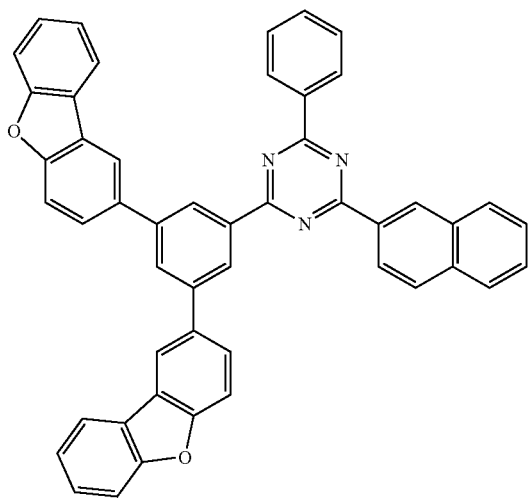

147
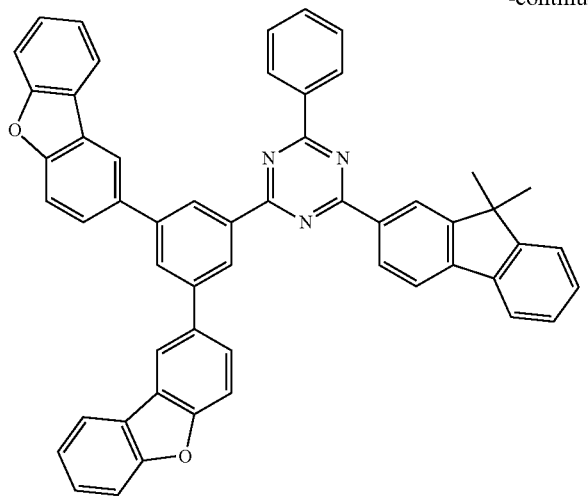
[Formula 33]
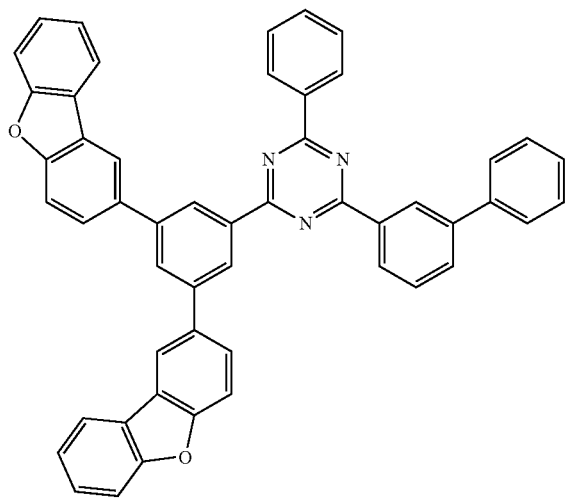
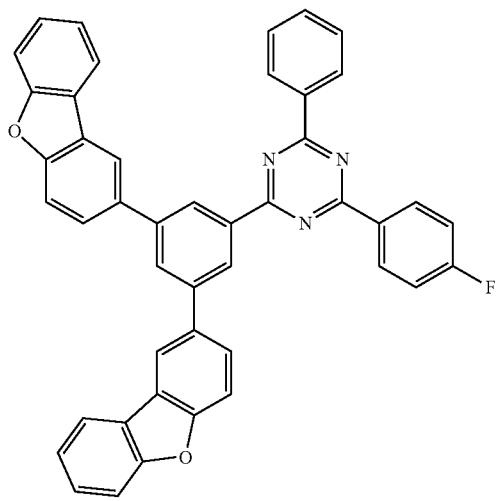
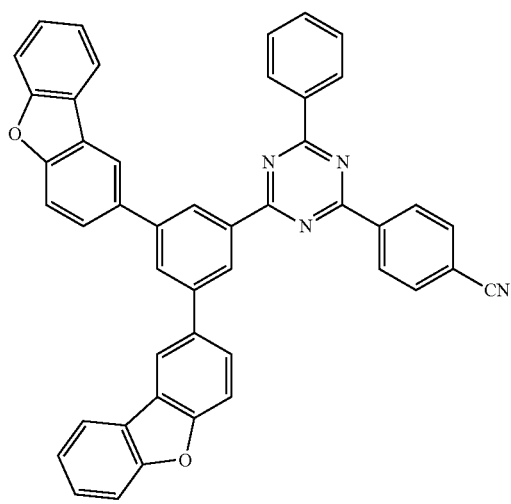
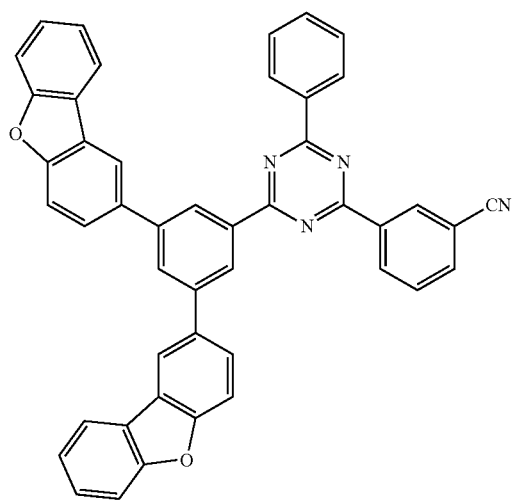

-continued
[Formula 34]
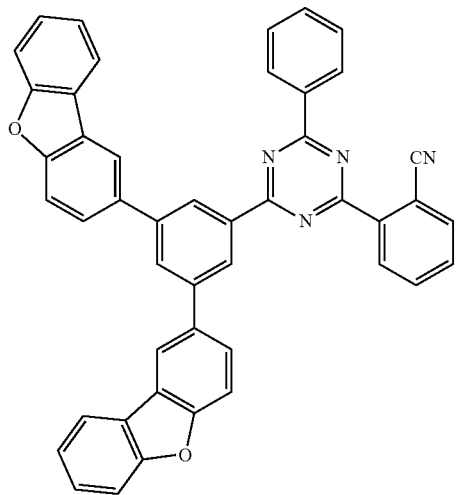
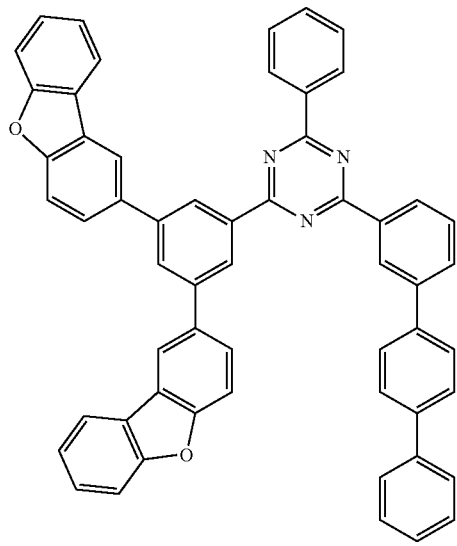
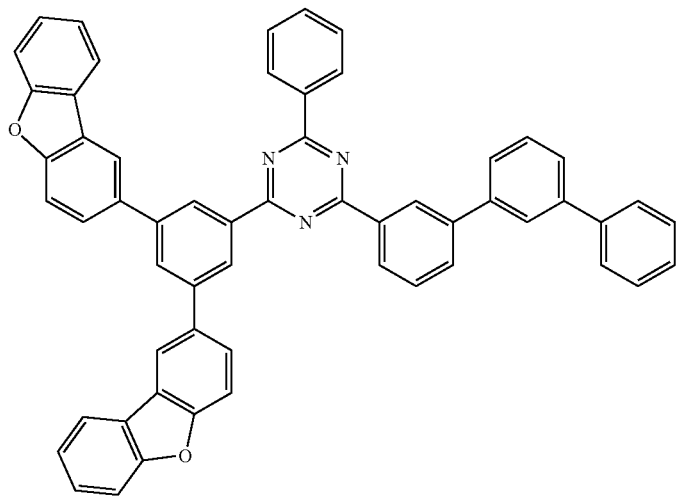
[Formula 35]
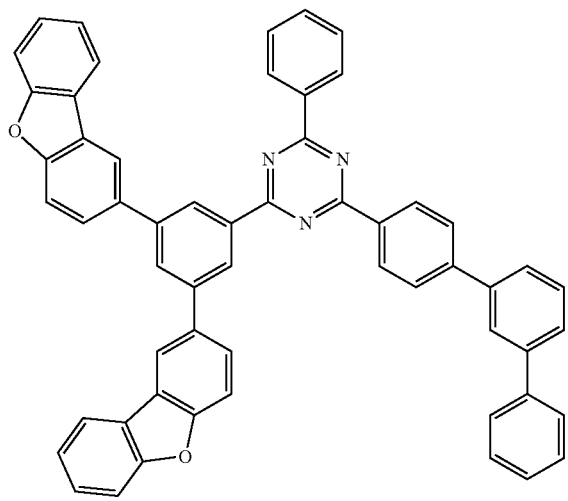
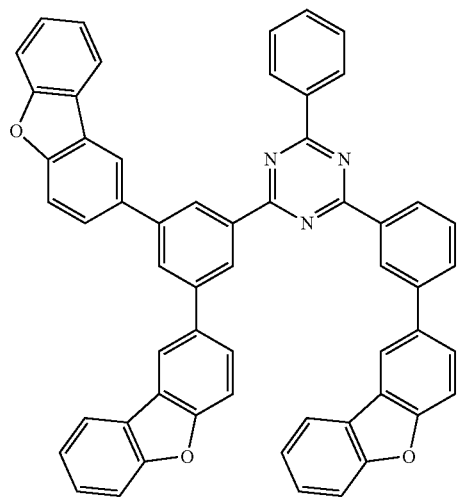

-continued
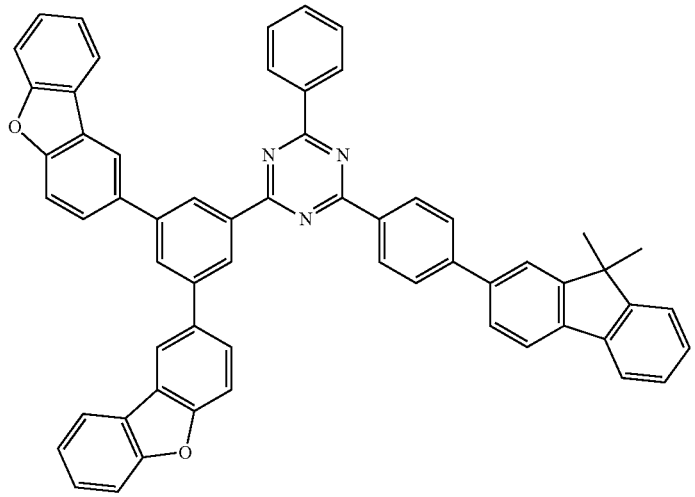
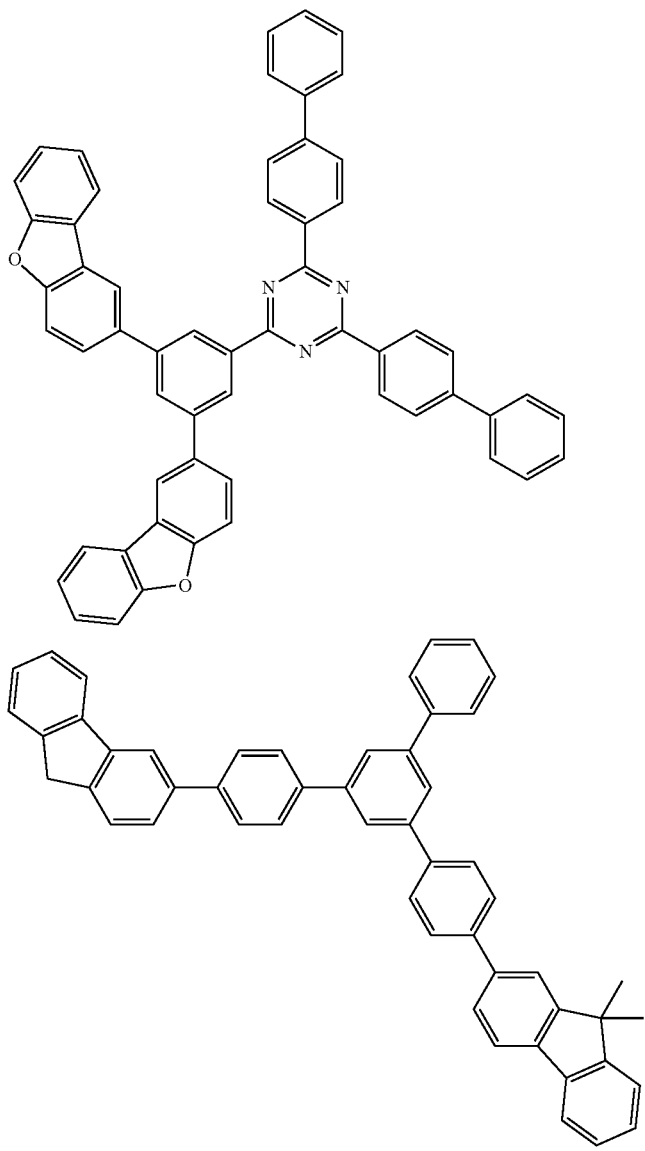

[Formula 36]
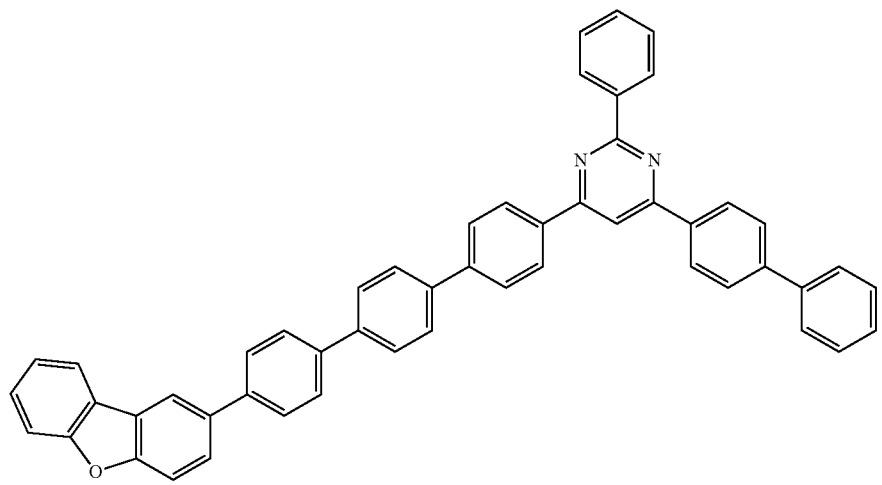
[Formula 37]
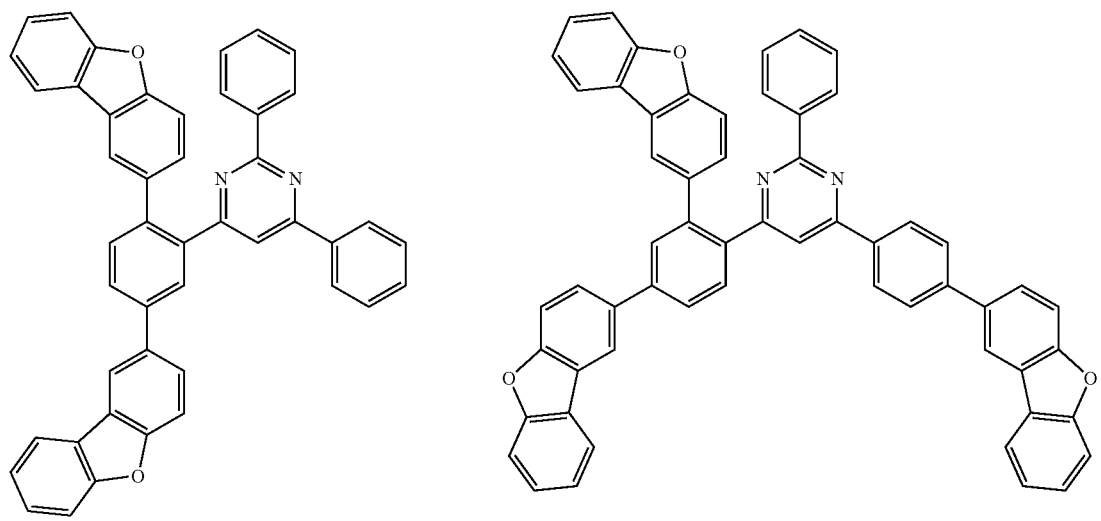
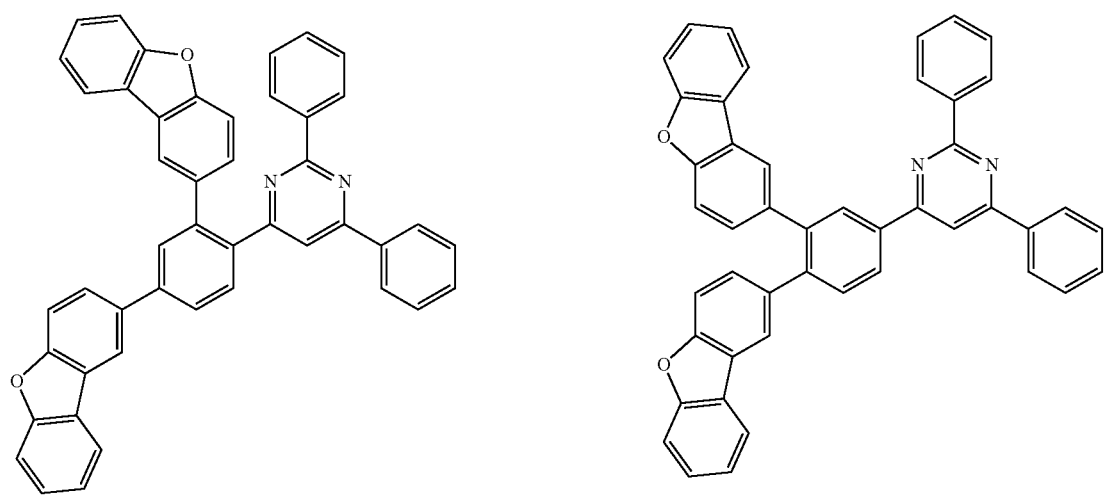

-continued
[Formula 38]
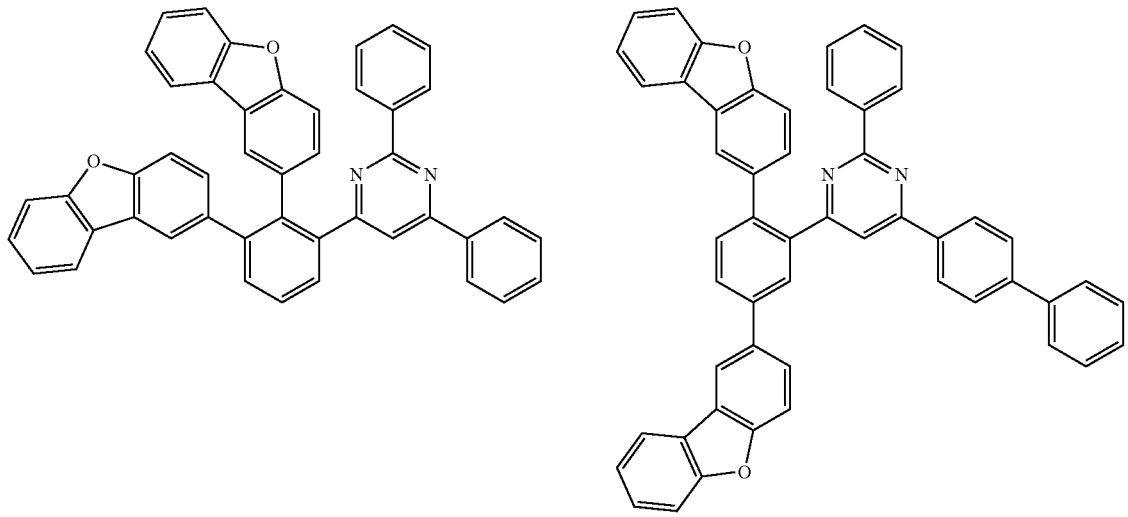
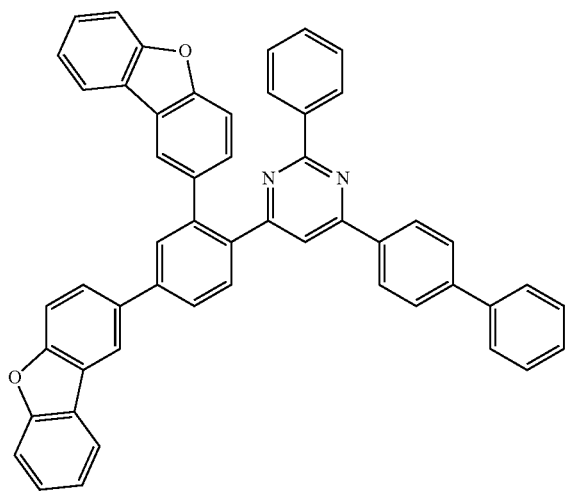
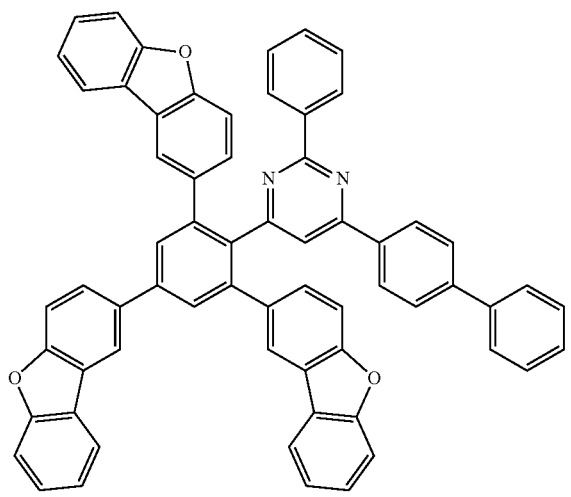

[Formula 39]
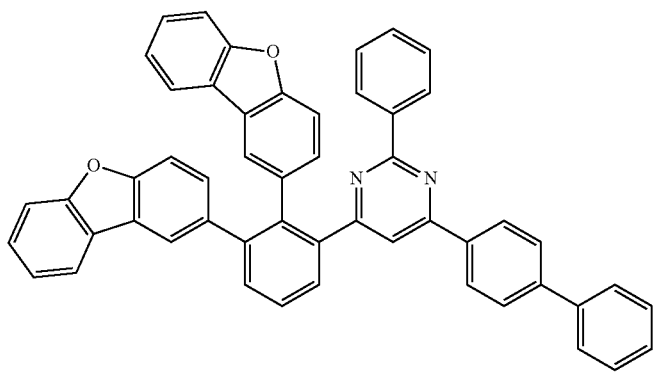
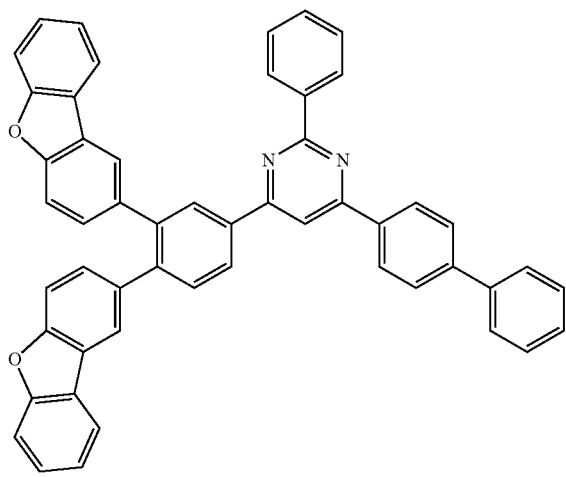
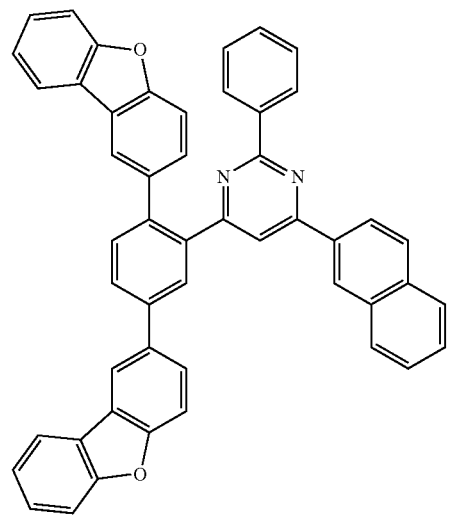
[Formula 40]
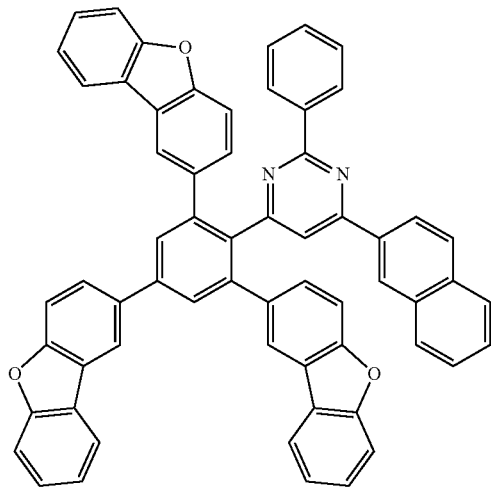
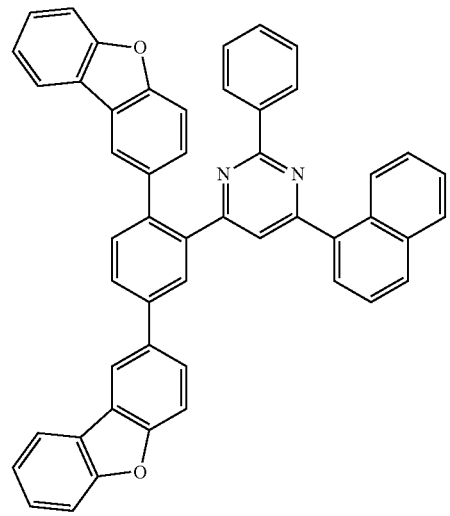

-continued
159
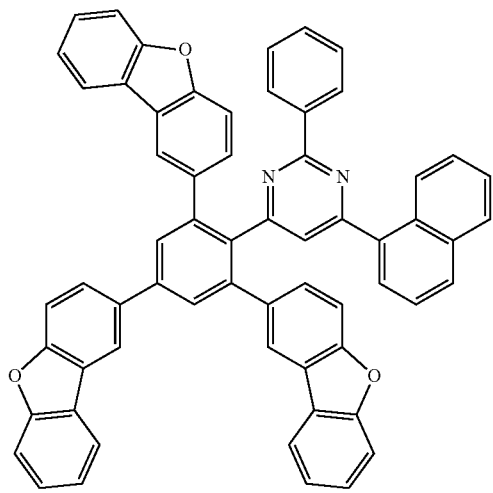
160
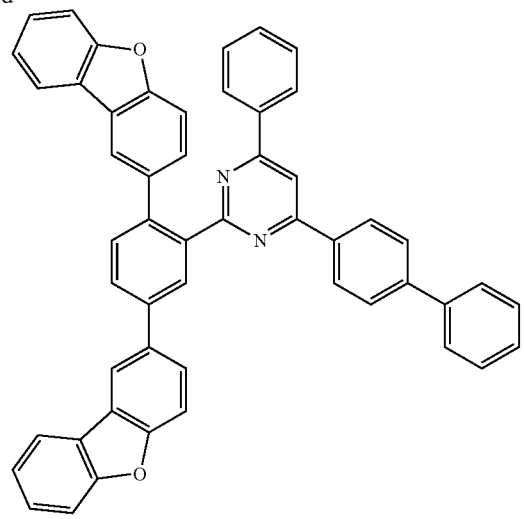
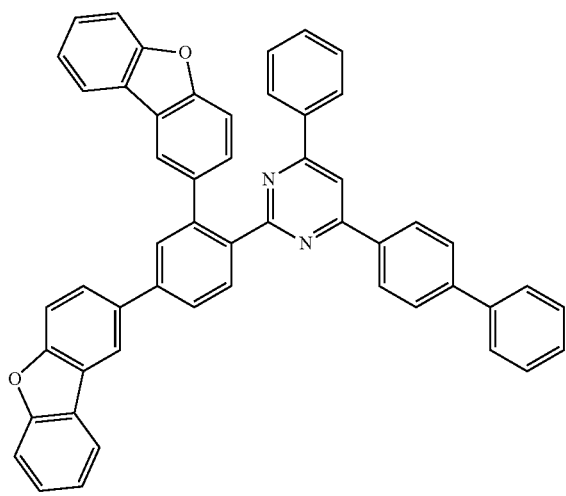
[Formula 41]
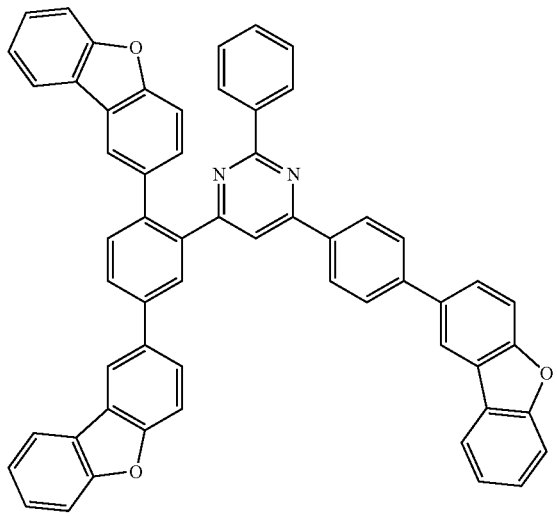
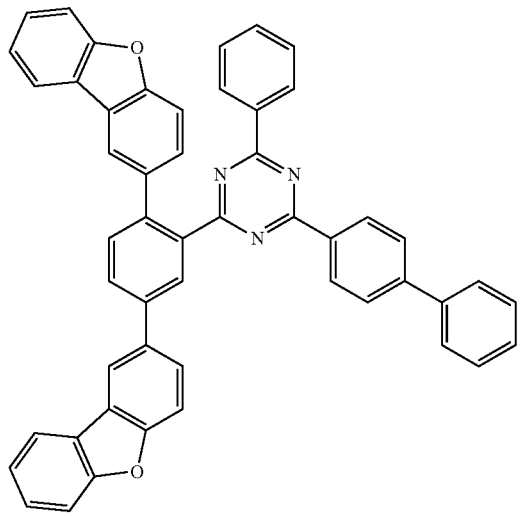

161
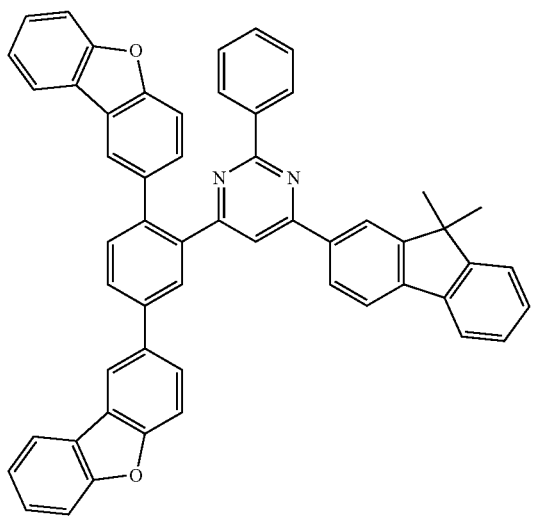
162
-continued
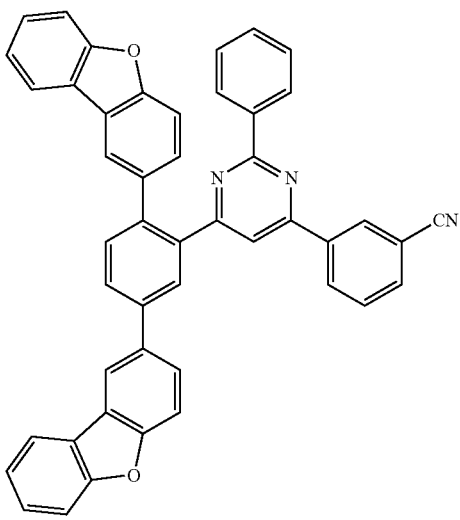
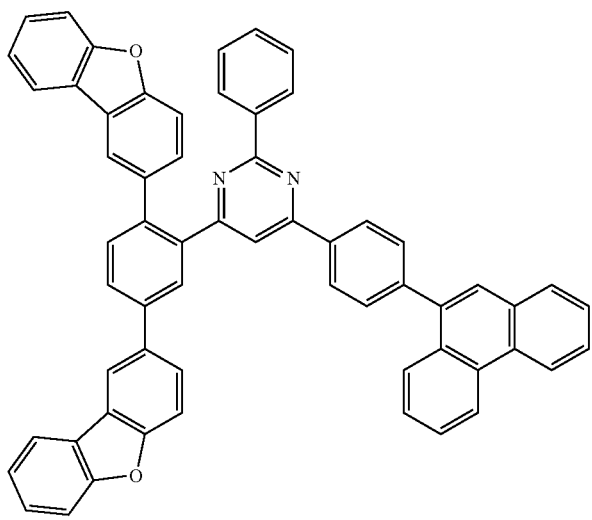
[Formula 42]
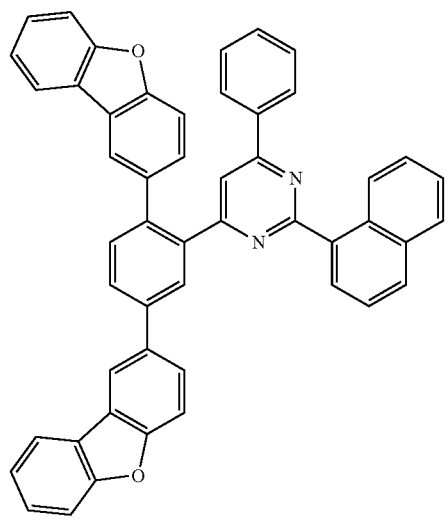
[Formula 43]
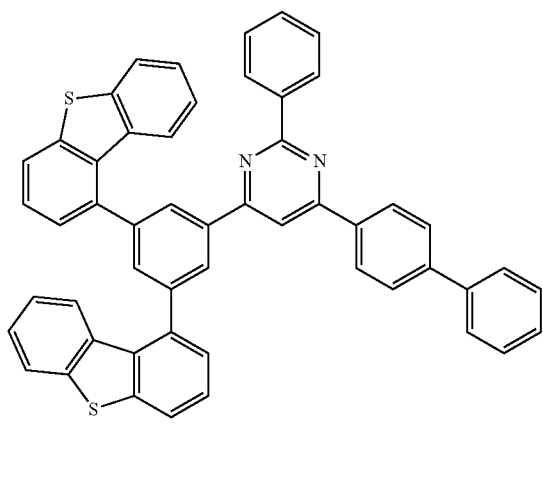
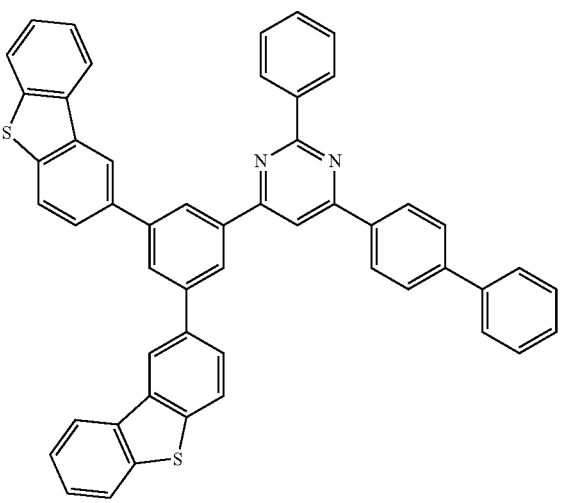

-continued
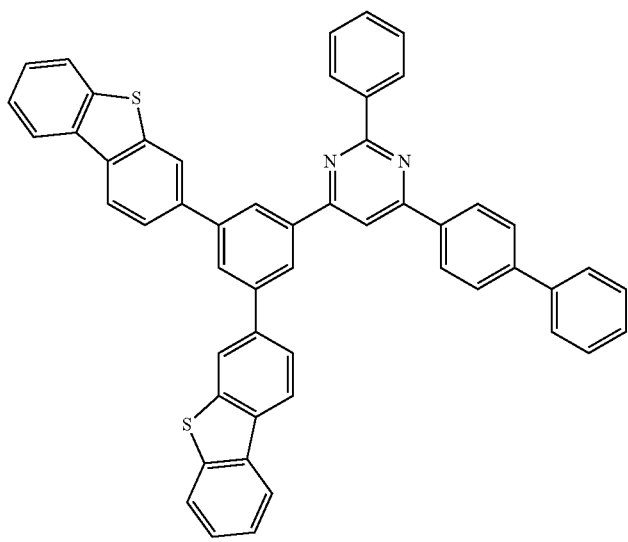
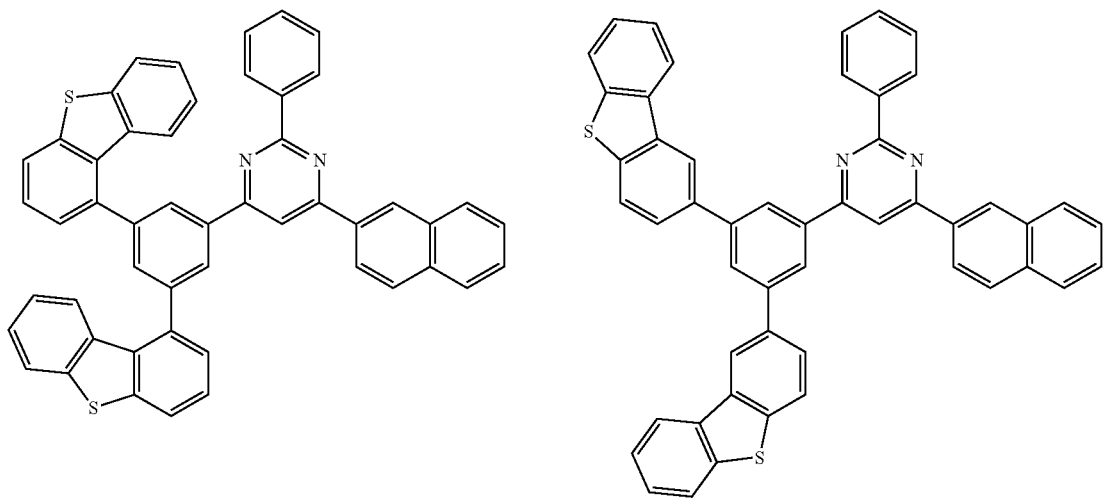
[Formula 44]
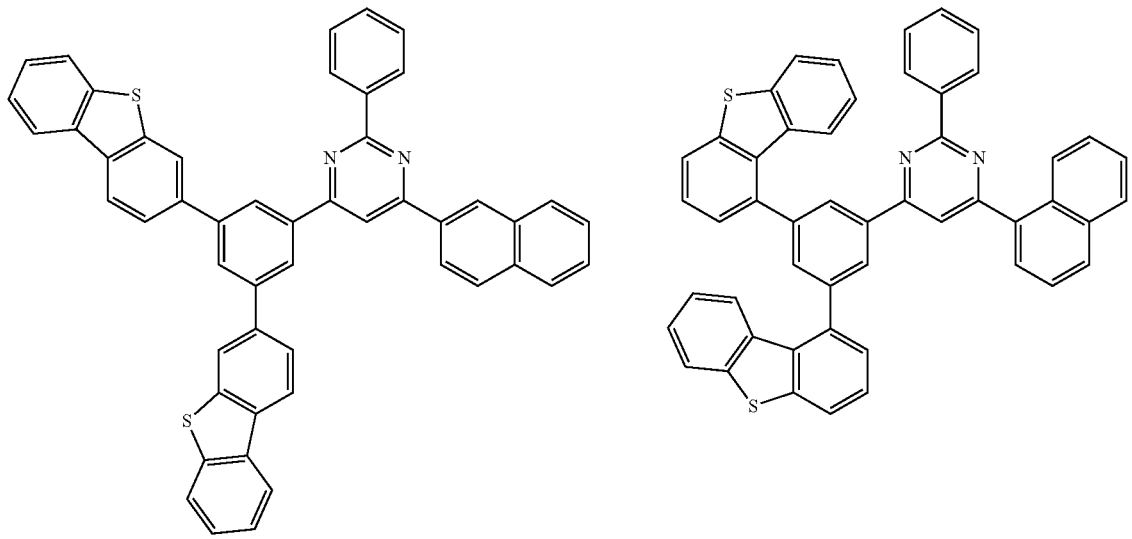

165 166
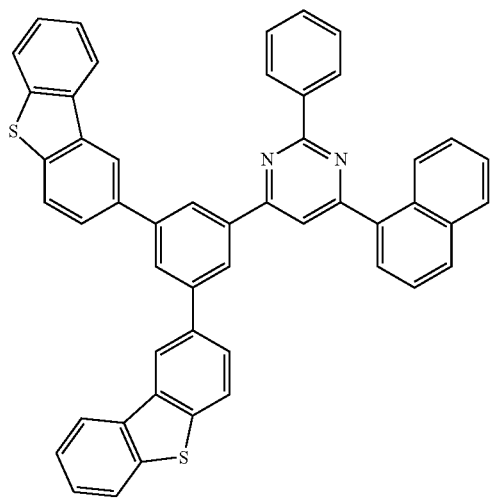
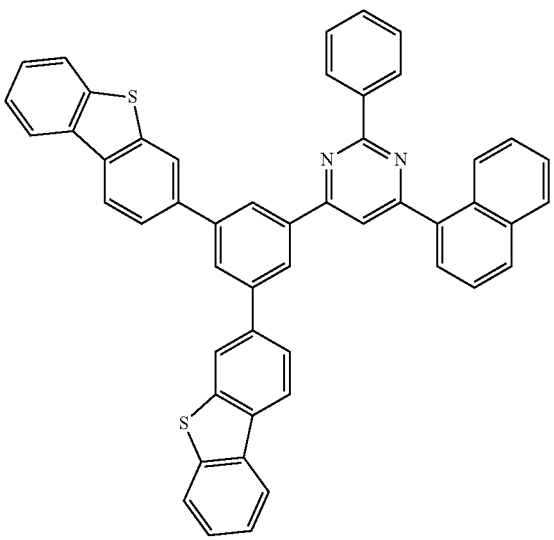
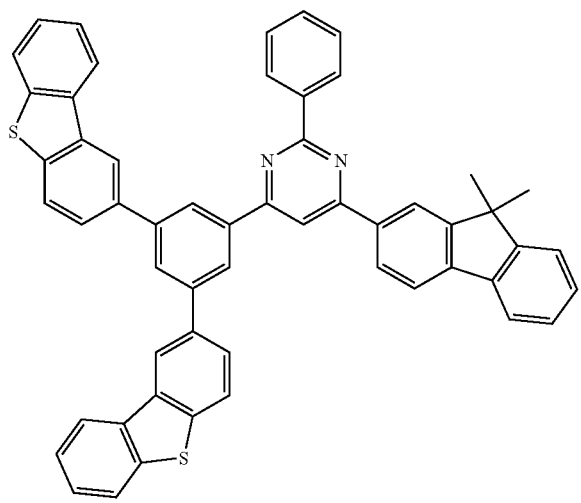
[Formula 45]
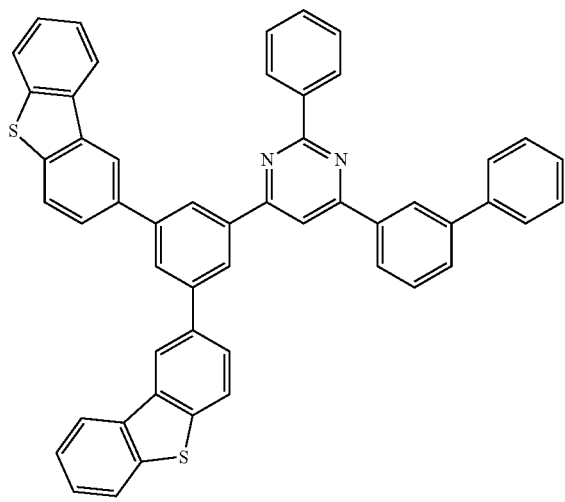
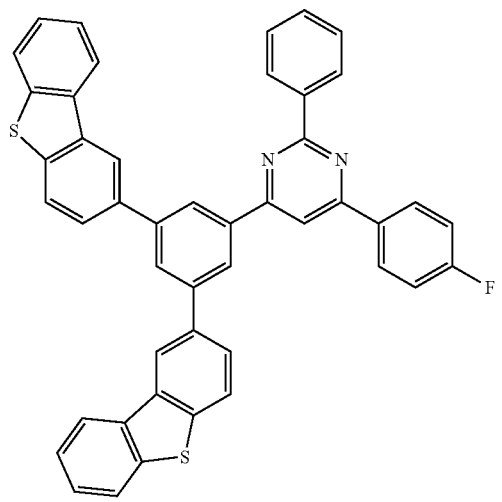

-continued
167
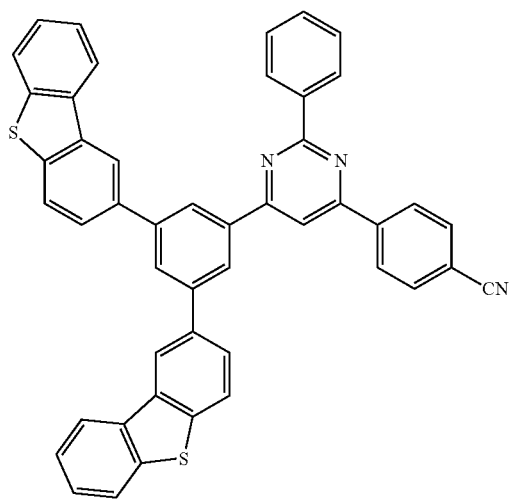
168
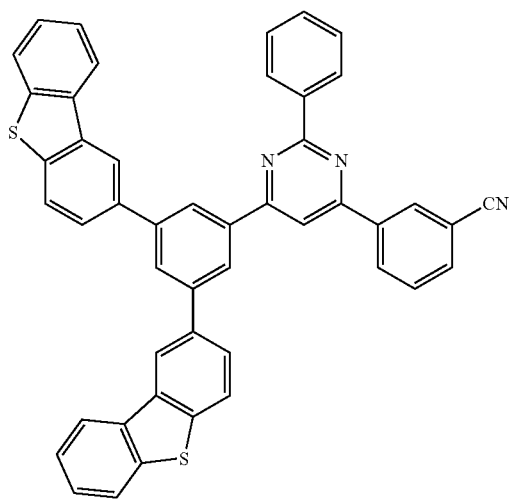
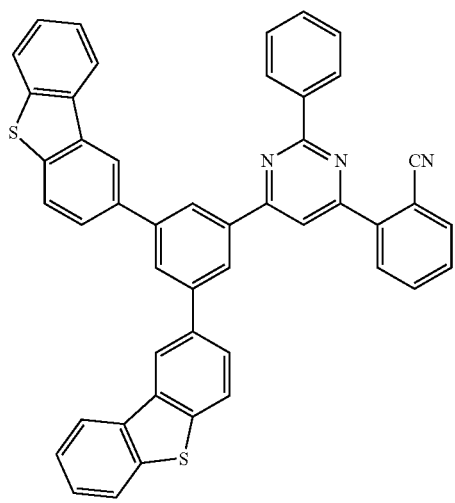
[Formula 46]
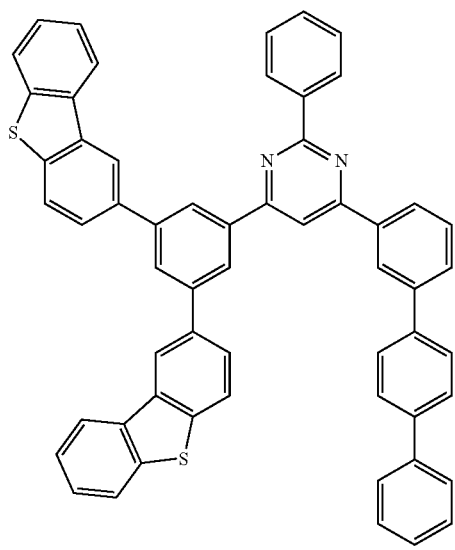
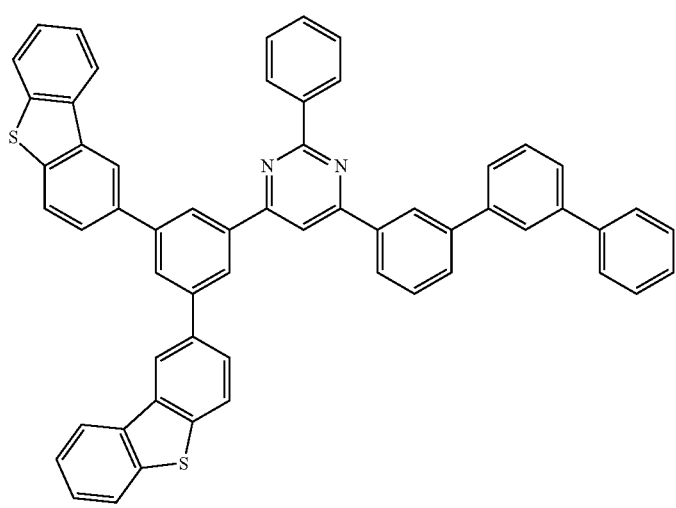

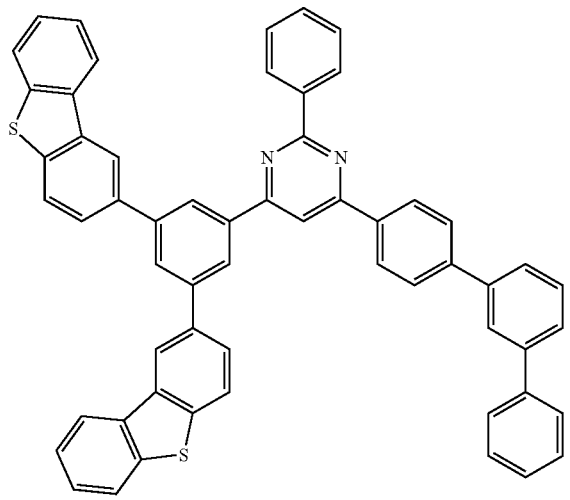
[Formula 47]
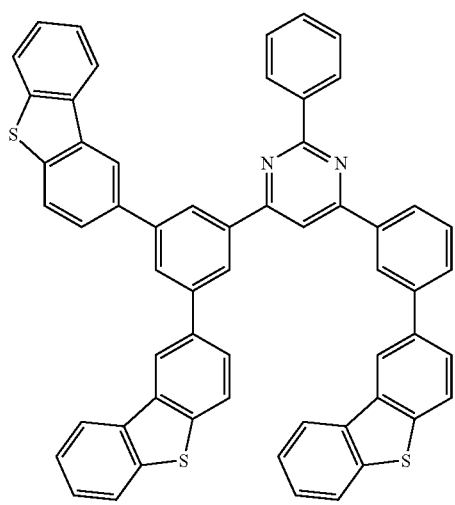
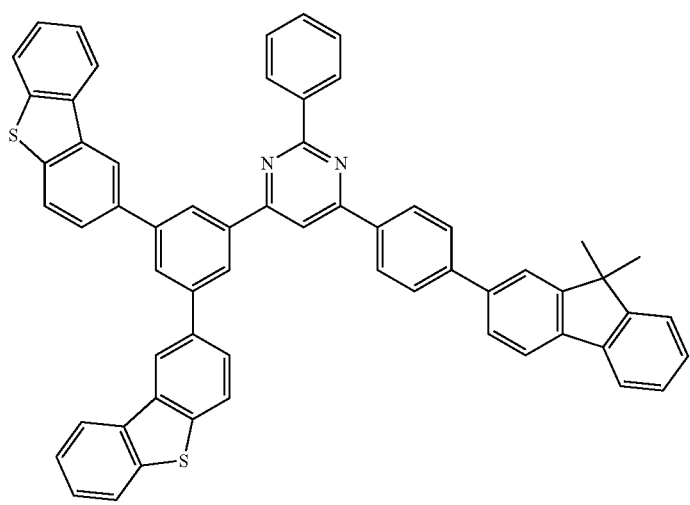

-continued
171
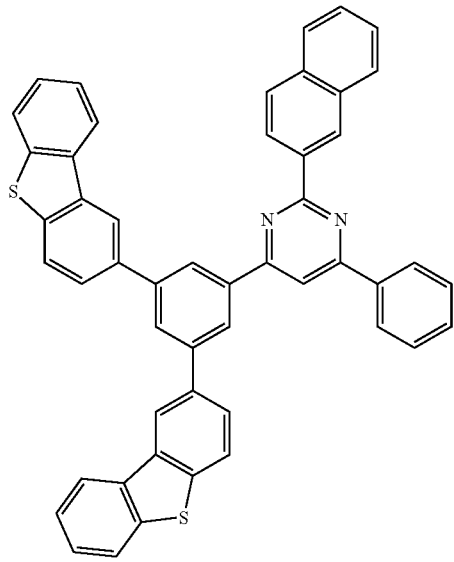
172
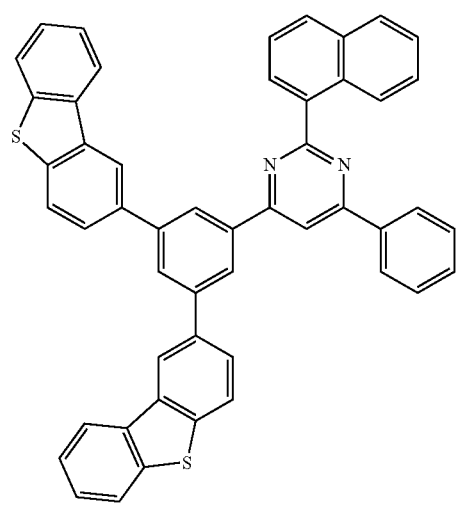
[Formula 48]
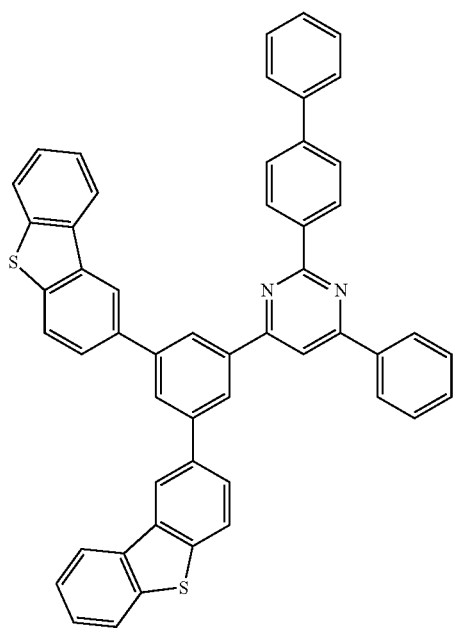
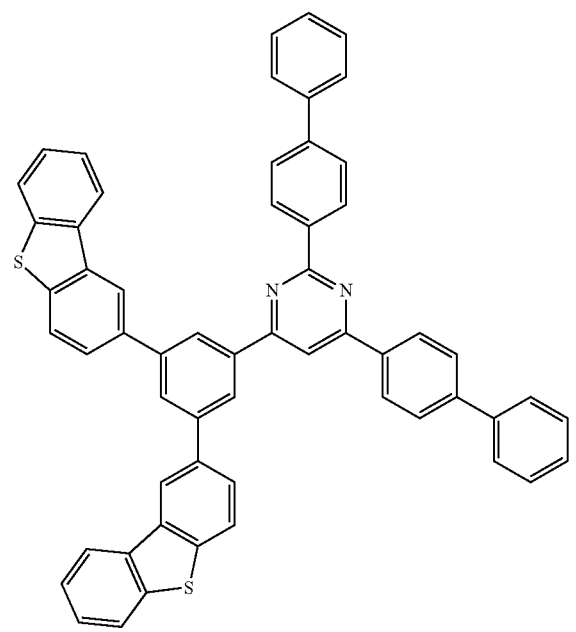
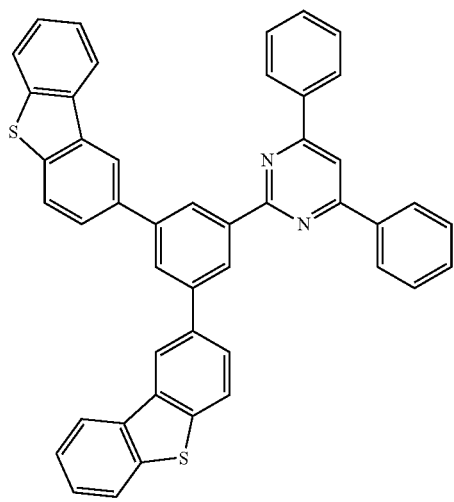
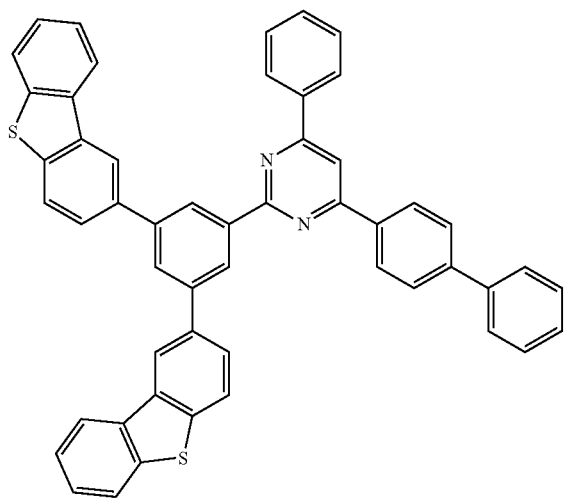

-continued
[Formula 49]
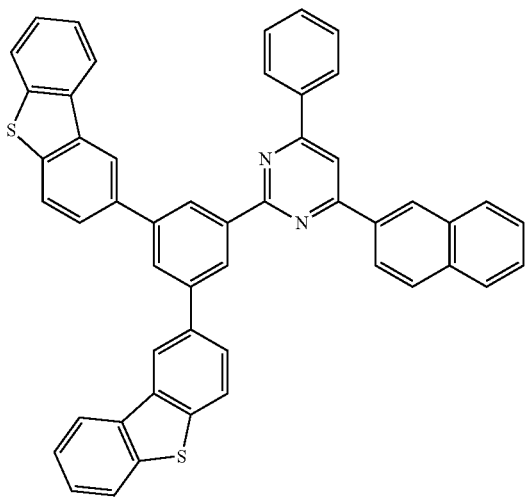
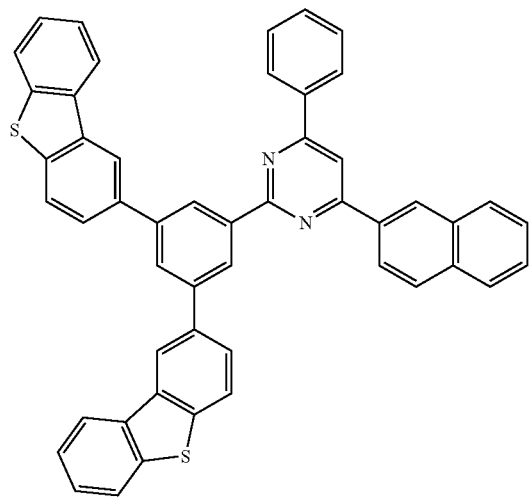
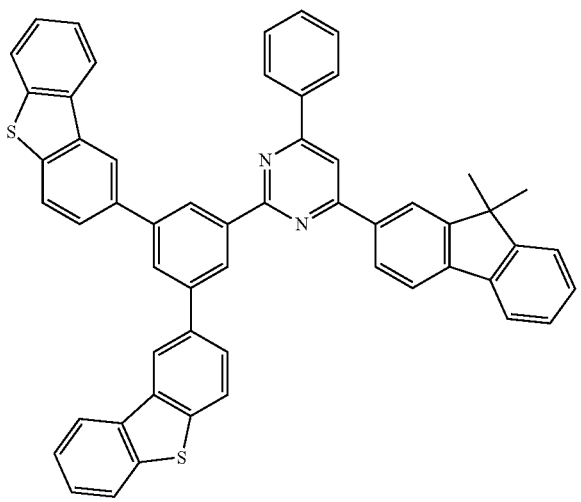
[Formula 50]
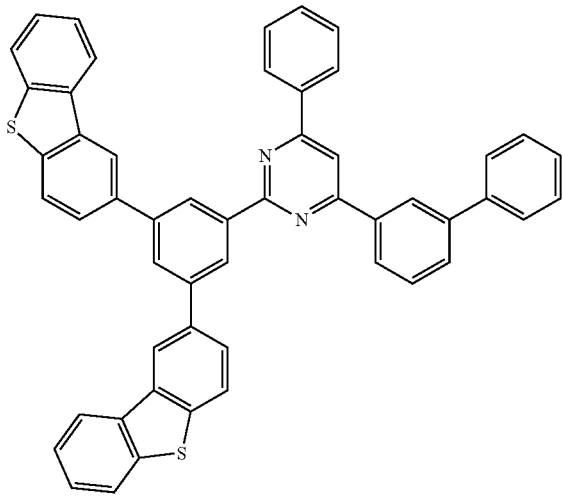
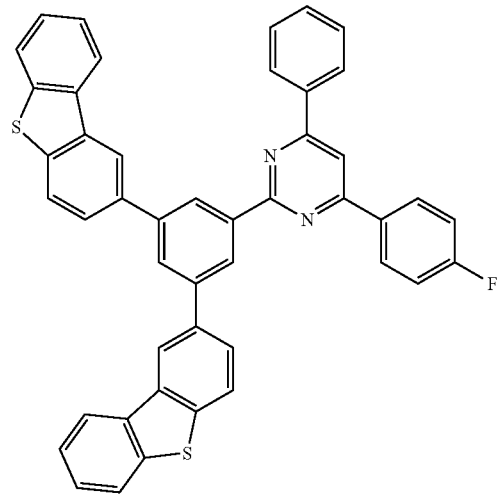

-continued
175
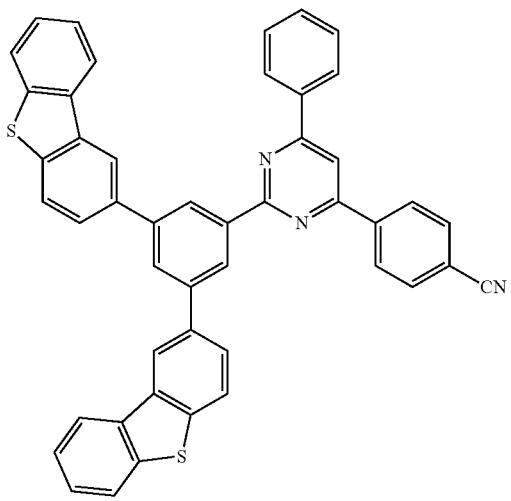
176
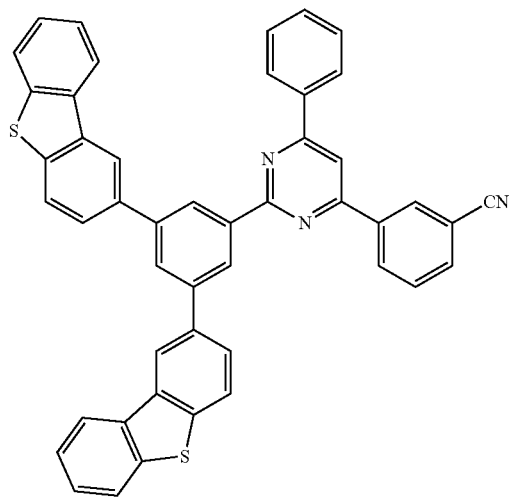
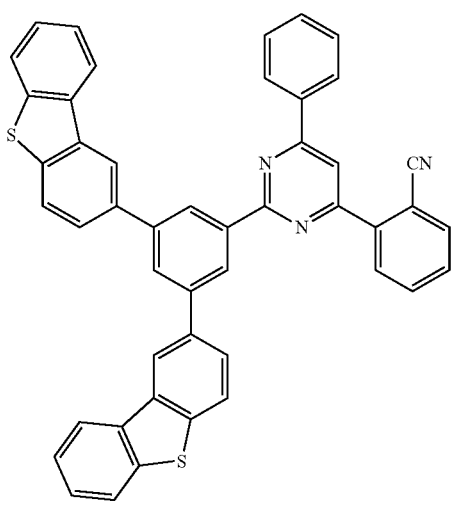
[Formula 51]
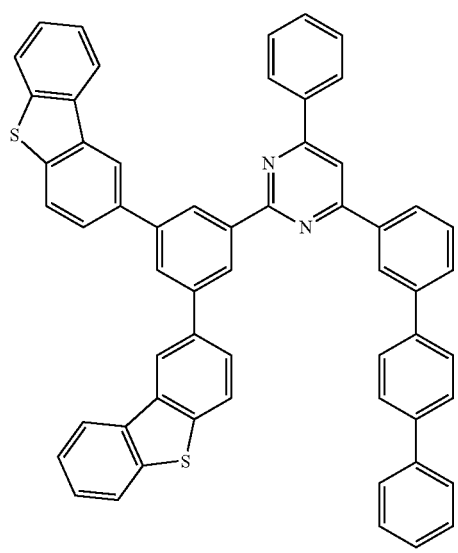
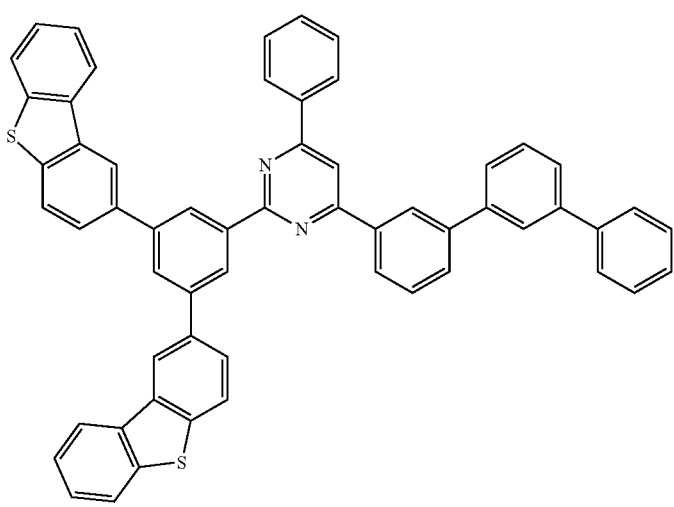

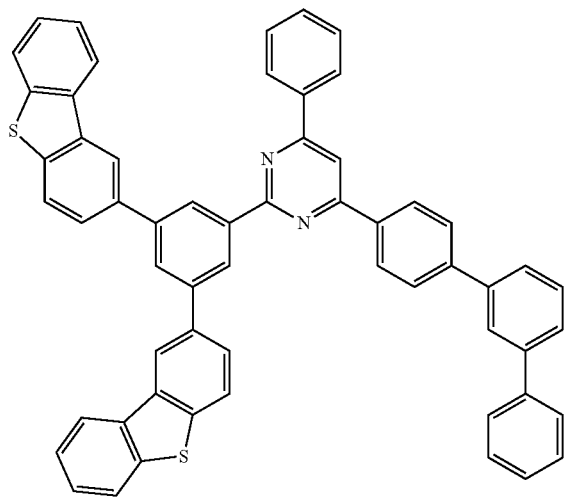
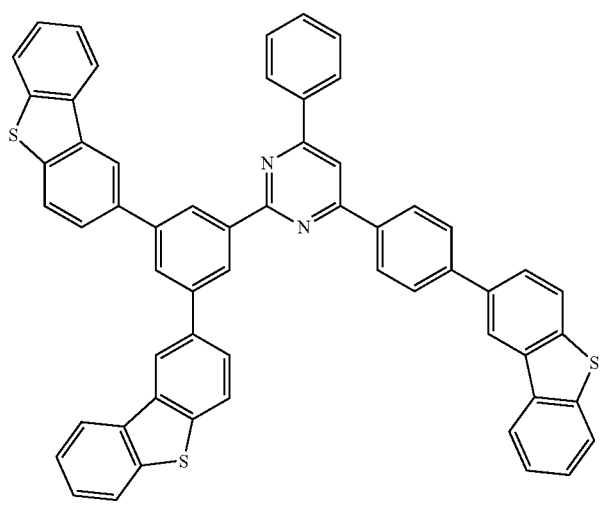
[Formula 52]
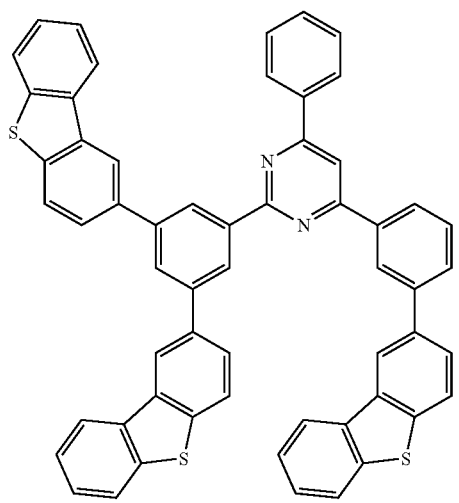

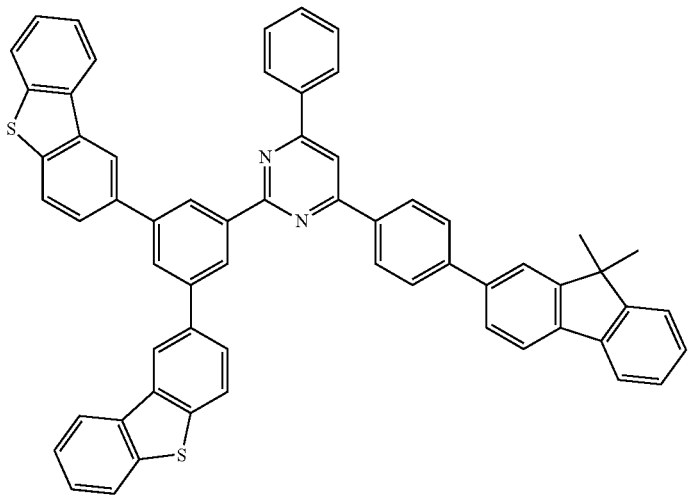
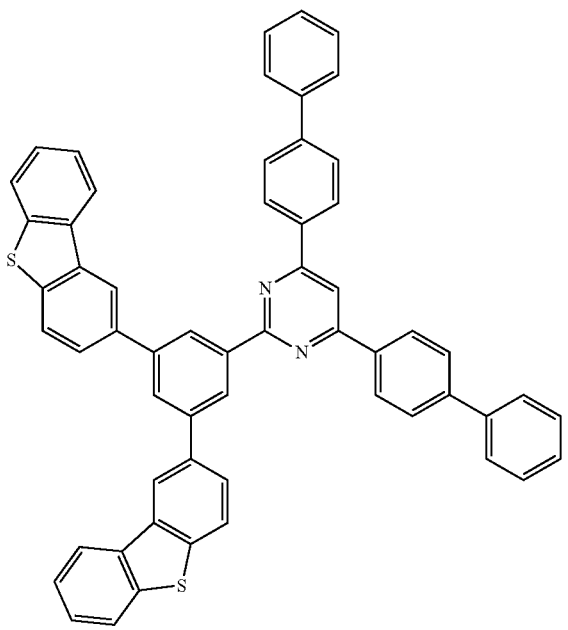
[Formula 53]
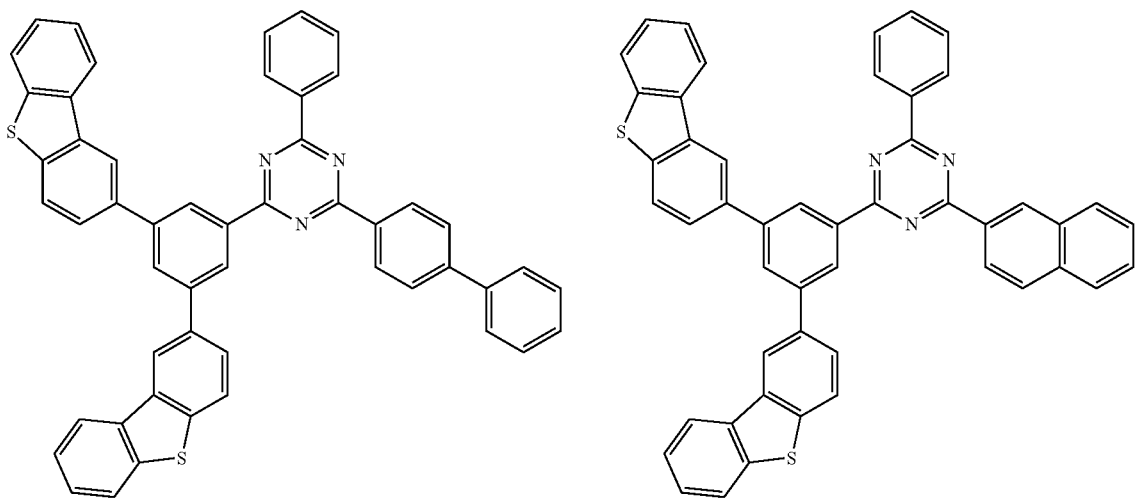

181
-continued
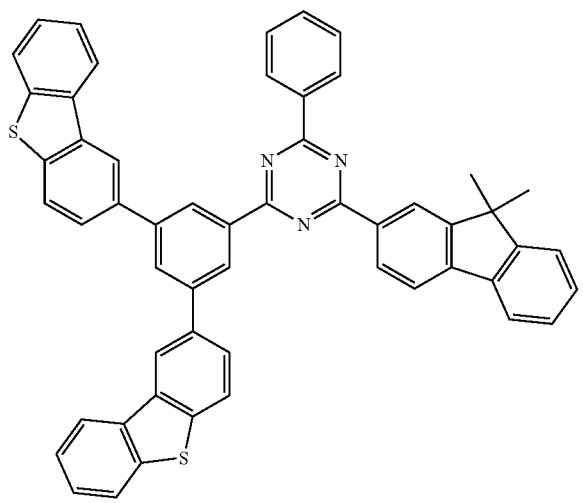
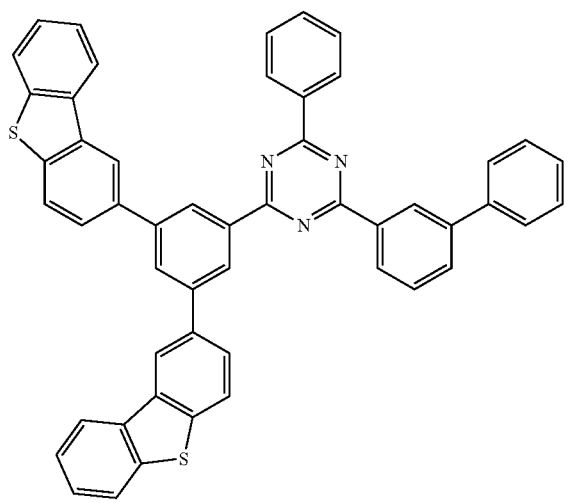
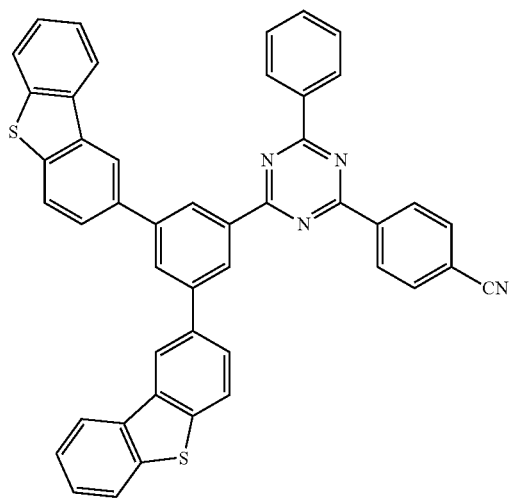
182
[Formula 54]
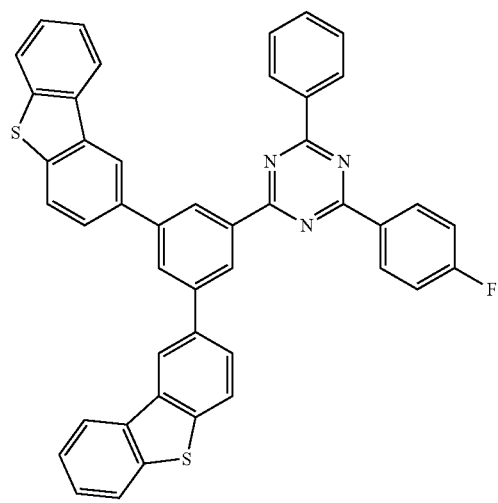
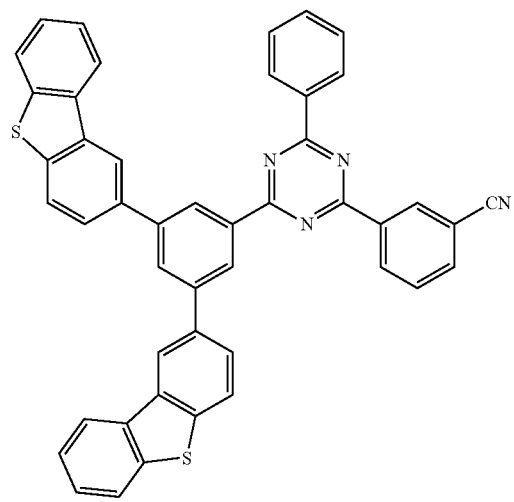

183
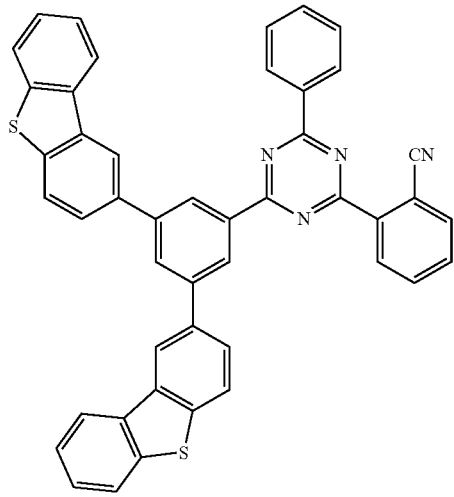
184
-continued
[Formula 55]
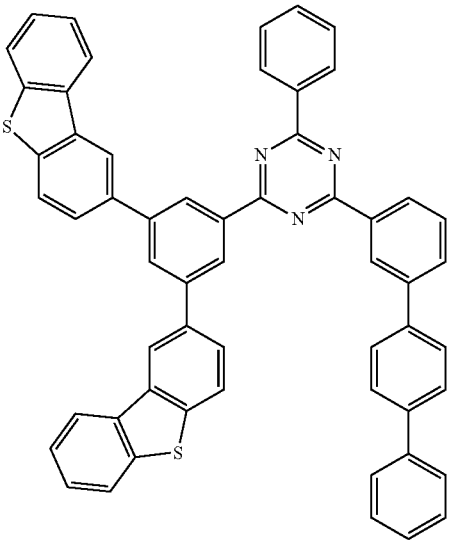
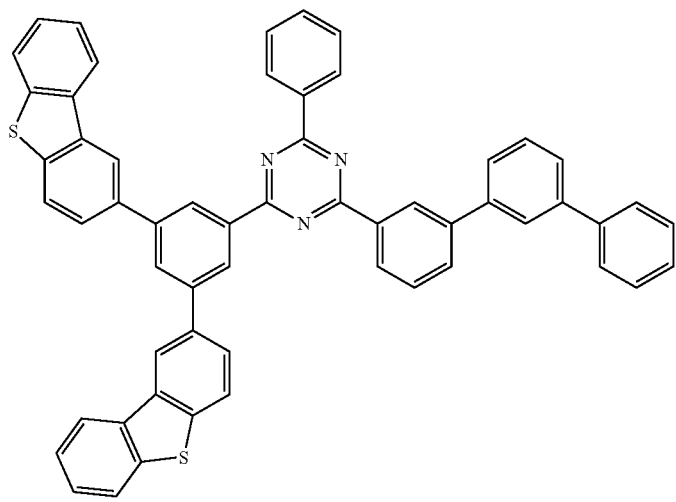
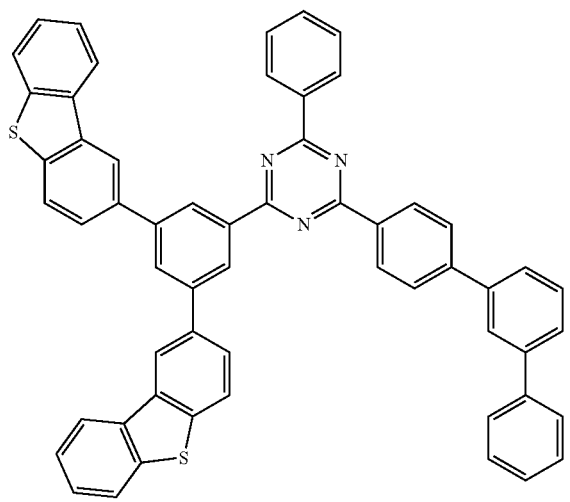

-continued
[Formula 56]
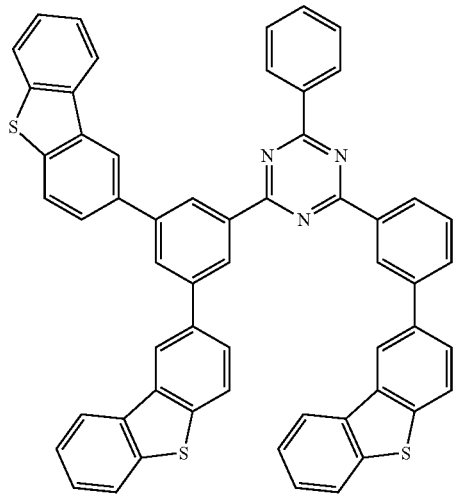
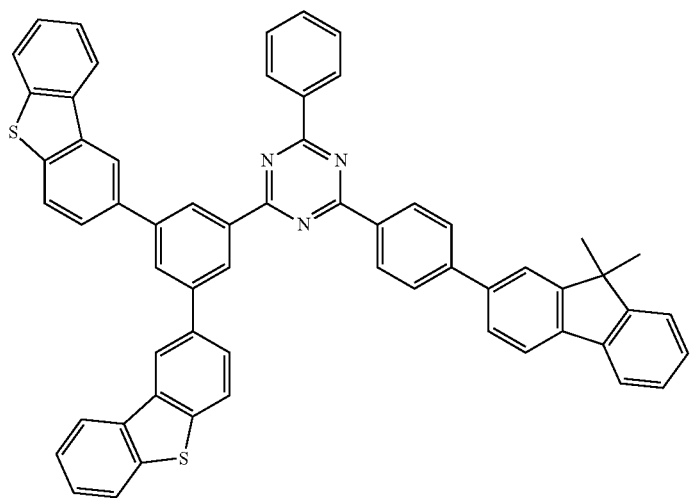
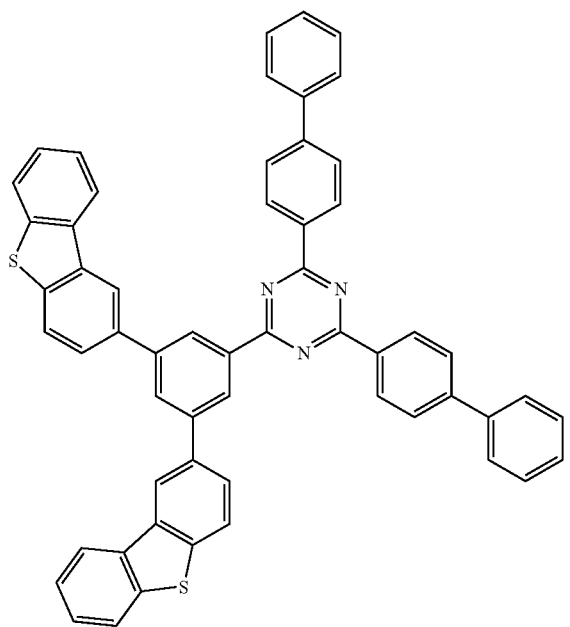

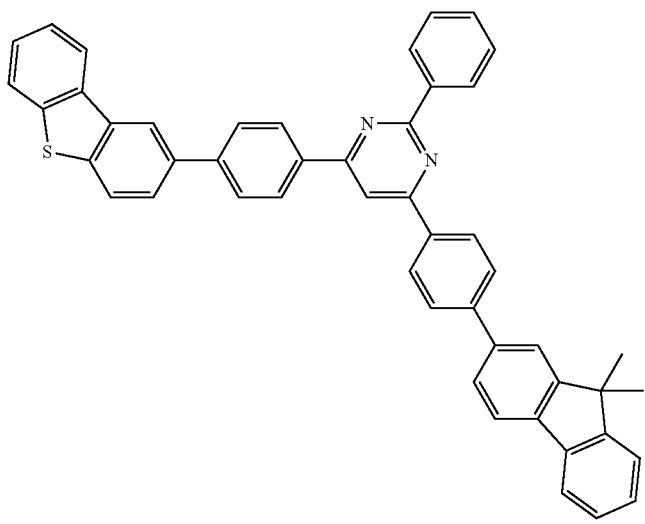
[Formula 57]
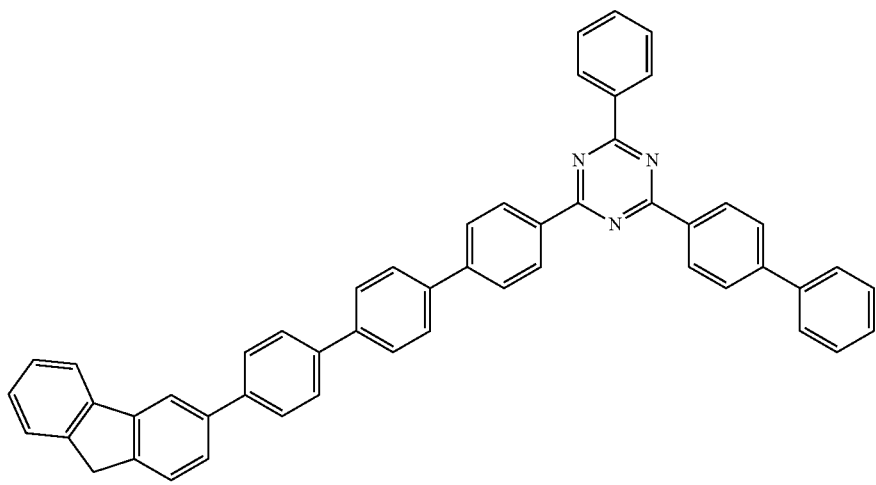
[Formula 58]
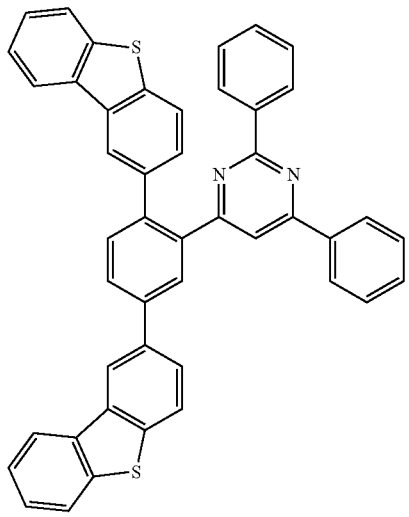
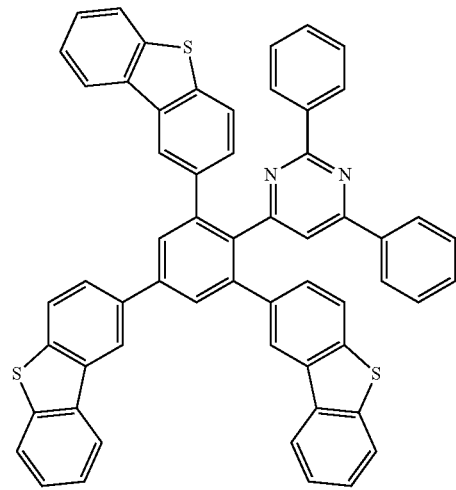

-continued
189
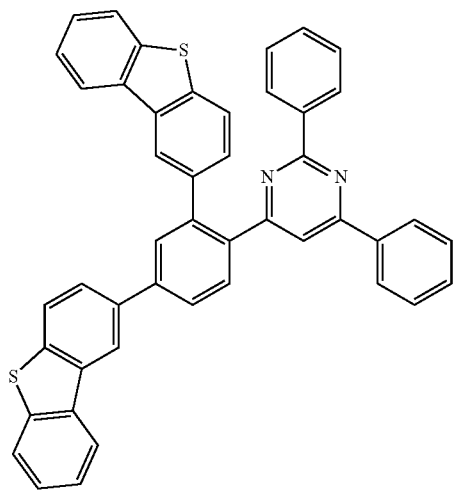
190
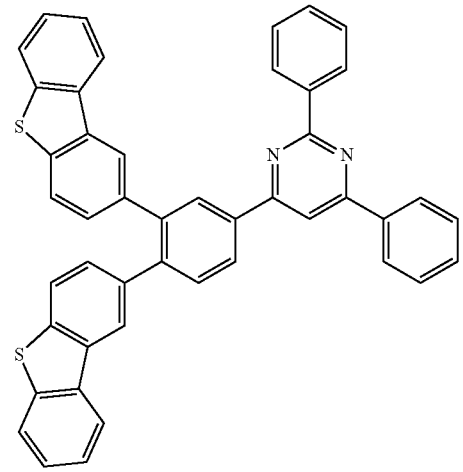
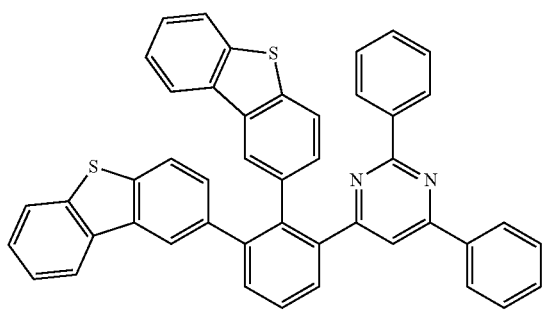
[Formula 59]
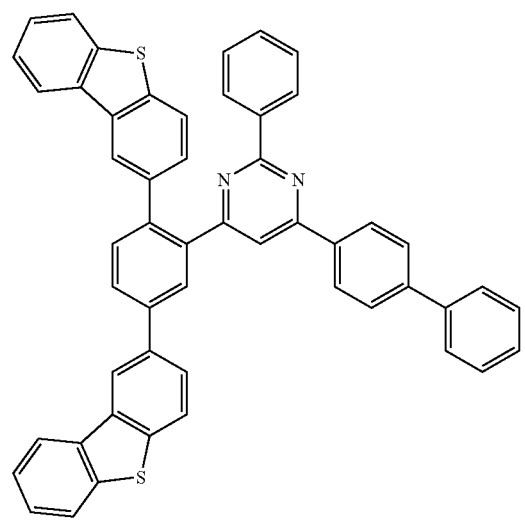
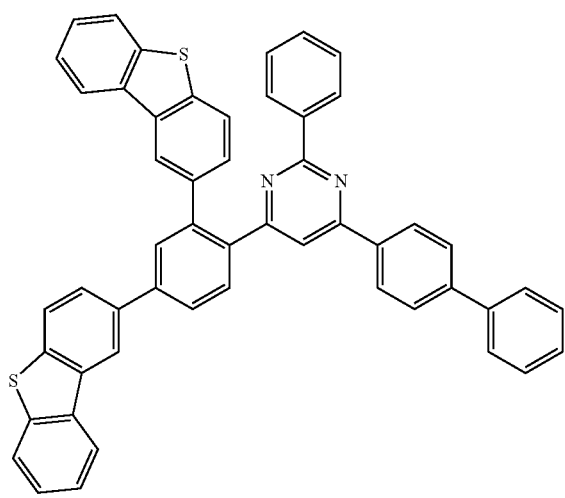

-continued
[Formula 60]
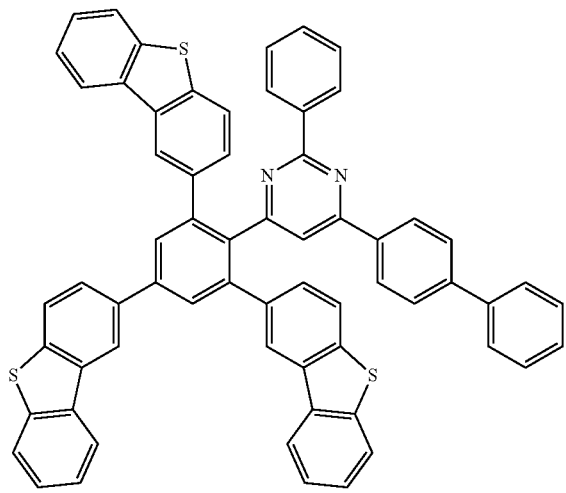
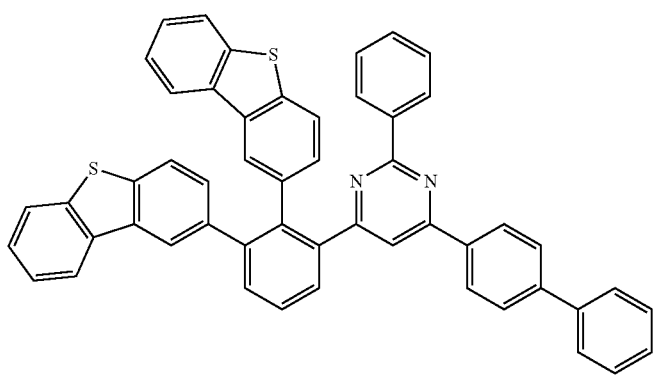
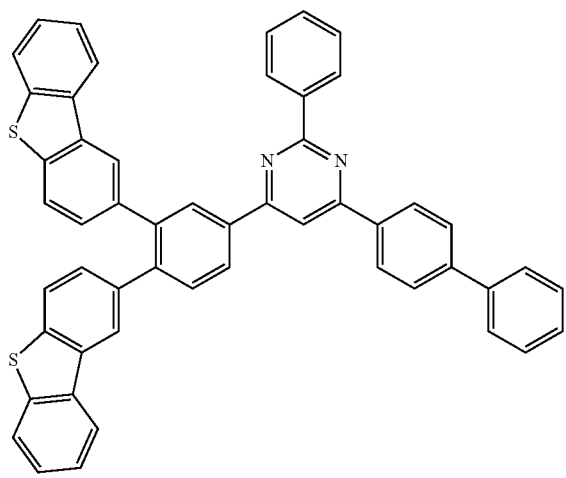
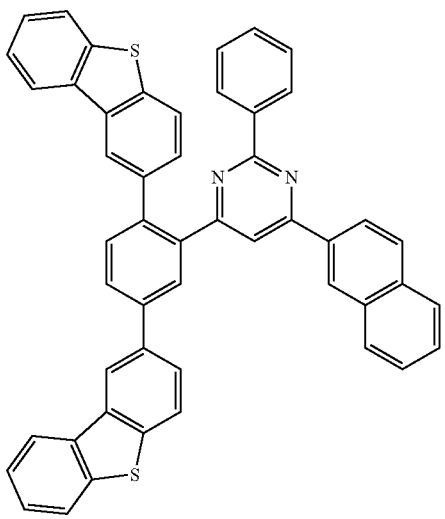

[Formula 61]
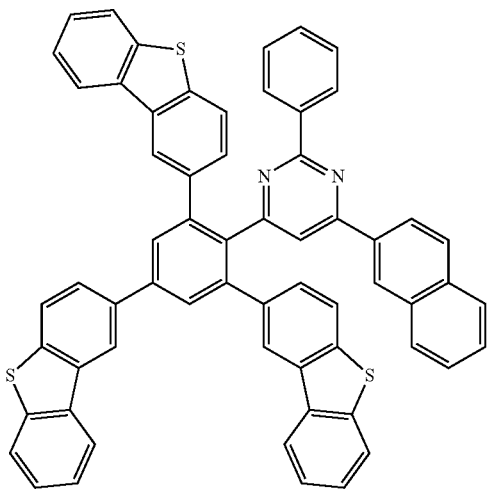
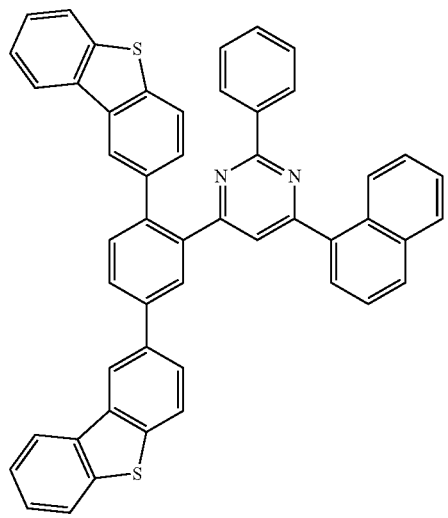
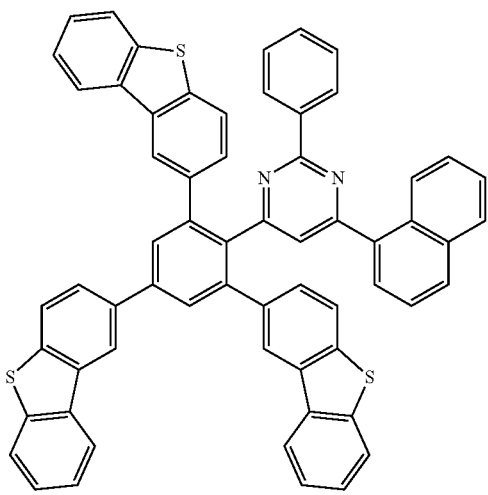
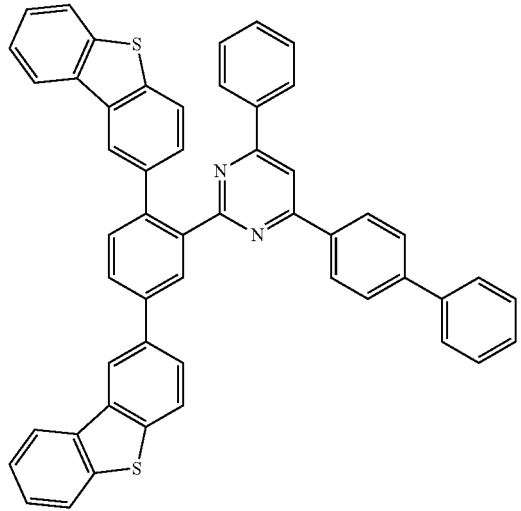
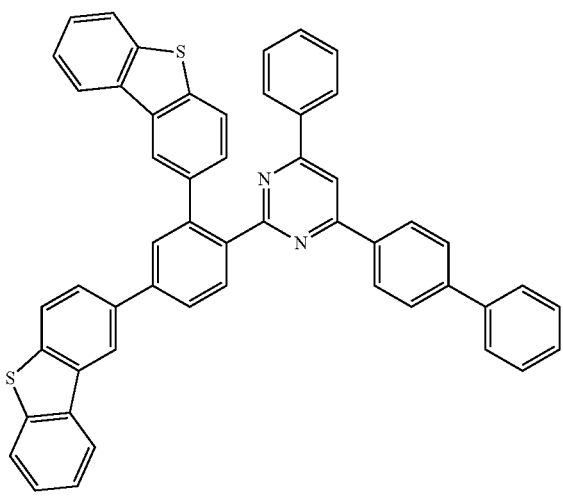

-continued
[Formula 62]
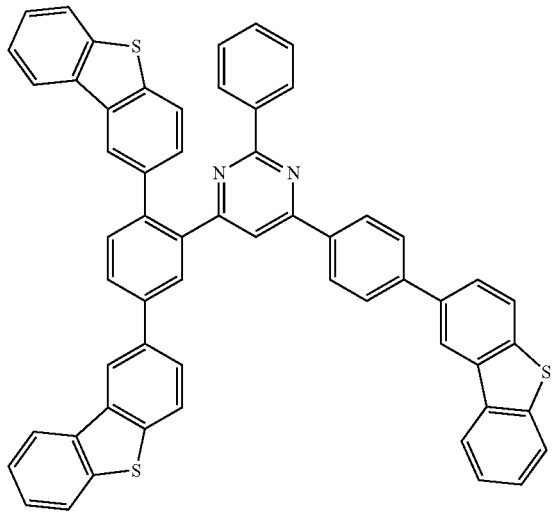
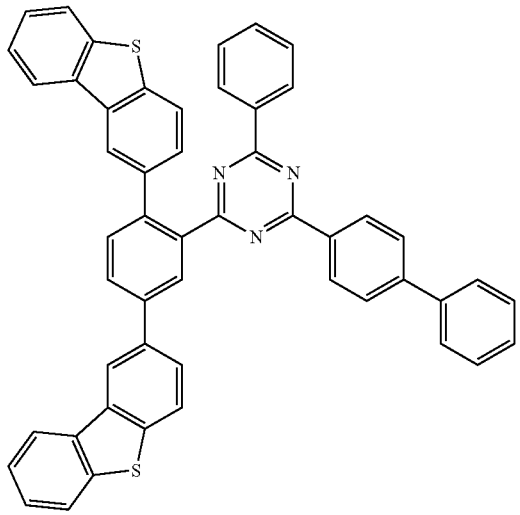
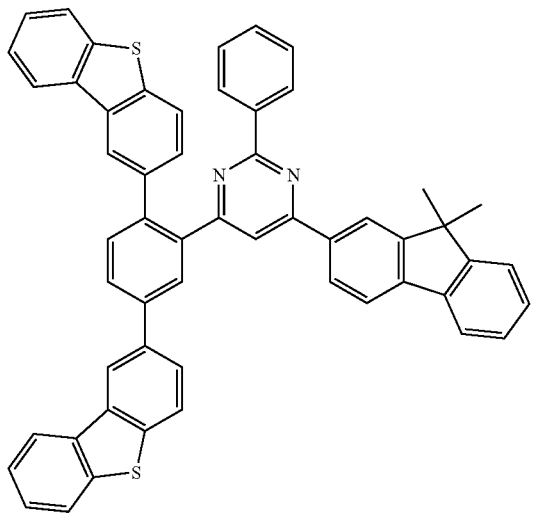
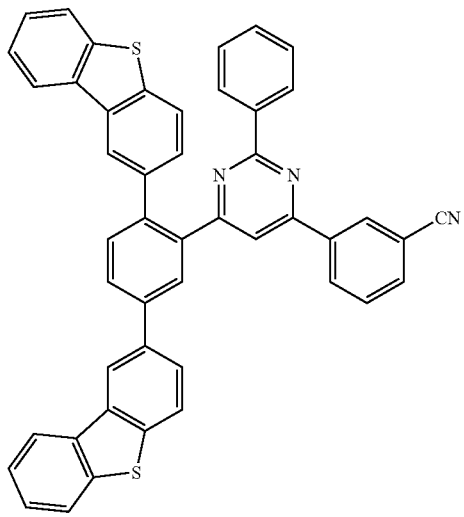
[Formula 63]
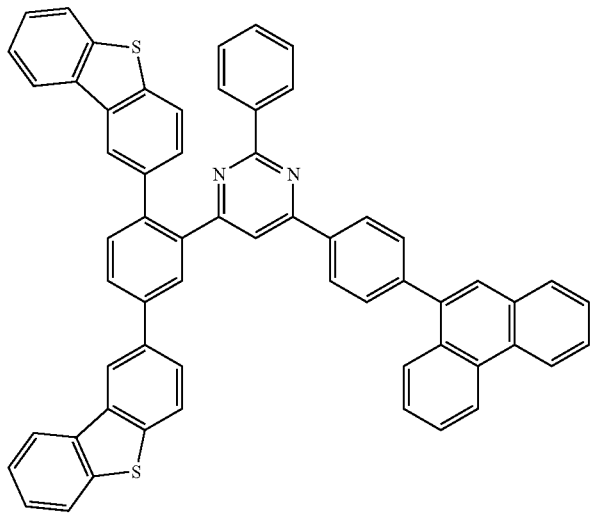
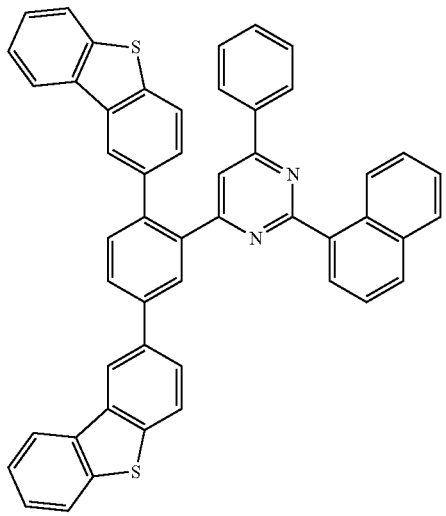

-continued
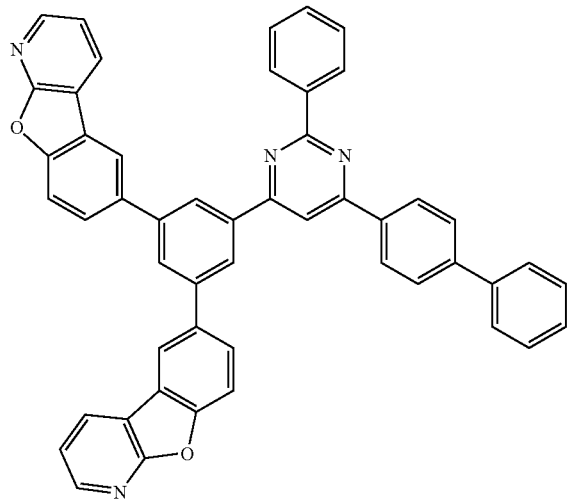
[Formula 64]
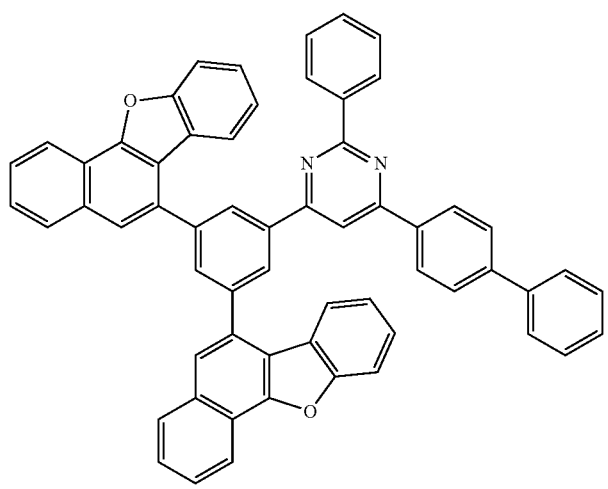
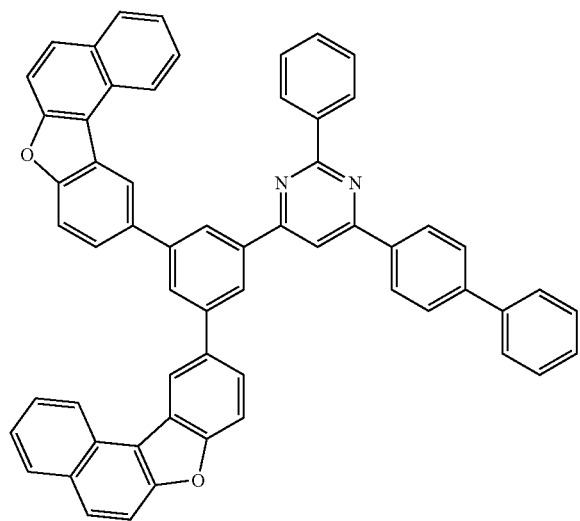

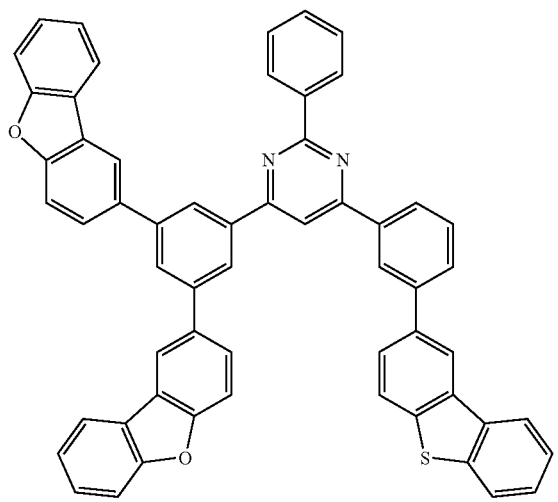
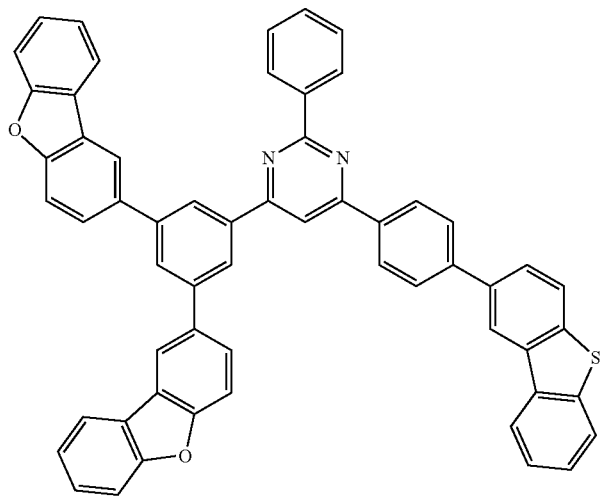
[Formula 65]
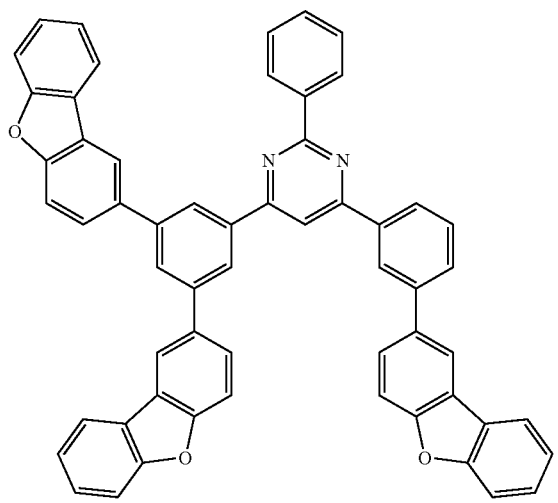

[Formula 66]
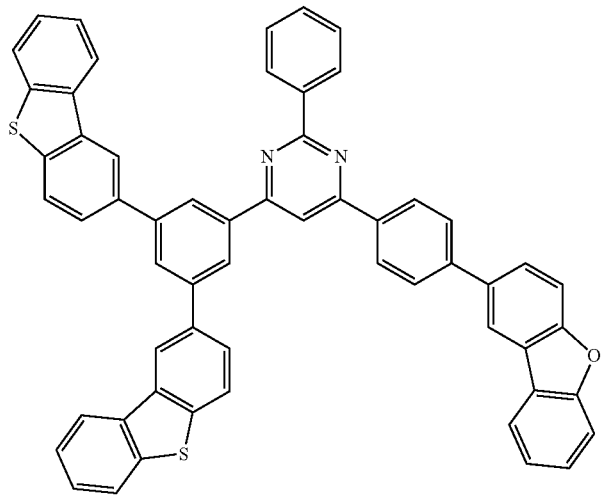
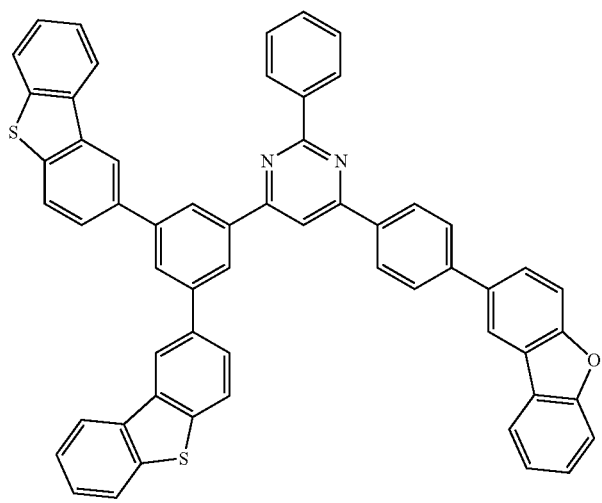
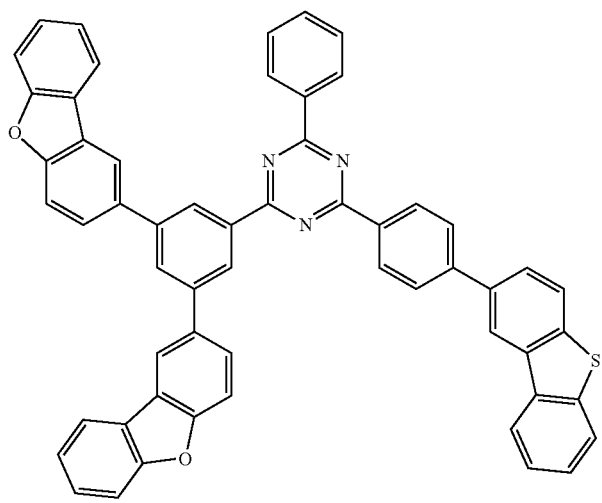

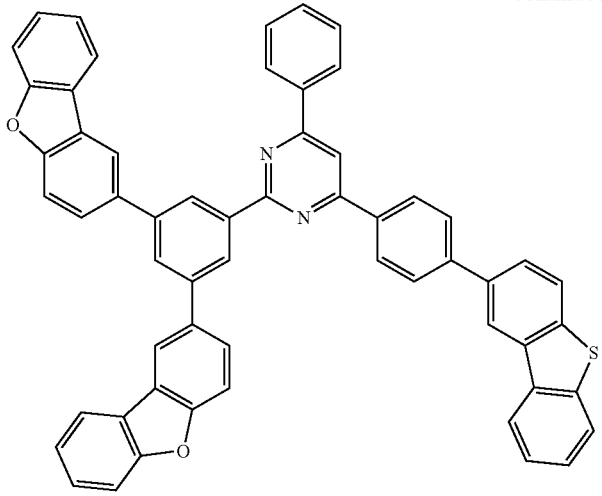

Organic-EL-Device Material

The aromatic heterocyclic derivative of the invention is usable as an organic-EL-device material. The organic-EL-device material may only contain the aromatic heterocyclic derivative of the invention, or alternatively, may further contain another compound. The organic-EL-device material containing the aromatic heterocyclic derivative according to the exemplary embodiment is usable, for instance, as a material for an electron transporting zone, e.g., a material for a blocking layer. It should be noted that, in the invention, the electron transporting zone means any one of an electron transporting layer, an electron injecting layer and a blocking layer, or combination of two or more thereof.

Organic EL Device
First Exemplary Embodiment

This exemplary embodiment utilizes TTF phenomenon. The TTF phenomenon will be initially described below.

Holes and electrons respectively injected from an anode and a cathode are recombined in an emitting layer to generate excitons. As for the spin state, as is conventionally known, singlet excitons account for 25% and triplet excitons account for 75%. In a conventionally known fluorescent device, light is emitted when singlet excitons of 25% are relaxed to the ground state. The remaining triplet excitons of 75% are returned to the ground state without emitting light through a thermal deactivation process. Accordingly, the theoretical limit value of the internal quantum efficiency of a conventional fluorescent device is believed to be 25%.

The behavior of triplet excitons generated within an organic substance has been theoretically examined. According to S. M. Bachilo et al. (J. Phys. Chem. A, 104, 7711 (2000)), assuming that high-order excitons such as quintet excitons are quickly returned to triplet excitons, triplet excitons (hereinafter abbreviated as $^3A^*$) collide with one another with an increase in the density thereof, whereby a reaction shown by the following formula occurs. In the formula, $^1A$ represents the ground state and $^1A^*$ represents the lowest singlet excitons.

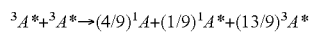

$$^3A^* + ^3A^* \rightarrow (4/9)^1A + (1/9)^1A^* + (13/9)^3A^*$$

In other words, $5\,^3A^* \rightarrow 4\,^1A + ^1A^*$, and it is expected that, among triplet excitons initially generated, which account for 75%, one fifth thereof (i.e., 20%) is changed to singlet excitons. Accordingly, the amount of singlet excitons which contribute to emission is 40%, which is a value obtained by adding 15% (75%×(1/5)=15%) to 25%, which is the amount ratio of initially generated singlet excitons. At this time, a ratio of luminous intensity derived from TTF (TTF ratio) relative to the total luminous intensity is 15/40, i.e., 37.5%. Assuming that singlet excitons are generated by collision of initially-generated triplet excitons which account for 75% (i.e., one singlet exciton is generated from two triplet excitons), a significantly high internal quantum efficiency of 62.5% is obtained which is a value obtained by adding 37.5% (75%×(1/2)=37.5%) to 25%, which is the amount ratio of initially generated singlet excitons. At this time, the TTF ratio is 60% (37.5/62.5).

Figure 2:
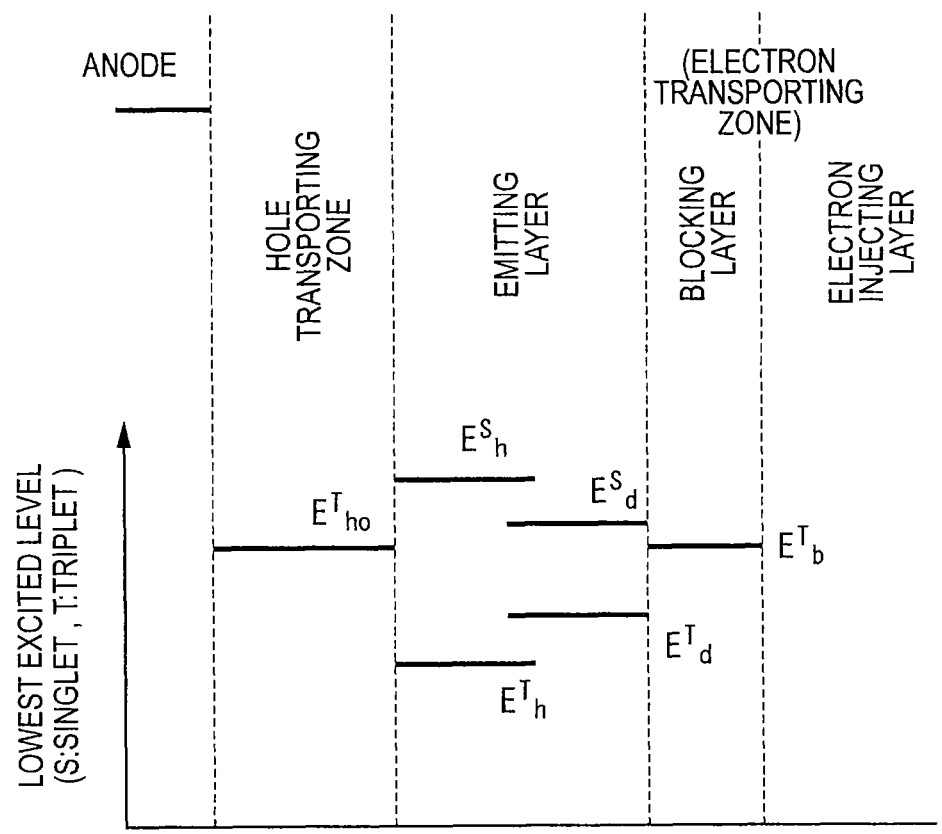
FIG. 2 is a view showing a relationship of energy gaps between layers of the invention.

FIG. 1 is schematic view showing one example of an organic EL device according to a first exemplary embodiment of the invention. FIG. 2 is a view showing a relationship between a triplet energy of the emitting layer and a triplet energy of an electron transporting zone in the organic EL device according to the first exemplary embodiment. In the exemplary embodiment, the triplet energy is referred to as a difference between energy in the lowest triplet state and energy in the ground state. The singlet energy (occasionally referred to as energy gap) is referred to as a difference between energy in the lowest singlet state and energy in the ground state.

An organic EL device 1 shown in FIG. 1 includes an anode 10, a hole transporting zone 60, an emitting layer 20, an electron transporting zone 70, and a cathode 50 in sequential order. These components are adjacent to one another in the organic EL device 1 in the exemplary embodiment. The electron transporting zone 70 in the exemplary embodiment includes a blocking layer 30 and an electron injecting layer 40. It is preferred that the hole transporting zone 60 is interposed between the anode 10 and the emitting layer 20. The hole transporting zone includes at least one of a hole injecting layer and a hole transporting layer.

In the invention, a simply-called blocking layer means a layer functioning as a barrier against triplet energy. Accordingly, the blocking layer functions differently from a hole blocking layer and a charge blocking layer.

The emitting layer includes a host material and a dopant material. The dopant material is preferably a dopant material exhibiting fluorescence (hereinafter, also referred to as a fluorescent dopant material). A fluorescent dopant material having a main peak wavelength of 550 nm or less is preferable. A fluorescent dopant material having a main peak wavelength of 500 nm or less is more preferable. A main peak wavelength means a peak wavelength of luminescence spectrum exhibiting a maximum luminous intensity among luminous spectra measured in a toluene solution with a concentration from $10^{-5}$ mol/liter to $10^{-6}$ mol/liter. The main peak wavelength of 550 nm is substantially equivalent to a green emission. In this wavelength zone, improvement in luminous efficiency of a fluorescent device utilizing the TTF phenomenon is desired. In a blue-emitting fluorescent device of 480 nm or less, further improvement in luminous efficiency is expectable. In a red-emitting fluorescent device of 550 nm or more, a phosphorescent device exhibiting a high internal quantum efficiency has already been at a practical level. Accordingly, improvement in luminous efficiency as a fluorescent device is not desired.

In FIG. 2, the holes injected from the anode are injected to the emitting layer via the hole transporting zone. The electrons injected from the cathode are injected to the emitting layer via the electron injecting layer and the blocking layer. Subsequently, the holes and the electrons are recombined in the emitting layer to generate singlet excitons and triplet excitons. There are two manners as for the occurrence of recombination: recombination may occur either on host material molecules or on dopant material molecules.

In this exemplary embodiment, as shown in FIG. 2, when the triplet energy of the host material and that of the dopant material are respectively taken as $E^T_h$ and $E^T_d$, a relationship of the following formula (2A) is satisfied.

$$E^T_h < E^T_d \quad (2A)$$

Figure 3:
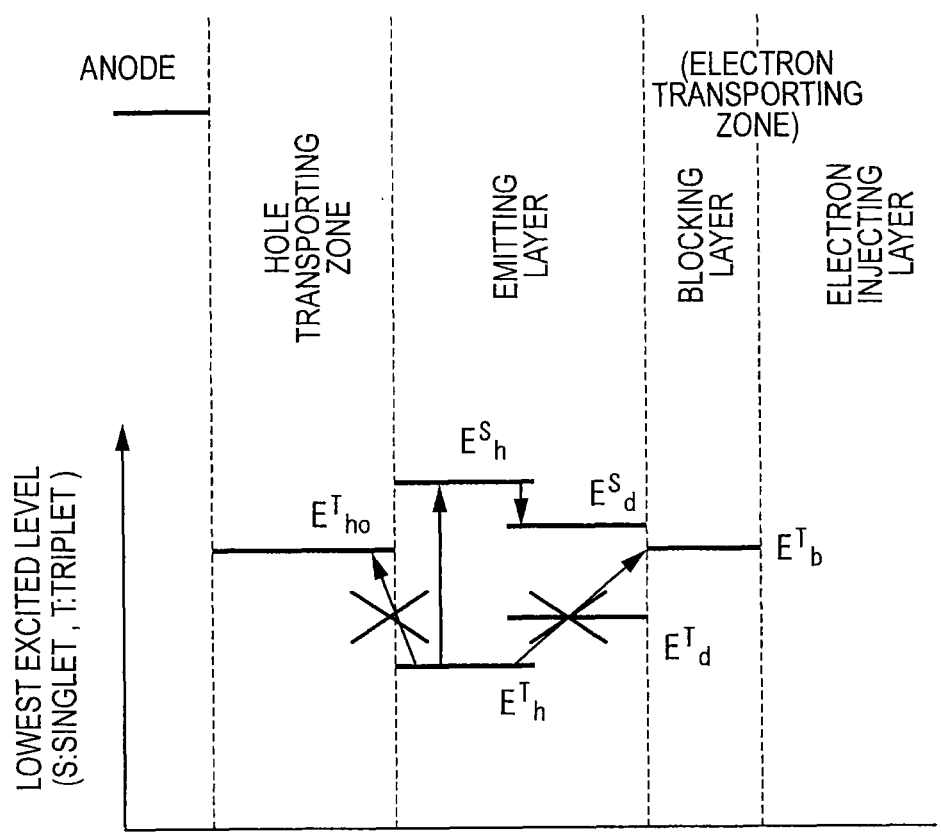
FIG. 3 is a view showing an action based on the relationship of the energy gaps between the layers of the invention.

When this relationship of the formula (2A) is satisfied, triplet excitons generated by recombination on the host material do not transfer to the dopant material which has a higher triplet energy, as shown in FIG. 3. Triplet excitons generated by recombination on dopant material molecules quickly energy-transfer to host material molecules. In other words, triplet excitons on the host material do not transfer to the dopant material but collide with one another efficiently on the host material to generate singlet excitons by the TTF phenomenon. Moreover, since the singlet energy $E^S_d$ of the dopant material is smaller than the singlet energy $E^S_h$ of the host material, a relationship of the following formula (2B) is satisfied.

$$E^S_d < E^S_h \quad (2B)$$

Since the relationship of the formula (2B) is satisfied, the singlet excitons generated by the TTF phenomenon energy-transfer from the host material to the dopant material, thereby contributing to fluorescence of the dopant material. In the dopant material which is usually used in a fluorescent device, transition from the triplet state to the ground state should be inhibited. In such a transition, triplet excitons are not optically energy-deactivated, but are thermally energy-deactivated. By causing the triplet energy of a host material and the triplet energy of a dopant material to satisfy the above-mentioned relationship, singlet excitons are generated efficiently due to the collision of triplet excitons before they are thermally deactivated, whereby luminous efficiency is improved. As a consequence, luminous efficiency is improved.

In the exemplary embodiment, the blocking layer is adjacent to the emitting layer. The blocking layer has a function of preventing triplet excitons generated in the emitting layer to be diffused to the electron transporting zone and confining the triplet excitons within the emitting layer to increase a density of the triplet excitons therein, thereby causing the TTF phenomenon efficiently.

The blocking layer also serves for efficiently injecting the electrons to the emitting layer. When the electron injecting properties to the emitting layer are deteriorated, the density of the triplet excitons is decreased since the electron-hole recombination in the emitting layer is decreased. When the density of the triplet excitons is decreased, the frequency of collision of the triplet excitons is reduced, whereby the TTF phenomenon does not occur efficiently.

The blocking layer of the organic EL device according to the exemplary embodiment contains an aromatic heterocyclic derivative represented by a formula (1) below.

[Formula 67]

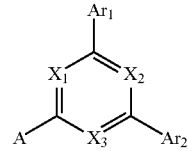

(1)

In the formula (1), $X_1$ to $X_3$ are a nitrogen atom or $CR_1$.

However, at least one of $X_1$ to $X_3$ is a nitrogen atom.

$R_1$ independently represents a hydrogen atom, a halogen atom, a cyano group, a substituted or unsubstituted aryl group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted alkenyl group having 2 to 30 carbon atoms, a substituted or unsubstituted alkynyl group having 2 to 30 carbon atoms, a substituted or unsubstituted alkylsilyl group having 3 to 30 carbon atoms, a substituted or unsubstituted arylsilyl group having 6 to 30 ring carbon atoms, a substituted or unsubstituted alkoxy group having 1 to 30 carbon atoms, a substituted or unsubstituted aralkyl group having 6 to 30 ring carbon atoms, and a substituted or unsubstituted aryloxy group having 6 to 30 ring carbon atoms.

In the formula (1), A is represented by a formula (2) below.

[Formula 68]

$$(HAr)_a\text{-}L_1\text{-} \quad (2)$$

In the formula (2), HAr is represented by a formula (3) below.

In the formula (2), a is an integer of 1 to 5.

When a is 1, $L_1$ is a single bond or a divalent linking group.

When a is in a range of 2 to 5, $L_1$ is a trivalent to hexavalent linking group and HAr is the same or different.

The linking group is a substituted or unsubstituted aryl group having 6 to 30 ring carbon atoms, substituted or unsubstituted heterocyclic group having 5 to 30 ring atoms, or a residue having 2 to 6 valences induced from any one of a group formed by bonding two or three of the above groups.

The mutually bonded groups are the same or different.

[Formula 69]

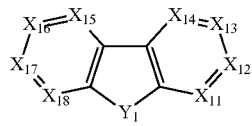

(3)

In the formula (3), $X_{11}$ to $X_{18}$ each are independently a nitrogen atom, $CR_{13}$ or a carbon atom bonded to $L_1$ by a single bond.

In the formula (3), $Y_1$ is a nitrogen atom, a sulfur atom, $SiR_{11}R_{12}$ or a silicon atom bonded to each of $R_{11}$ and $L_1$ by a single bond.

However, $L_1$ is bonded by one of a carbon atom at $X_{11}$ to $X_{18}$ and $R_{11}$ to $R_{12}$ and a silicon atom at $Y_1$.

$R_{11}$ and $R_{12}$ represent the same as $R_1$ in the formula (1). $R_{11}$ and $R_{12}$ are the same or different.

$R_{13}$ independently represents a hydrogen atom, a halogen atom, a cyano group, a substituted or unsubstituted aryl group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted alkenyl group having 2 to 30 carbon atoms, a substituted or unsubstituted alkynyl group having 2 to 30 carbon atoms, a substituted or unsubstituted alkylsilyl group having 3 to 30 carbon atoms, a substituted or unsubstituted arylsilyl group having 6 to 30 ring carbon atoms, a substituted or unsubstituted alkoxy group having 1 to 30 carbon atoms, a substituted or unsubstituted aralkyl group having 6 to 30 ring carbon atoms, or a substituted or unsubstituted aryloxy group having 6 to 30 ring carbon atoms. A plurality of $R_{13}$ are mutually the same or different. Adjacent $R_{13}$ may bond to each other to form a ring.

In the above formula (1), $Ar_1$ and $Ar_2$ each are independently represented by the formula (2), or represent a substituted or unsubstituted aryl group having 6 to 30 ring carbon atoms or a substituted or unsubstituted heterocyclic group having 5 to 30 ring atoms.

In the formula (3), $X_{13}$ or $X_{16}$ is preferably a carbon atom bonded to $L_1$ by a single bond. Alternatively, in the formula (3), $X_{11}$ or $X_{18}$ is preferably a carbon atom bonded to $L_1$ by a single bond.

In the formula (2), a is an integer in a range of 1 to 5, more preferably of 1 to 3, particularly preferably 1 or 2.

When a is 1, $L_1$ is a single bond or a divalent linking group and the formula (2) is represented by a formula (2-1) below.

When a is in a range of 2 to 5, $L_1$ is a trivalent to hexavalent linking group. When a is 2, the formula (2) is represented by a formula (2-2) below. At this time, HAr is the same or different.

[Formula 70]

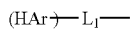

(2-1)

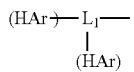

(2-2)

The linking group is a substituted or unsubstituted aryl group having 6 to 30 ring carbon atoms, substituted or unsubstituted heterocyclic group having 5 to 30 ring atoms, or a divalent or trivalent residue induced from any one of a group formed by bonding two or three of the above groups.

The group formed by bonding two or three of the above groups means a group formed by bonding, with a single bond, two or three of the divalent or trivalent residue induced from the aryl group having 6 to 30 ring carbon atoms and the heterocyclic group having 5 to 30 ring atoms. In the linking group, the mutually bonded groups are the same or different.

In the formulae (2), (2-1) and (2-2), $L_1$ is preferably a linking group. The linking group is a substituted or unsubstituted aryl group having 6 to 30 ring carbon atoms, substituted or unsubstituted heterocyclic group having 5 to 30 ring atoms, or a divalent or trivalent residue induced from any one of a group formed by bonding two or three of the above groups. Further, the linking group is preferably a substituted or unsubstituted aryl group having 6 to 30 ring carbon atoms, or substituted or unsubstituted heterocyclic group having 5 to 30 ring atoms.

In the formula (2), it is preferable that when a is 1 (see the formula (2-1)) and $L_1$ is a linking group, the linking group is a divalent residue of a substituted or unsubstituted aryl group having 6 to 30 ring carbon atoms, or a divalent residue of a substituted or unsubstituted heterocyclic group having 5 to 30 ring atoms. More specifically, $L_1$ is preferably a divalent residue induced from any one of benzene, biphenyl, terphenyl, naphthalene and phenanthrene.

In the formula (2), it is preferable that when a is 2 (see the formula (2-2)) and $L_1$ is a linking group, the linking group is a trivalent residue of a substituted or unsubstituted aryl group having 6 to 30 ring carbon atoms, or a trivalent residue of a substituted or unsubstituted heterocyclic group having 5 to 30 ring atoms. More specifically, $L_1$ is preferably a divalent residue induced from any one of benzene, biphenyl, terphenyl, naphthalene and phenanthrene.

In the formula (3), $Y_1$ is preferably an oxygen atom or a sulfur atom. Moreover, in the formula (3), it is preferable that $Y_1$ is an oxygen atom or a sulfur atom, one of $X_{11}$ to $X_{18}$ is a carbon atom bonded to $L_1$ by a single bond and the rest of $X_{11}$ to $X_{18}$ are $CR_{13}$.

In the formula (1), two or three of $X_1$ to $X_3$ are more preferably a nitrogen atom.

In the formula (2), $L_1$ is preferably a divalent or trivalent residue induced from any one of benzene, biphenyl, terphenyl, naphthalene and phenanthrene.

Specific examples of each group for $Ar^1$, $Ar^2$, $L_1$, $R_1$, $R_{11}$ to $R_{13}$, $X_{11}$ to $X_{18}$ and $Y_1$ in the formulae (1) to (3) and (2-1) to (2-2) are the groups described in relation to the aromatic heterocyclic derivative represented by the formula (4).

Examples of specific structures of the aromatic heterocyclic derivative represented by the formula (1) and contained in the blocking layer of the organic EL device according to this exemplary embodiment are as follows. However, the exemplary embodiment is not limited to the aromatic derivative having these structures.

[Formula 71]
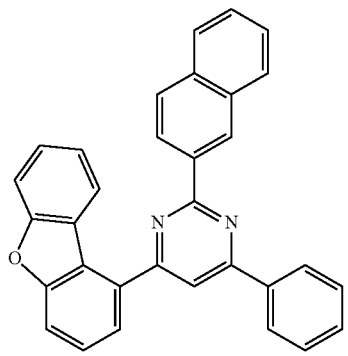
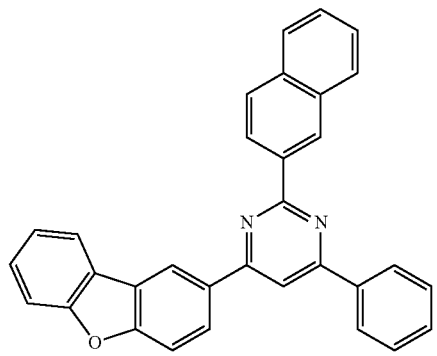
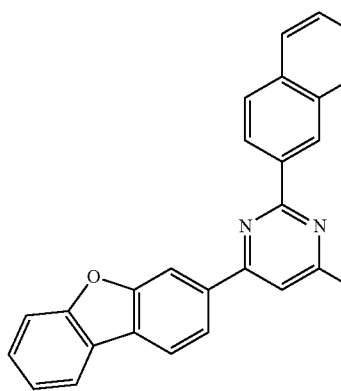
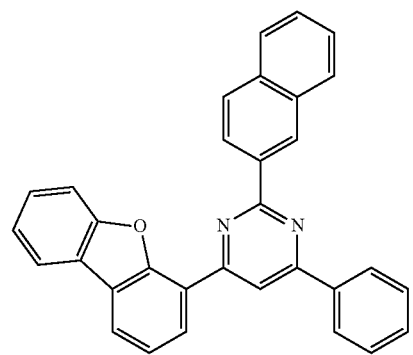
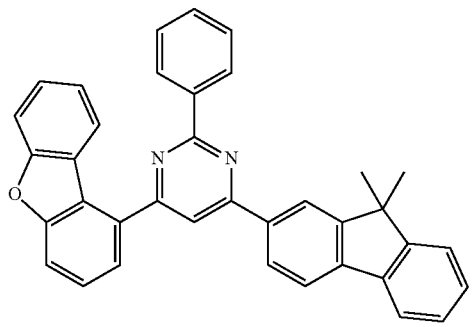
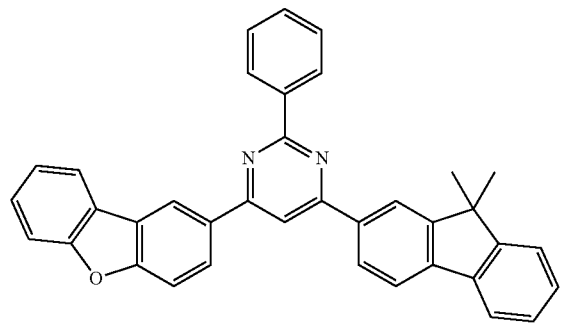
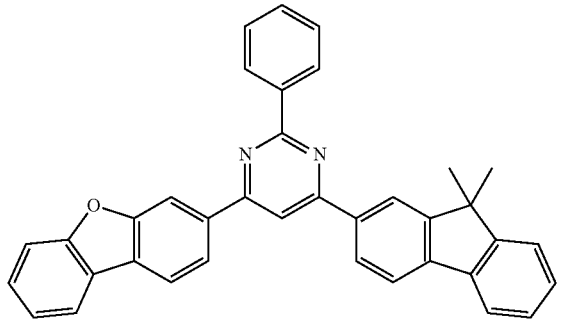
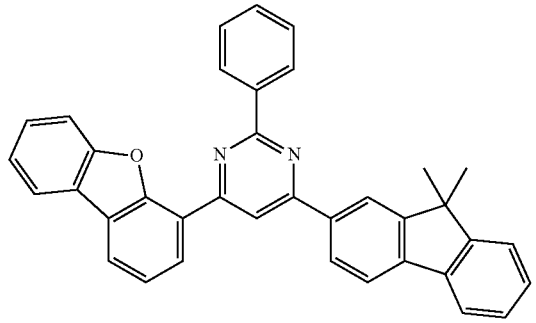

211
212
-continued
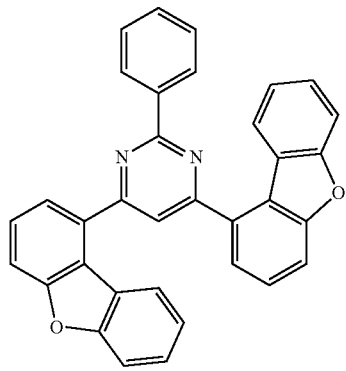
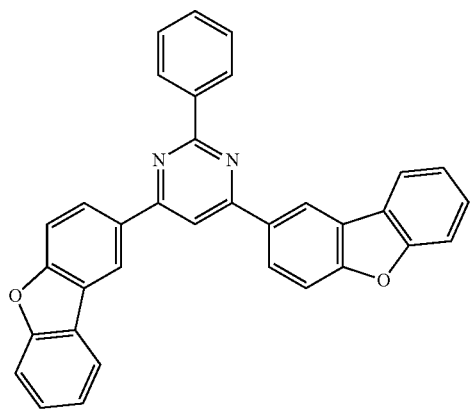
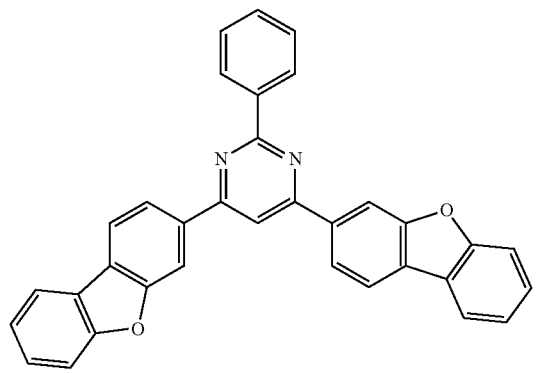
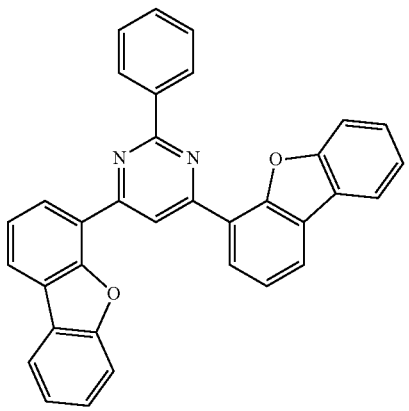
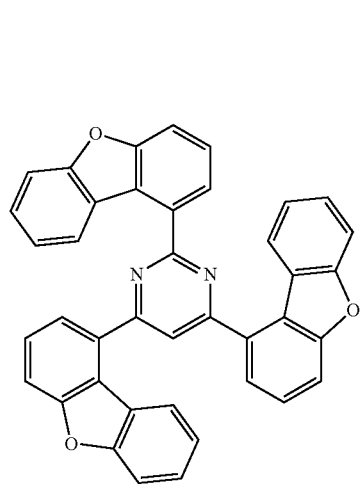
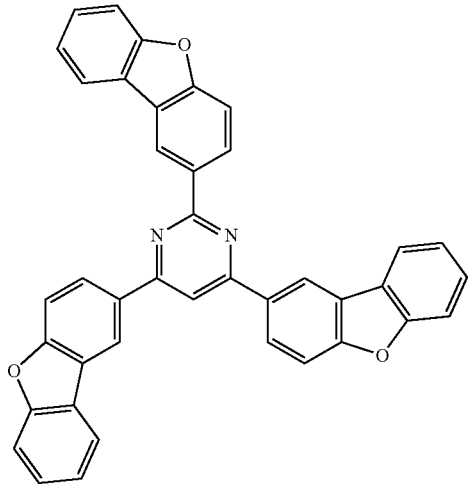

-continued
213
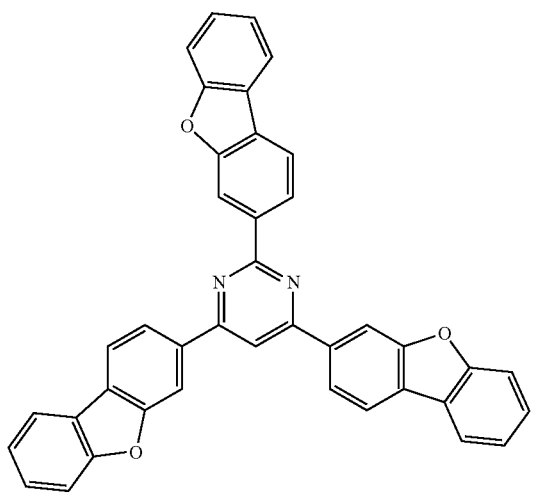
214
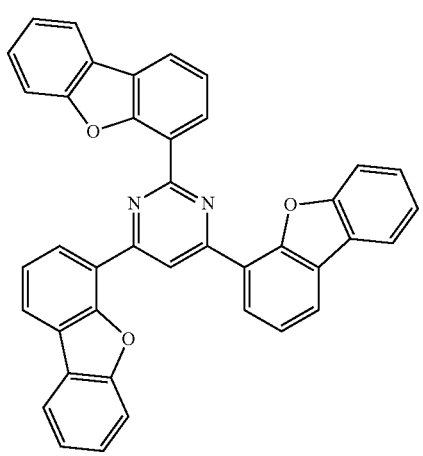
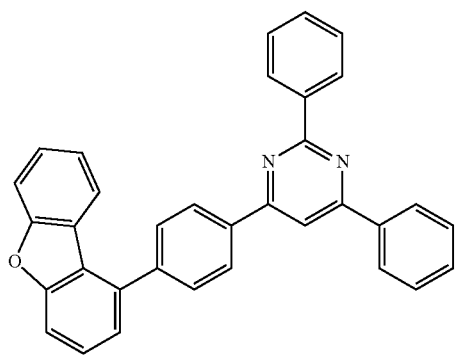
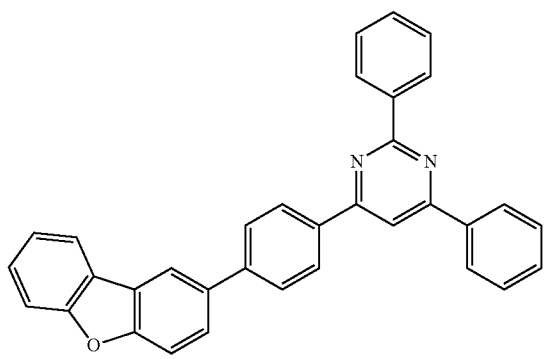
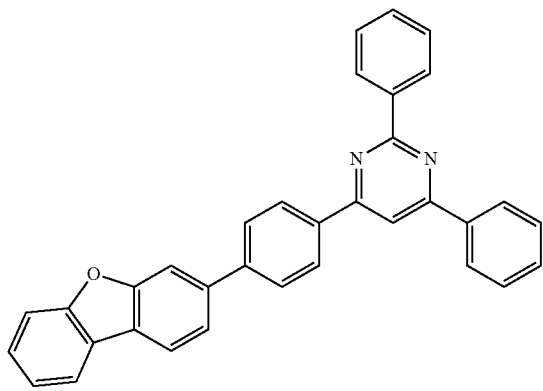
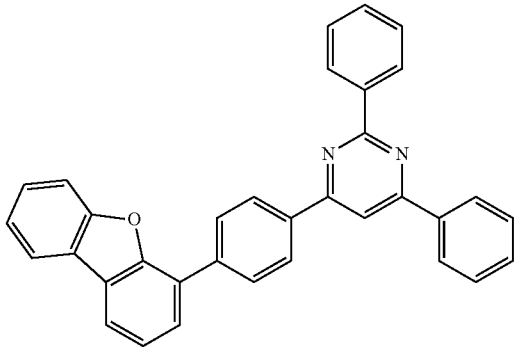

-continued
215
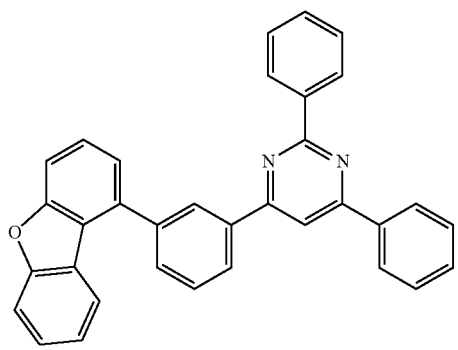
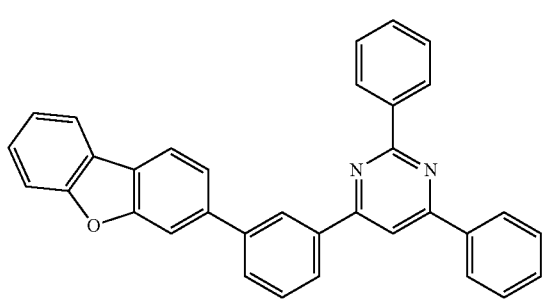
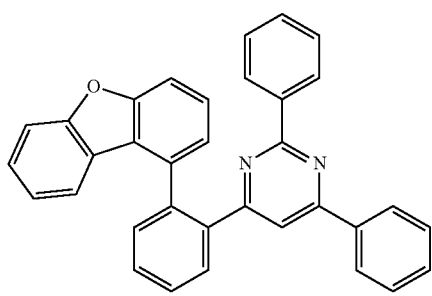
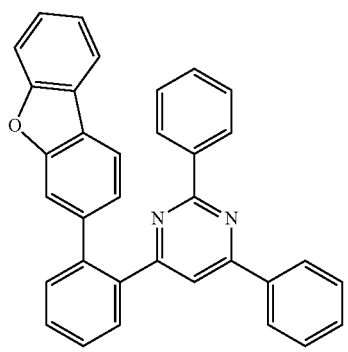
216
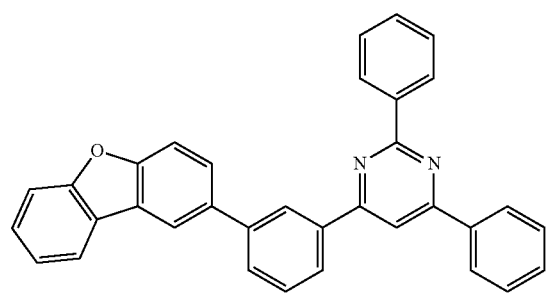
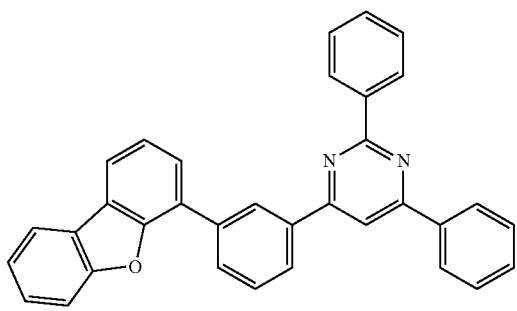
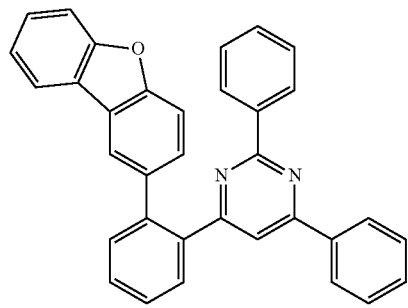
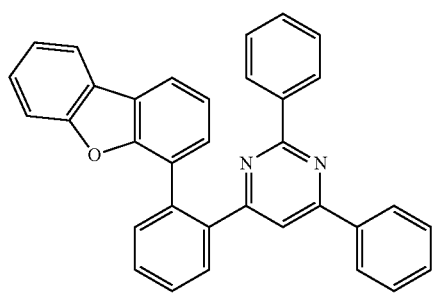

-continued
217
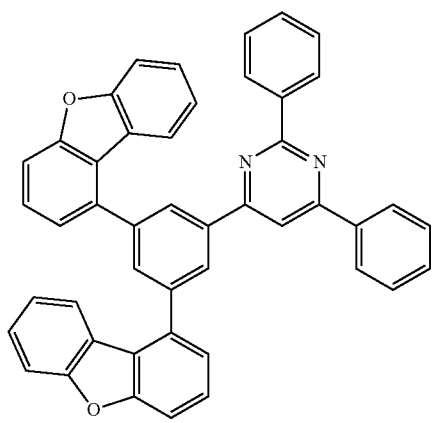
218
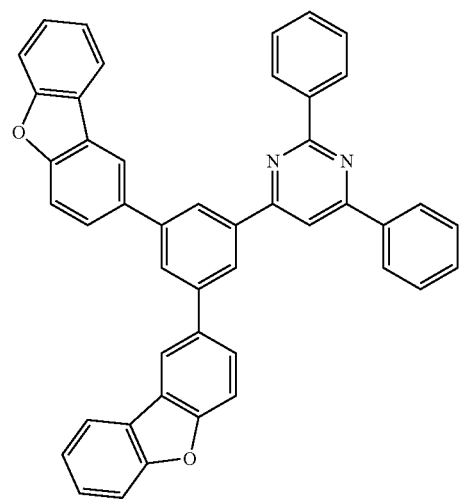
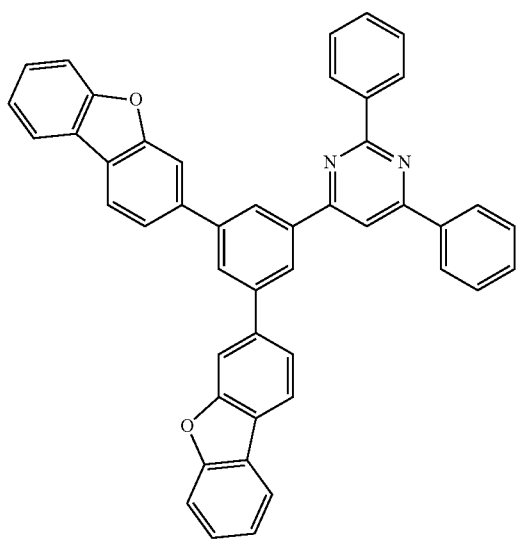
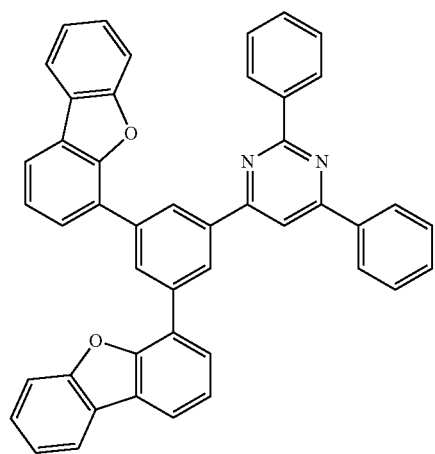
[Formula 72]
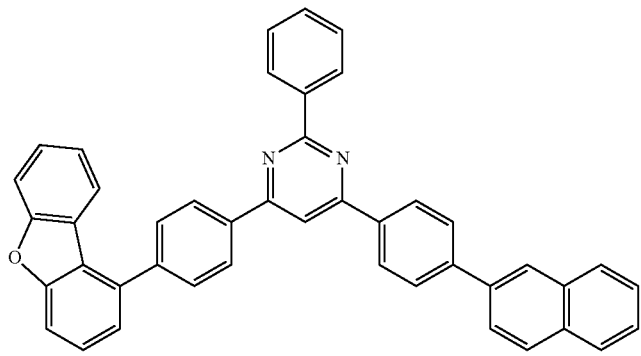

-continued
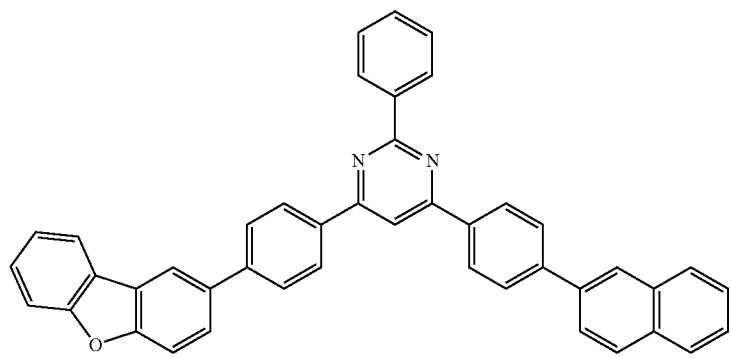
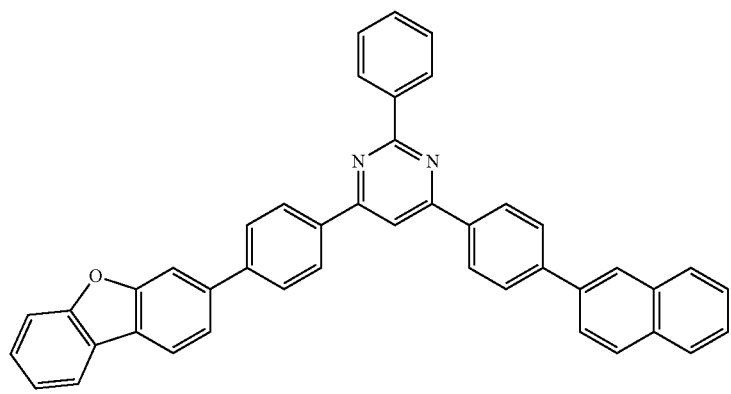
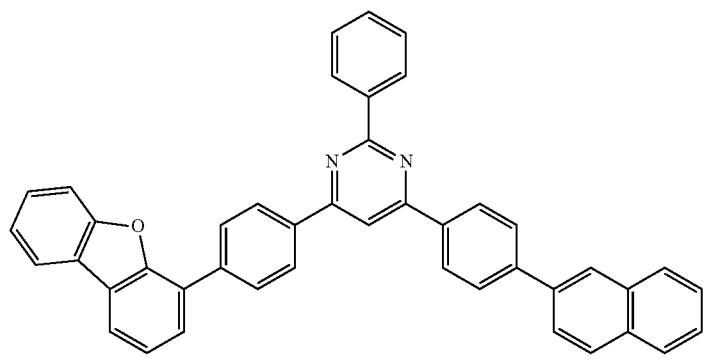
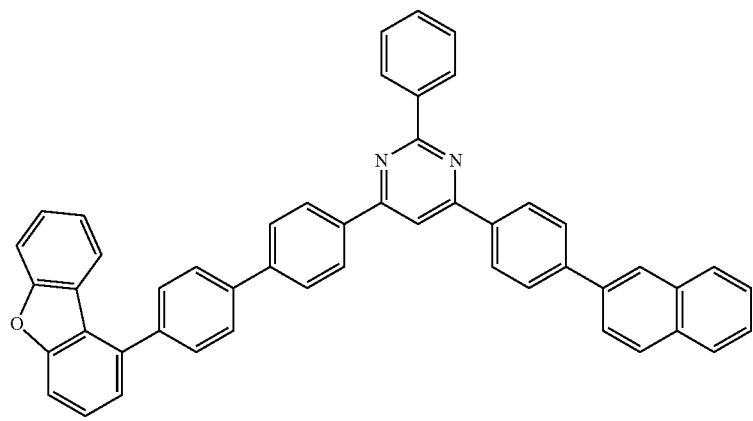

-continued
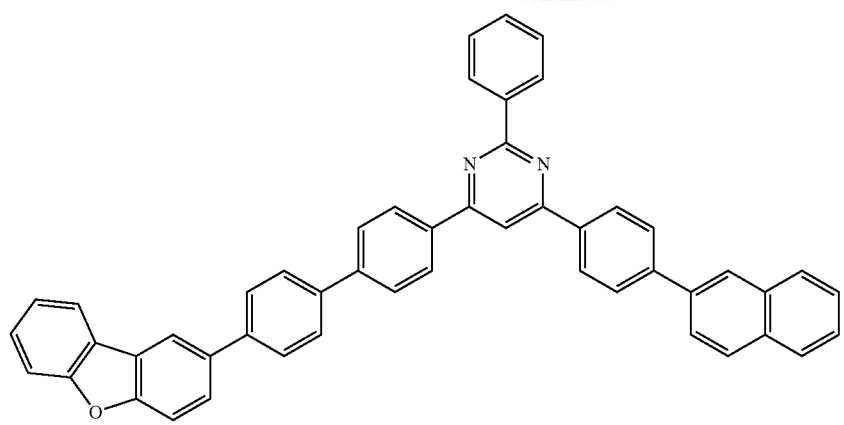
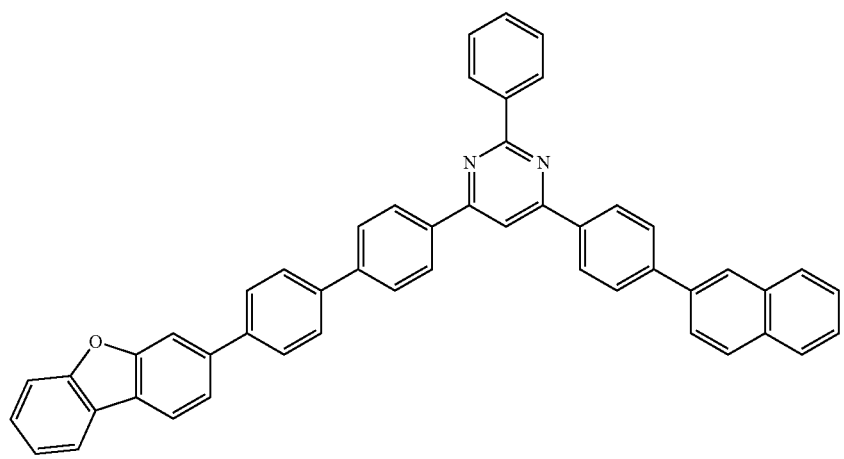
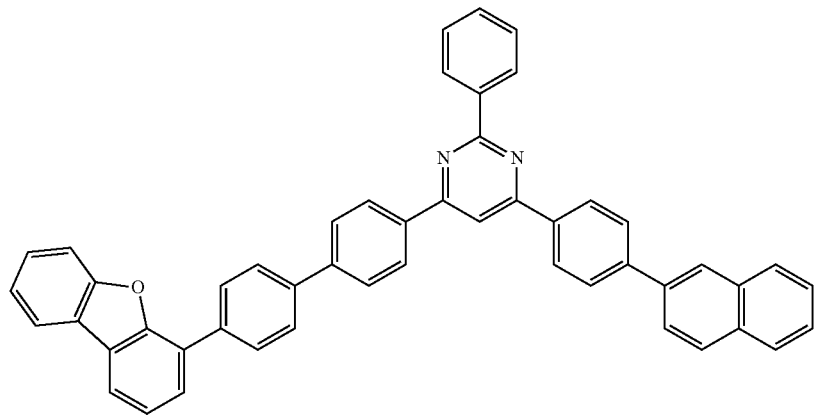
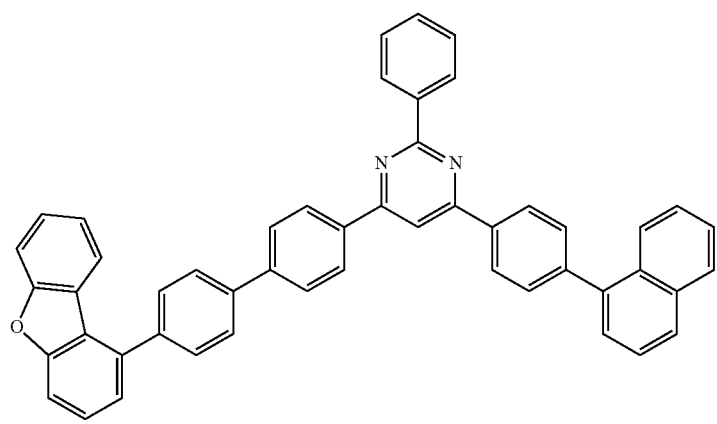

-continued
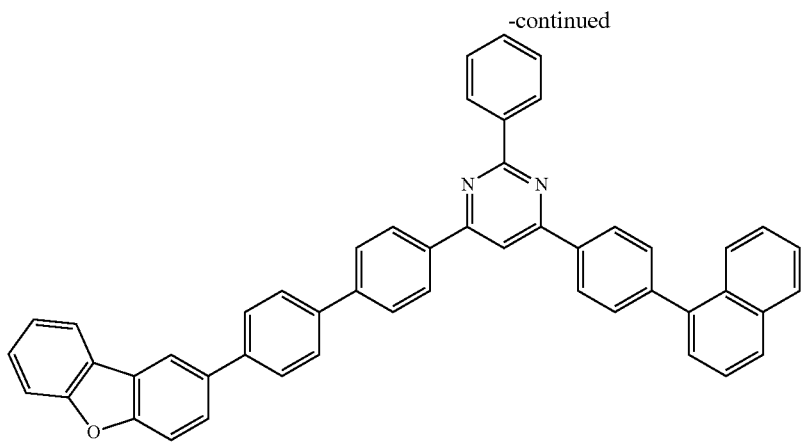
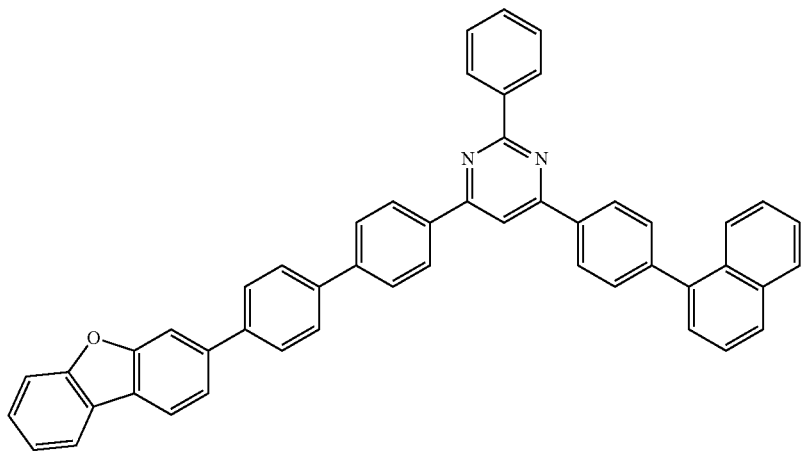
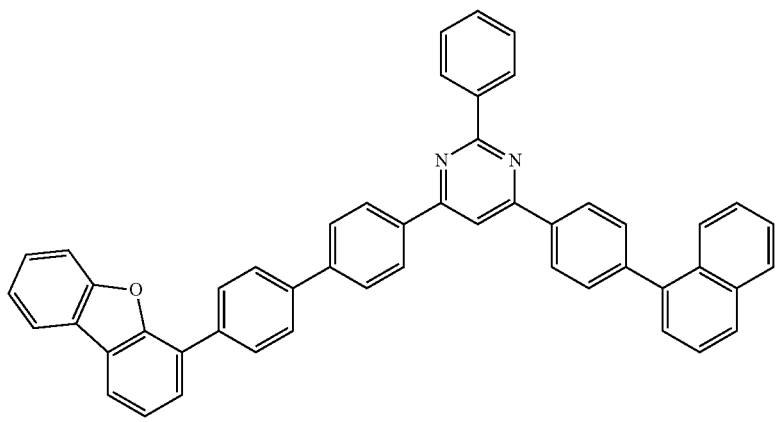

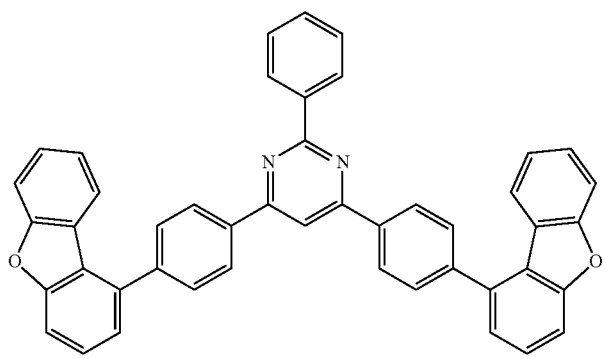
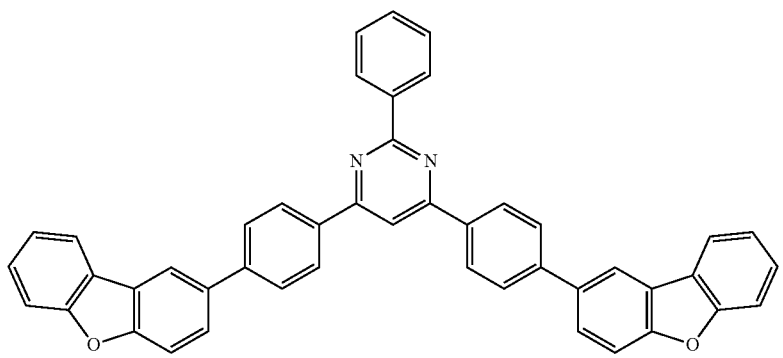
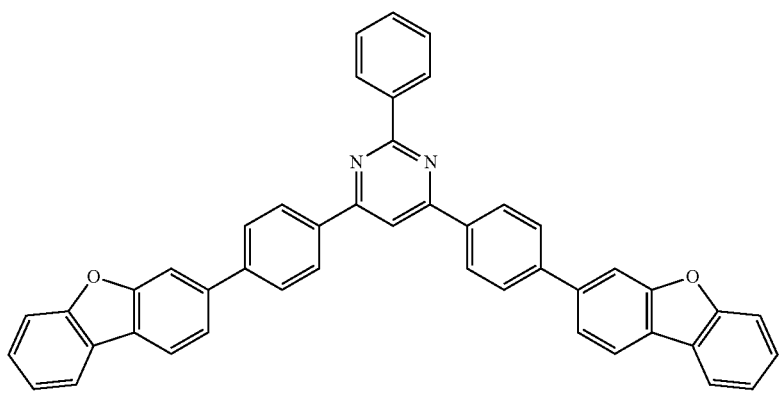

-continued
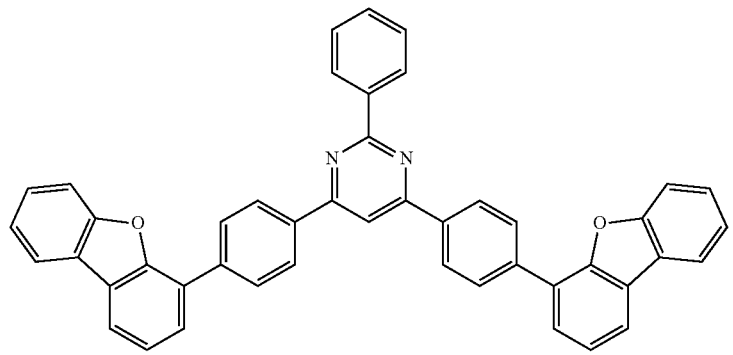
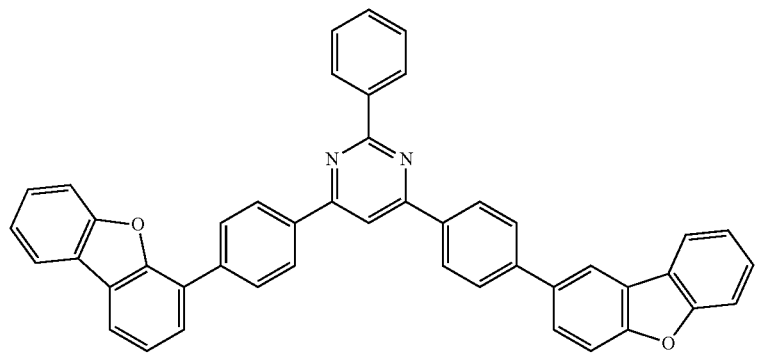
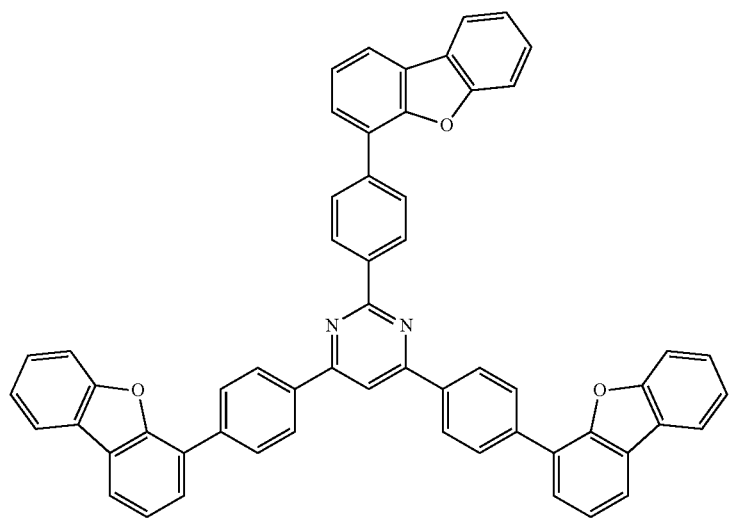

-continued
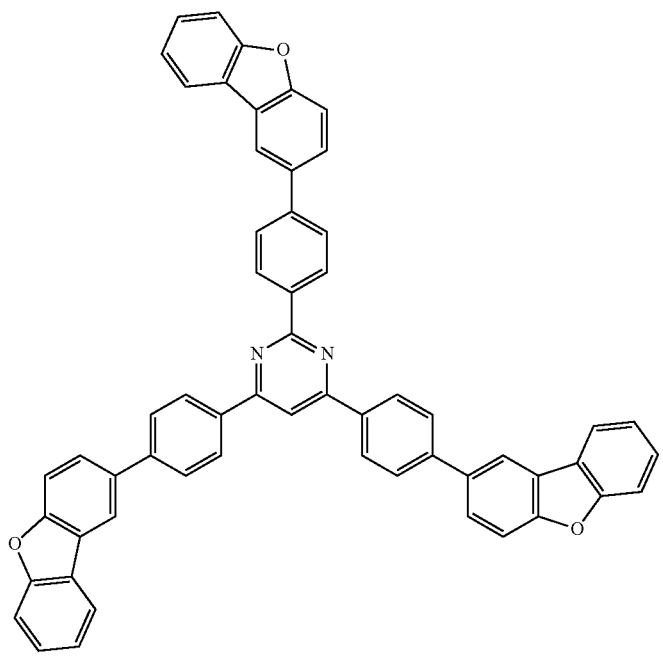
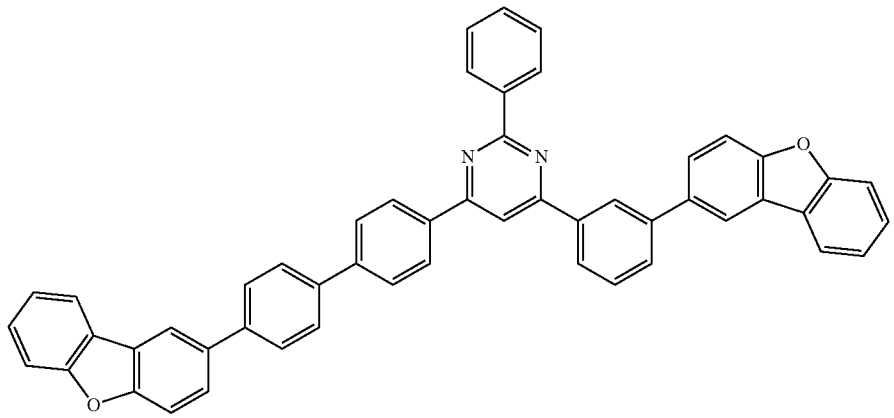
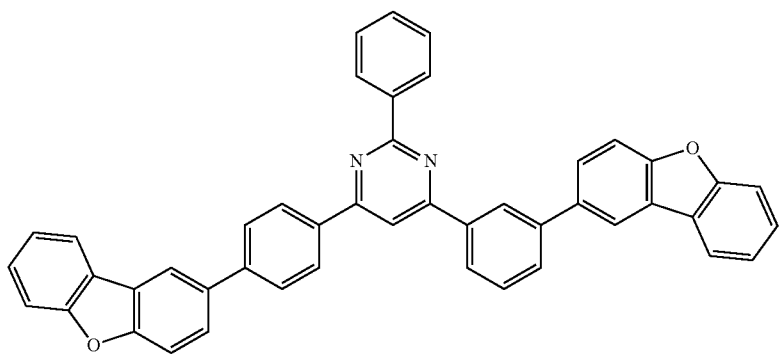

-continued
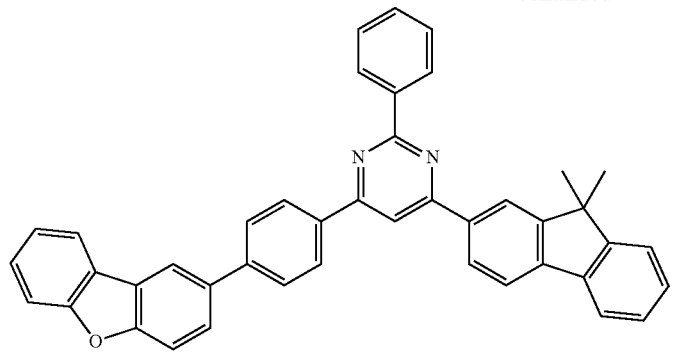
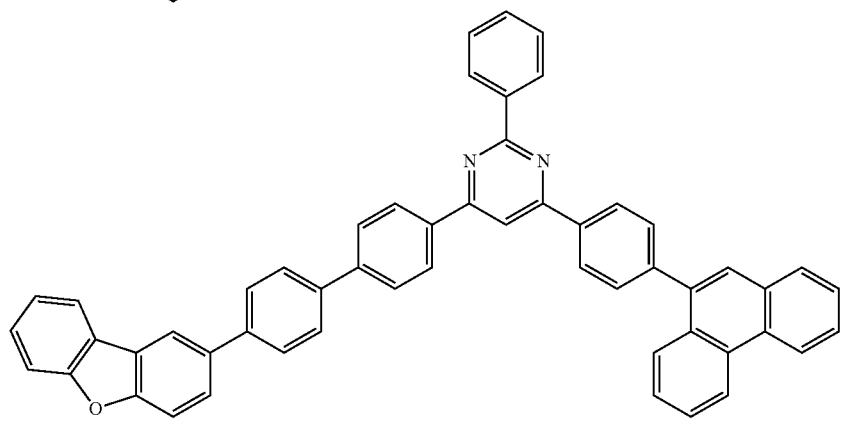
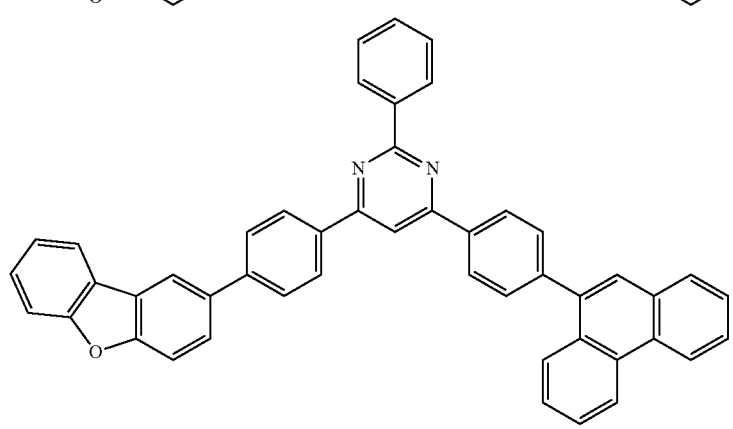
[Formula 73]
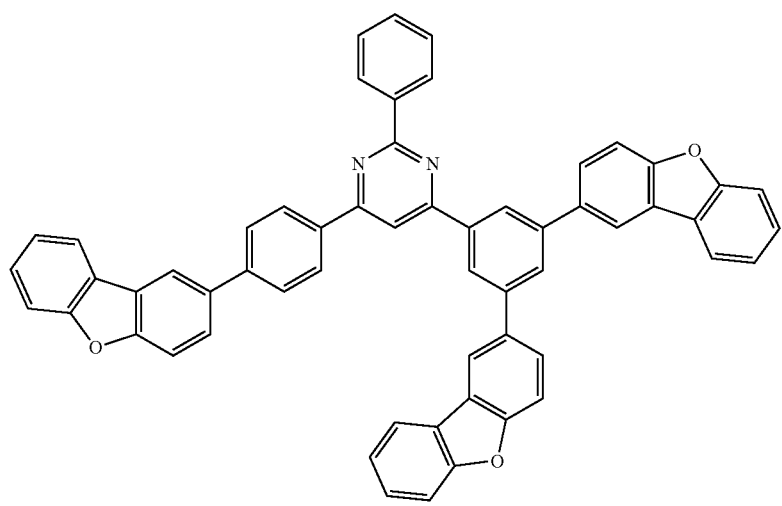

-continued
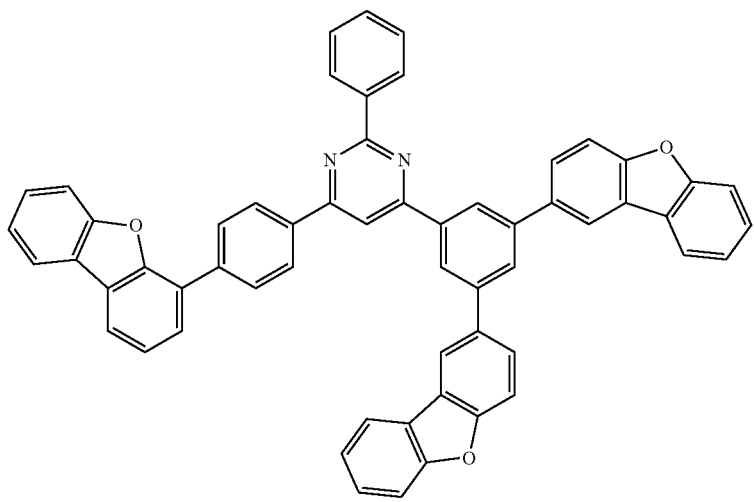
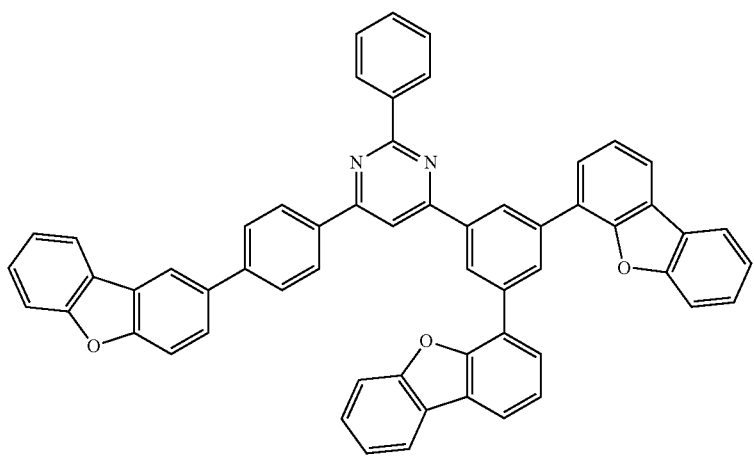
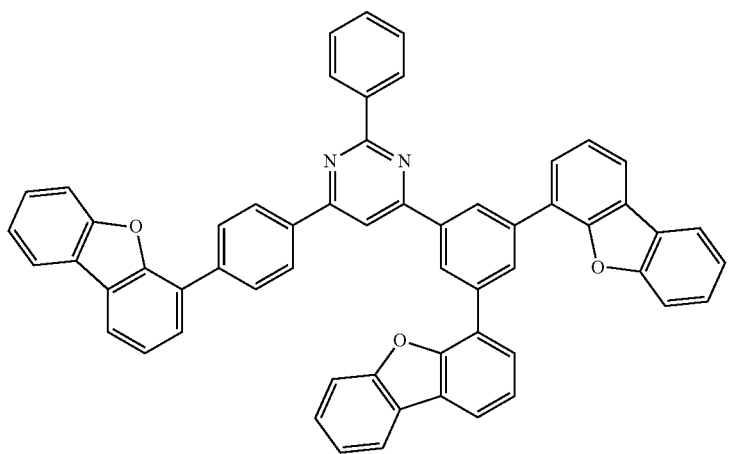

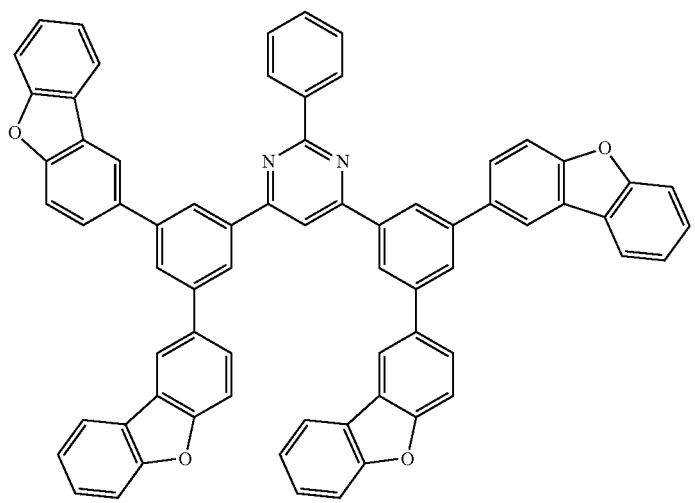
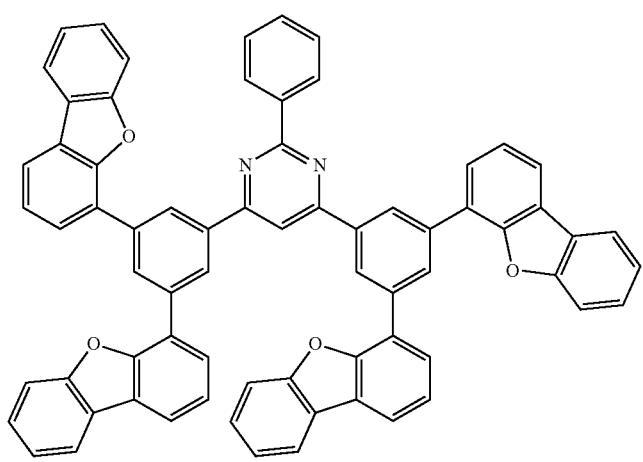
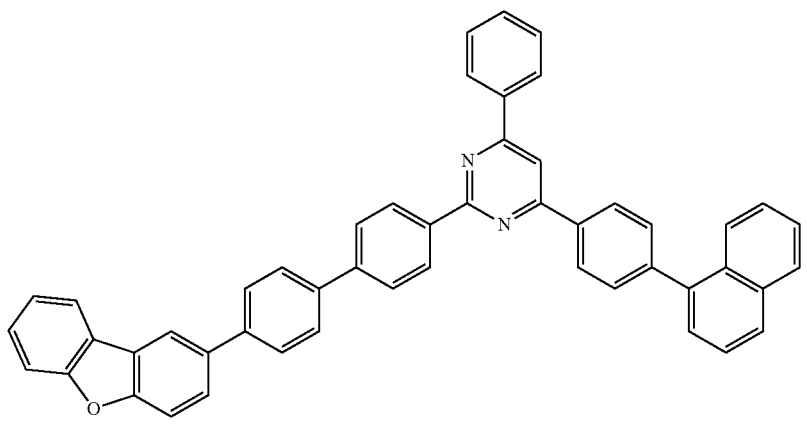

-continued
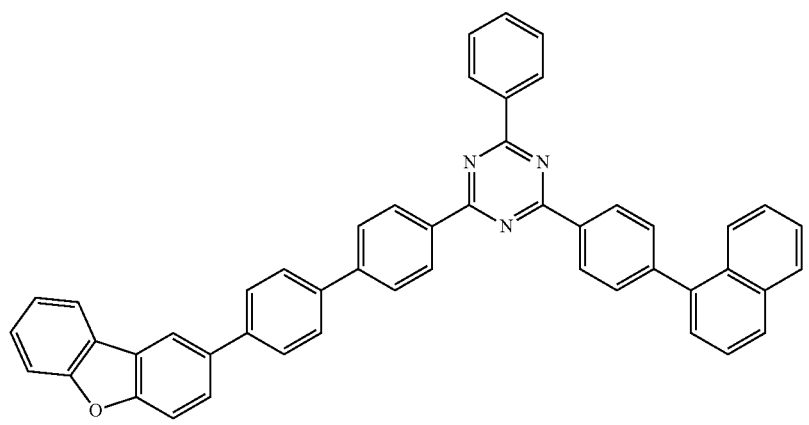
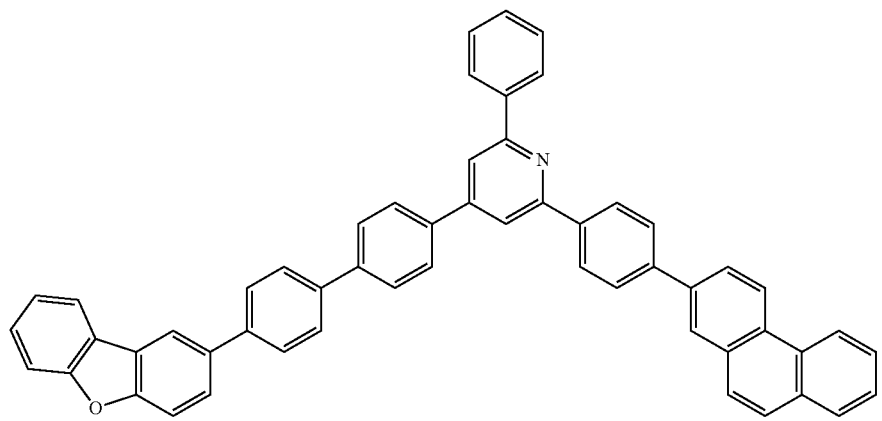
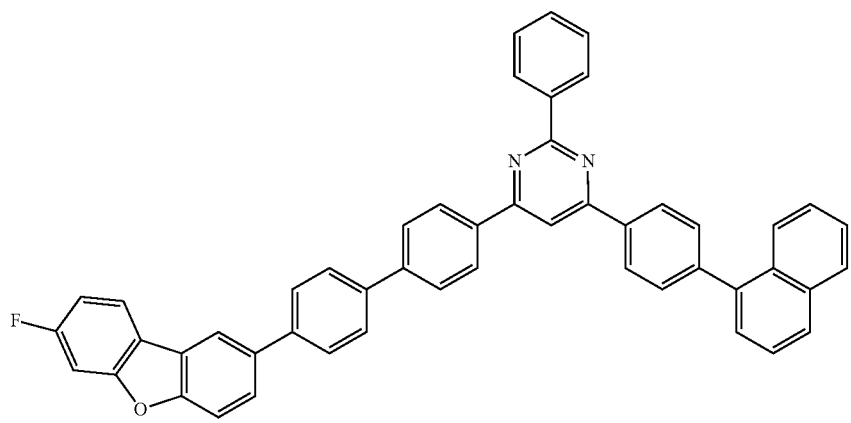
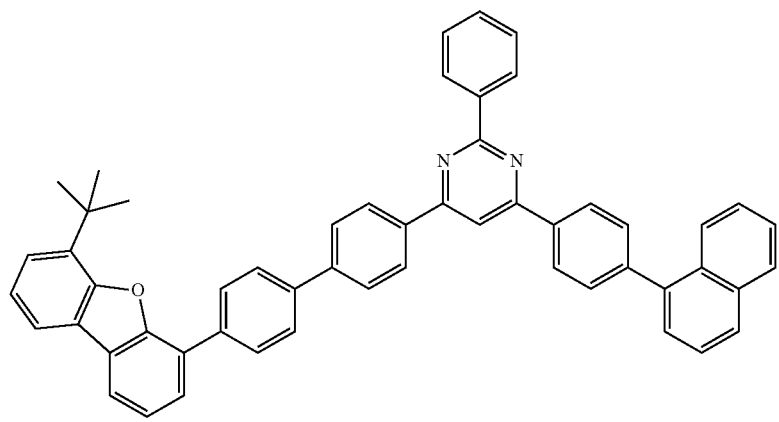

-continued
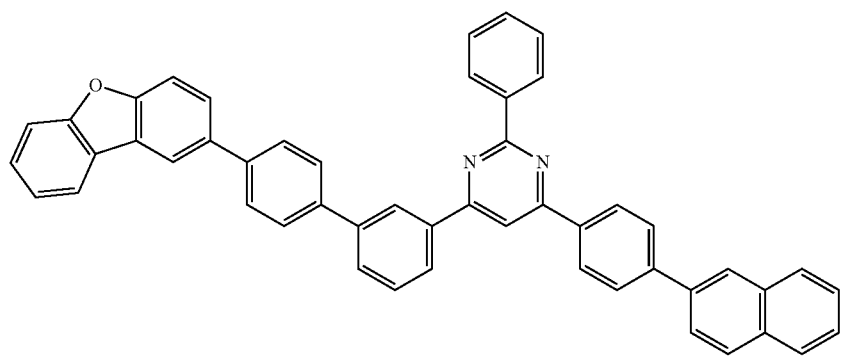
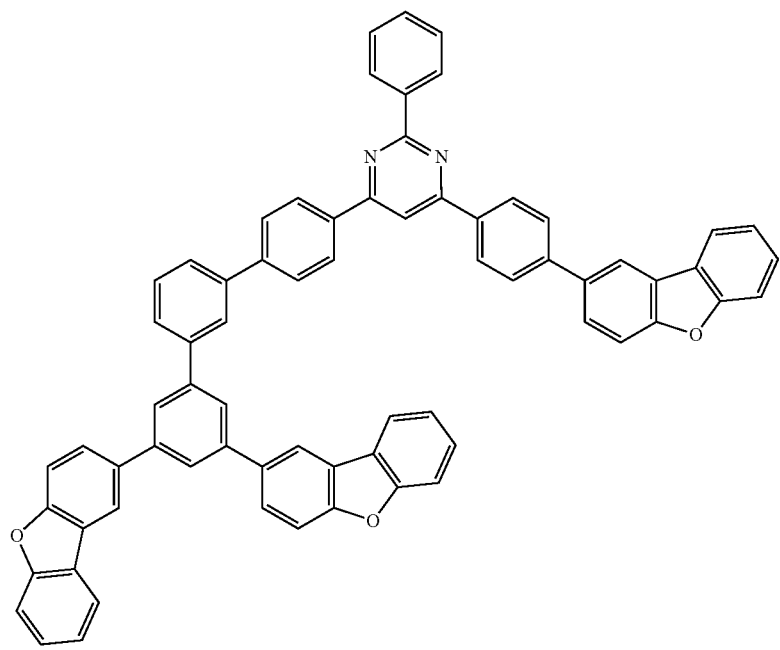
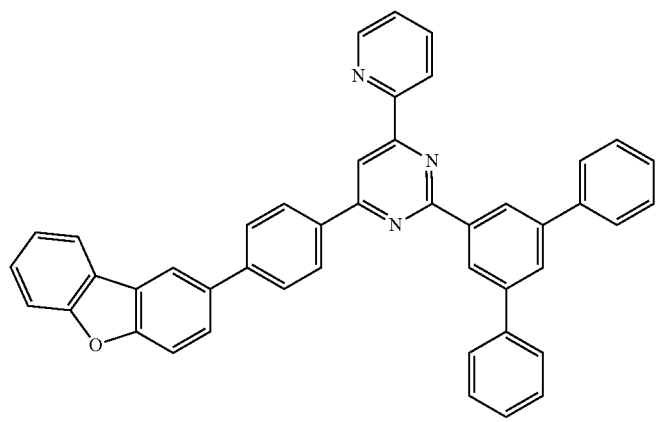

-continued
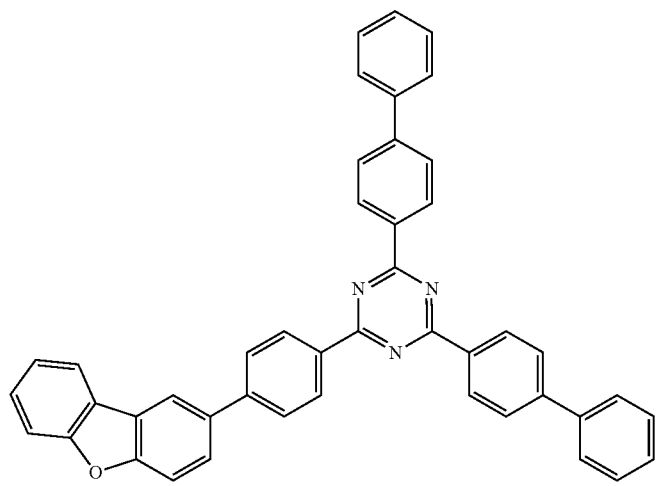
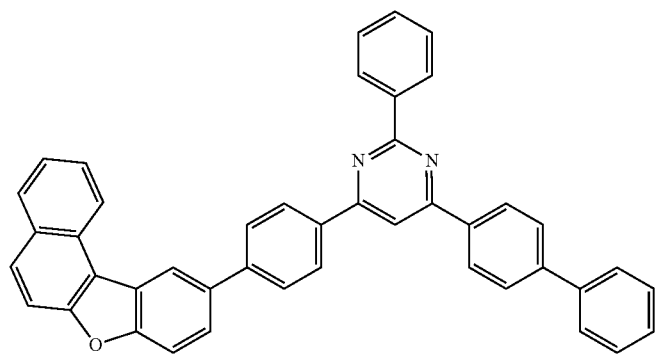
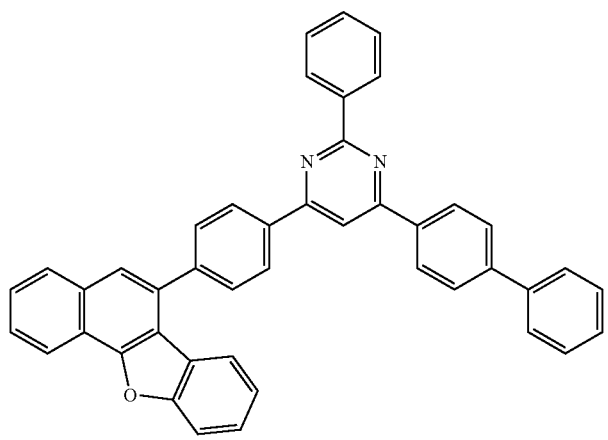
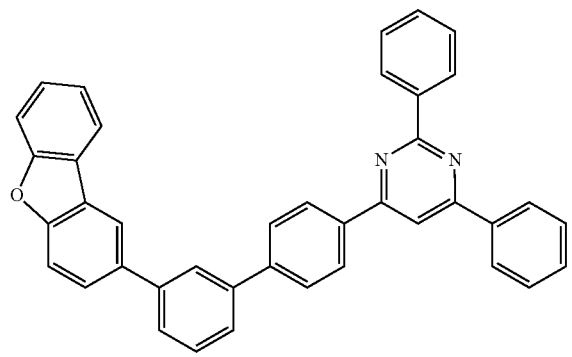

-continued
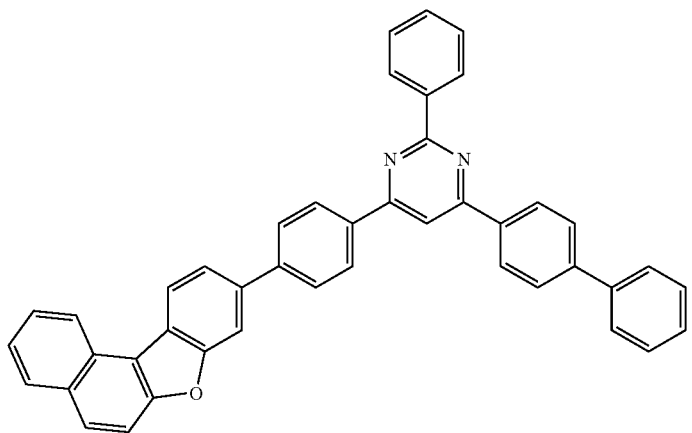
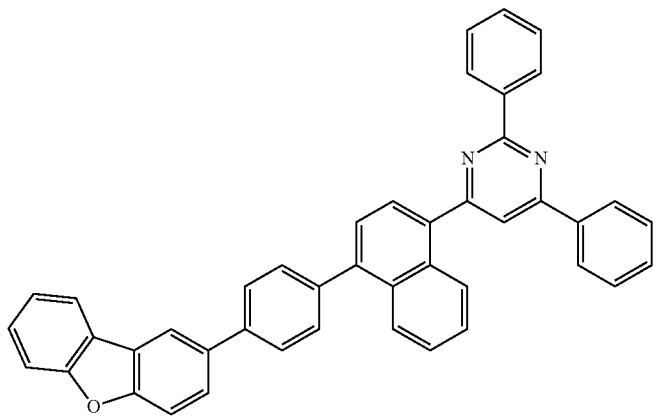
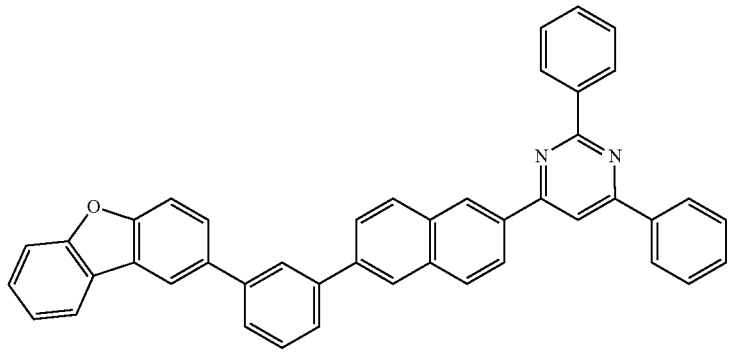
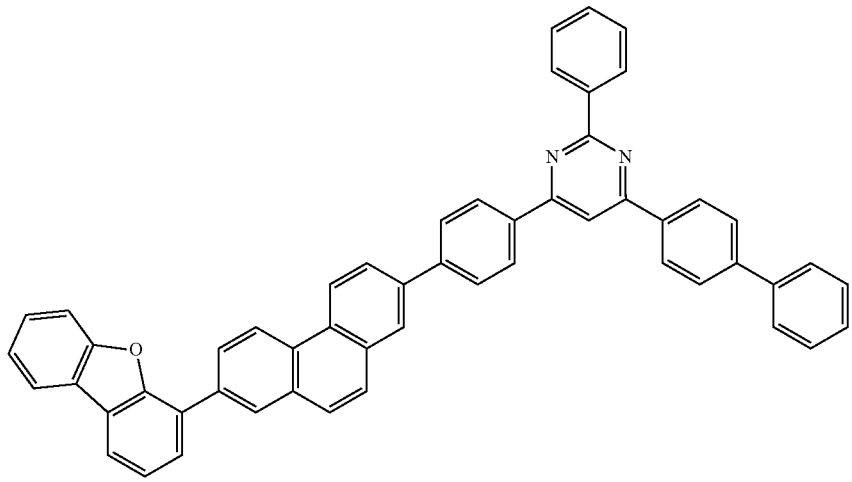

-continued
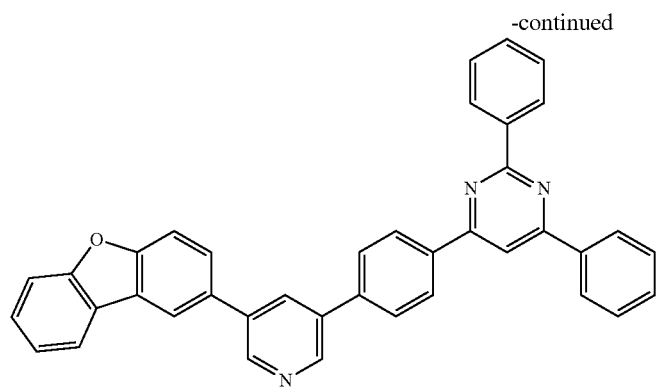
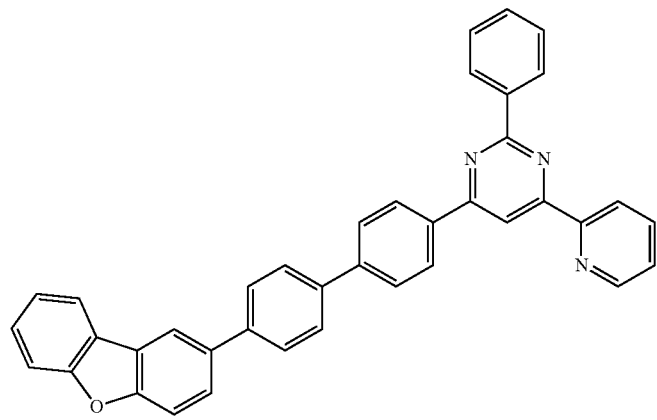
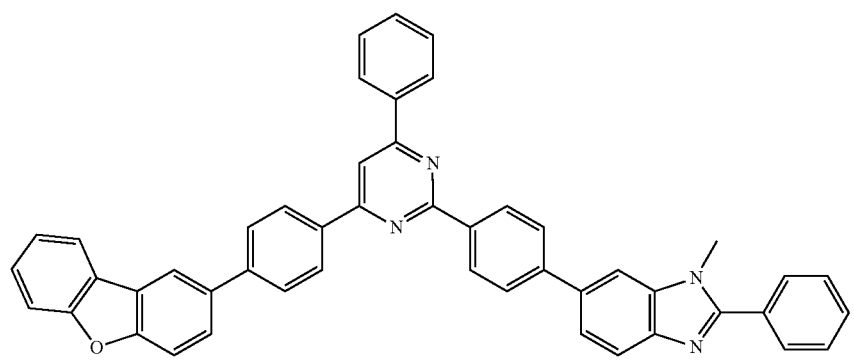
[Formula 74]
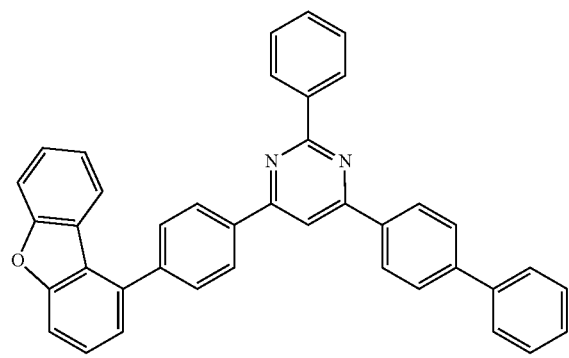

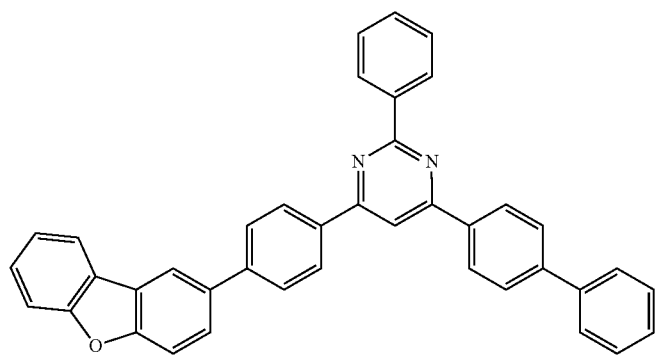
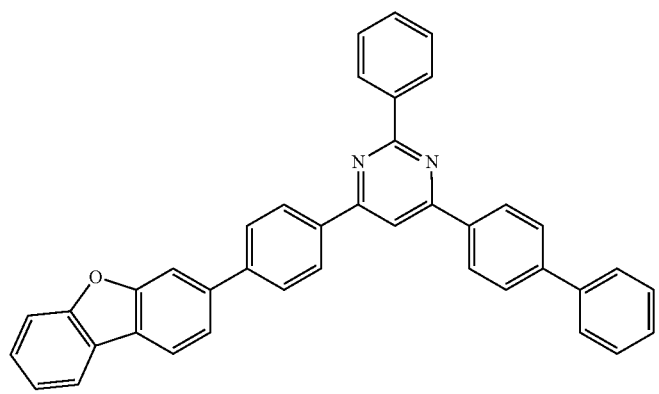
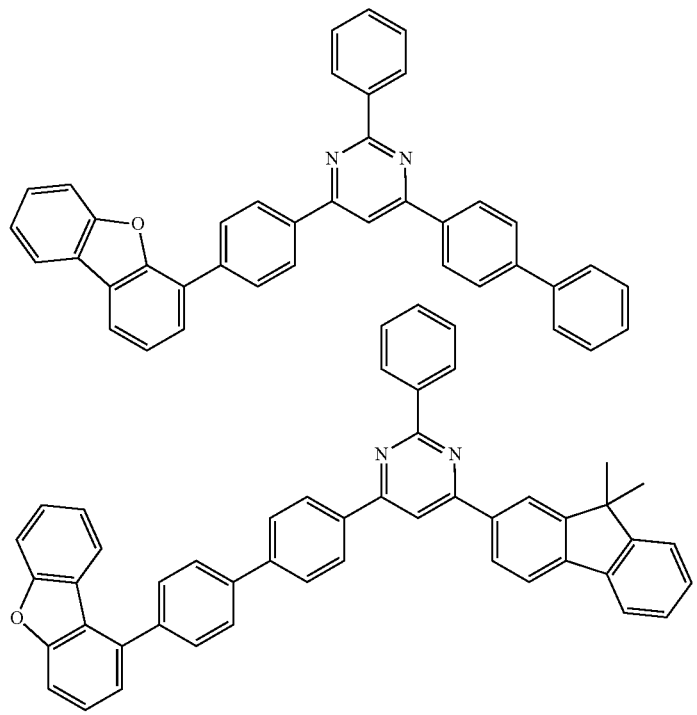

-continued
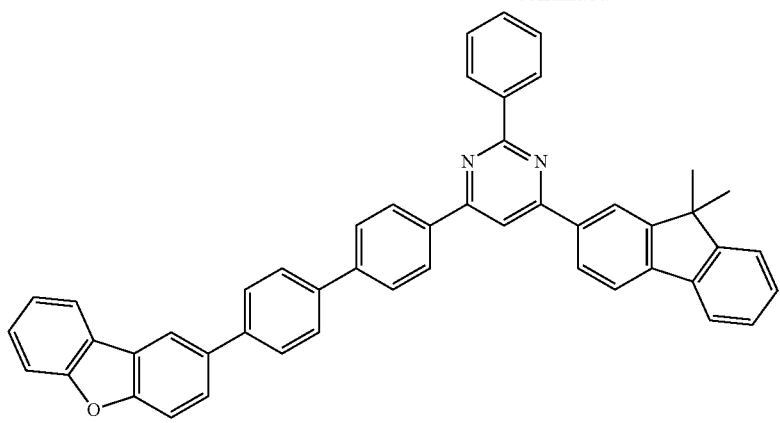
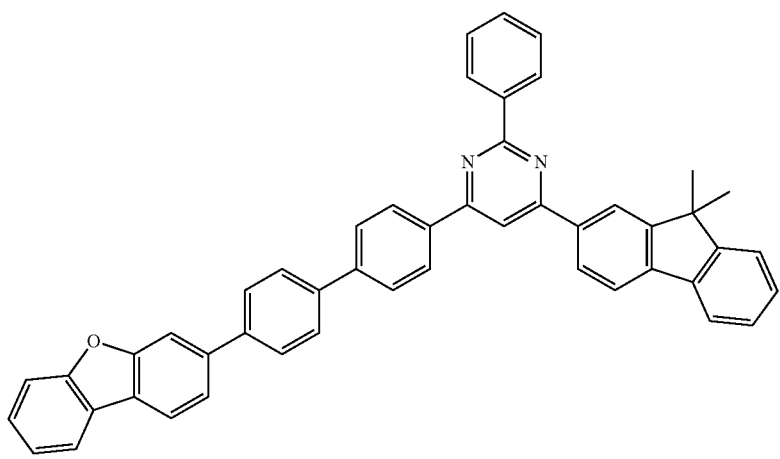
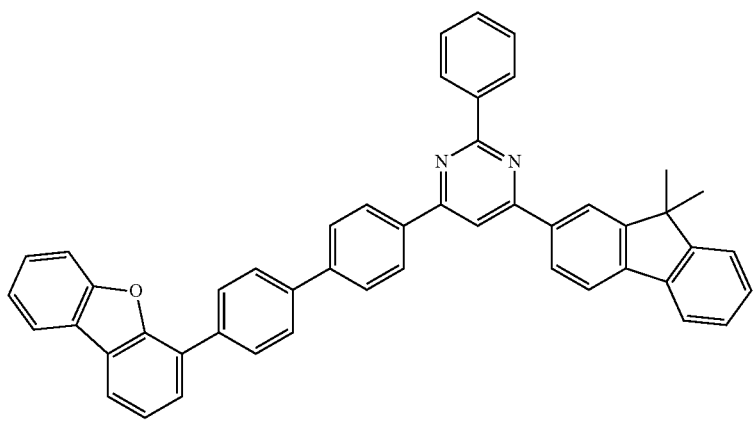
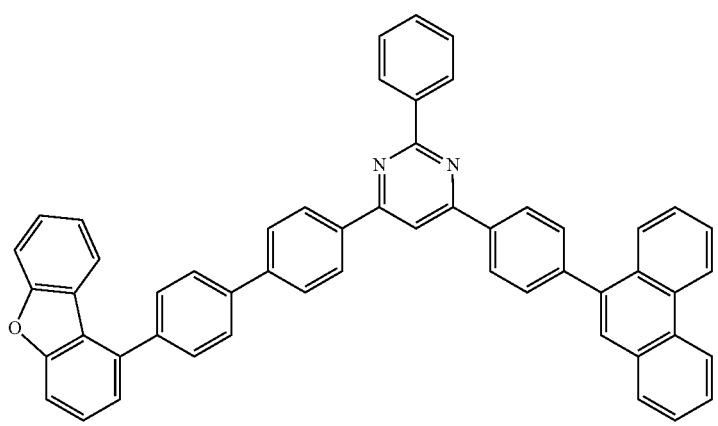

-continued
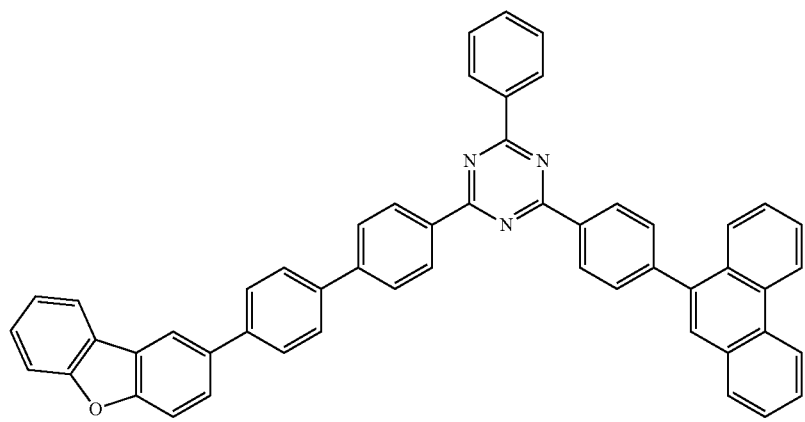
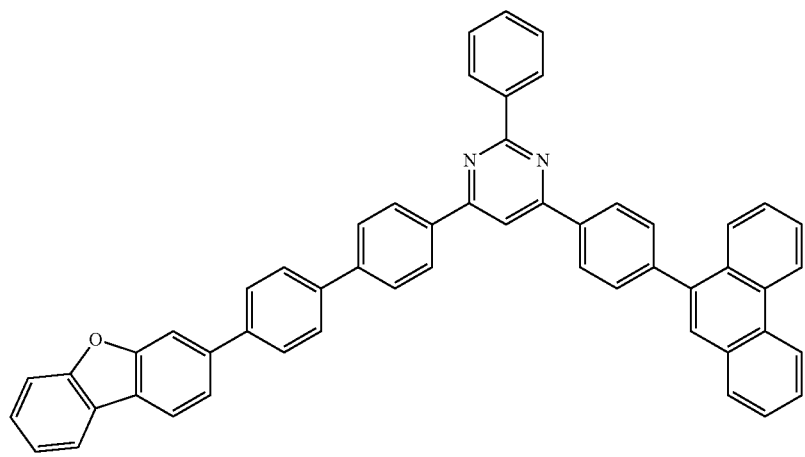
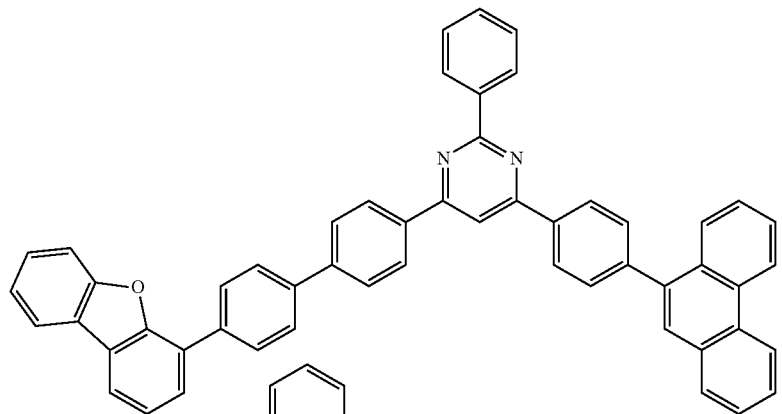
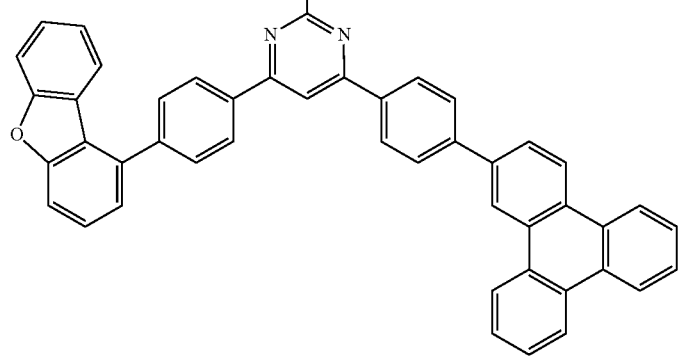

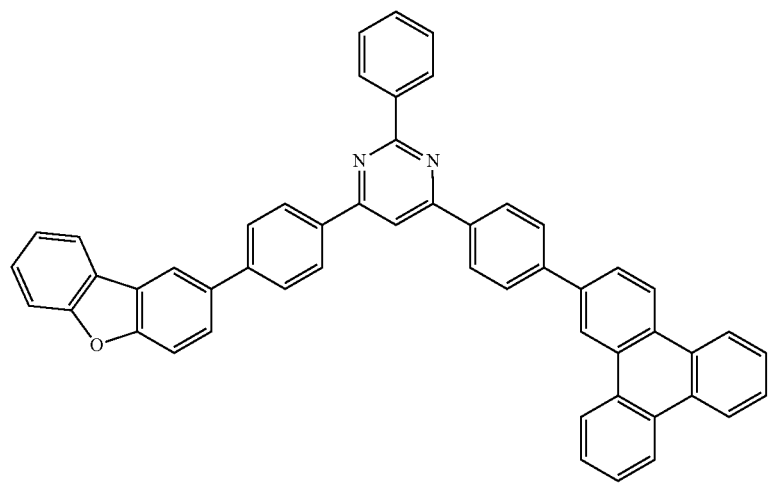
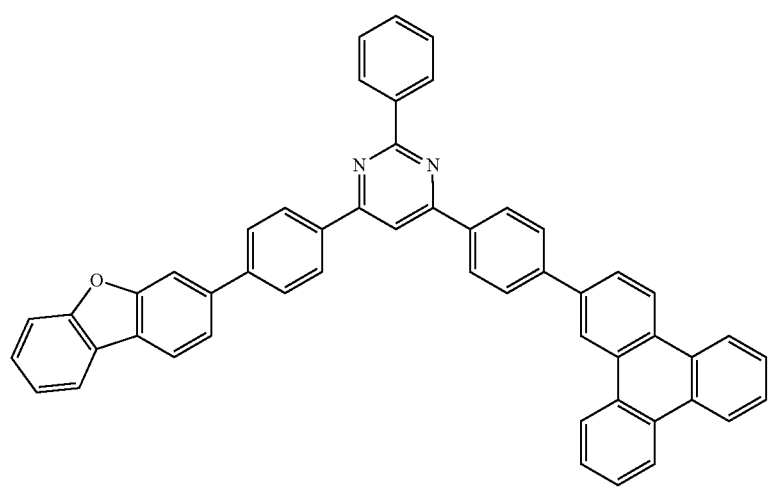
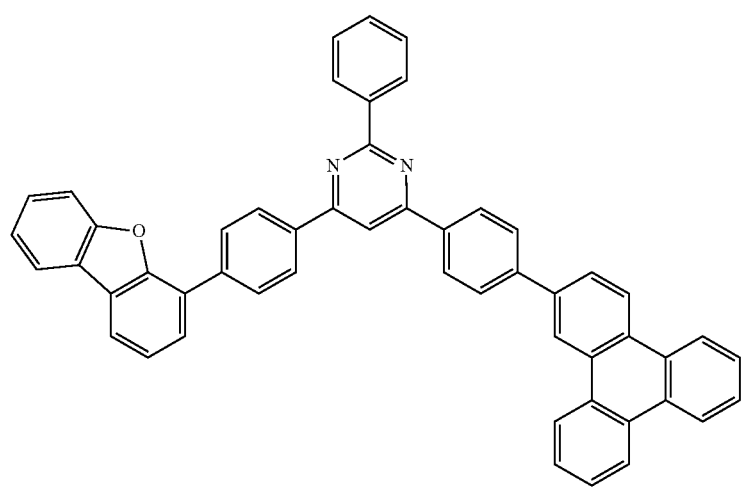

-continued
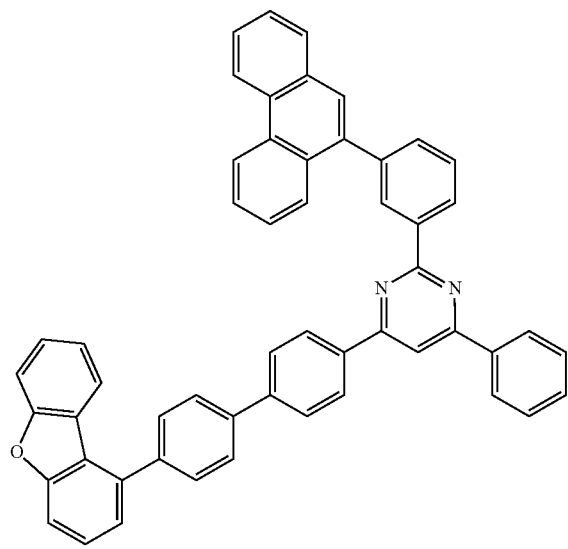
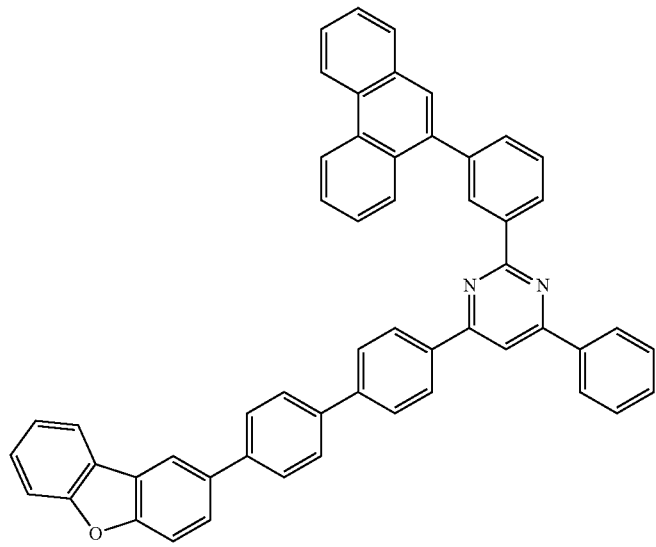
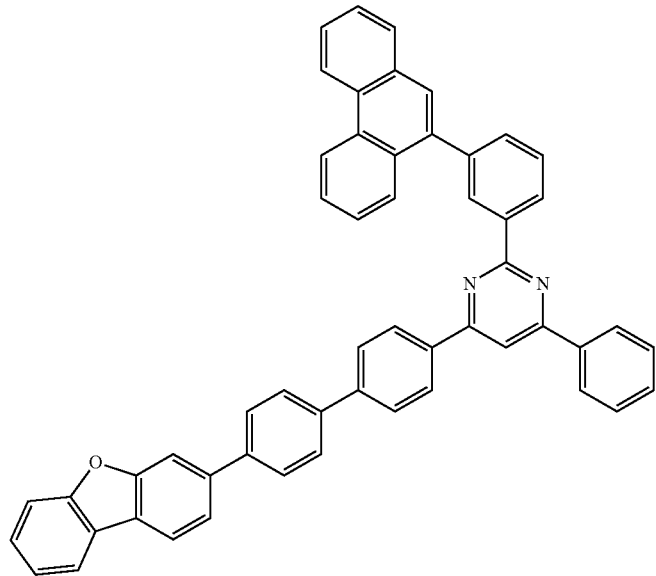

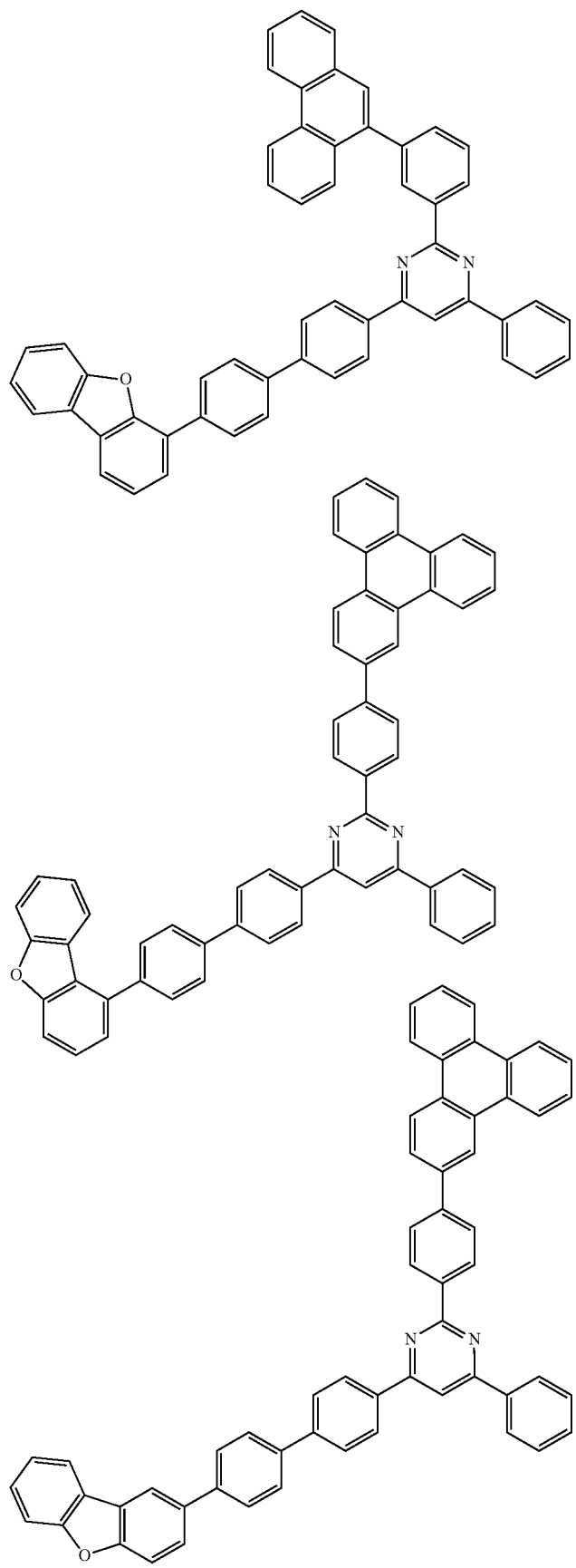

-continued
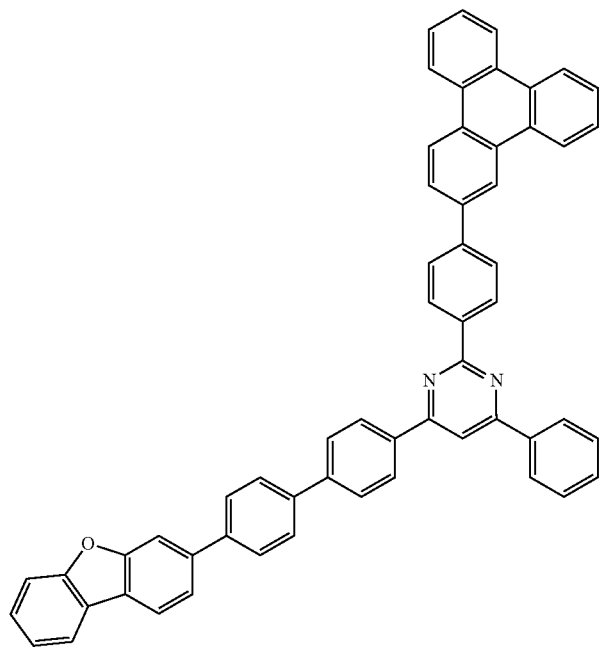
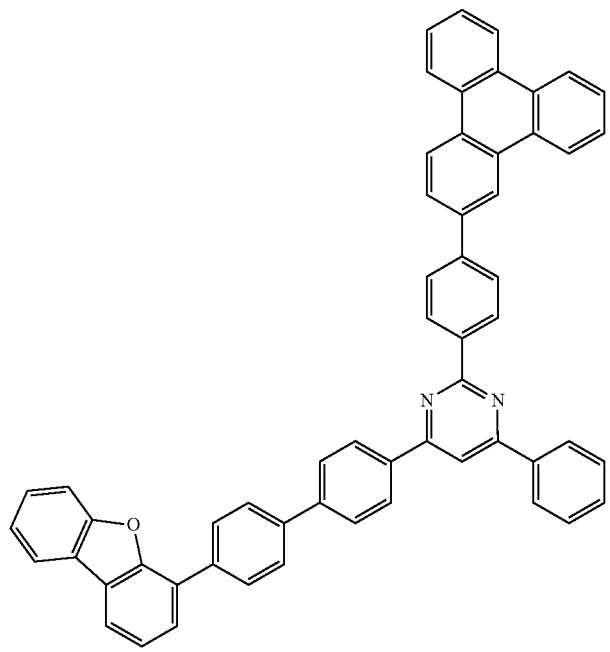
[Formula 75]
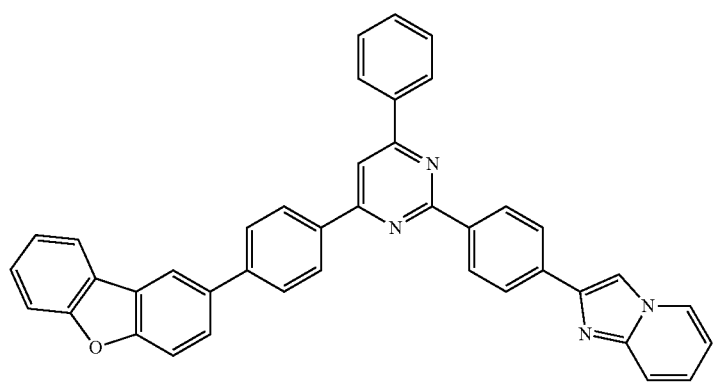

-continued
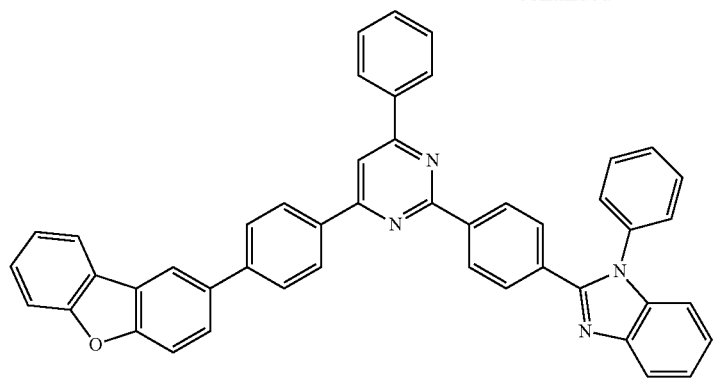
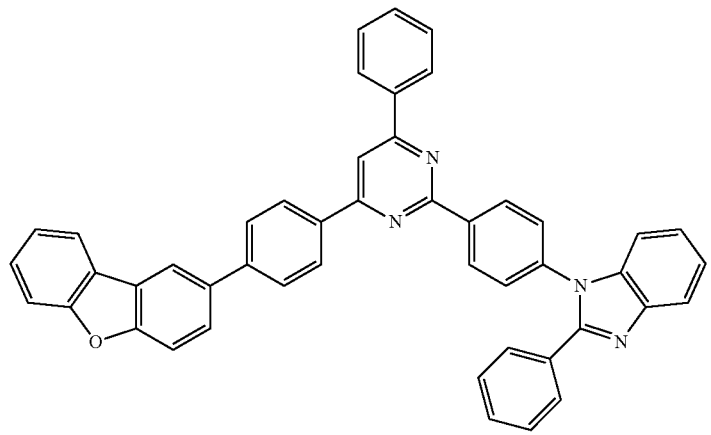
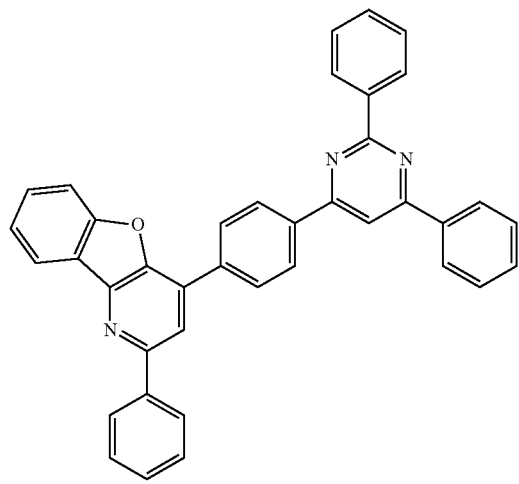
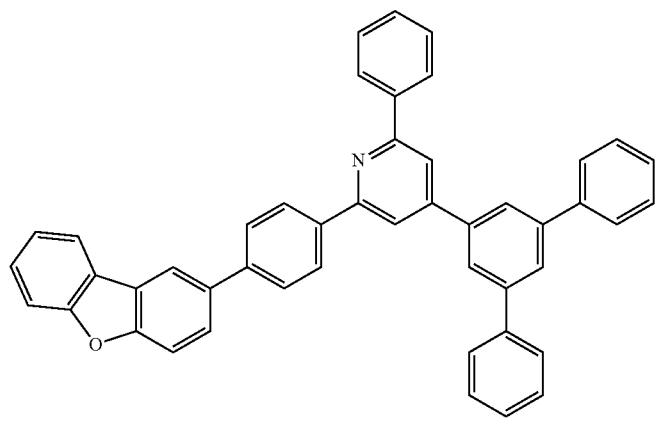

-continued
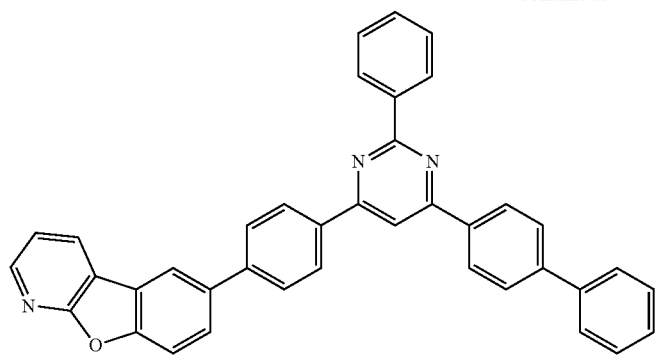
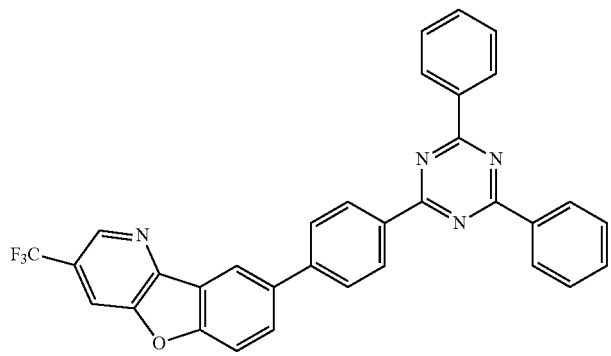
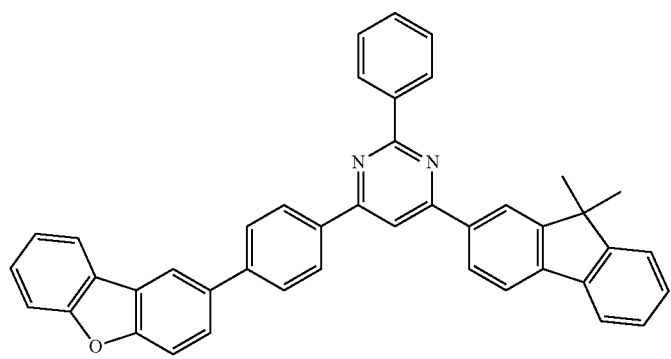
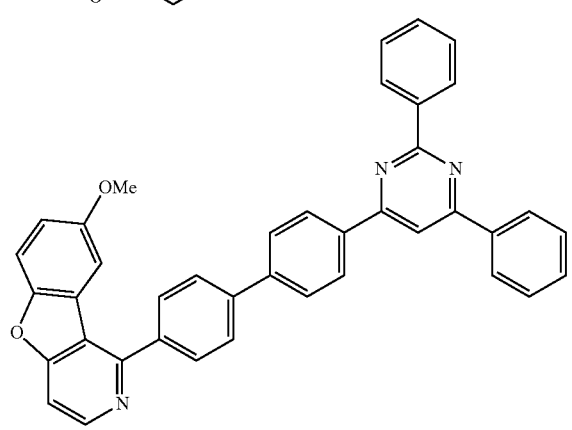

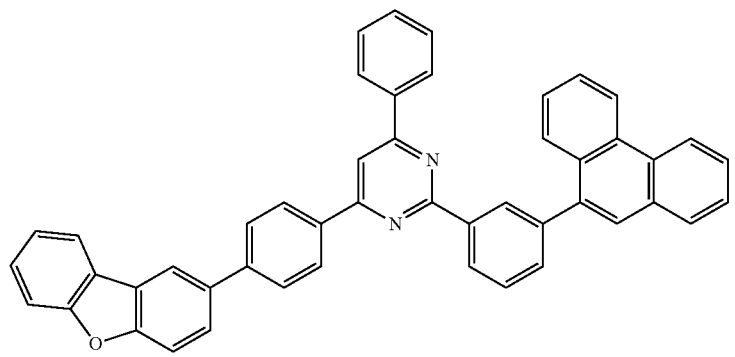
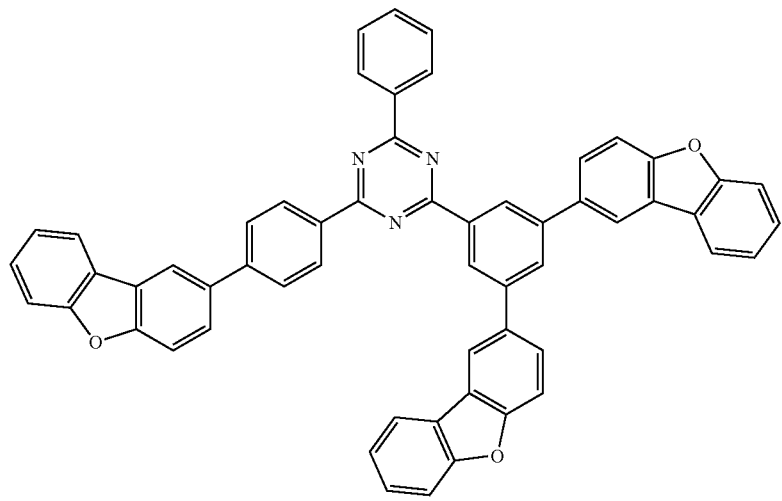
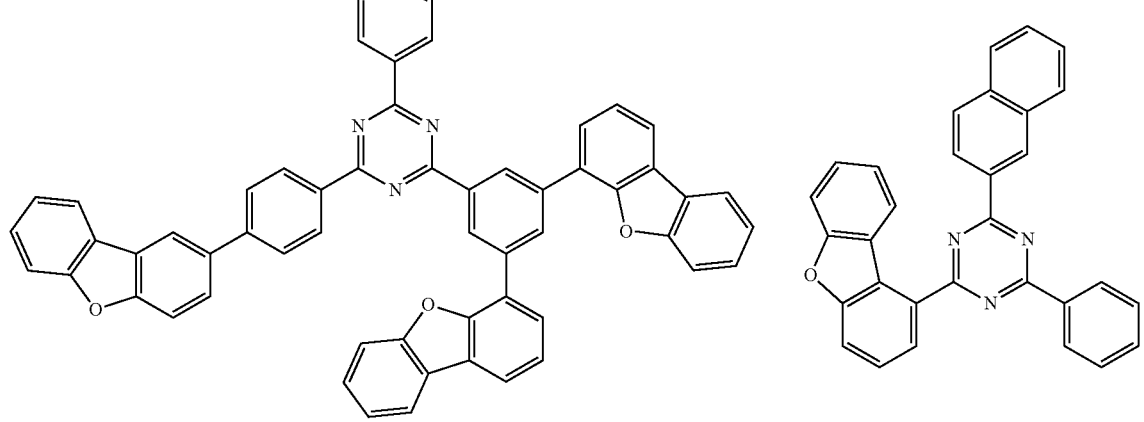
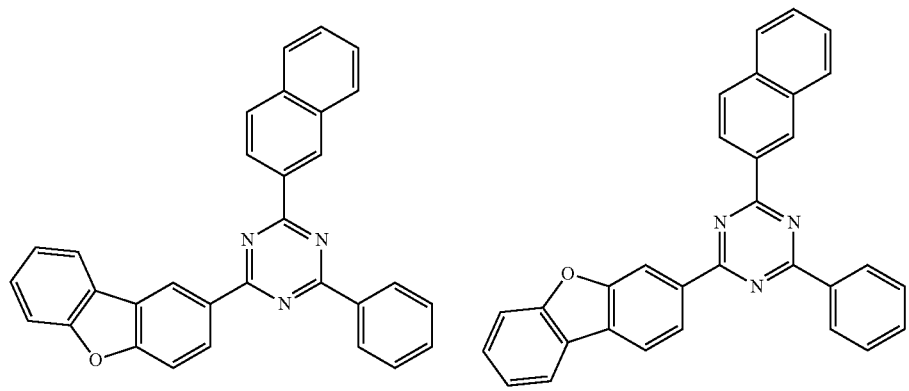

267
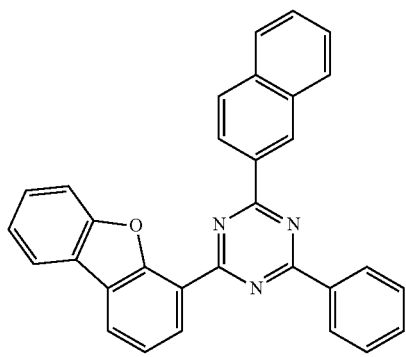
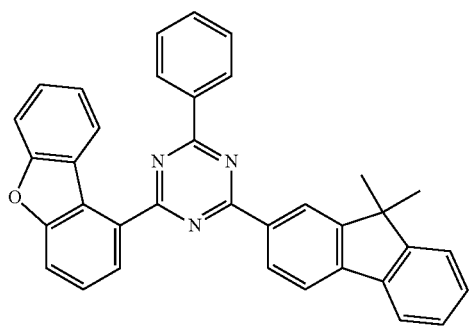
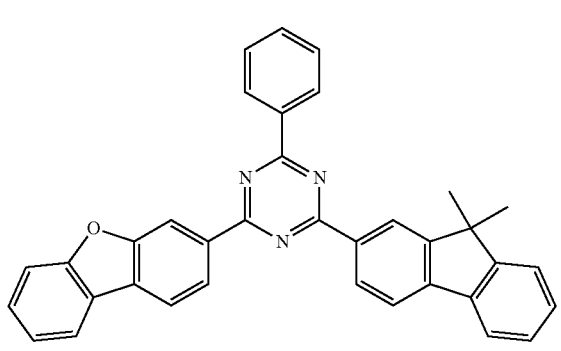
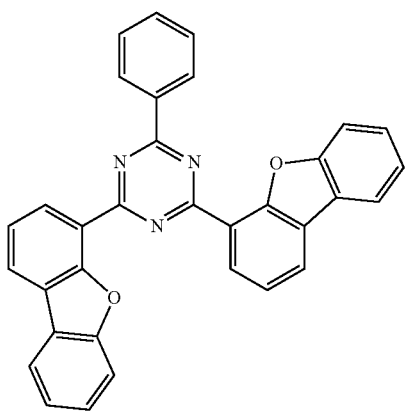
268
-continued
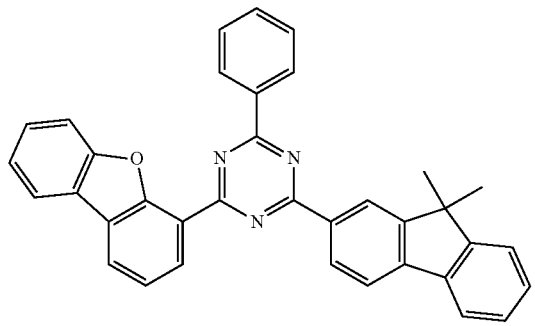
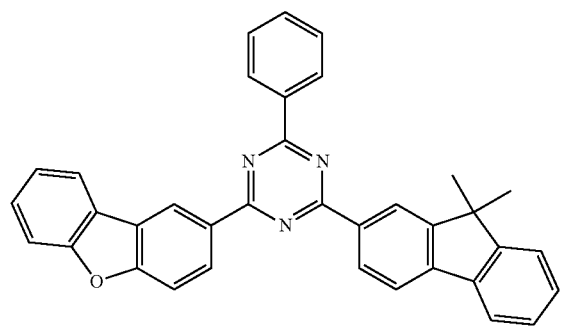
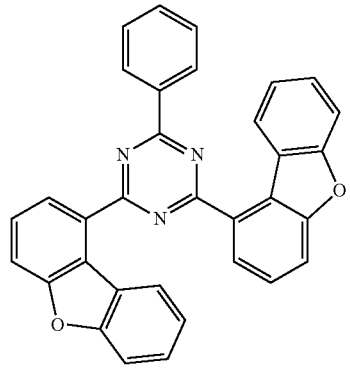
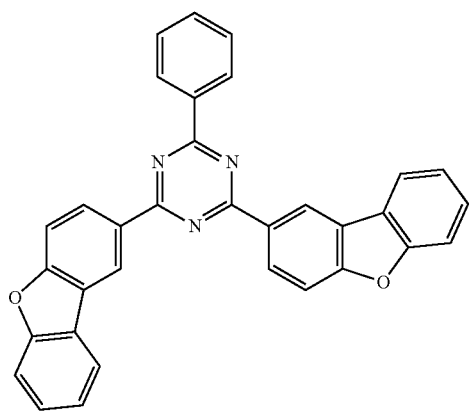

269
270
-continued
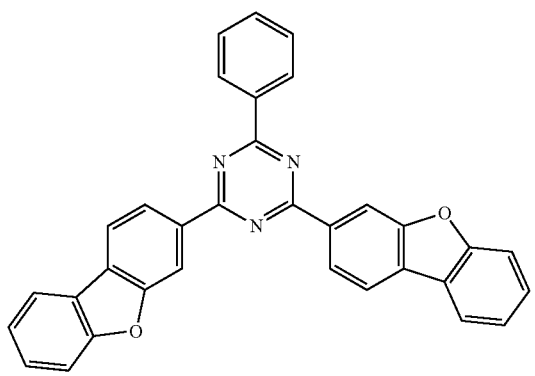
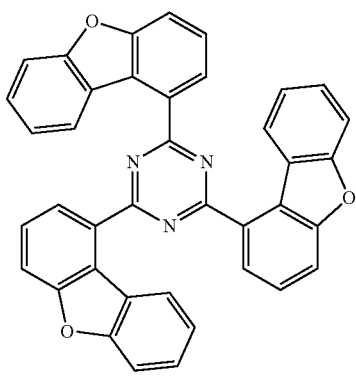
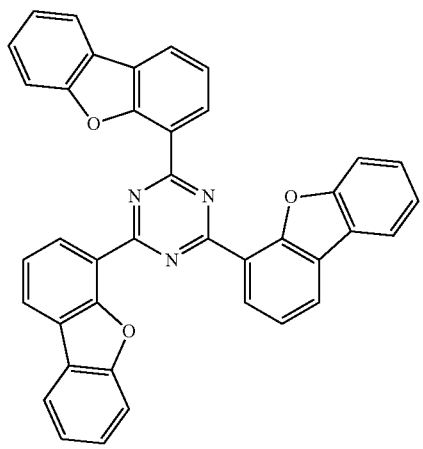
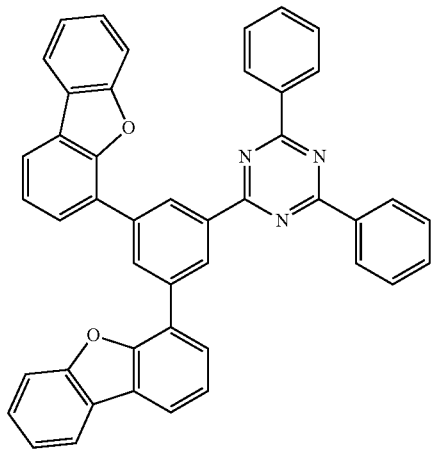
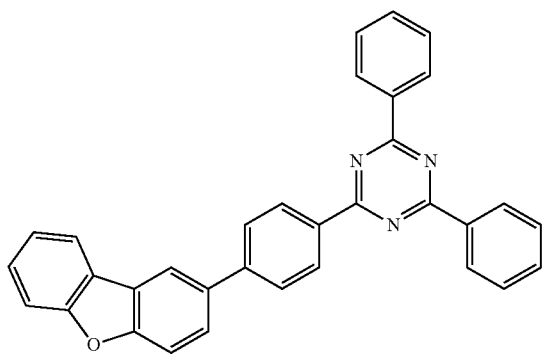
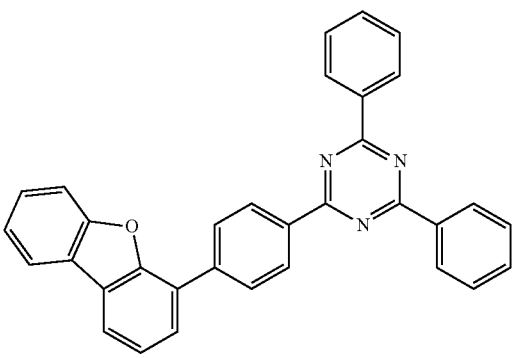
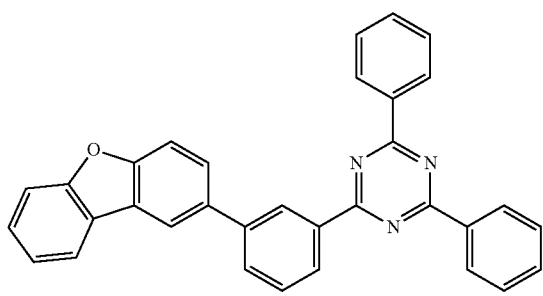
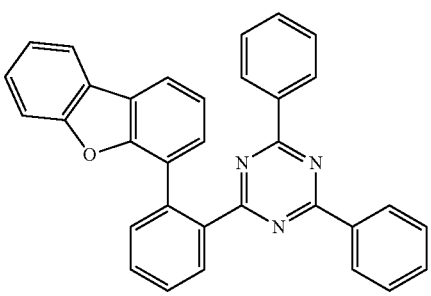

-continued
271 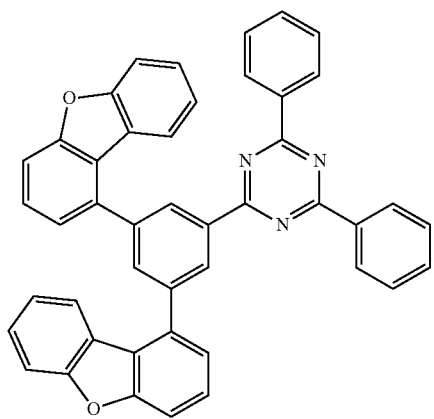
272 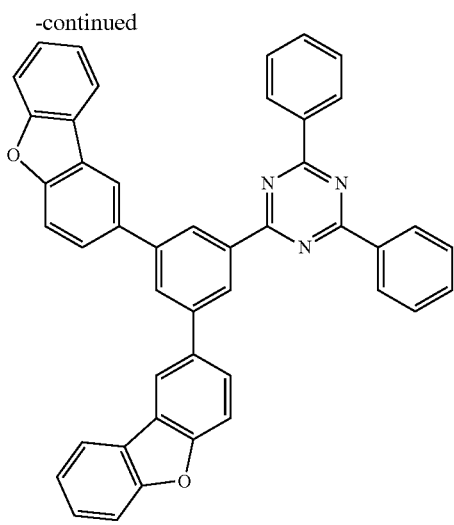
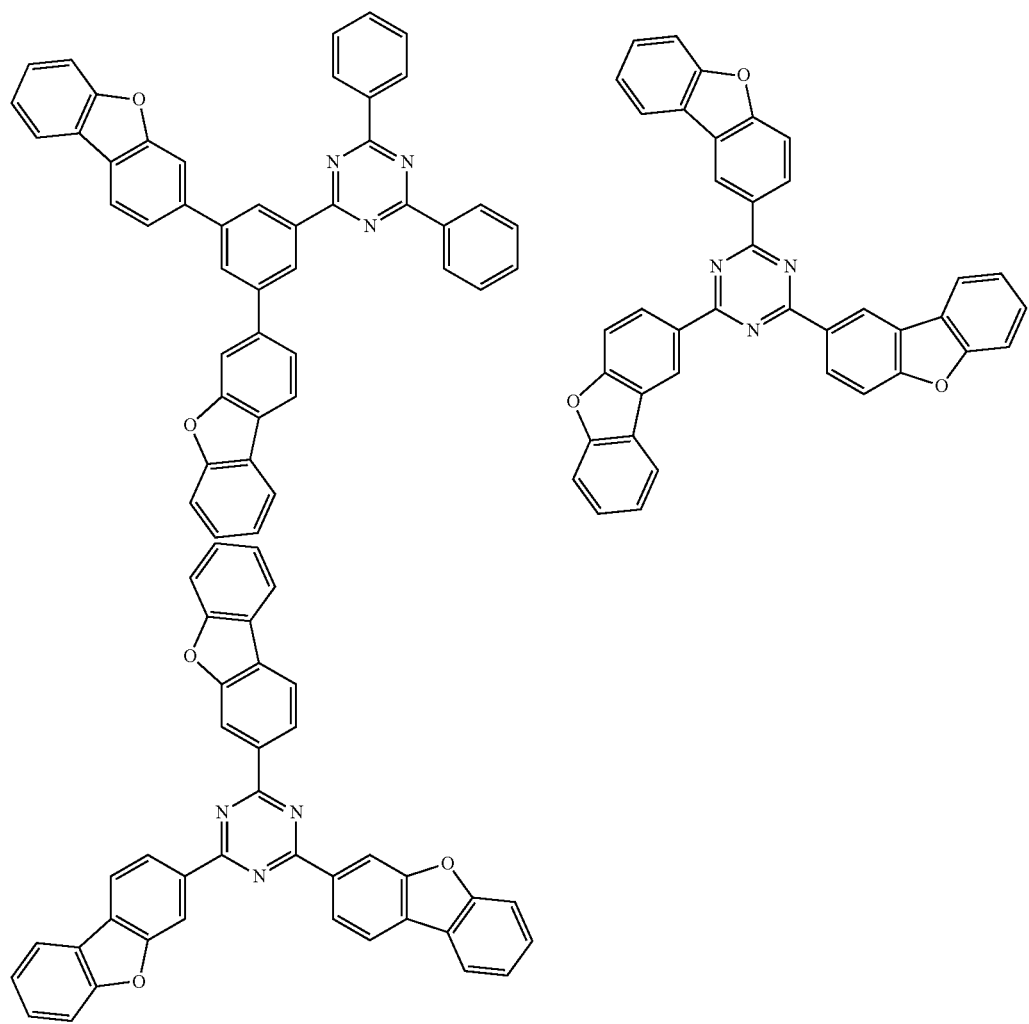

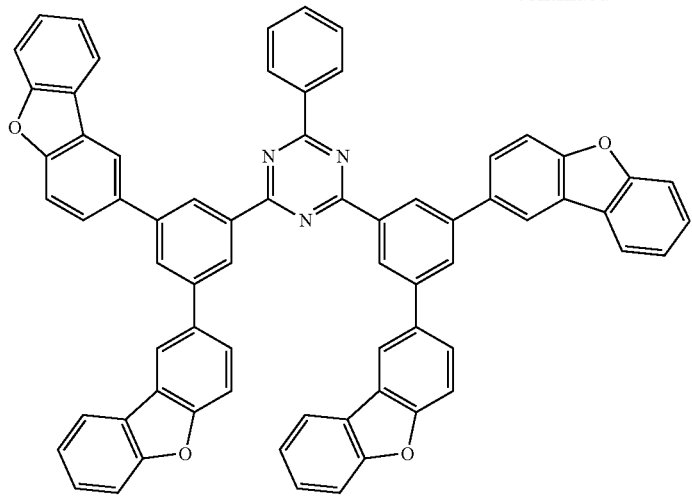
[Formula 76]
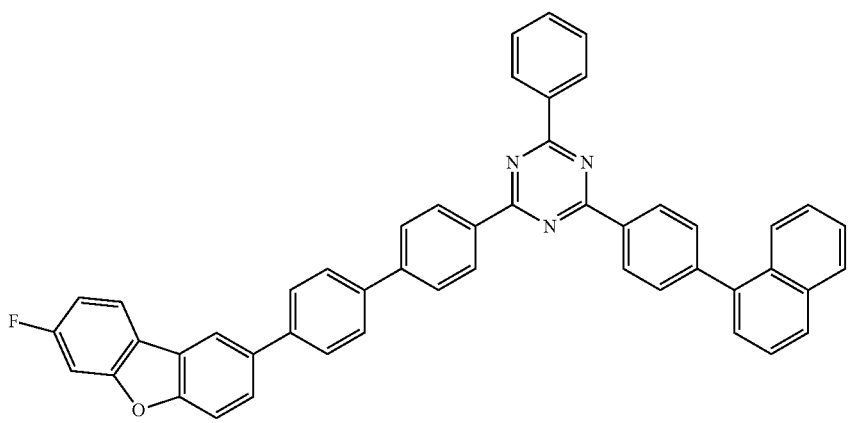
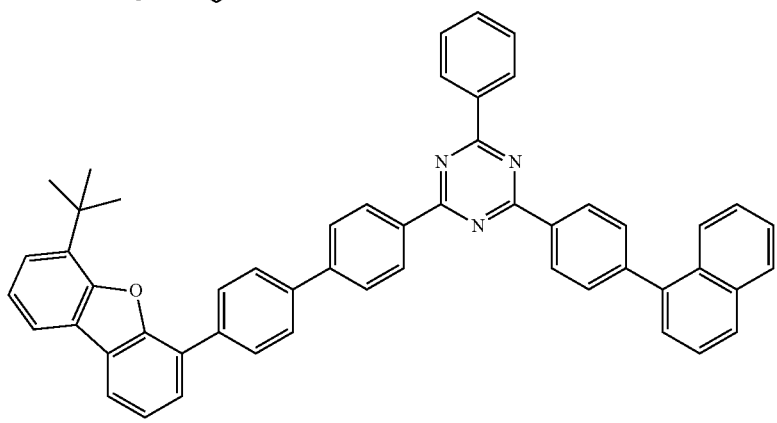
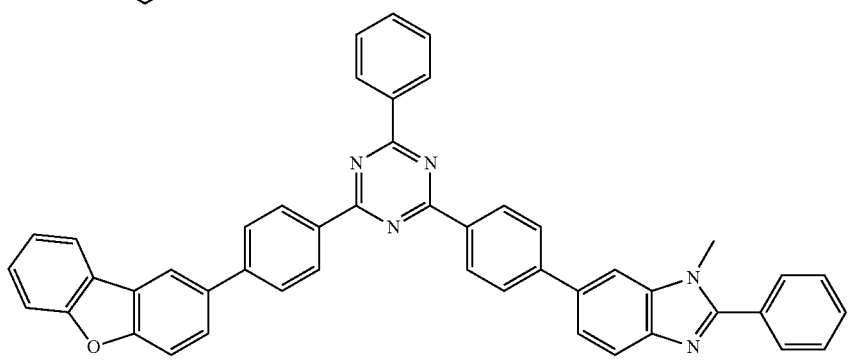

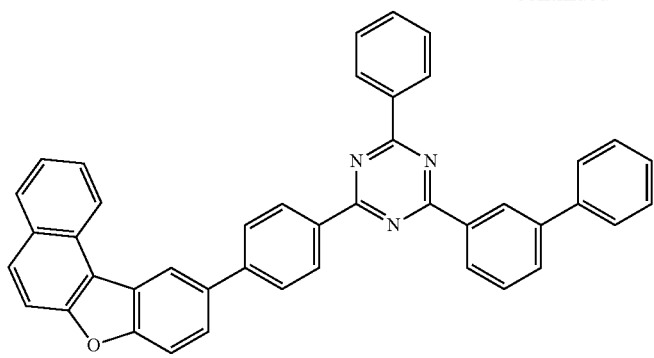
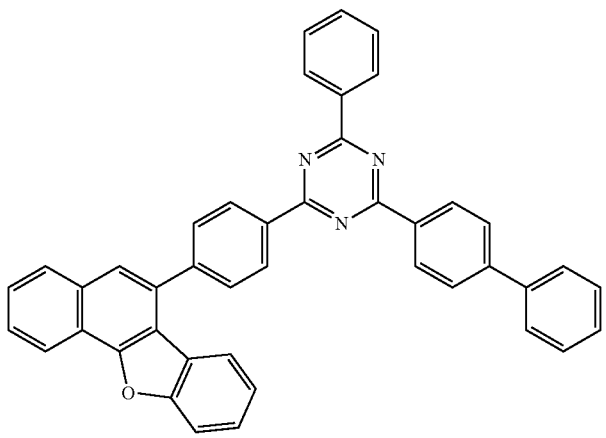
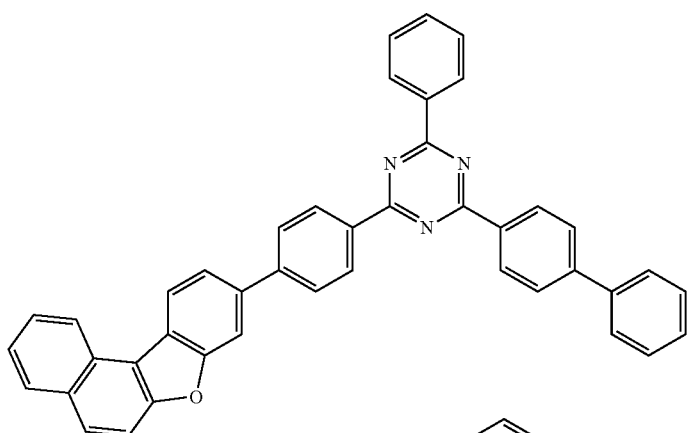
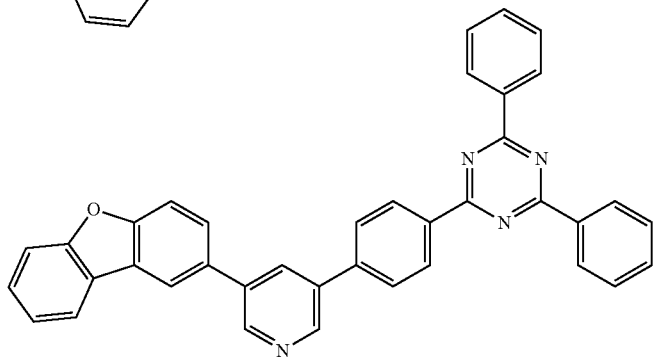

-continued
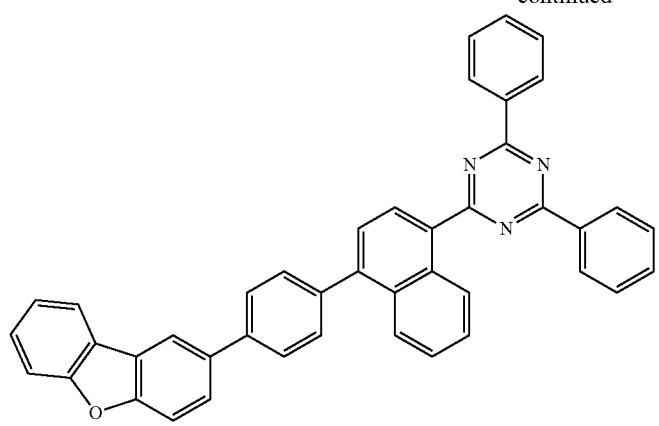
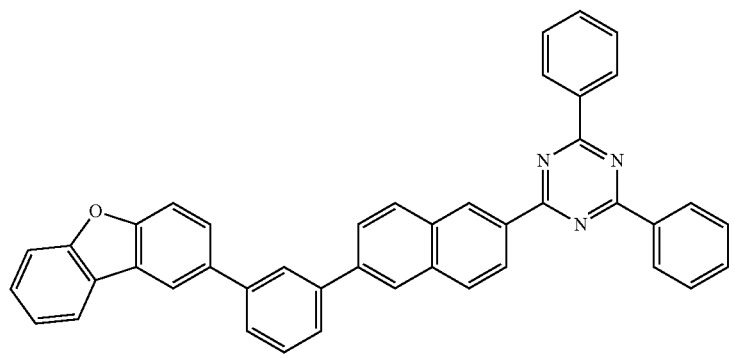
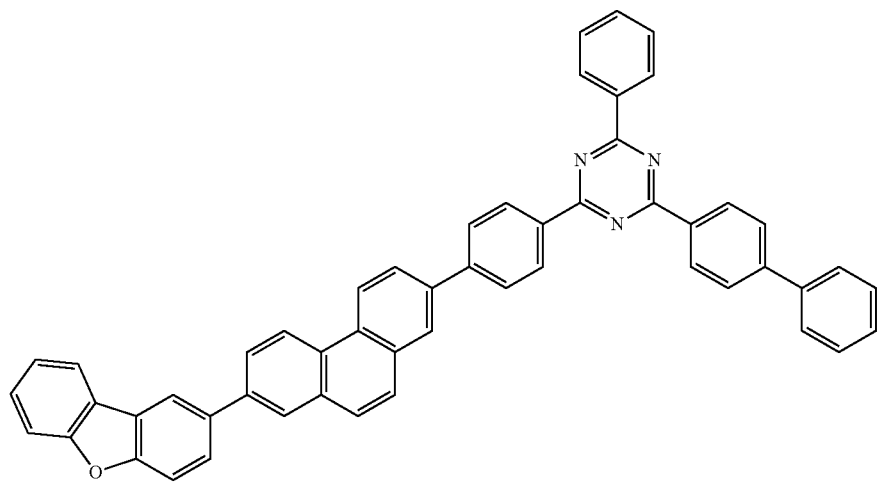
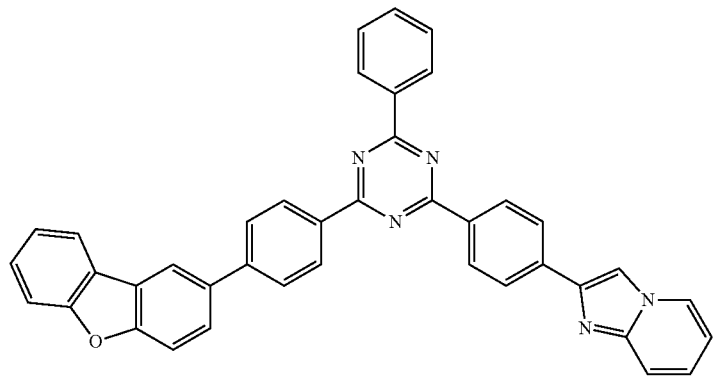

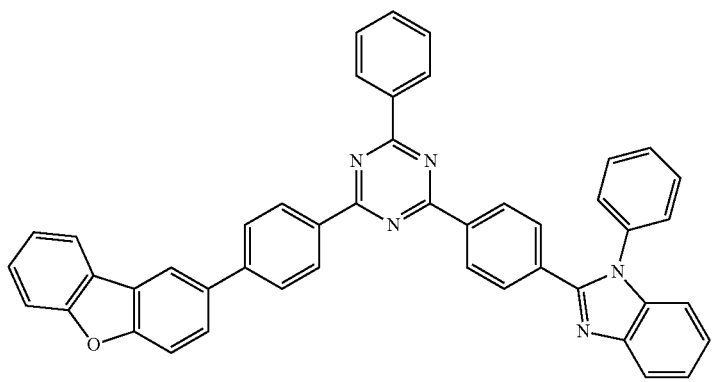
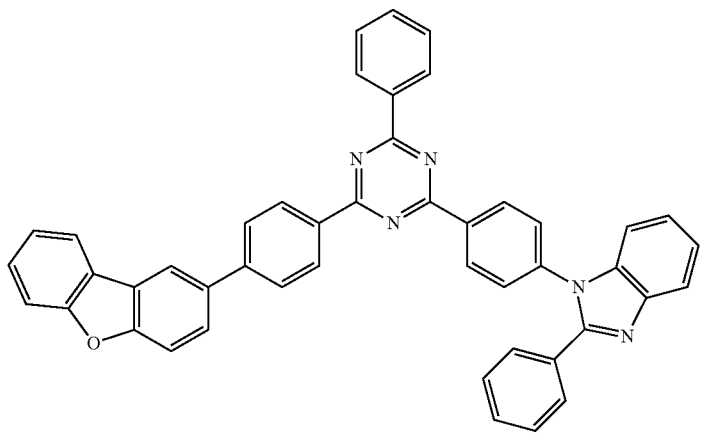
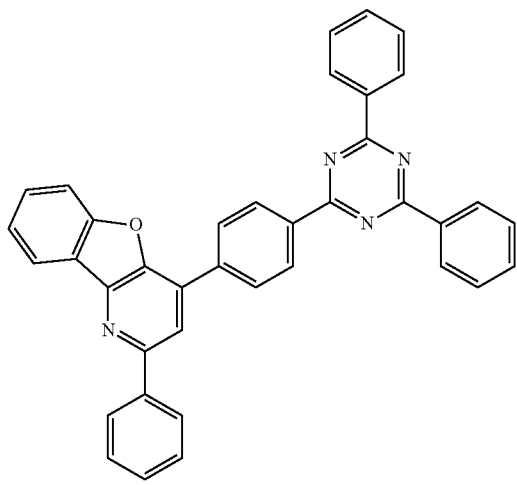
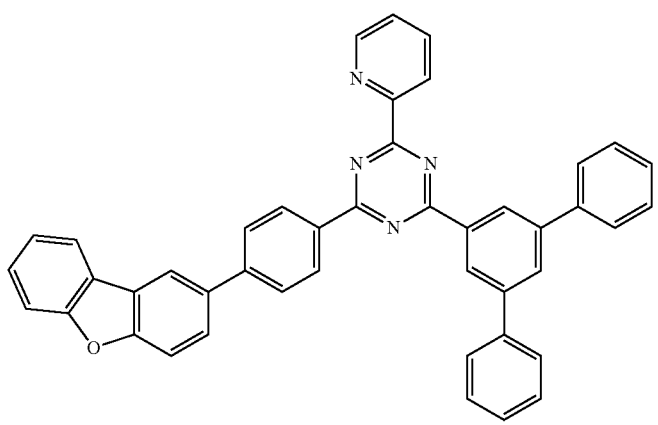

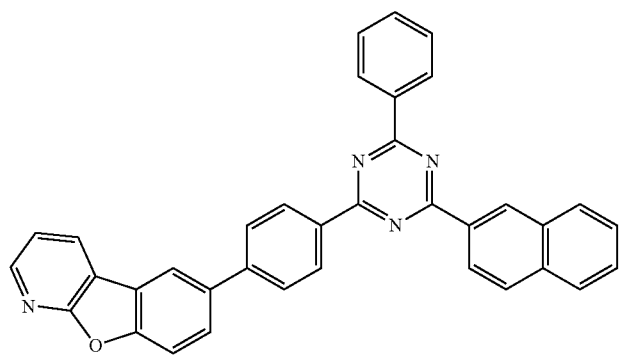
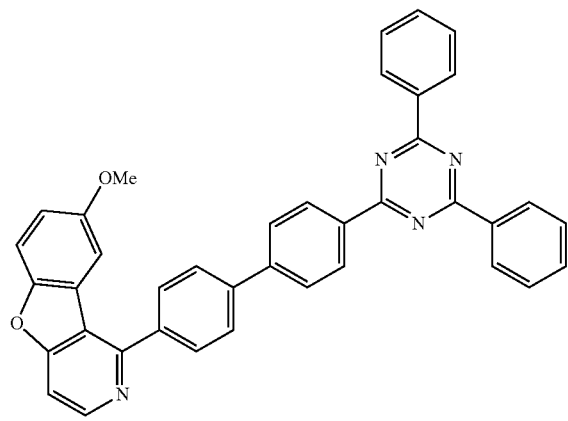
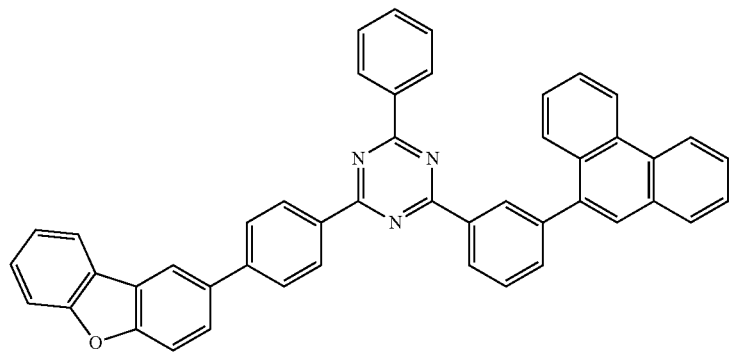
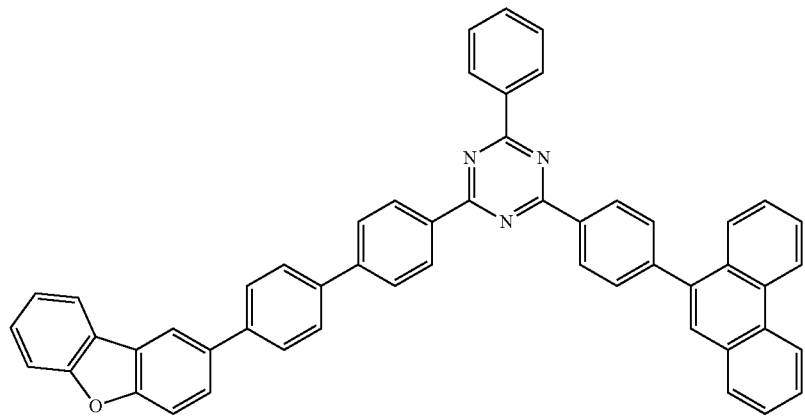

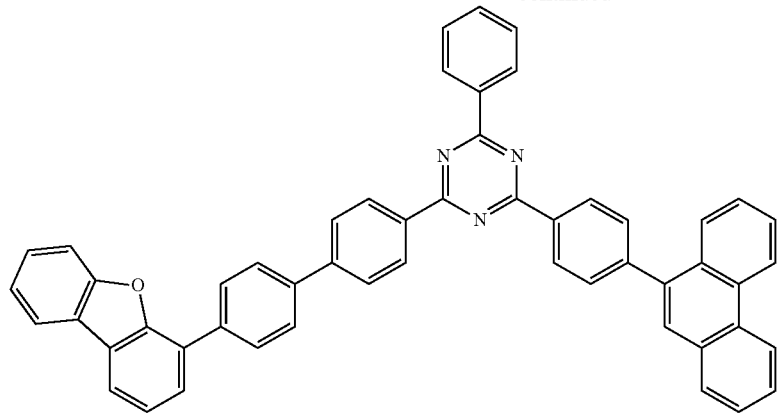
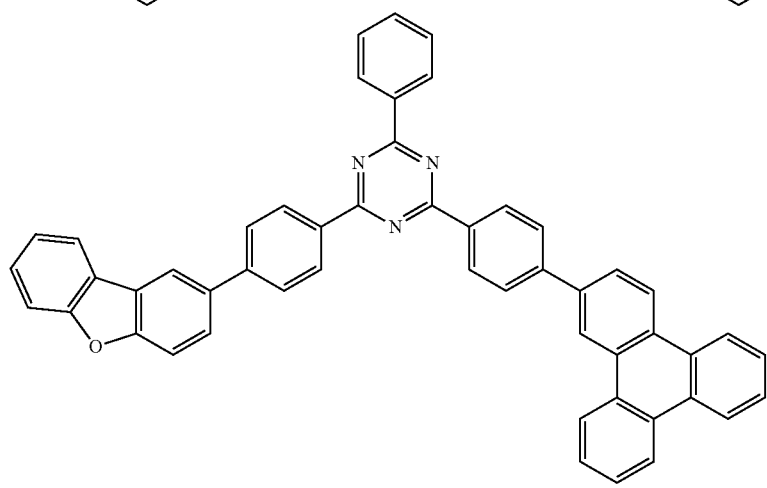
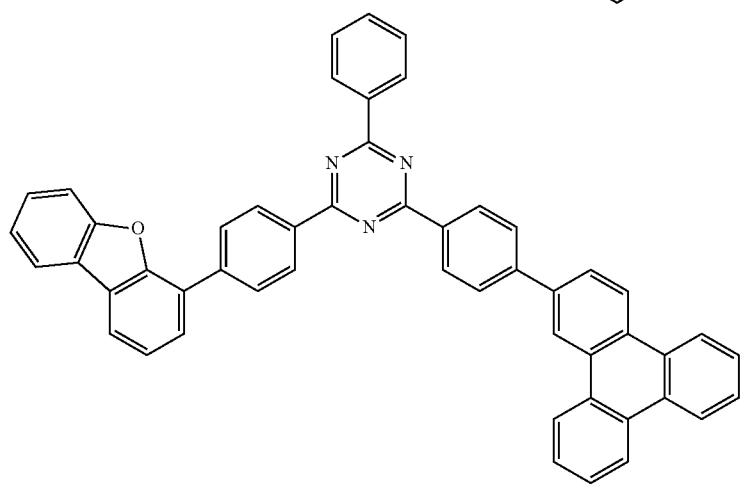
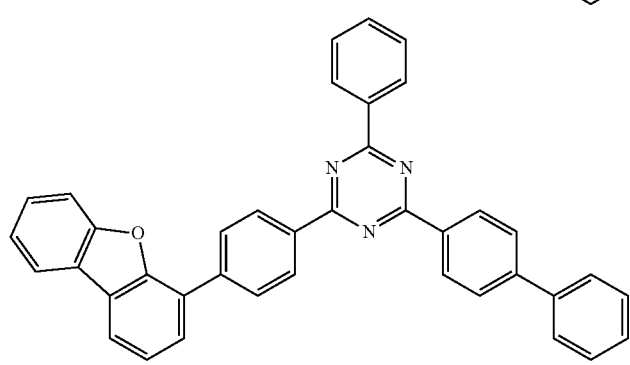

-continued
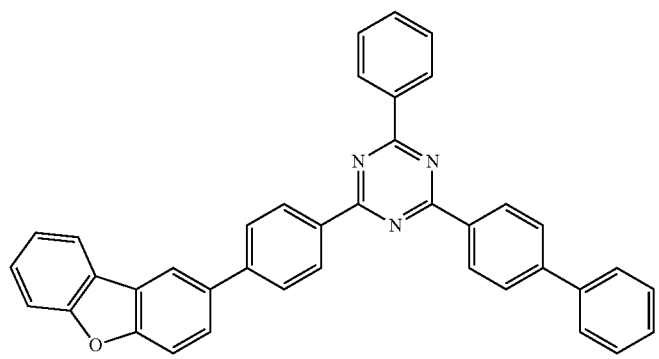
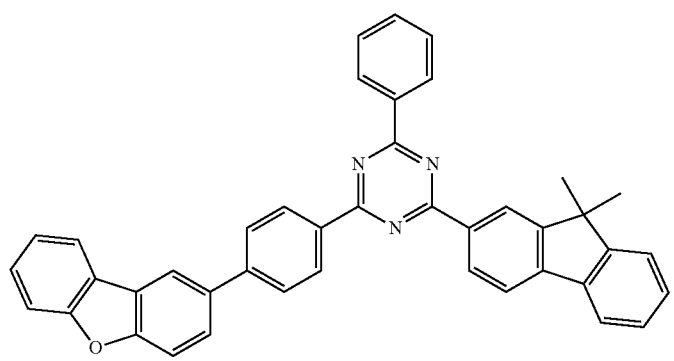
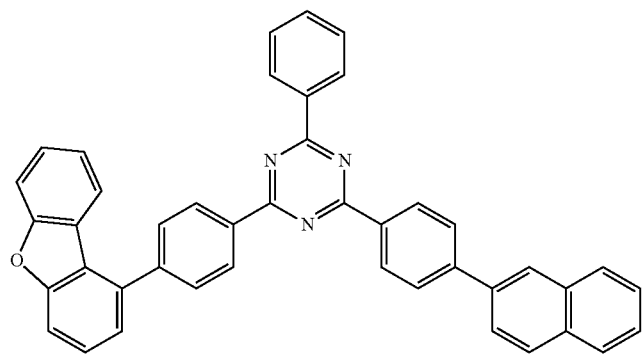
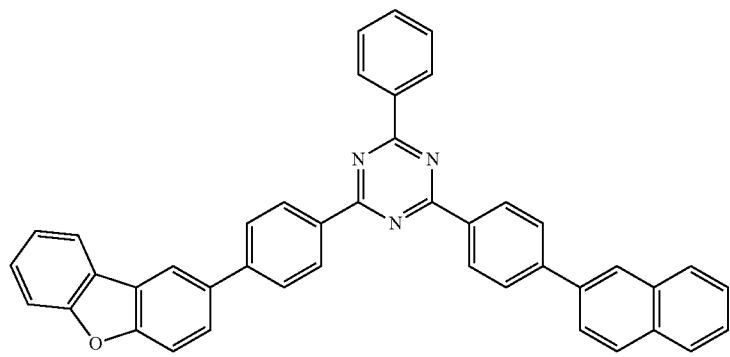

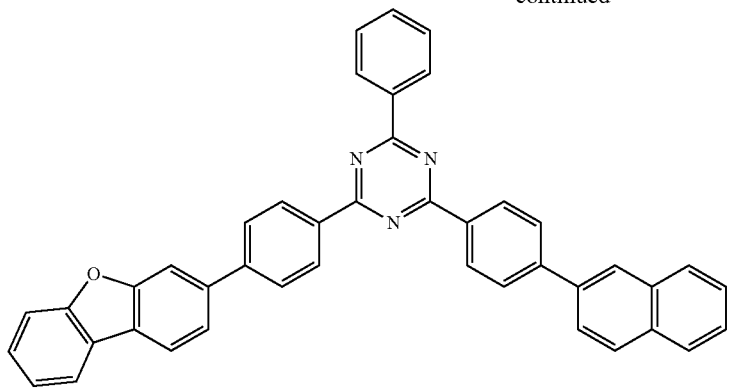
[Formula 77]
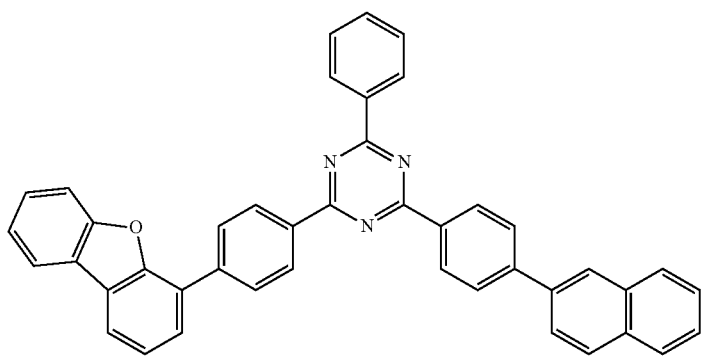
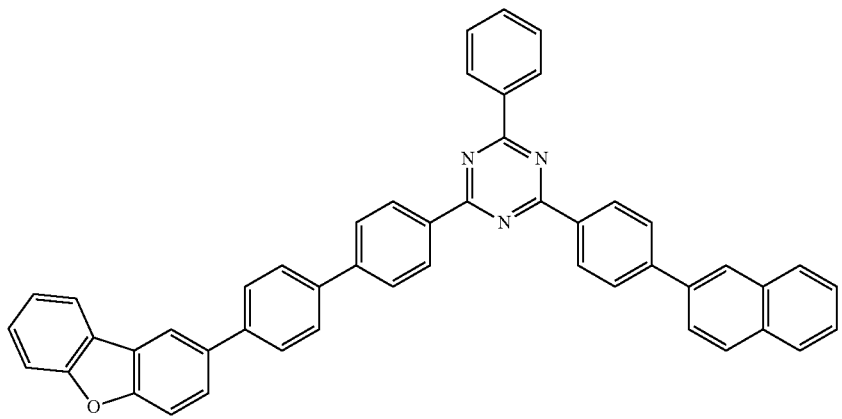
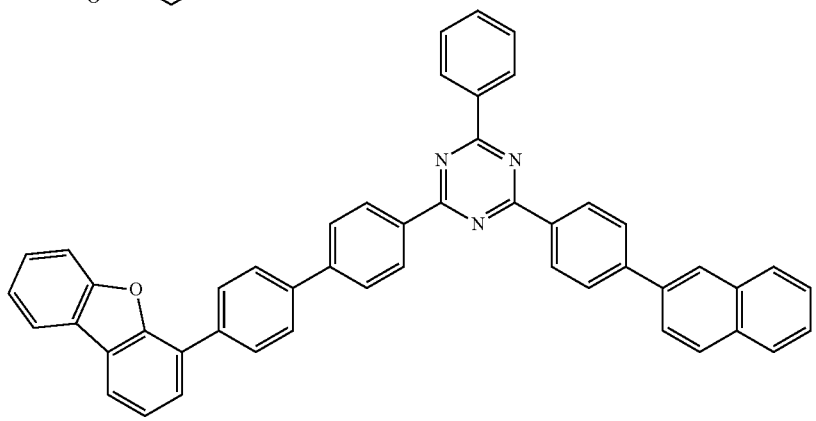

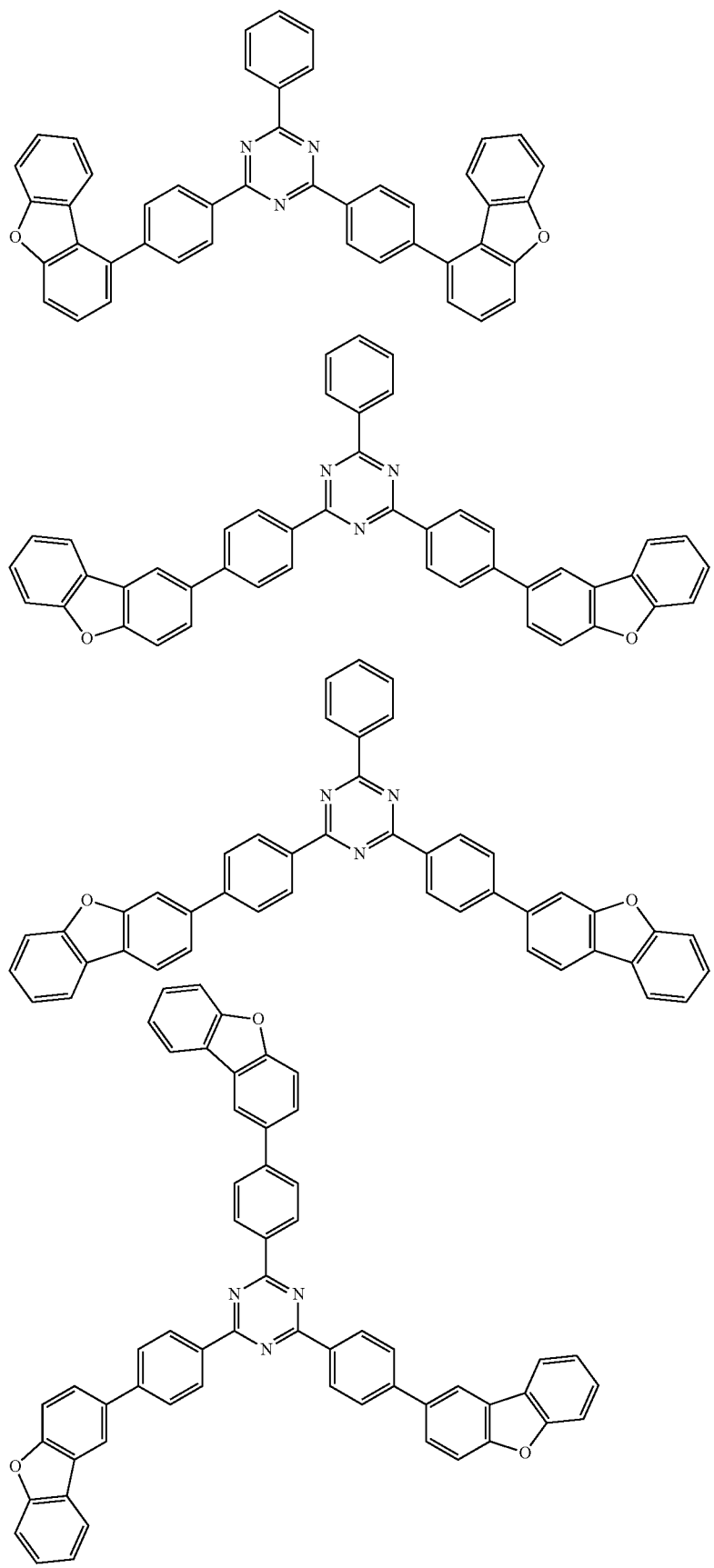

-continued
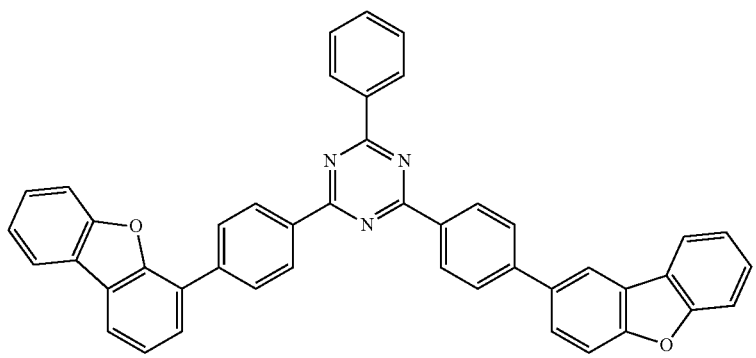
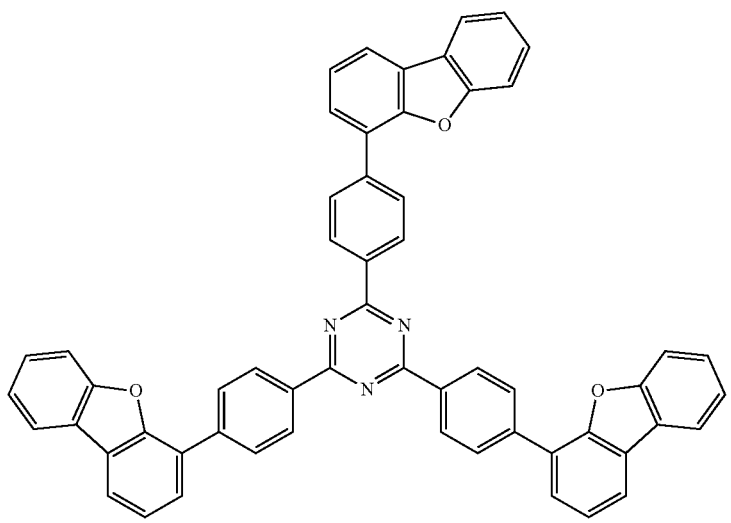
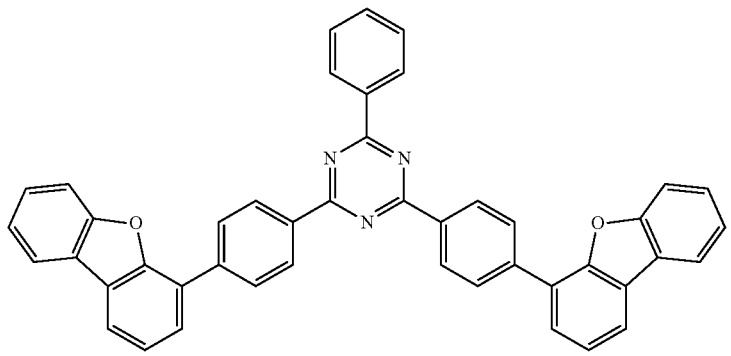
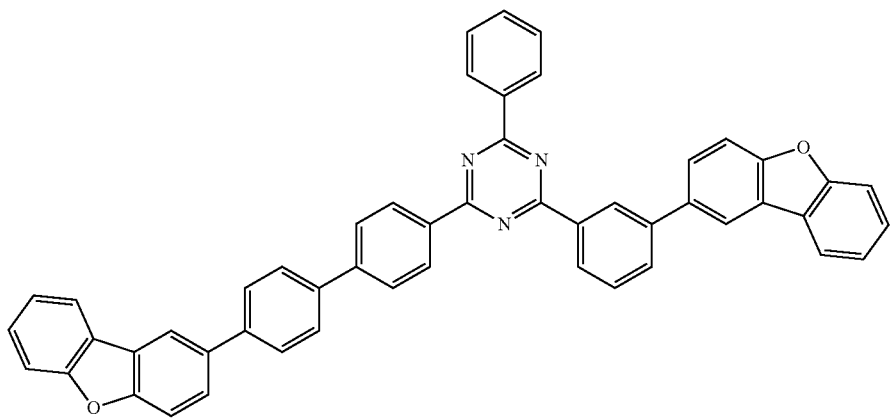

-continued
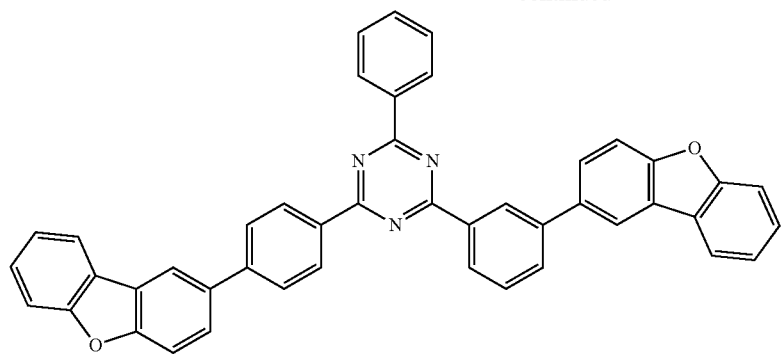
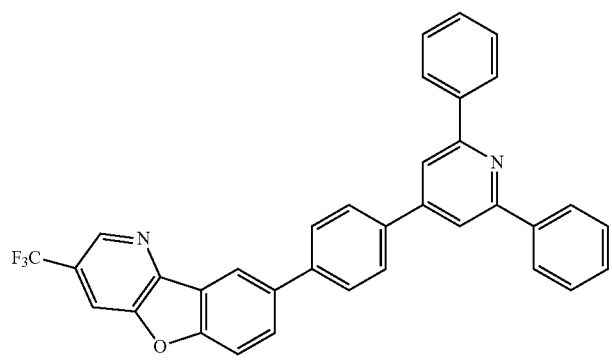
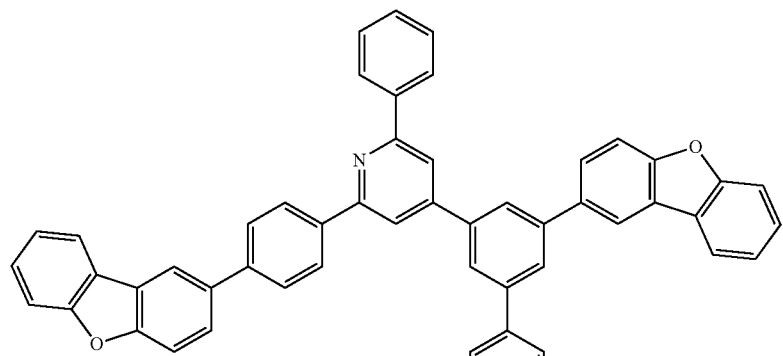
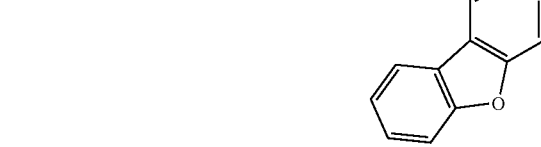
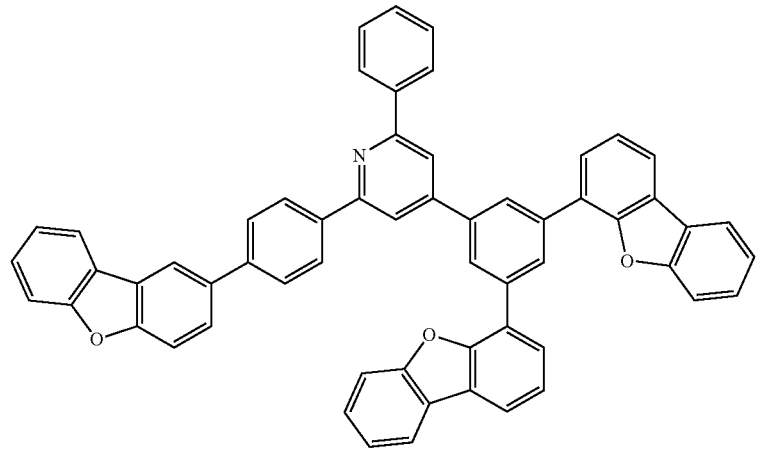

295
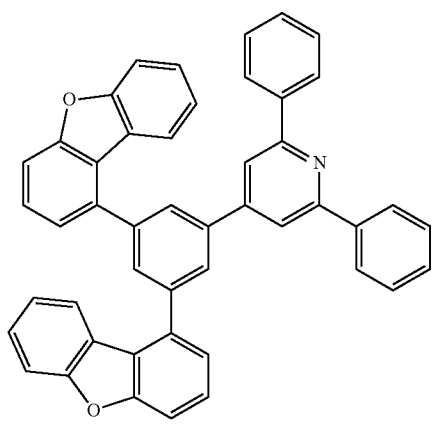
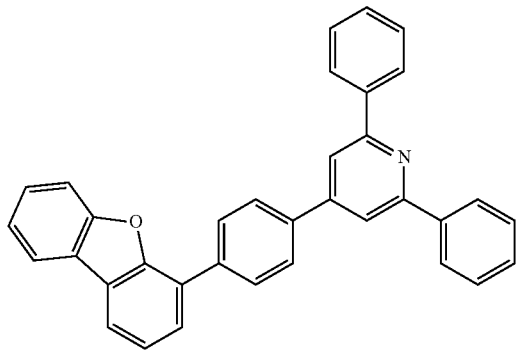
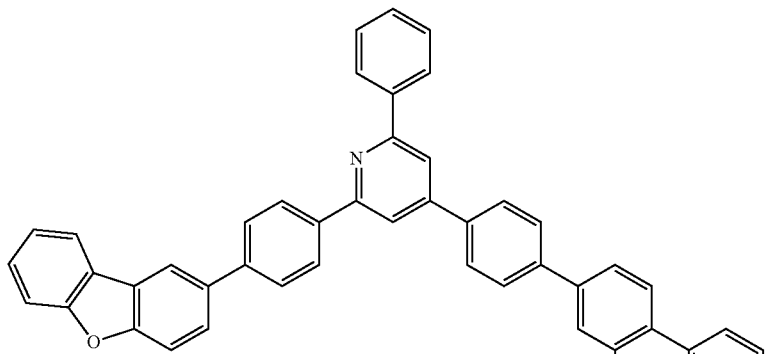
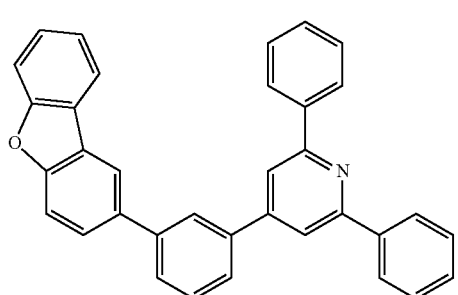
-continued
296
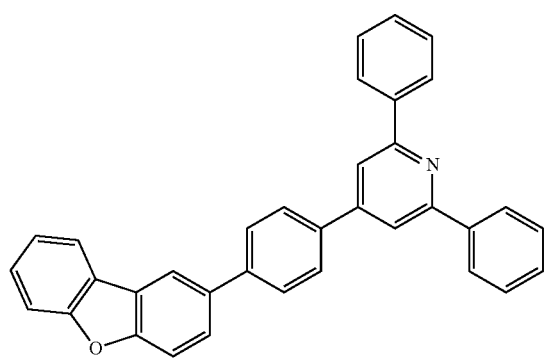
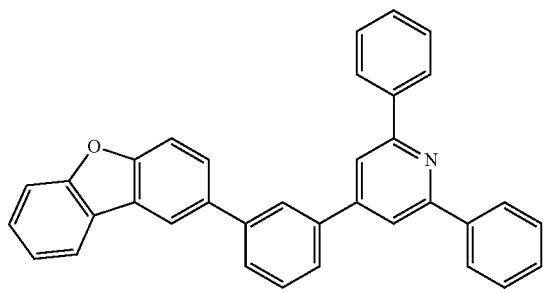
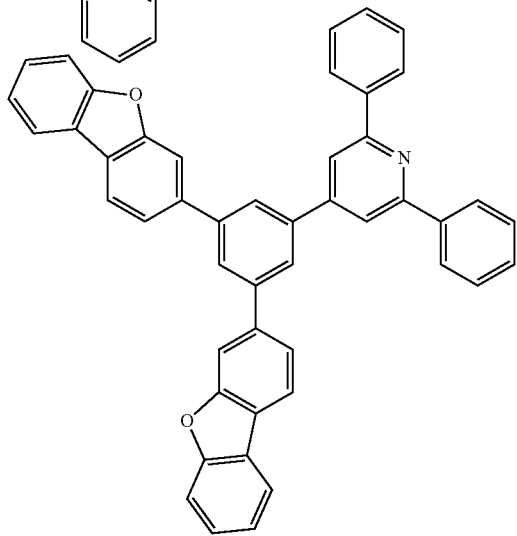

-continued
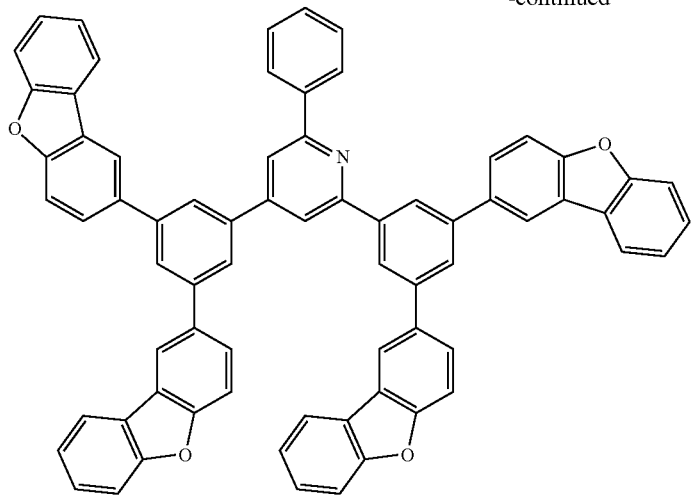
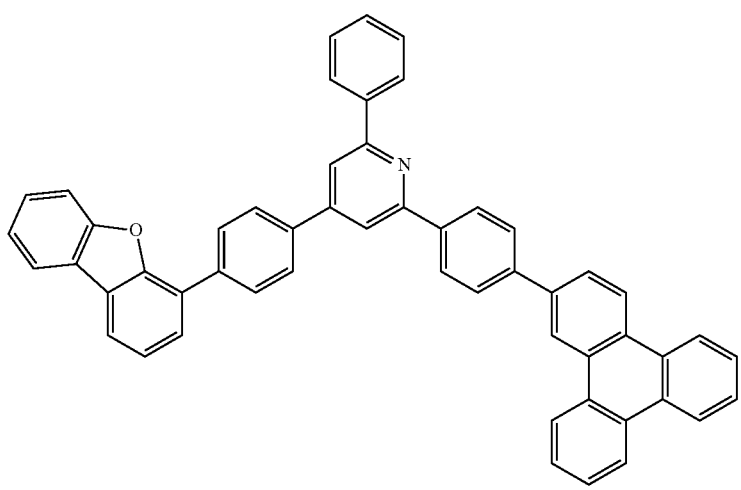
[Formula 78]
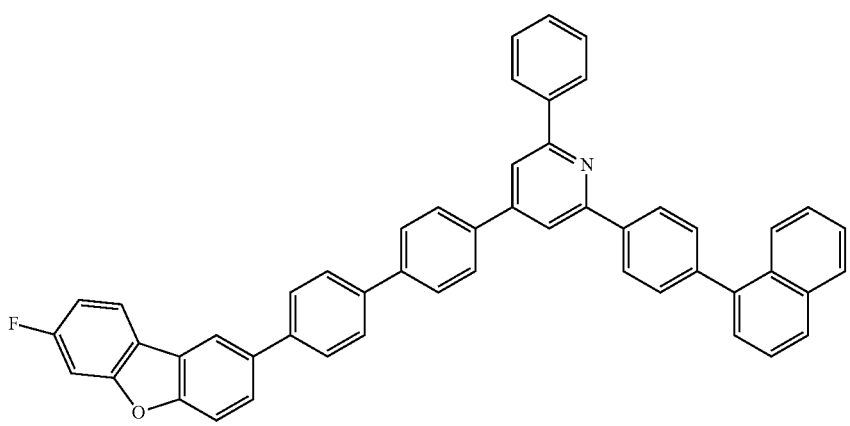

-continued
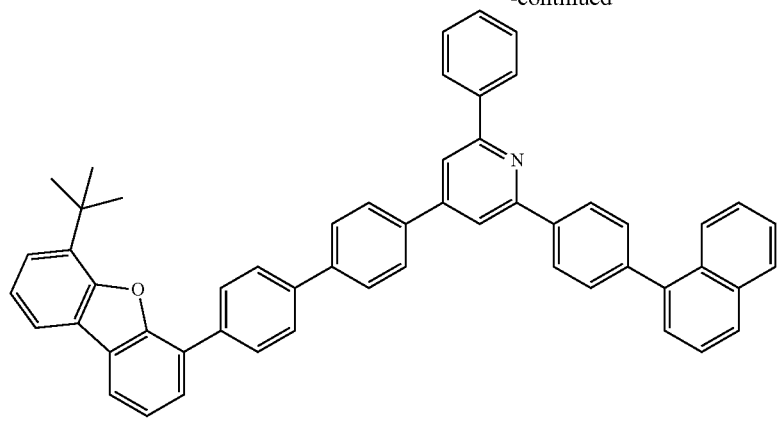
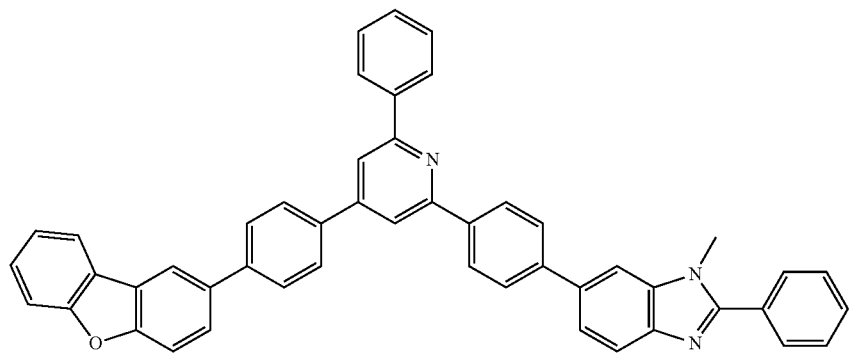
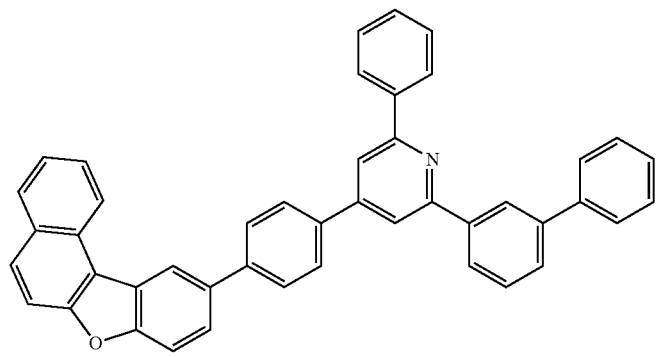
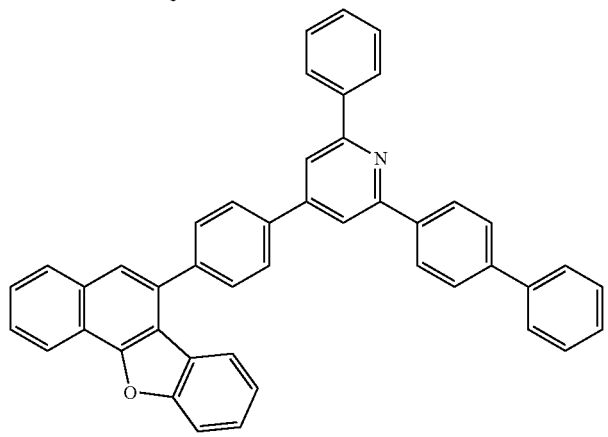

-continued
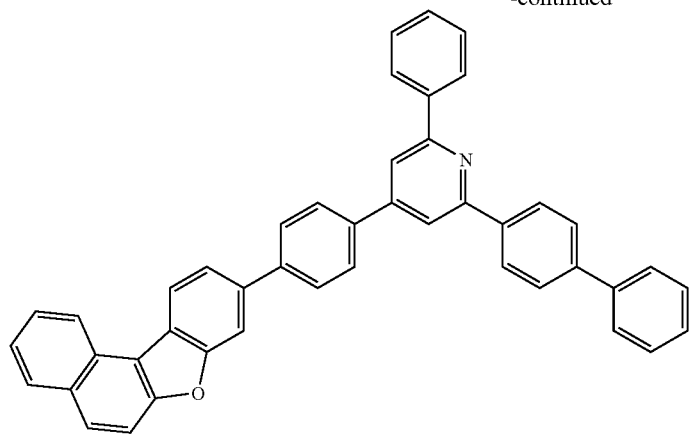
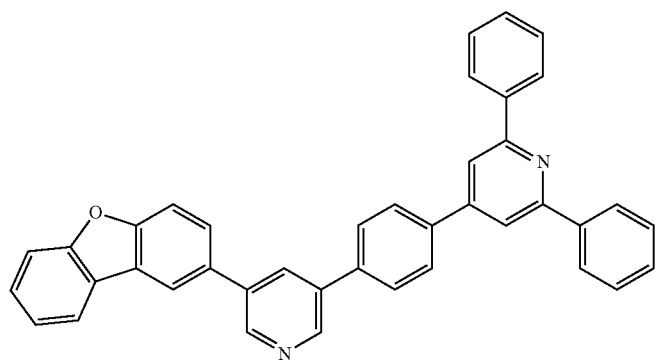
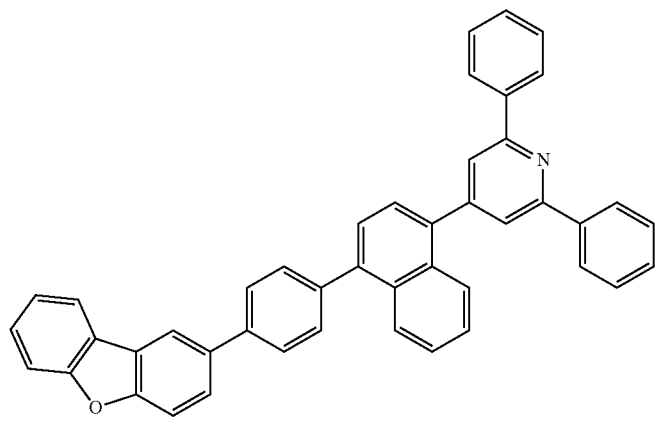
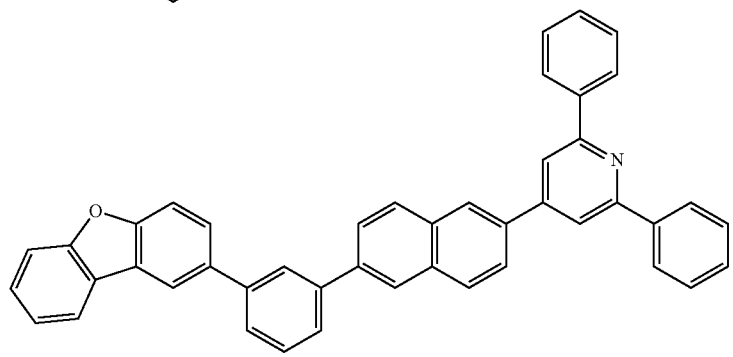

-continued
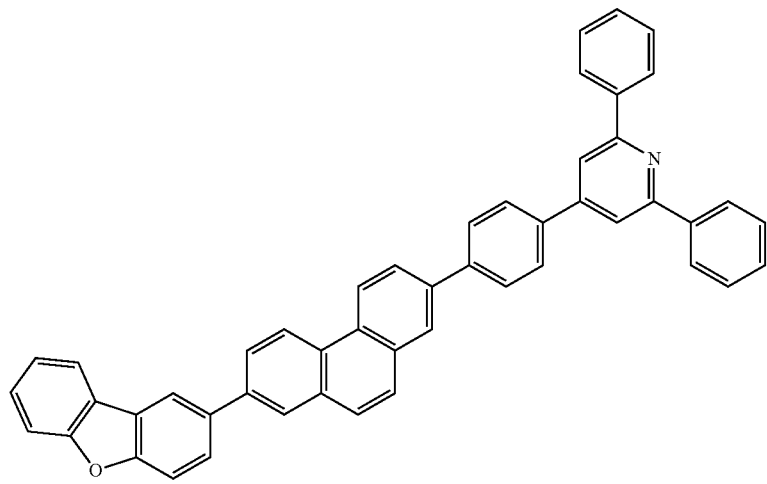
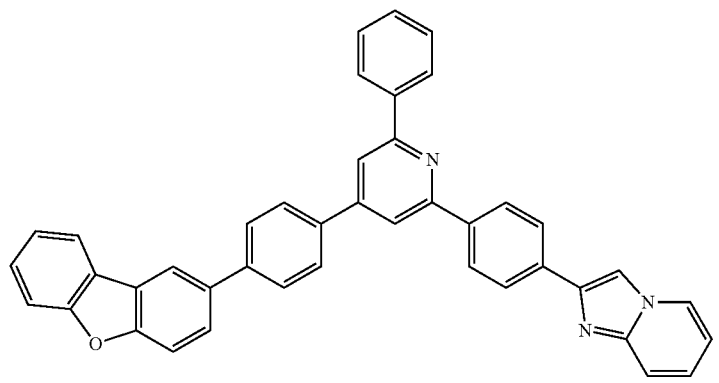
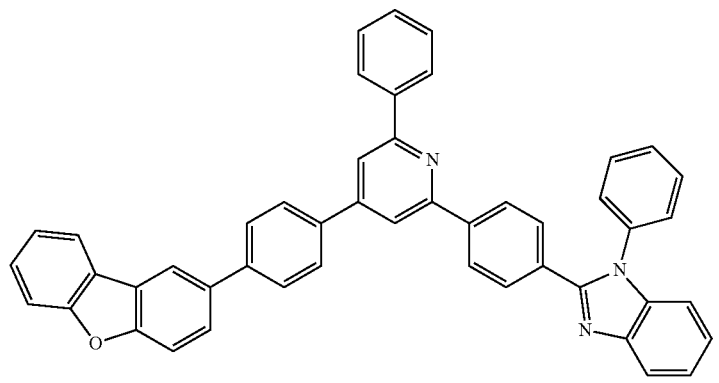
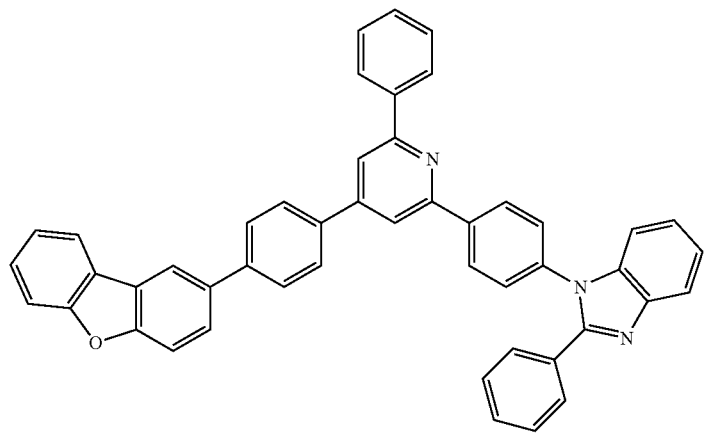

-continued
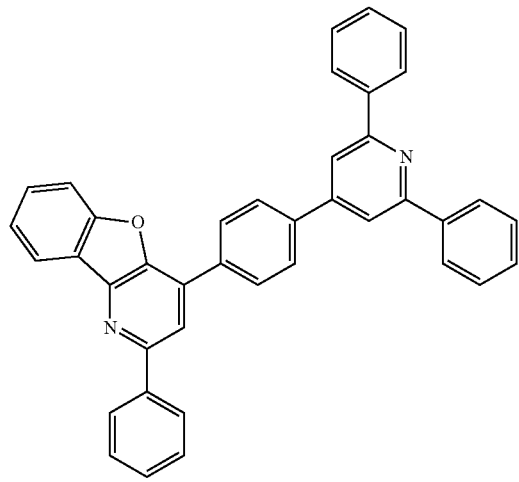
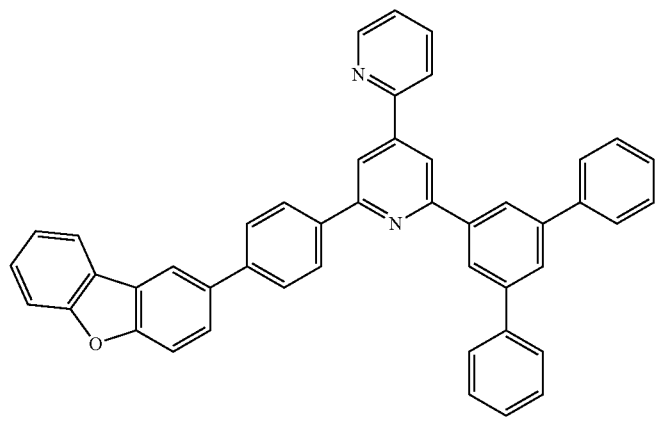
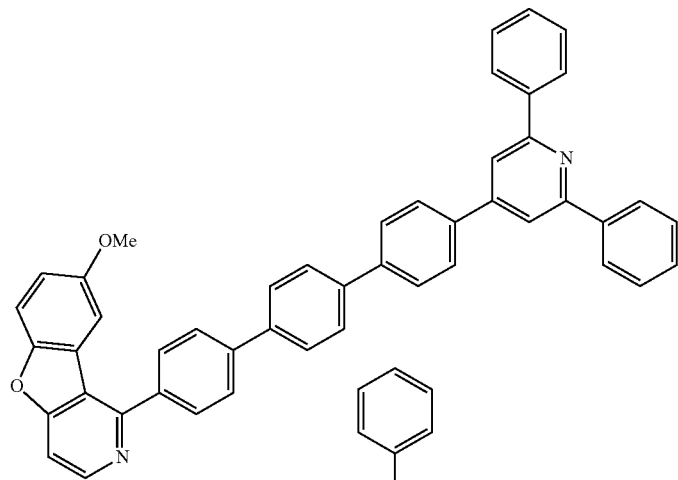
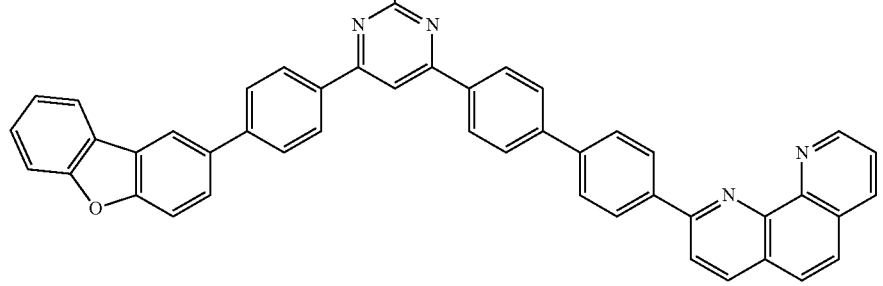

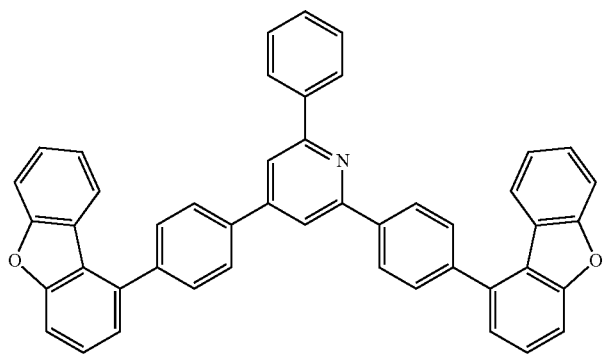
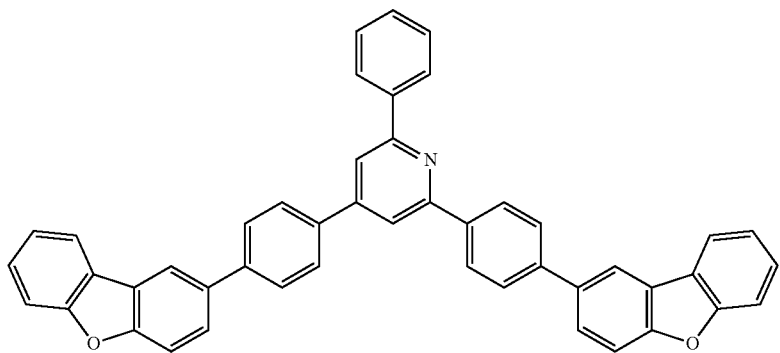
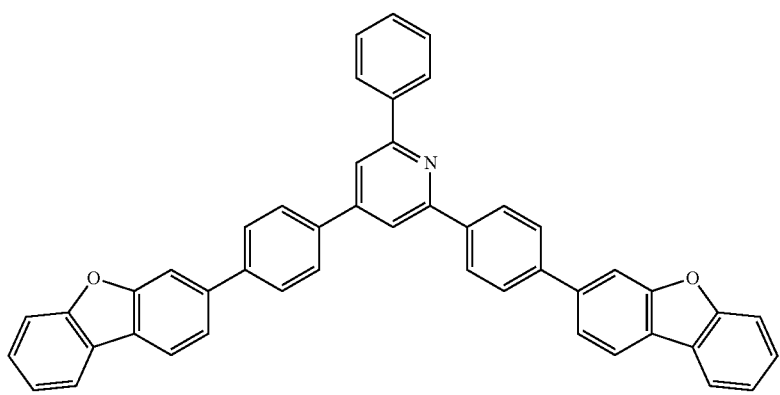
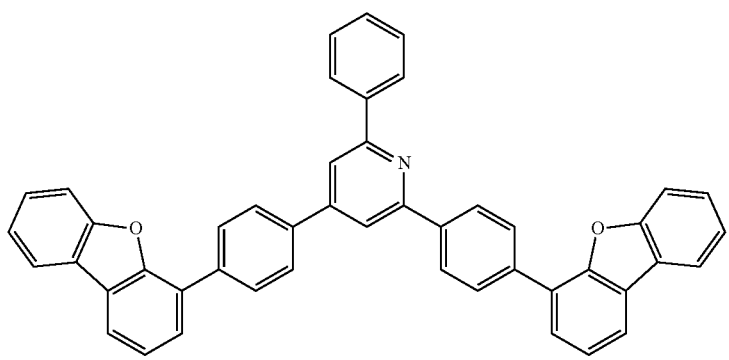

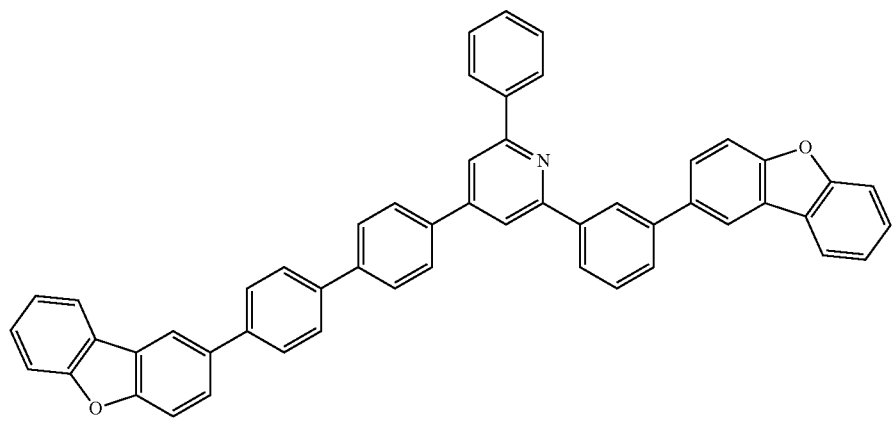
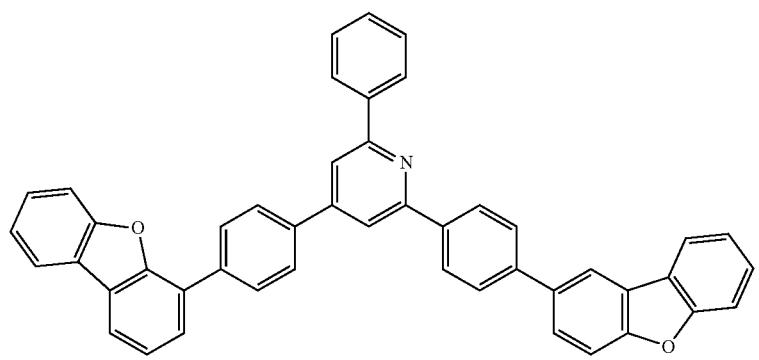
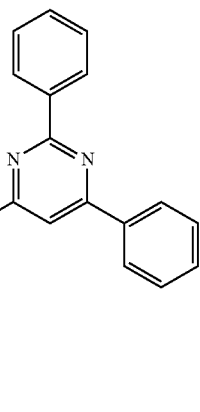
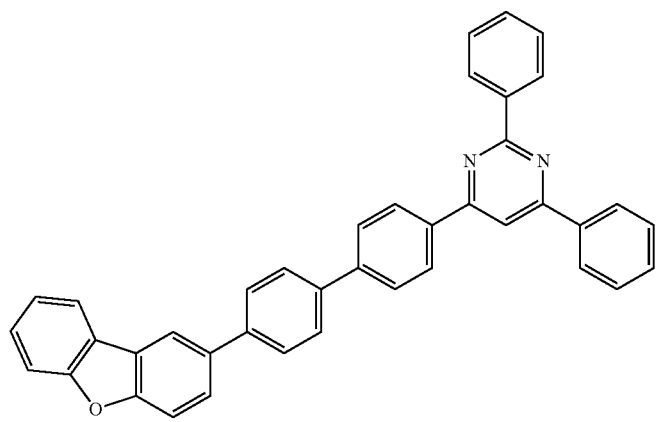

-continued
311
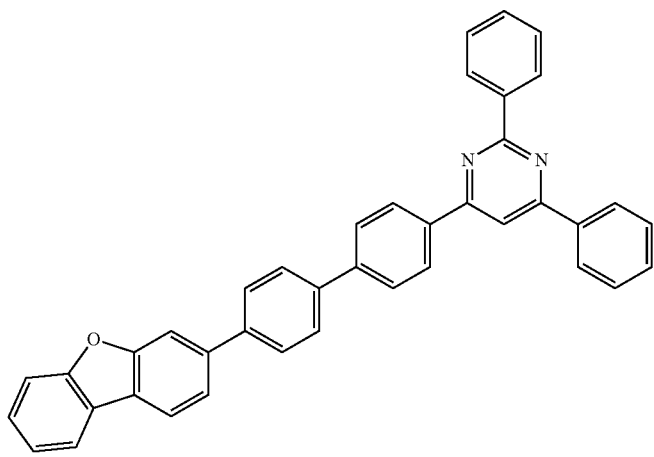
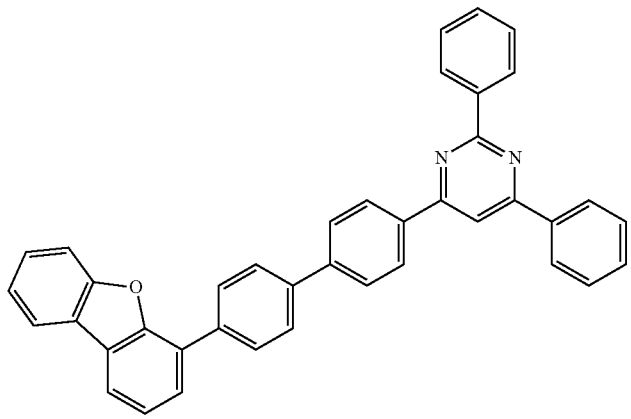
[Formula 79]
312
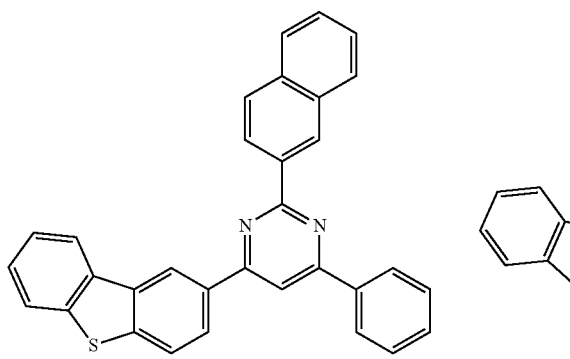 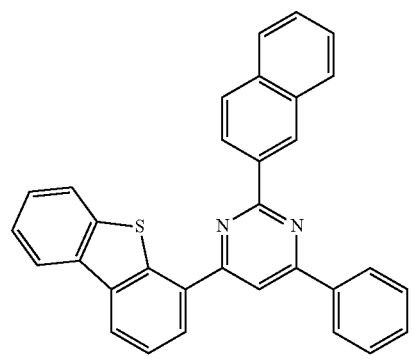
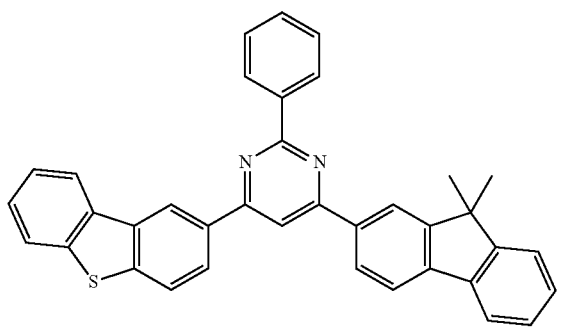 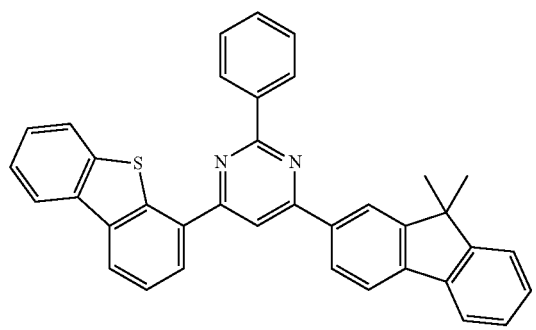

-continued
313
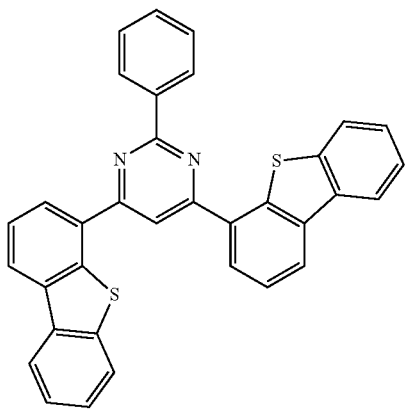
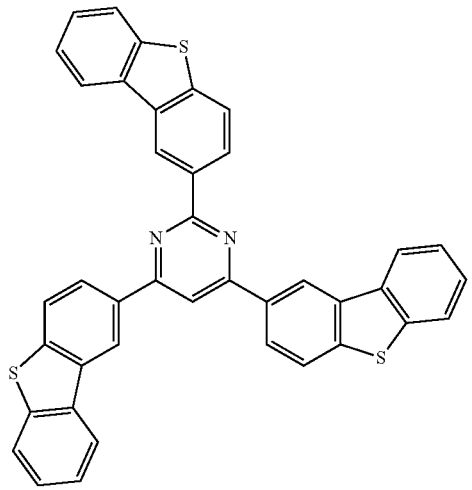
314
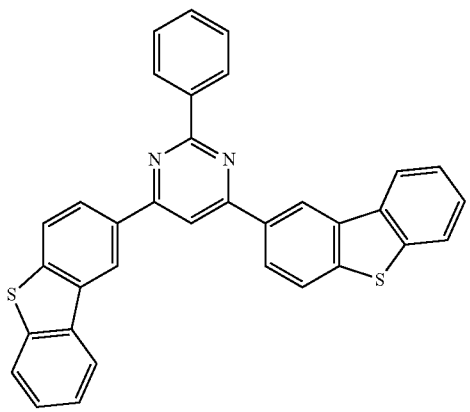
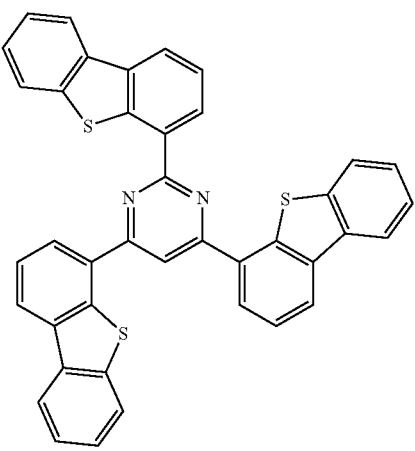
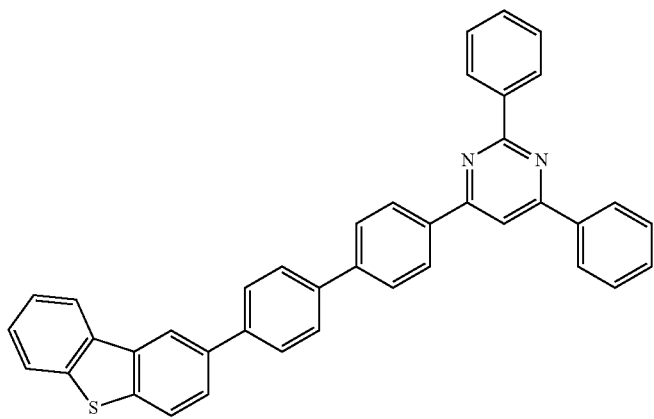
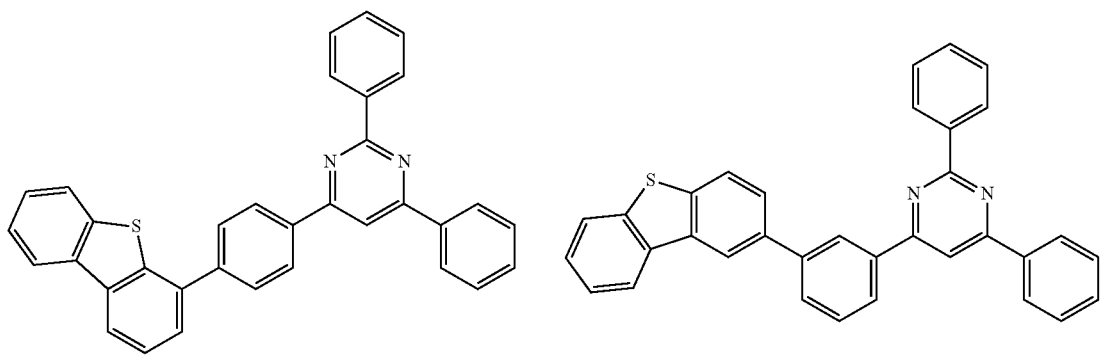

-continued
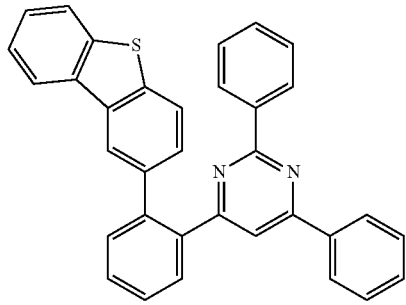
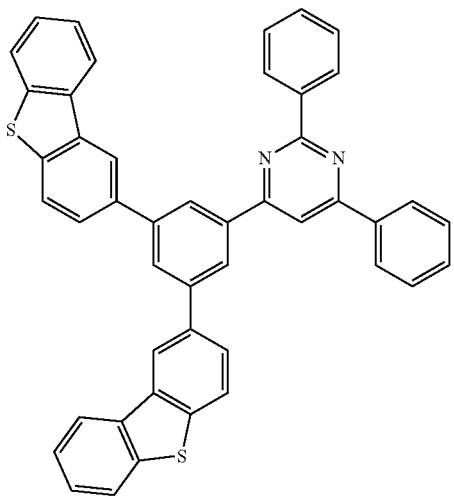
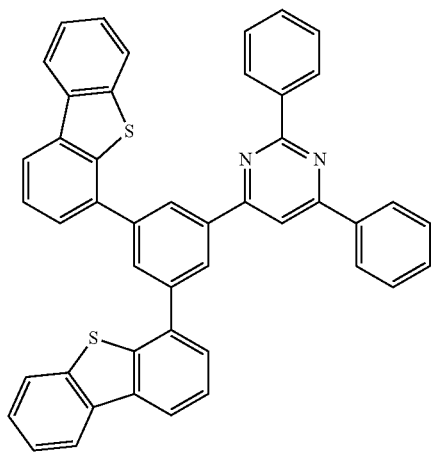
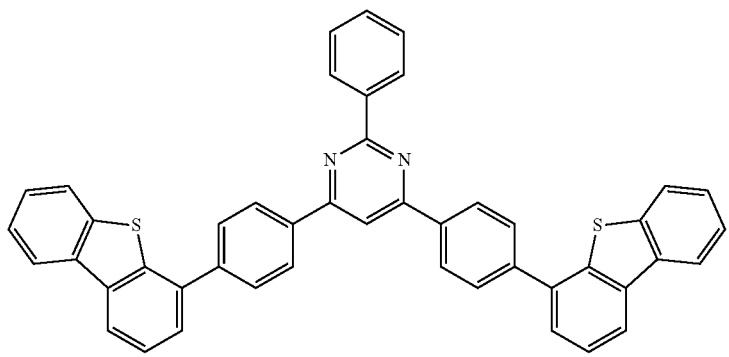
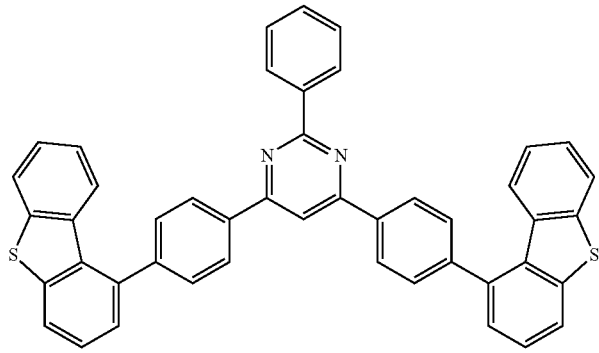

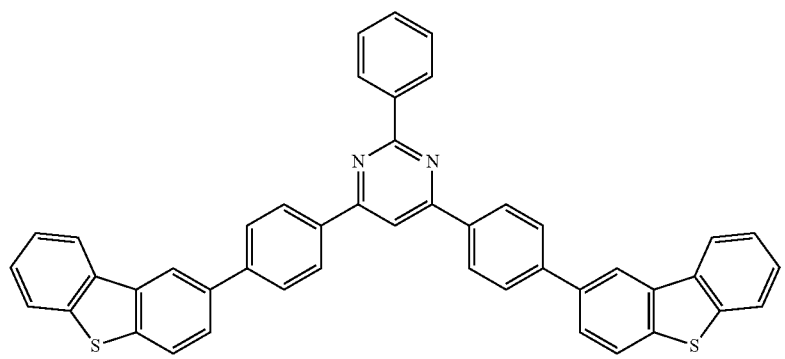
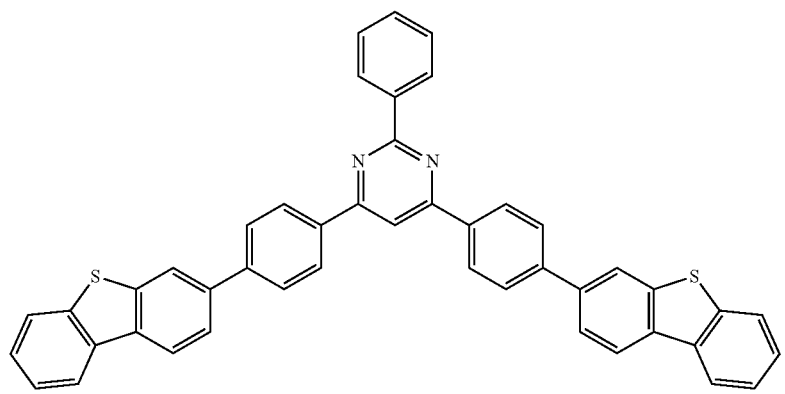
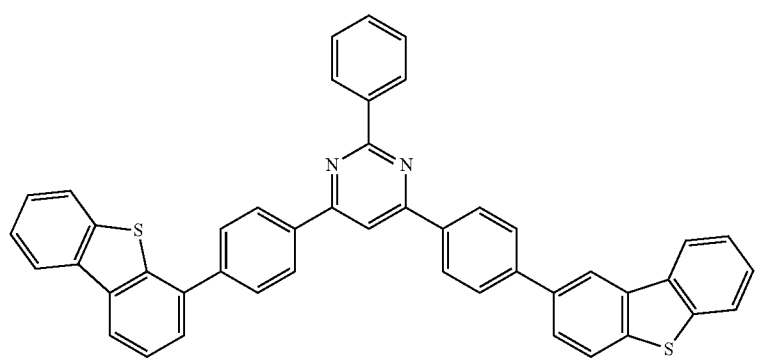
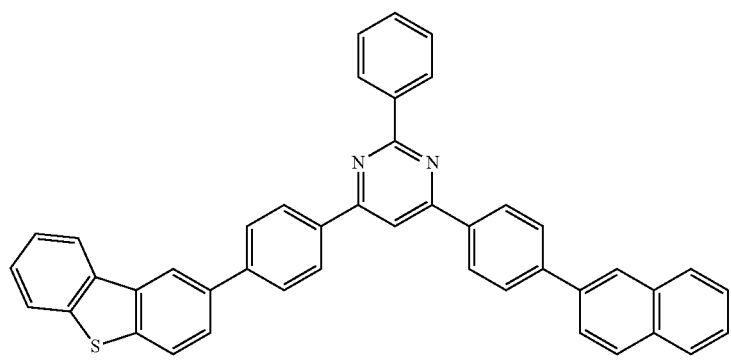

-continued
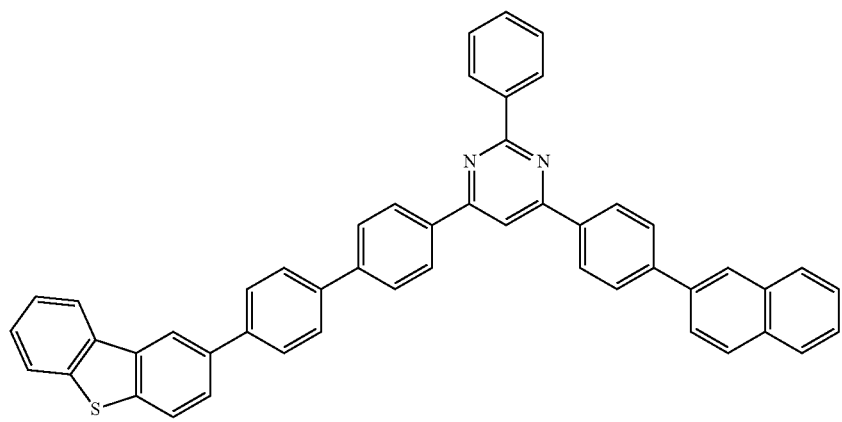
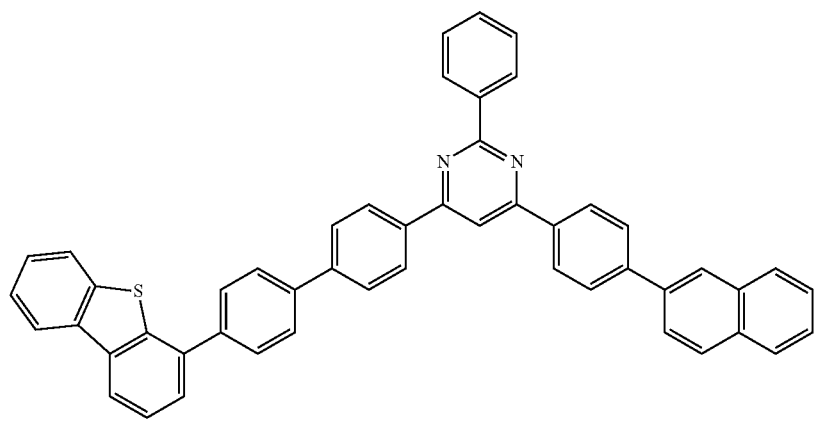
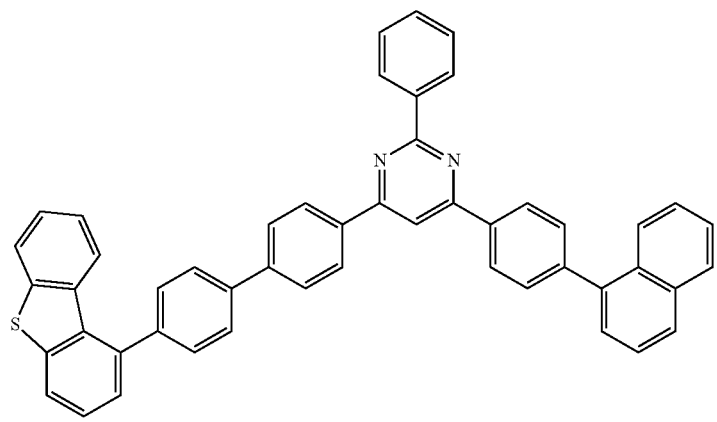
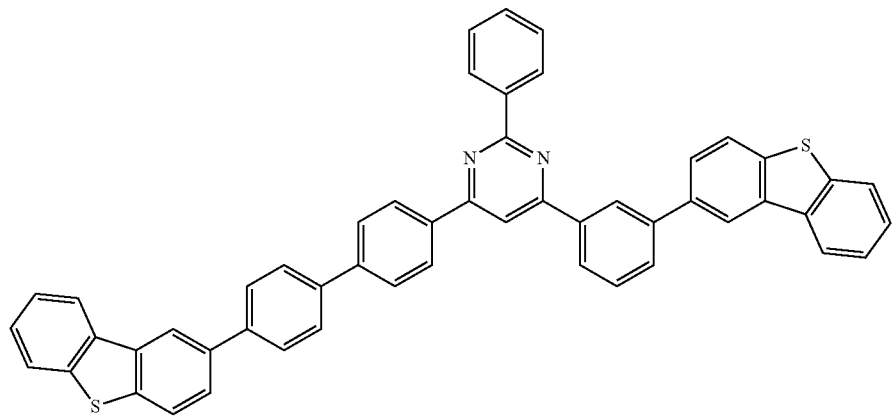

-continued
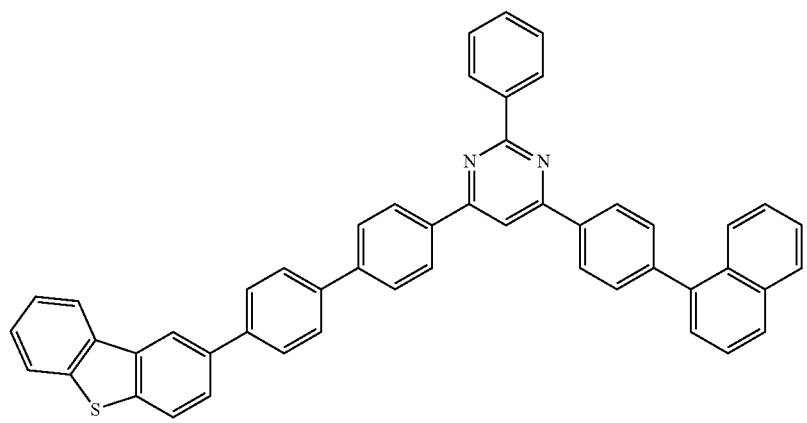
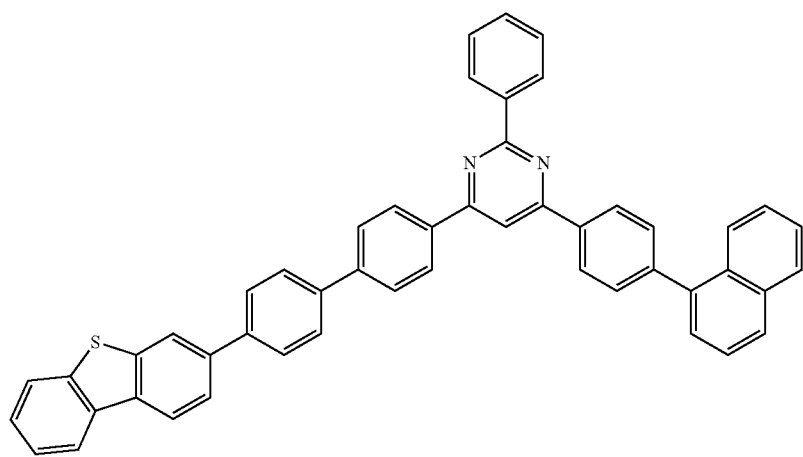
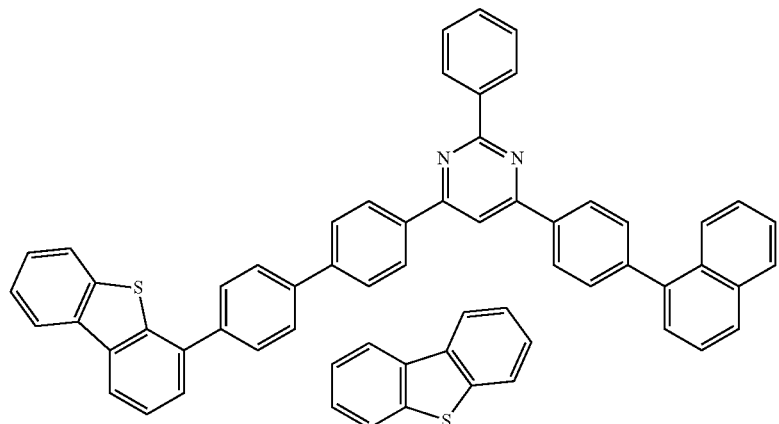
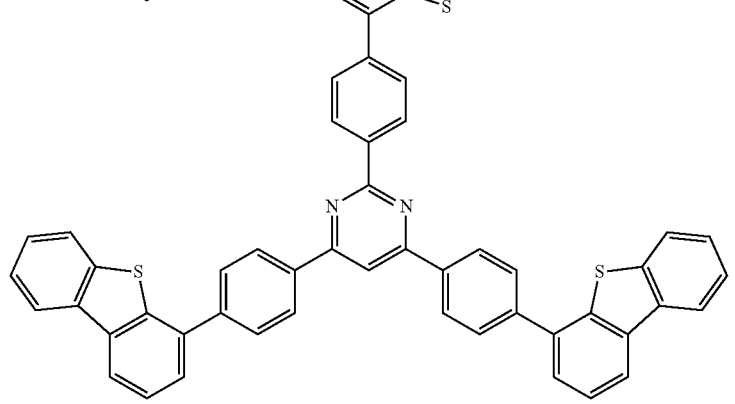

323
324
-continued
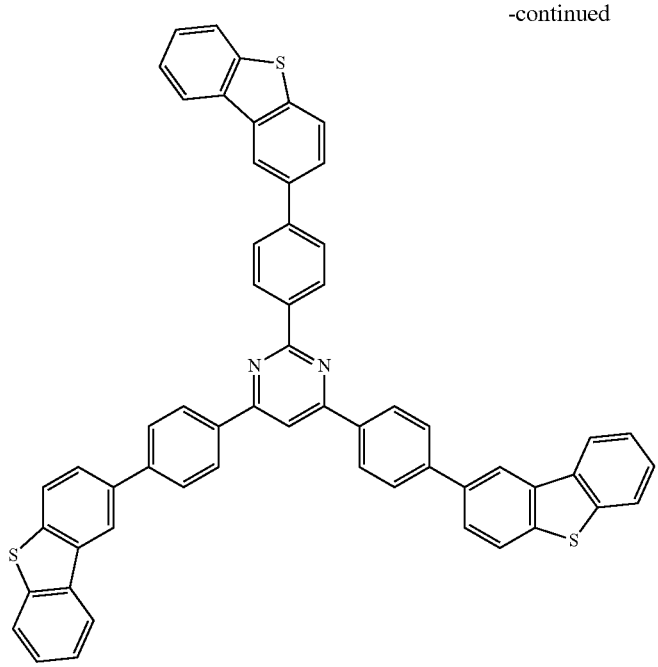
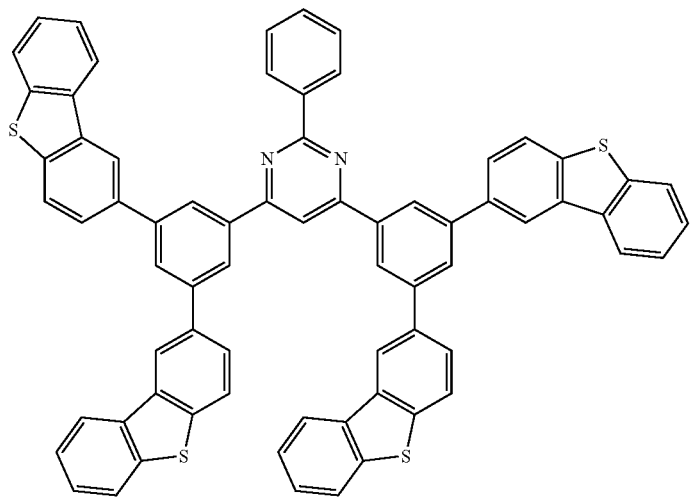
[Formula 80]
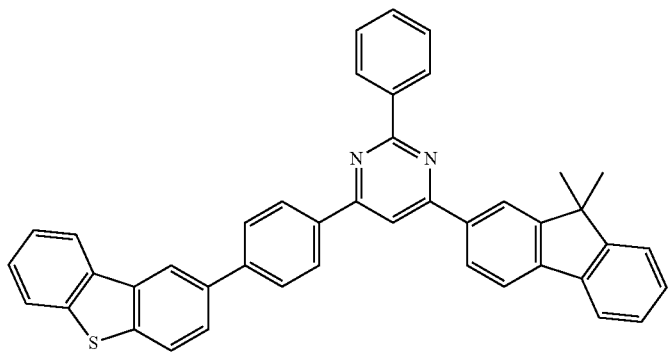

-continued
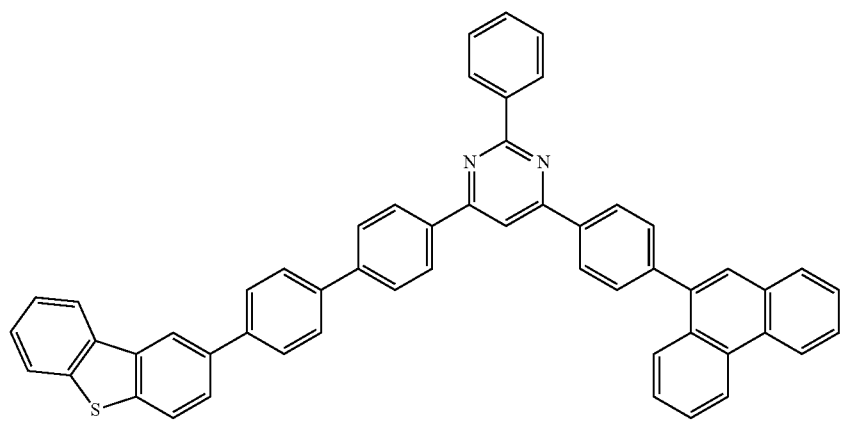
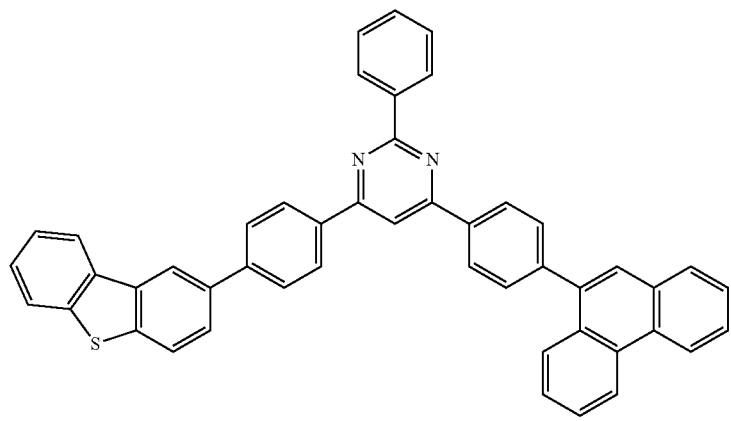
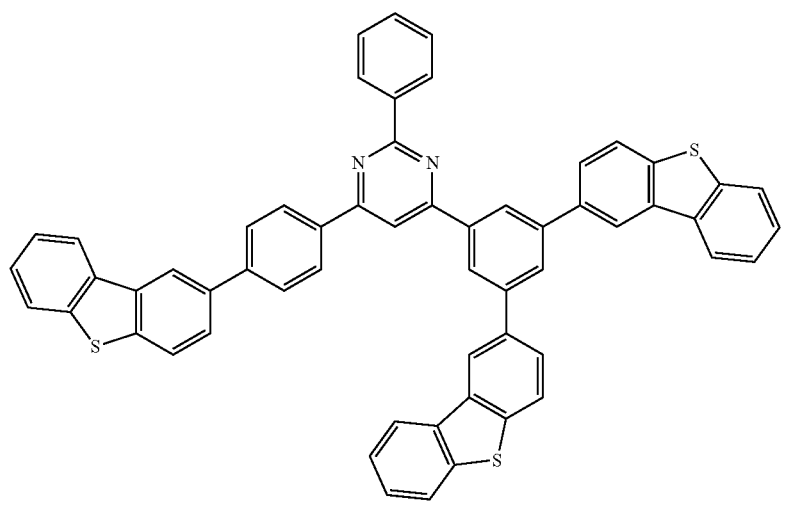

-continued
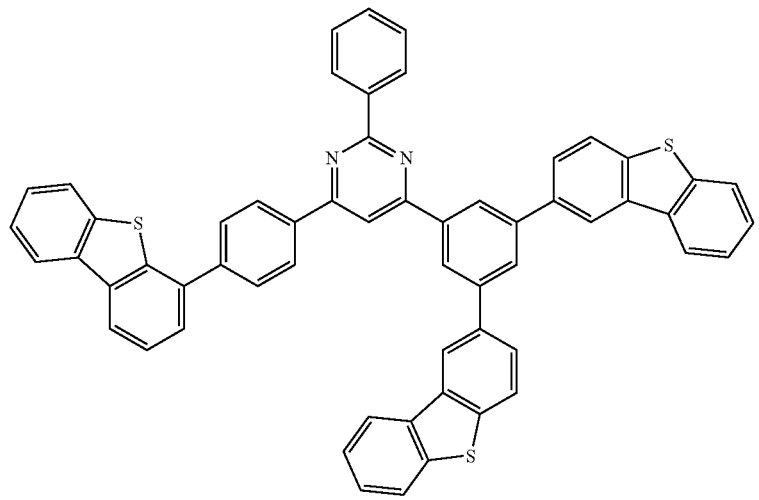
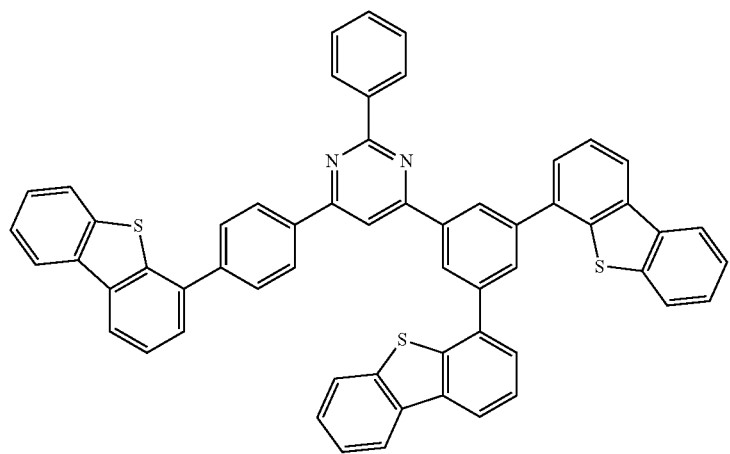
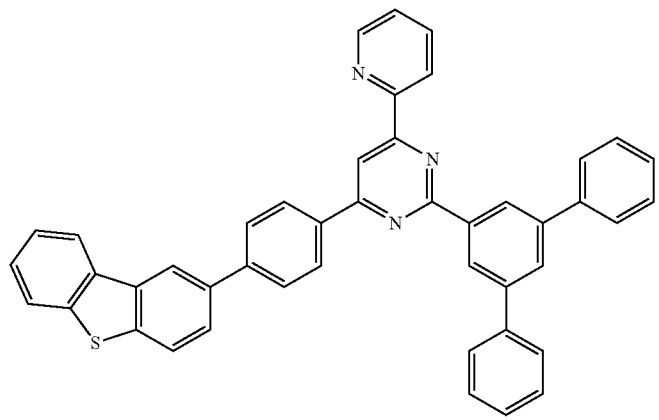

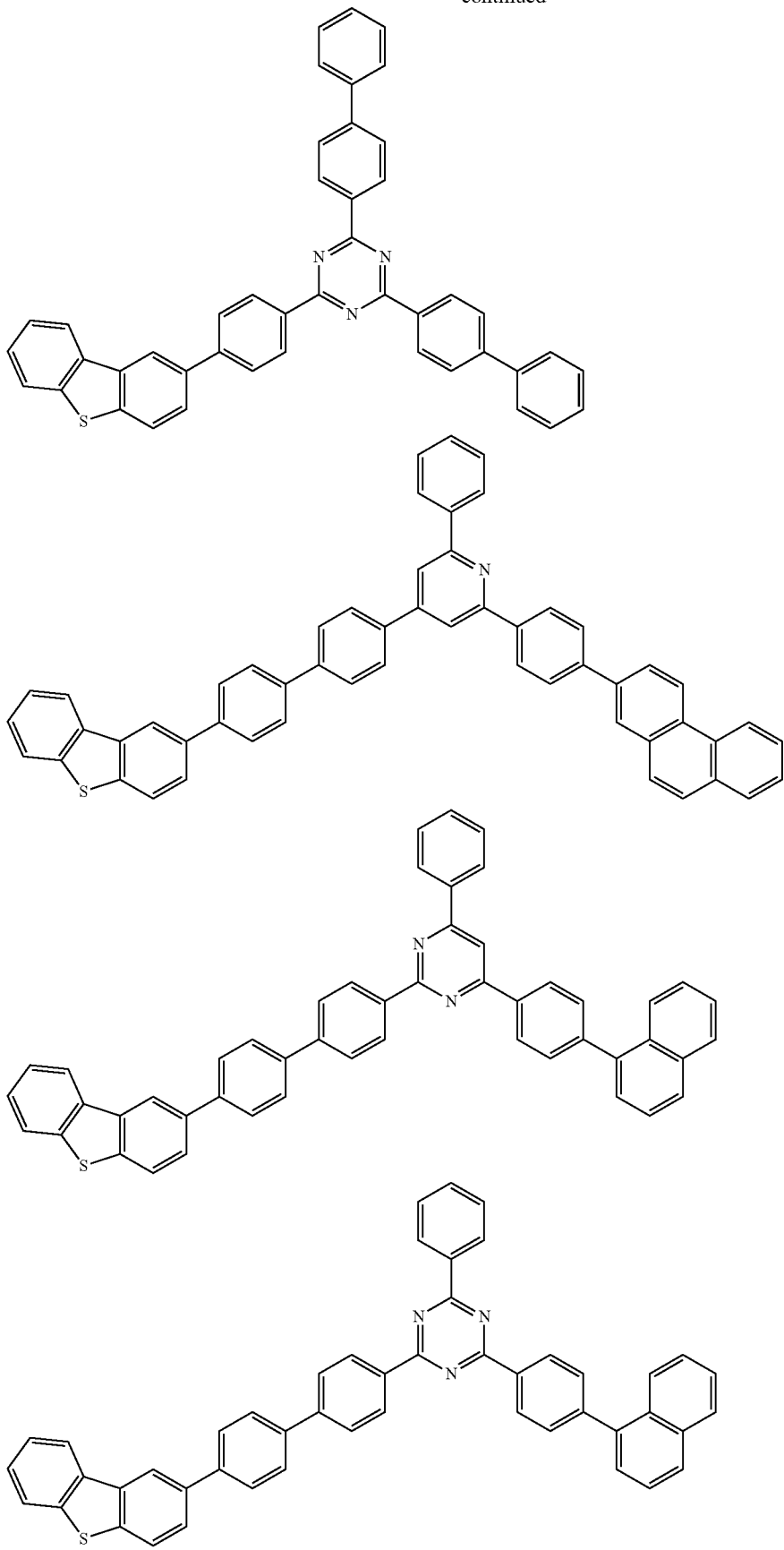

-continued
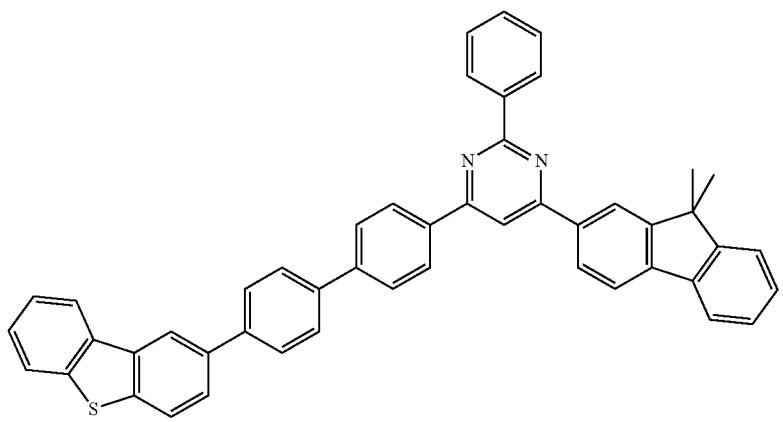
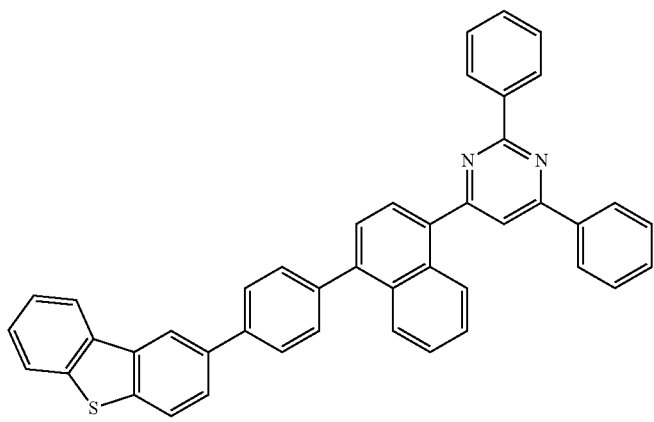
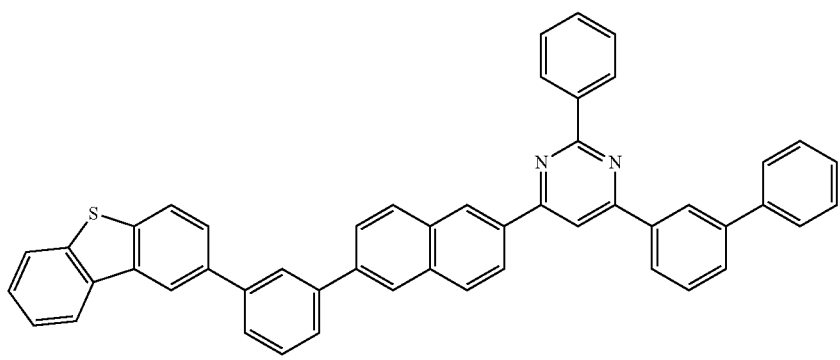
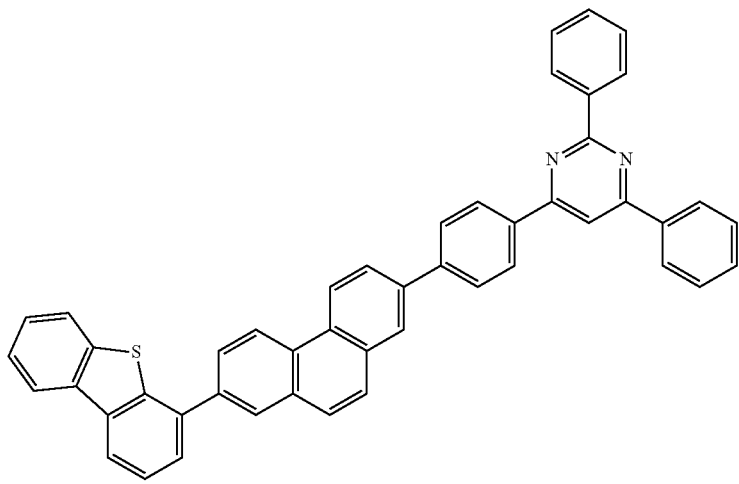

-continued
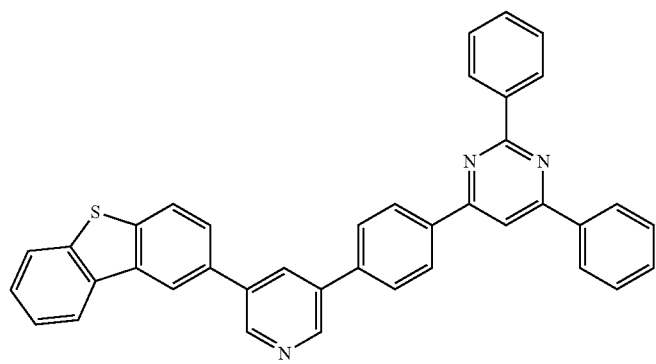
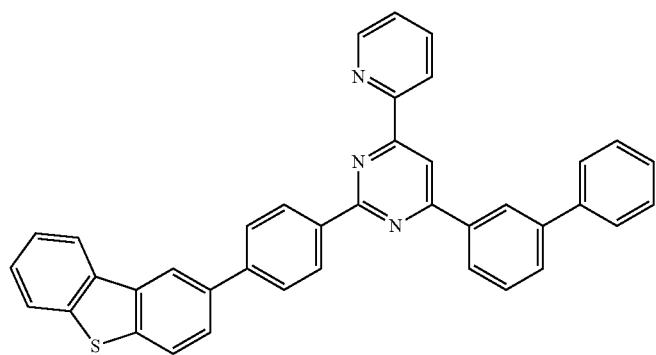
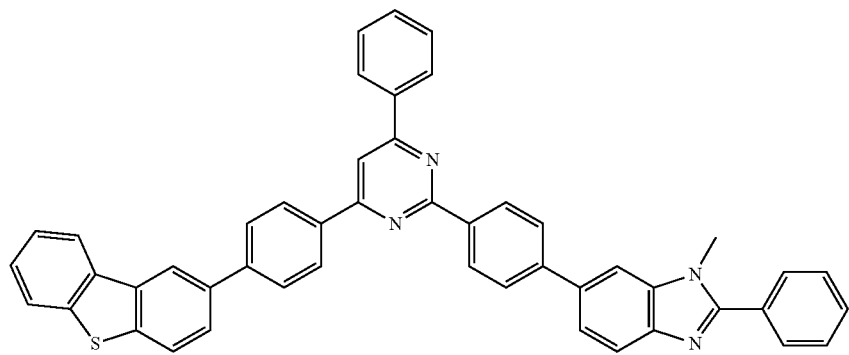
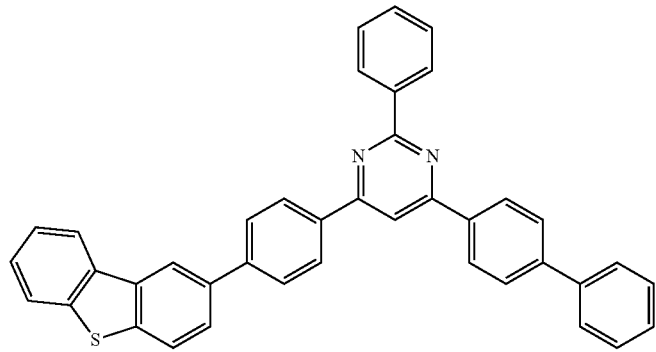

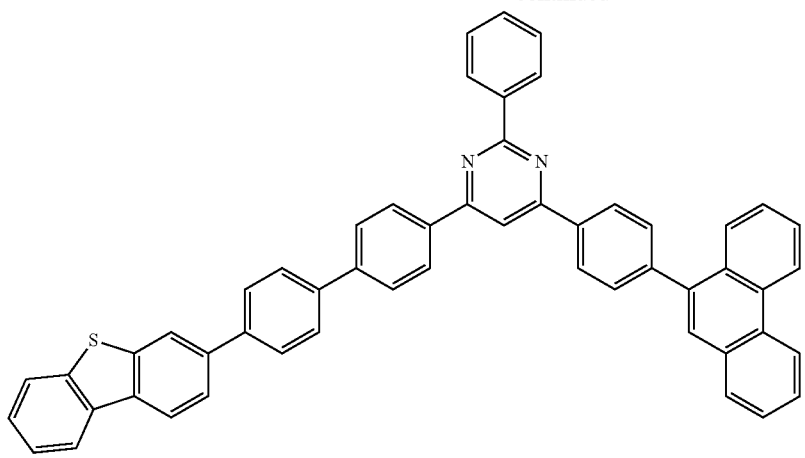
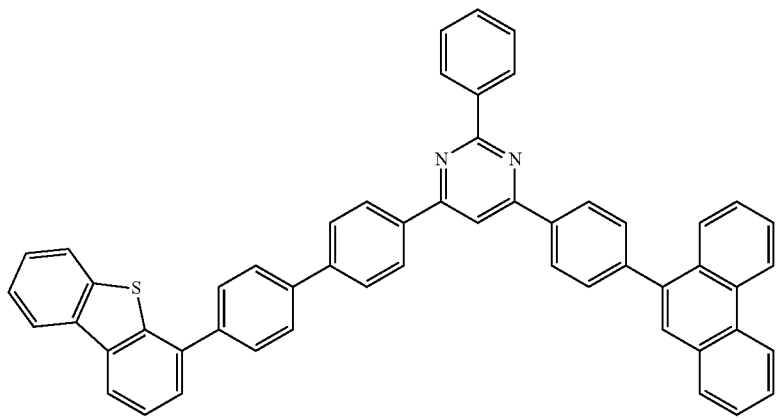
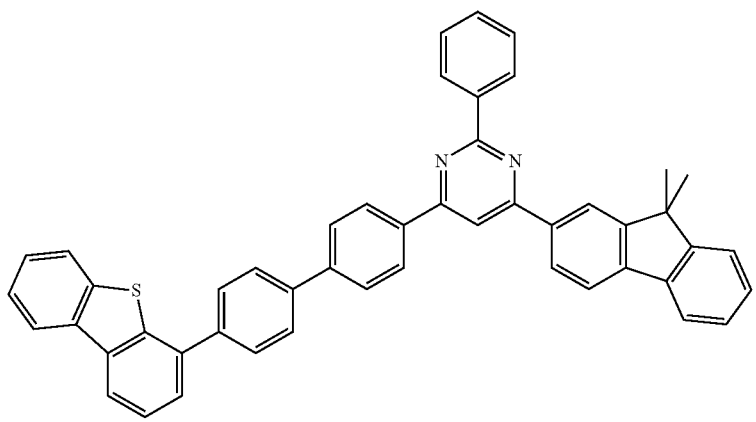
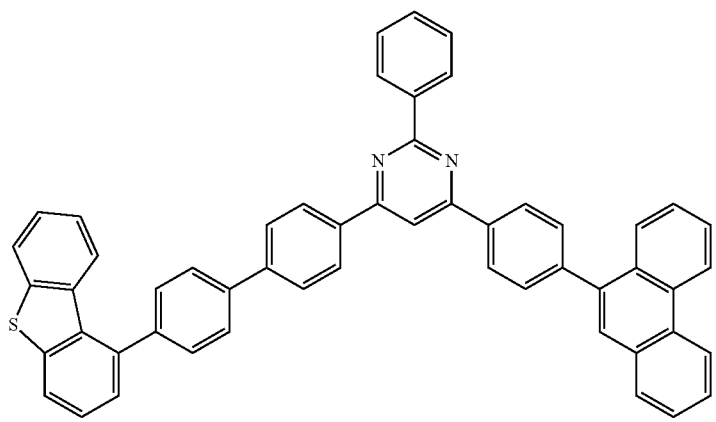

-continued
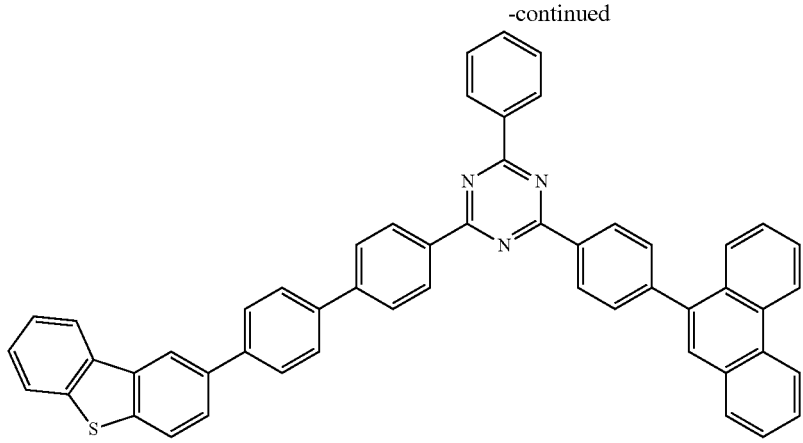
[Formula 81]
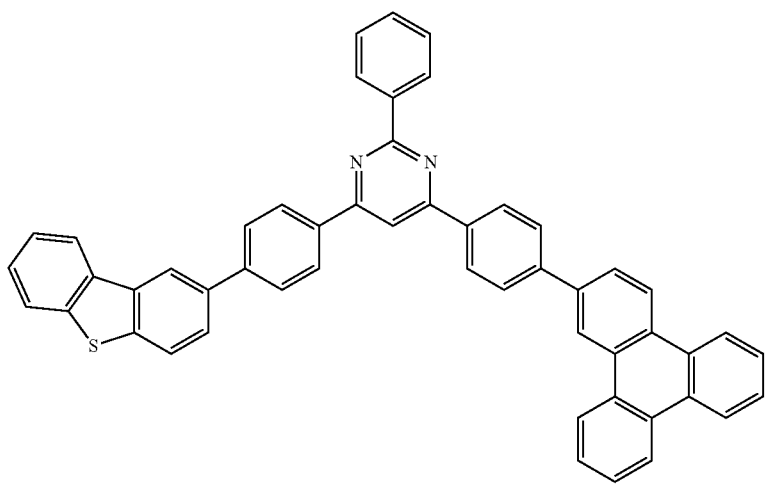
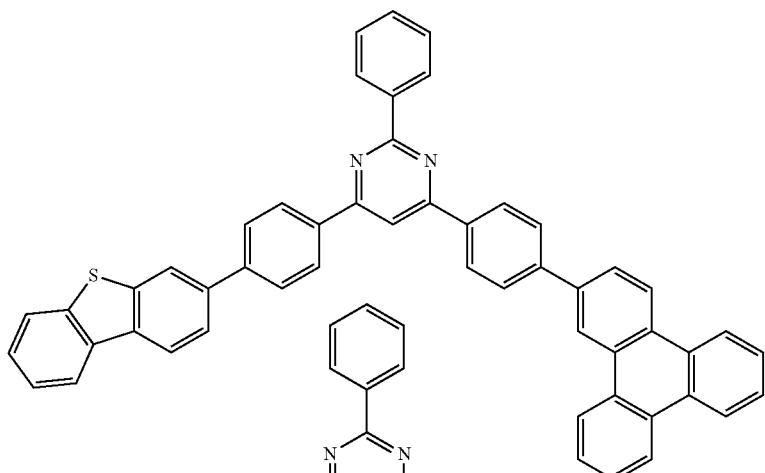
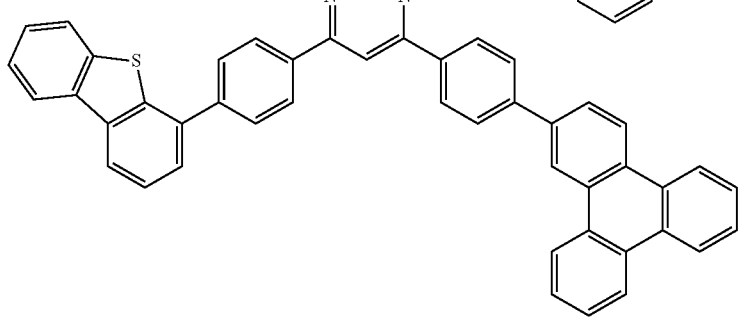

-continued
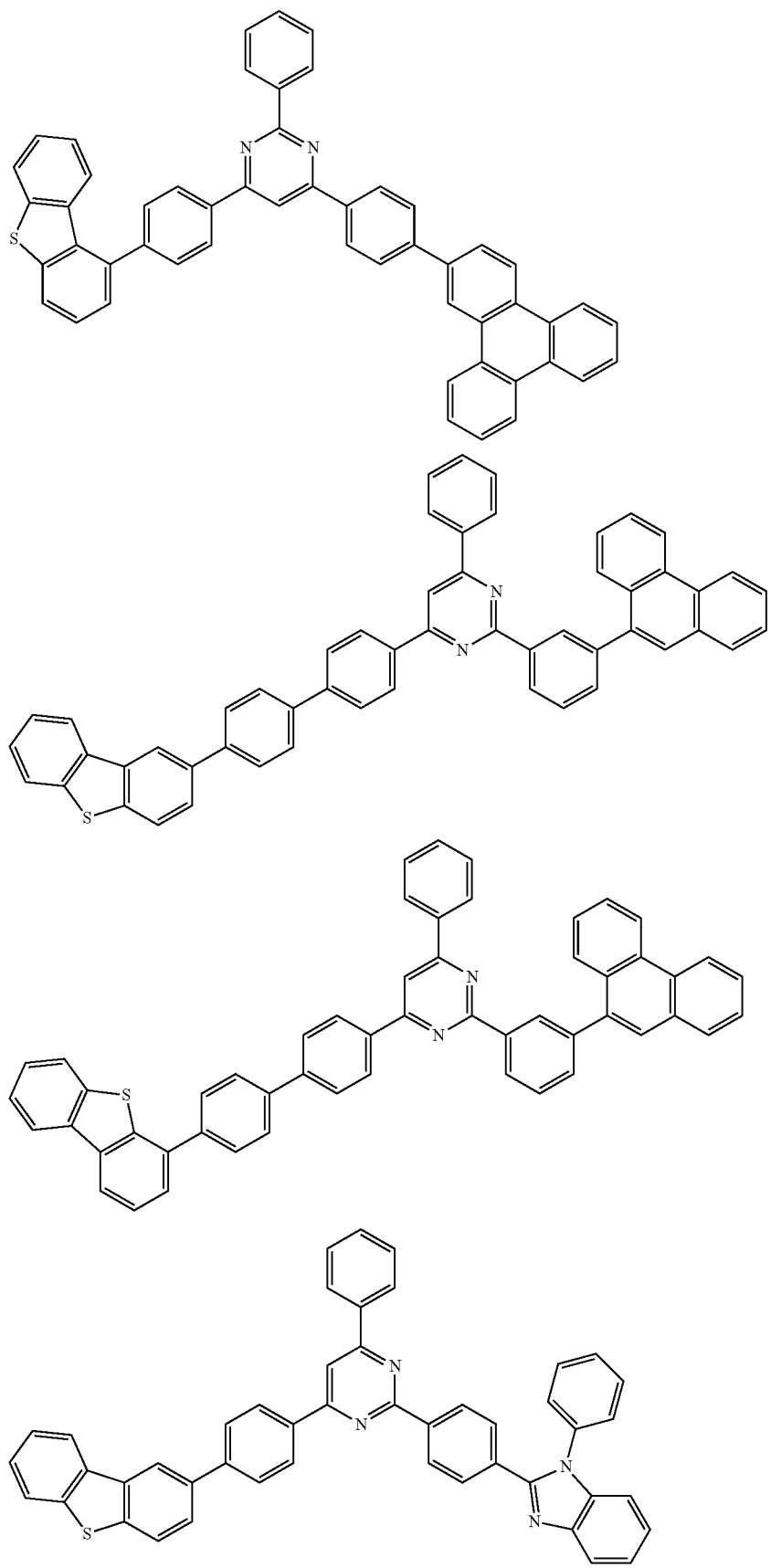

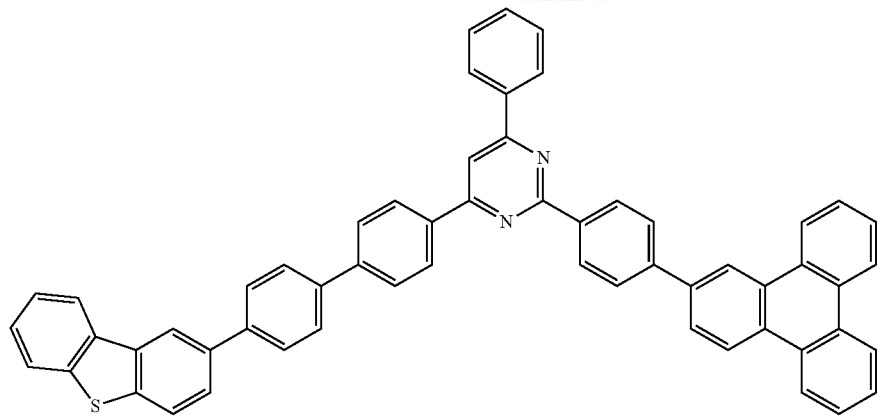
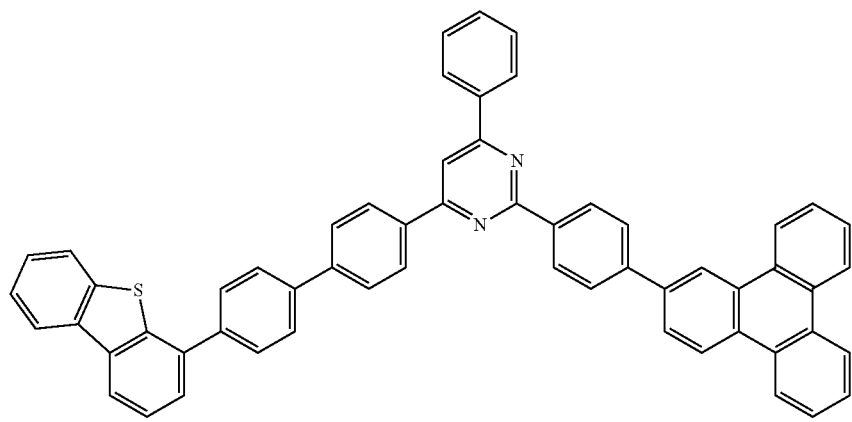
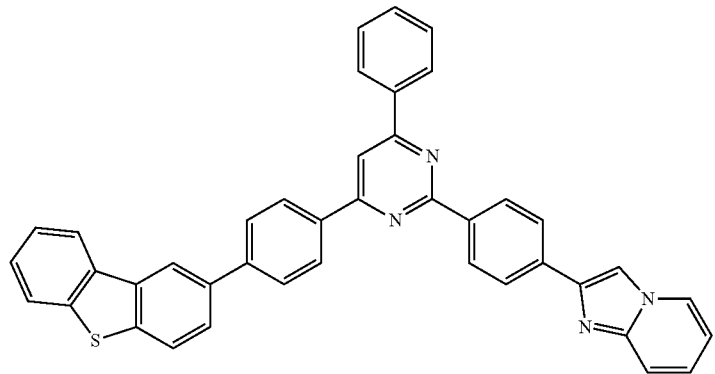
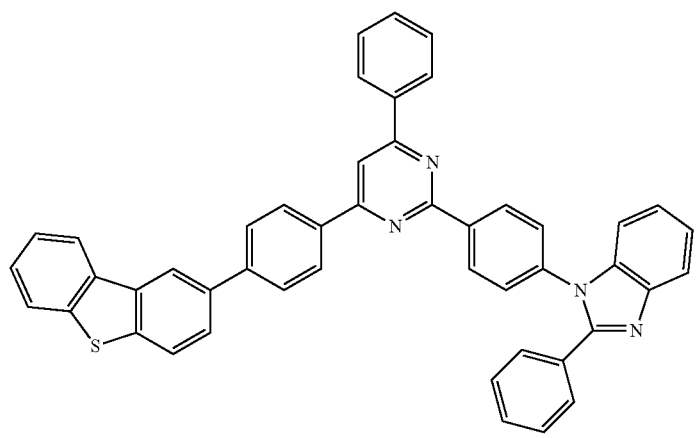

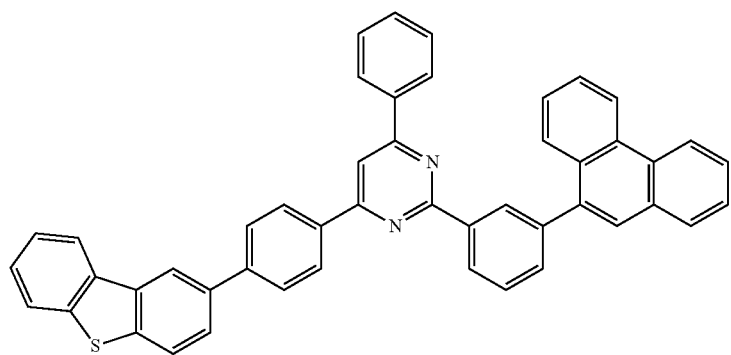
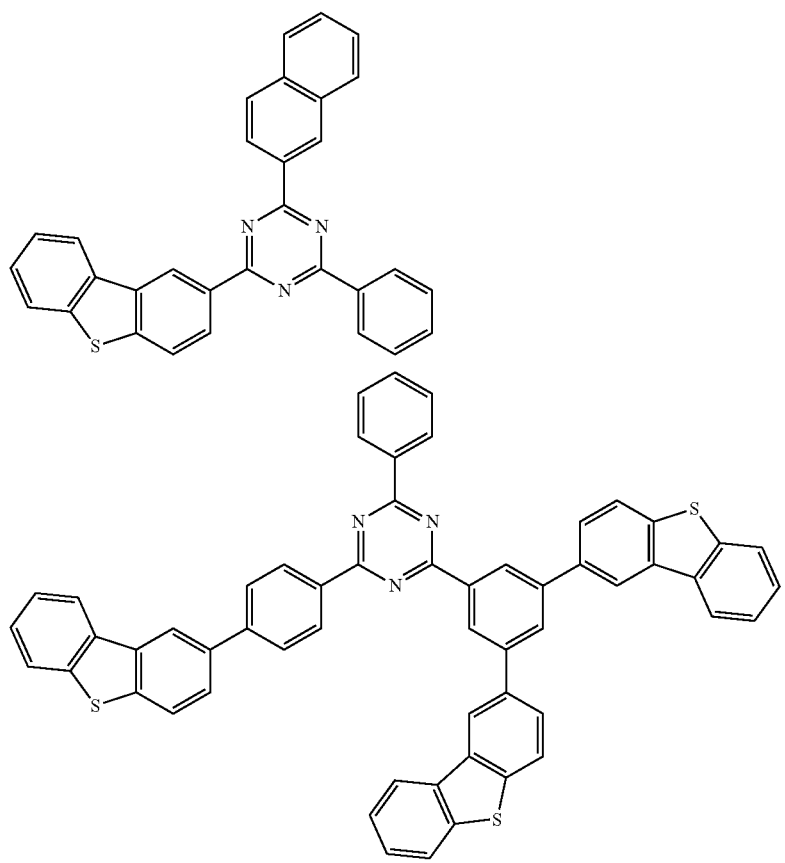
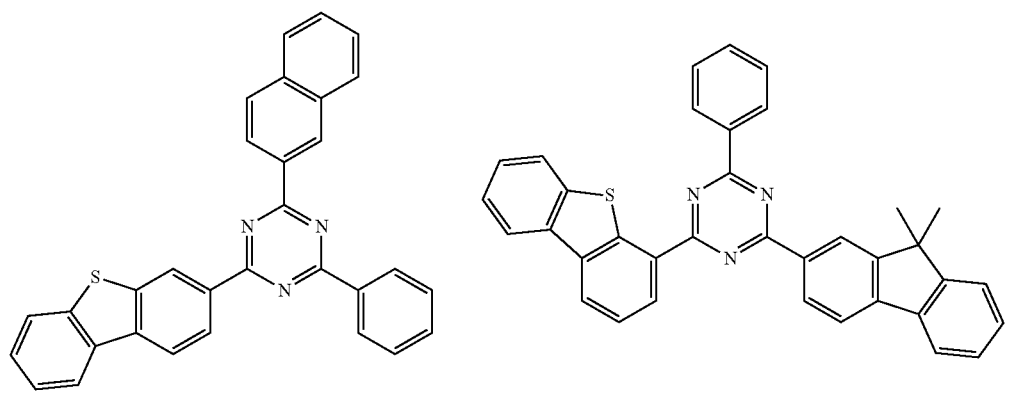

-continued
345
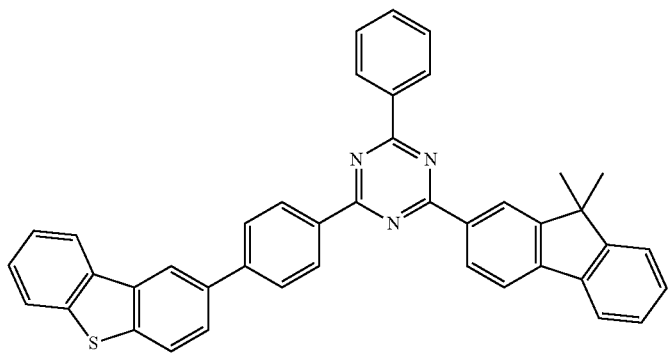
346
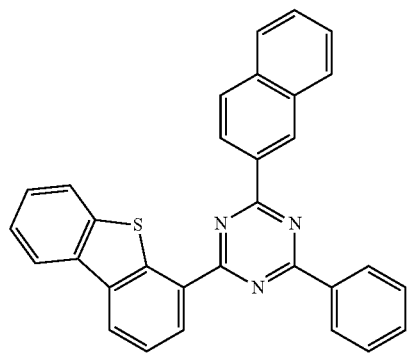
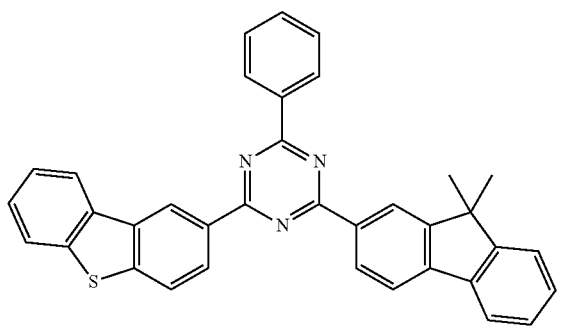
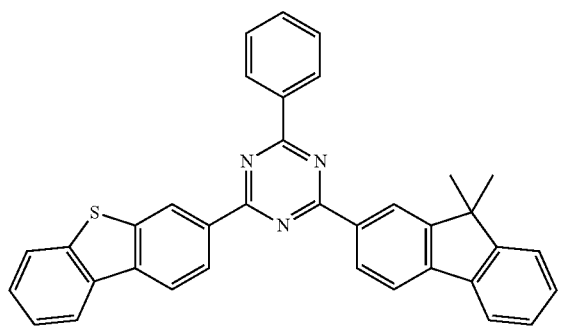
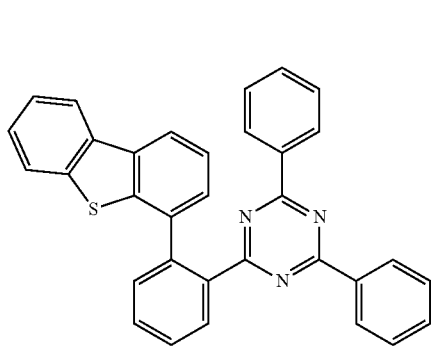
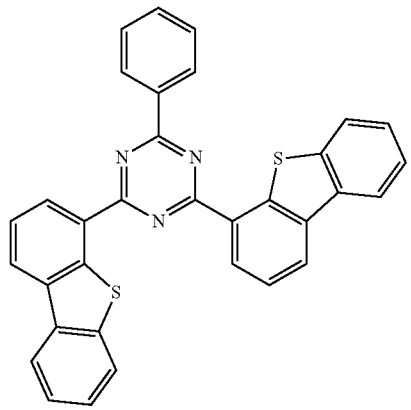
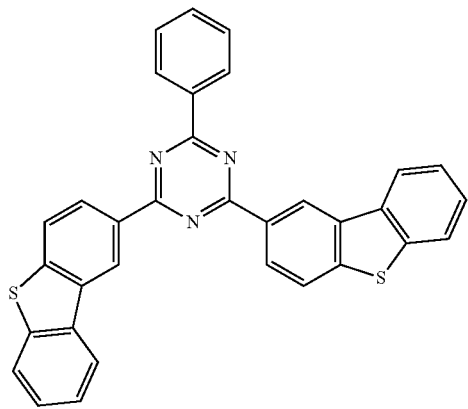
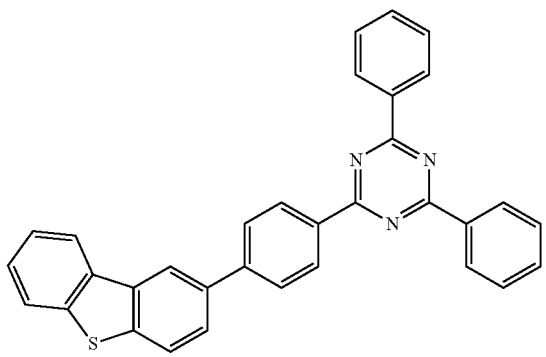

-continued
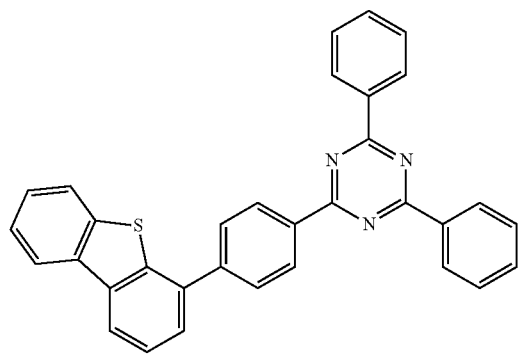
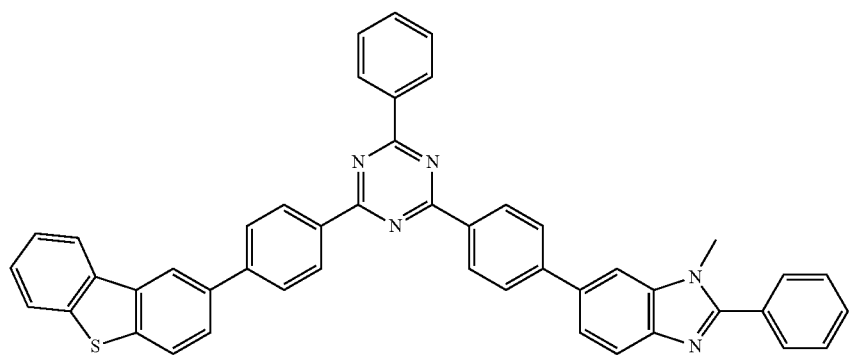
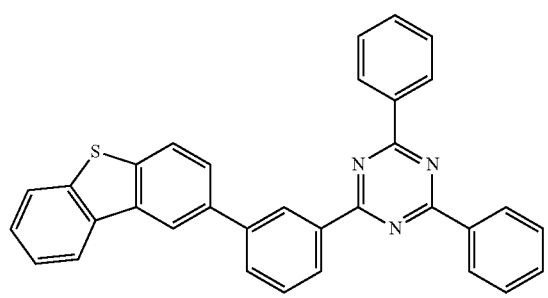
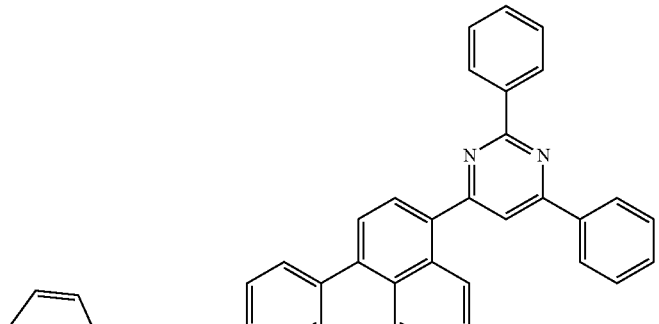

-continued
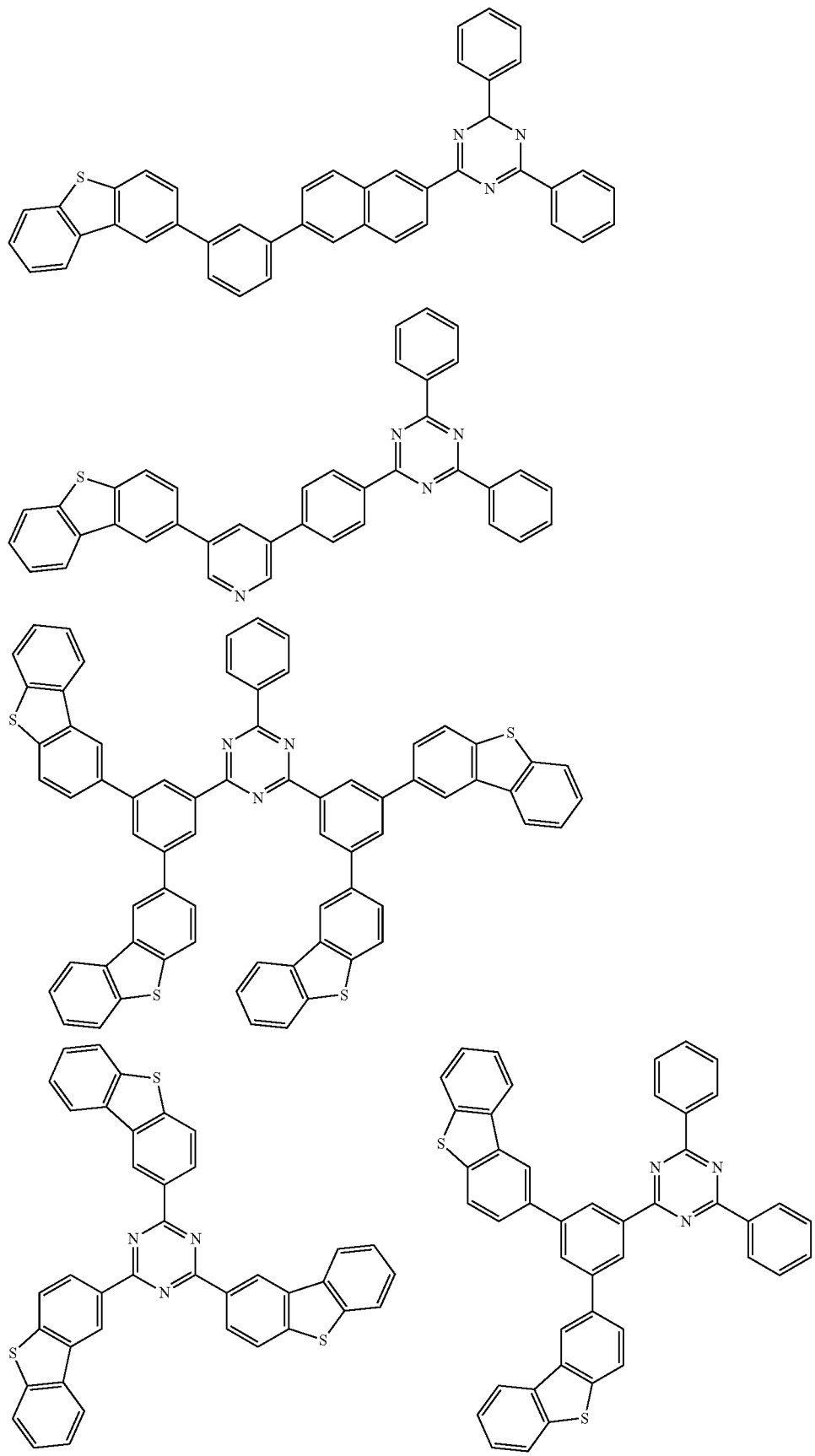

351
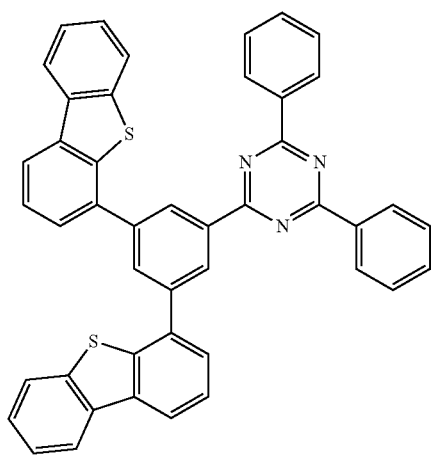
352
-continued
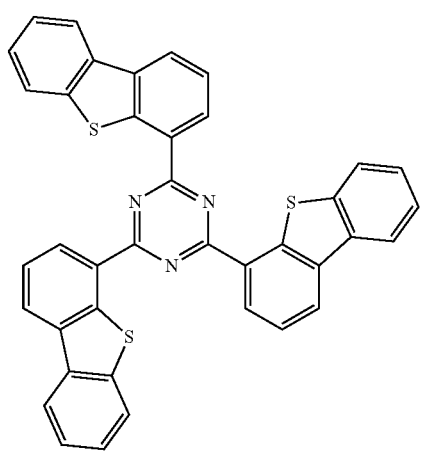
[Formula 82]
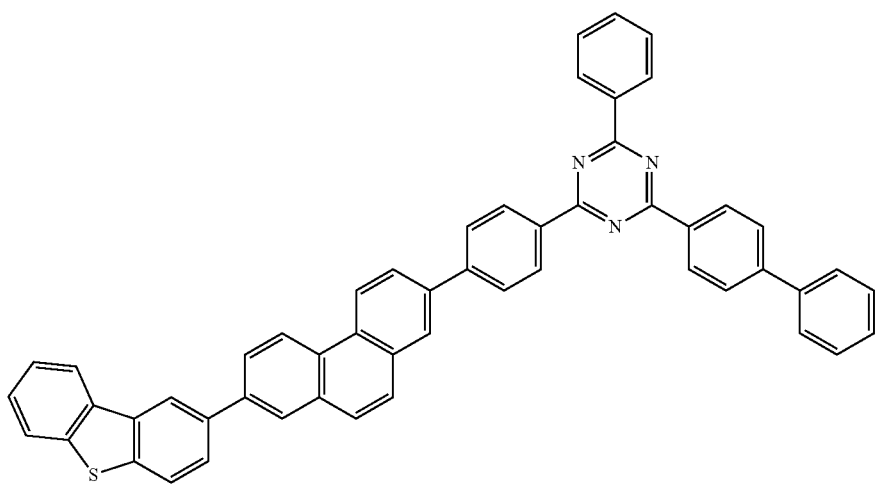
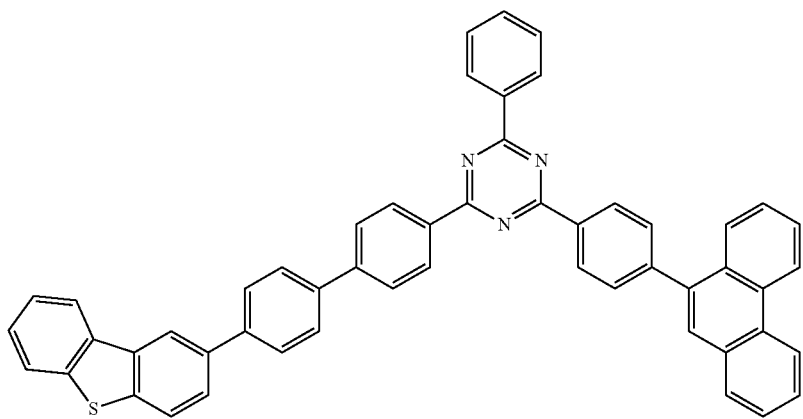

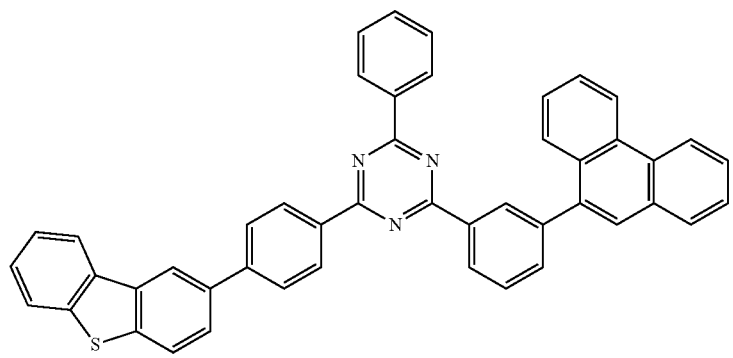
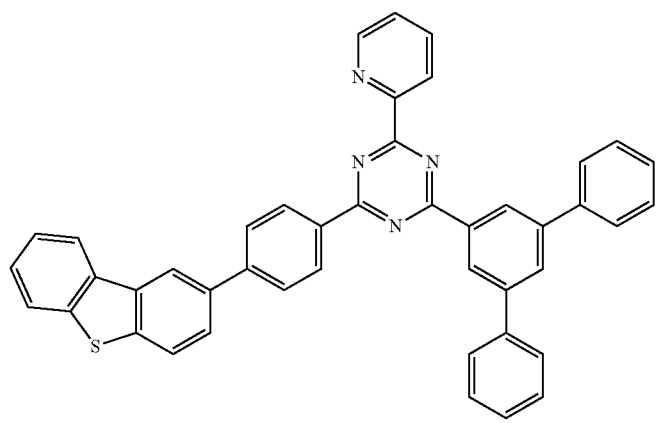
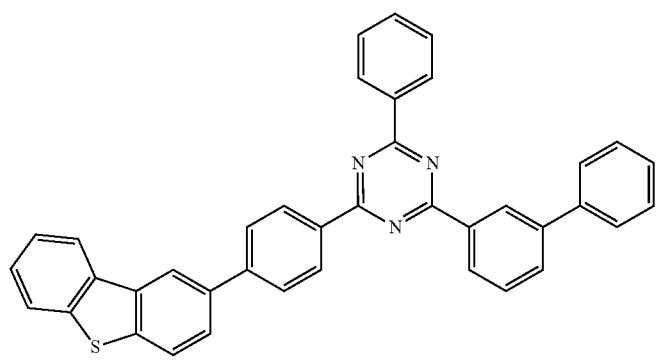
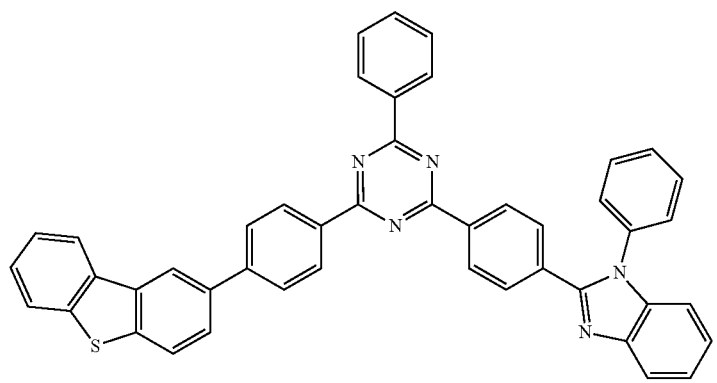

-continued
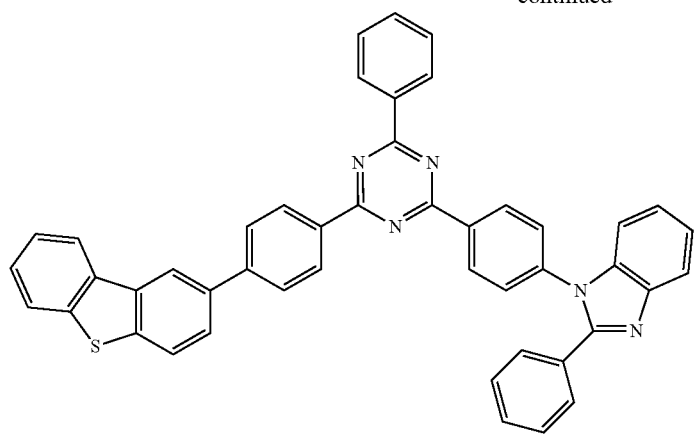
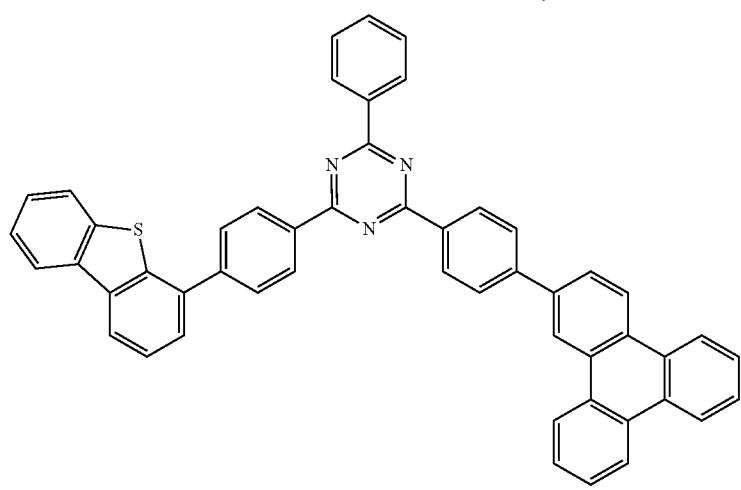
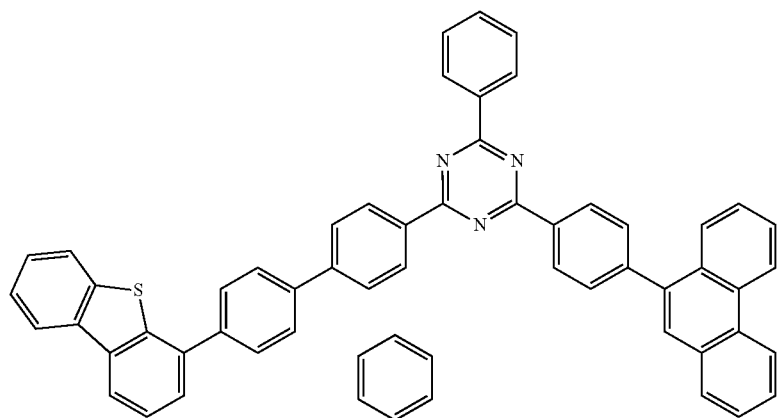
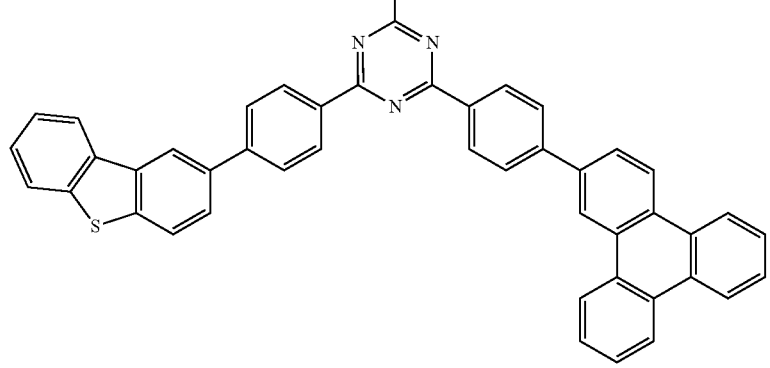

-continued
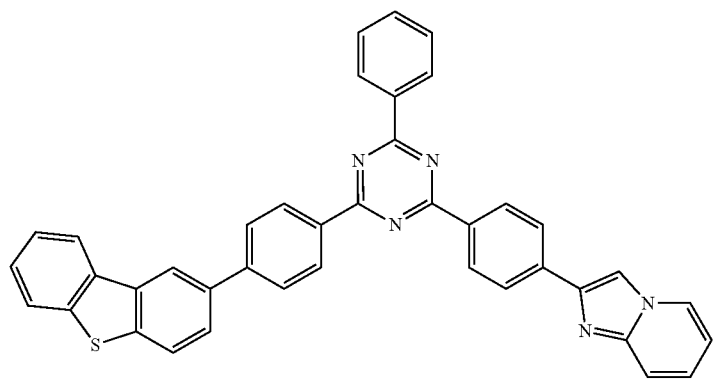

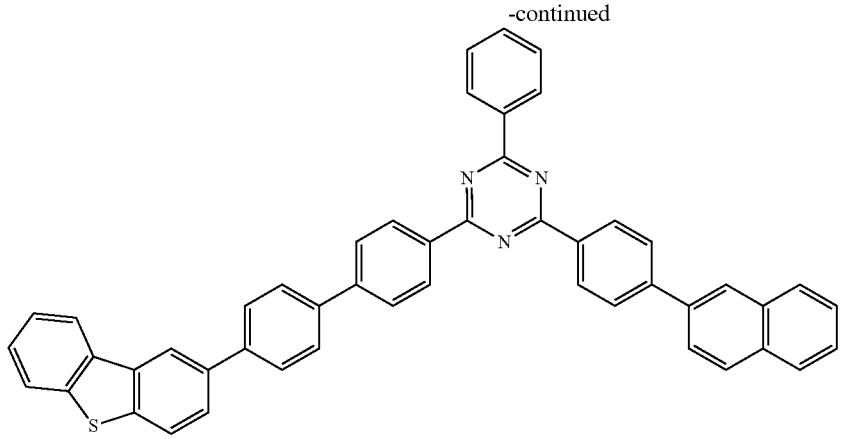
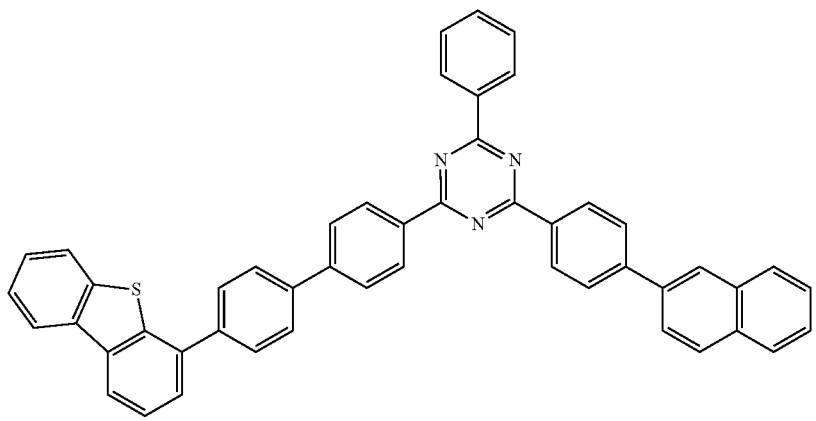
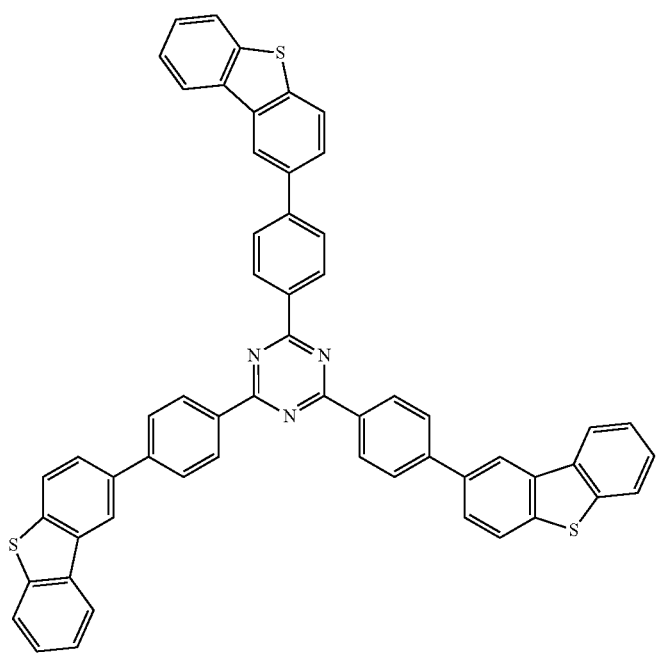

-continued
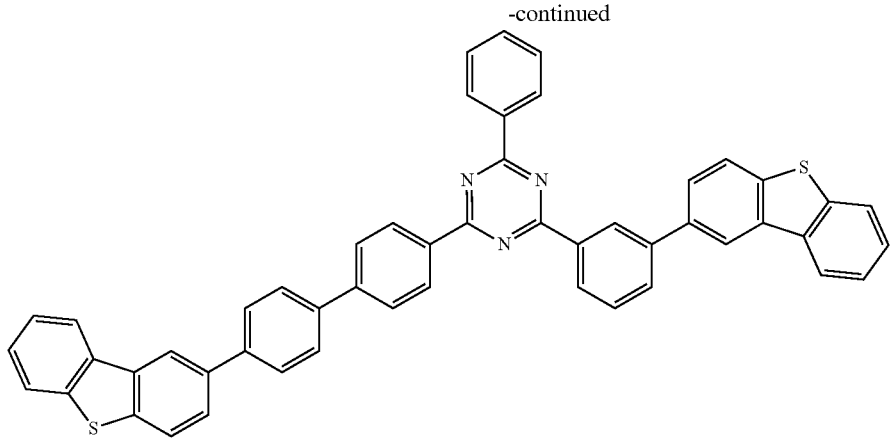
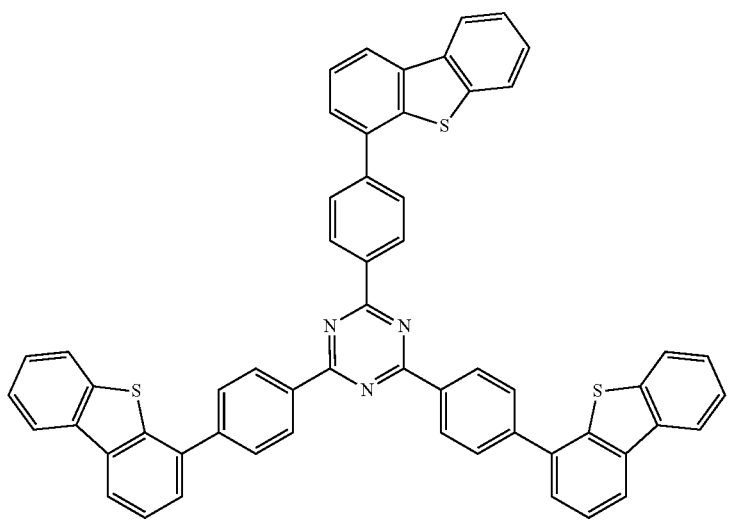
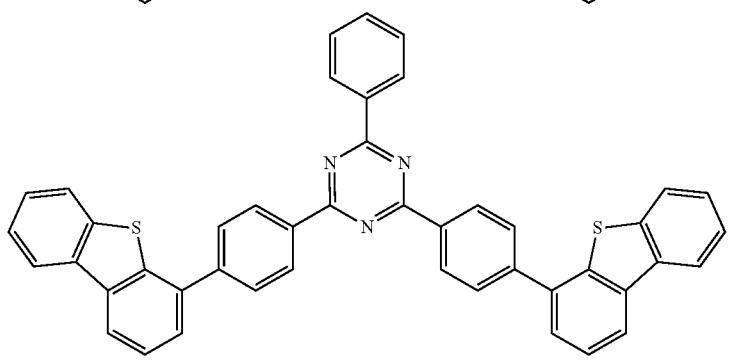
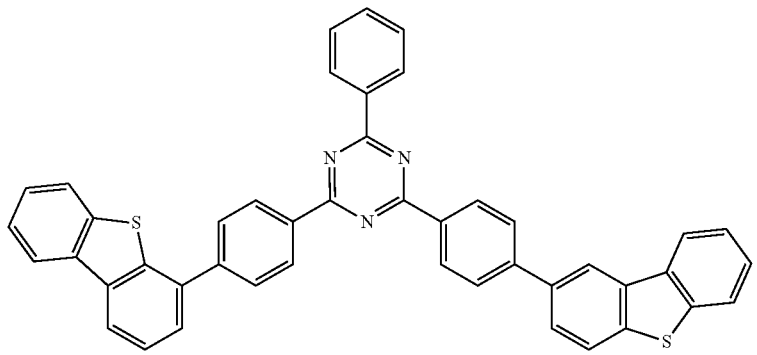

-continued
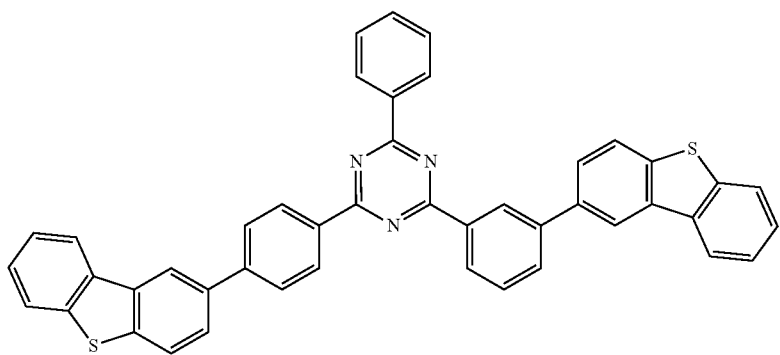
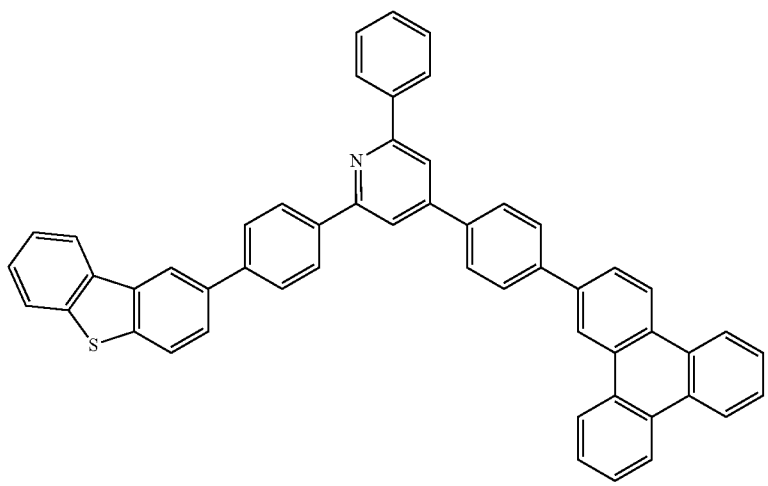
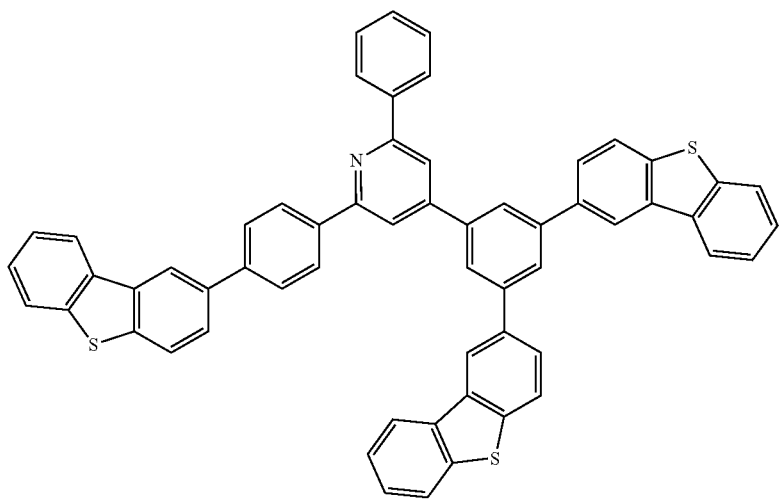
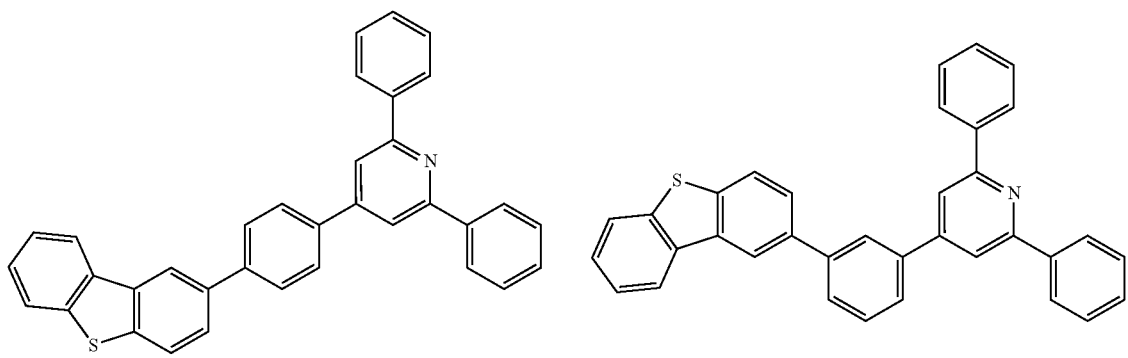

365
366
-continued
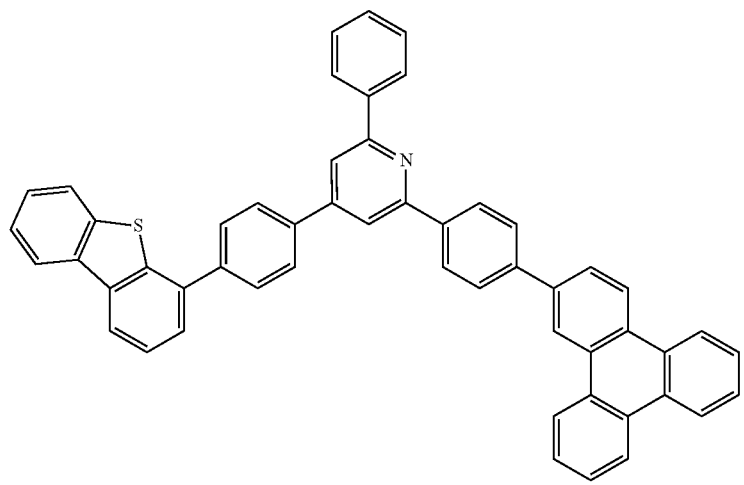
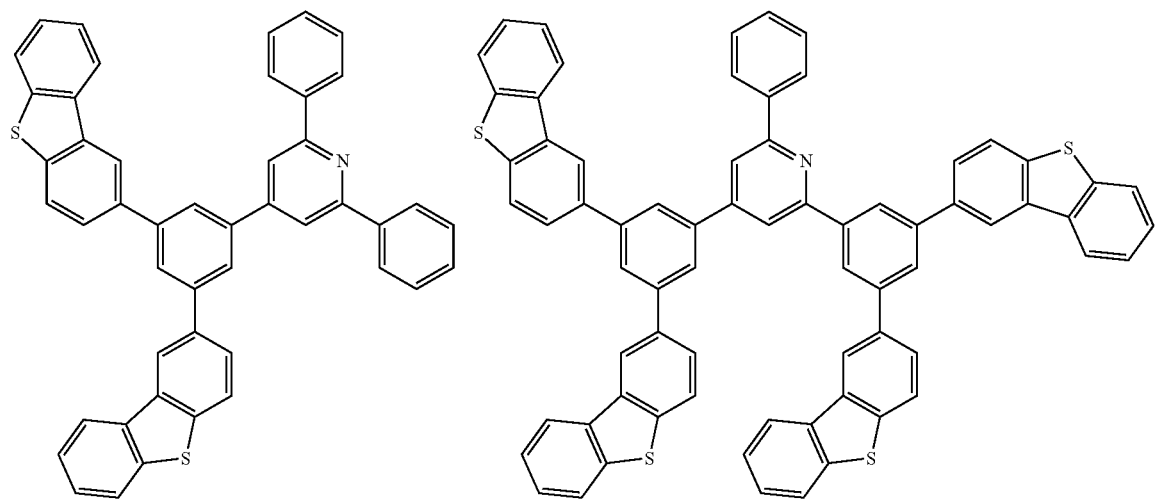
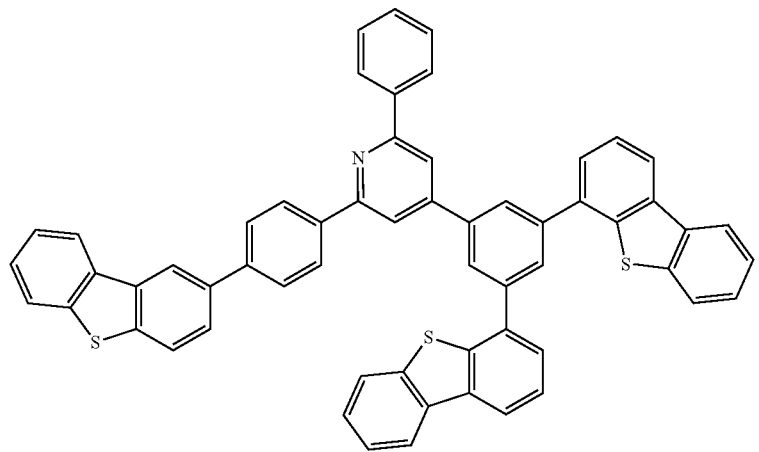

[Formula 83]
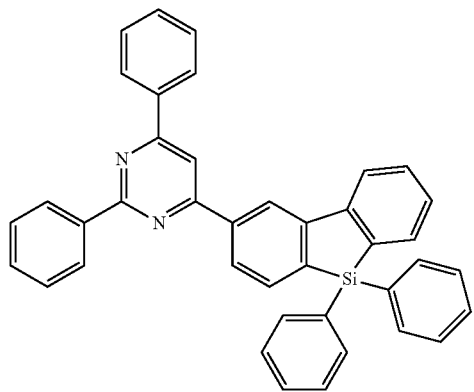
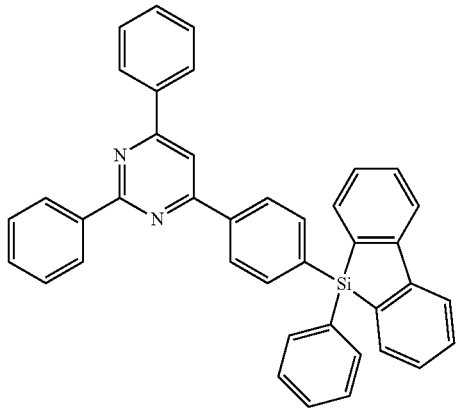
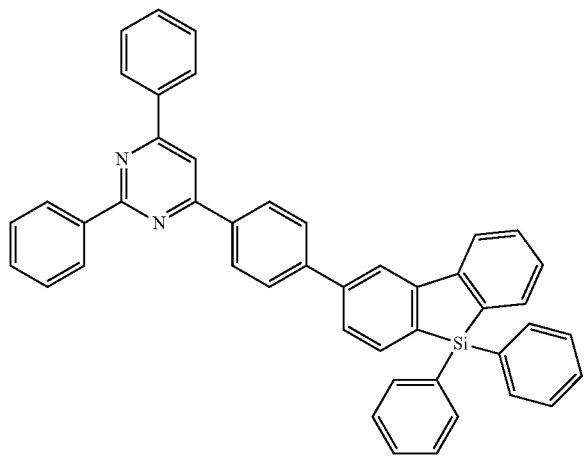
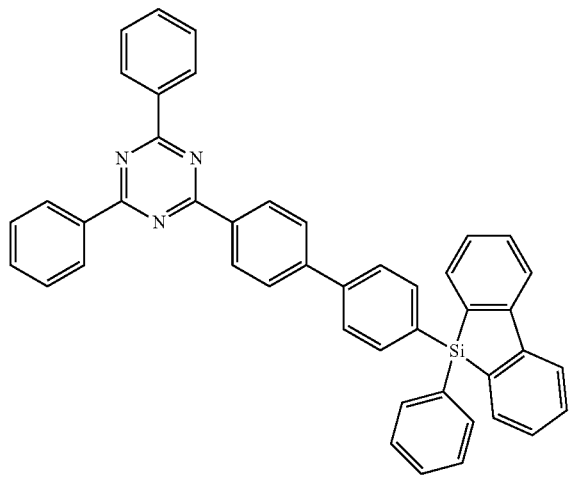

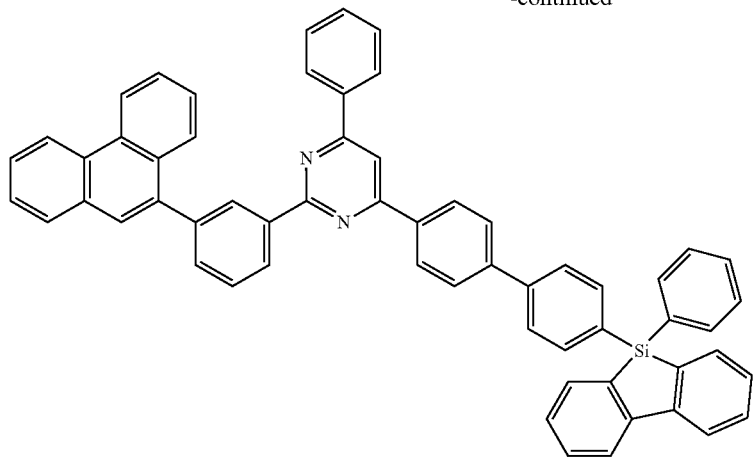
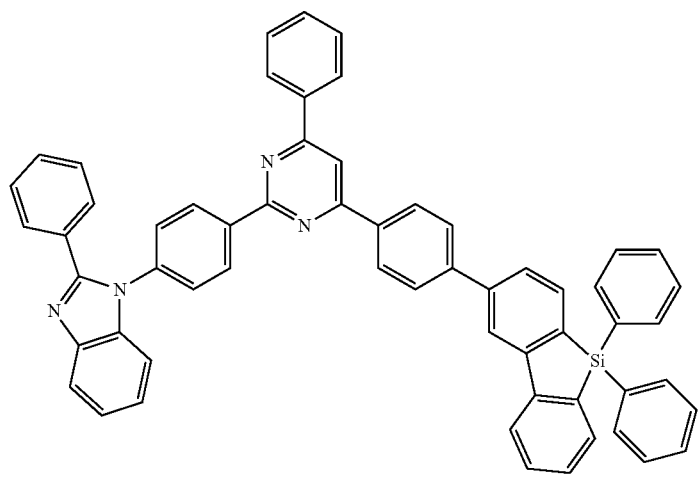
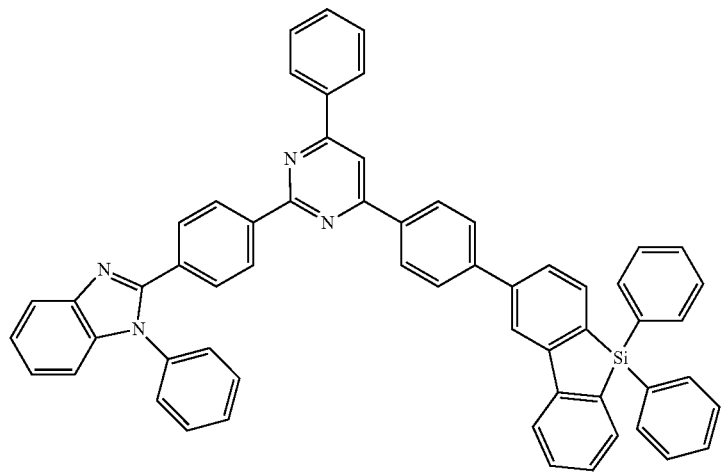

-continued
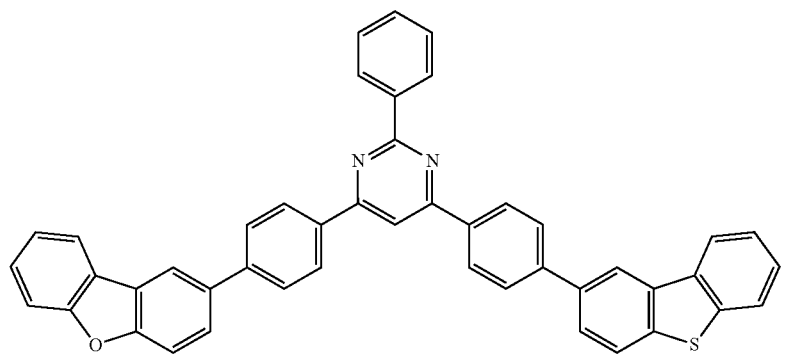
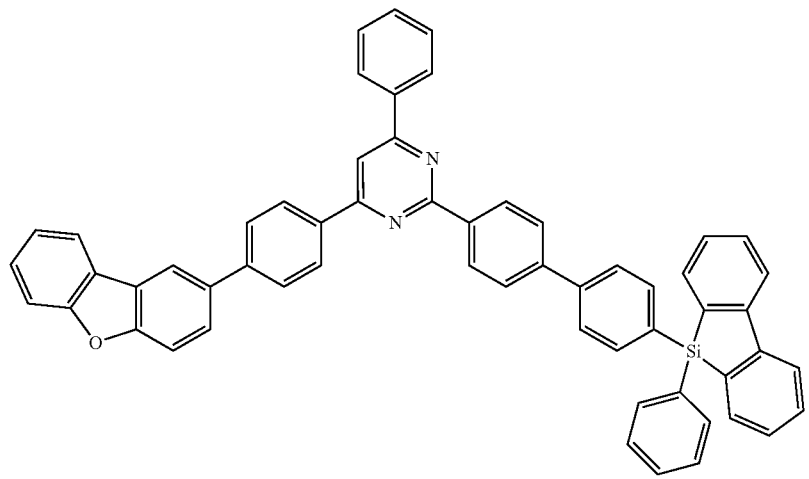
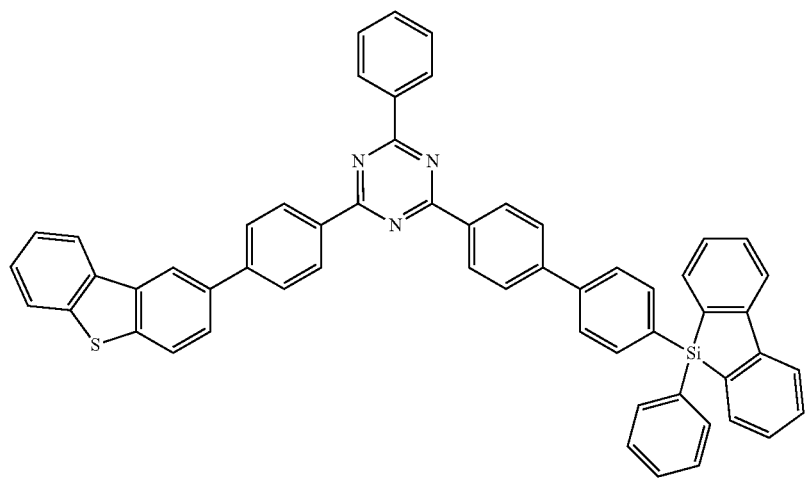

373
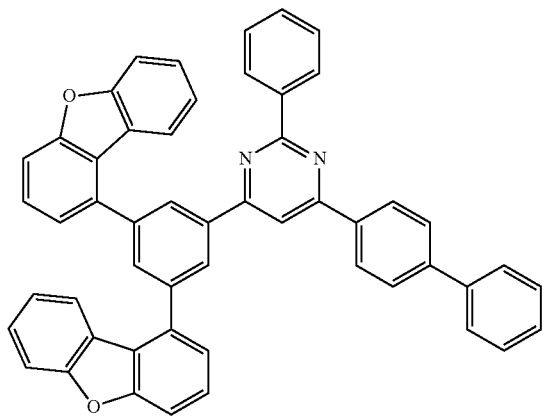
374
-continued
[Formula 84]
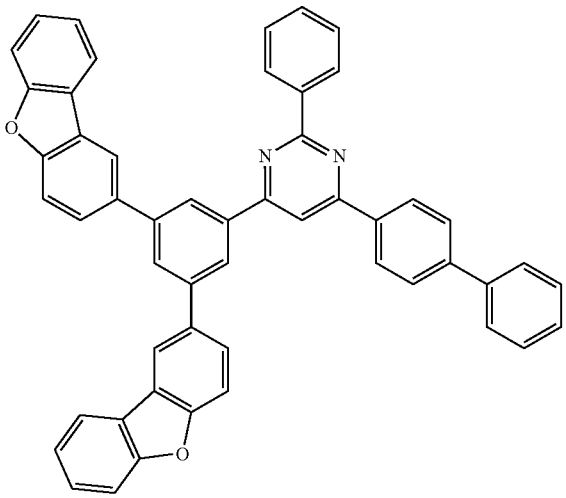
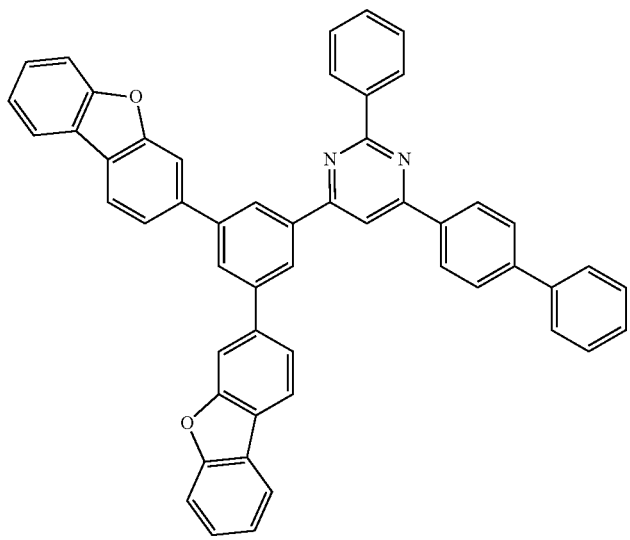
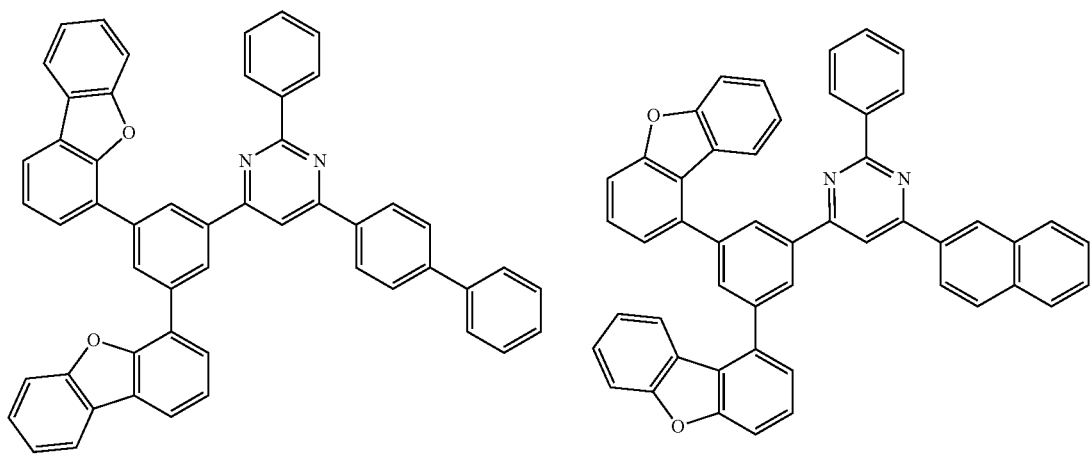

-continued
375
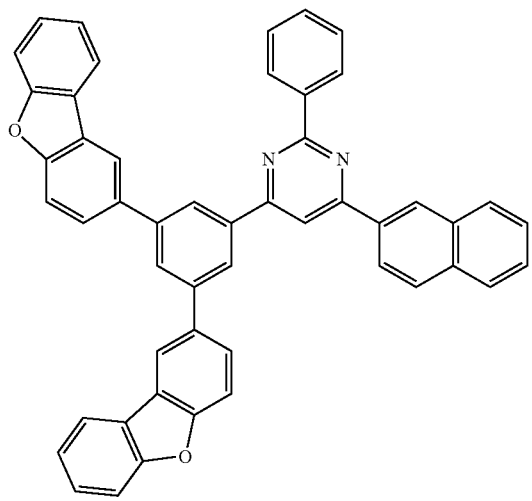
376
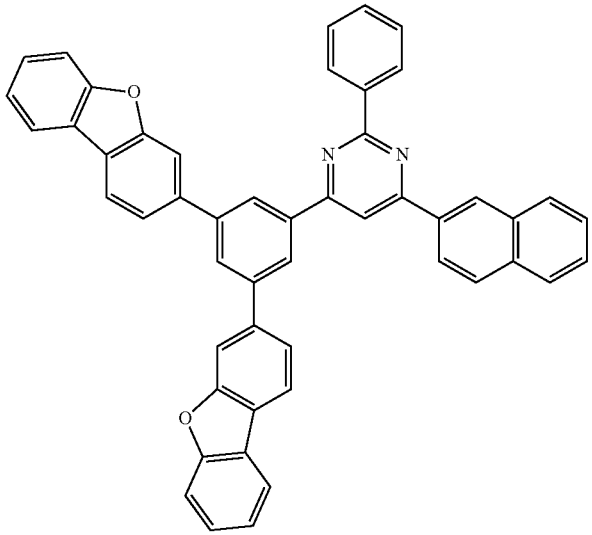
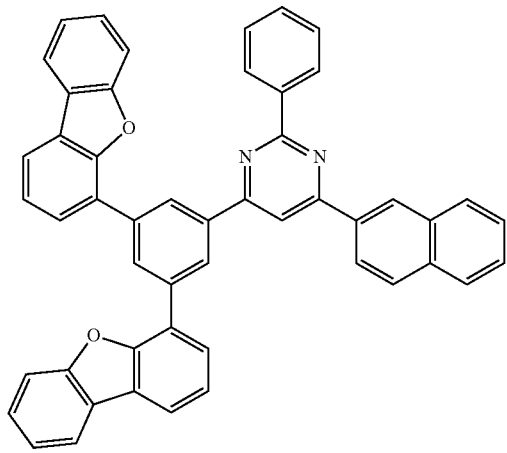
[Formula 85]
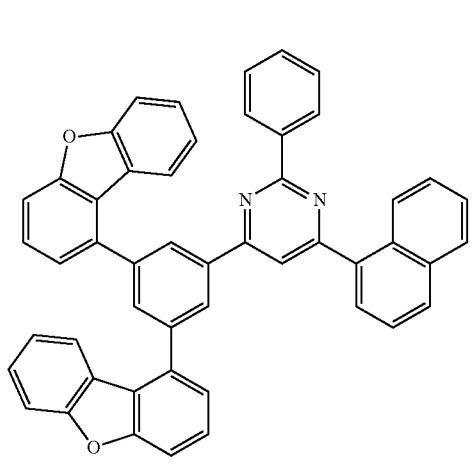
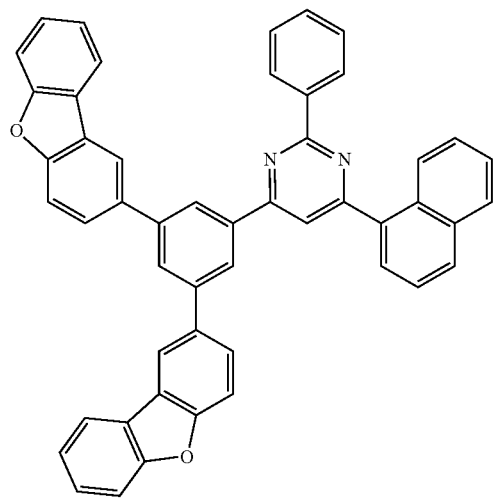

-continued
377
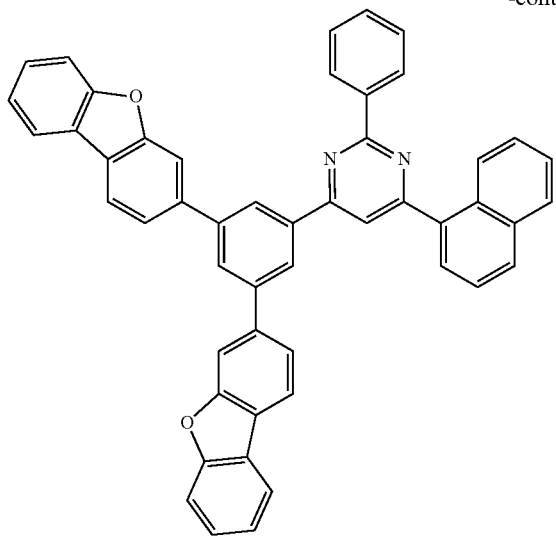
378
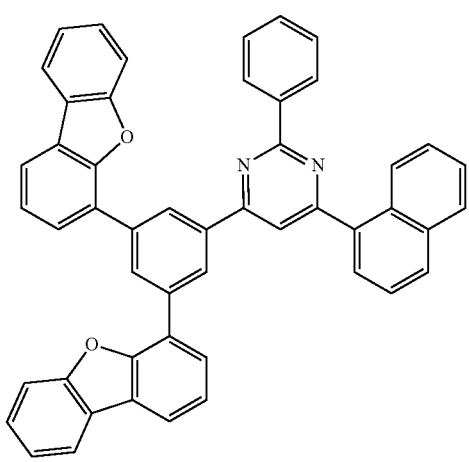
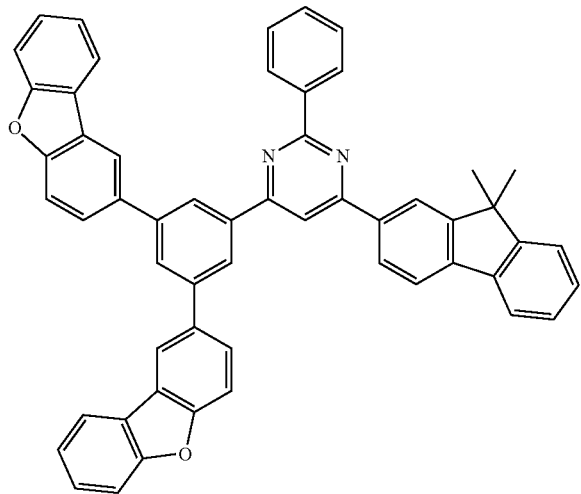
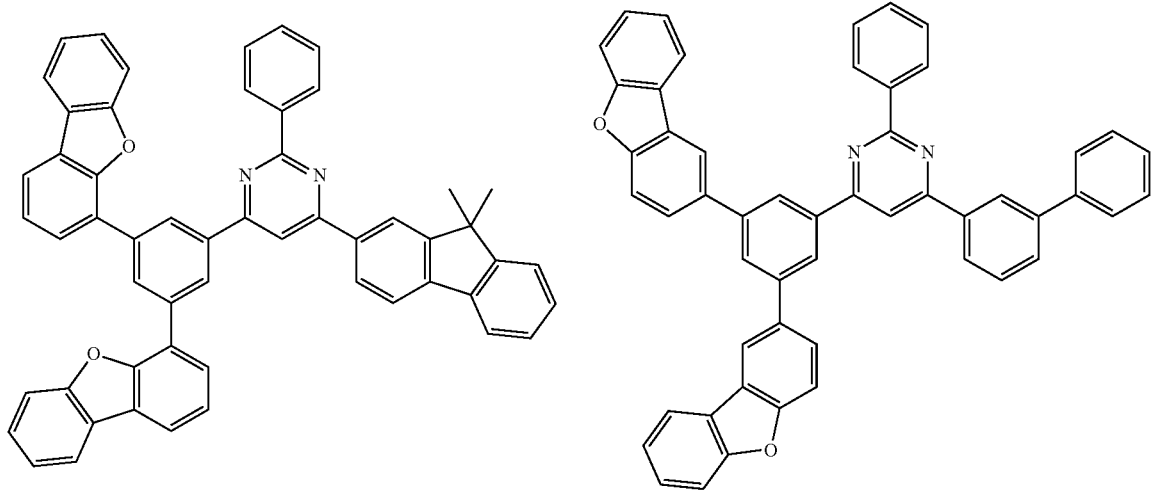

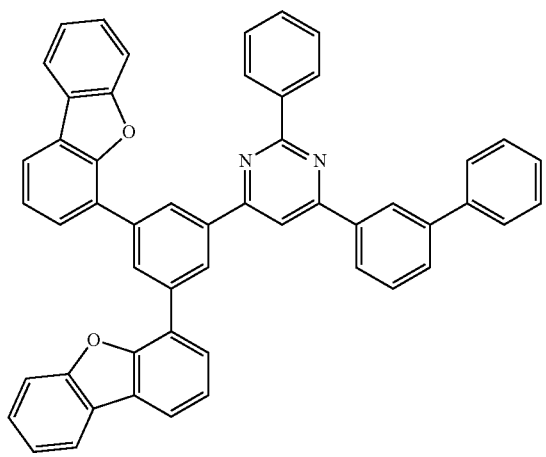
[Formula 86]
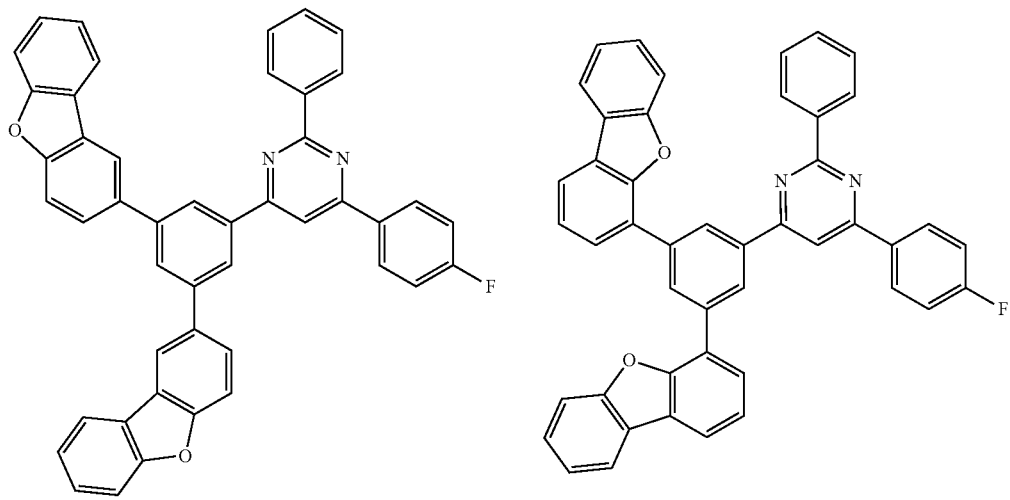
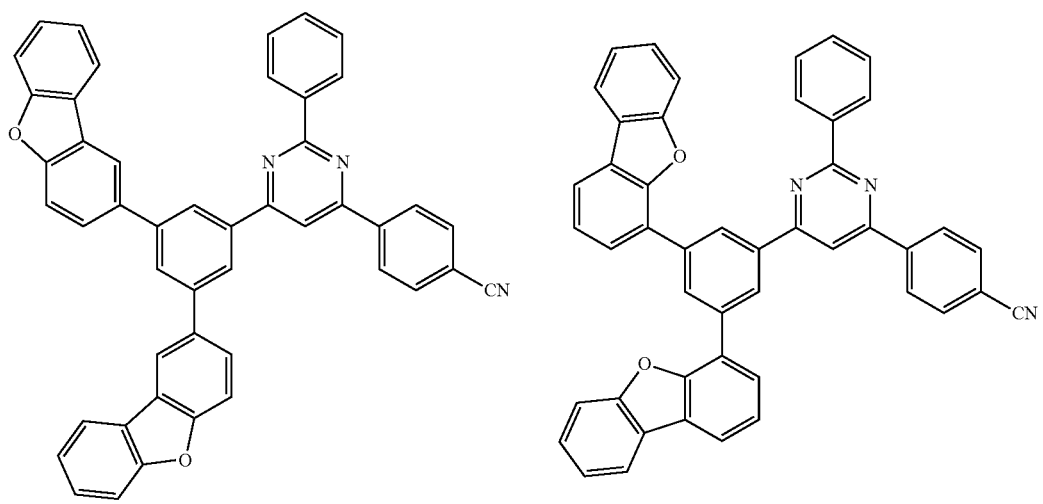

-continued
381 382
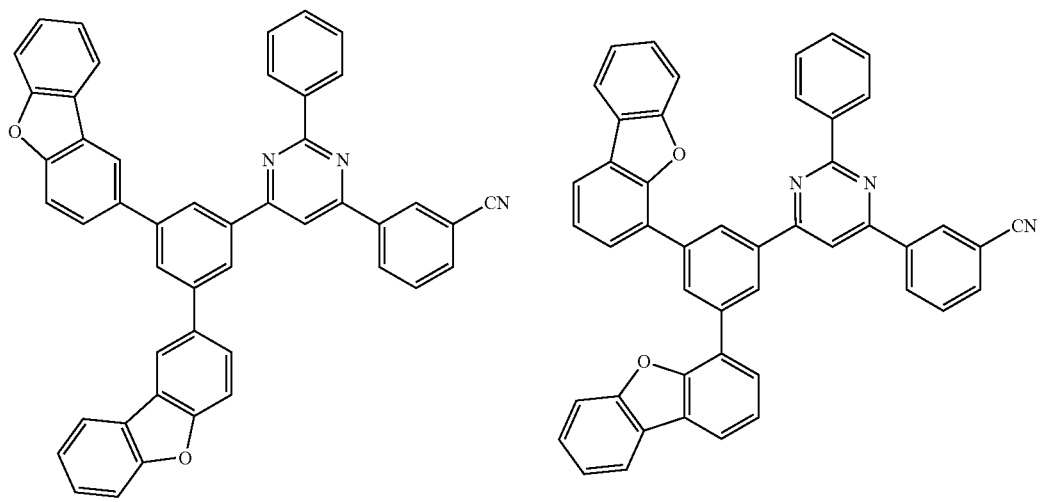
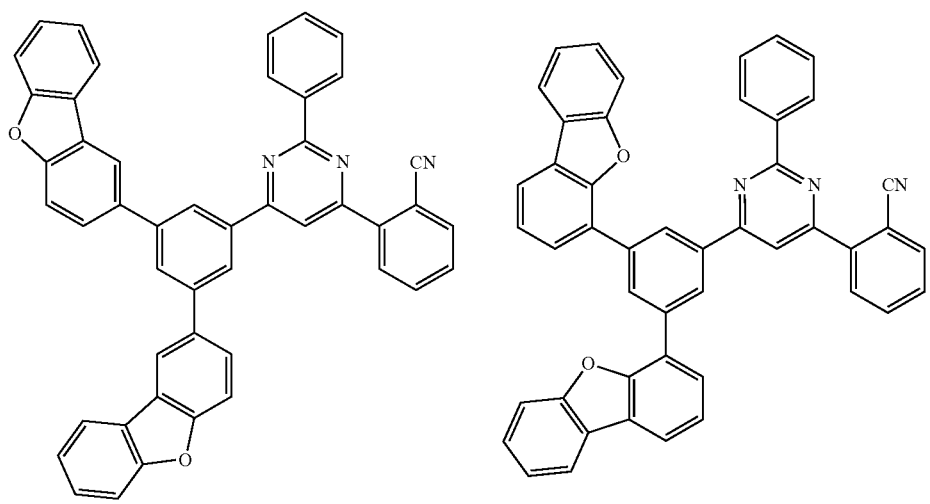
[Formula 87]
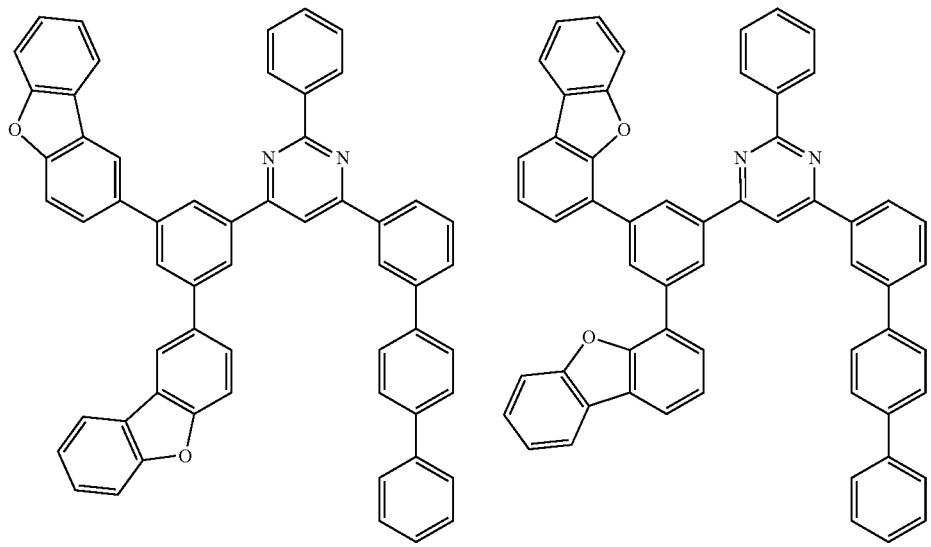

383 384
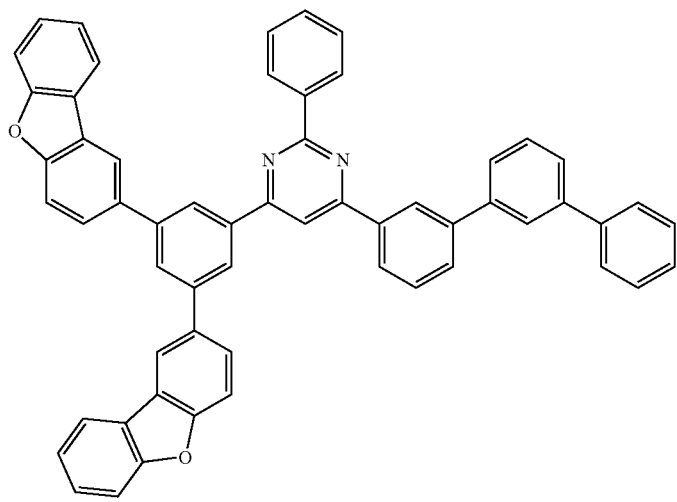

-continued
385
386
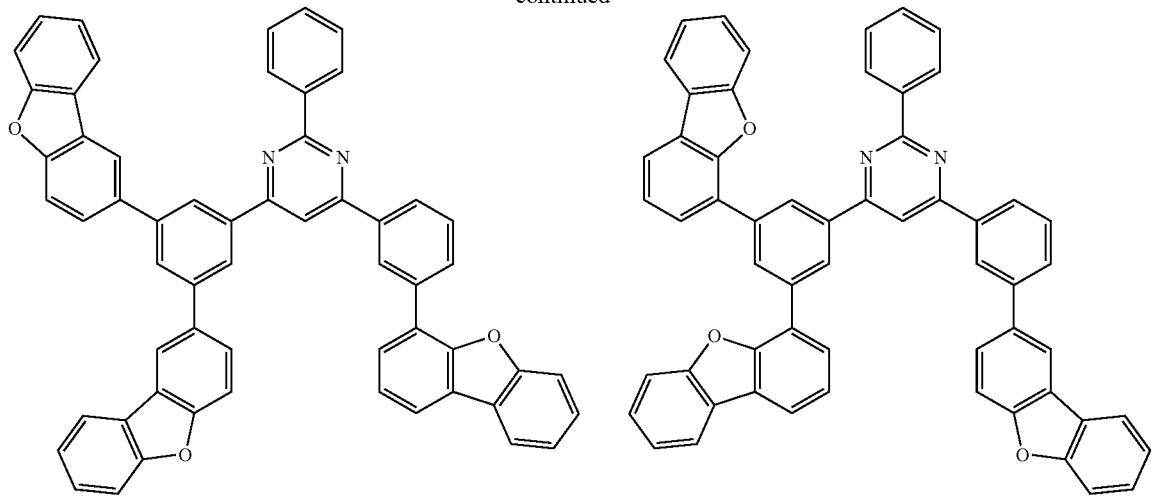
[Formula 88]
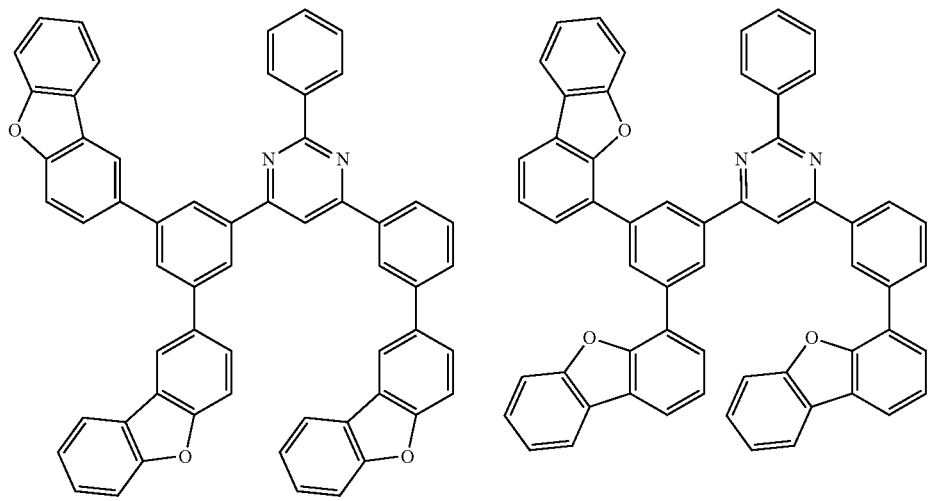
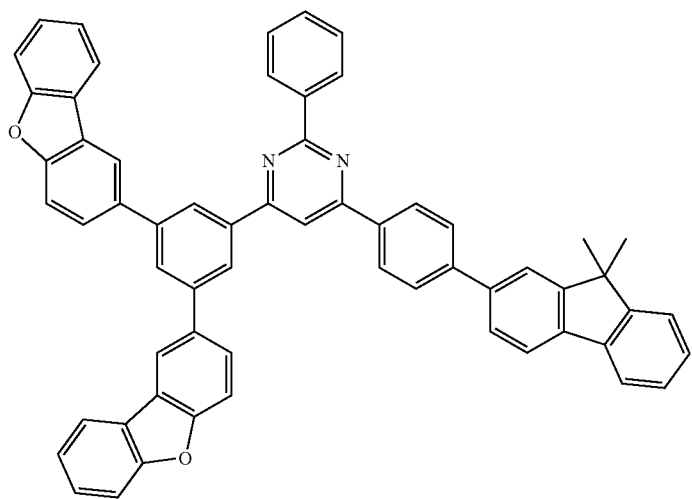

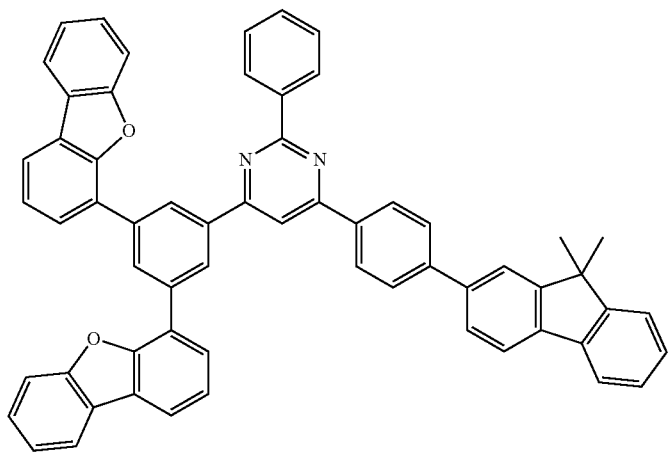
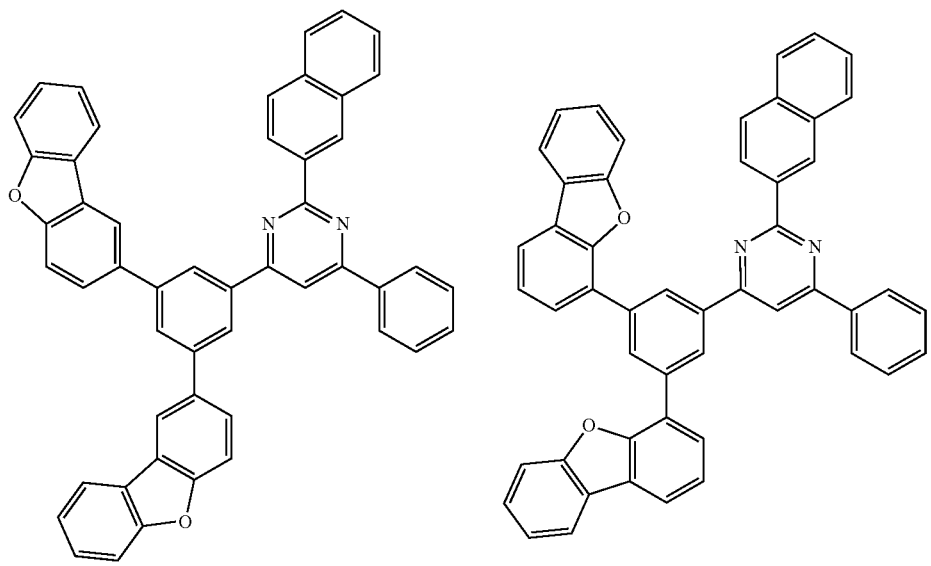
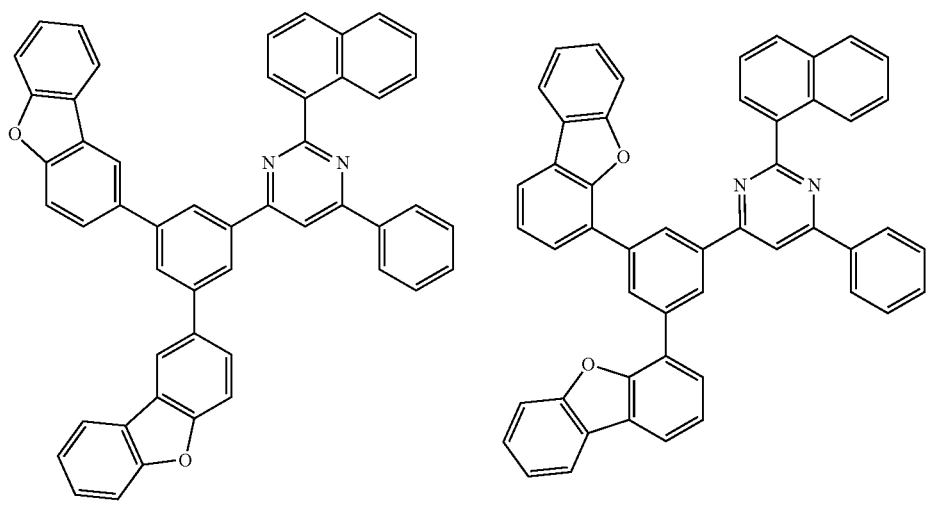

[Formula 89]
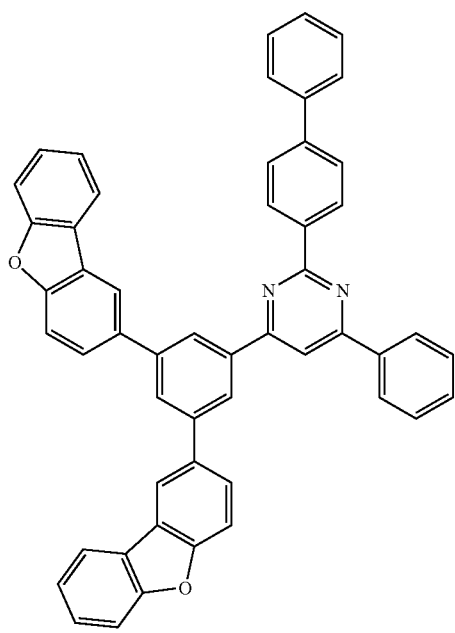
389
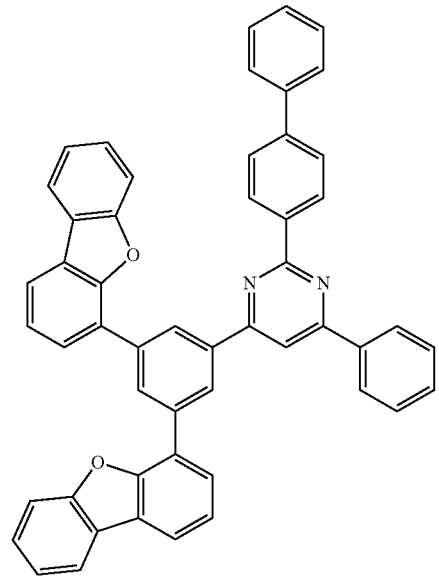
390
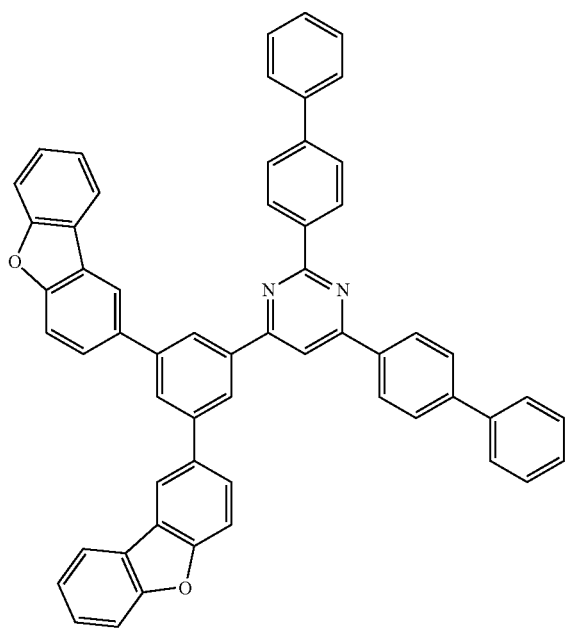
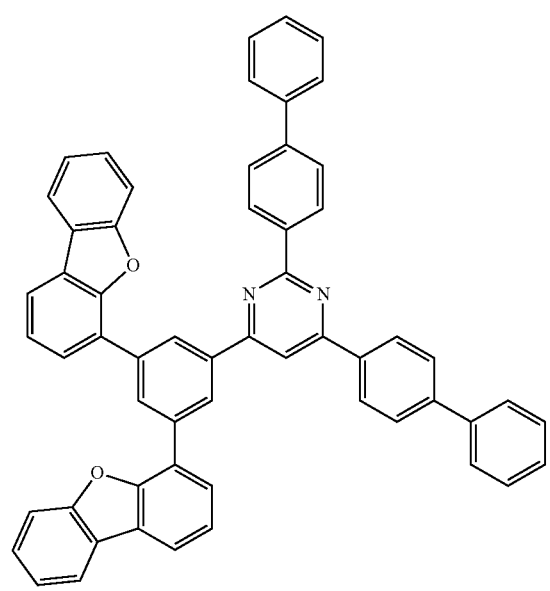

-continued
391
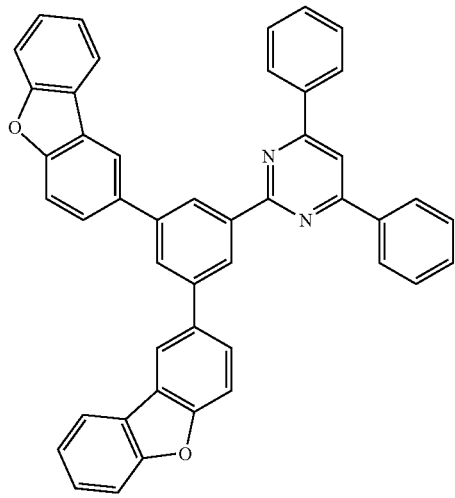
392
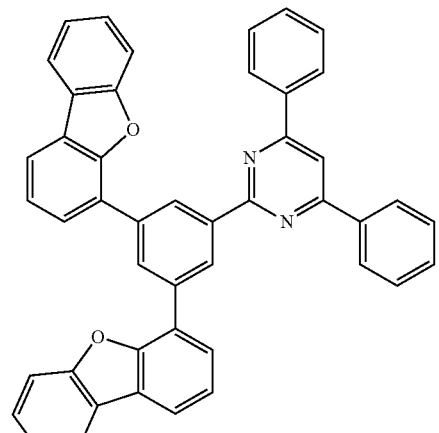
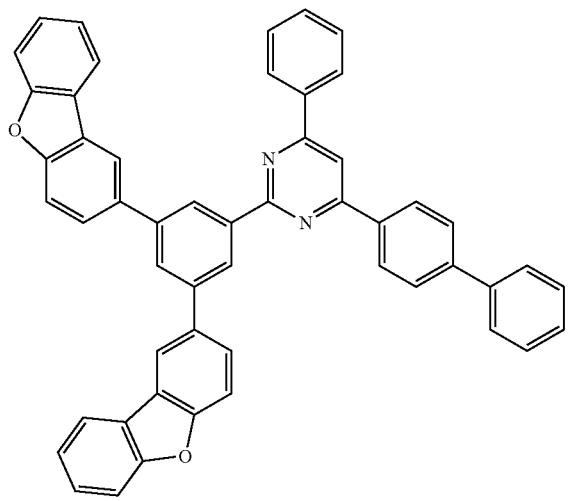
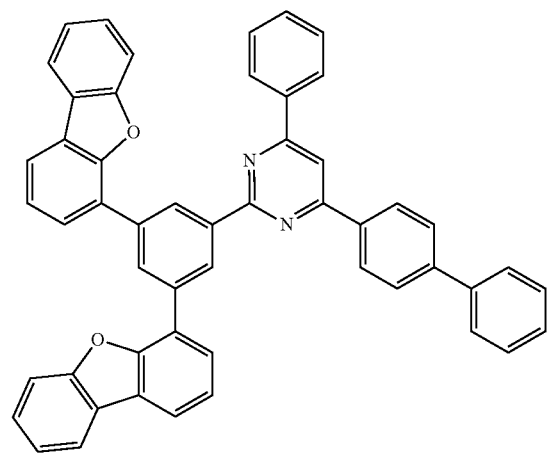
[Formula 90]
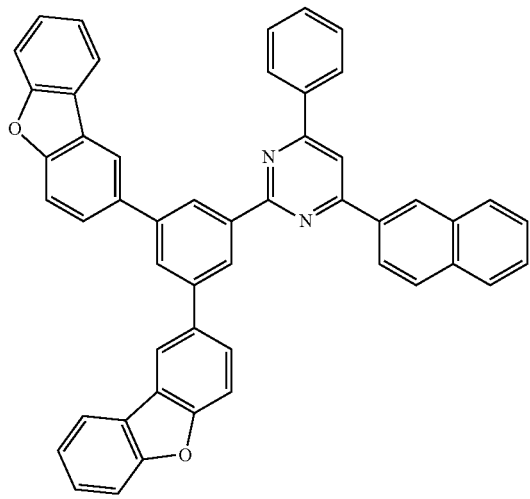
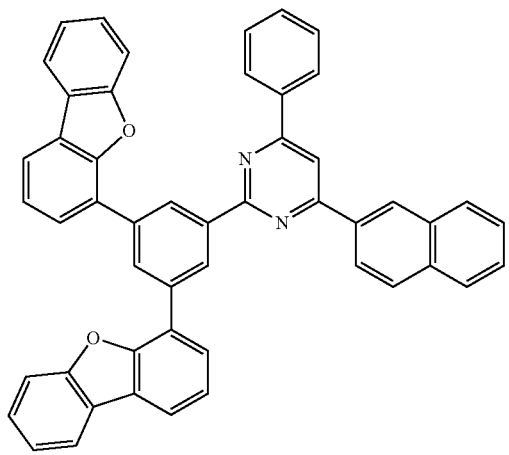

-continued
393 394
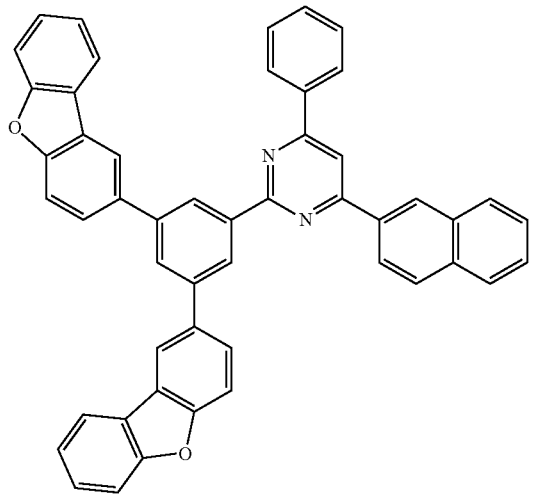
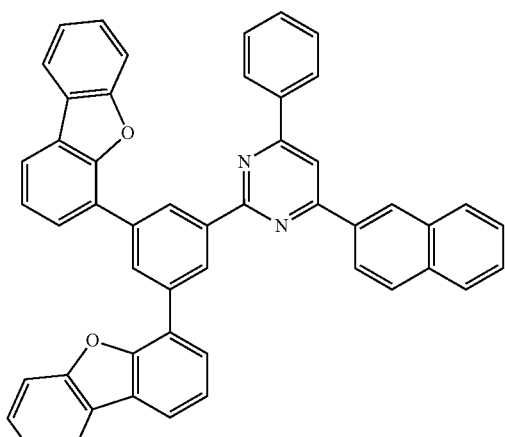
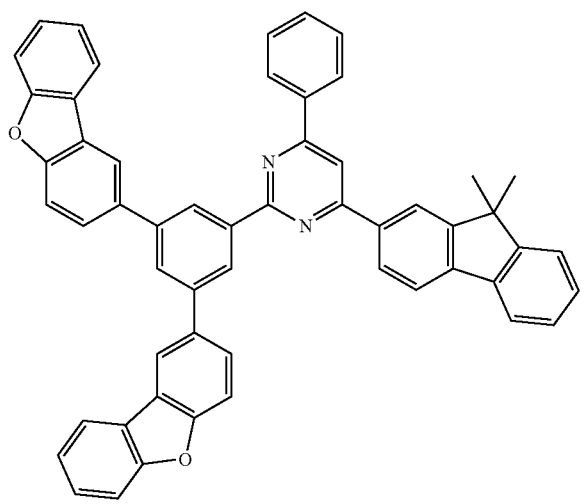
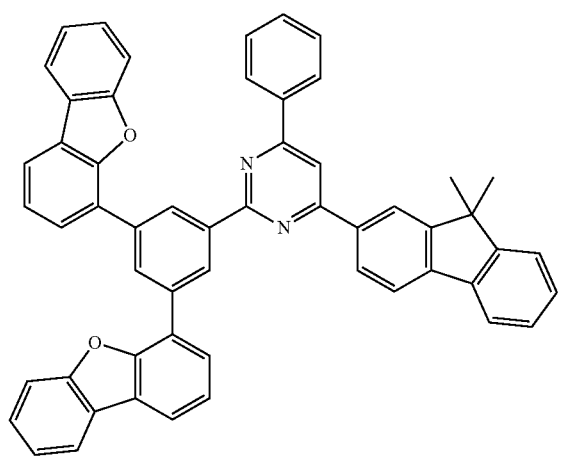
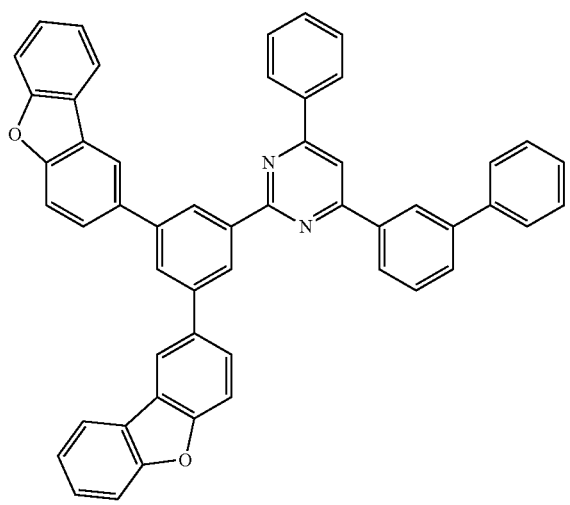
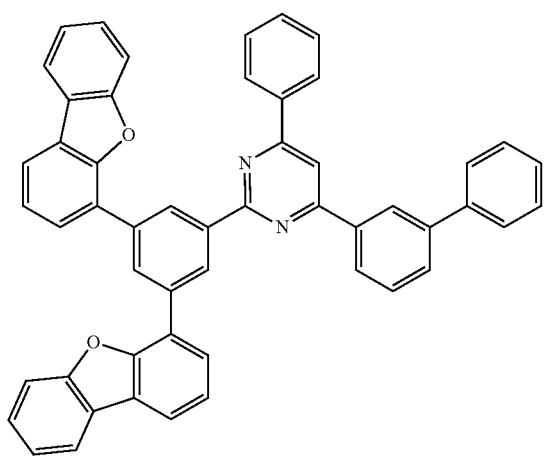

-continued
[Formula 91]
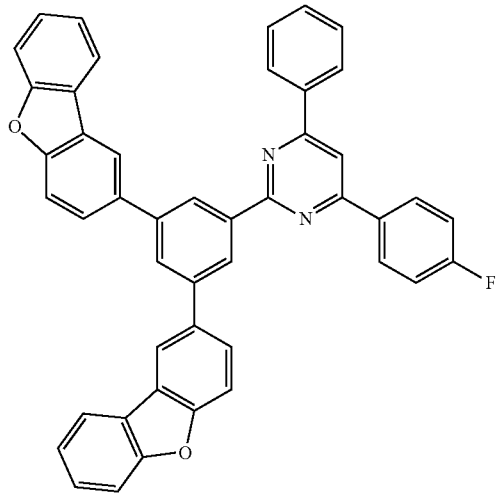
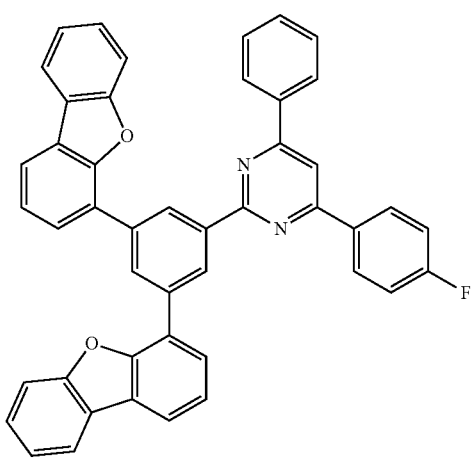
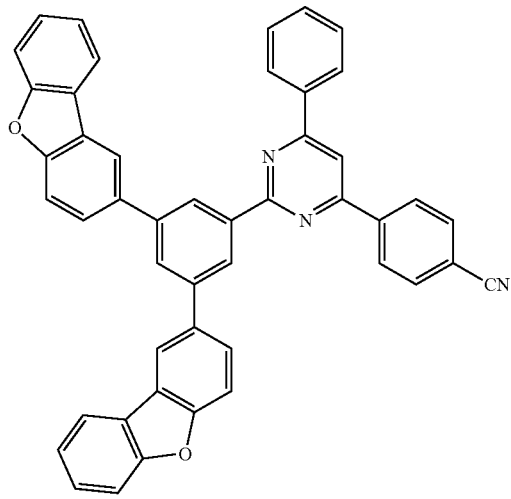
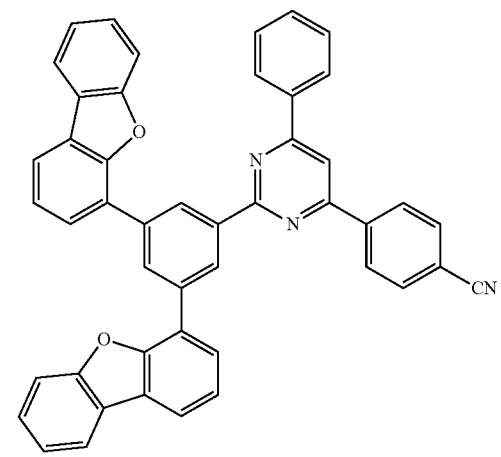
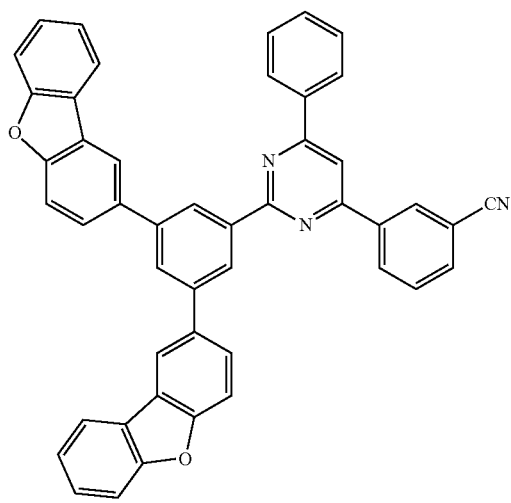
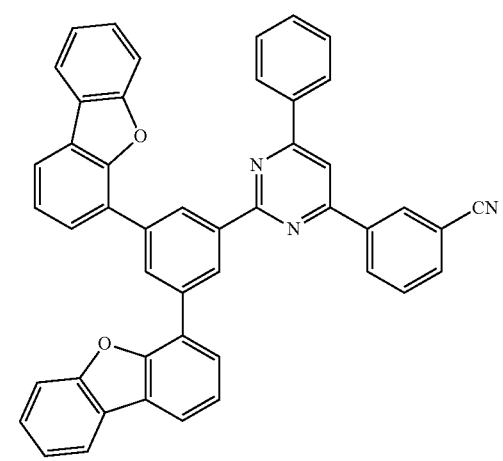

-continued
397
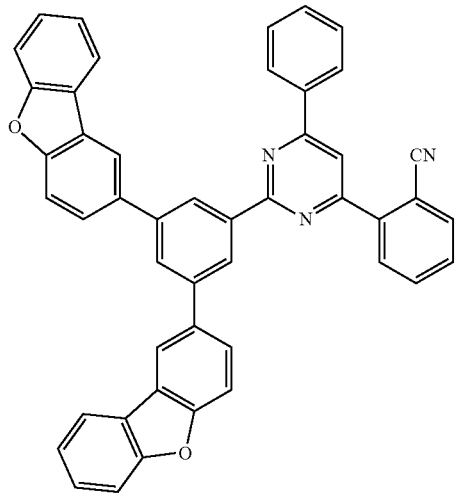
398
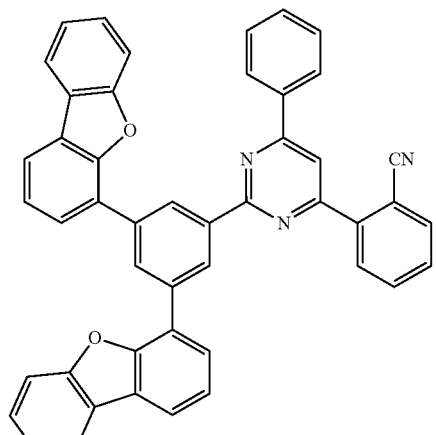
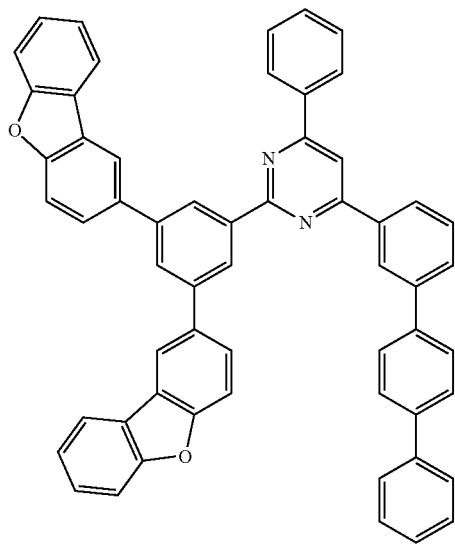
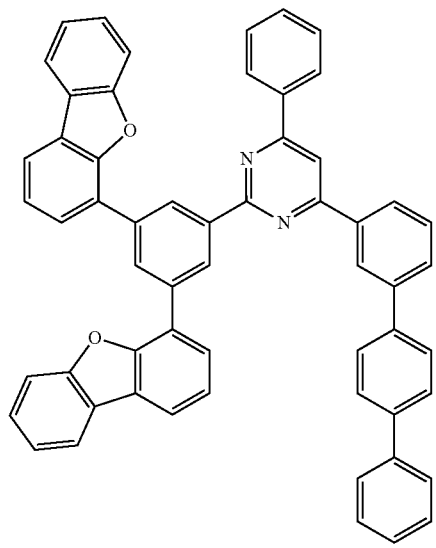
[Formula 92]
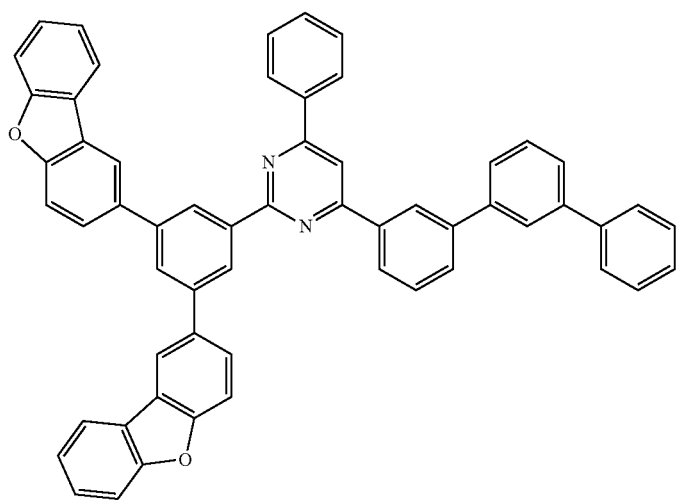

-continued
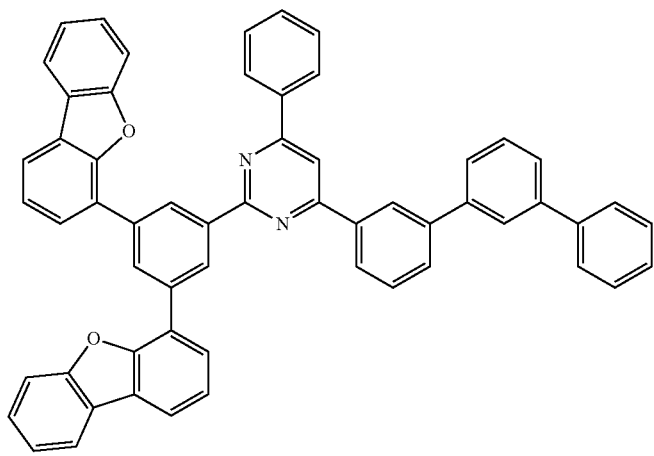
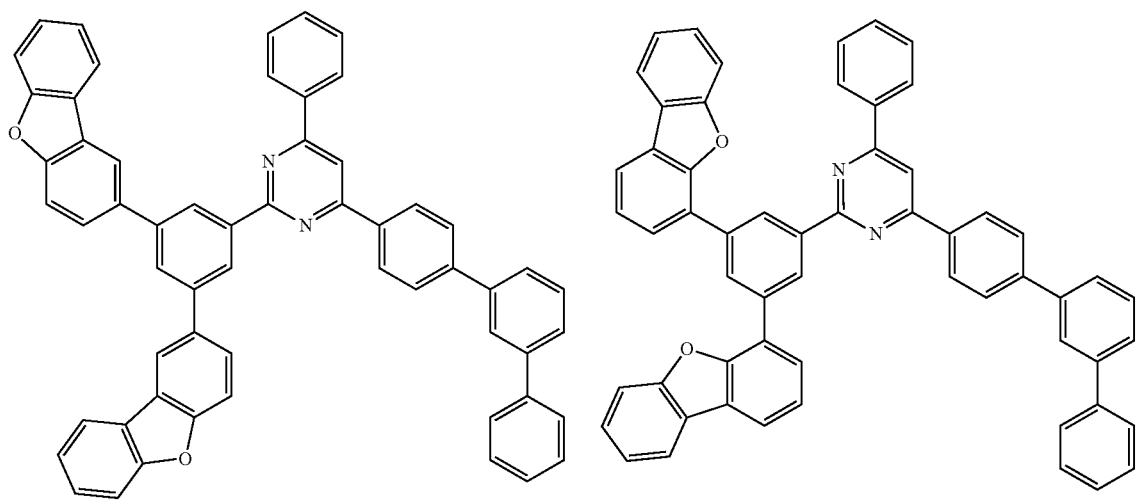
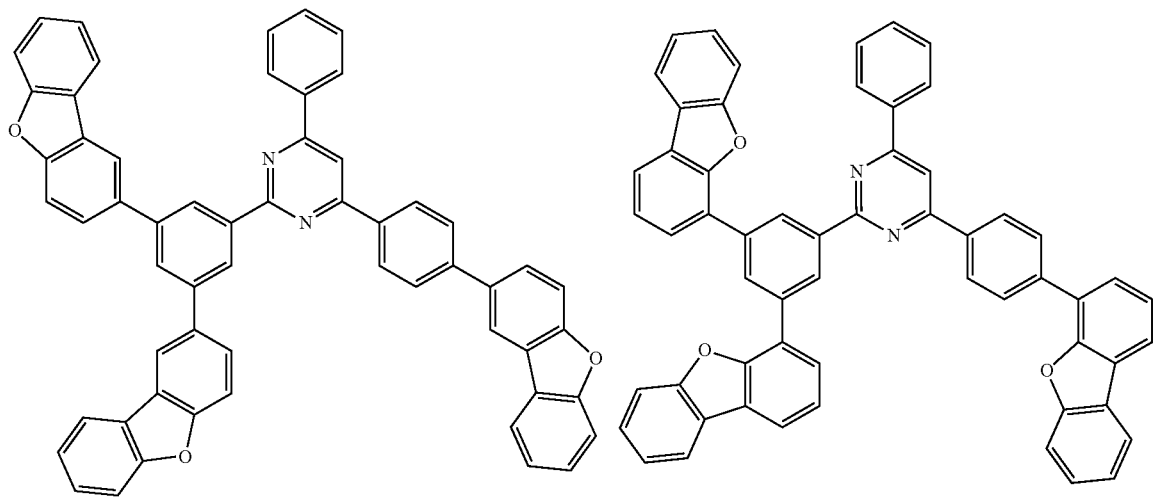

-continued
[Formula 93]
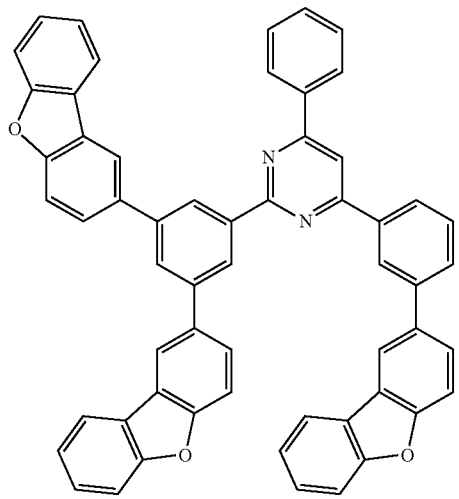
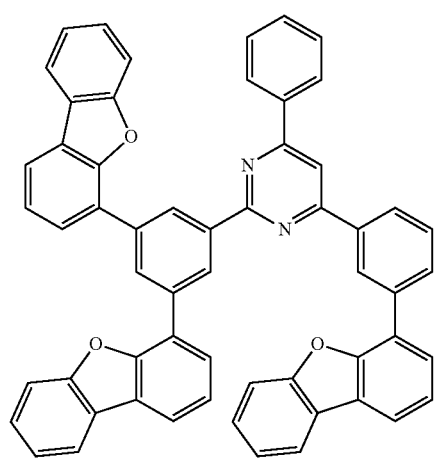
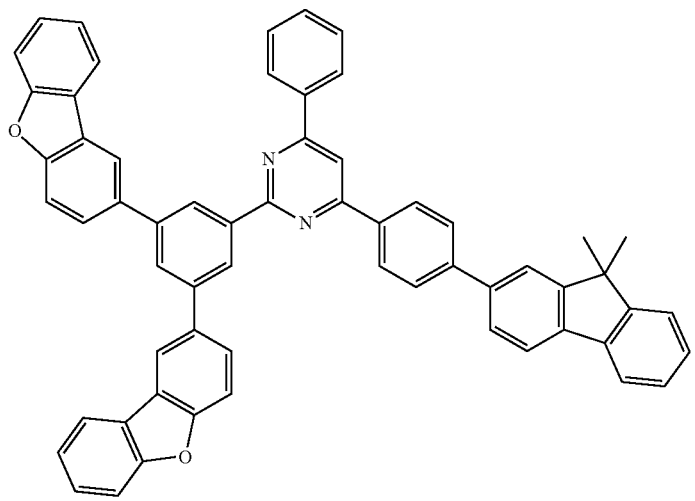
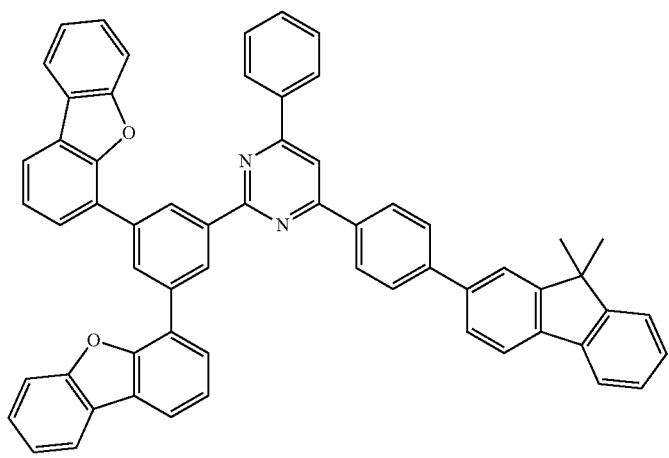

-continued
403
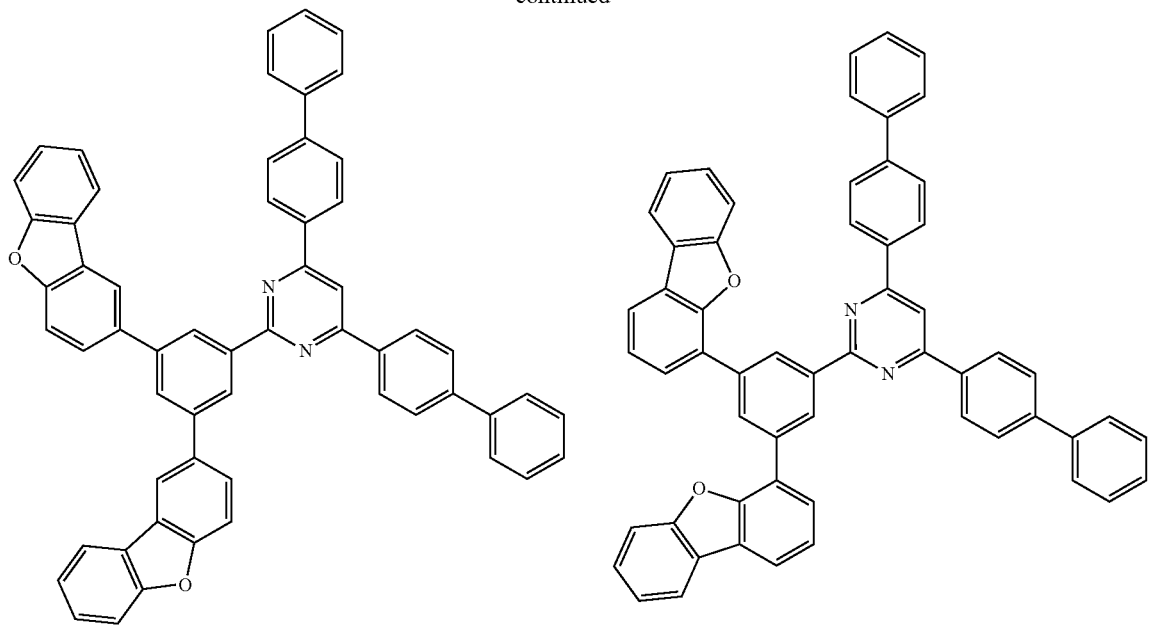
404
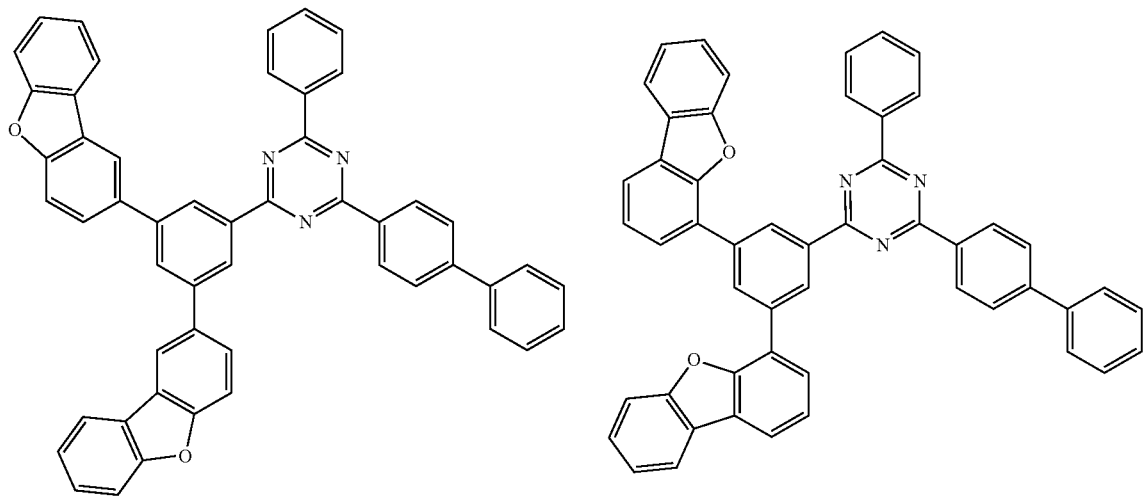
[Formula 94]
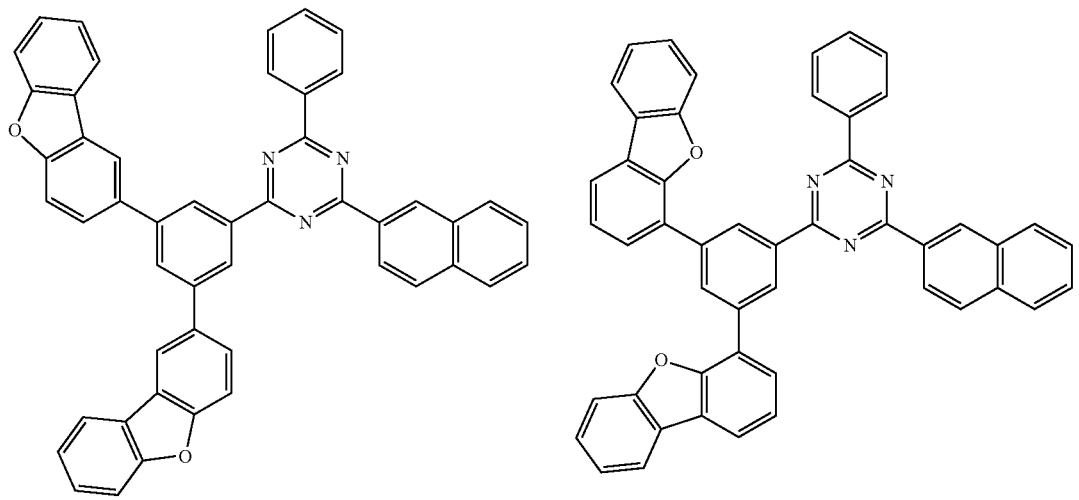

405
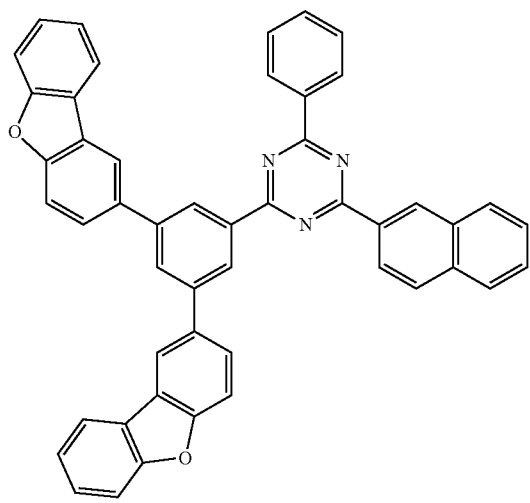
406
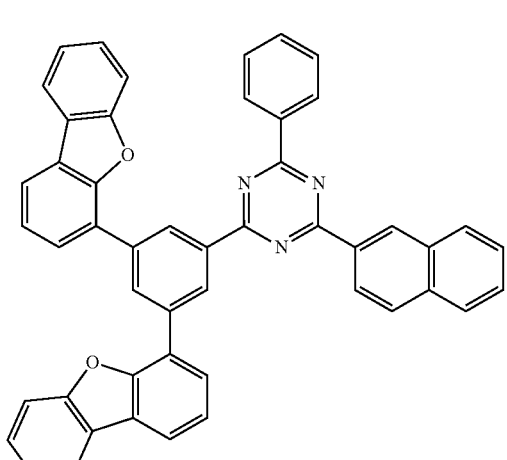
-continued
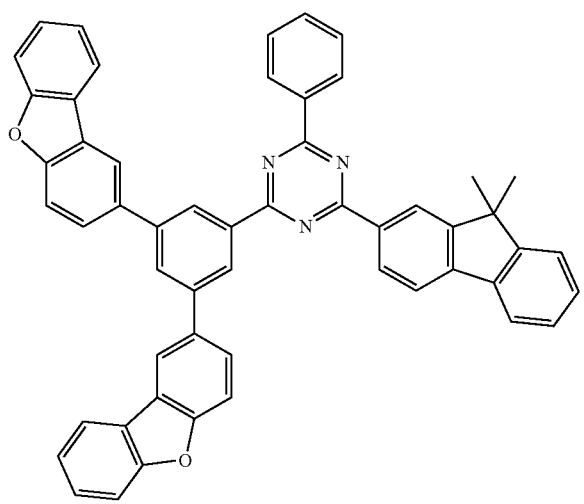
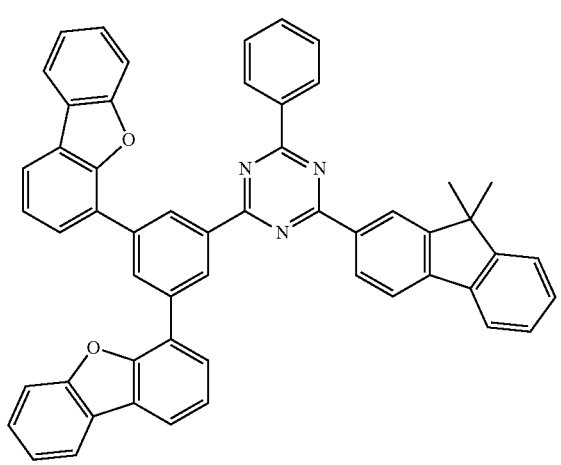
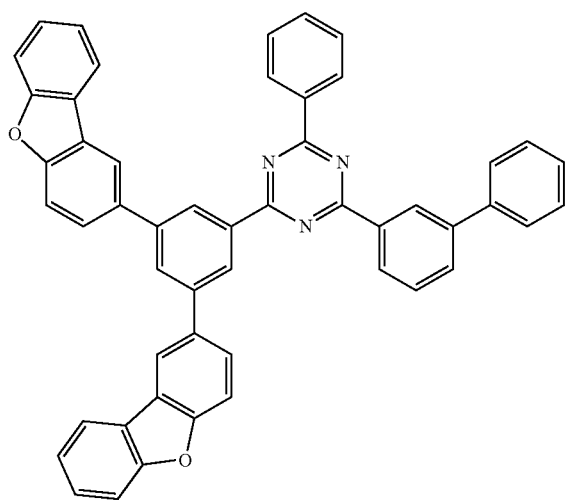
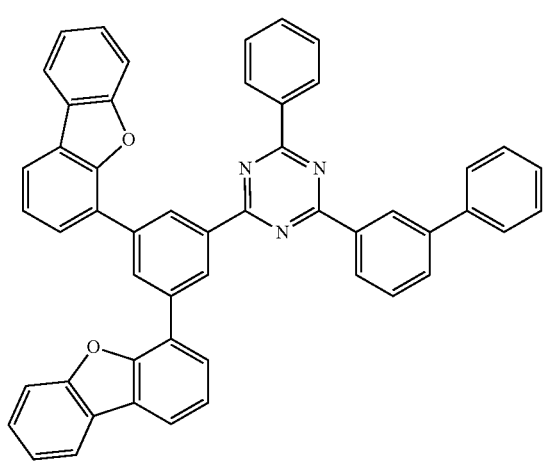

-continued
[Formula 95]
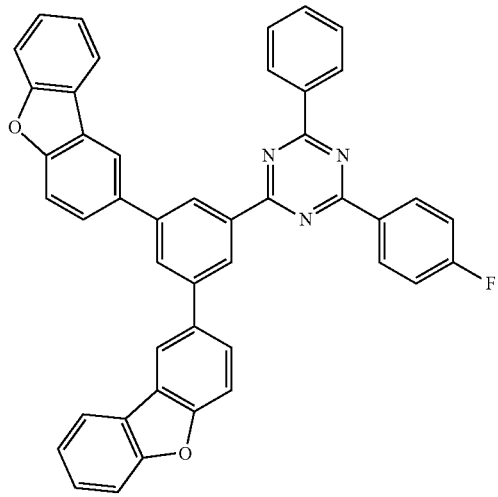
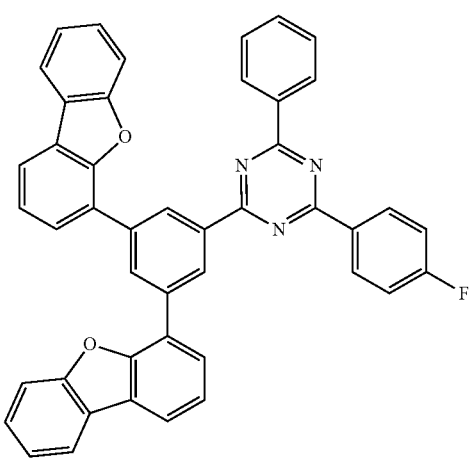
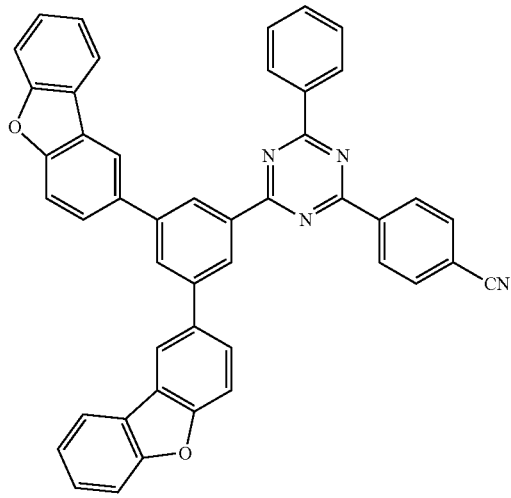
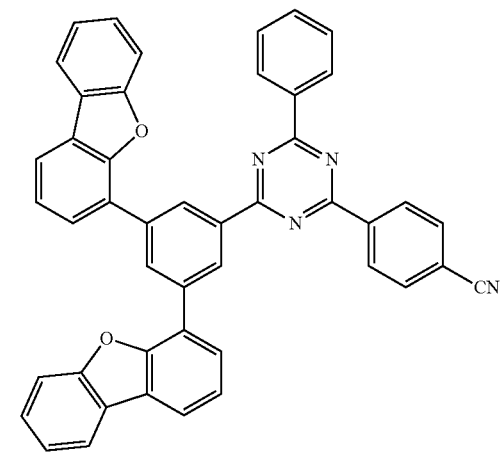
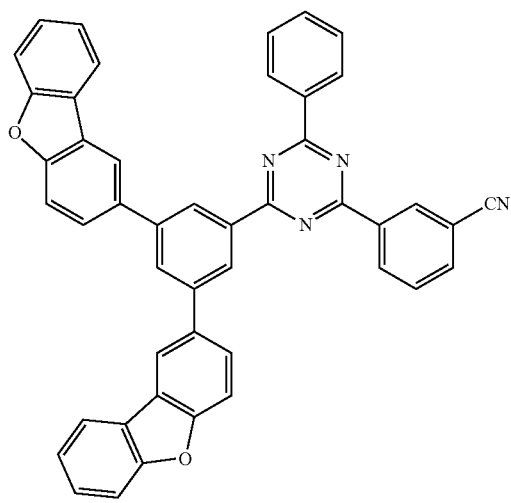
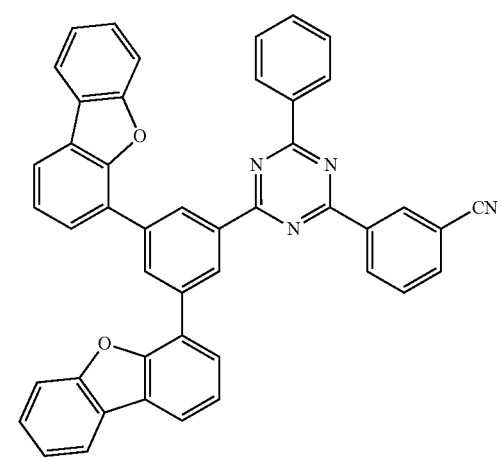

409
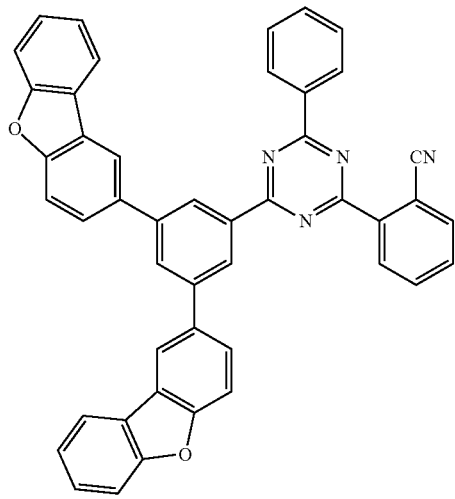
410
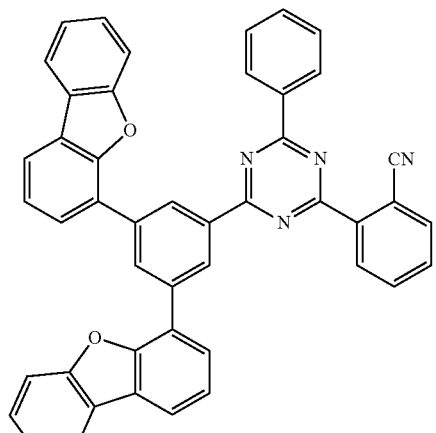
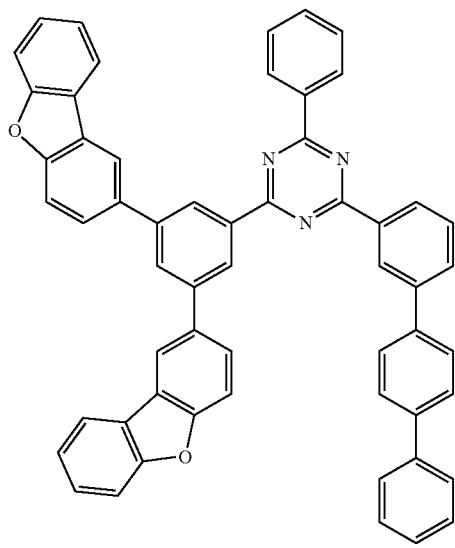
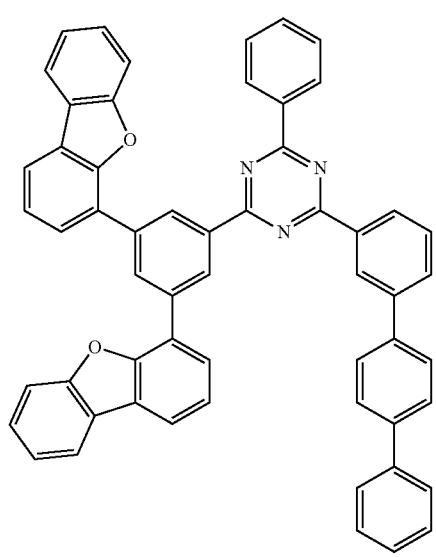
[Formula 96]
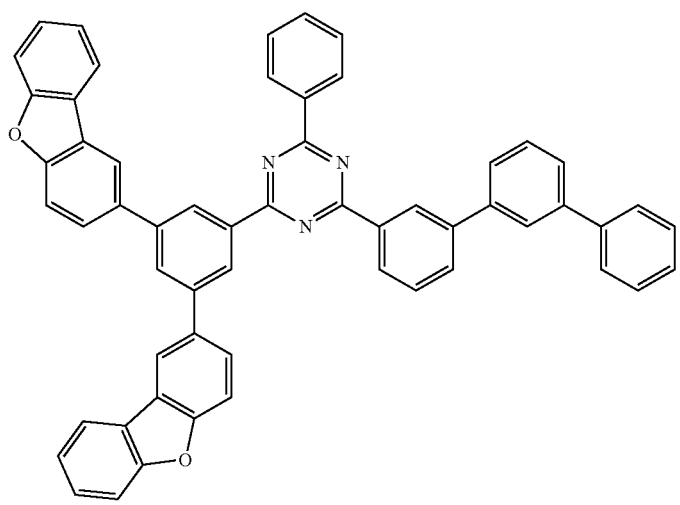

411 412
-continued
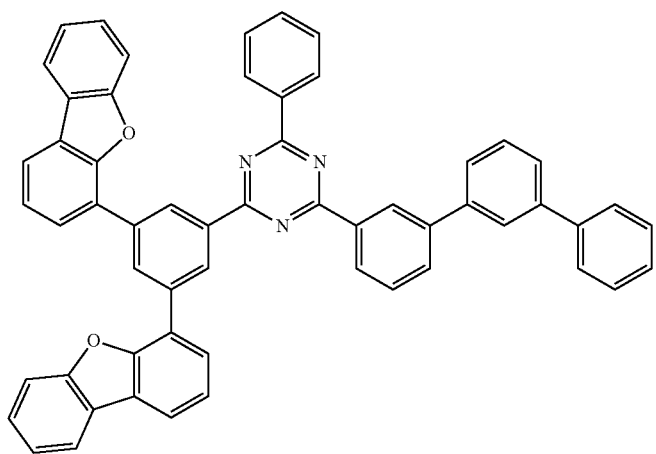
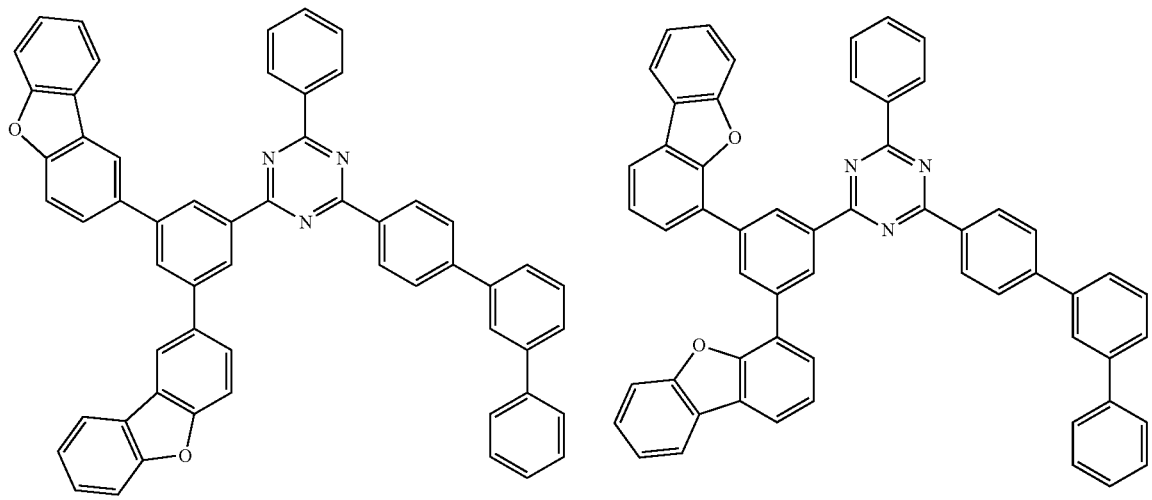
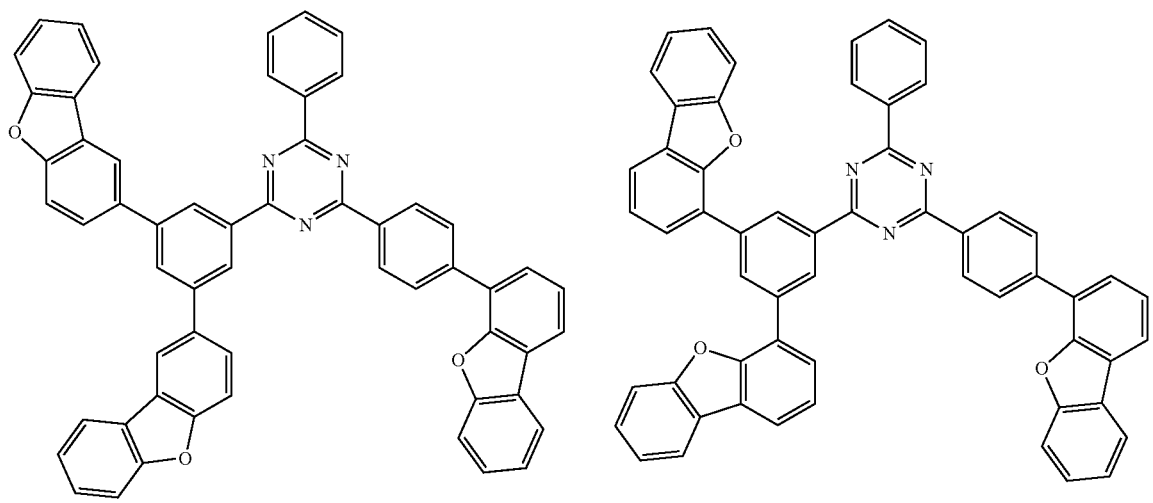

[Formula 97]
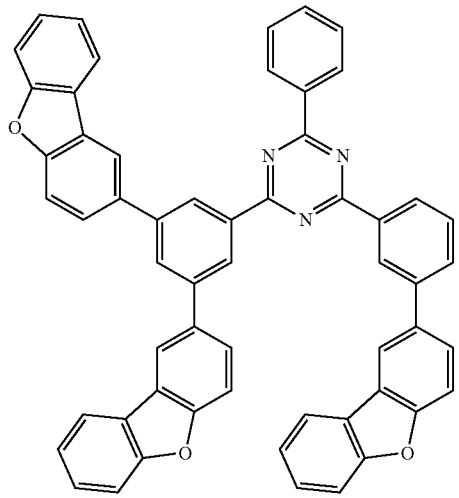
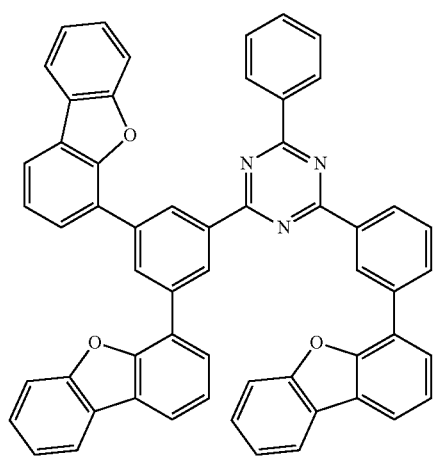
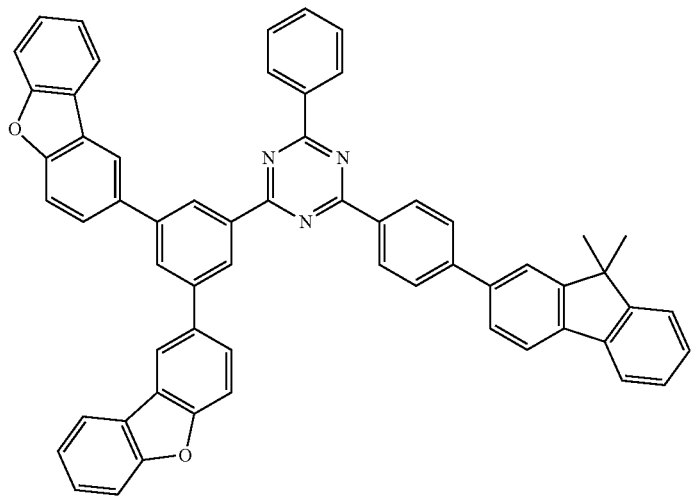
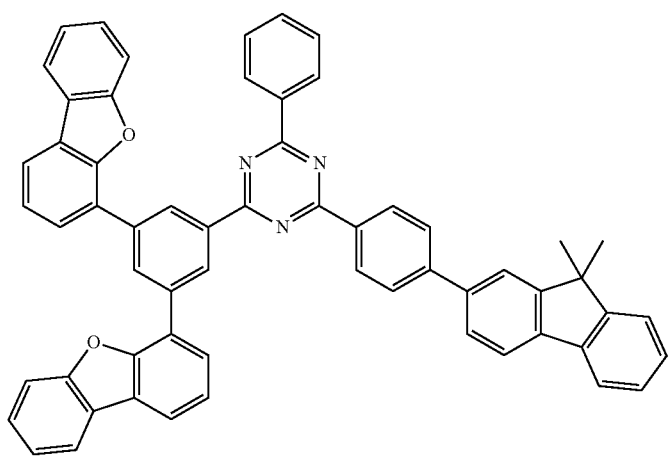

415
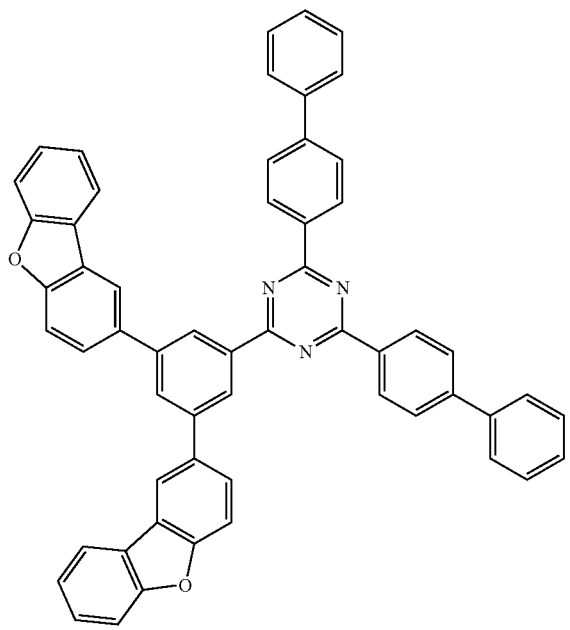
416
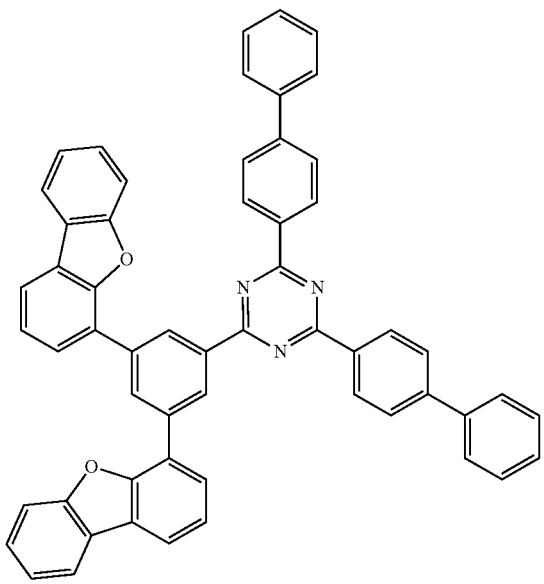
-continued
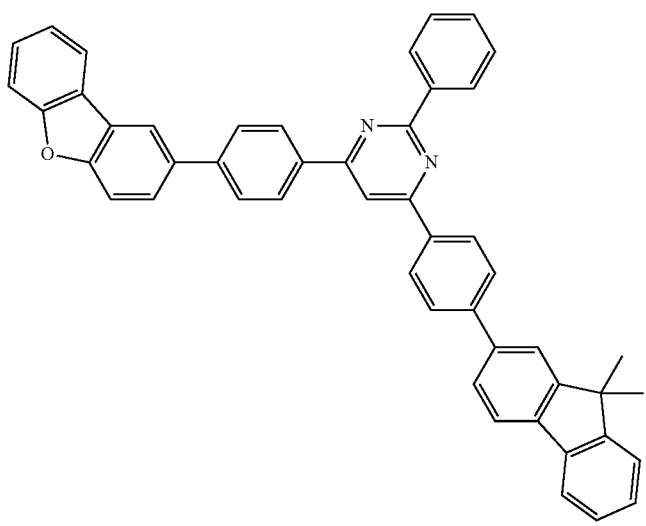
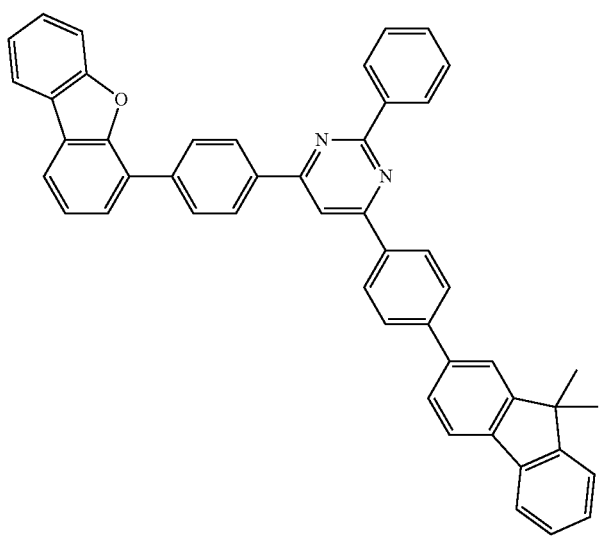

[Formula 98]
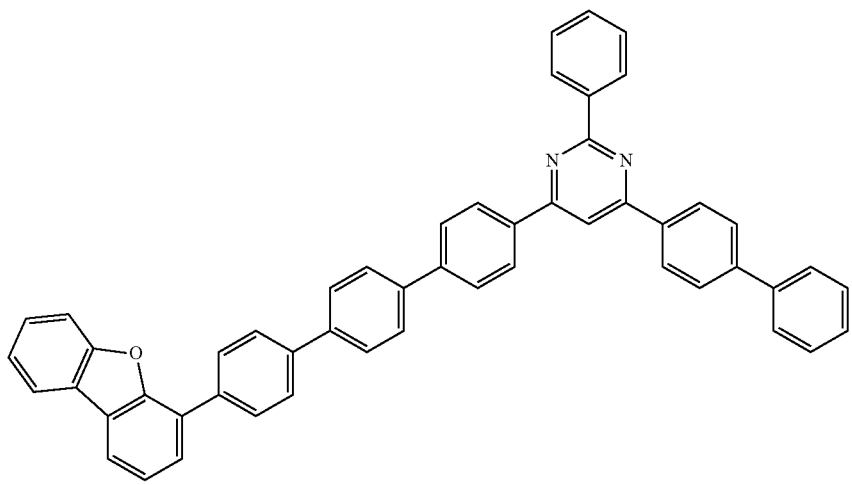
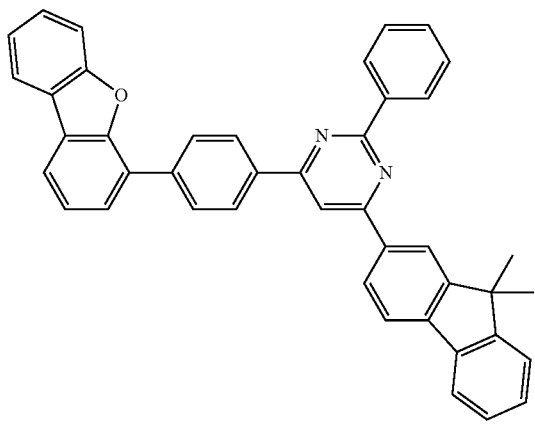
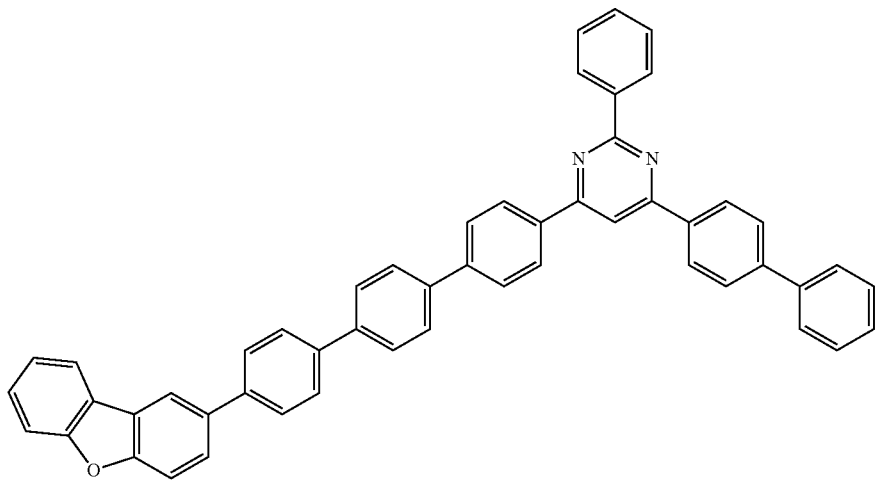

419
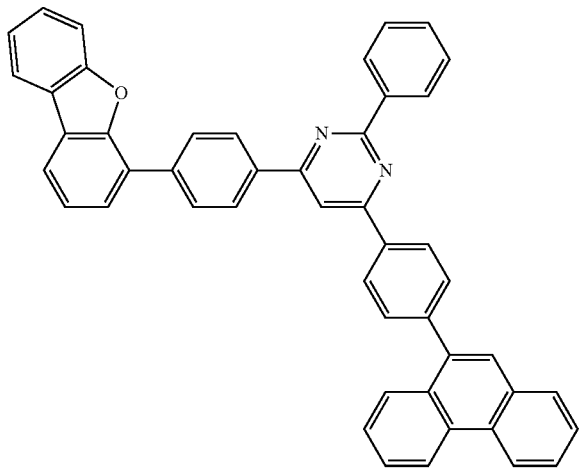
-continued
420
[Formula 99]
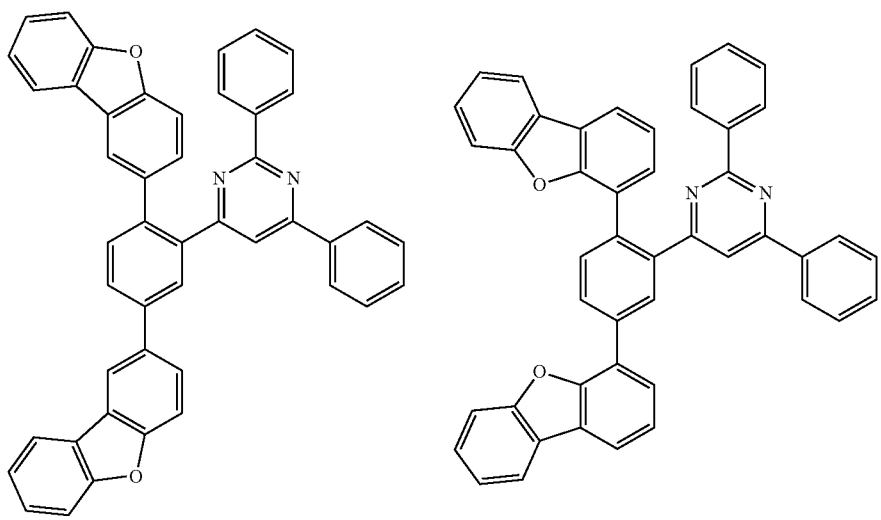
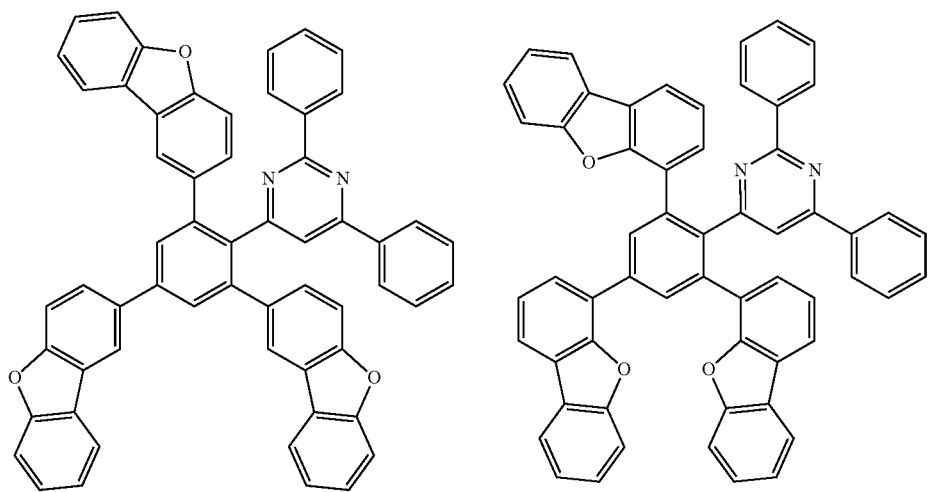

-continued
421
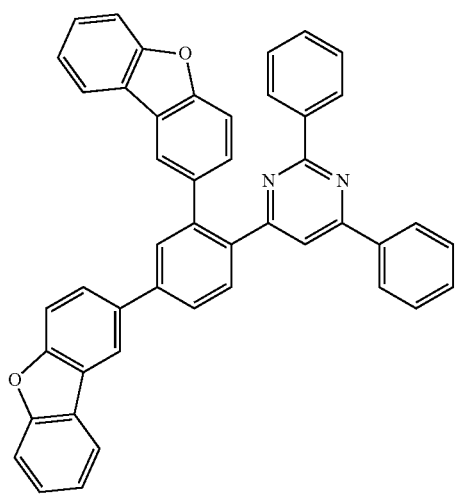
422
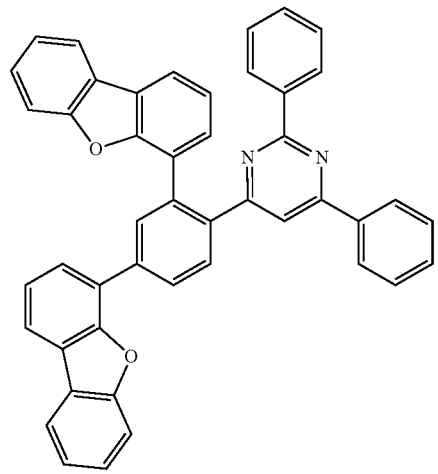
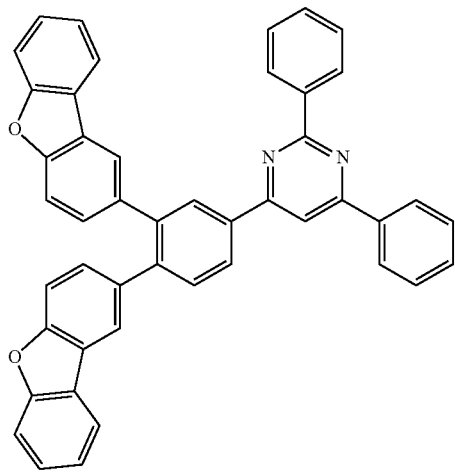
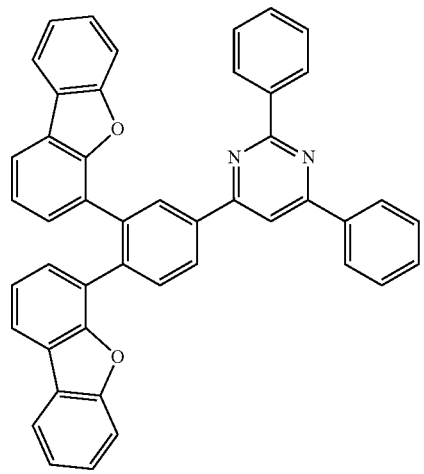
[Formula 100]
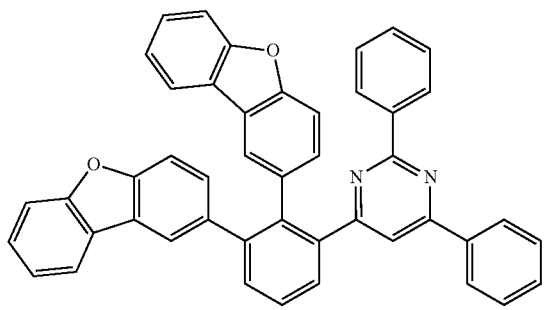
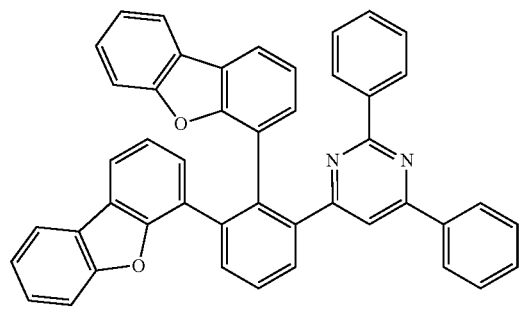

-continued
423
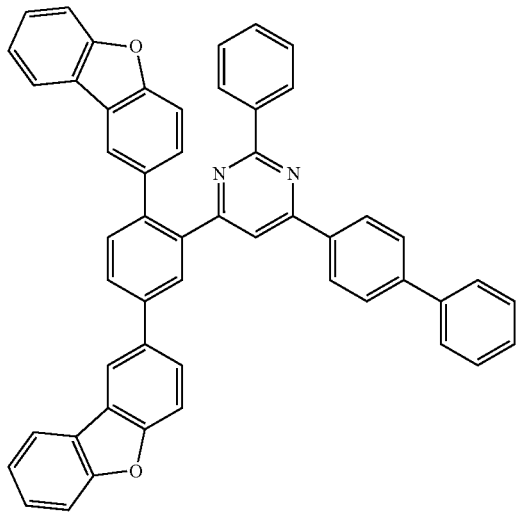
424
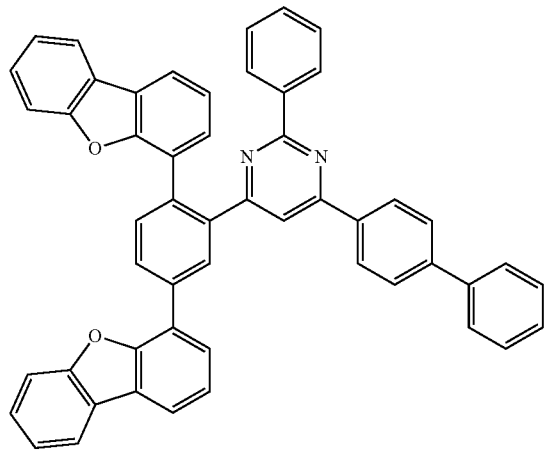
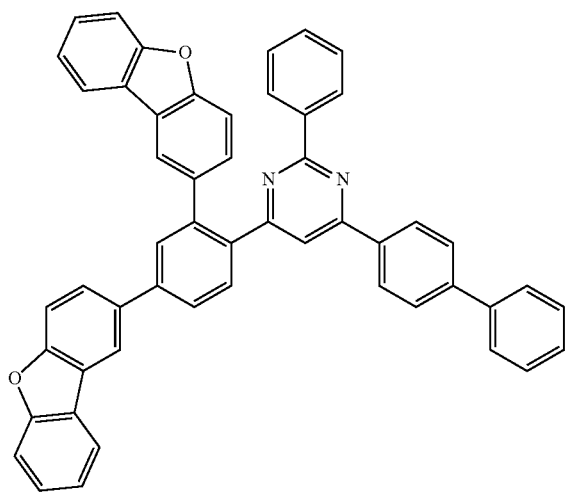
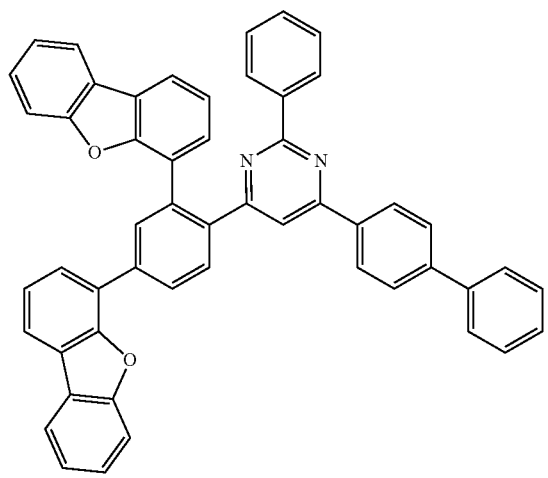
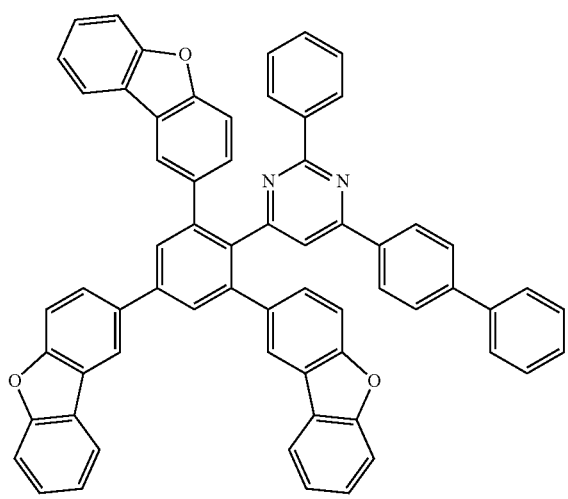
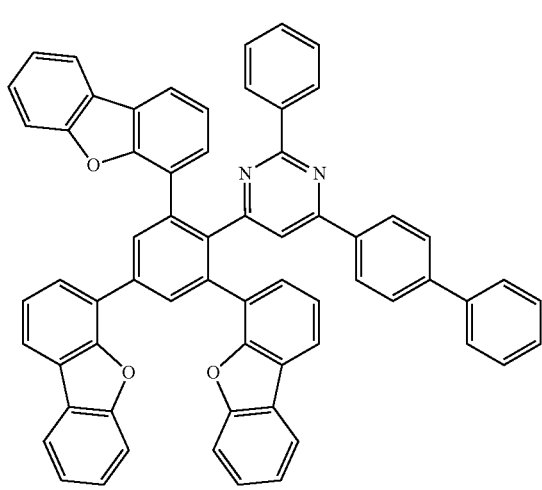

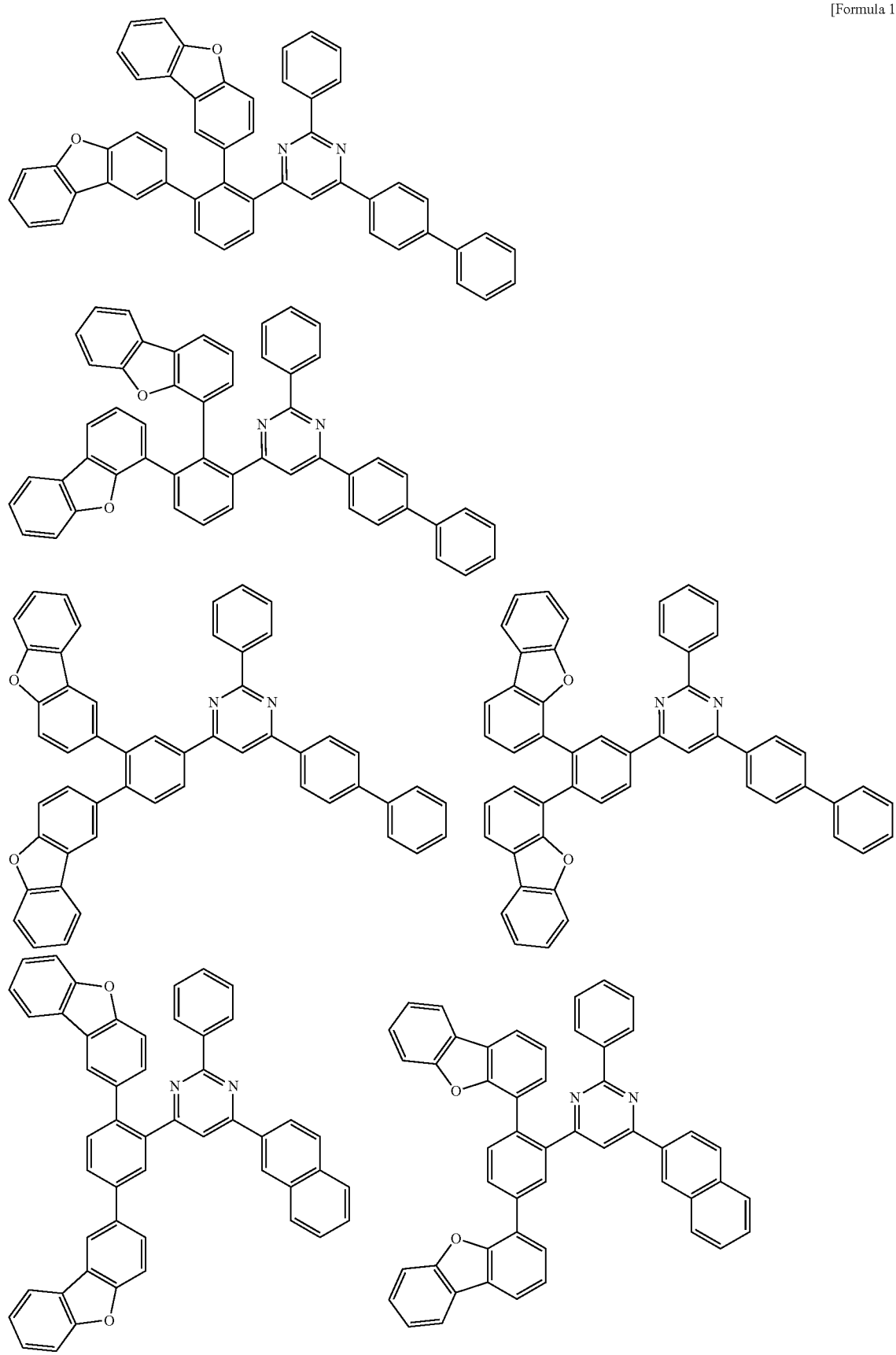
[Formula 101]

427
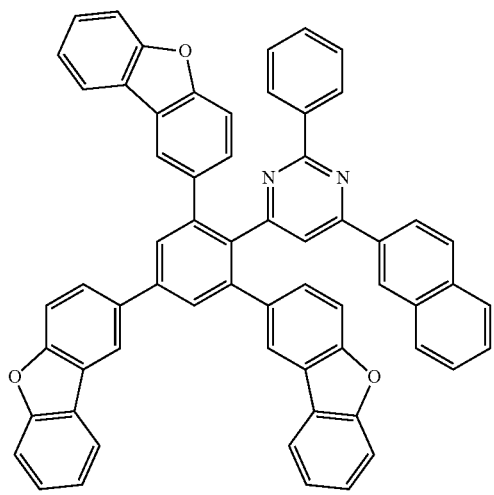
428
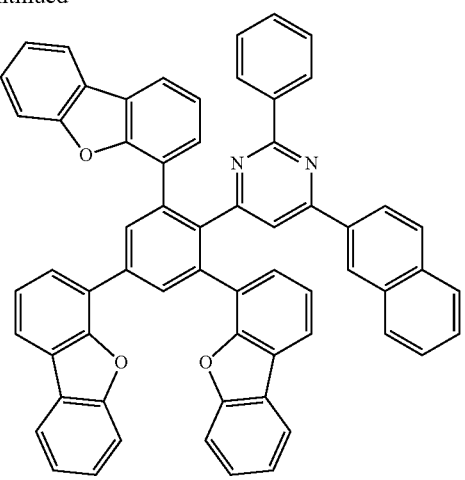
[Formula 102]
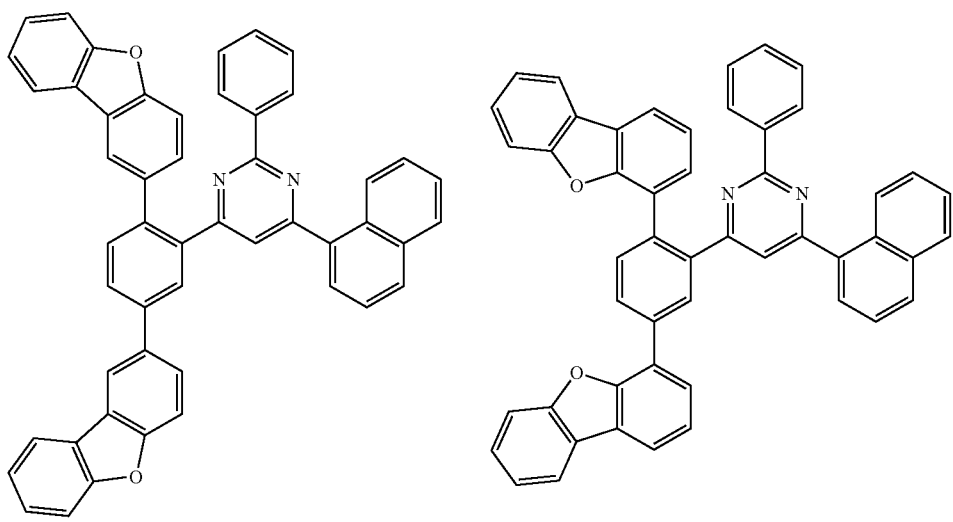
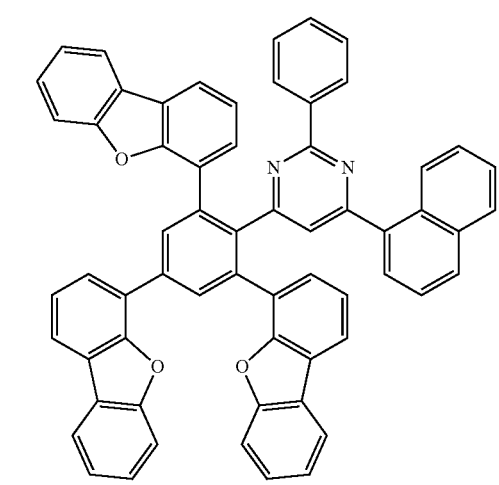

429
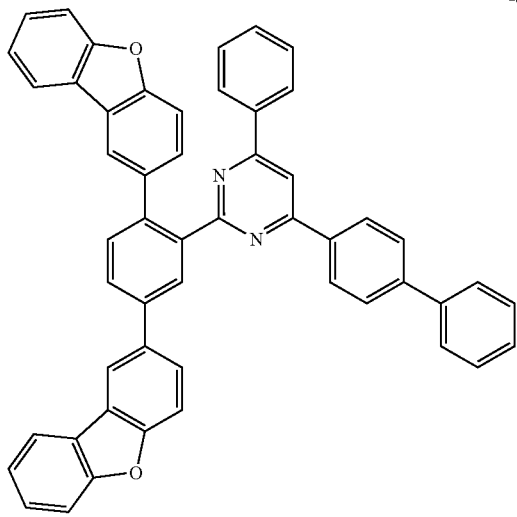
430
-continued
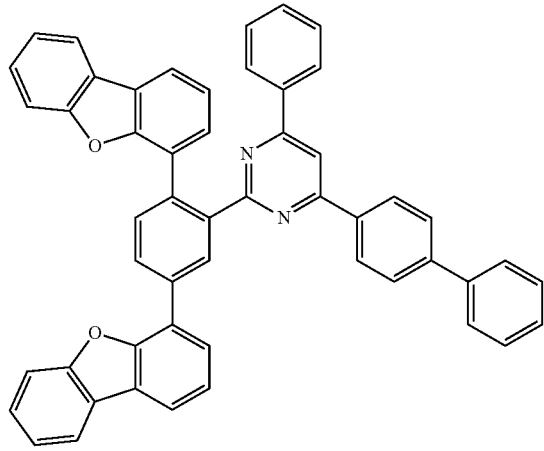
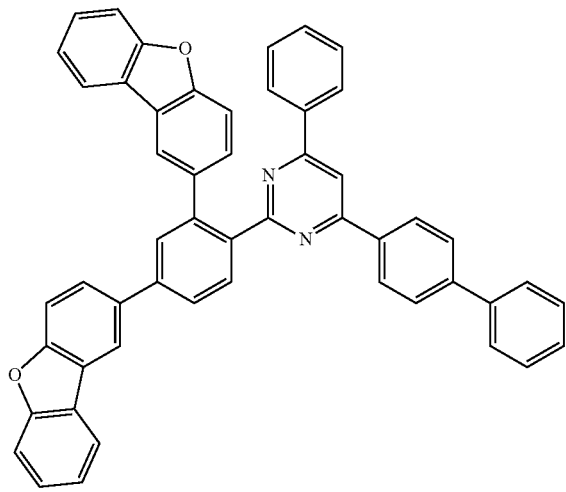
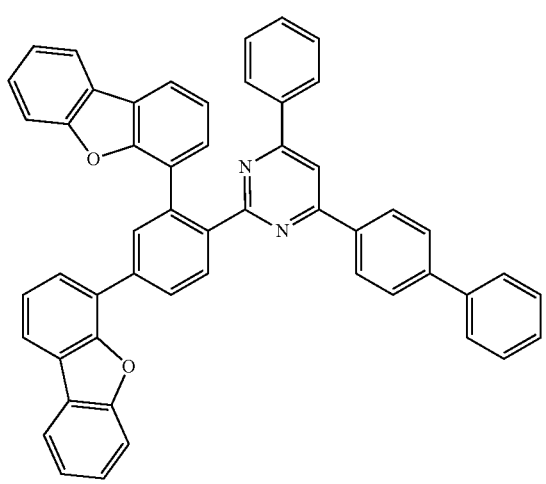
[Formula 103]
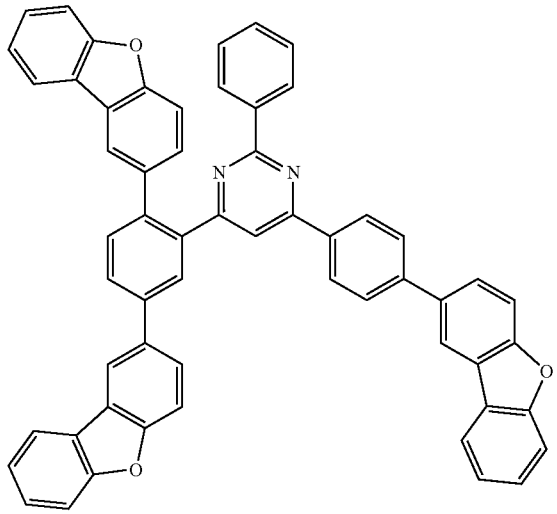
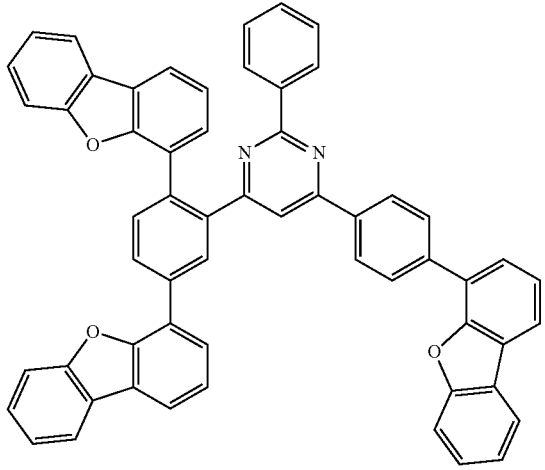

-continued
431
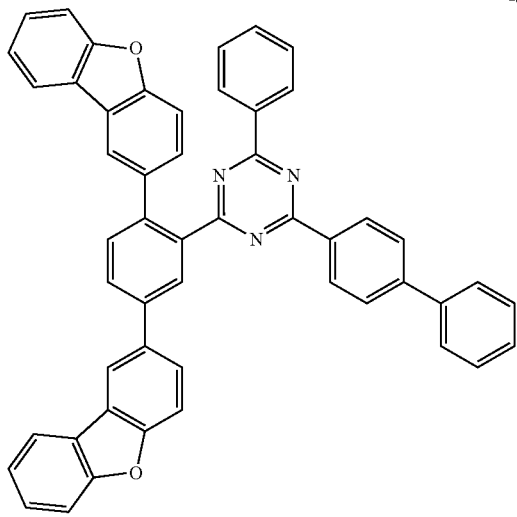
432
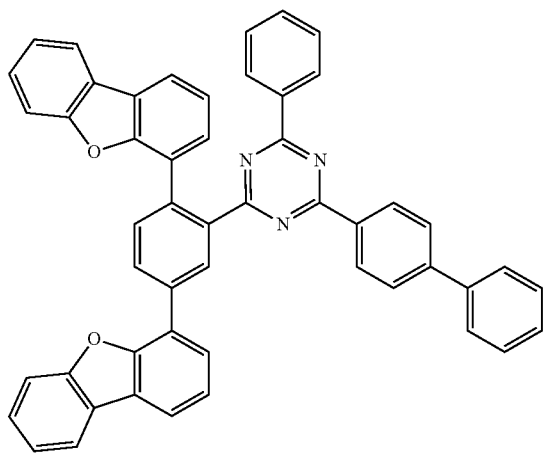
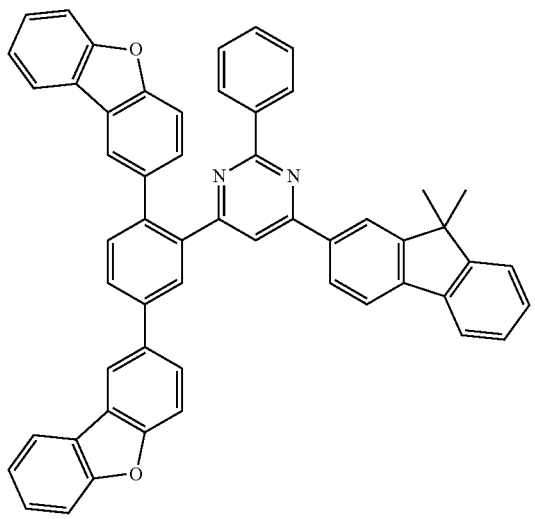
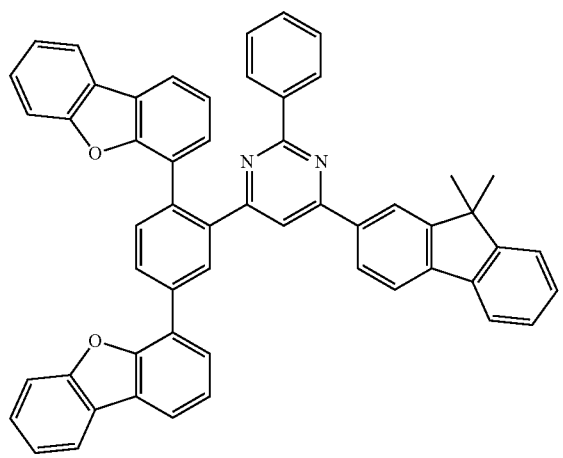
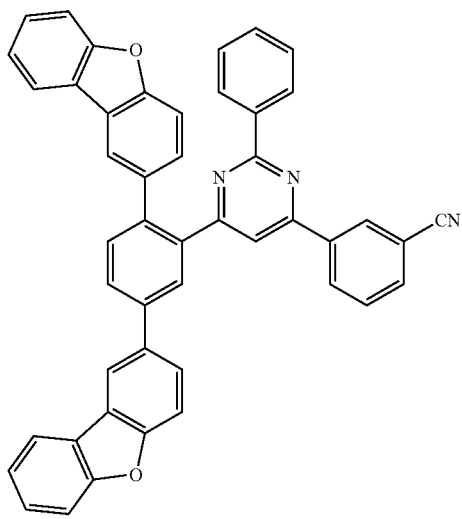
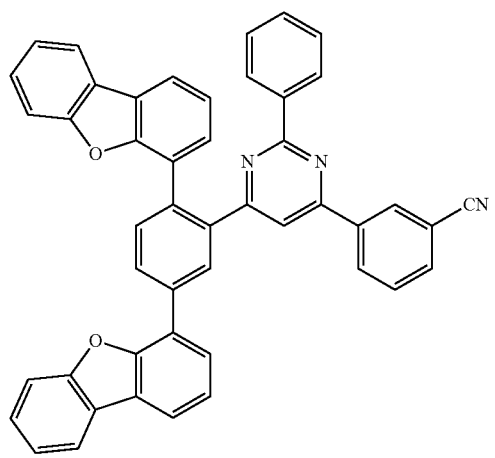

[Formula 104]
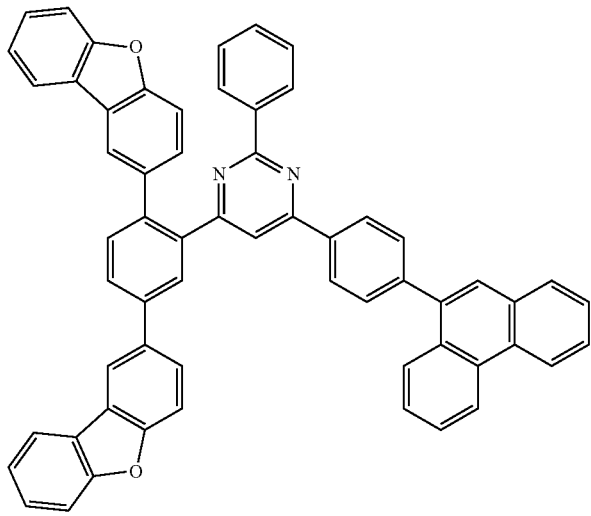
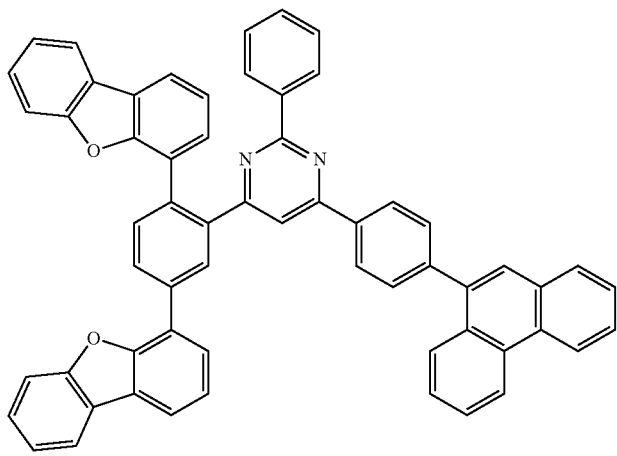
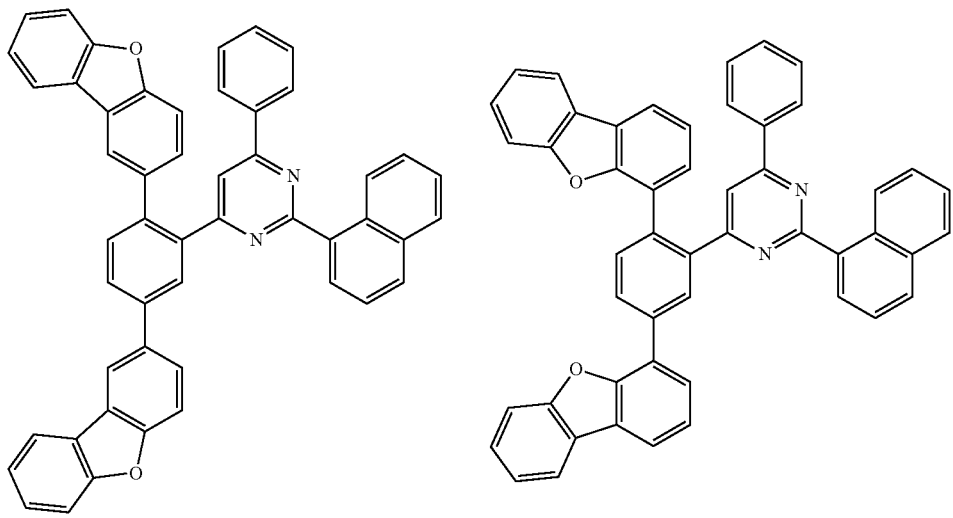

-continued
435
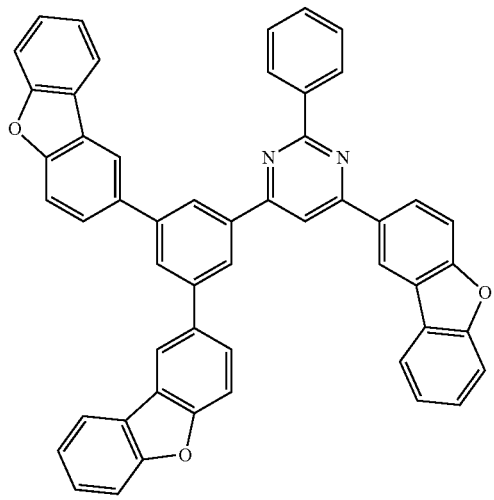
436
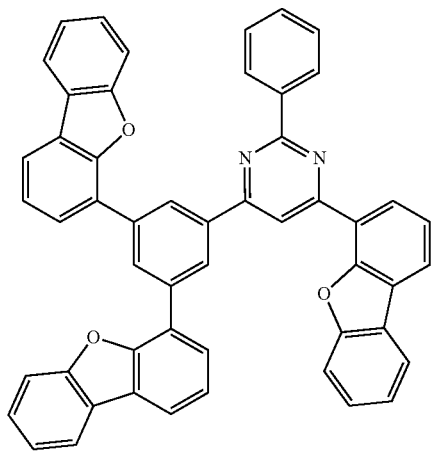
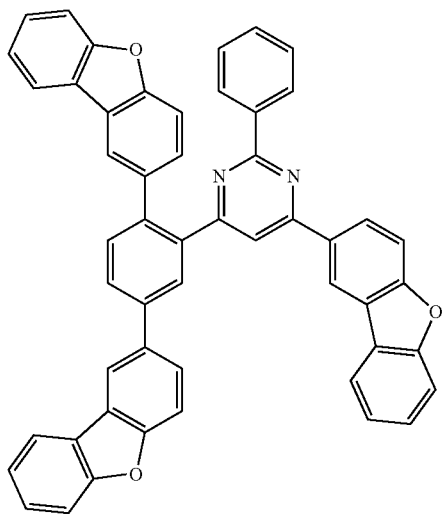
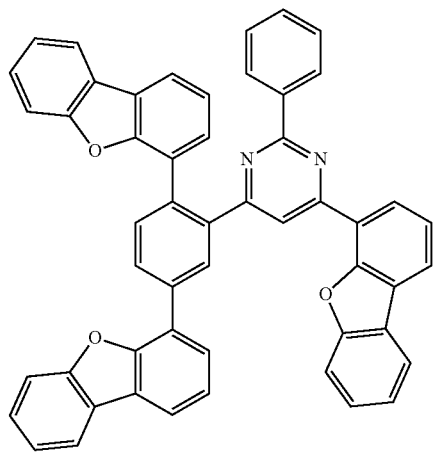
[Formula 105]
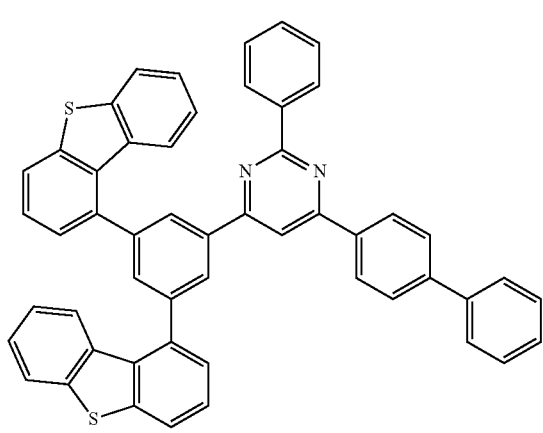
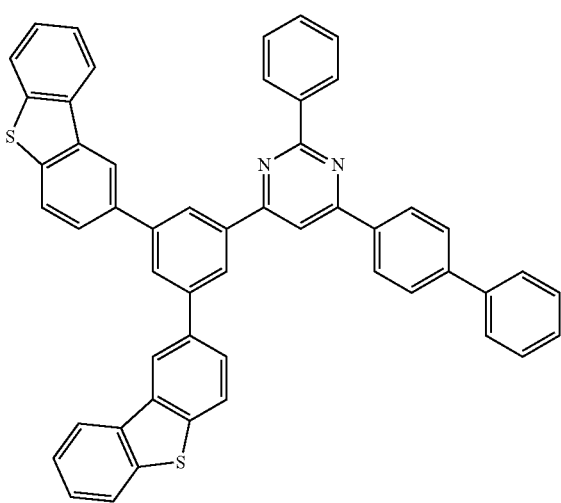

-continued
437
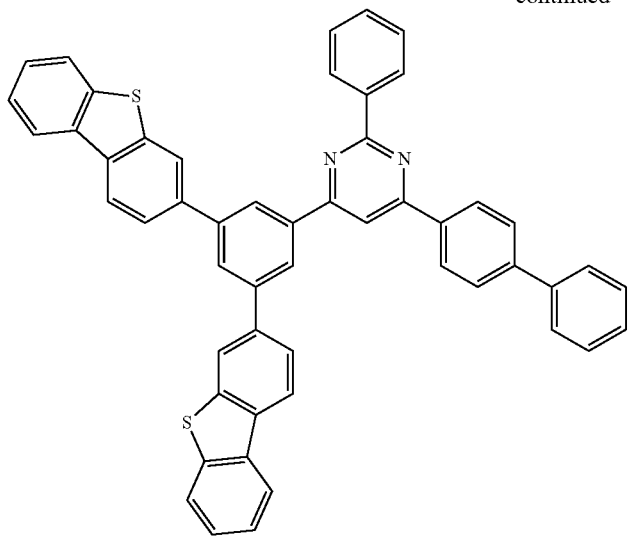
438
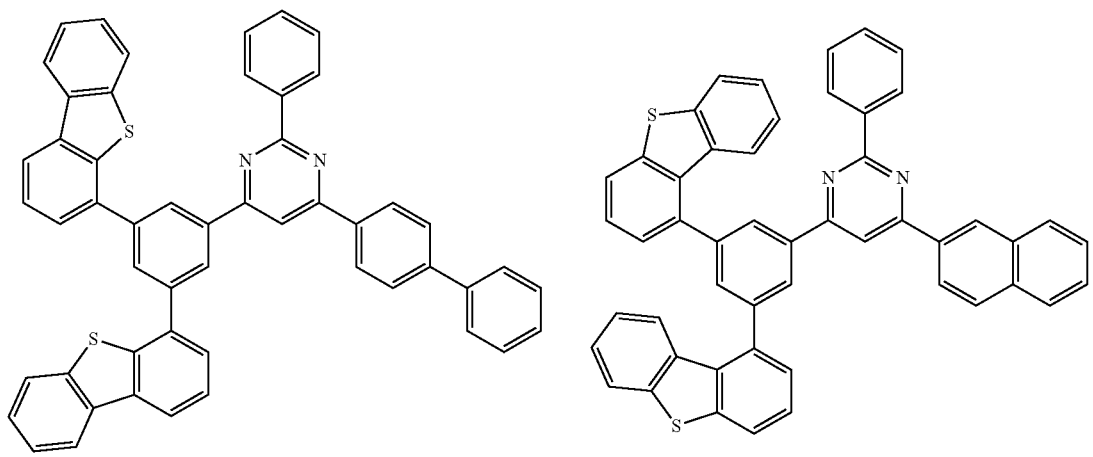
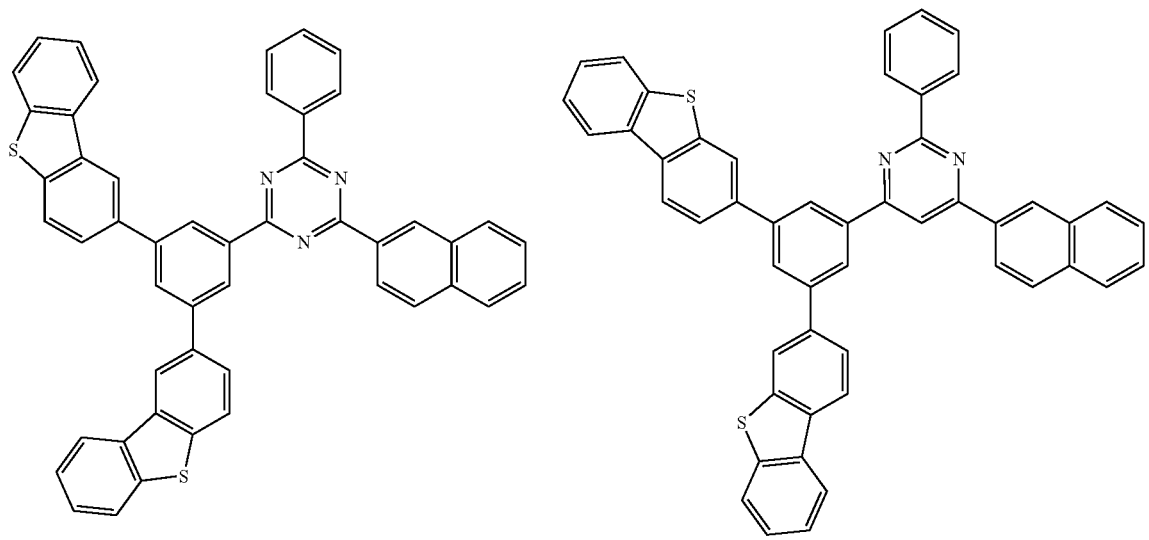

439
-continued
440
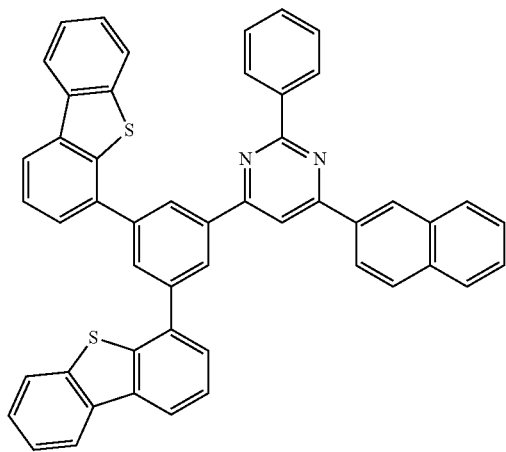
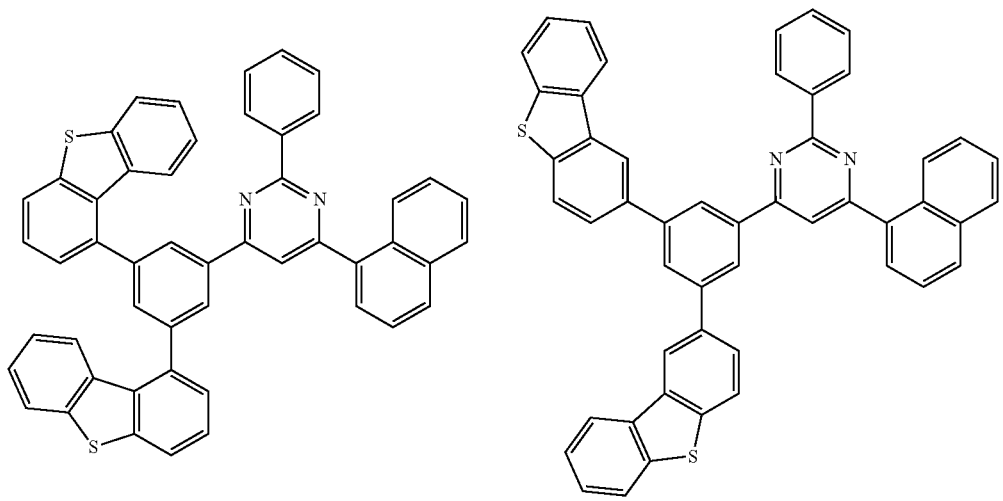
[Formula 106]
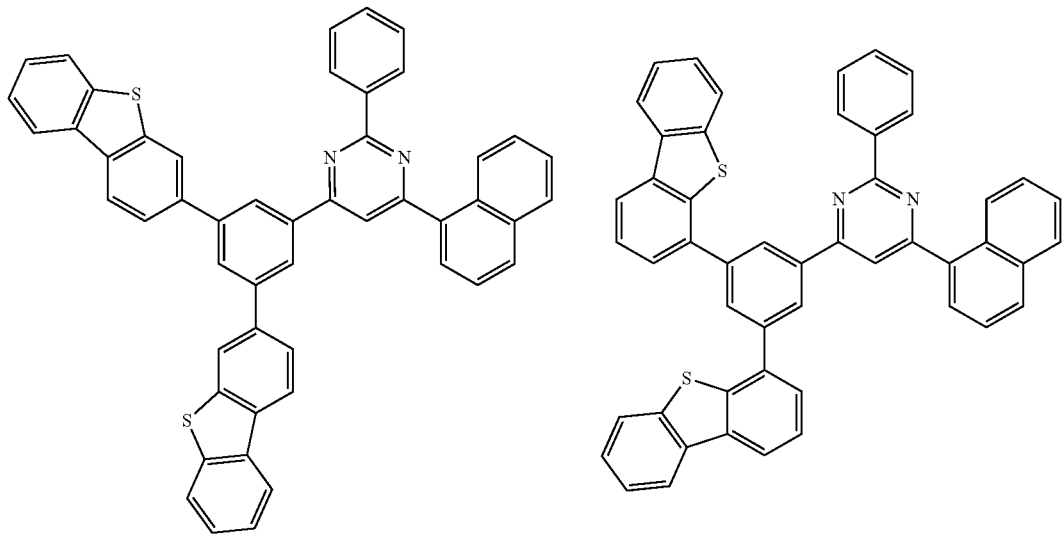

-continued
441
442
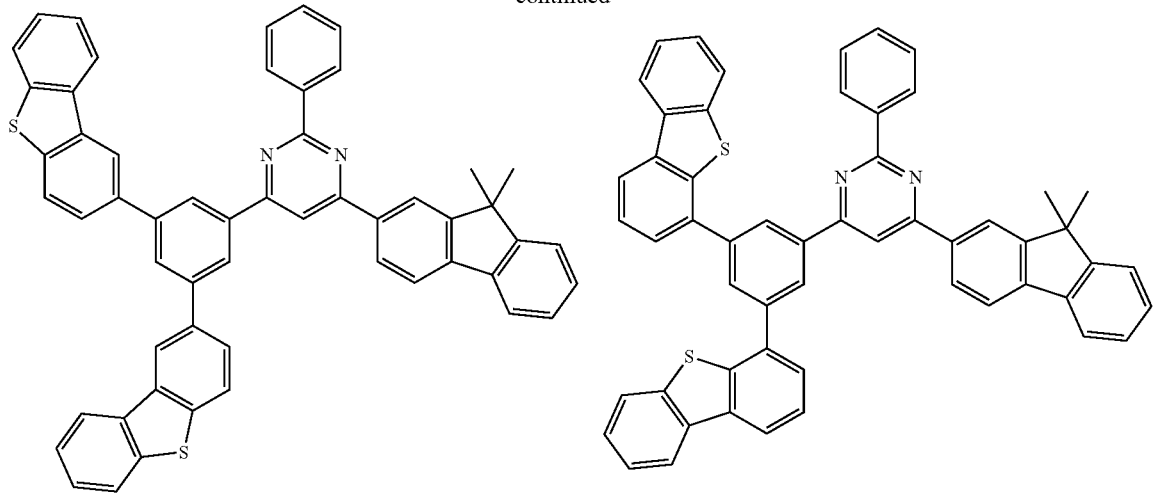
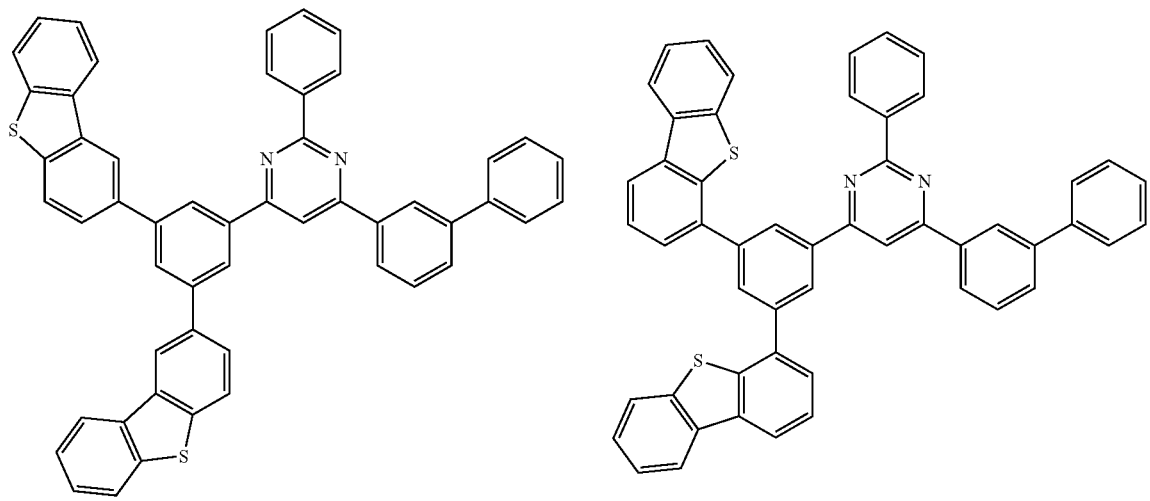
[Formula 107]
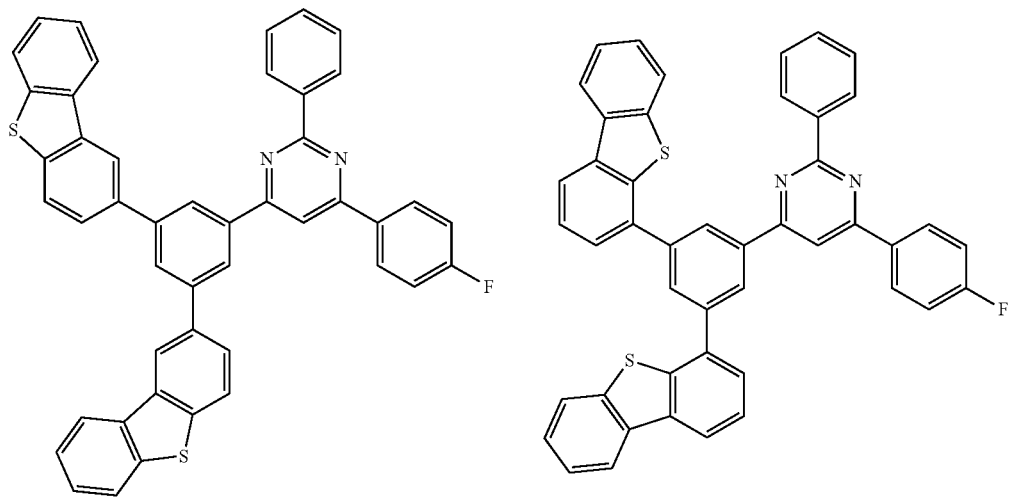

443 444
-continued
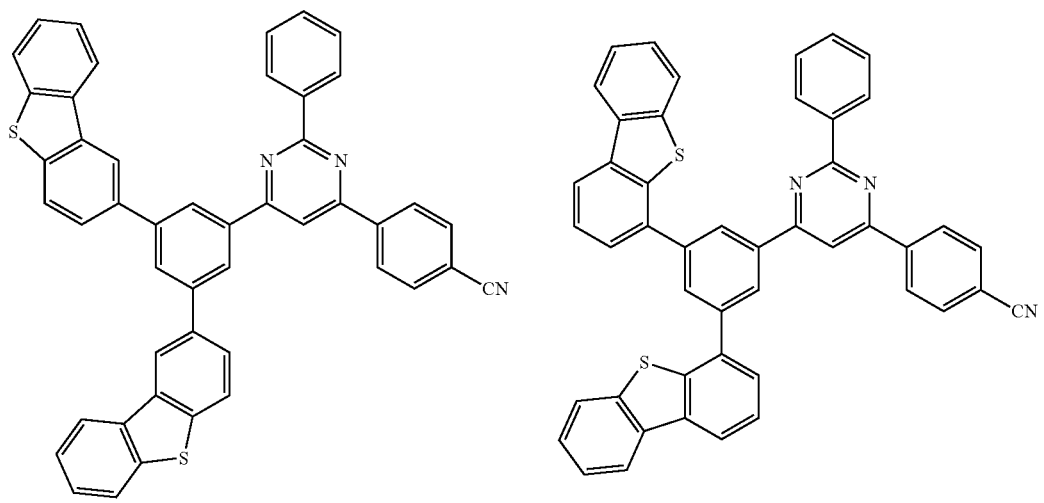
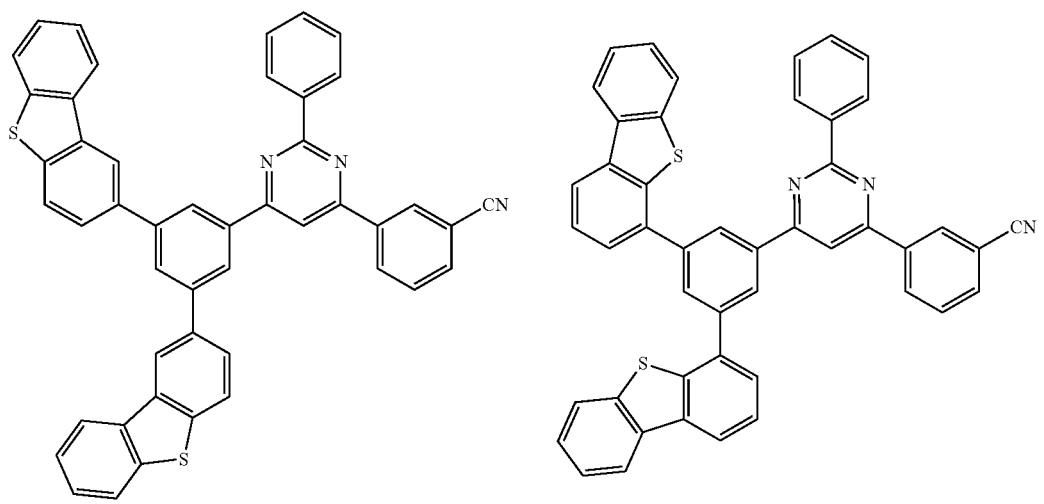
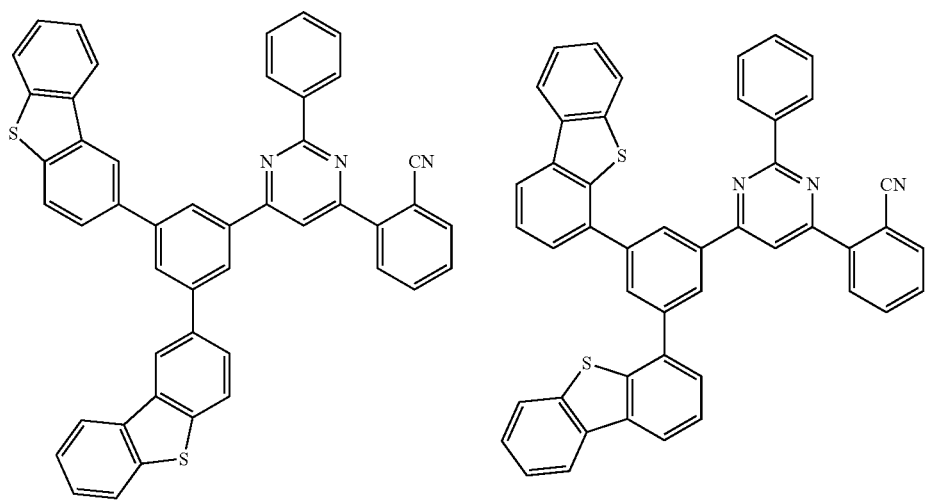

[Formula 108]
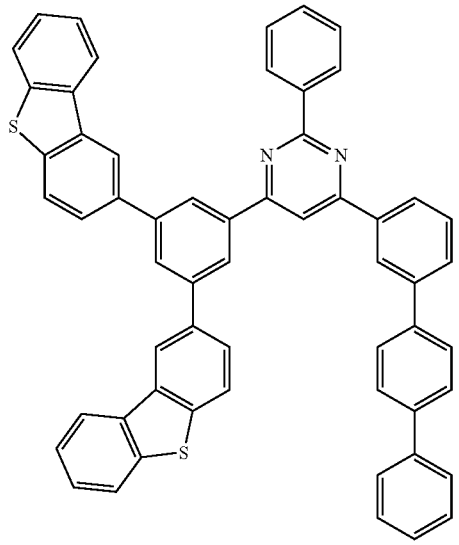
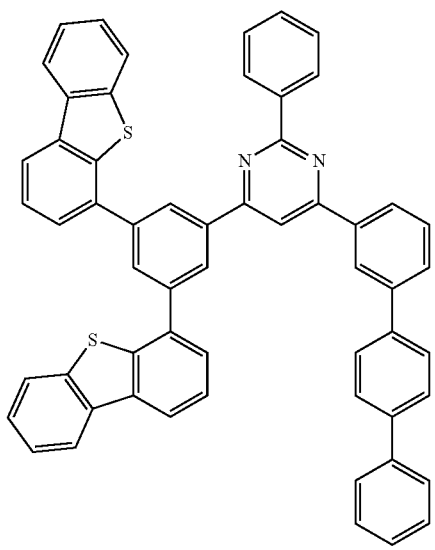
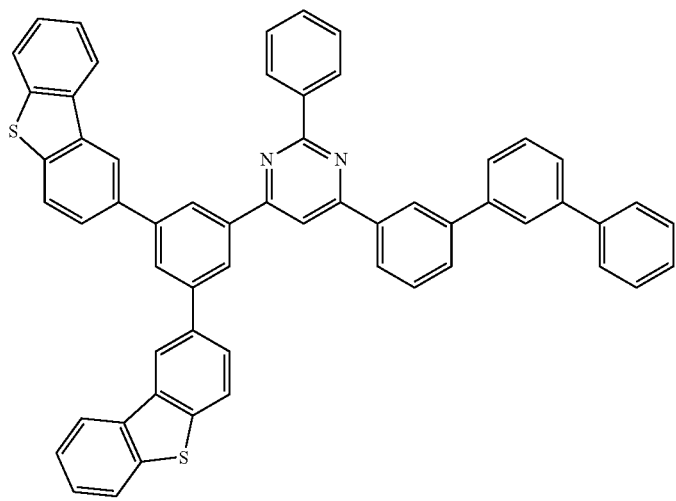
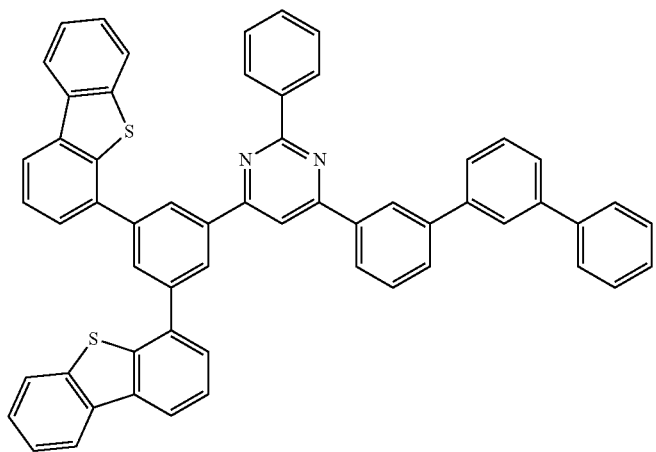

447 448
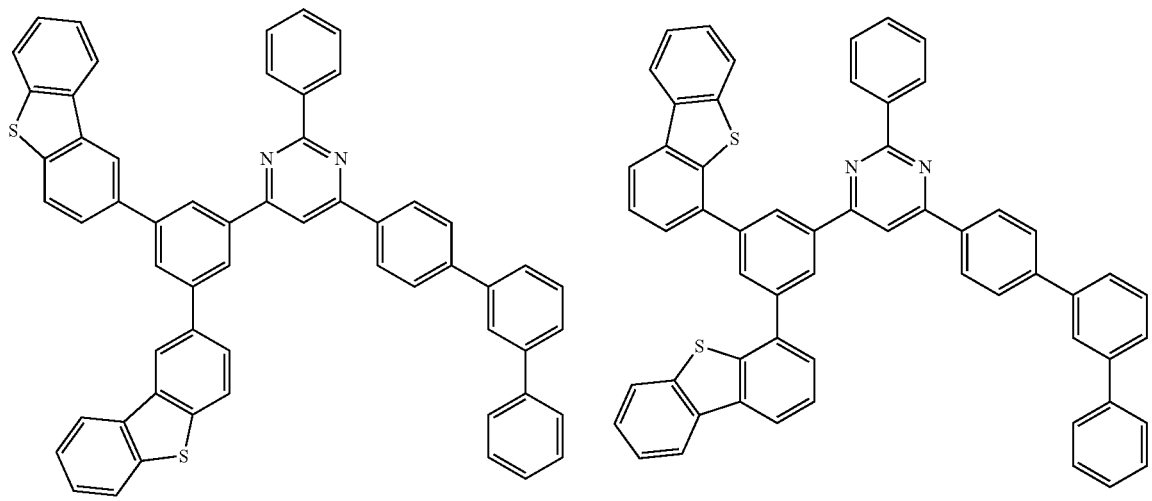
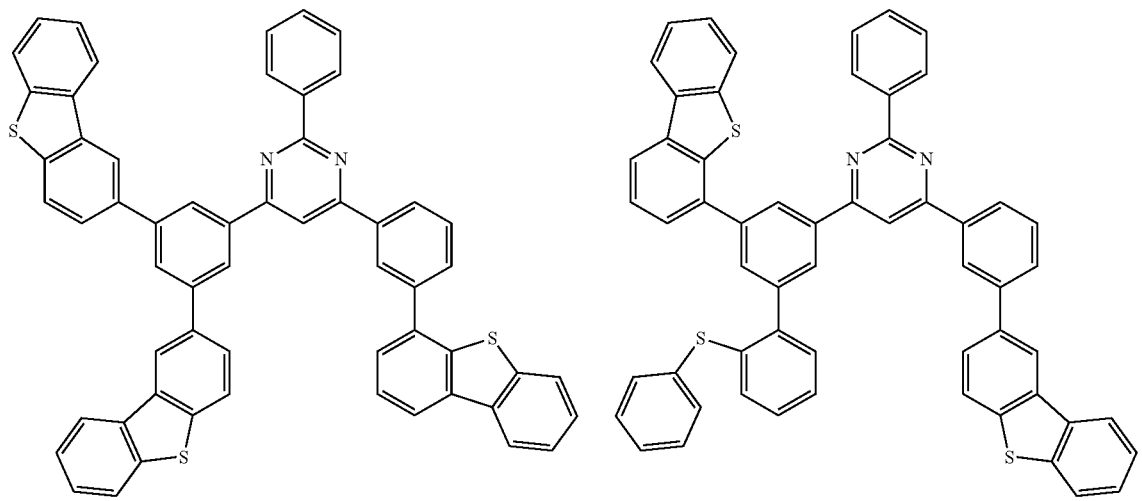
[Formula 109]
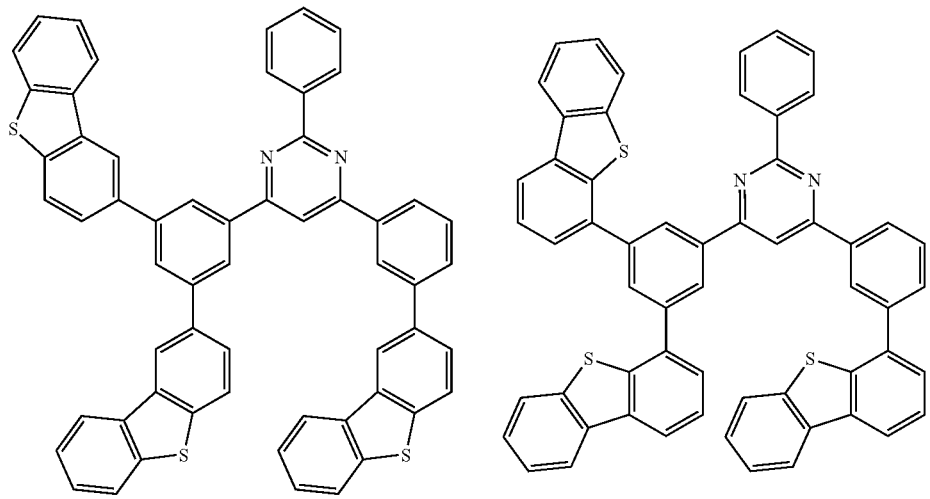

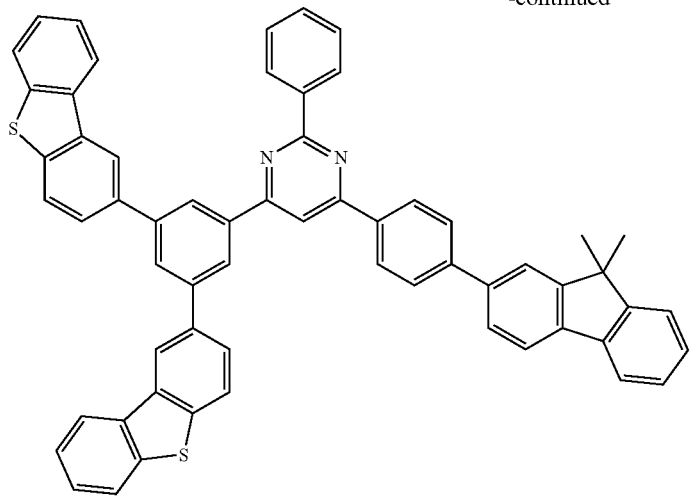
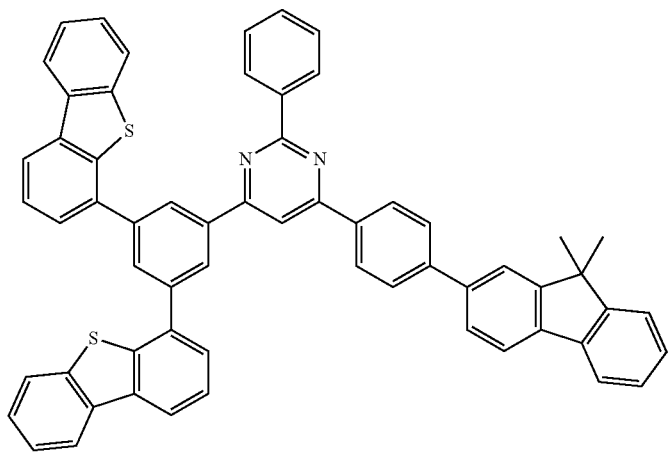
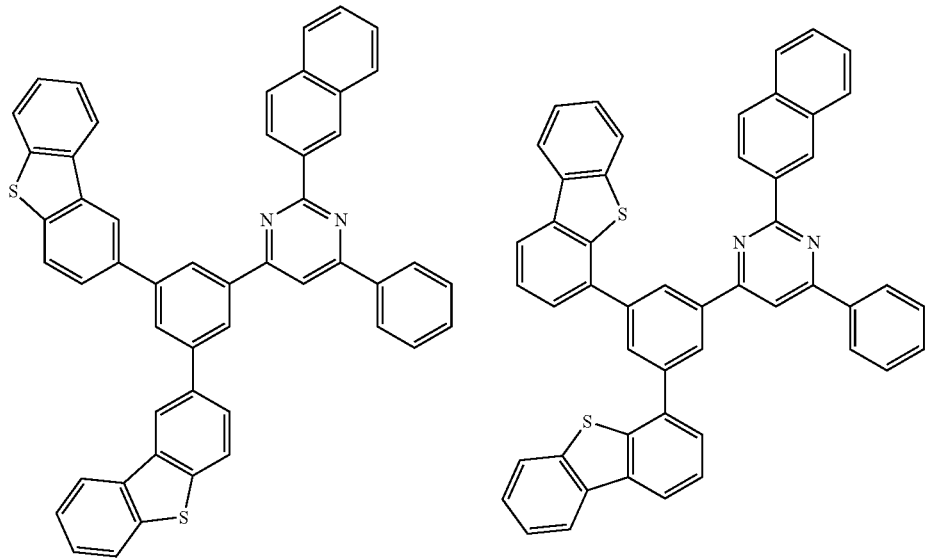

-continued
451
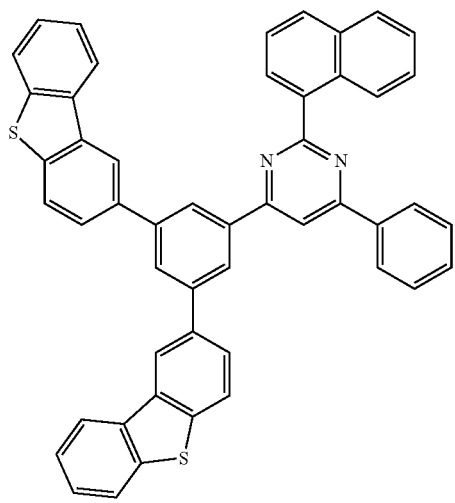
452
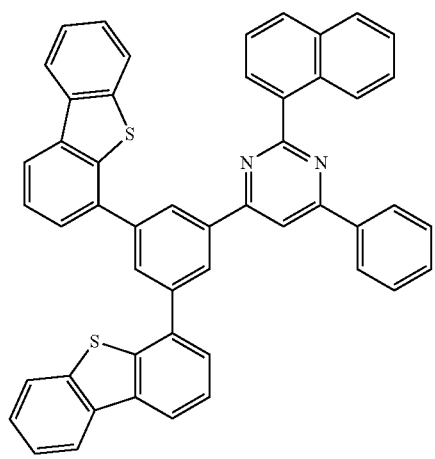
[Formula 110]
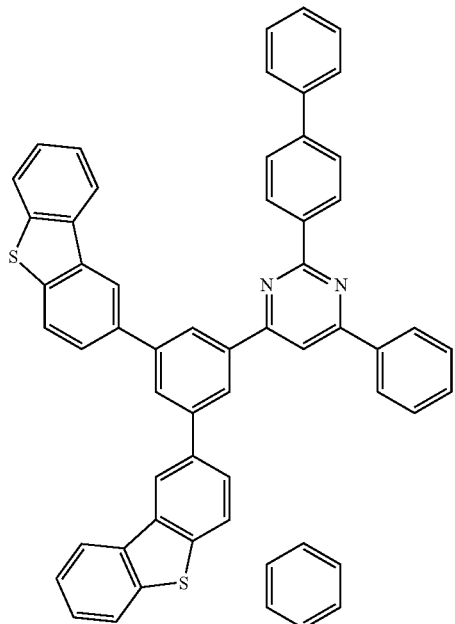
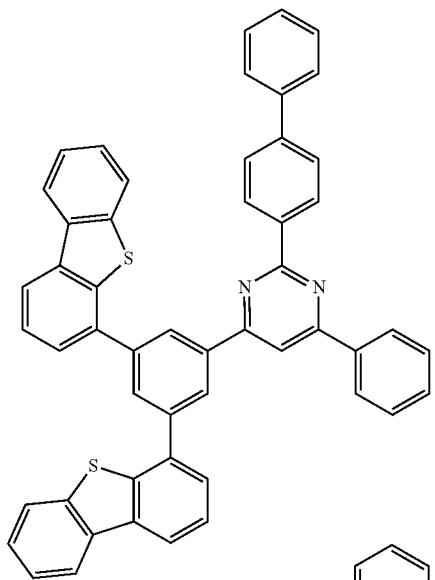
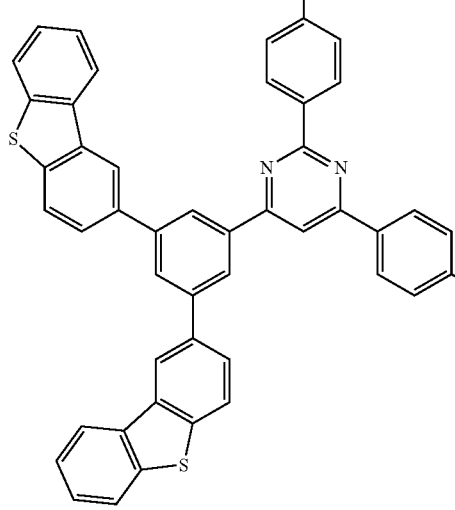
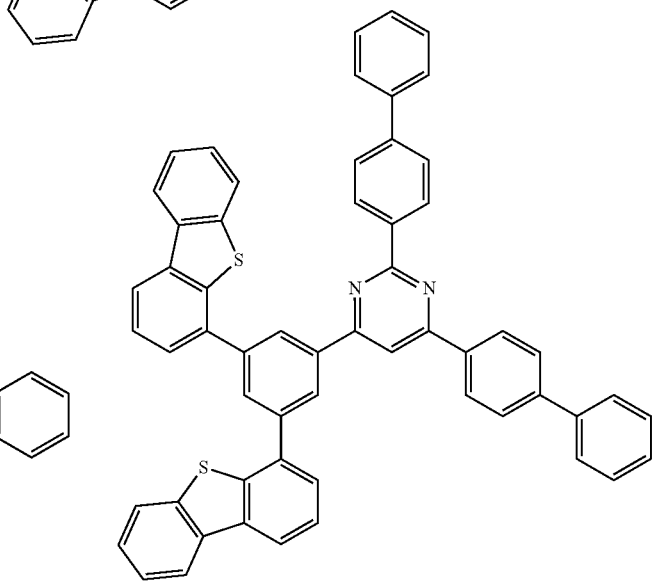

-continued
453
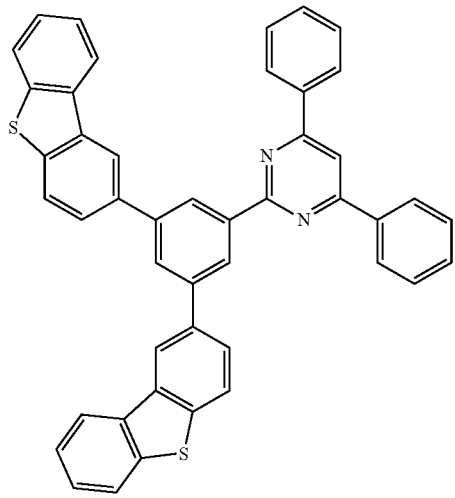
454
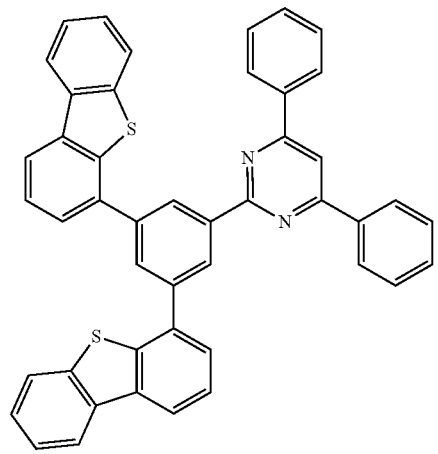
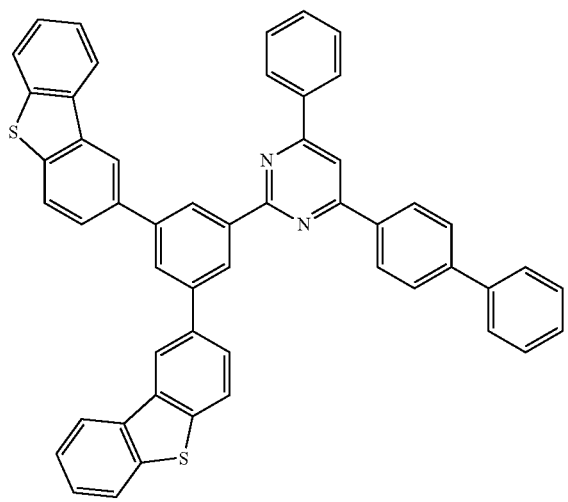
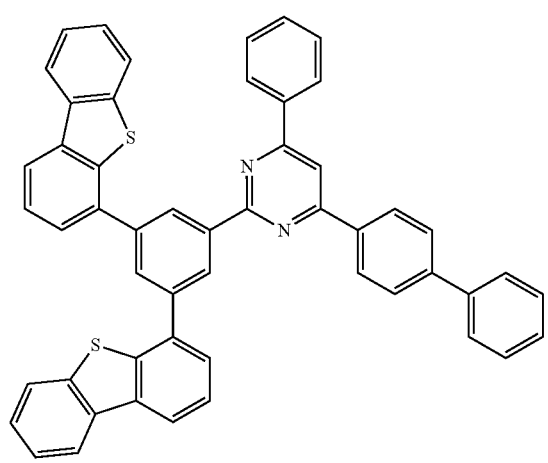
[Formula 111]
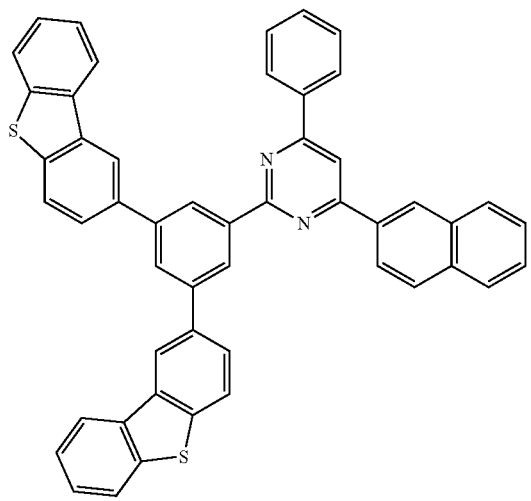
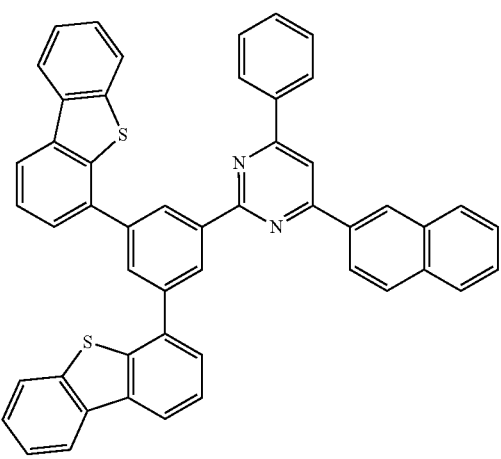

455
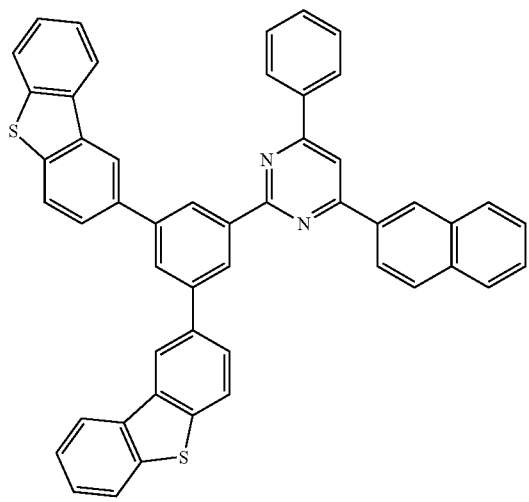
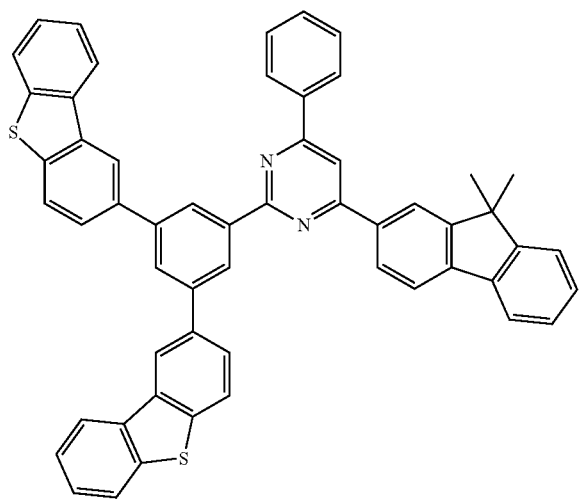
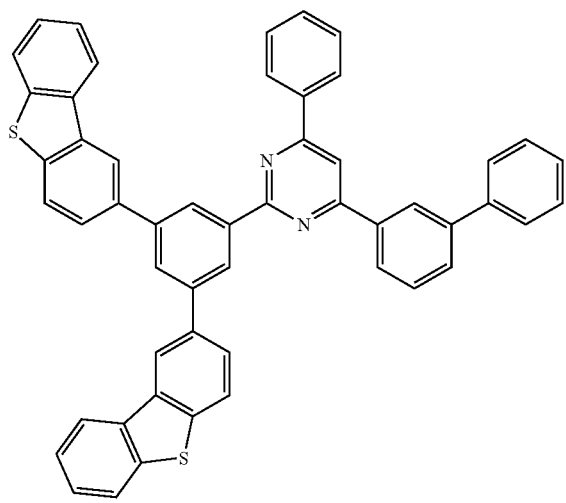
456
-continued
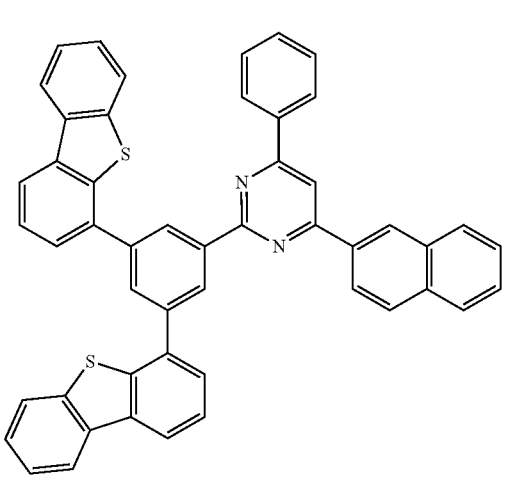
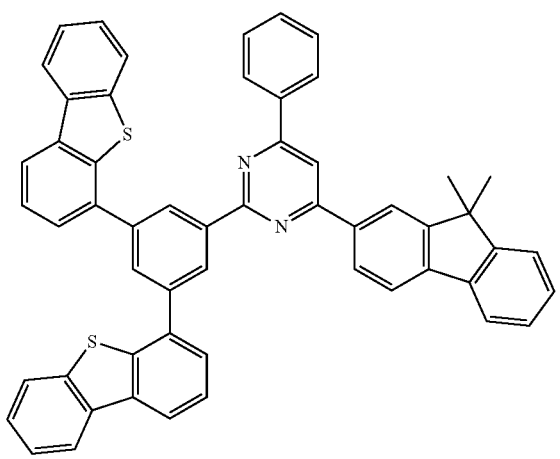
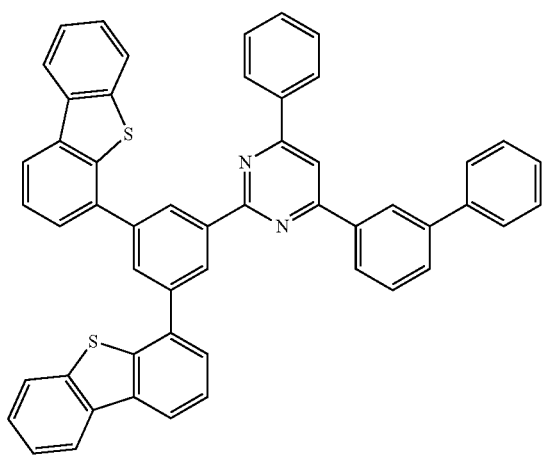

-continued
[Formula 112]
457
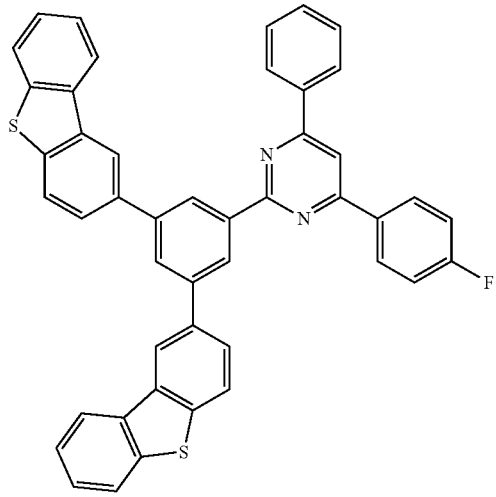
458
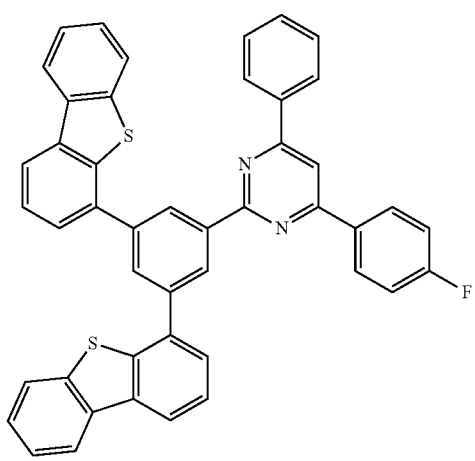
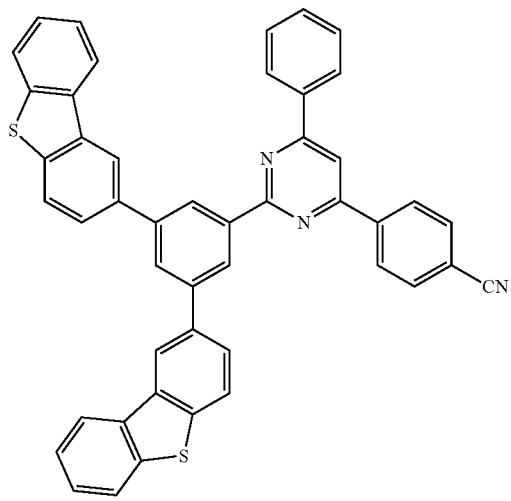
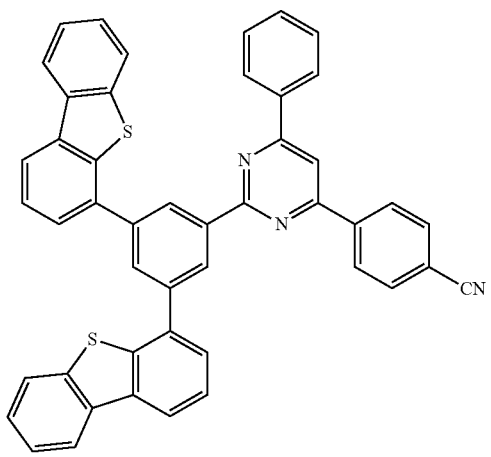
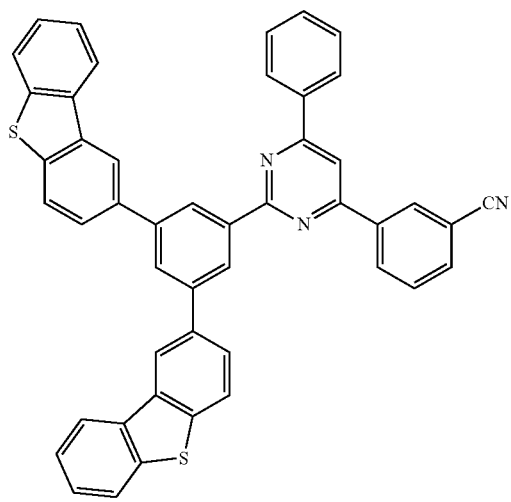
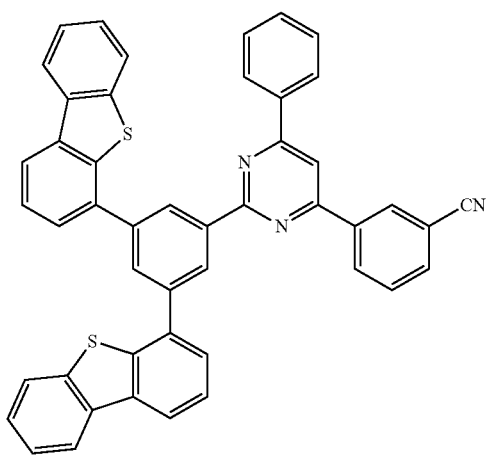

459       460
-continued
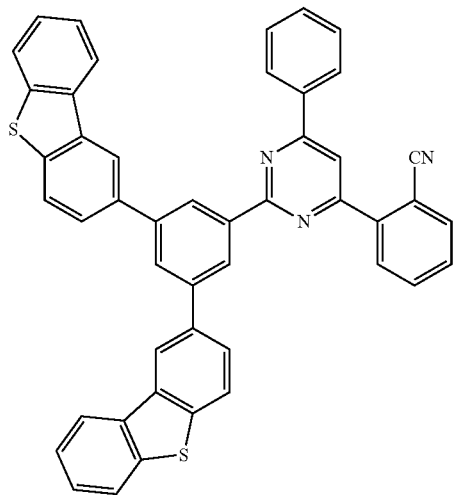
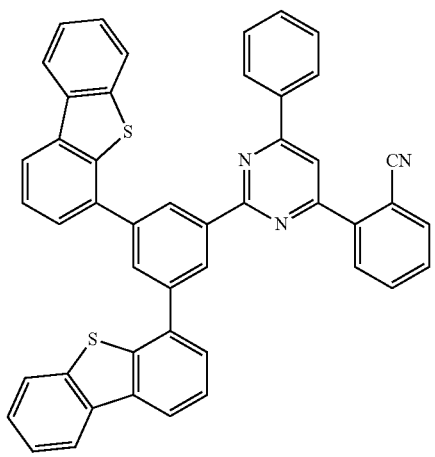
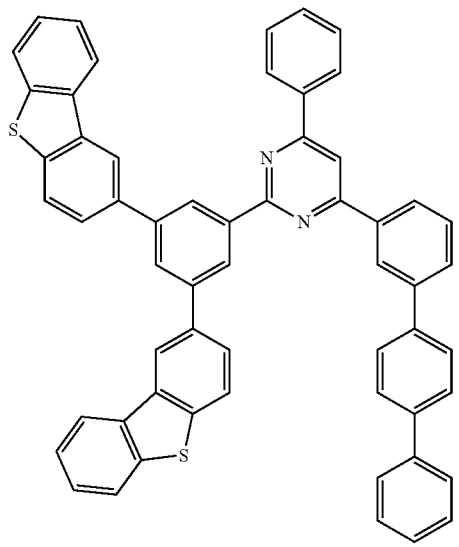
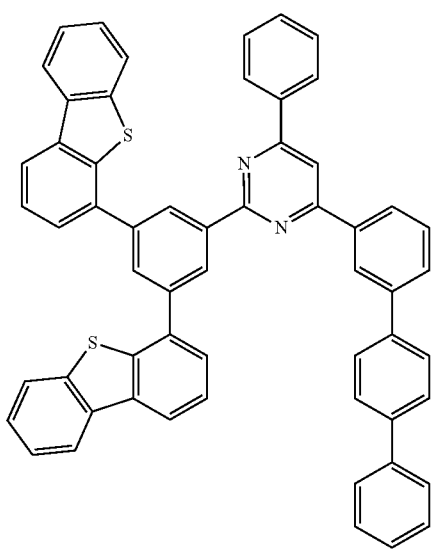
[Formula 113]
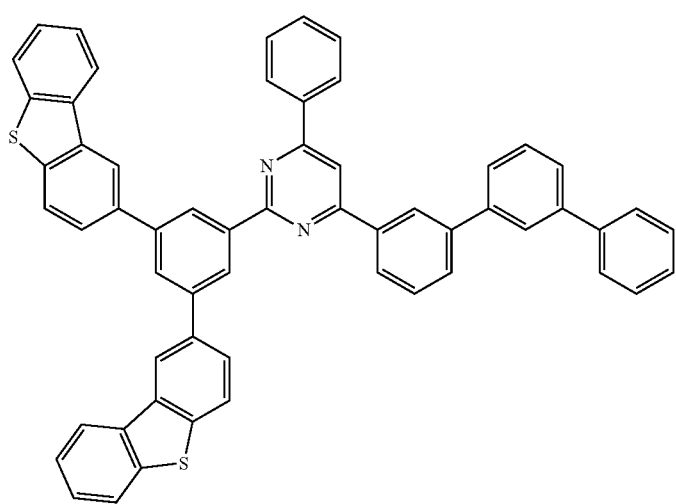

461
-continued
462
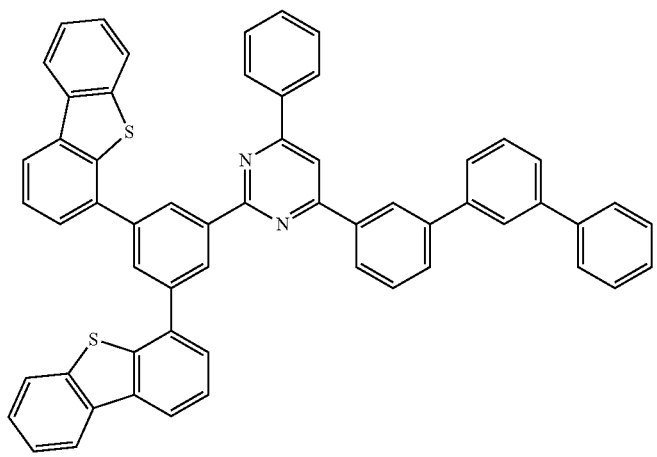
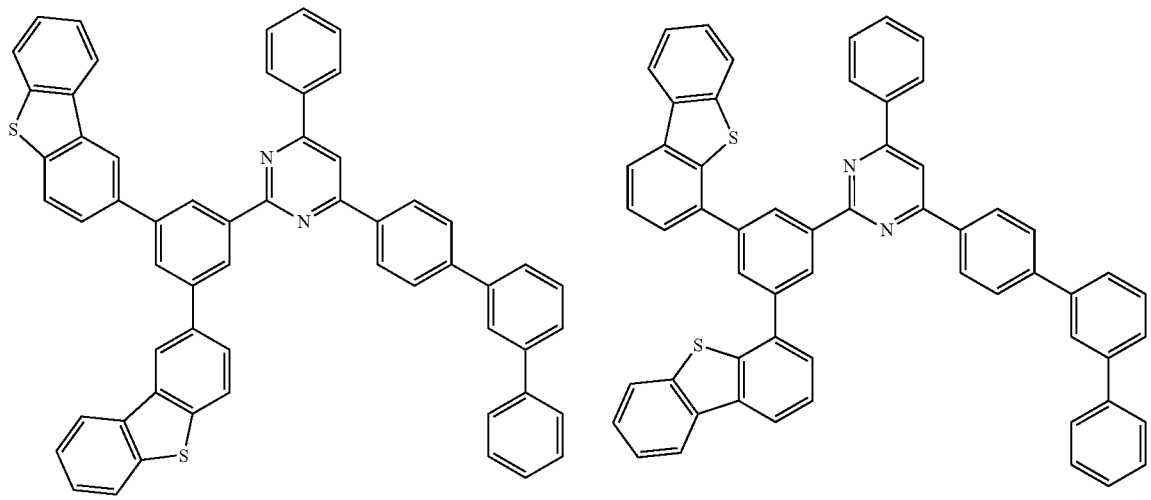
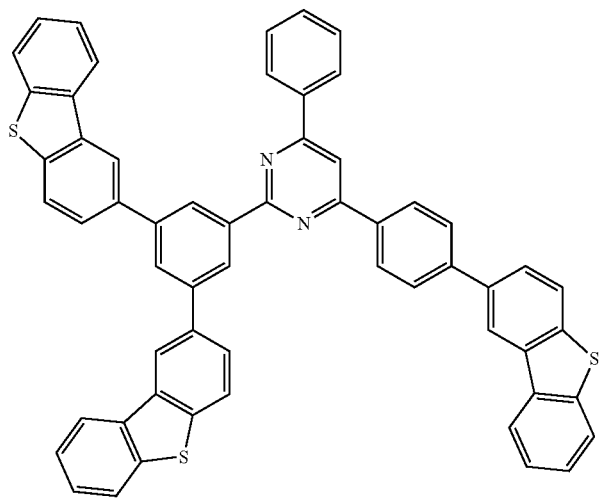

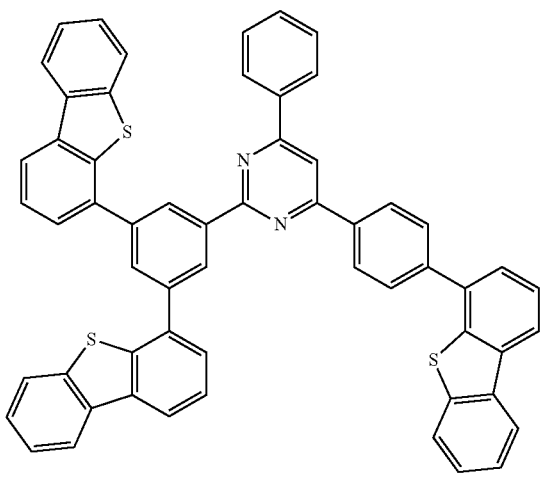
[Formula 114]
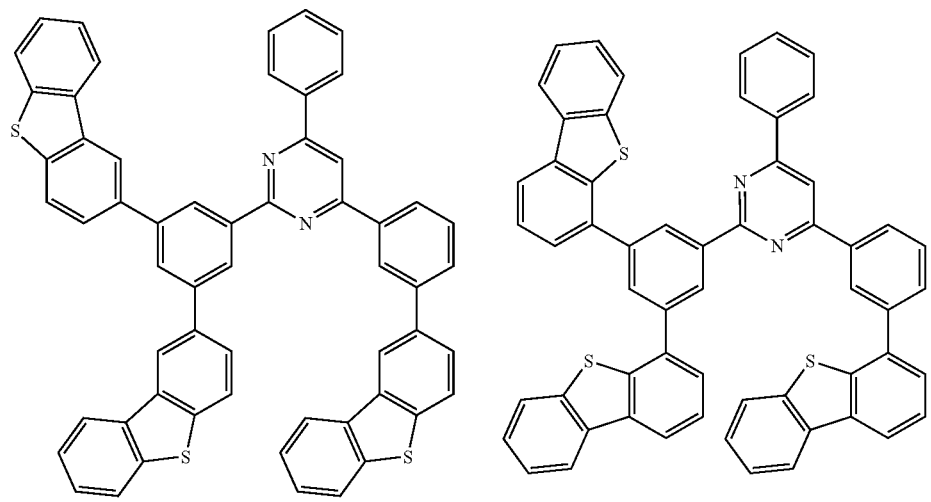
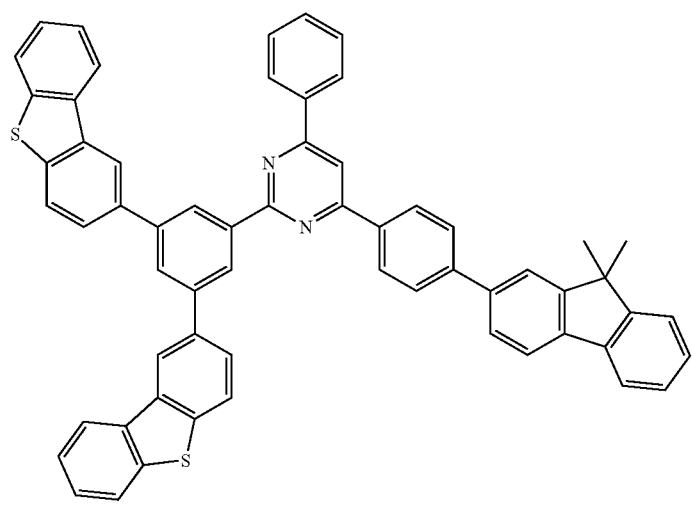

465 466
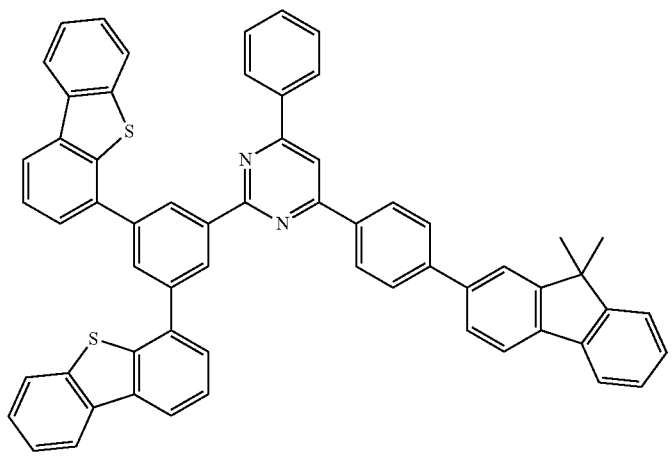
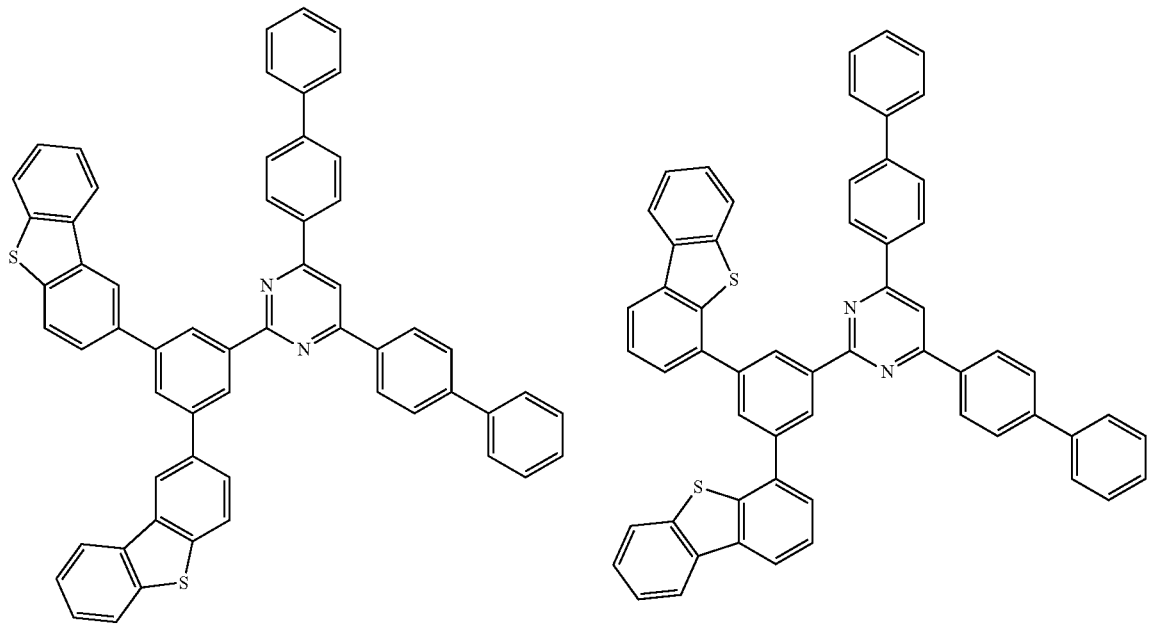
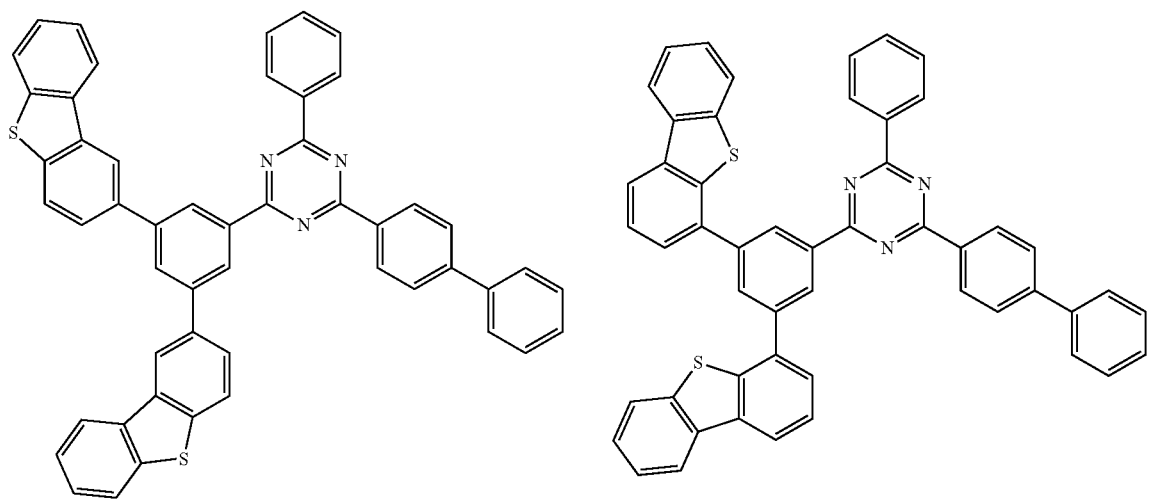

[Formula 115]
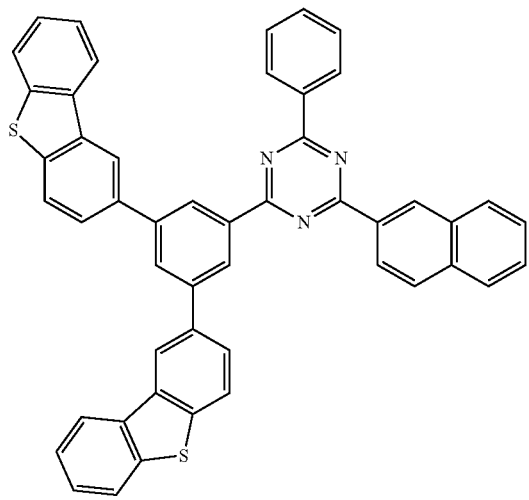
467
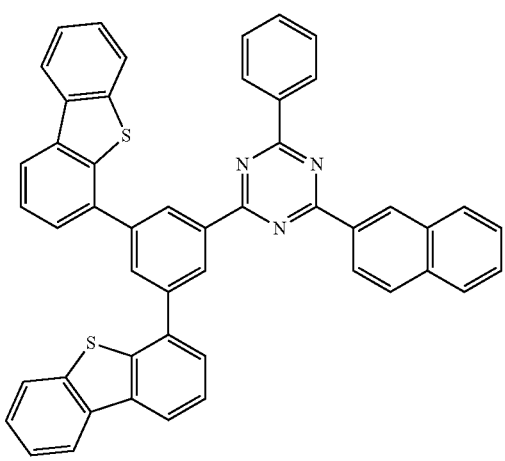
468
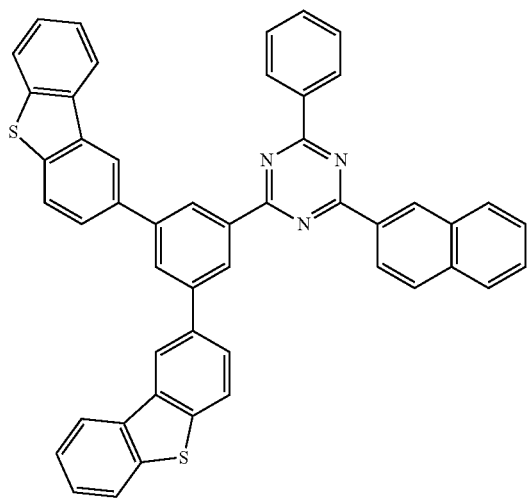
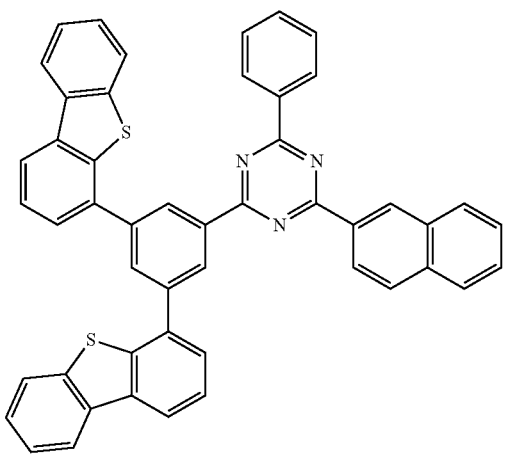
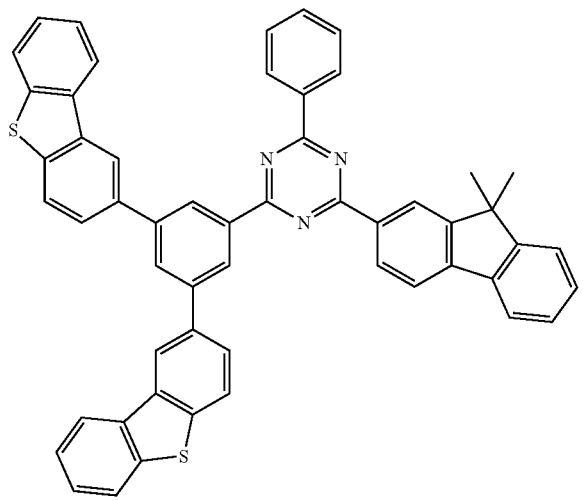
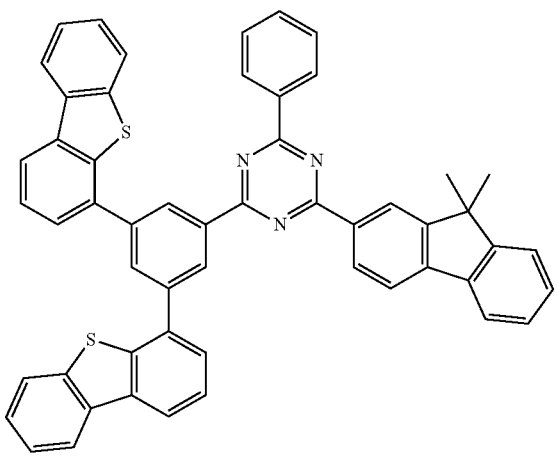

-continued
469
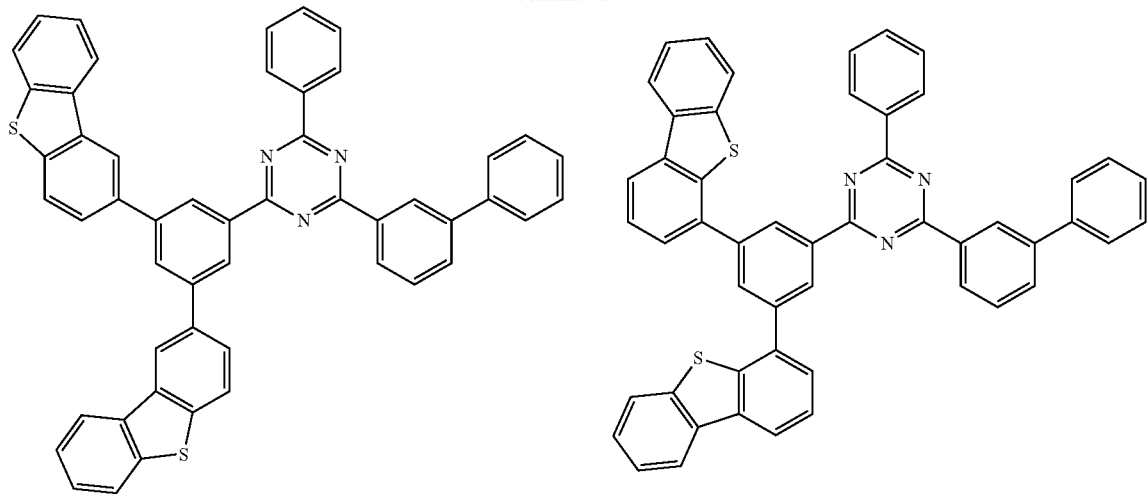
470
[Formula 116]
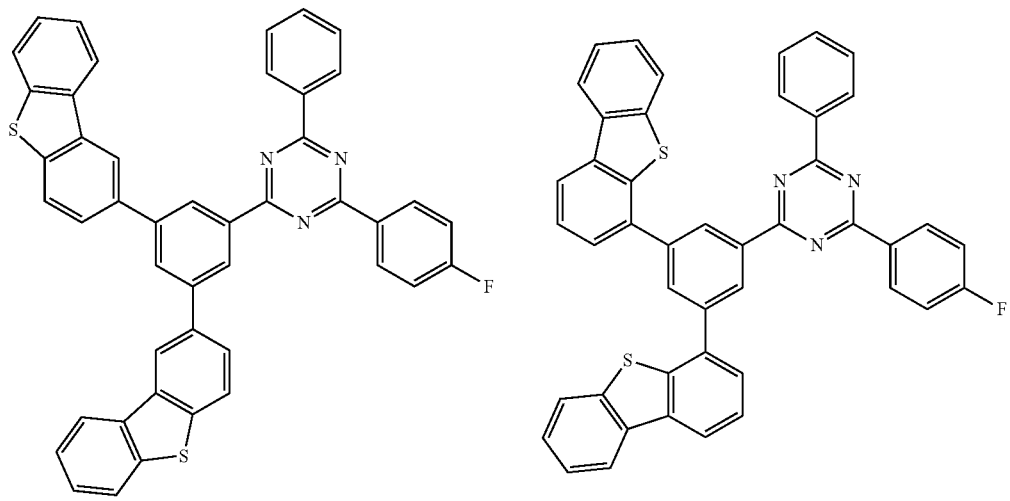
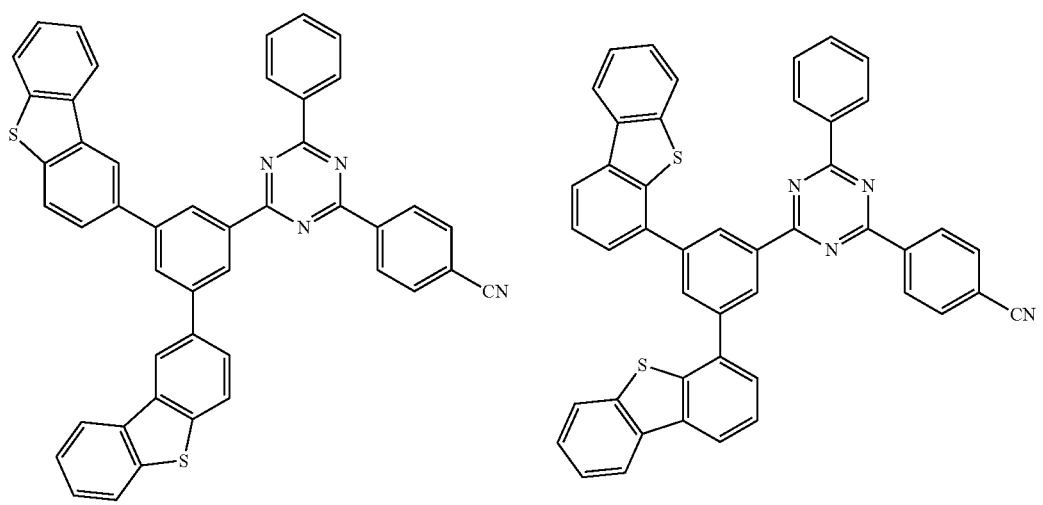

471 472
-continued
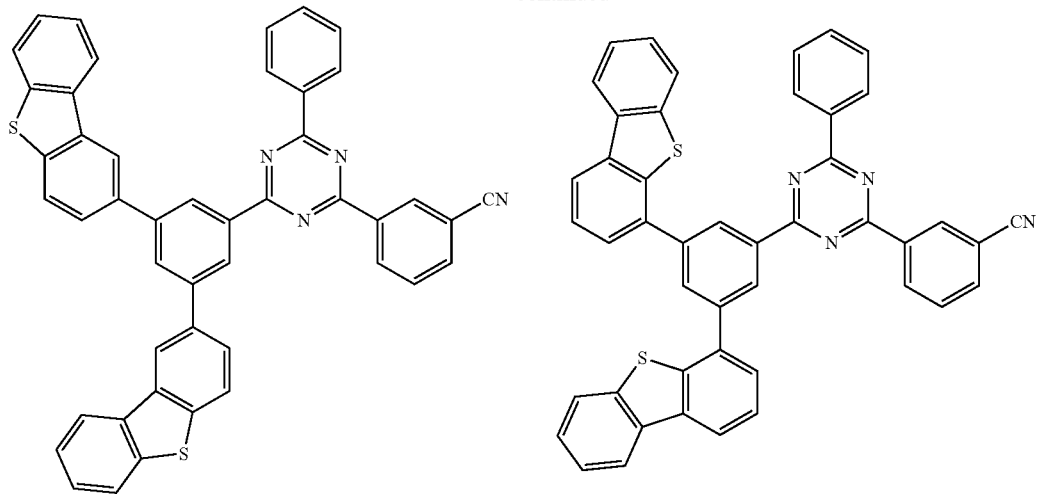
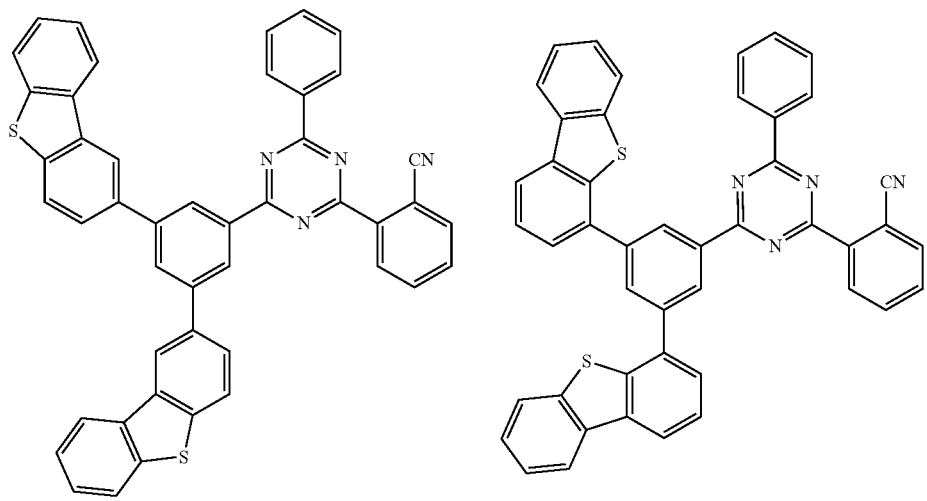
[Formula 117]
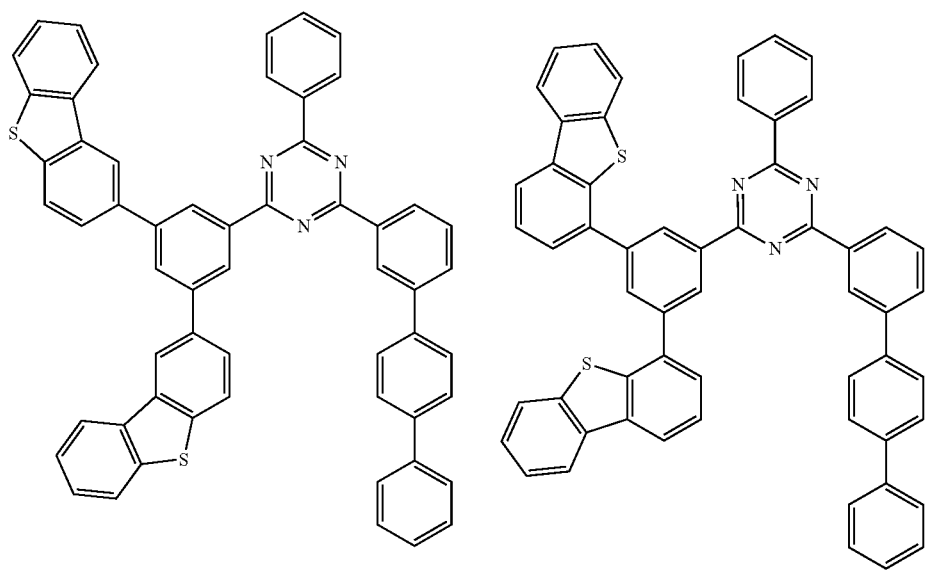

473
474
-continued
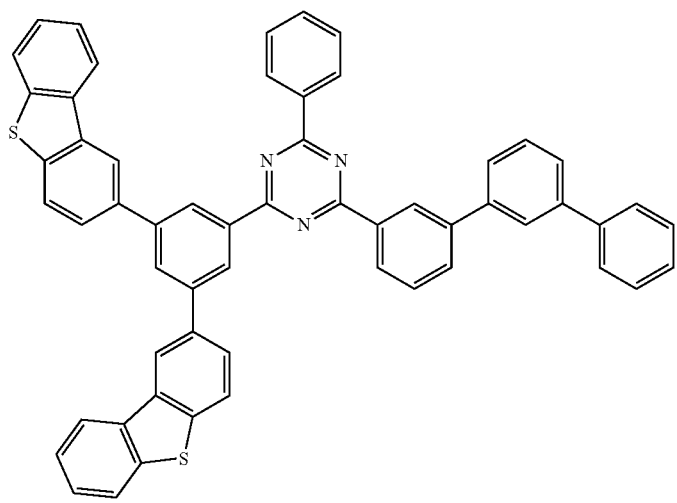
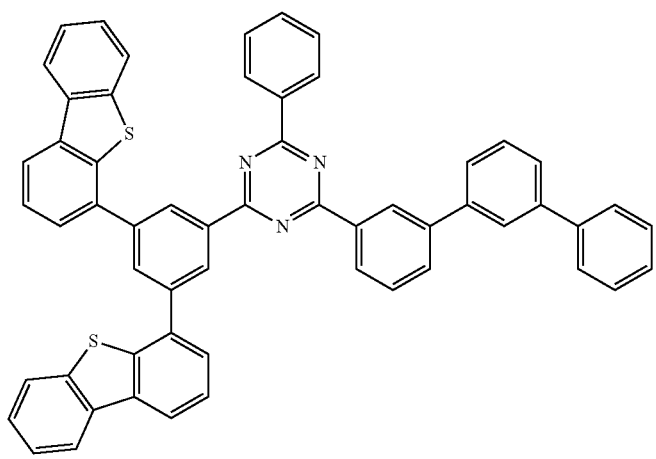
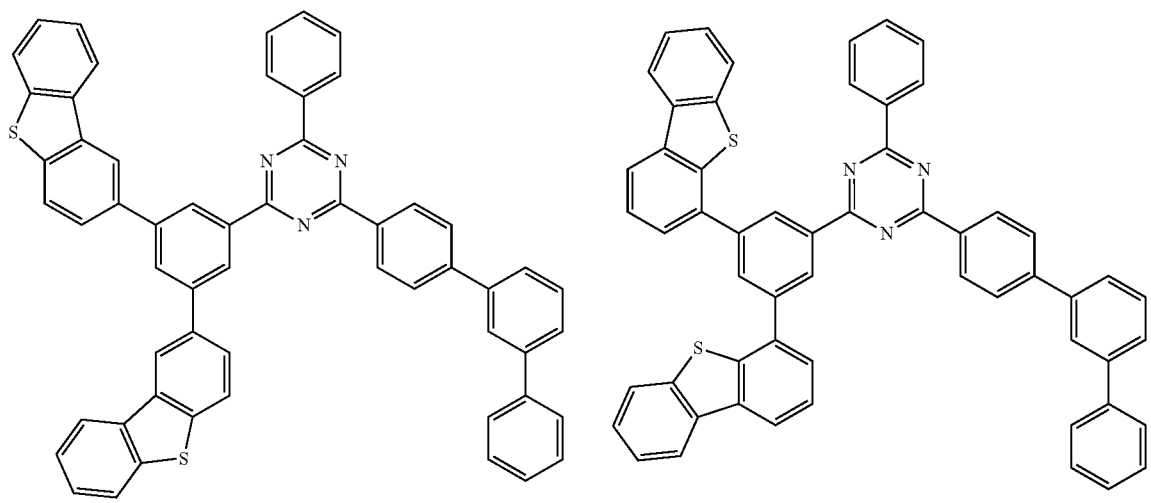

-continued
475
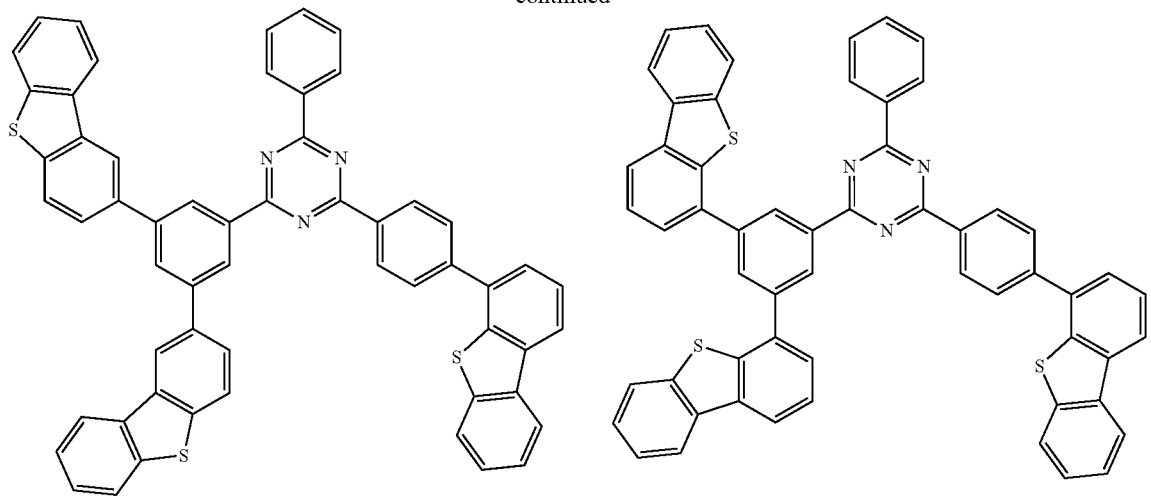
476
[Formula 118]
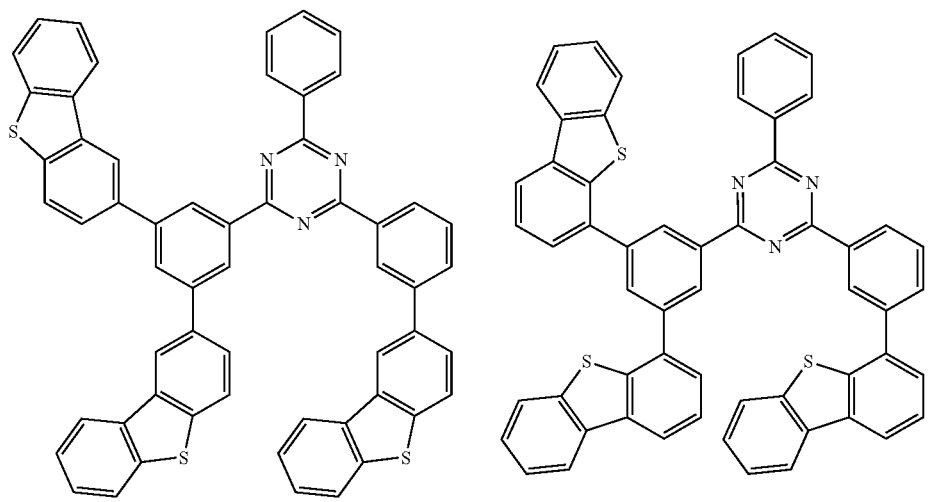
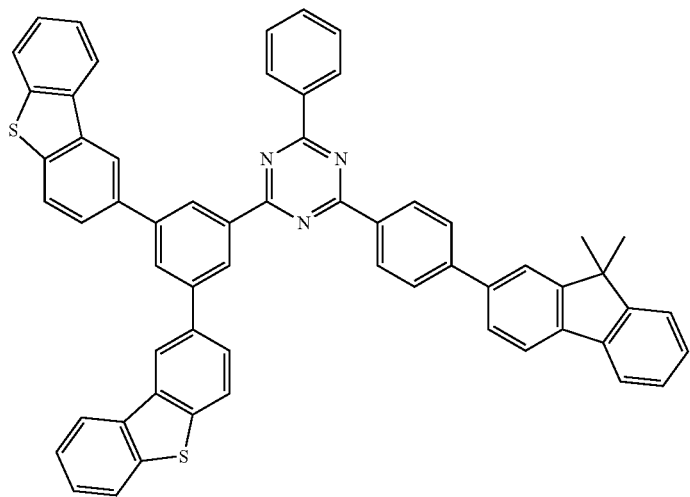

-continued
477 478
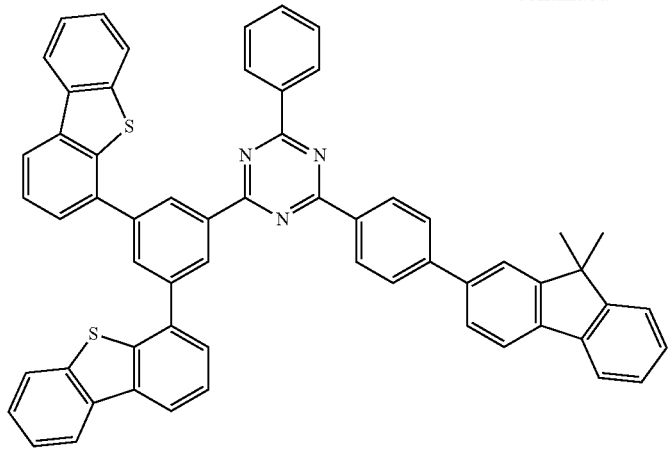
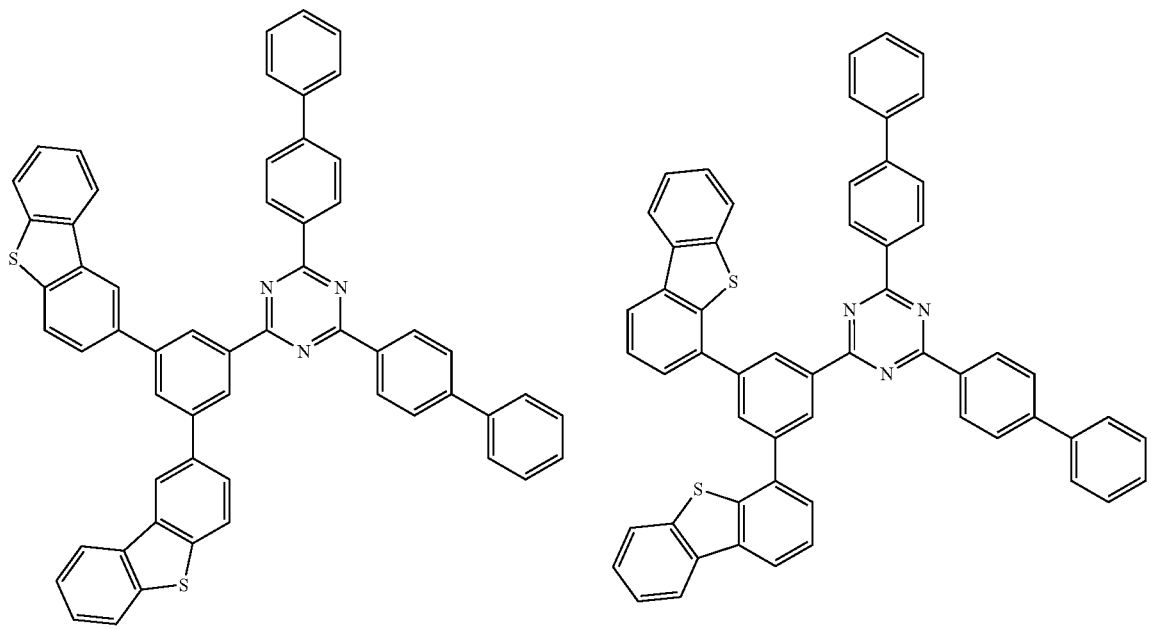
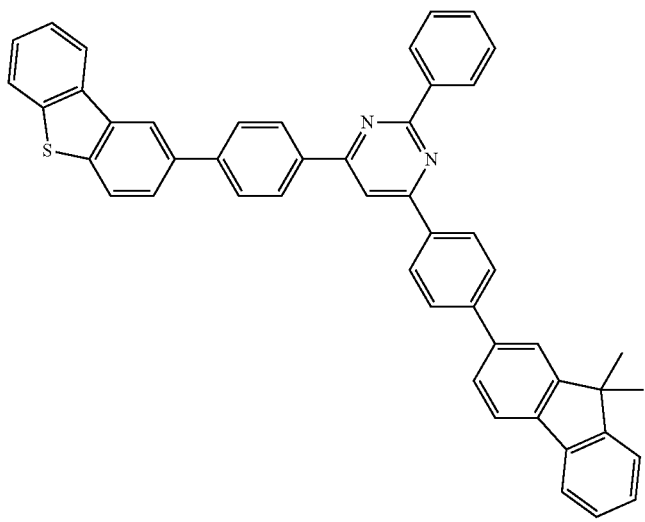

479
-continued
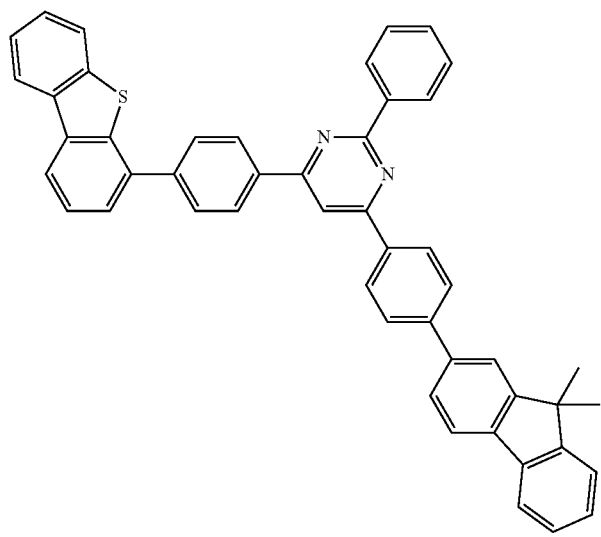
[Formula 119]
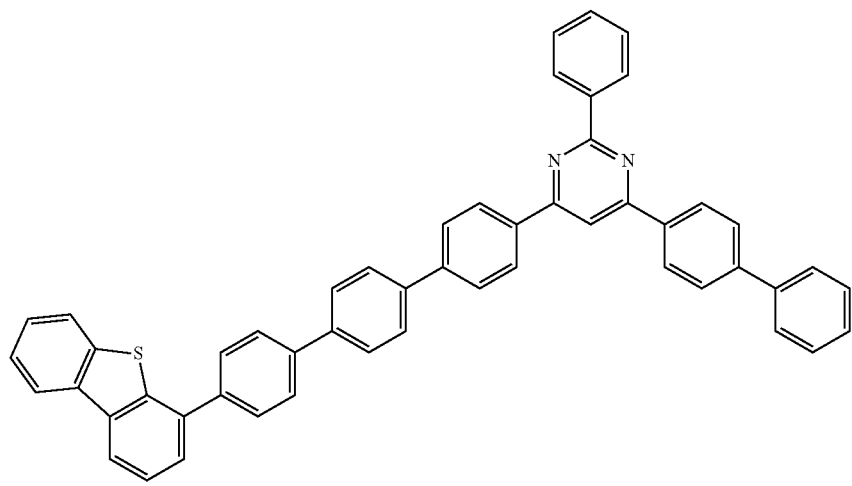
480
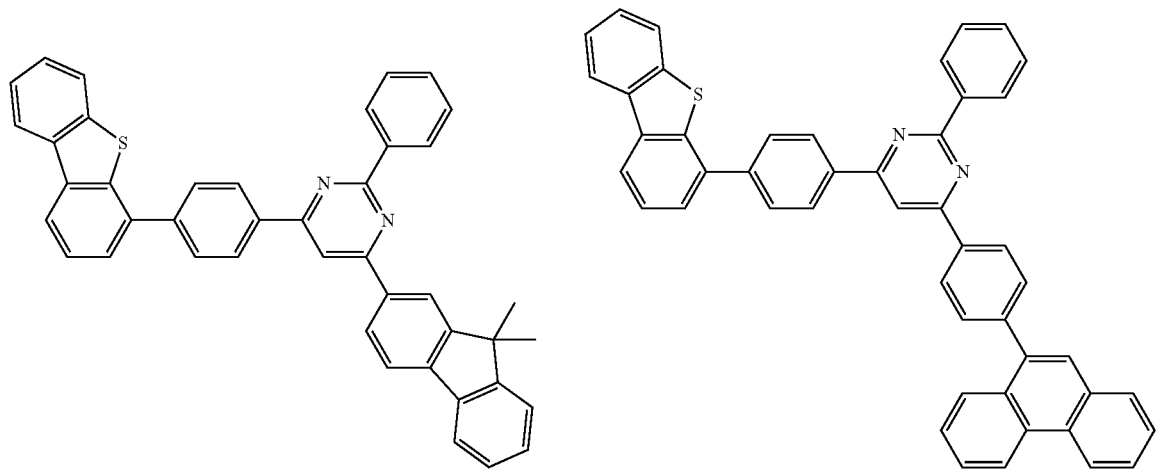

-continued
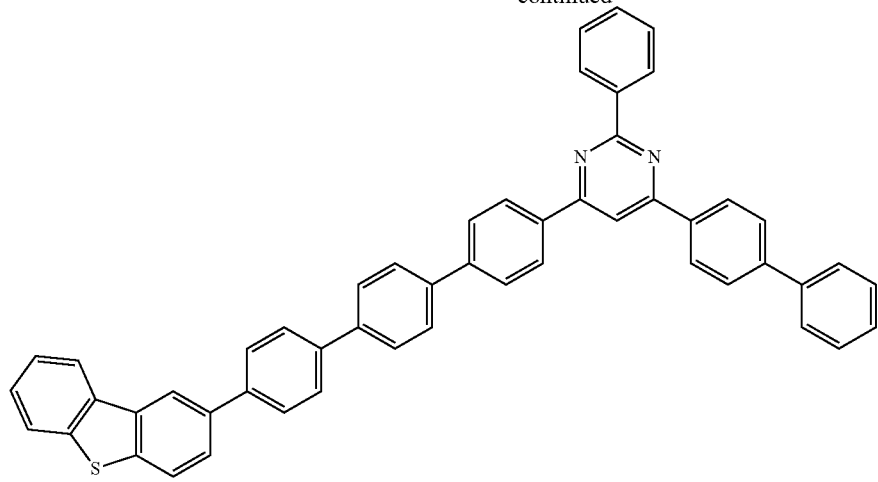
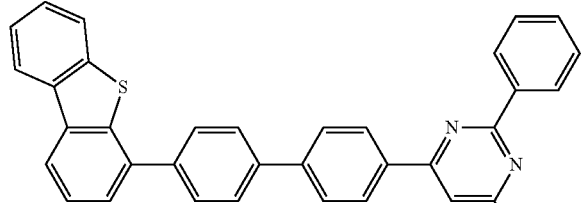
[Formula 120]
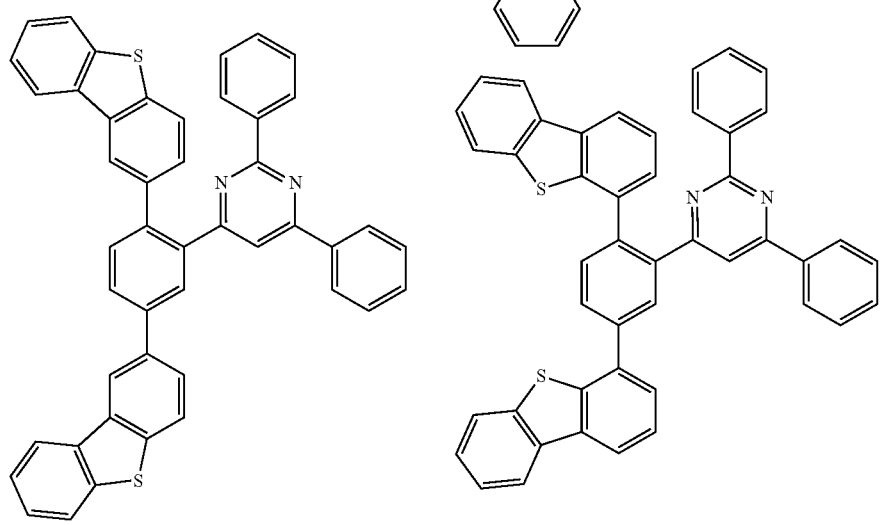
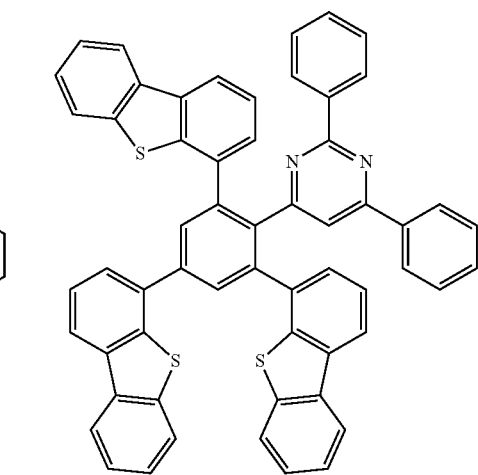

-continued
483
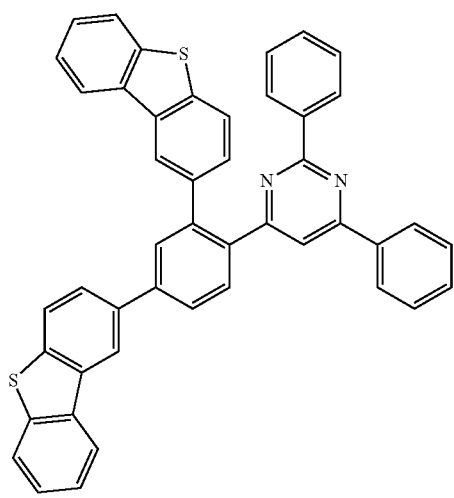
484
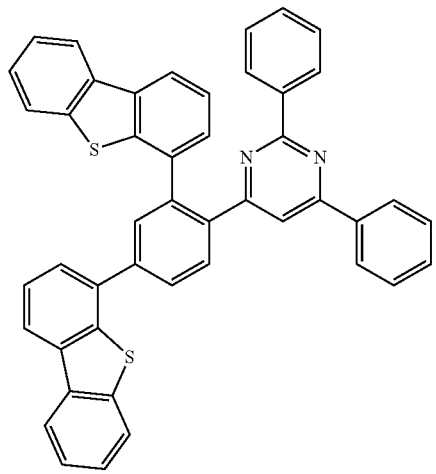
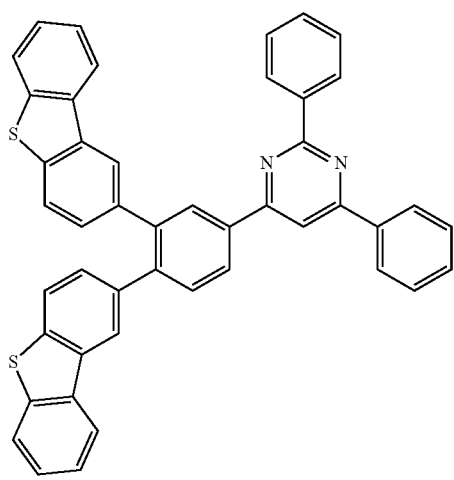
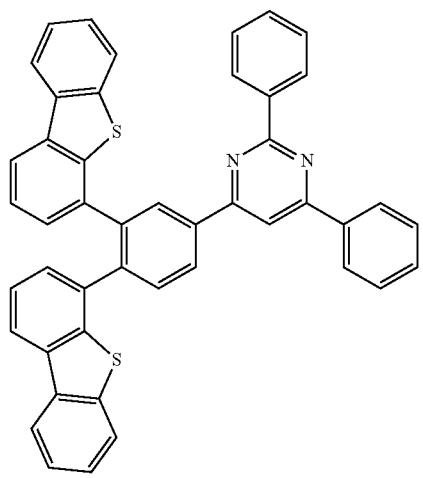
[Formula 121]
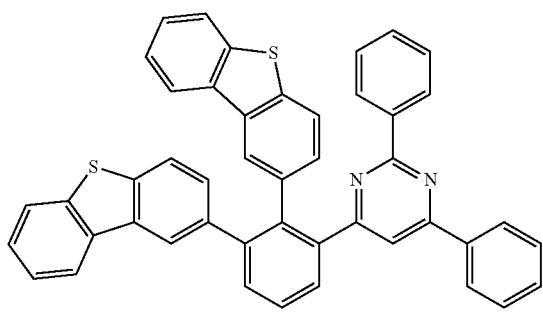
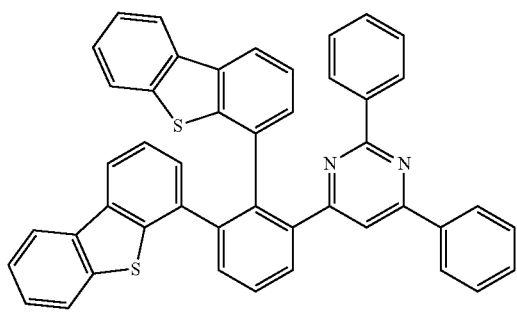

-continued
485
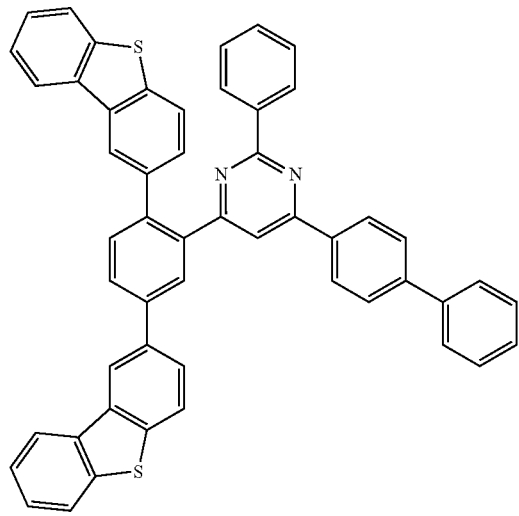
486
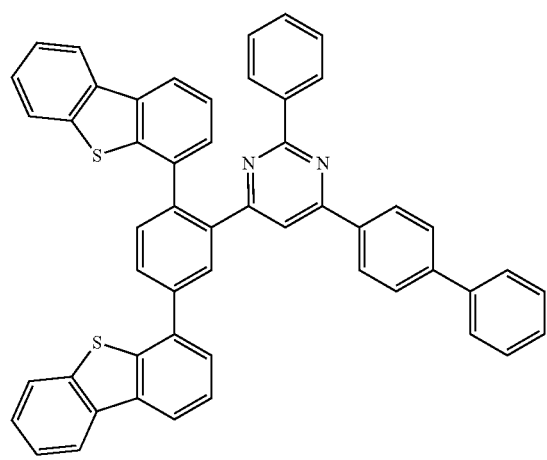
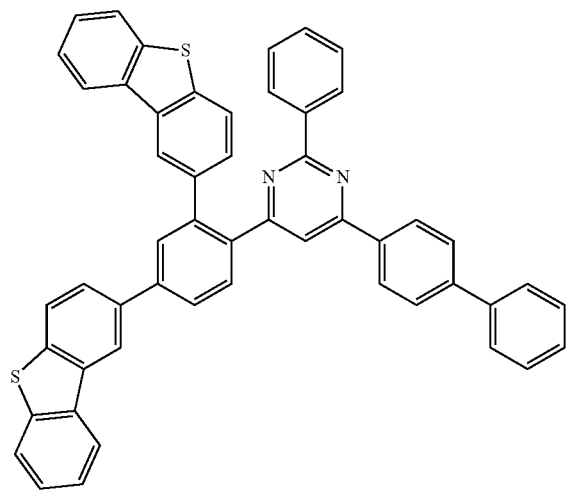
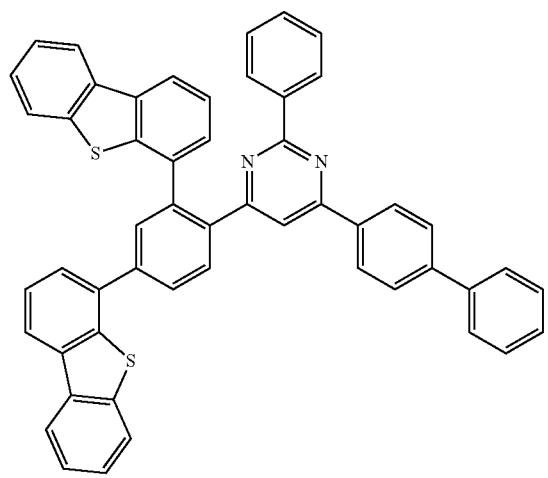
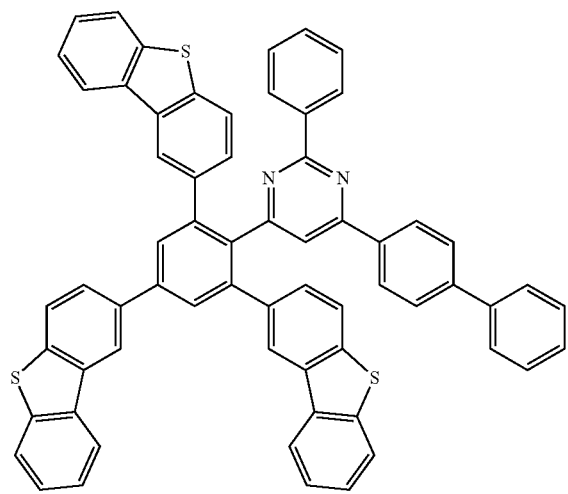
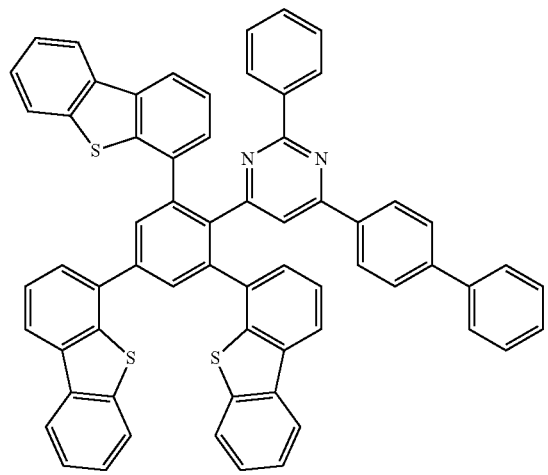

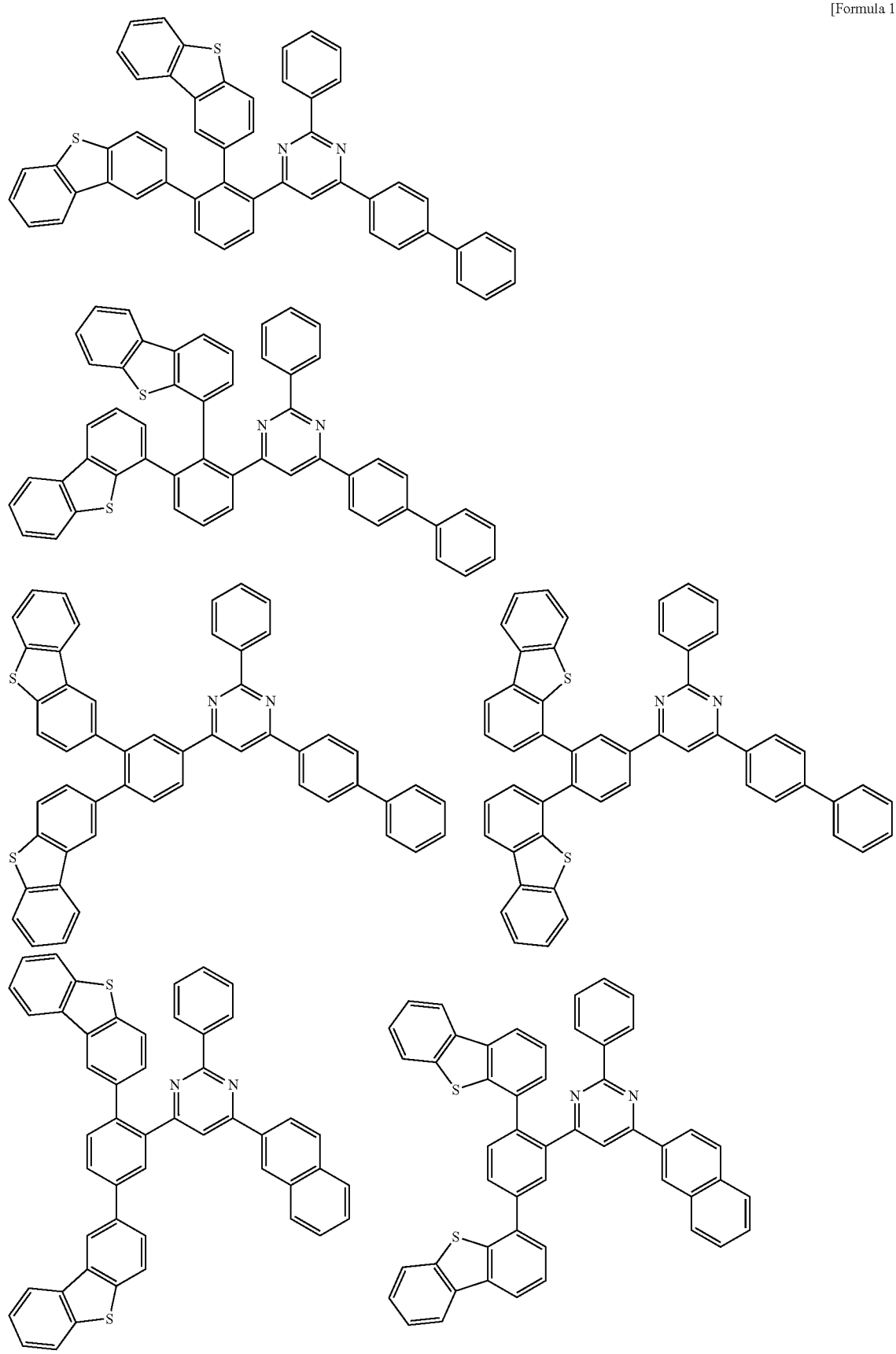
[Formula 122]

-continued
489
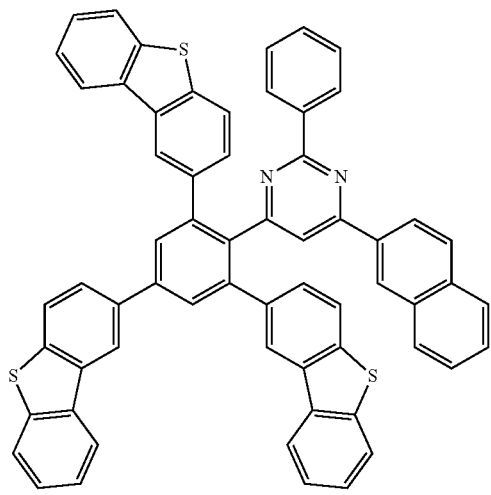
490
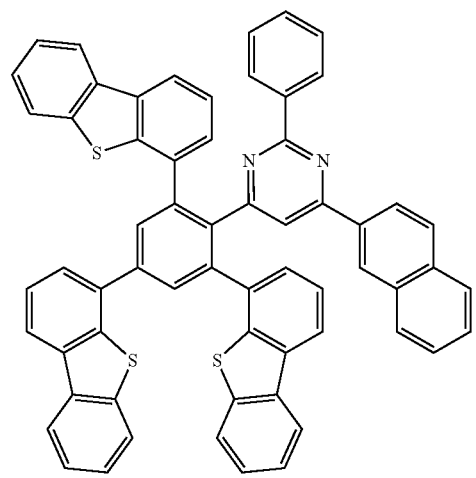
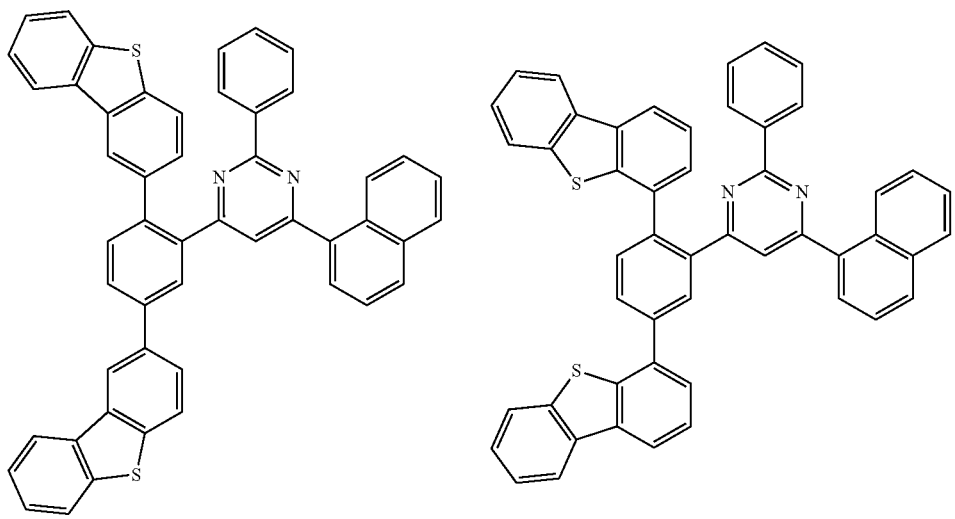
[Formula 123]
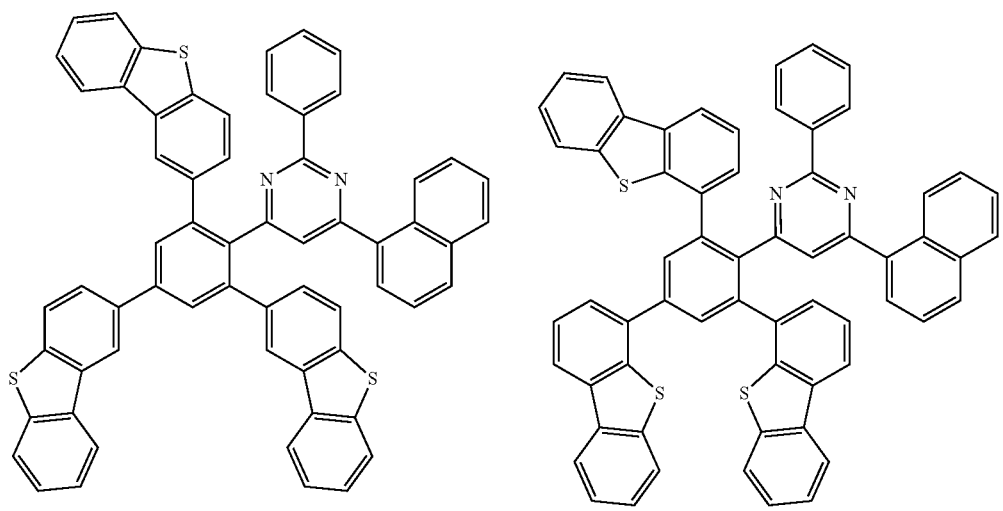

491
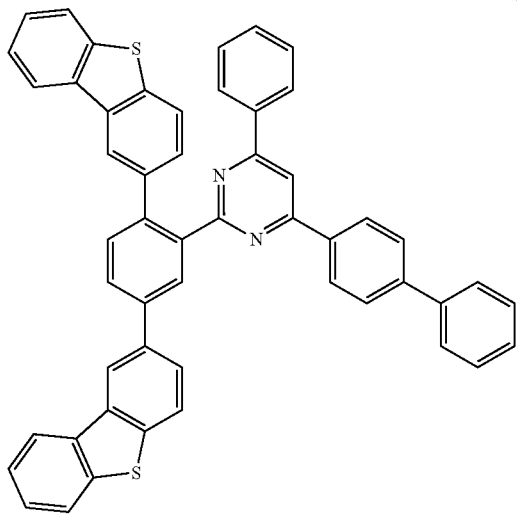
492
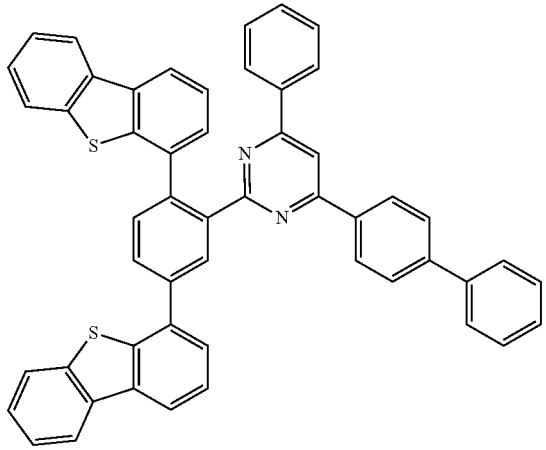
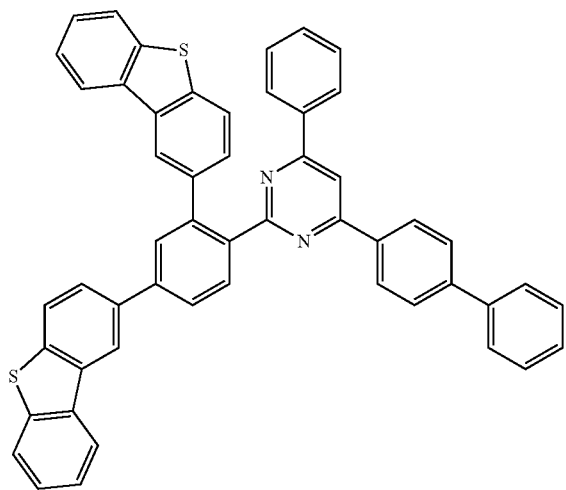
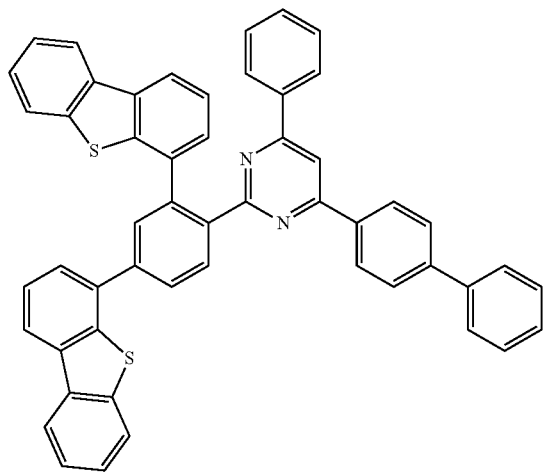
[Formula 124]
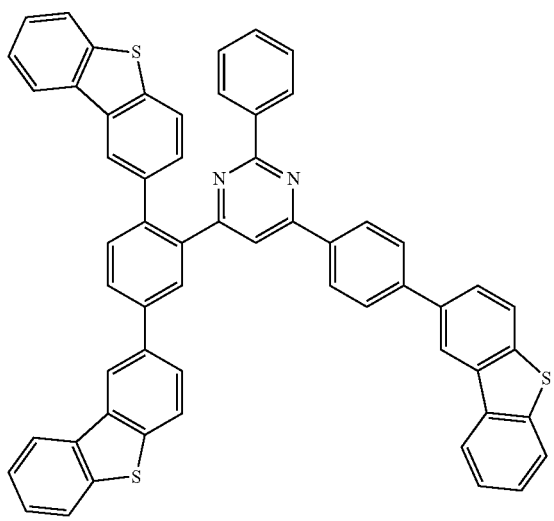
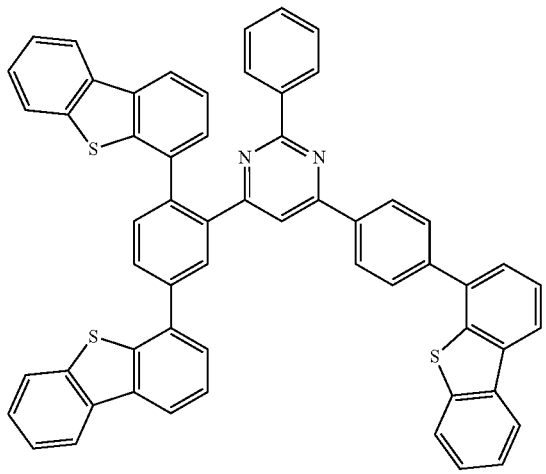

-continued
493
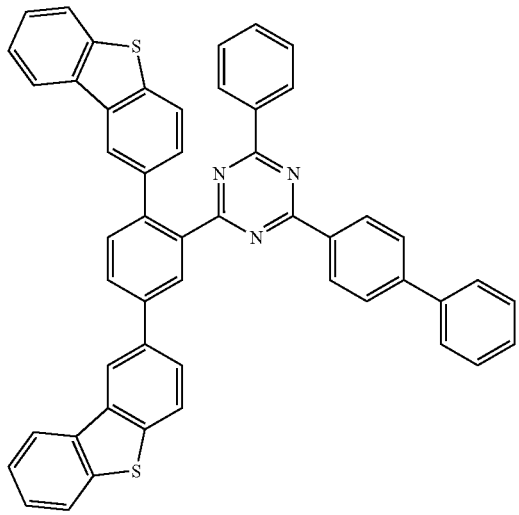
494
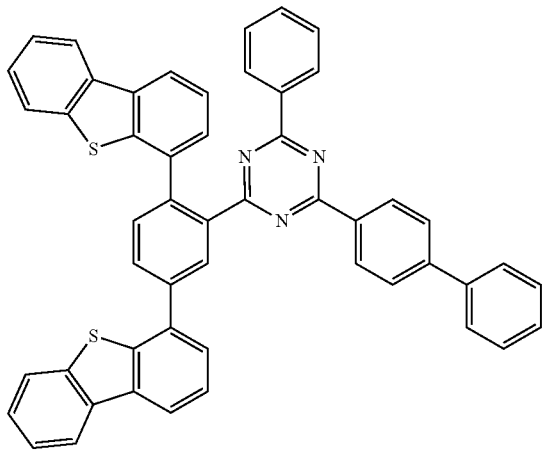
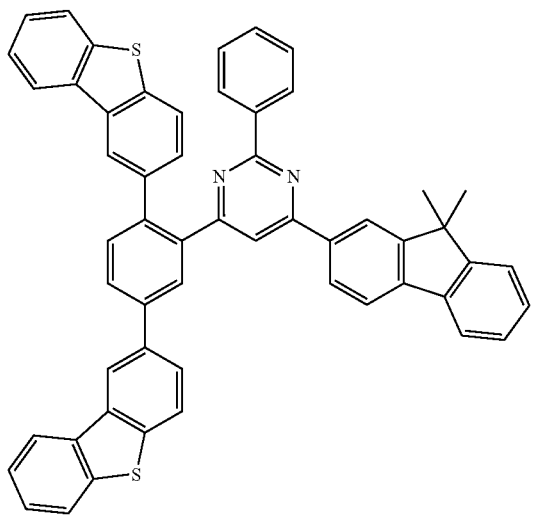
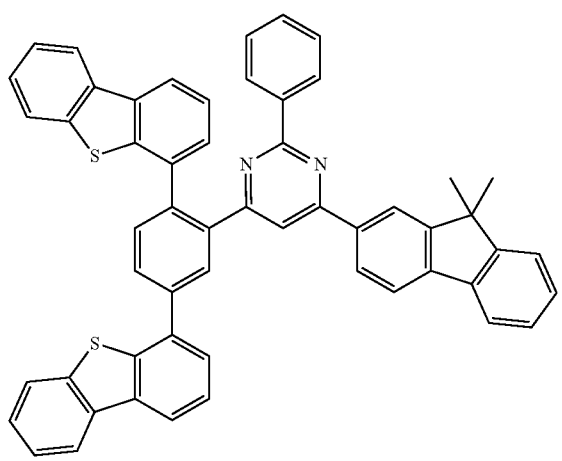
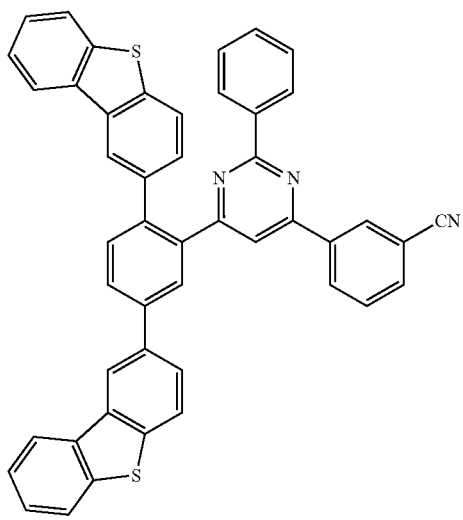
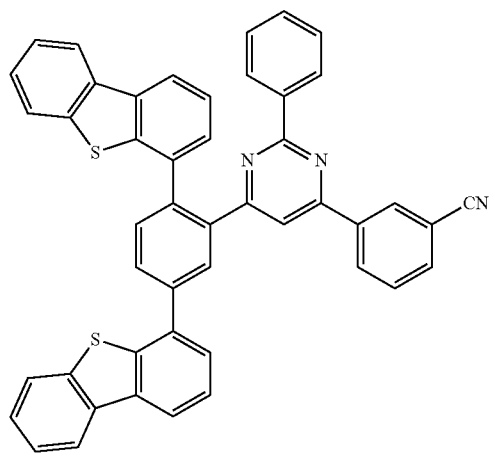

[Formula 125]
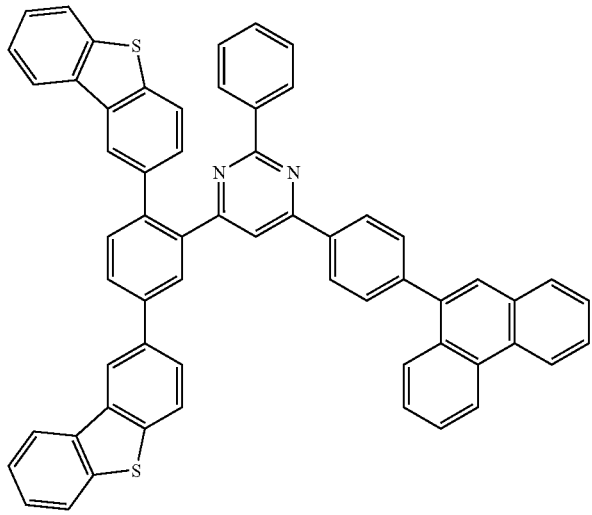
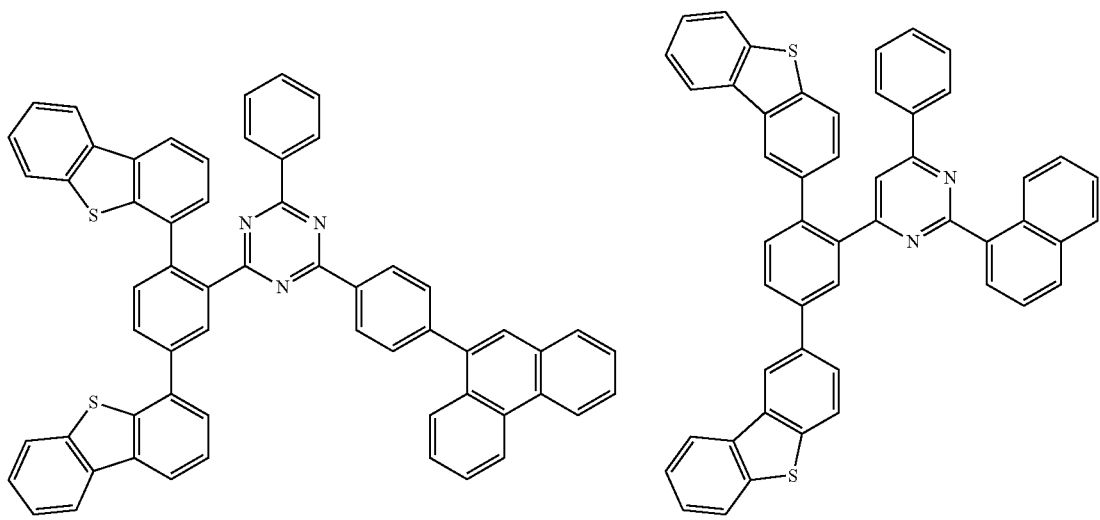
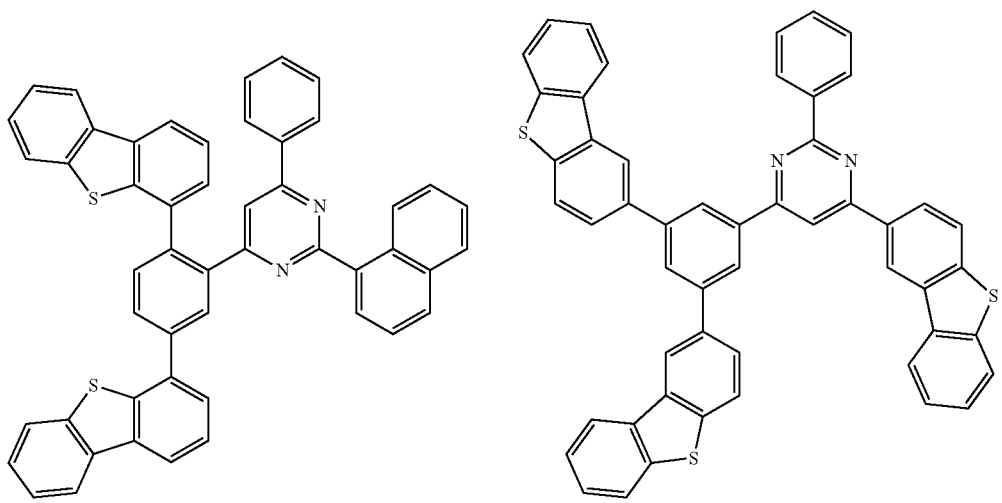

-continued
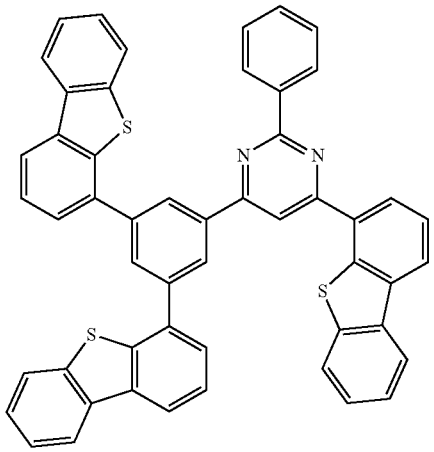
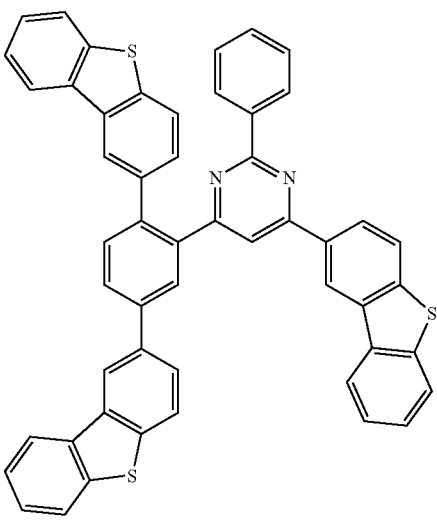
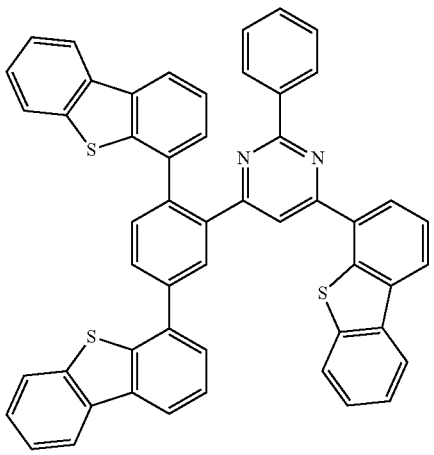
[Formula 126]
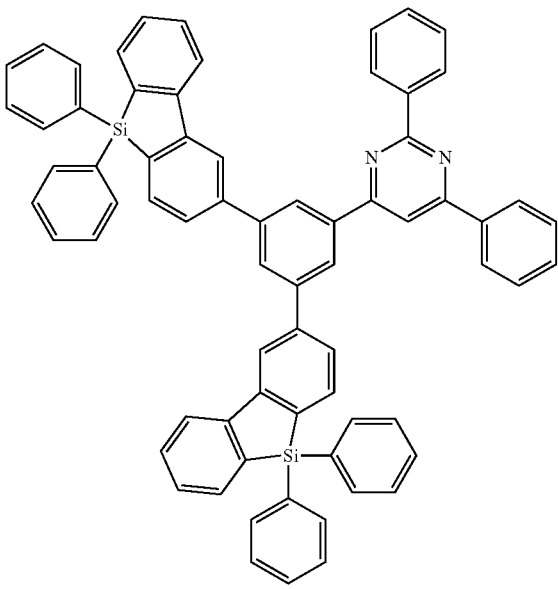

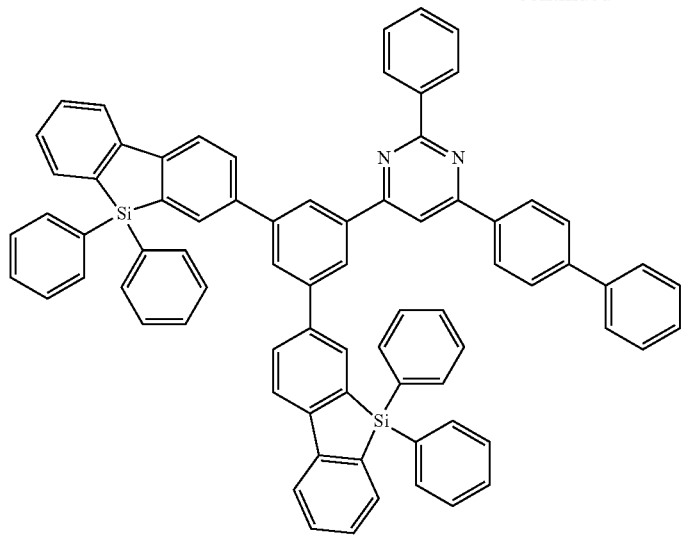 [SMILES: c1ccc(-c2ccc(-c3cc(-c4cc(-c5ccc6c(c5)[Si](c5ccccc5)(c5ccccc5)c5ccccc5-6)cc(-c5ccc6c(c5)[Si](c5ccccc5)(c5ccccc5)c5ccccc5-6)c4)nc(-c4ccccc4)n3)cc2)cc1]
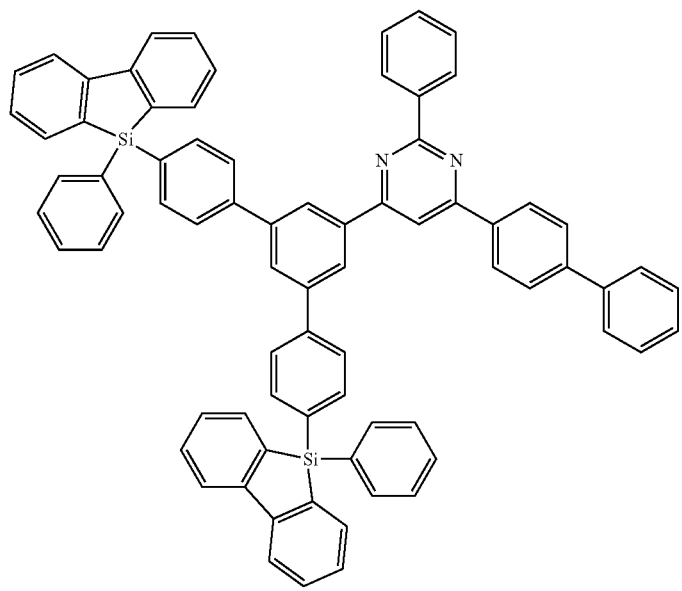
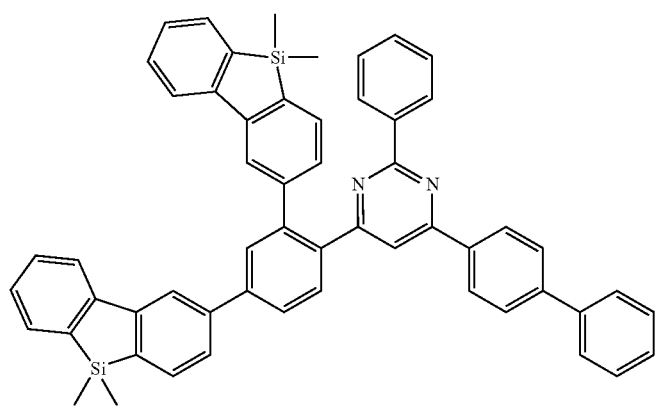

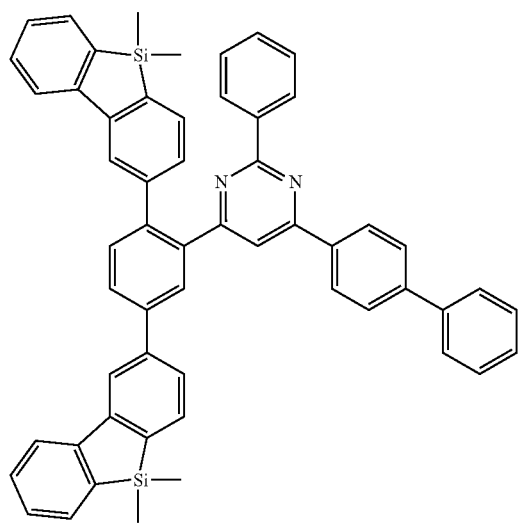
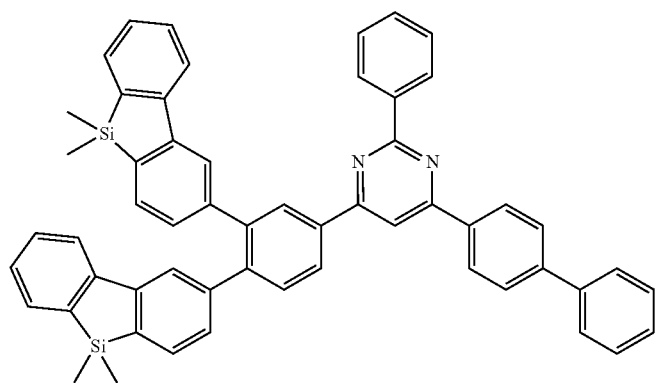
[Formula 127]
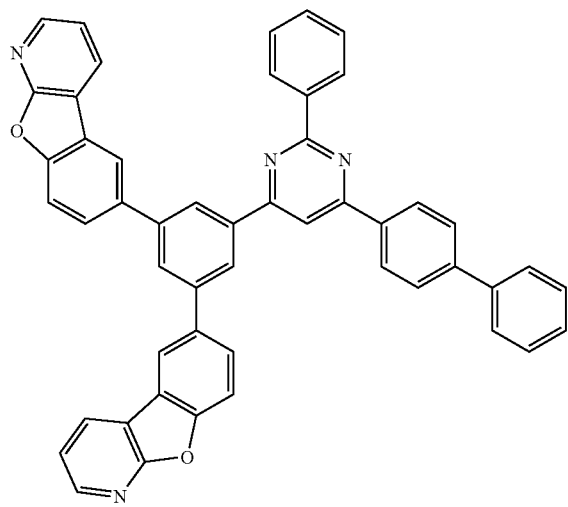

503
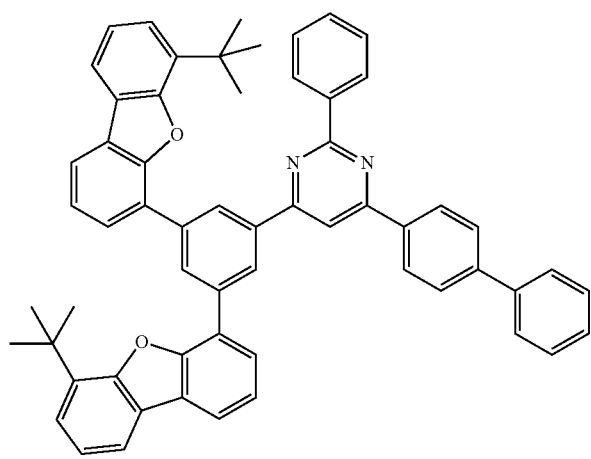
504
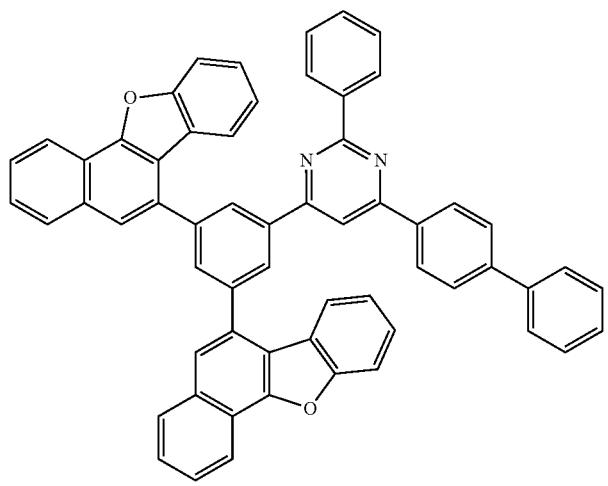
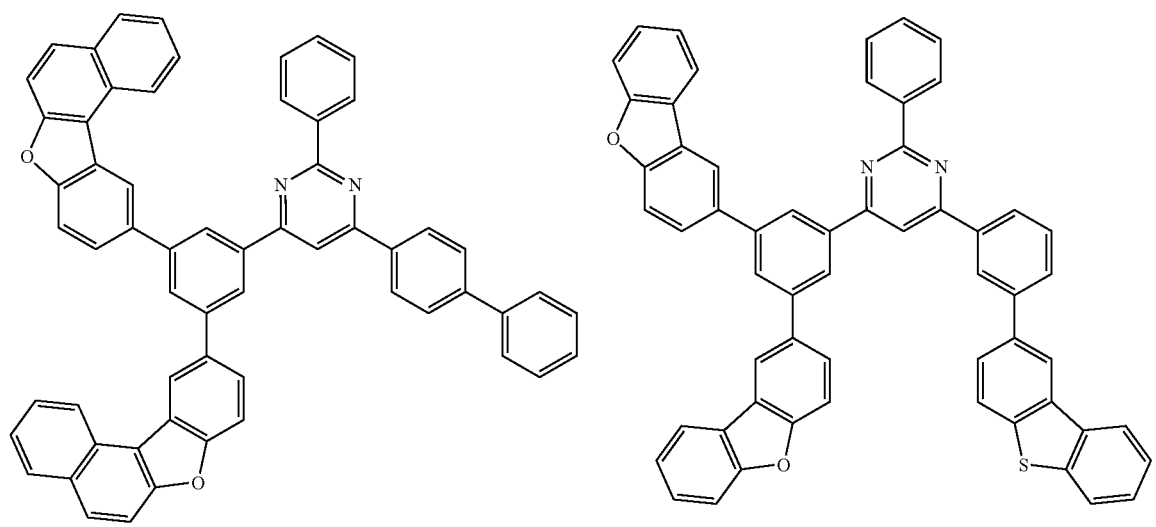

-continued
505
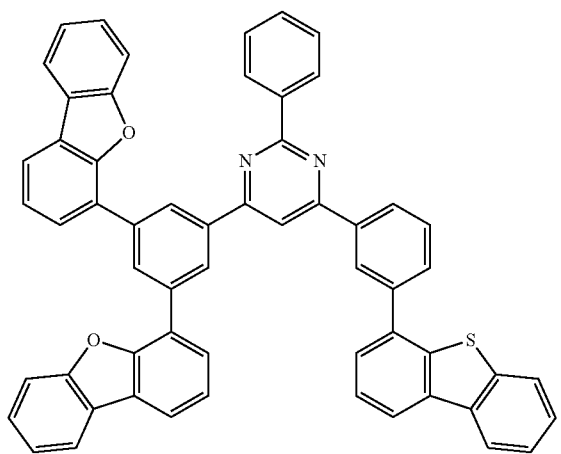
506
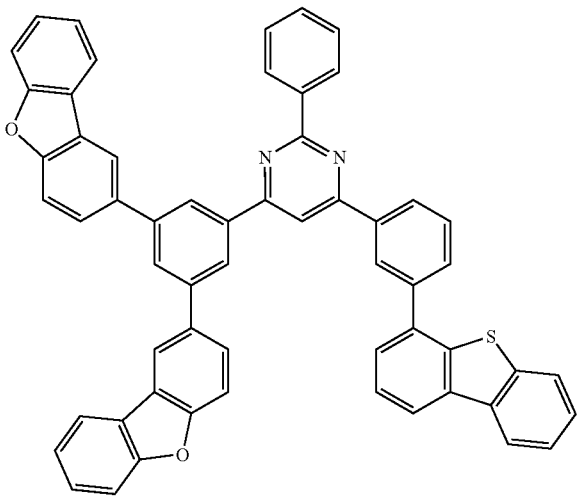
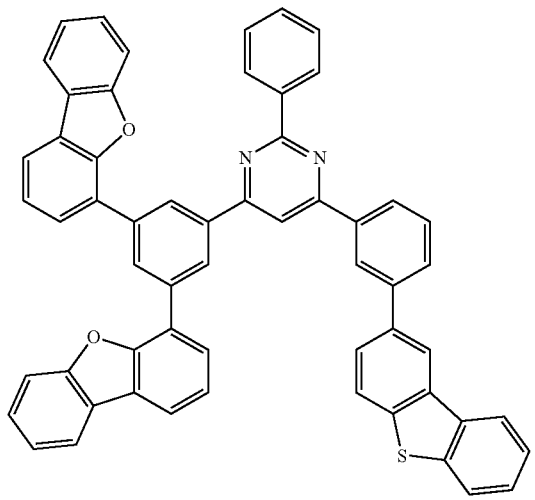
[Formula 128]
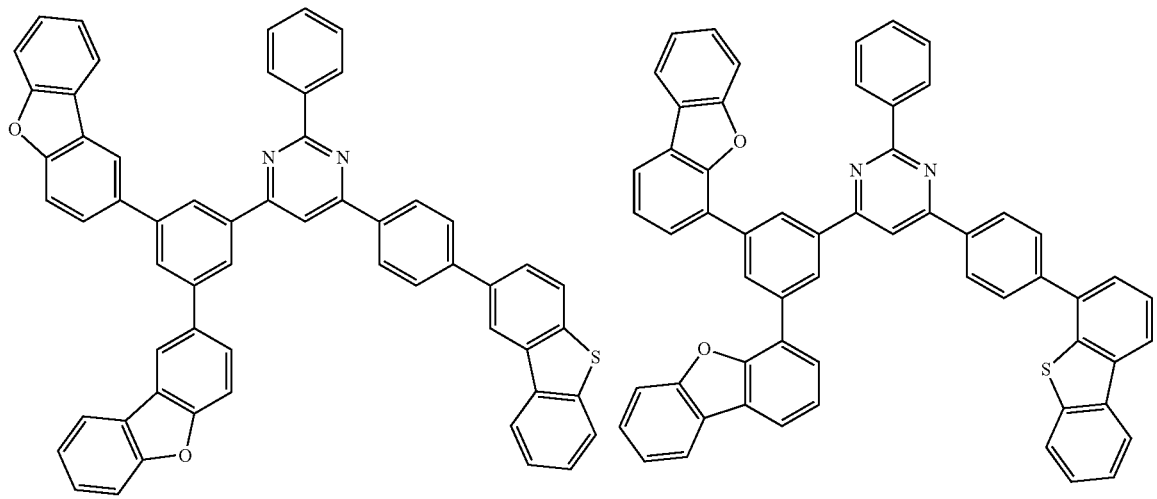

507
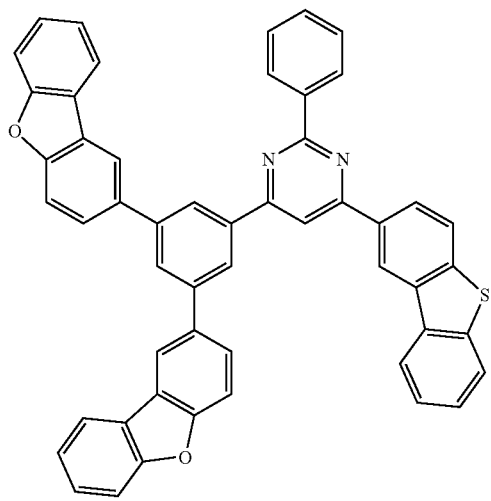
508
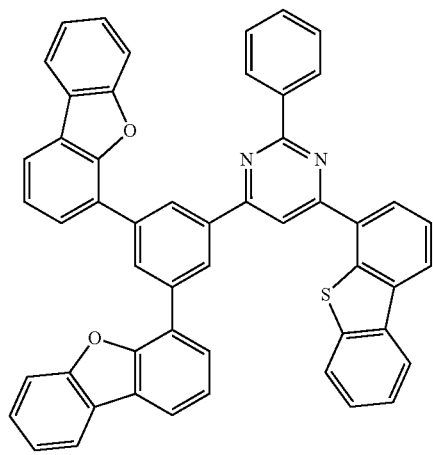
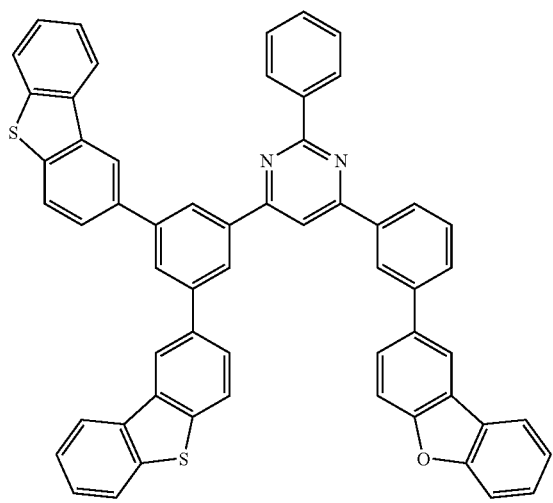
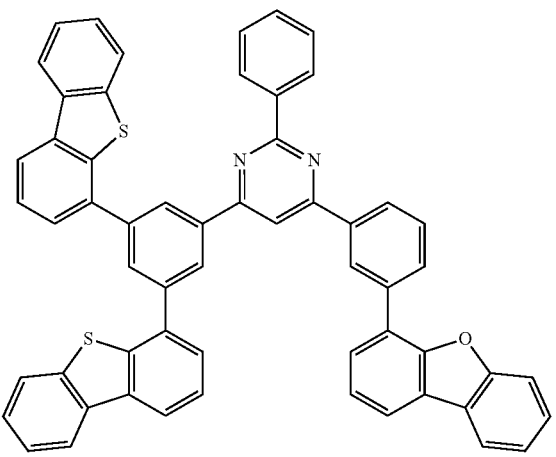
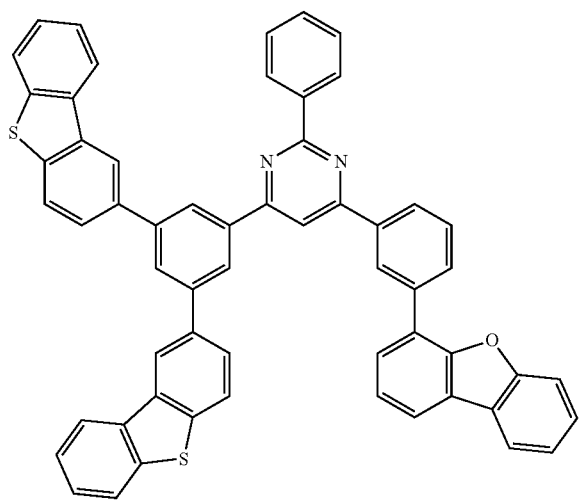
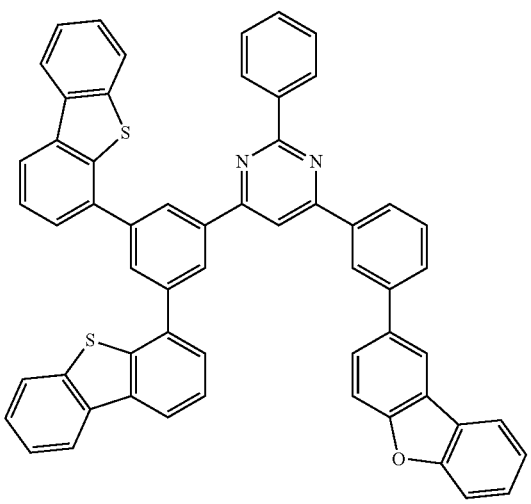

[Formula 129]
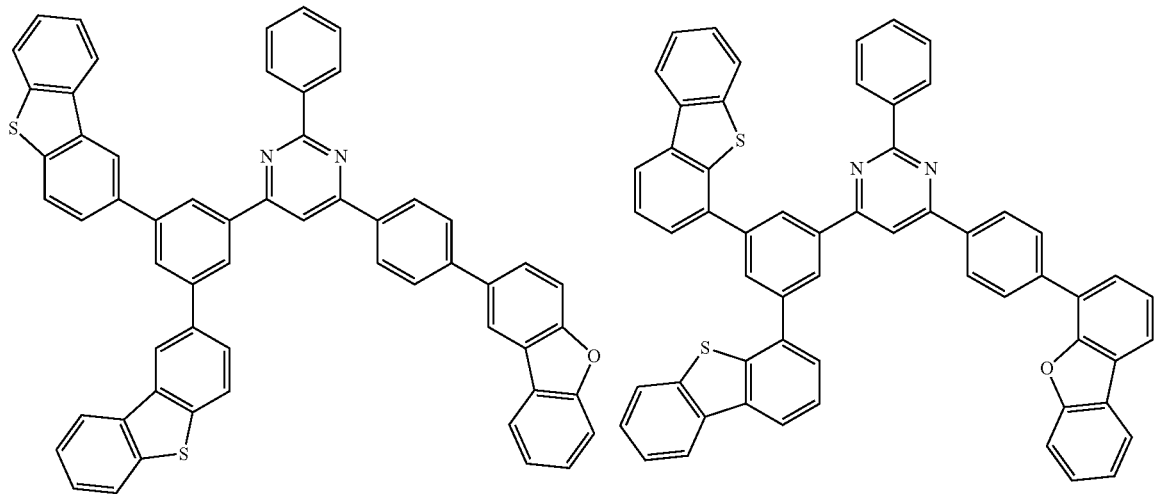
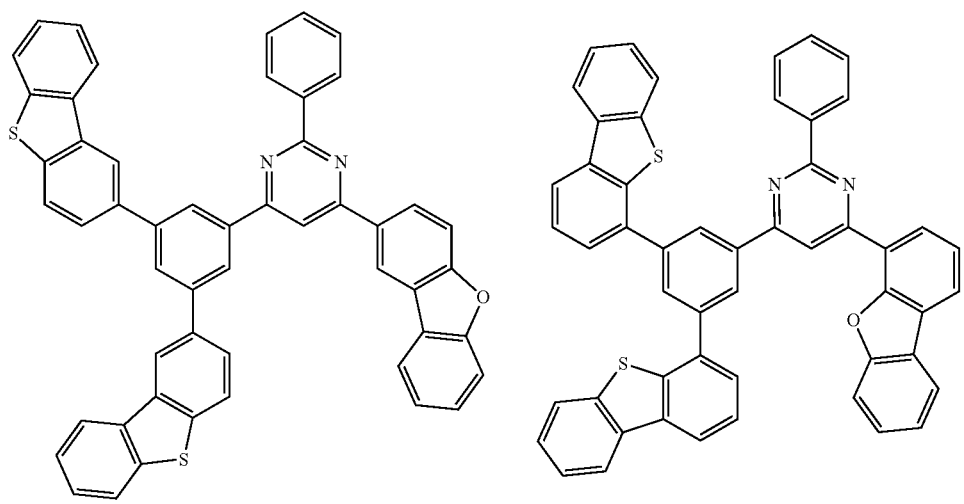
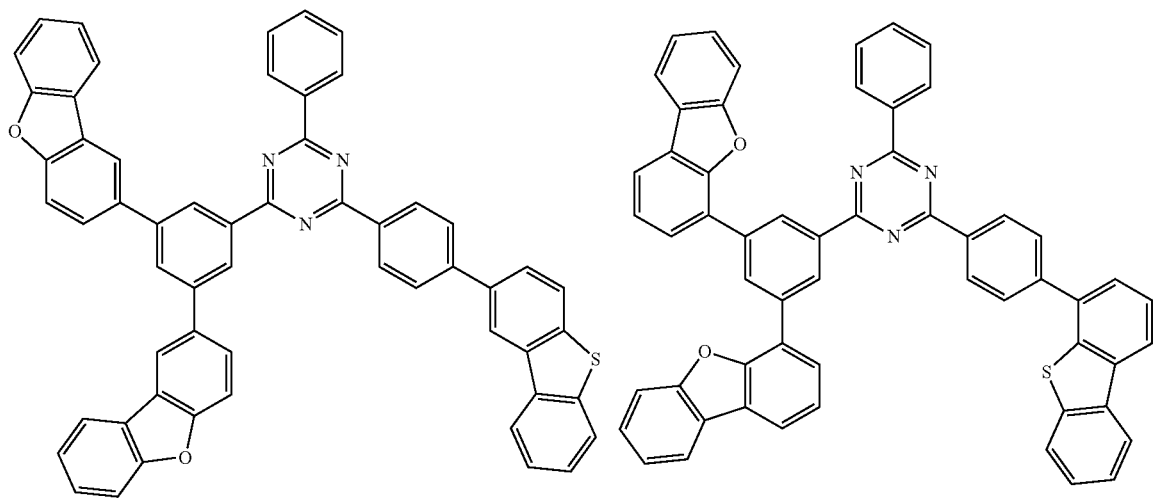

-continued

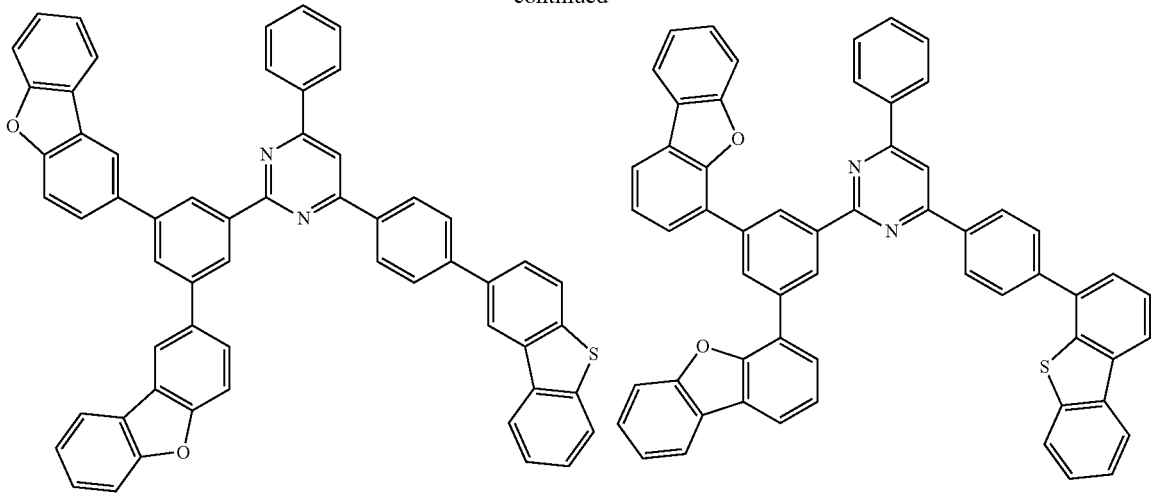

The organic EL device 1 in the exemplary embodiment includes the electron injecting layer 40 between the blocking layer 30 and the cathode 50 as described above. The electron injecting layer 40 preferably contains the aromatic heterocyclic derivative represented by the formula (1). Herein, the aromatic heterocyclic derivative contained in the blocking layer 30 and the aromatic heterocyclic derivative contained in the electron injecting layer 40 may be the same or different.

The electron injecting layer facilitates electron injection from the cathode. Specifically, for instance, the electron injecting layer may be provided by a laminate of a typical electron transporting material and at least one of an electron-donating dopant material and an organic metal complex. Alternatively, the electron injecting layer may be provided by adding at least one of the electron-donating dopant material and the organic metal complex to a material for forming the blocking layer, specifically, in a vicinity of an interface of the electron injecting layer to the cathode.

The electron-donating dopant material may be at least one selected from an alkali metal, an alkali metal compound, an alkaline-earth metal, an alkaline-earth metal compound, a rare-earth metal, a rare-earth metal compound and the like.

The organic metal complex may be at least one selected from an organic metal complex including an alkali metal, an organic metal complex including an alkaline-earth metal, an organic metal complex including a rare-earth metal, and the like.

Examples of the alkali metal are lithium (Li) (work function: 2.93 eV), sodium (Na) (work function: 2.36 eV), potassium (K) (work function: 2.28 eV), rubidium (Rb) (work function: 2.16 eV) and cesium (Cs) (work function: 1.95 eV), which particularly preferably has a work function of 2.9 eV or less. Among the above, the alkali metal is preferably K, Rb or Cs, more preferably Rb or Cs, the most preferably Cs.

Examples of the alkaline-earth metal are calcium (Ca) (work function: 2.9 eV), strontium (Sr) (work function: 2.0 to 2.5 eV), and barium (Ba) (work function: 2.52 eV), among which a substance having a work function of 2.9 eV or less is particularly preferable.

Examples of the rare-earth metal are scandium (Sc), yttrium (Y), cerium (Ce), terbium (Tb), and ytterbium (Yb), among which a substance having a work function of 2.9 eV or less is particularly preferable.

Since the above preferred metals have particularly high reducibility, addition of a relatively small amount of the metals to an electron injecting zone can enhance luminance intensity and lifetime of the organic EL device.

Examples of the alkali metal compound are an alkali oxide such as lithium oxide ($Li_2O$), cesium oxide ($Cs_2O$) and potassium oxide ($K_2O$), and an alkali halogenide such as sodium fluoride (NaF), cesium fluoride (CsF) and potassium fluoride (KF), among which lithium fluoride (LiF), lithium oxide ($Li_2O$) and sodium fluoride (NaF) are preferable.

Examples of the alkaline-earth metal compound are barium oxide (BaO), strontium oxide (SrO), calcium oxide (CaO) and a mixture thereof, i.e., barium strontium oxide ($Ba_xSr_{1-x}O$) (0<x<1), barium calcium oxide (Ba, $Ca_{1-x}O$) (0<x<1), among which BaO, SrO and CaO are preferable.

Examples of the rare earth metal compound are ytterbium fluoride ($YbF_3$), scandium fluoride ($ScF_3$), scandium oxide ($ScO_3$), yttrium oxide ($Y_2O_3$), cerium oxide ($Ce_2O_3$), gadolinium fluoride ($GdF_3$) and terbium fluoride ($TbF_3$), among which $YbF_3$, $ScF_3$, and $TbF_3$ are preferable.

The organic metal complex is not specifically limited as long as containing at least one metal ion of an alkali metal ion, an alkaline-earth metal ion and a rare earth metal ion. A ligand for each of the complexes is preferably quinolinol, benzoquinolinol, acridinol, phenanthridinol, hydroxyphenyl oxazole, hydroxyphenyl thiazole, hydroxydiaryl oxadiazole, hydroxydiaryl thiadiazole, hydroxyphenyl pyridine, hydroxyphenyl benzoimidazole, hydroxybenzo triazole, hydroxy fluborane, bipyridyl, phenanthroline, phthalocyanine, porphyrin, cyclopentadiene, β-diketones, azomethines, or a derivative thereof, but the ligand is not limited thereto.

The electron-donating dopant material and the organic metal complex are added to preferably form a layer or an island pattern in an interfacial region. A layer or an island pattern of the electron-donating dopant and the organic metal complex is preferably formed by evaporating at least one of the electron-donating dopant material and the organic metal complex by resistance heating evaporation while an emitting material for forming the interfacial region or an organic substance as an electron-injecting material are simultaneously evaporated, so that at least one of the electron-donating dopant material and an organic metal complex reduction-causing dopant is dispersed in the organic substance. Dispersion concentration at which the electron-donating dopant is dispersed in the organic substance is a mole ratio (the organic substance to the electron-donating dopant or the organic metal complex) of 100:1 to 1:100, preferably 5:1 to 1:5.

When at least one of the electron-donating dopant material and the organic metal complex forms a layer, the emitting material or the electron injecting material for forming the organic layer of the interfacial region is initially layered, and then, at least one of the electron-donating dopant material and the organic metal complex is singularly evaporated thereon by resistance heating evaporation to preferably form a layer having a thickness of 0.1 nm to 15 nm.

When at least one of the electron-donating dopant material and the organic metal complex forms an island pattern, the emitting material or the electron injecting material for forming the organic layer of the interfacial region is initially layered, and then, at least one of the electron-donating dopant material is singularly evaporated thereon by resistance heating evaporation to preferably form an island pattern having a thickness of 0.05 nm to 1 nm.

A ratio of the main component to at least one of the electron-donating dopant material and the organic metal complex in the organic EL device according to the exemplary embodiment is preferably a mole ratio (the main component to the electron-donating dopant or the organic metal complex) of 5:1 to 1:5, more preferably 2:1 to 1:2.

A compound other than the electron-donating dopant material and the organic metal complex, which is used in the electron injecting layer, is exemplified by a compound represented by the following formula (EIL-1).

[Formula 130]

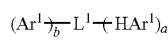

(EIL-1)

In the formula (EIL-1), HAr¹ is a substituted or unsubstituted nitrogen-containing heterocyclic group, preferably having the following structures.

[Formula 131]

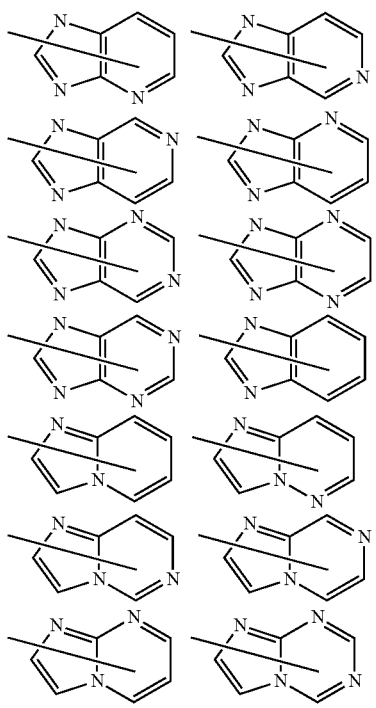

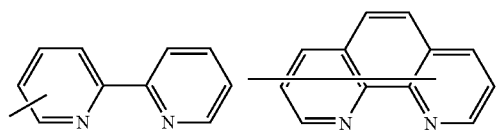

-continued

Examples of a substituent for HAr¹ in the formula (EIL-1) are a fluorine atom, a cyano group, a substituted or unsubstituted alkyl group having 1 to 20 carbon atoms, a substituted or unsubstituted cycloalkyl group having 3 to 20 carbon atoms, a substituted or unsubstituted alkylsilyl group having 3 to 20 carbon atoms, a substituted or unsubstituted arylsilyl group having 8 to 30 carbon atoms, a substituted or unsubstituted alkoxy group having 1 to 20 carbon atoms, a substituted or unsubstituted aryloxy group having 6 to 30 carbon atoms, a substituted or unsubstituted aryl group having 6 to 30 ring carbon atoms, or a substituted or unsubstituted heterocyclic group having 5 to 30 ring atoms.

In the formula (EIL-1), Ar¹ is a substituted or unsubstituted fused cyclic group having 10 to 30 ring carbon atoms, preferably having the following fused cyclic structures.

[Formula 132]

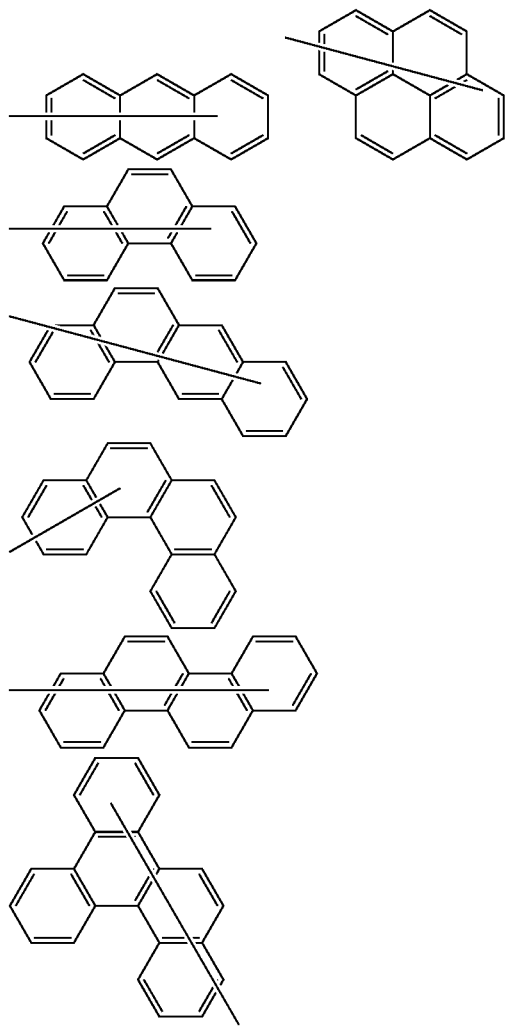

-continued

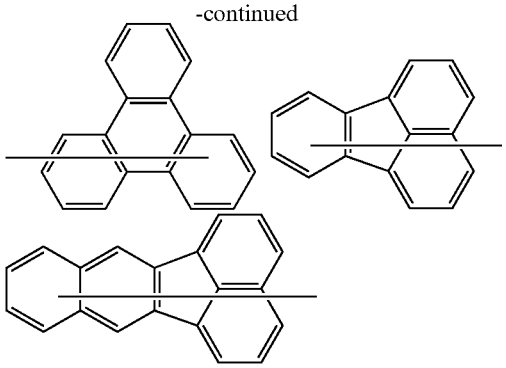

Examples of a substituent for Ar¹ in the formula (EIL-1) are a fluorine atom, a cyano group, a substituted or unsubstituted alkyl group having 1 to 20 carbon atoms, a substituted or unsubstituted cycloalkyl group having 3 to 20 carbon atoms, a substituted or unsubstituted alkylsilyl group having 3 to 20 carbon atoms, a substituted or unsubstituted arylsilyl group having 8 to 30 carbon atoms, a substituted or unsubstituted alkoxy group having 1 to 20 carbon atoms, a substituted or unsubstituted aryloxy group having 6 to 30 carbon atoms, a substituted or unsubstituted aryl group having 6 to 30 ring carbon atoms, or a substituted or unsubstituted heterocyclic group having 5 to 30 ring atoms.

$L^1$ in the formula (EIL-1) represents a single bond, a substituted or unsubstituted a+b valent aromatic hydrocarbon ring group having 6 to 30 ring carbon atoms, a substituted or unsubstituted a+b valent heterocyclic group having 5 to 30 ring atoms, a substituted or unsubstituted hydrocarbon ring group having 6 to 30 ring carbon atoms, or an a+b valent group formed by bonding a plurality of substituted or unsubstituted heterocyclic groups having 5 to 30 ring atoms.

Examples of a substituent for $L^1$ in the formula (EIL-1) are a fluorine atom, a cyano group, a substituted or unsubstituted alkylsilyl group having 3 to 20 carbon atoms, a substituted or unsubstituted arylsilyl group having 8 to 30 carbon atoms, a substituted or unsubstituted aryl group having 6 to 30 ring carbon atoms, or a substituted or unsubstituted heterocyclic group having 5 to 30 ring atoms.

In the formula (EIL-1), a is an integer of 1 to 3, preferably a=1.

In the formula (EIL-1), b is an integer of 1 to 3, preferably b=1.

A compound used for the electron injecting layer is exemplified by a compound represented by the following formula (EIL-2).

[Formula 133]

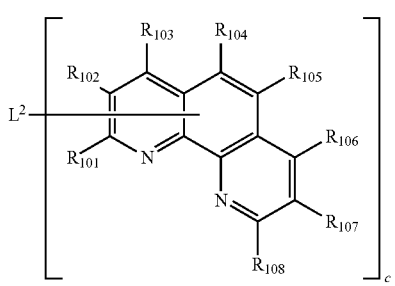
(EIL-2)

In the formula (EIL-2), one of $R_{101}$ to $R_{108}$ is bonded to $L^2$ by a single bond. The rest of $R_{101}$ to $R_{108}$ are a hydrogen atom or a substituent.

Examples of the substituent for $R_{101}$ to $R_{108}$ in the formula (EIL-2) are the same as those listed in the formula (EIL-1). A preferred example is an alkyl group having 1 to 20 carbon atoms or an aryl group having 6 to 30 ring carbon atoms.

In the formula (EIL-2), $L^2$ represents a single bond or a linking group, in which the linking group is a c-valent aromatic hydrocarbon group or c-valent group having a structure represented by the following formula (EIL-2-1).

[Formula 134]

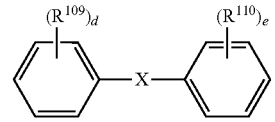
(EIL-2-1)

In the formula (EIL-2-1), $R_{109}$ to $R_{110}$ are a hydrogen atom or a substituent.

In the formula (EIL-2-1), d and e are independently an integer of 1 to 5.

In the formula (EIL-2-1), X is selected from the following structures.

[Formula 135]

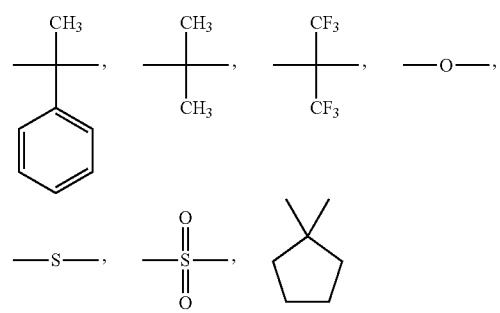

In the formula (EIL-2), c is an integer of 2 to 4, preferably c is 2.

Among the compounds represented by the formula (EIL-2), a compound bonded to $L^2$ in $R_{101}$ and represented by the following formula (EIL-2-2) is preferable.

[Formula 136]

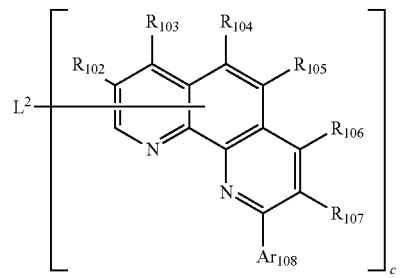
(EIL-2-2)

In the formula (EIL-2-2), $R_{102}$ to $R_{107}$ are a hydrogen atom or a substituent, preferably a hydrogen atom.

In the formula (EIL-2-2), c and $L^2$ are the same as those in the formula (EIL-2).

In the formula (EIL-2-2), c is preferably 2.

In the formula (EIL-2-2), $L^2$ is preferably a substituted or unsubstituted phenylene group or a substituted or unsubstituted naphthylene group.

In the formula (EIL-2-2), $Ar^{108}$ represents a hydrogen atom, alkyl group having 1 to 20 carbon atoms, or substituted or unsubstituted aryl group having 6 to 30 ring carbon atoms, more preferably a methyl group, t-butyl group, substituted or unsubstituted phenyl group, or substituted or unsubstituted naphthyl group.

In order to efficiently cause The TTF phenomenon, it is preferable to adjust a relationship between an affinity of the host material and an affinity of the dopant material as described below. Hereinafter, the affinity of the host material is described as $A_h$, the affinity of the dopant material as $A_d$, ionization potential of the host material as $I_h$ and ionization potential of the dopant material as $I_d$.

Now, the following cases will be described.

[1] Case of $A_h > A_d$

[2] Case of $A_h < A_d$

[3] Case where a dopant material satisfying $A_h < A_d$ and a dopant material satisfying $A_h > A_d$ coexist

[1] Case of $A_h > A_d$

A case where a relationship of $A_h > A_d$ is satisfied will be described. The dopant material used in this exemplary embodiment is a dopant material emitting fluorescence of a main peak wavelength of 550 nm or less and exhibiting a relatively large energy gap. Accordingly, when the relationship of $A_h > A_d$ is satisfied, a relationship of $I_h > I_d$ is simultaneously satisfied. Consequently, the dopant material easily functions as a hole trap.

Figure 4:
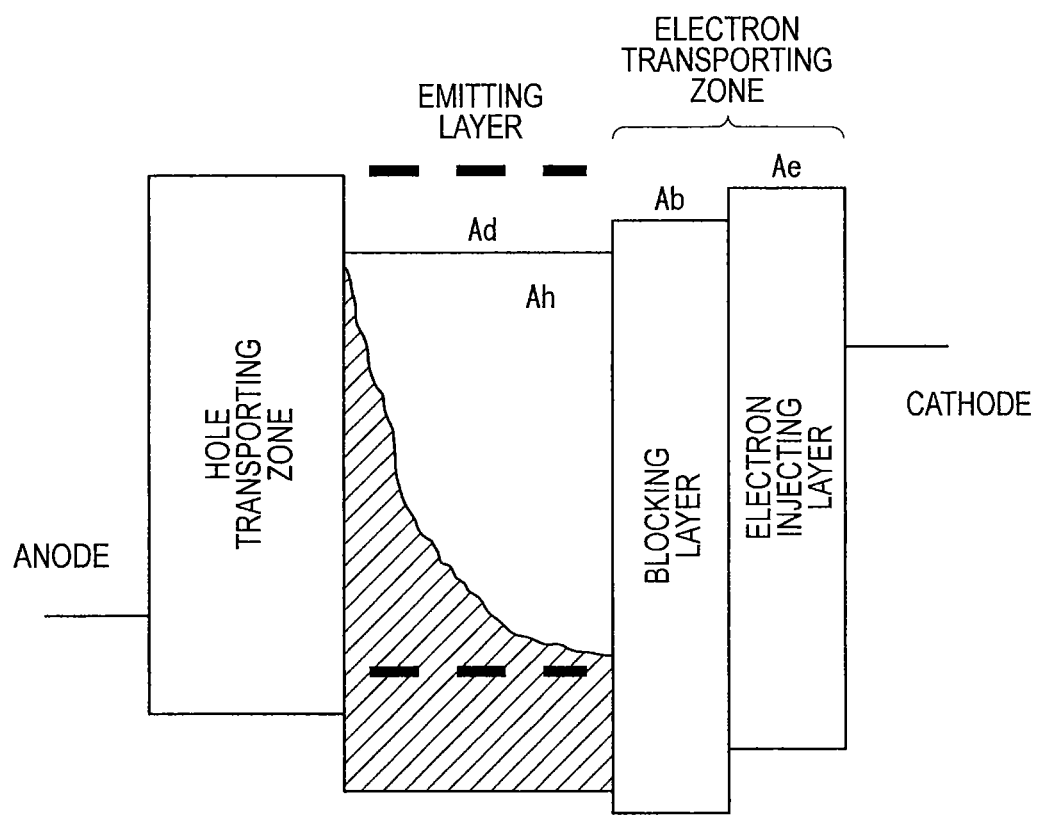
FIG. 4 is an energy band diagram showing a case where an affinity of a host material (Ah)>an affinity of a dopant material (Ad) is satisfied.

For instance, FIG. 4 shows an Ip (ionization potential)-Af (affinity) relationship of the host material and the dopant material in the emitting layer in the above case. In FIG. 4, a shaded area in the emitting layer shows an exciton-density distribution. The same applies to FIGS. 5 to 7. FIG. 4 shows the relationship in the case of $A_h > A_b > A_e$.

When a gap in ionization potential between the host material and the dopant material becomes large, the dopant material is likely to have a hole-trapping property, whereby triplet excitons are generated not only on the host material molecule but directly on the dopant material molecule. Consequently, the triplet excitons generated directly on the dopant material are increased. When a relationship of $E^T_h < E^T_d$ is satisfied, triplet exciton energy on the dopant material molecule is transferred onto the host molecule by Dexter energy transfer, resulting in that all the triplet excitons gather on the host material. As a result, The TTF phenomenon occurs efficiently.

In the exemplary embodiment, it is preferred that the hole transporting layer is adjacent to the emitting layer in the hole transporting zone and a triplet energy $E^T_{ho}$ of the hole transporting layer is larger than a triplet energy $E^T_h$ of the host material.

When the dopant material has a hole-trapping property, the holes injected from the hole transporting zone to the emitting layer are trapped by the dopant material. Accordingly, recombination often occurs in the emitting layer near the anode. A typically-known hole transporting material used for the hole transporting zone often exhibits a larger triplet energy than the host material. Accordingly, diffusion of the triplet excitons on holes-side has not been a problem.

However, even though recombination often occurs near the anode, the triplet exciton density in the interface of the electron transporting zone cannot be ignored. Even under such conditions, highly efficient recombination can be achieved by increasing the triplet energy of the blocking layer.

Other factors to determine recombination areas are a carrier mobility, ionization potential, affinity and thickness of each of the hole transporting zone and the electron transporting zone. For instance, when the thickness of the hole transporting zone is thicker than that of the electron transporting zone, an amount of the electrons injected to the emitting layer is relatively decreased. As a result, the recombination areas are shifted near the electron transporting zone. In such a case, when the blocking layer having a large triplet energy as in the invention is used, the TTF phenomenon can be efficiently induced.

The host material and the dopant material that satisfy the above relationship in the affinity are selected from, for instance, the following compounds (see JP-A-2010-50227 (Japanese Patent Application No. 2008-212102) and the like).

The host material is an anthracene derivative and a polycyclic aromatic skeleton-containing compound, preferably the anthracene derivative.

The dopant material is at least one compound selected from the group consisting of a pyrene derivative, aminoanthracene derivative, aminochrysene derivative and aminopyrene derivative.

Examples of preferable combinations of the host material and the dopant material are the anthracene derivative as the host material and at least one compound selected from the group consisting of a pyrene derivative, aminoanthracene derivative, aminochrysene derivative and aminopyrene derivative as the dopant material.

The aminoanthracene derivative is specifically exemplified by a compound represented by the following formula (20A).

[Formula 137]

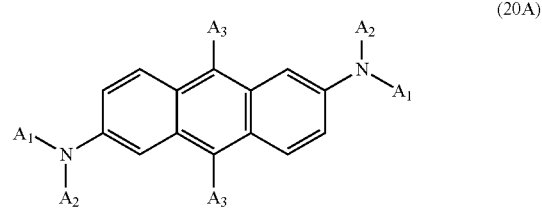

(20A)

In the formula (20A), $A_1$ and $A_2$ independently represent a substituted or unsubstituted aliphatic hydrocarbon group having 1 to 6 carbon atoms, substituted or unsubstituted aromatic hydrocarbon group having 6 to 20 ring carbon atoms, or substituted or unsubstituted heterocyclic aromatic hydrocarbon group having 5 to 19 ring atoms and containing nitrogen, sulfur or oxygen atom.

$A_3$ independently represents a substituted or unsubstituted aliphatic hydrocarbon group having 1 to 6 carbon atoms, substituted or unsubstituted aromatic hydrocarbon group having 6 to 20 ring carbon atoms, substituted or unsubstituted heterocyclic aromatic hydrocarbon group having 5 to 19 ring atoms, or a hydrogen atom. The heterocyclic aromatic hydrocarbon group includes nitrogen, sulfur or oxygen atom.

The aminochrysene derivative is specifically exemplified by a compound represented by the following formula (20B).

[Formula 138]

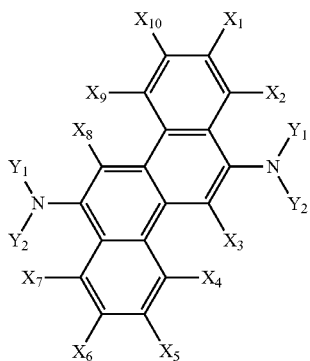

(20B)

In the formula (20B), $X_1$ to $X_{10}$ each represent a hydrogen atom or a substituent. $Y_1$ and $Y_2$ each represent a substituent.

$X_1$ to $X_{10}$ are preferably a hydrogen atom. $Y_1$ and $Y_2$ are preferably a substituted or unsubstituted aromatic ring having 6 to 30 ring carbon atoms. The substituent of the aromatic ring is preferably an alkyl group having 1 to 6 carbon atoms. The aromatic ring is preferably an aromatic ring having 6 to 10 ring carbon atoms or a phenyl group.

The aminopyrene derivative is exemplified by a compound represented by the following formula (20C).

[Formula 139]

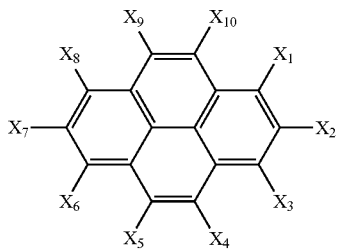

(20C)

In the formula (20C), $X_1$ to $X_{10}$ each represent a hydrogen atom or a substituent. $X_3$ and $X_8$ or $X_2$ and $X_7$ each represent —$NY_1Y_2$($Y_1$ and $Y_2$: substituents). When $X_3$ and $X_8$ each represent —$NY_1Y_2$, it is preferred that $X_{2,4,5,7,9,10}$ represent a hydrogen atom, $X_1$ and $X_6$ represent a hydrogen atom, alkyl group or cycloalkyl group. When $X_2$ and $X_7$ each represent —$NY_1Y_2$, it is preferred that $X_{1,3-6,8-10}$ are a hydrogen atom. $Y_1$ and $Y_2$ are preferably a substituted or unsubstituted aromatic ring, e.g., a phenyl group and a naphthyl group. The substituent of the aromatic ring is exemplified by an alkyl group having 1 to 6 carbon atoms.

The anthracene derivative is preferably a compound represented by the formula (20D).

In the formula (20D), $Ar^{11}$ and $Ar^{12}$ each independently represent a substituted or unsubstituted monocyclic group having 5 to 30 ring atoms, a substituted or unsubstituted fused cyclic group having 10 to 30 ring atoms or a combination of the monocyclic group and the fused cyclic group.

The monocyclic group in the formula (20D) is a group formed only by ring structure(s) having no fused structure.

The monocyclic group has 5 to 30 ring atoms, preferably 5 to 20 ring atoms. Examples of the monocyclic group include: an aromatic group such as a phenyl group, biphenyl group, terphenyl group and quarter-phenyl group; and a heterocyclic group such as a pyridyl group, pyrazyl group, pyrimidyl group, triazinyl group, furyl group and thienyl group. Among the monocyclic group, a phenyl group, biphenyl group and terphenyl group are preferable.

The fused cyclic group in the formula (20D) is a group formed by fusing two or more ring structures.

The fused cyclic group has 10 to 30 ring atoms, preferably 10 to 20 ring atoms. Examples of the fused cyclic group include: a fused aromatic cyclic group such as a naphthyl group, phenanthryl group, anthryl group, chrysenyl group, benzoanthryl group, benzophenanthryl group, triphenylenyl group, benzochrysenyl group, indenyl group, fluorenyl group, 9,9-dimethylfluorenyl group, benzofluorenyl group, dibenzofluorenyl group, fluoranthenyl group and benzofluoranthenyl group; and a fused heterocyclic group such as a benzofuranyl group, benzothiophenyl group, indolyl group, dibenzofuranyl group, dibenzothiophenyl group, carbazolyl group, quinolyl group and phenanthrolinyl group. Among the fused cyclic group, a naphthyl group, phenanthryl group, anthryl group, 9,9-dimethylfluorenyl group, fluoranthenyl group, benzoanthryl group, dibenzothiophenyl group, dibenzofuranyl group and carbazolyl group are preferable.

The group formed in a combination of the monocyclic group and the fused cyclic group in the formula (20D) is exemplified by a group combined by sequentially bonding a phenyl group, a naphthyl group and a phenyl group to an anthracene ring.

Specific examples of the alkyl group, silyl group, alkoxy group, aryloxy group, aralkyl group and the halogen atom for $R^{101}$ to $R^{108}$ in the formula (20D) are the same as those described in relation to $R_1$ in the formula (1). Examples of the cycloalkyl group are the same as the above examples of the cycloalkyl group. The same applies to the description of "substituted or unsubstituted" in these substituents.

Preferable examples of the "substituted or unsubstituted" substituent for $Ar^{11}$ and $Ar^{12}$ and $R^{101}$ to $R^{108}$ in the formula (20D) are a monocyclic group, fused cyclic group, alkyl group, cycloalkyl group, silyl group, alkoxy group, cyano group and halogen atom (particularly, fluorine). The monocyclic group and the fused cyclic group are particularly preferable. Preferable specific examples of the substituents are the same as the above examples of the groups in the formula (20D) and the above examples of the groups in the formula (1).

[2] Case of $A_h<A_d$

Using the combination of the host material and the dopant material which allows $A_h<A_d$, the advantageous effects of the blocking layer provided within the electron transporting zone is exhibited outstandingly, whereby improvement in efficiency due to the TTF phenomenon can be attained. Description will be given in the following cases of [2-1] and [2-2]. In general, an organic material has a broadening of a LUMO level in a range larger than the measured affinity level by approximately 0.2 eV.

[2-1] Difference Between $A_d$ and $A_h$ is Smaller than 0.2 eV

Figure 5:
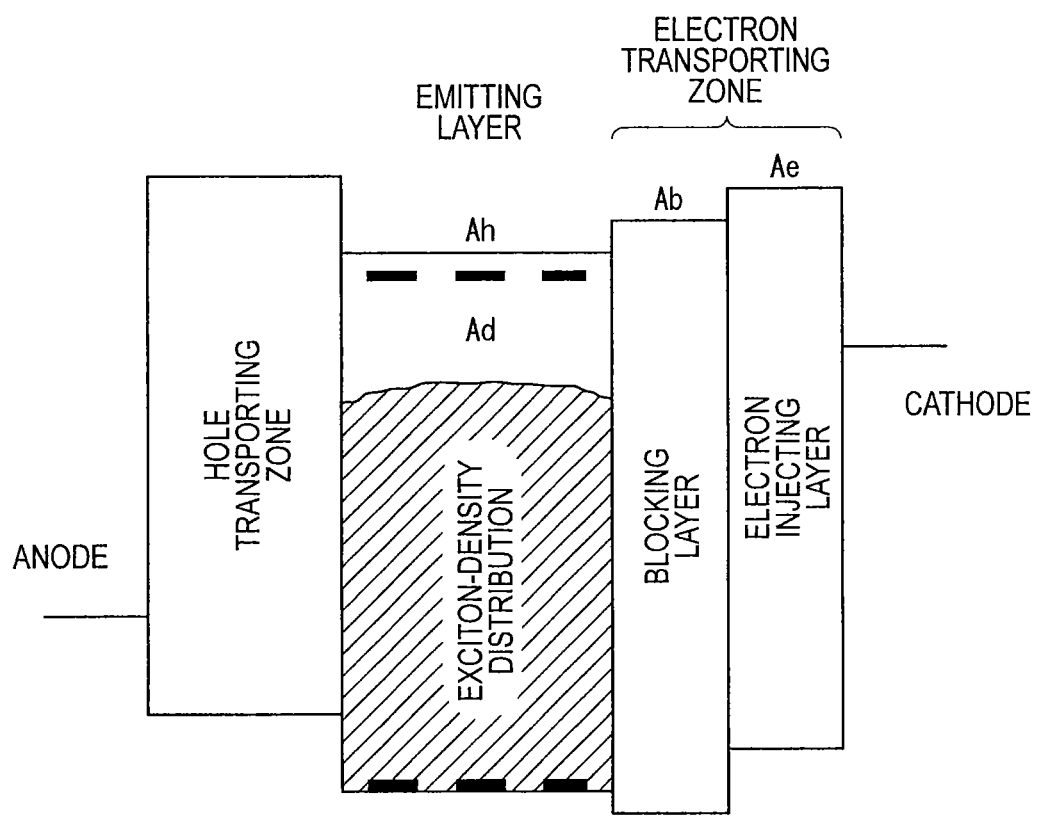
FIG. 5 is an energy band diagram showing a case where Ah<Ad is satisfied and a difference between Ah and Ad is less than 0.2 eV.

FIG. 5 shows one example of an energy band diagram in this case. Dotted lines in the emitting layer show an energy level of the dopant material. As shown in FIG. 5, when a difference between $A_d$ and $A_h$ is smaller than 0.2 eV, the LUMO level of the dopant material is included in the range of the broadening of the LUMO level of the host material, so that the electrons carried within the emitting layer is less likely to be trapped by the dopant material. In other words, the dopant material is less likely to exhibit an electron-trapping property. Moreover, the dopant material in the exemplary embodiment is a wide-gap fluorescent dopant material having a main peak wavelength of 550 nm or less. When the relationship of $A_h<A_d$ is satisfied, since the difference between $A_h$ and $A_d$ is approximately 0.2 eV, a difference between the ionization potential of the host material and the ionization potential of the dopant material is reduced. As a result, the dopant material does not tend to exhibit an outstanding hole-trapping property. FIG. 5 shows the relationship in the case of $A_h>A_b>A_e$.

In other words, the dopant material in this case does not tend to exhibit an outstanding trapping property for both electrons and holes. In this case, as shown by the shaded area of the emitting layer in FIG. 5, the electron-hole recombination occur mainly on the host material molecule in the broad whole area in the emitting layer, thereby generating 25% of singlet excitons and 75% of triplet excitons mainly on the host material molecule. Energy of the singlet excitons generated on the host material is transferred to the dopant material by Forster energy transfer to contribute to a fluorescent emission of the dopant material molecule. On the other hand, the transfer direction of the energy of triplet excitons depends on the triplet energy relationship of the host material and the dopant material. When the relationship is $E^T_h>E^T_d$, the triplet excitons generated on the host material are transferred to a dopant material which exists in the vicinity by the Dexter energy transfer. A concentration of the dopant material in the emitting layer of a fluorescent device is typically as low as at a few mass % to approximately 20 mass %. Accordingly, triplet excitons which have transferred to the dopant material collide with one another less frequently, resulting in a less possibility of occurrence of the TTF phenomenon. However, when the relationship of $E^T_h<E^T_d$ is satisfied as in this exemplary embodiment, since the triplet excitons are present on the host material molecule, the frequency of collision is increased, so that the TTF phenomenon easily and efficiently occur.

In the exemplary embodiment, the blocking layer is adjacent to the emitting layer. Since the triplet energy $E^T_b$ of the blocking layer is set to be larger than the triplet energy $E^T_h$ of the host material, the triplet excitons is prevented from dispersing in the electron transporting zone, so that the TTF phenomenon can occur efficiently in the emitting layer.

[2-2] Difference Between $A_d$ and $A_h$ is Larger than 0.2 eV

Figure 6:
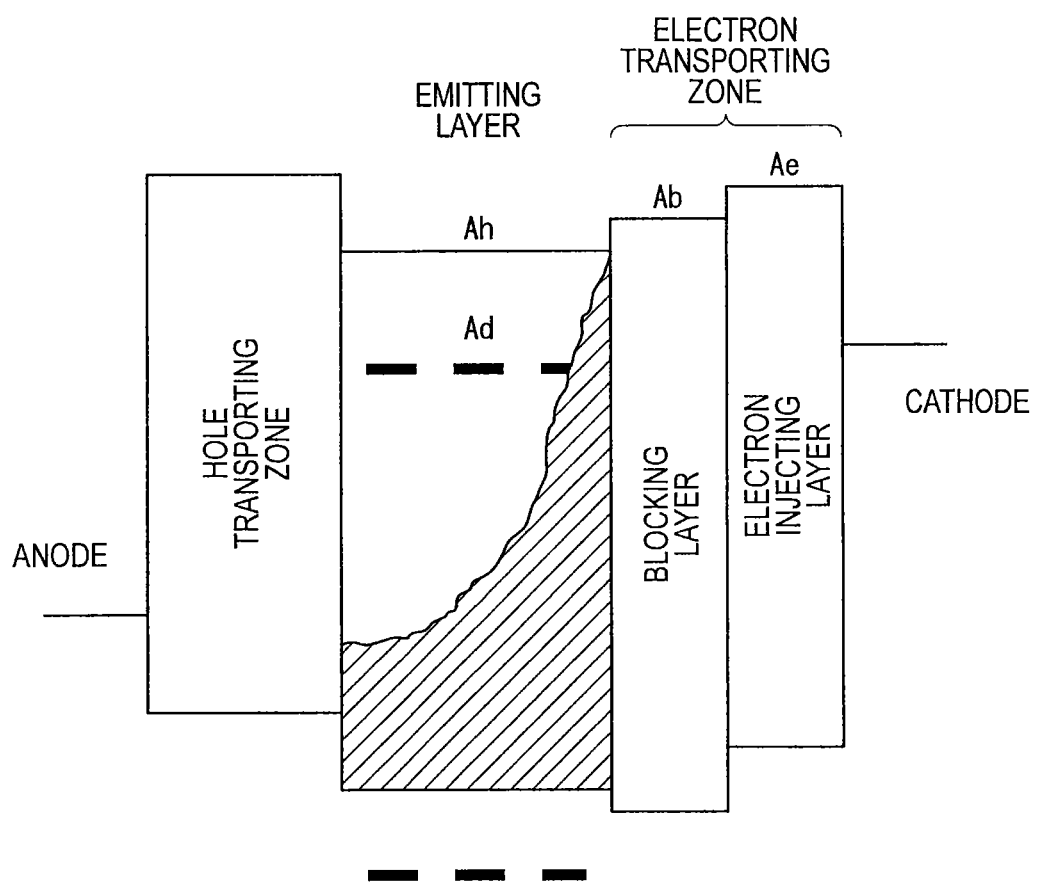
FIG. 6 is an energy band diagram showing a case where Ah<Ad is satisfied and a difference between Ah and Ad is more than 0.2 eV.

FIG. 6 shows one example of an energy band diagram in this case. The difference in affinity between the dopant material and the host material is increased, so that a LUMO level of the dopant material is present at a position further higher than the LUMO level broadening of the host material. Accordingly, the dopant material is more likely to exhibit a significant electron-trapping property. Electrons trapped by the dopant material are recombined with holes after the holes are transferred from the host material to the dopant material. In other words, unlike the condition shown in FIG. 5, the electrons and the holes are recombined in a pair not only on the host material molecule but also on the dopant material molecule. As a result, triplet excitons are generated not only on the host material molecule but also directly on the dopant material molecule. Under such conditions, when the relationship of $E^T_h<E^T_d$ is satisfied as in this exemplary embodiment, the triplet excitons generated directly on the dopant material also gather on the host material by Dexter energy transfer, so that the TTF phenomenon occurs efficiently.

When the affinities satisfy the above-mentioned relationship, the possibility of trapping of electrons by the dopant material is increased toward the interface between the emitting layer and the blocking layer. As a result, recombination occurs frequently in the vicinity of the interface between the emitting layer and the blocking layer. In this case, the efficiency of confining triplet excitons by the blocking layer is increased as compared with the case mentioned in [2-1], resulting in an increase in density of triplet excitons at the interface between the emitting layer and the blocking layer. FIG. 6 shows the relationship in the case of $A_h>A_b>A_e$.

The host material and the dopant material that satisfy the above relationship in the $A_h<A_d$ can be selected from, for instance, the following compounds (see JP-A-2010-50227 (Japanese Patent Application No. 2008-212102) and the like).

Examples of the host material are an anthracene derivative and a polycyclic aromatic skeleton-containing compound, preferably an anthracene derivative.

Examples of the dopant material are a fluoranthene derivative, pyrene derivative, arylacetylene derivative, fluorene derivative, boron complex, perylene derivative, oxadiazole derivative and anthracene derivatives, preferably fluoranthene derivative, pyrene derivative, and boron complex, more preferably fluoranthene derivative and boron complex. As for the combination of the host material and the dopant material, it is preferred that the host material is an anthracene derivative and the dopant material is a fluoranthene derivative or a boron complex.

The fluoranthene derivative is exemplified by the following compound.

[Formula 140]

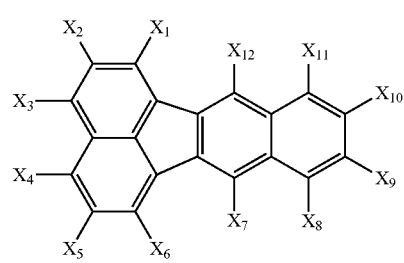

(30A)

In the formula (30A), $X_1$ to $X_{12}$ each represent a hydrogen atom or a substituent. Preferably, in the compound, $X_1$ to $X_2$, $X_4$ to $X_6$ and $X_8$ to $X_{11}$ are a hydrogen atom, and $X_3$, $X_7$ and $X_{12}$ are a substituted or unsubstituted aryl group having 5 to 50 ring atoms. Preferably, in the compound, $X_1$ to $X_2$, $X_4$ to $X_6$ and $X_8$ to $X_{11}$ are a hydrogen atom, $X_3$, $X_7$ and $X_{12}$ are a substituted or unsubstituted aryl group having 5 to 50 ring atoms. $X_3$ is —$Ar_1$—$Ar_2$, in which $Ar_1$ is a substituted or unsubstituted arylene group having 5 to 50 ring atoms, and $Ar_2$ is a substituted or unsubstituted aryl group having 5 to 50 ring atoms.

More preferably, in the compound, $X_1$ to $X_2$, $X_4$ to $X_6$ and $X_8$ to $X_{11}$ are a hydrogen atom and $X_7$ and $X_{12}$ are a substituted or unsubstituted aryl group having 5 to 50 ring atoms. $X_3$ is —$Ar_1$—$Ar_2$—$Ar_3$, in which $Ar_1$ and $Ar_3$ are each a substituted or unsubstituted arylene group having 5 to 50 ring atoms, and $Ar_2$ is a substituted or unsubstituted aryl group having 5 to 50 ring atoms.

The boron complex is exemplified by the following compound.

[Formula 141]

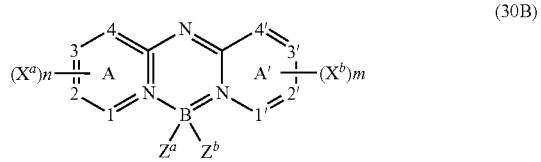

(30B)

In the formula (30B), A and A' represent an independent azine ring system corresponding to a six-membered aromatic ring containing one or more nitrogen. $X^a$ and $X^b$ represent independently-selected substituents, which are bonded together to form a fused ring for the ring A or the ring A'. The fused ring contains an aryl or heteroaryl substituent. m and n independently represent 0 to 4. $Z^a$ and $Z^b$ each represent an independently-selected halide. 1, 2, 3, 4, 1', 2', 3' and 4' each represent an independently-selected carbon atom or nitrogen atom.

Desirably, the azine ring is preferably a quinolinyl ring or isoquinolinyl ring in which all of 1, 2, 3, 4, 1', 2', 3' and 4' are carbon atoms, m and n each are 2 or more, and $X^a$ and $X^b$ are a substituent having 2 or more carbon atoms that combine with each other to form an aromatic ring. $Z^a$ and $Z^b$ are desirably fluorine atoms.

The anthracene derivatives as the host material in the case of [2] are the same as those described in the above "[1] Case of $A_h > A_d$."

Figure 7:
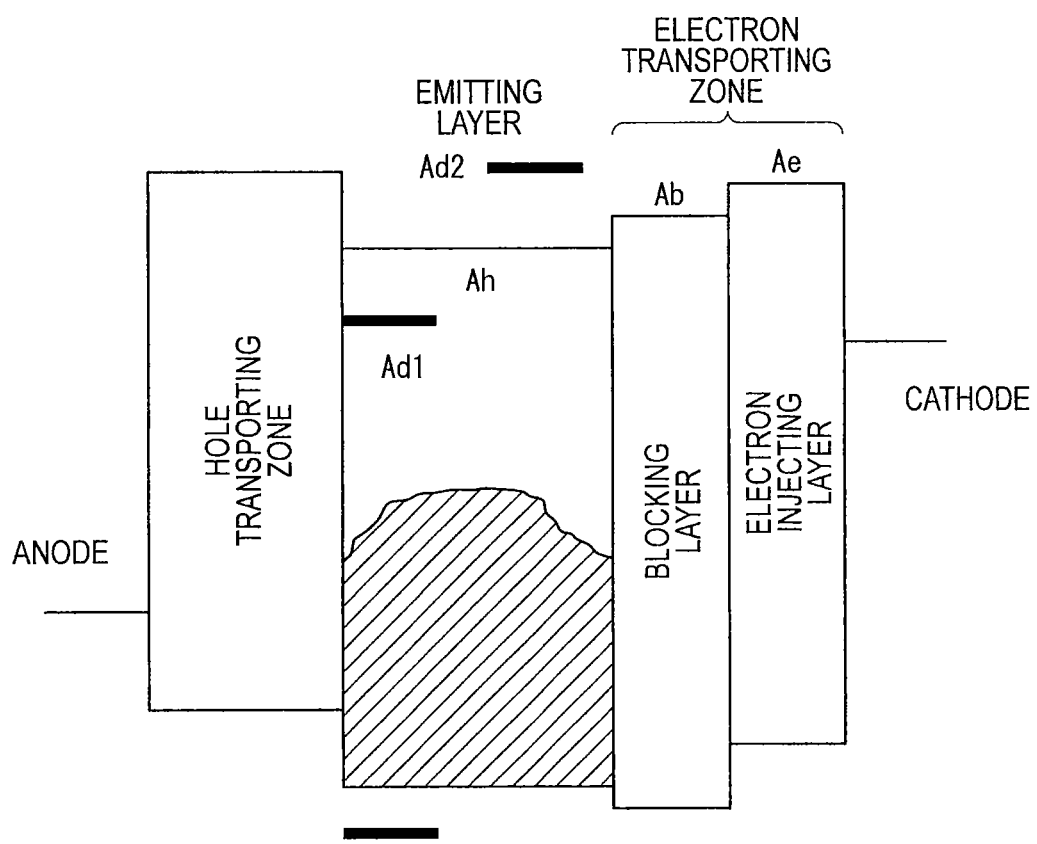
FIG. 7 is an energy band diagram showing a case where a dopant material satisfying Ah<Ad and a dopant material satisfying Ah>Ad coexist.

[3] Case where a Dopant Material Satisfying $A_h < A_d$ and a Dopant Material Satisfying $A_h > A_d$ Coexist FIG. 7 shows one example of an energy band diagram when a dopant material satisfying $A_h < A_d$ and a dopant material satisfying $A_h > A_d$ are both contained in the emitting layer. In such a case, both electrons and holes are trapped properly, whereby recombination occurs in the entire region of the emitting layer. Accordingly, recombination occurs frequently also on the cathode side. By providing a blocking layer that has a large triplet energy, the TTF phenomenon occurs efficiently. FIG. 7 shows the relationship in the case of $A_h > A_b > A_e$.

In the exemplary embodiment, the density of excitons is large in the interface between the emitting layer and the blocking layer. In this case, holes which do not contribute to recombination in the emitting layer are injected in the blocking layer with a high probability. Accordingly, among the above-mentioned aromatic heterocyclic derivatives, one having an excellent oxidation resistance is preferable as the material to be used in the blocking layer.

The blocking layer material desirably exhibits a reversible oxidation process in a cyclic voltammetry measurement.

The emitting layer may contain two or more fluorescent dopant materials of which the main peak wavelength is 550 nm or less. When the emitting layer contains two or more fluorescent dopant materials, the affinity $A_d$ of at least one dopant material is equal to or larger than the affinity $A_h$ of the host material, and the triplet energy $E^T_d$ of this dopant material is larger than the triplet energy $E^T_h$ of the host material. For instance, the affinity $A_d$ of at least one dopant material of the rest of the dopant materials may be smaller than the affinity $A_h$ of the host material. Containing such two kinds of dopant materials means containing both of a dopant material satisfying $A_h < A_d$ and a dopant material satisfying $A_h > A_d$ as described above. Efficiency can be significantly improved by providing the blocking layer having a large triplet energy.

Examples of the dopant material having the affinity $A_d$ that is smaller than the affinity $A_h$ of the host material include a pyrene derivative, aminoanthracene derivative, aminochrysene derivative, and aminopyrene derivative.

In addition to the above-mentioned host materials, dibenzofuran compounds disclosed in WO05/113531 and JP2005-314239, fluorene compounds disclosed in WO02/14244, and benzanthracene compounds disclosed in WO08/145,239 can be used.

In addition to the above-mentioned dopant materials, pyrene compounds disclosed in JP2004-204238, WO05/108348, WO04/83162, WO09/84512, KR10-2008-79956, KR10-2007-115588 and KR10-2010-24894, chrysene compounds disclosed in WO04/44088, and anthracene compounds disclosed in WO07/21117 can be used.

Preferably, the host material and the dopant material are each a compound formed by bonding ring structures or single atoms (including bonding of a ring structure and a single atom), in which the bonding is a single bond. A compound having a carbon-carbon double bond in the part other than the ring structure thereof is not preferable The reason thereof is that the triplet energies generated on the host material and the dopant material are used for the structural change of the double bond, not for a TTF phenomenon.

Formation Method of Each Layer of Organic EL Device

Each layer of the organic EL device in the exemplary embodiment may be formed by any one of dry film-forming such as vacuum deposition, sputtering, plasma deposition and ion plating, and wet film-forming such as spin coating, dipping, flow coating and ink jet.

In the wet film-forming, materials for forming each layer are dissolved or dispersed in an appropriate solvent such as ethanol, chloroform, tetrahydrofuran and dioxane to form a thin-film. Any one of the solvents is usable.

As a solution suitable for the wet film-forming, an organic-EL-material-containing solution, which contains an aromatic amine derivative of the invention as an organic-EL-device material and a solvent, is usable.

In any one of the organic thin-film layer, a resin or an additive suitable for improving film-forming performance and preventing pin holes on a film may be used.

Thickness of Each Layer of Organic EL Device

Although a thickness is not limited, an appropriate thickness needs to be set. When the thickness is excessively thick, a large voltage is required to be applied in order to obtain a predetermined emission, so that an efficiency is deteriorated. When the thickness is excessively thin, pin holes or the like generate. Accordingly, even when the electrical field is applied to the film, a sufficient luminescence intensity is not obtained. A thickness of the blocking layer is preferably 20 nm or less. A thickness of each of other layers is typically preferably in a range of 5 nm to 10 μm, more preferably in a range of 10 nm to 0.2 μm.

Second Exemplary Embodiment

Figure 8:
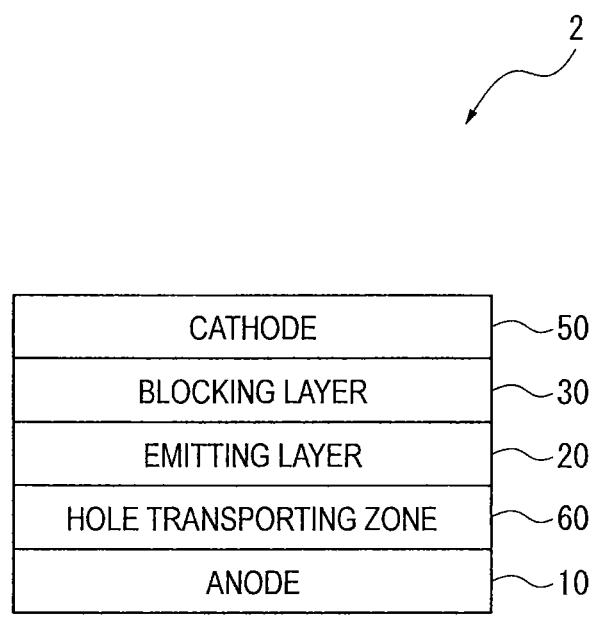
FIG. 8 is a view showing one example of an organic EL device according to a second exemplary embodiment of the invention.

FIG. 8 shows one example of an organic EL device 2 according to a second exemplary embodiment.

The organic EL device according to the second exemplary embodiment may not include an electron injecting layer. As shown in FIG. 8, the organic EL device 2 according to the second exemplary embodiment includes the anode 10, the hole transporting zone 60, the emitting layer 20, the electron transporting zone (the blocking layer 30 in the exemplary embodiment), and the cathode 50 in this sequence. These layers are adjacent to one another in the organic EL device in the exemplary embodiment.

The blocking layer 30 of the organic EL device 2 contains the aromatic heterocyclic derivative represented by the formula (1) in the same manner as in the first exemplary embodiment. Other layers forming the organic EL device 2 are also the same as those in the first exemplary embodiment.

Third Exemplary Embodiment

Figure 9:
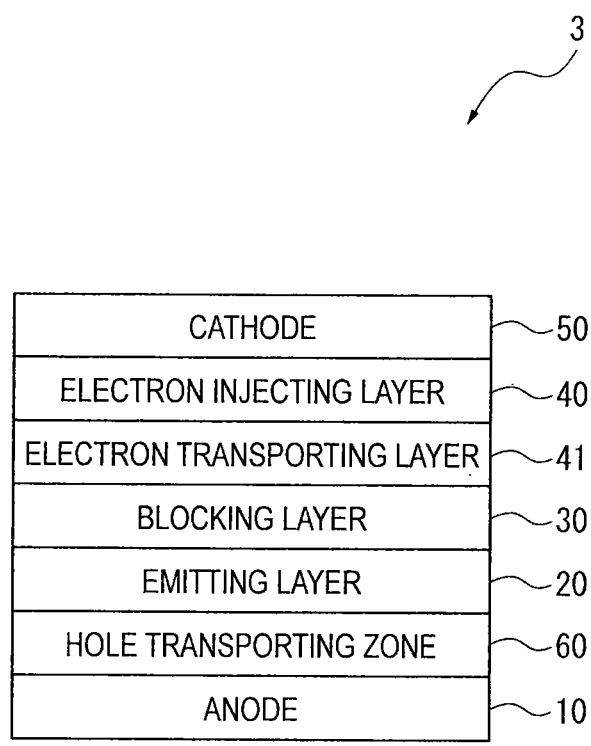
FIG. 9 is a view showing one example of an organic EL device according to a third exemplary embodiment of the invention.

FIG. 9 shows one example of an organic EL device 3 according to a third exemplary embodiment.

The organic EL device according to the third exemplary embodiment may include an electron injecting layer on a side of the electron transporting layer near the cathode. As shown in FIG. 9, the organic EL device 3 according to the third exemplary embodiment includes the anode 10, the hole transporting zone 60, the emitting layer 20, the electron transporting zone (the blocking layer 30, the electron transporting layer 41 and the electron injecting layer 40 in the exemplary embodiment), and the cathode 50 in this sequence. These layers are adjacent to one another in the exemplary embodiment.

In the organic EL device 3, at least one of the electron injecting layer 40 and the electron transporting layer 41 preferably contains the aromatic heterocyclic derivative according to the above exemplary embodiment. A material to be contained in the electron transporting layer can be the material described in relation to the above electron injecting layer and known electron transporting materials. Moreover, the electron injecting layer 40 and the electron transporting layer 41 may further include other material(s) in addition to the aromatic heterocyclic derivative according to the above exemplary embodiment.

The blocking layer 30 of the organic EL device 3 contains the aromatic heterocyclic derivative represented by the formula (1) in the same manner as in the first exemplary embodiment. Other layers forming the organic EL device 3 are also the same as those in the first exemplary embodiment.

Fourth Exemplary Embodiment

An organic EL device in the fourth exemplary embodiment may have a tandem device configuration in which at least two organic layer units including emitting layers are provided. An intermediate layer (intermediate conductive layer, charge generation layer or CGL) is interposed between the two emitting layers. An electron transporting zone can be provided in each unit. At least one emitting layer is a fluorescent emitting layer and the unit including the emitting layer satisfies the above-mentioned requirements.

Figure 10:
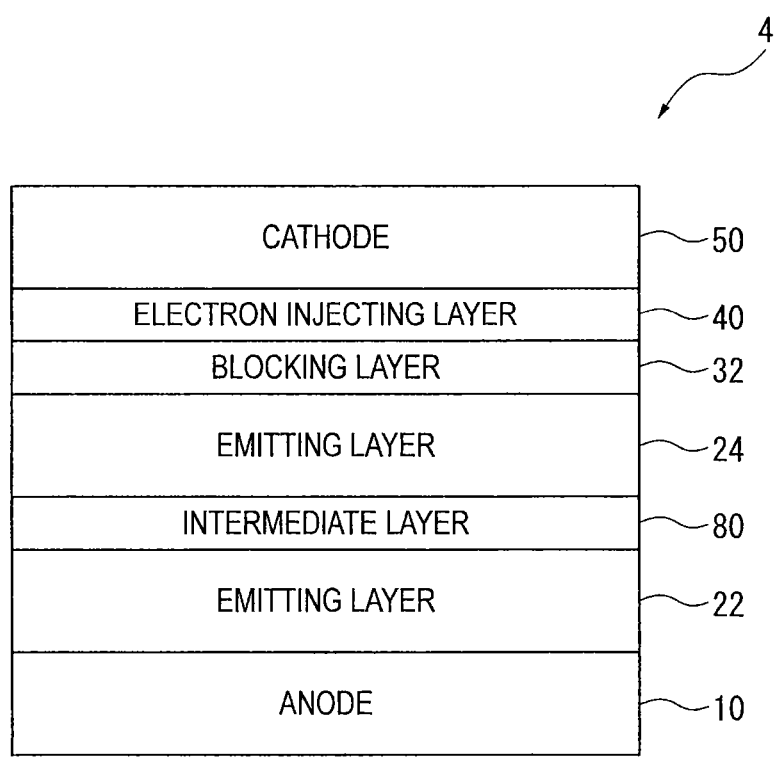
FIG. 10 is a view showing one example of an organic EL device according to a third exemplary embodiment of the invention.

FIG. 10 shows one example of the organic EL device according to the fourth exemplary embodiment. An organic EL device 4 includes the anode 10, emitting layers 22 and 24 and the cathode 50 in this sequence. An intermediate layer 80 is interposed between the emitting layers 22 and 24. A blocking layer 32 is adjacent to the emitting layer 24. The electron injecting layer 40 is interposed between the blocking layer 32 and the cathode 50. The blocking layer 32, the electron injecting layer 40 and the emitting layer 24 are respectively a blocking layer, an electron injecting layer and a fluorescent emitting layer which satisfy the requirements of the invention. The other emitting layer may be either a fluorescent emitting layer or a phosphorescent emitting layer. Another blocking layer and another electron injecting layer are provided adjacent to the emitting layer 22 in sequential order. These blocking layer and electron injecting layer and the emitting layer 22 may be respectively used as the blocking layer, the electron injecting layer, and the fluorescent emitting layer which satisfy the requirements of the invention.

Note that, in the exemplary embodiment, the blocking layer 32 and the electron injecting layer 40 correspond to the electron transporting zone.

At least one of an electron transporting zone and hole transporting zone may be interposed between the two emitting layers 22 and 24. Three or more emitting layers may be provided, and two or more intermediate layers may be provided. When three or more emitting layers are present, an intermediate layer may or may not be present between all of the emitting layers.

The intermediate layer is a layer including at least one of the intermediate conductive layer and the charge generation layer, or at least one of the intermediate conductive layer and the charge generation layer. The intermediate layer serves as a source for supplying electrons or holes to be injected in an emitting unit. In addition to charges injected from a pair of electrodes, charges supplied from the intermediate layer are injected into the emitting unit. Accordingly, by providing the intermediate layer, luminous efficiency (current efficiency) relative to injected current is improved.

Examples of the intermediate layer include a metal, metal oxide, mixture of metal oxides, composite oxide, and electron-accepting organic compound. Examples of the metal are preferably Mg, Al, and a film formed by co-evaporating Mg and Al. Examples of the metal oxide include $ZnO$, $WO_3$, $MoO_3$ and $MoO_2$. Examples of the mixture of the metal oxides include ITO, IZO (registered trade mark), and ZnO:Al. Examples of the electron-accepting organic compound include an organic compound having a CN group as a substituent. The organic compound having a CN group is preferably a triphenylene derivative, tetracyanoquinodimethane derivative and indenofluorene derivative. The triphenylene derivative is preferably hexacyanohexaazatriphenylene. The tetracyanoquinodimethane derivative is preferably tetrafluoroquinodimethane and dicyanoquinodimethane. The indenofluorene derivative is preferably a compound disclosed in WO2009/011327, WO2009/069717, or WO2010/064655. The electron accepting substance may be a single substance, or a mixture with other organic compounds.

In order to easily accept the electrons from the charge generation layer, at least one of the electron-donating dopant represented by an alkali metal and the organic metal complex is added in the vicinity of the interface of the charge generation layer in the electron transporting layer. Examples of the electron-donating dopant and the organic metal complex are those described above in the first exemplary embodiment.

Specific examples of the compounds usable for the electron-donating dopant and the organic metal complex are compounds disclosed in International Patent Application No. PCT/JP2010/003434 (International Publication No. WO2010/134352).

Fifth Exemplary Embodiment

In the fifth exemplary embodiment, an anode, a plurality of emitting layers, an electron transporting zone that includes a blocking layer adjacent to one of the emitting layers and an electron injecting layer adjacent to the blocking layer, and a cathode are provided in sequential order. A charge blocking layer is provided between two emitting layers of the plurality of the emitting layers. The emitting layers in contact with the charge blocking layer are fluorescent emitting layers. The fluorescent emitting layer, and the blocking layer and the electron injecting layer in the electron transporting zone satisfy the above requirements.

Figure 11:
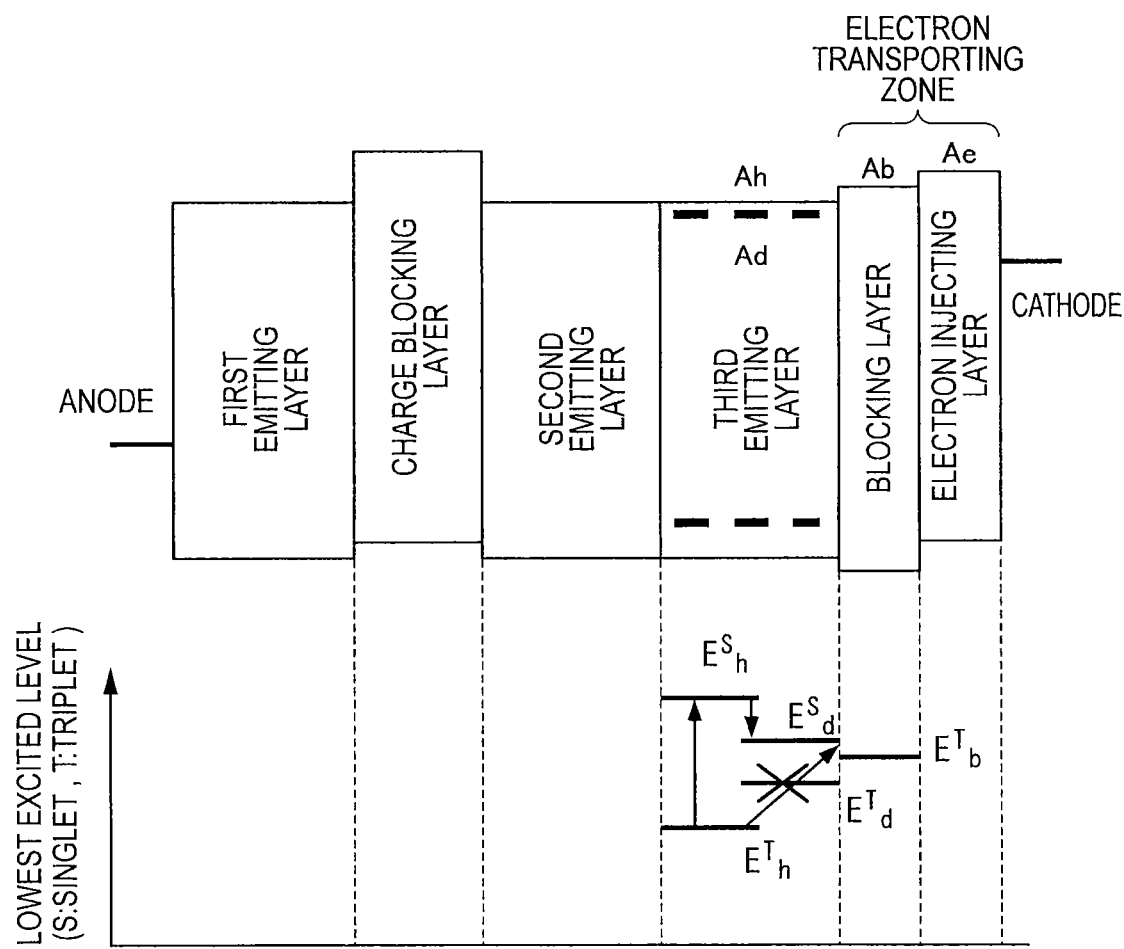
FIG. 11 is a view showing one example of an organic EL device according to a fifth exemplary embodiment of the invention.

As a configuration of a suitable organic EL device according to the fifth exemplary embodiment, there can be given a configuration as disclosed in Japanese Patent No. 4134280, US patent publication US2007/0273270A1 and International Publication WO2008/023623A1. Specifically, the configuration in which an anode, a first emitting layer, a charge blocking layer, a second emitting layer and a cathode are sequentially stacked, and an electron-transporting zone having a blocking layer and an electron injecting layer for preventing diffusion of triplet excitons is further provided between the second emitting layer and the cathode. Here, the charge blocking layer means a layer to control the carrier injection to an emitting layer and the carrier balance between electrons and holes injected in the emitting layer by providing an energy barrier of a HOMO level or a LUMO level between adjacent emitting layers Specific examples of such a configuration are given below.
anode/first emitting layer/charge blocking layer/second emitting layer/electron transporting zone/cathode
anode/first emitting layer/charge blocking layer/second emitting layer/third emitting layer/electron transporting zone/cathode It is preferred that a hole transporting zone is provided between the anode and the first emitting layer in the same manner as in other embodiments FIG. 11 shows one example of an organic EL device according to the fifth exemplary embodiment. An upper view in FIG. 11 shows a device configuration, and the HOMO and LUMO energy levels of each layer. A lower view in FIG. 11 shows a relationship between energy gaps of the third emitting layer and the blocking layer. The upper view in FIG. 11 shows the relationship in the case of $A_h > A_b > A_e$.

The organic EL device includes the anode, first emitting layer, second emitting layer, third emitting layer, electron transporting zone, and cathode in sequential order. A charge blocking layer is interposed between the first and second emitting layers. The electron transporting zone is formed of the blocking layer. This blocking layer and third emitting layer are the blocking layer and the fluorescent emitting layer that satisfy the requirements of the invention. The first and second emitting layers may be either a fluorescent emitting layer or a phosphorescent emitting layer.

The device of this embodiment is suitable as a white emitting device. The device can be a white emitting device by adjusting the emission colors of the first emitting layer, second emitting layer and third emitting layer. Moreover, the device can be a white emitting device by arranging only the first emitting layer and the second emitting layer and adjusting the emission colors of these two emitting layers. In this case, the second emitting layer is a fluorescent emitting layer satisfying the requirements of the invention.

In particular, by using a hole transporting material as the host in the first emitting layer, by adding a fluorescent dopant material of which the main peak wavelength is larger than 550 nm, by using an electron transporting material as the host material in the second emitting layer (and the third emitting layer), and by adding a fluorescent dopant material of which the main peak wavelength is equal to or smaller than 550 nm, it is possible to achieve a white emitting device that exhibits a higher luminous efficiency as compared with conventional white emitting devices, even though all of them are entirely formed of fluorescent materials.

Reference is made particularly to a hole transporting layer which is adjacent to the emitting layer. In order to allow the TTF phenomenon to occur effectively, it is preferred that the triplet energy of the hole transporting material is larger than the triplet energy of the host material, when the triplet energy of the hole transporting material and that of the host material are compared.

Sixth Exemplary Embodiment

In a sixth exemplary embodiment, a blue pixel, a green pixel and a red pixel are arranged in parallel on a substrate. Of these three color pixels, at least one of the blue pixel and the green pixel has the configuration of the first exemplary embodiment or second exemplary embodiment.

Figure 12:
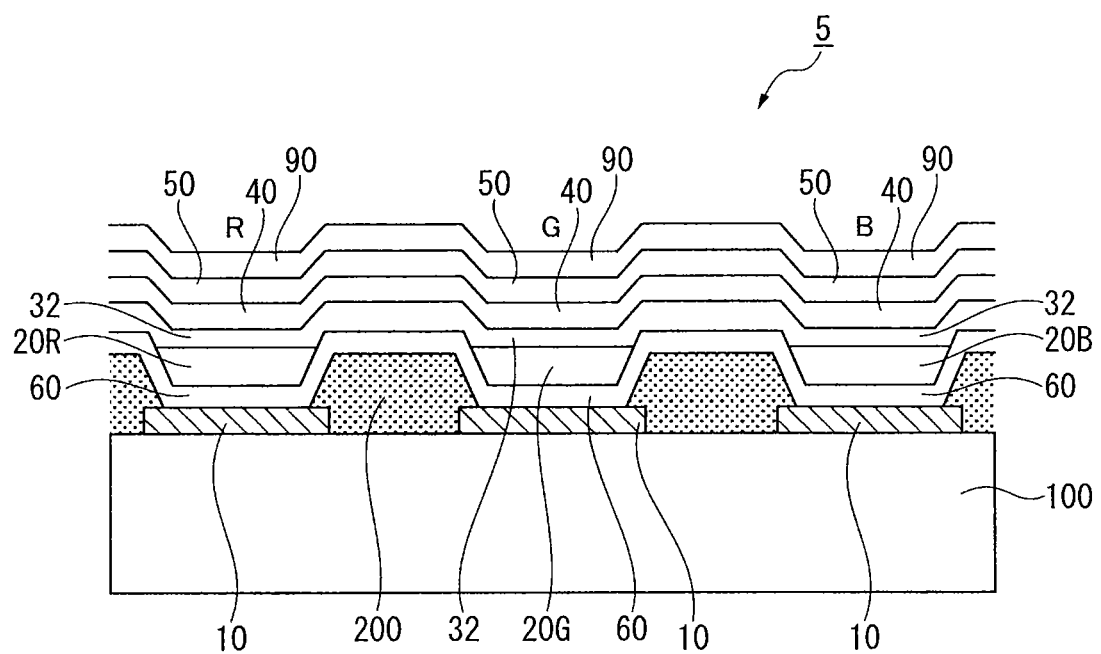
FIG. 12 is a view showing one example of an organic EL device according to a sixth exemplary embodiment of the invention.

FIG. 12 shows one example of an organic EL device according to the fifth exemplary embodiment.

In a top-emission type organic EL device 5 shown in FIG. 12, a blue pixel B, a green pixel G and a red pixel R are arranged in parallel on a common substrate 100.

The blue pixel B includes the anode 10, the hole transporting zone 60, a blue emitting layer 20B, the blocking layer 32, the electron injecting layer 40, the cathode 50, and a protection layer 90 on the substrate 100 in sequential order.

The green pixel G includes the anode 10, the hole transporting zone 60, a green emitting layer 20G, the blocking layer 32, the electron injecting layer 40, the cathode 50, and the protection layer 90 on the substrate 100 in sequential order.

The red pixel R includes the anode 10, the hole transporting zone 60, a red emitting layer 20R, the blocking layer 32, the electron injecting layer 40, the cathode 50, and the protection layer 90 on the substrate 100 in sequential order.

An insulating film 200 is formed between the anodes of adjacent pixels so as to keep the insulation between the pixels. The electron transporting zone is formed of the blocking layer 32 and the electron injecting layer 40.

In the organic EL device 5, the blocking layer is provided as a common blocking layer for the blue pixel B, the red pixel R and the green pixel G.

The advantageous effects brought by the blocking layer are outstanding comparing to the luminous efficiency conventionally attained in a blue fluorescent device. In a green fluorescent device and a red fluorescent device, similar advantageous effects, such as confining triplet energies in the emitting layer, can be attained, and improvement in luminous efficiency can also be expected.

On the other hand, in a phosphorescent emitting layer, it is possible to attain the advantageous effects of confining triplet energies in the emitting layer, and as a result, diffusion of triplet energies is prevented, thereby contributing to improvement in luminous efficiency of a phosphorescent dopant material.

The hole transporting zone is formed of, for instance, a hole transporting layer, or a combination of a hole transporting layer and a hole injecting layer. A common hole transporting zone may be provided or different hole transporting zones may be provided for the blue pixel B, the red pixel R and the green pixel G. Typically, the hole transporting zones respectively have a configuration suited to the color of emitted light.

The configuration of the organic layer formed of the emitting layers 20B, G and R and the blocking layer is not limited to that shown in the figure and is changeable appropriately.

The host material and the dopant material usable in the exemplary embodiment are the same as described above. In particular, emitting layers for each color will be described below.

A green emitting layer is preferably formed of the following host material and dopant material.

The host material is preferably a fused aromatic ring derivative. As the fused aromatic ring derivative, an anthracene derivative, pyrene derivative and the like are more preferable in view of luminous efficiency and luminous lifetime.

The host material is exemplified by a heterocycle-containing compound. Examples of the heterocycle-containing compound are a carbazole derivative, dibenzofuran derivative, ladder-type furan compound and pyrimidine derivative.

The dopant material is not particularly limited so long as it functions as a dopant, but an aromatic amine derivative is preferable in view of luminous efficiency and the like. As the aromatic amine derivative, a fused aromatic ring derivative having a substituted or unsubstituted arylamino group is preferable. Examples of such a compound are pyrene, anthracene and chrysene having an arylamino group.

A styrylamine compound is also preferable as the dopant material. Examples of the styrylamine compound are styrylamine, styryldiamine, styryltriamine and styryltetraamine. Here, the styrylamine means a compound in which a substituted or unsubstituted arylamine is substituted with at least one arylvinyl group. The arylvinyl group may be substituted with a substituent such as an aryl group, silyl group, alkyl group, cycloalkyl group, or arylamino group, which may have a further substituent.

Furthermore, as the dopant material, a boron complex and a fluoranthene compound are preferable. A metal complex is also preferable as the dopant material. The metal complex is exemplified by an iridium complex or platinum complex.

A red emitting layer is preferably formed of the following host material and dopant material. The host material is preferably a fused aromatic ring derivative. As the fused aromatic ring derivative, a naphthacene derivative, pentacene derivative and the like are more preferable in view of luminous efficiency and luminous lifetime.

The host material is exemplified by a fused polycyclic aromatic compound. Examples of the fused polycyclic aromatic compound are a naphthalene compound, phenanthrene compound and fluoranthene compound.

The dopant material is preferably an aromatic amine derivative. As the aromatic amine derivative, a fused aromatic ring derivative having a substituted or unsubstituted arylamino group is preferable. Such a compound is exemplified by periflanthene having an arylamino group.

A metal complex is also preferable as the dopant material. The metal complex is exemplified by an iridium complex or platinum complex.

The organic EL device of the sixth exemplary embodiment is prepared in the following manner.

On a substrate, an APC (Ag—Pd—Cu) layer as a silver alloy layer (reflective layer) and a transparent conductive layer such as a zinc oxide (IZO) film and a tin oxide film are sequentially formed. Next, by a typical lithographic technology, this conductive material layer is patterned by etching using a mask with a resist pattern, thereby forming an anode. Then, by the spin coating method, an insulating film formed of a photosensitive resin such as a polyimide is formed by coating on the anode. Thereafter, the resulting film is exposed, developed and cured to allow the anode to be exposed, whereby the anodes for a blue emitting region, a green emitting region and a red emitting region are patterned.

There are three types of electrodes, i.e. an electrode for the red pixel, an electrode for the green pixel and an electrode for a blue pixel. They respectively correspond to the blue emitting region, the green emitting region and the red emitting region, and respectively correspond to the anode. After conducting cleaning for 5 minutes in isopropyl alcohol, a UV ozone cleaning is conducted for 30 minutes. When the hole injecting layer and the hole transporting layer are formed thereafter, the hole injecting layer is stacked over the entire surface of the substrate, and the hole transporting layer is stacked thereon. Emitting layers are formed to be correspondingly arranged to the positions of the anode for the red pixel, the anode for the green pixel and the anode for the blue pixel When vacuum evaporation method is used, the blue emitting layer, the green emitting layer and the red emitting layer are finely patterned using a shadow mask.

Next, a blocking layer is stacked over the entire surface. Subsequently, an electron injecting layer is stacked over the entire surface. Thereafter, Mg and Ag are formed into a film by evaporation, thereby forming a semi-transparent cathode formed of an Mg—Ag alloy.

As for the other members used in the exemplary embodiment, such as the substrate, the anode, the cathode, the hole injecting layer and the hole transporting layer, known members disclosed in PCT/JP2009/053247, PCT/JP2008/073180, U.S. patent application Ser. No. 12/376,236, U.S. patent application Ser. No. 11/766,281, U.S. patent application Ser. No. 12/280,364 or the like can be appropriately selected and used.

It is preferred that the hole transporting layer include an aromatic amine derivative represented by any one of the following formulae (a-1) to (a-5).

[Formula 142]

(a-1)

(a-2)

(a-3)

(a-4)

(a-5)

In the formulae (a-1) to (a-5), $Ar_1$ to $Ar_{24}$ are independently a substituted or unsubstituted aryl group having 6 to 50 ring carbon atoms, or a substituted or unsubstituted heteroaryl group having 5 to 50 ring atoms.

$L_1$ to $L_9$ are independently a substituted or unsubstituted arylene group having 6 to 50 ring carbon atoms or a substituted or unsubstituted heteroarylene group having 5 to 50 ring atoms.

Examples of a substituent which $Ar_1$ to $Ar_{24}$ and $L_1$ to $L_9$ may have include a linear or branched alkyl group having 1 to 15 carbon atoms, a cycloalkyl group having 3 to 15 ring carbon atoms, a trialkylsilyl group having a linear or branched alkyl group having 1 to 15 carbon atoms, a triarylsilyl group having an aryl group having 6 to 14 ring carbon atoms, an alkylarylsilyl group having a linear or branched alkyl group having 1 to 15 carbon atoms and an aryl group having 6 to 14 ring carbon atoms, an aryl group having 6 to 50 ring carbon atoms, a heteroaryl group having 5 to 50 ring atoms, a halogen atom, and a cyano group. Adjacent substituents may bond to each other to form a saturated or unsaturated divalent group forming a ring.

At least one of the above $Ar_1$ to $Ar_{24}$ is preferably a substituent represented by the following formula (a-6) or (a-7).

[Formula 143]

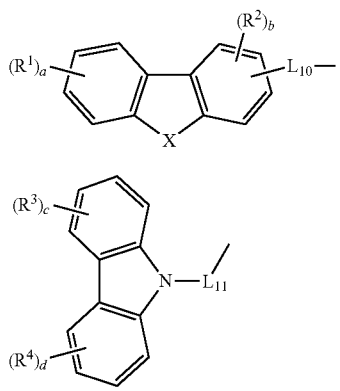

(a-6)

(a-7)

In the formula (a-6), X is an oxygen atom, sulfur atom or N—Ra. Ra is a linear or branched alkyl group having 1 to 15 carbon atoms, a cycloalkyl group having 3 to 15 ring carbon atoms, an aryl group having 6 to 50 ring carbon atoms or a heteroaryl group having 5 to 50 ring atoms.

$L_{10}$ is a single bond, a substituted or unsubstituted arylene group having 6 to 50 ring carbon atoms, or a substituted or unsubstituted heteroarylene group having 5 to 50 ring atoms.

In the formula (a-7), $L_{11}$ is a substituted or unsubstituted arylene group having 6 to 50 ring carbon atoms, or a substituted or unsubstituted heteroarylene group having 5 to 50 ring atoms.

In the formulae (a-6) and (a-7), $R^1$ to $R^4$ are independently a linear or branched alkyl group having 1 to 15 carbon atoms, a cycloalkyl group having 3 to 15 ring carbon atoms, a trialkylsilyl group having a linear or branched alkyl group having 1 to 15 carbon atoms, a triarylsilyl group having an aryl group having 6 to 14 ring carbon atoms, an alkylarylsilyl group having a linear or branched alkyl group having 1 to 15 carbon atoms and an aryl group having 6 to 14 ring carbon atoms, an aryl group having 6 to 14 ring carbon atoms, a heteroaryl group having 5 to 50 ring atoms, a halogen atom, or a cyano group. Adjacent groups of $R^1$ s to $R^4$ s may bond to each other to form a ring.

a, c and d are each an integer of 0 to 4.

b is an integer of 0 to 3.

The compound represented by the formula (a-1) is preferably a compound represented by the following formula (a-8).

[Formula 144]

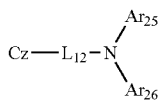

(a-8)

In the formula (a-8), Cz is a substituted or unsubstituted carbazolyl group.

$L_{12}$ is a substituted or unsubstituted arylene group having 6 to 50 ring carbon atoms, or a substituted or unsubstituted heteroarylene group having 5 to 50 ring atoms.

$Ar_{25}$ and $Ar_{26}$ are independently a substituted or unsubstituted aryl group having 6 to 50 ring carbon atoms or a substituted or unsubstituted heteroaryl group having 5 to 50 ring atoms.

The compound represented by the formula (a-8) is preferably a compound represented by the following formula (a-9).

[Formula 145]

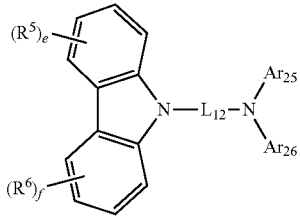

(a-9)

In the formula (a-9), $R^5$ and $R^6$ are independently a linear or branched alkyl group having 1 to 15 carbon atoms, a cycloalkyl group having 3 to 15 ring carbon atoms, a trialkylsilyl group having a linear or branched alkyl group having 1 to 15 carbon atoms, a triarylsilyl group having an aryl group having 6 to 14 ring carbon atoms, an alkylarylsilyl group having a linear or branched alkyl group having 1 to 15 carbon atoms and an aryl group having 6 to 14 ring carbon atoms, an aryl group having 6 to 14 ring carbon atoms, a heteroaryl group having 5 to 50 ring atoms, a halogen atom, or a cyano group. Adjacent groups of $R^5$ s to $R^6$ s may bond to each other to form a ring. e and f are each an integer of 0 to 4.

$L_{12}$, $Ar_{25}$ and $Ar_{26}$ are the same as $L_{12}$, $Ar_{25}$ and $Ar_{26}$ in the formula (a-8).

The compound represented by the formula (a-9) is preferably a compound represented by the following formula (a-10).

[Formula 146]

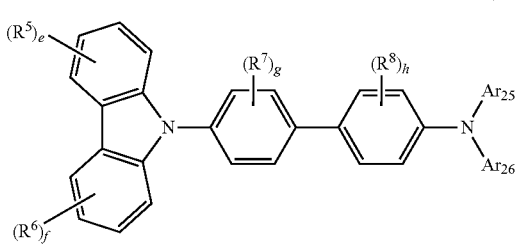

(a-10)

In the formula (a-10), $R^7$ and $R^8$ are independently a linear or branched alkyl group having 1 to 15 carbon atoms, a cycloalkyl group having 3 to 15 ring carbon atoms, a trialkylsilyl group having a linear or branched alkyl group having 1 to 15 carbon atoms, a triarylsilyl group having an aryl group having 6 to 14 ring carbon atoms, an alkylarylsilyl group having a linear or branched alkyl group having 1 to 15 carbon atoms and an aryl group having 6 to 14 ring carbon atoms, an aryl group having 6 to 14 ring carbon atoms, a heteroaryl group having 5 to 50 ring atoms, a halogen atom, or a cyano group. Adjacent groups of $R^5$ s to $R^6$ s may bond to each other to form a ring.

g and h are each an integer of 0 to 4.

$R^5$, $R^6$, e, f, $Ar_{25}$ and $Ar_{26}$ are the same as $R^5$, $R^6$, e, f, $Ar_{25}$ and $Ar_{26}$ in the formula (a-9).

Seventh Exemplary Embodiment

An organic EL device according to the seventh exemplary embodiment may include the electron transporting layer in place of the blocking layer 30 as the electron transporting zone in the organic EL device 2 according to the second exemplary embodiment in FIG. 8. Specifically, the organic EL device according to the seventh exemplary embodiment (not shown) include the anode 10, the hole transporting zone 60, the emitting layer 20, the electron transporting layer and the cathode 50 in this sequence. The electron transporting layer includes the aromatic heterocyclic derivative of the invention and may further include other material(s). In the seventh exemplary embodiment, the emitting layer 20 preferably contains a dopant material exhibiting phosphorescence as the dopant material.

Note that other layers forming the organic EL device in the seventh exemplary embodiment are the same as those in the first and second exemplary embodiments.

EXAMPLES

Examples of the invention will be described below. However, the invention is not limited by these Examples.

Synthesis of Compound(s)

Synthesis Example 1

Synthesis of Compound 7

A synthesis scheme of a compound 7 is shown below.

[Formula 147]

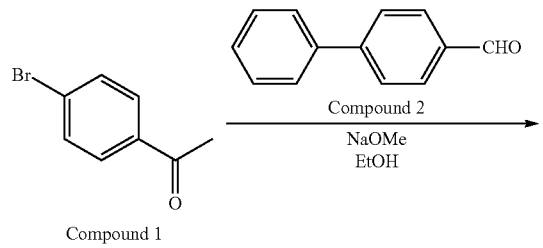

Compound 1

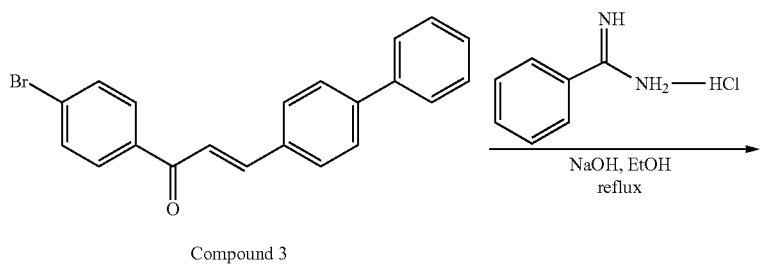

Compound 3

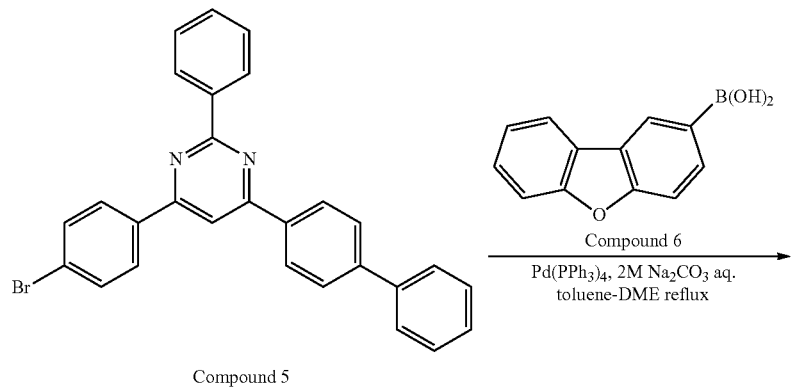

Compound 5

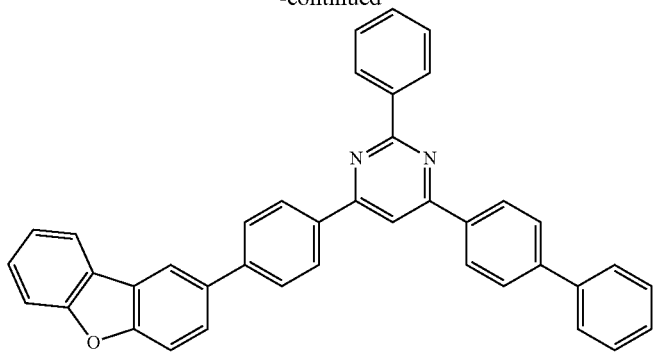

Compound 7

(1-1) Synthesis of Compound 3

4'-bromoacetophenone (a compound 1) (22 g, 120 mmol), 4-phenylbenzaldehyde (a compound 2) (25 g, 126 mmol), sodium methoxide (8.4 g, 156 mmol) and ethanol (200 mL) were mixed and stirred for 12 hours at the room temperature. A precipitated solid was separated by filtration and suspended in and washed with ethanol. Subsequently, the obtained solid was dried under reduced pressure, so that a compound 3 (42 g, a yield of 96%) in a form of a white solid was obtained.

(1-2) Synthesis of Compound 5

Ethanol (450 mL) was added with the compound 3 (40 g, 111 mmol), benzamidine hydrochloride (a compound 4) (26 g, 166 mmol) and sodium hydroxide (12 g, 299 mmol), and was heated to reflux for nine hours. After the reaction, a precipitated solid was separated by filtration and refined by silica-gel column chromatography (eluent: toluene). The reactant was recrystallized using toluene, so that a compound 5 in a form of a white solid (24 g, a yield of 47%) was obtained.

(1-3) Synthesis of Compound 7

The compound 5 (6.0 g, 13 mmol) and a compound 6 (3.3 g, 16 mmol) were dissolved in toluene (200 mL) and 1,2-dimethoxyethane (200 mL), to which tetrakis(triphenylphosphine)palladium (0) (0.75 g, 0.65 mmol) and an aqueous solution of 2M sodium carbonate (26 mL) were added. The obtained solution was heated to reflux for 15 hours. After the reaction, the reactant solution was cooled to the room temperature and extracted with toluene. The obtained organic layer was washed with water and saturated saline in sequential order and dried with sodium sulfate. The solvent was distilled away under reduced pressure. The residue was added with toluene and heated to reflux to be dissolved. The reactant solution was cooled and precipitated in a crystal form. The crystal was separated by filtration and washed with toluene. Subsequently, the obtained solid was dried under reduced pressure, so that a compound 7 (5.5 g, a yield of 77%) in a form of a white solid was obtained. As a result of FD-MS (Field Desorption Mass Spectrometry) analysis, the reactant was identified as the compound 7.

Synthesis Example 2

Synthesis of Compound 9

A synthesis scheme of a compound 9 is shown below.

[Formula 148]

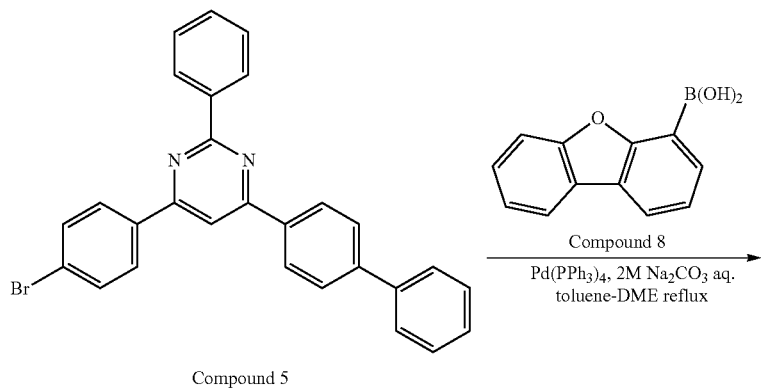

Compound 5

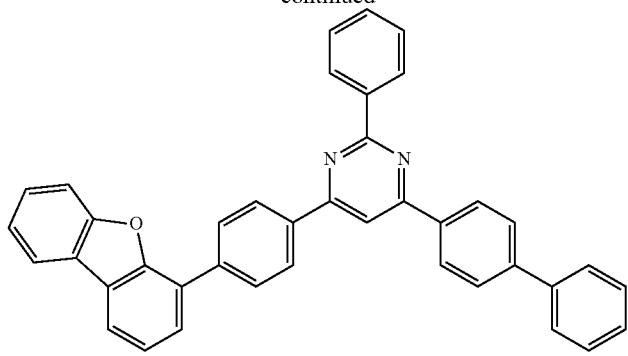

Compound 9

(2-1) Synthesis of Compound 9

Synthesis was made by the same method as in (1-3) synthesis of the compound 7, except for using a compound 8 (2.7 g, 13 mmol) in place of the compound 6, so that a compound 9 (5.5 g, a yield of 92%) in a form of a white solid was obtained. As a result of FD-MS (Field Desorption Mass Spectrometry) analysis, the reactant was identified as the compound 9.

Synthesis Example 3

Synthesis of Compound 13

A synthesis scheme of a compound 13 is shown below.

[Formula 149]

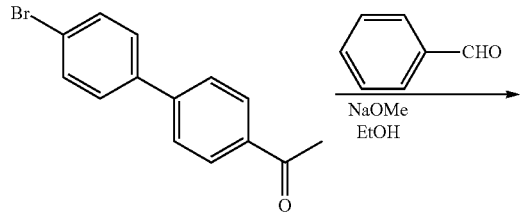

Compound 10

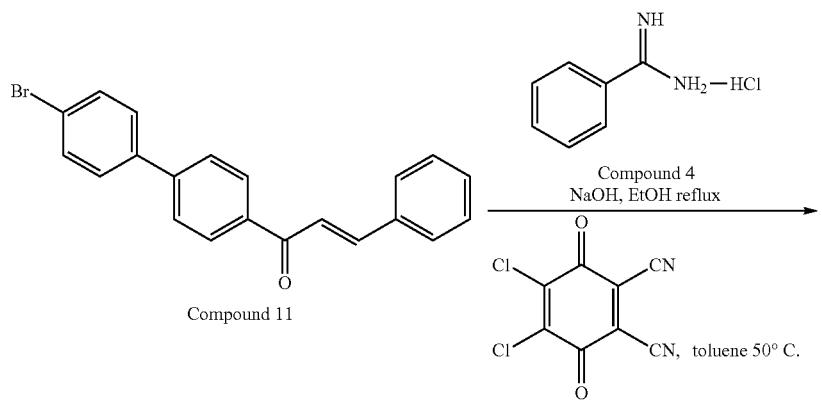

Compound 11

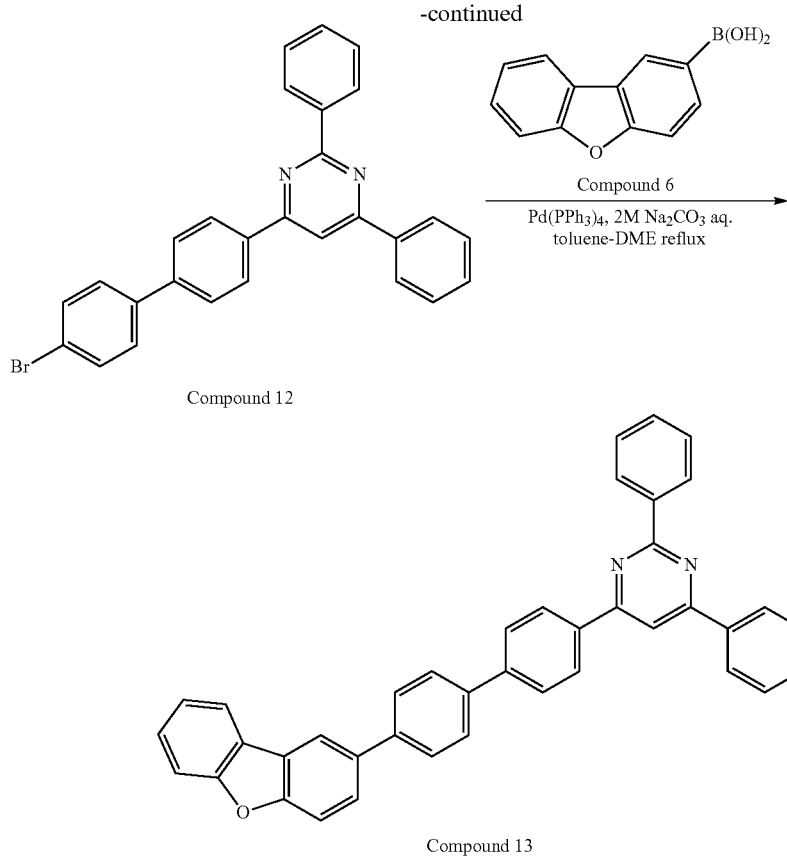

Compound 12

Compound 13

(3-1) Synthesis of Compound 12

4'-(p-bromophenyl)acetophenone (a compound 10) (30 g, 110 mmol) and benzaldehyde (12 g, 110 mmol) were dissolved in ethanol (300 mL), into which sodium methoxide (about-5M methanol solution) (80 mL) was dropped. The obtained solution was stirred for three hours at the room temperature to synthesize a compound 11. Next, benzamidine hydrochloride (the compound 4) (17 g, 110 mmol) and sodium hydroxide (5.3 g, 132 mmol) were added to the above solution and was heated to reflux for 18 hours. After the reaction, the reactant solution was cooled to the room temperature and a precipitated solid was separated by filtration. Then, the obtained solid was washed with methanol. A crude product, 2,3-dichloro-5,6-dicyano-p-benzoquinone (19 g, 84 mmol) and toluene (400 mL) were mixed and stirred for one hour at 50 degrees C. After the reaction, methanol was added to the mixture and a precipitated solid was separated by filtration and refined by silica-gel column chromatography (eluent: toluene), so that a compound 12 (26 g, a yield of 51%) in a form of a white solid was obtained.

(3-2) Synthesis of Compound 13

Synthesis was made by the same method as in (1-3) synthesis of the compound 7, except for using the compound 12 (6.0 g, 13 mmol) in place of the compound 5, so that a compound 13 (4.9 g, a yield of 69%) in a form of a white solid was obtained. As a result of FD-MS (Field Desorption Mass Spectrometry) analysis, the reactant was identified as the compound 13.

Synthesis Example 4
Synthesis of Compound 14

A synthesis scheme of a compound 14 is shown below.

[Formula 150]

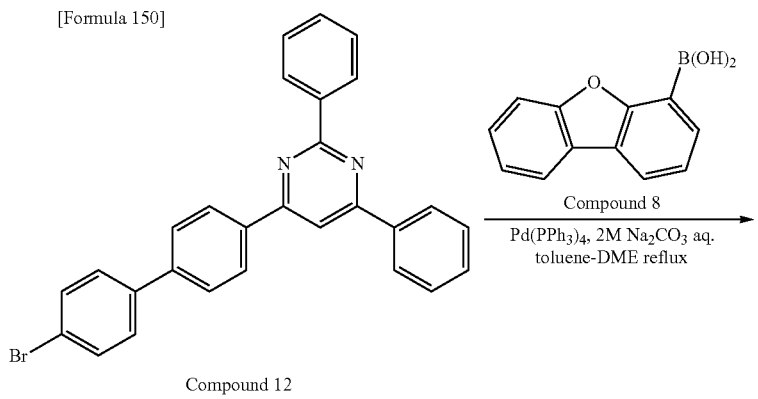

Compound 12

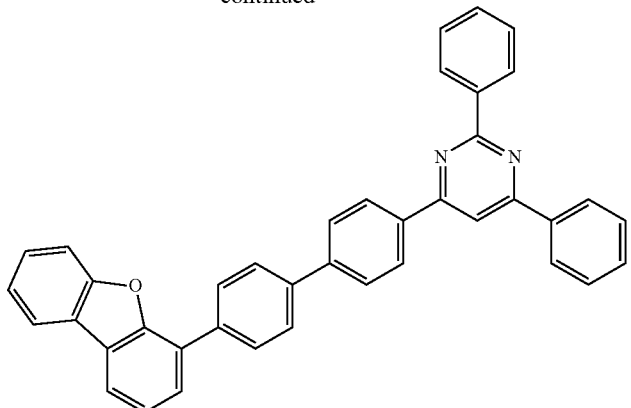

Compound 14

(4-1) Synthesis of Compound 14

Synthesis was made by the same method as in (1-3) synthesis of the compound 7, except for using the compound 12 (5.0 g, 11 mmol) in place of the compound 5 and the compound 8 (2.7 g, 13 mmol) in place of the compound 6, so that a compound 14 (5.5 g, a yield of 93%) in a form of a white solid was obtained. As a result of FD-MS (Field Desorption Mass Spectrometry) analysis, the reactant was identified as the compound 14.

Synthesis Example 5

Synthesis of Compound 16

A synthesis scheme of a compound 16 is shown below.

[Formula 151]

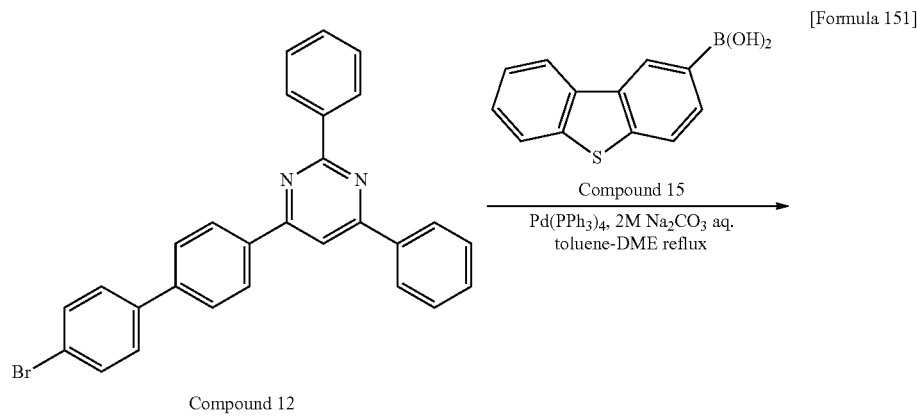

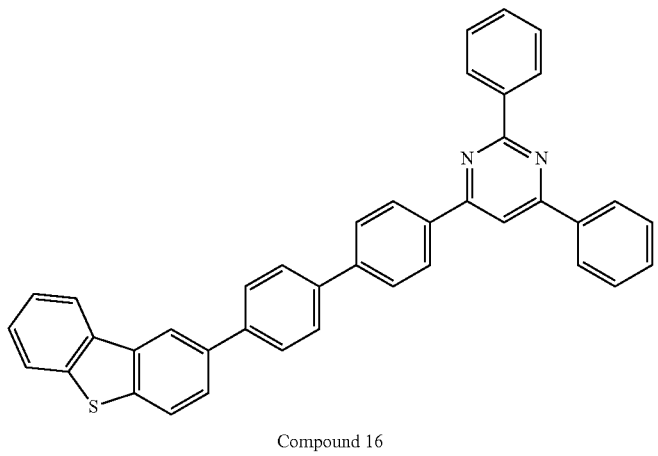

Compound 16

(5-1) Synthesis of Compound 16

Synthesis was made by the same method as in (1-3) synthesis of the compound 7, except for using the compound 12 (5.0 g, 11 mmol) in place of the compound 5 and the compound 15 (3.0 g, 13 mmol) in place of the compound 6, so that a compound 16 (4.5 g, a yield of 74%) in a form of a white solid was obtained. As a result of FD-MS (Field Desorption Mass Spectrometry) analysis, the reactant was identified as the compound 16.

Synthesis Example 6

Synthesis of Compound 22

A synthesis scheme of a compound 22 is shown below.

[Formula 152]

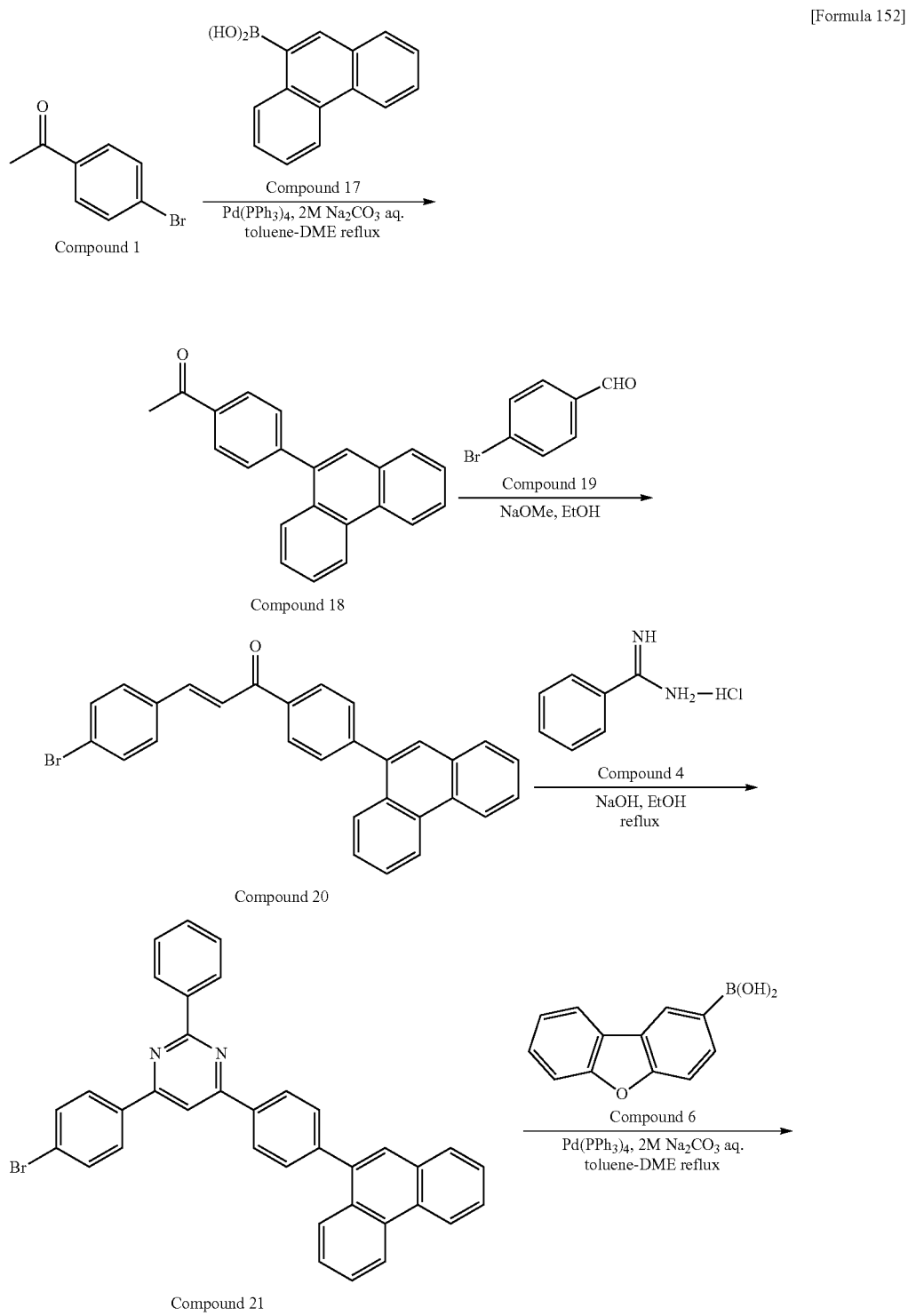

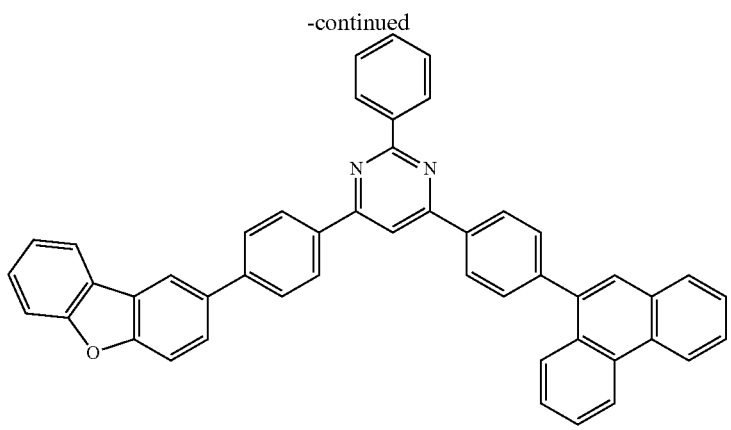

Compound 22

(6-1) Synthesis of Compound 18

Synthesis was made by the same method as in (1-3) synthesis of the compound 7, except for using the compound 1 (20 g, 100 mmol) in place of the compound 5 and a compound 17 (22 g, 100 mmol) in place of the compound 6, so that a compound 18 (25 g, a yield of 85%) in a form of a white solid was obtained.

(6-2) Synthesis of Compound 20

Synthesis was made by the same method as in (1-1) synthesis of the compound 7, except for using 4-bromobenzaldehyde (a compound 19) (17 g, 89 mmol) in place of the compound 2 and the compound 18 (25 g, 85 mmol) in place of the compound 1, so that a compound 20 (38 g, a yield of 97%) in a form of a white solid was obtained.

(6-3) Synthesis of Compound 21

Synthesis was made by the same method as in (1-2) synthesis of the compound 7, except for using the compound 20 (38 g, 82 mmol) in place of the compound 3, so that a compound 21 (16 g, a yield of 34%) in a form of a white solid was obtained.

(6-4) Synthesis of Compound 22

Synthesis was made by the same method as in (1-3) synthesis of the compound 7, except for using the compound 21 (5.0 g, 8.9 mmol) in place of the compound 5, so that a compound 22 (3.9 g, a yield of 68%) in a form of a white solid was obtained. As a result of FD-MS (Field Desorption Mass Spectrometry) analysis, the reactant was identified as the compound 22.

Synthesis Example 7

Synthesis of Compound 24

A synthesis scheme of a compound 22 is shown below.

[Formula 153]

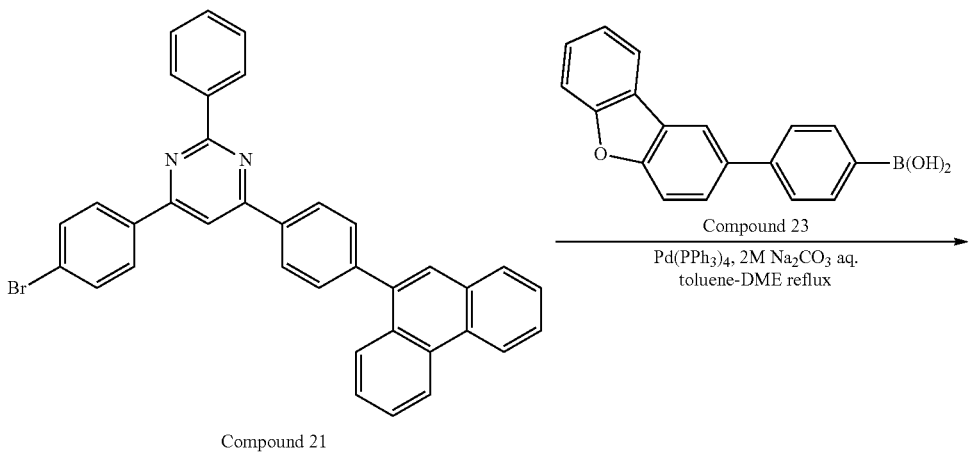

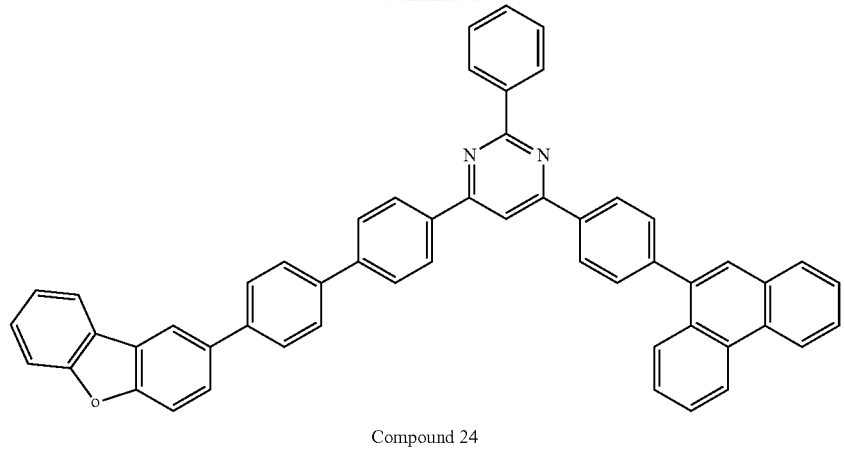

Compound 24

(7-1) Synthesis of Compound 24

Synthesis was made by the same method as in (1-3) synthesis of the compound 7, except for using the compound 21 (5.0 g, 8.9 mmol) in place of the compound 5 and a compound 23 (2.8 g, 9.8 mmol) in place of the compound 6, so that a compound 24 (25 g, a yield of 78%) in a form of a white solid was obtained. As a result of FD-MS (Field Desorption Mass Spectrometry) analysis, the reactant was identified as the compound 24.

Synthesis Example 8

Synthesis of Compound 28

A synthesis scheme of a compound 28 is shown below.

[Formula 154]

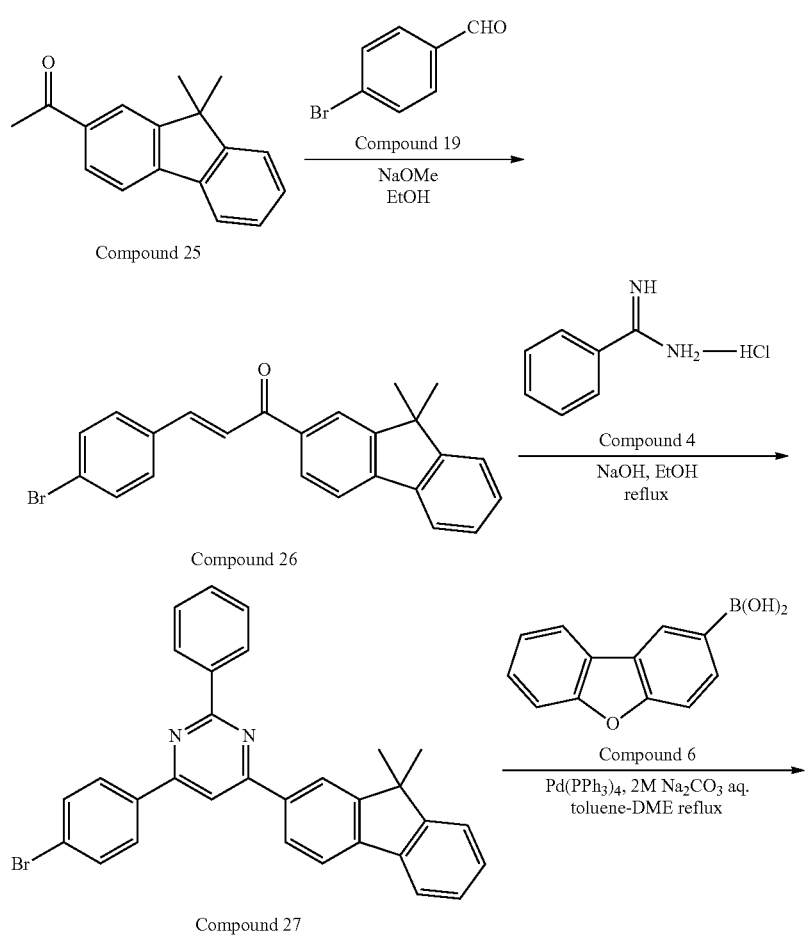

-continued

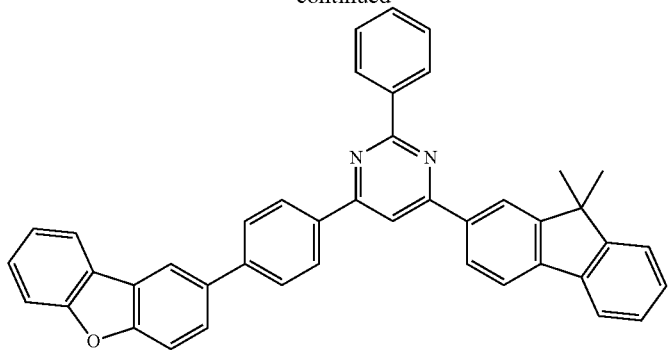

Compound 28

(8-1) Synthesis of Compound 26

Synthesis was made by the same method as in (1-1) synthesis of the compound 7, except for using the compound 19 (20 g, 109 mmol) in place of the compound 2 and a compound 25 (25 g, 106 mmol) in place of the compound 1, so that a compound 26 (27 g, a yield of 64%) in a form of a white solid was obtained.

(8-2) Synthesis of Compound 27

Synthesis was made by the same method as in (1-2) synthesis of the compound 7, except for using the compound 26 (27 g, 68 mmol) in place of the compound 3, so that a compound 27 (6.7 g, a yield of 20%) in a form of a white solid was obtained.

(8-3) Synthesis of Compound 28

Synthesis was made by the same method as in (1-3) synthesis of the compound 7, except for using the compound 27 (3.4 g, 6.8 mmol) in place of the compound 5, so that a compound 28 (3.3 g, a yield of 82%) in a form of a white solid was obtained. As a result of FD-MS (Field Desorption Mass Spectrometry) analysis, the reactant was identified as the compound 28.

Synthesis Example 9

Synthesis of Compound 31

A synthesis scheme of a compound 31 is shown below.

[Formula 155]

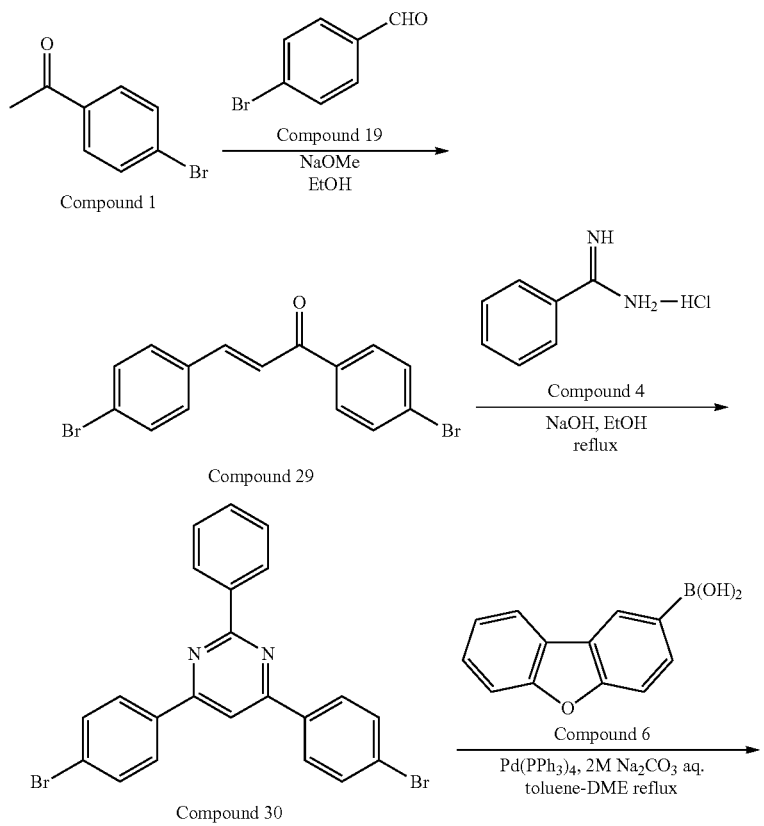

-continued

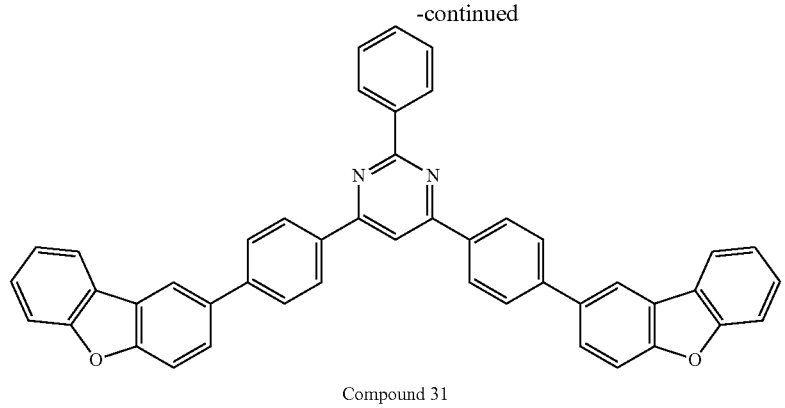

Compound 31

(9-1) Synthesis of Compound 29

Synthesis was made by the same method as in (1-1) synthesis of the compound 7, except for using the compound 19 (23 g, 125 mmol) in place of the compound 2, so that a compound 29 (41 g, a yield of 95%) in a form of a white solid was obtained.

(9-2) Synthesis of Compound 30

Synthesis was made by the same method as in (1-2) synthesis of the compound 7, except for using the compound 29 (20 g, 55 mmol) in place of the compound 3, so that a compound 30 (15 g, a yield of 61%) in a form of a white solid was obtained.

(9-3) Synthesis of Compound 31

Synthesis was made by the same method as in (1-3) synthesis of the compound 7, except for using a compound 30 (6.9 g, 15 mmol) in place of the compound 5 and using 2.1 mol equivalent weight of the compound 6 relative to the compound 30, so that a compound 31 (5.3 g, a yield of 56%) in a form of a white solid was obtained. As a result of FD-MS (Field Desorption Mass Spectrometry) analysis, the reactant was identified as the compound 31.

Synthesis Example 10

Synthesis of Compound 34

A synthesis scheme of a compound 34 is shown below.

[Formula 156]

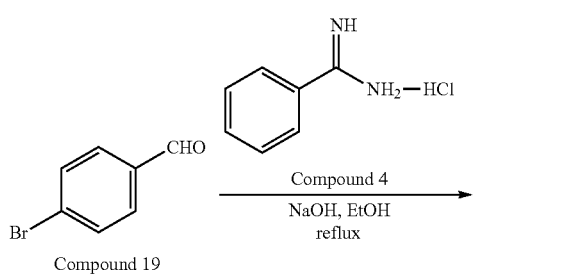

-continued

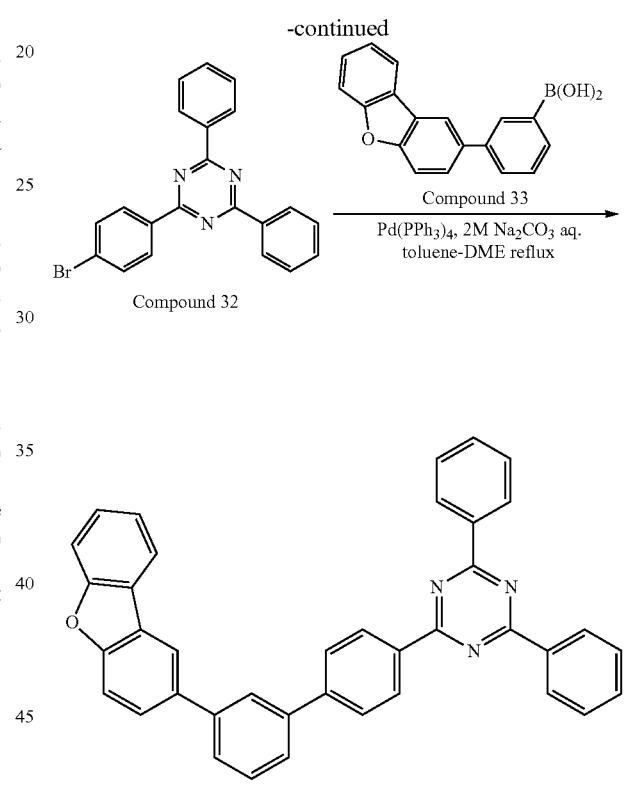

(10-1) Synthesis of Compound 32

Synthesis was made by the same method as in (1-2) synthesis of the compound 7, except for using the compound 19 (20 g, 108 mmol) in place of the compound 3 and using 2 mol equivalent weight of the compound 4 relative to the compound 19, so that a compound 32 (11 g, a yield of 26%) in a form of a white solid was obtained.

(10-2) Synthesis of Compound 34

Synthesis was made by the same method as in (1-3) synthesis of the compound 7, except for using the compound 32 (5.5 g, 14 mmol) in place of the compound 5 and using a compound 33 (4.9 g, 17 mmol) in place of the compound 6, so that a compound 34 (6.1 g, a yield of 78%) in a form of a white solid was obtained. As a result of FD-MS (Field Desorption Mass Spectrometry) analysis, the reactant was identified as the compound 34.

Synthesis Example 11

Synthesis of Compound 38

A synthesis scheme of a compound 38 is shown below.

[Formula 157]

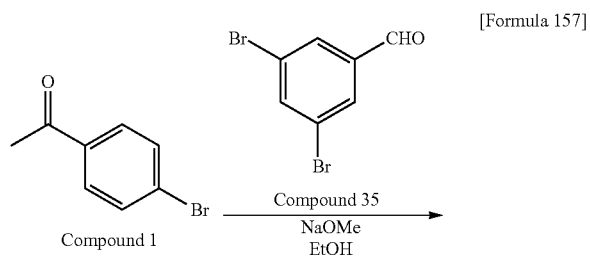

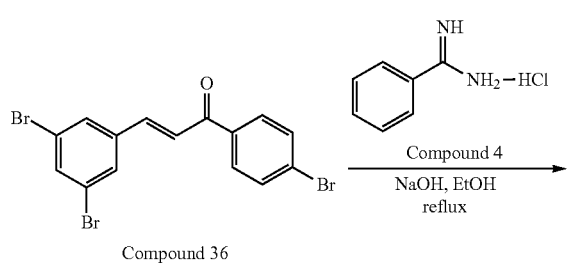

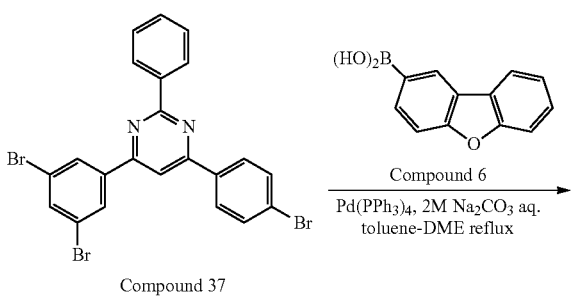

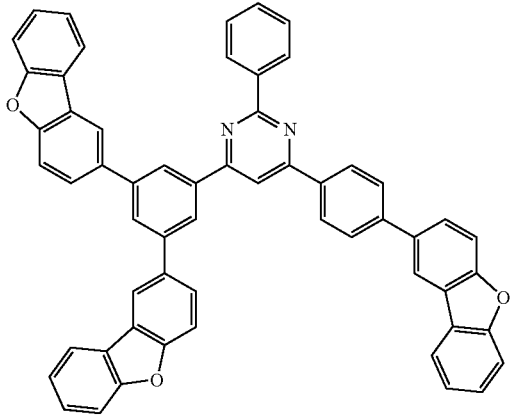

Compound 38

(11-1) Synthesis of Compound 36

Synthesis was made by the same method as in (1-1) synthesis of the compound 7, except for using a compound 35 (28 g, 105 mmol) in place of the compound 2, so that a compound 36 (44 g, a yield of 98%) in a form of a white solid was obtained.

(11-2) Synthesis of Compound 37

Synthesis was made by the same method as in (1-2) synthesis of the compound 7, except for using the compound 36 (44 g, 98 mmol) in place of the compound 3, so that a compound 37 (17 g, a yield of 23%) in a form of a white solid was obtained.

(11-3) Synthesis of Compound 38

Synthesis was made by the same method as in (1-3) synthesis of the compound 7, except for using the compound 37 (5.0 g, 9.2 mmol) in place of the compound 5 and using 3.1 mol equivalent weight of the compound 6 relative to the compound 37, so that a compound 38 (4.7 g, a yield of 64%) in a form of a white solid was obtained. As a result of FD-MS (Field Desorption Mass Spectrometry) analysis, the reactant was identified as the compound 38.

Synthesis Example 12

Synthesis of Compound 42

A synthesis scheme of a compound 42 is shown below.

[Formula 158]

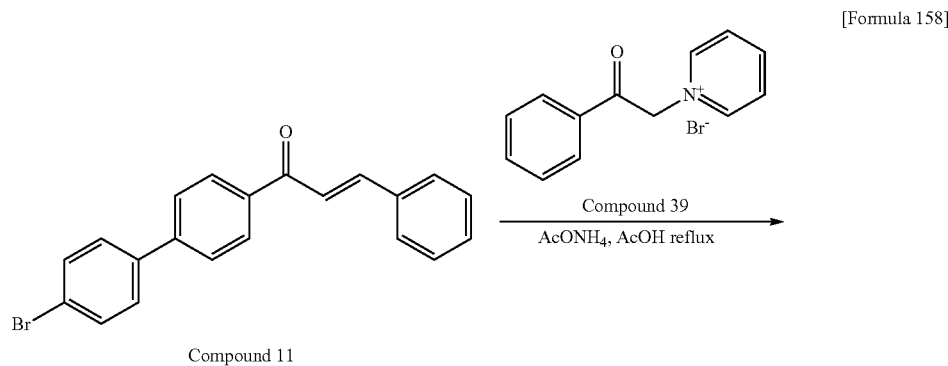

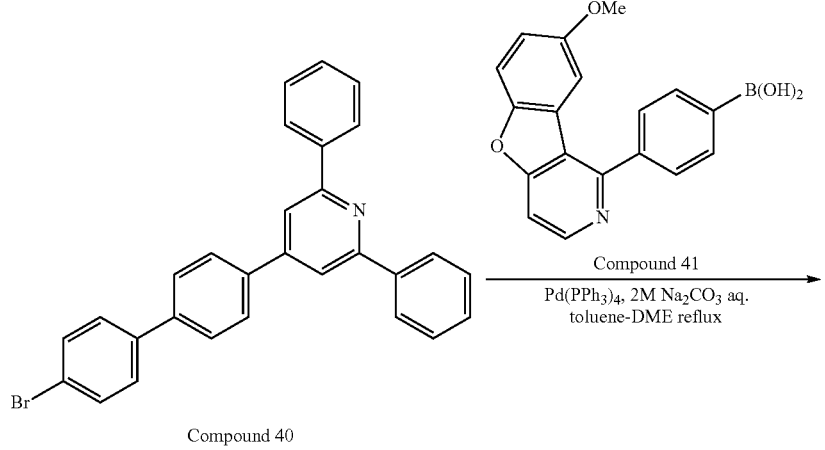

Compound 40

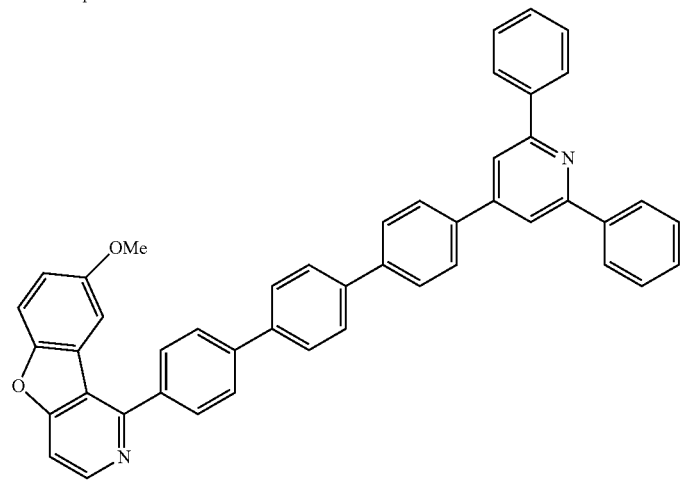

Compound 42

(12-1) Synthesis of Compound 40

The compound 11 (11 g, 31 mmol), 1-phenacylpyridinium bromide (a compound 39) (8.7 g, 31 mmol) and ammonium acetate (19 g, 250 mmol) were suspended in acetic acid (27 mL) and heated to reflux for 12 hours. After the reaction, the reactant solution was cooled to the room temperature, added with water and extracted with toluene. The obtained organic layer was washed with a 10-mass % aqueous sodium hydroxide and saturated saline in sequential order and dried with sodium sulfate. The solvent was distilled away under reduced pressure. The residue was added with ethanol and heated to reflux to be dissolved. The reactant solution was cooled and precipitated in a crystal form. The crystal was separated by filtration and washed with ethanol. Subsequently, the obtained solid was dried under reduced pressure, so that a compound 40 (13 g, a yield of 88%) in a form of a light-yellow solid was obtained.

(12-2) Synthesis of Compound 42

Synthesis was made by the same method as in (1-3) synthesis of the compound 7, except for using the compound 40 (5.0 g, 11 mmol) in place of the compound 5 and a compound 41 (3.8 g, 12 mmol) in place of the compound 6, so that a compound 42 (4.4 g, a yield of 62%) in a form of a white solid was obtained. As a result of FD-MS (Field Desorption Mass Spectrometry) analysis, the reactant was identified as the compound 42.

Synthesis Example 13

Synthesis of Compound 46

A synthesis scheme of a compound 46 is shown below.

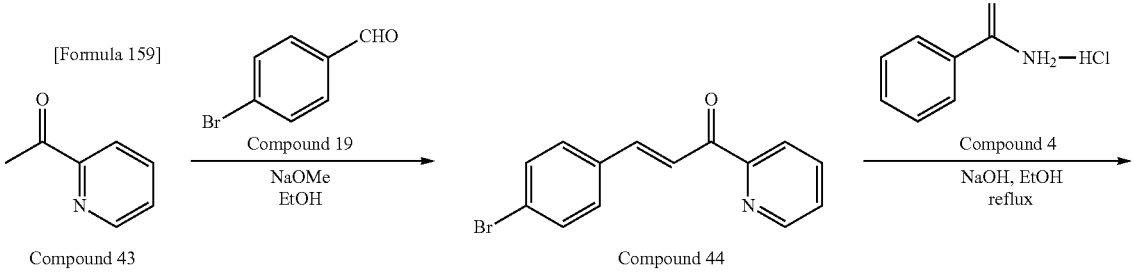

-continued

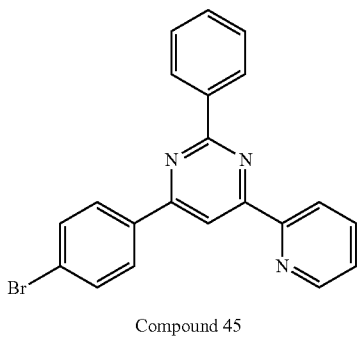
Compound 45

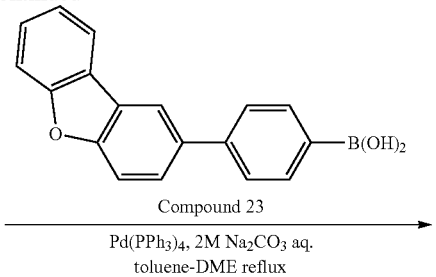
Compound 23

Pd(PPh₃)₄, 2M Na₂CO₃ aq.
toluene-DME reflux

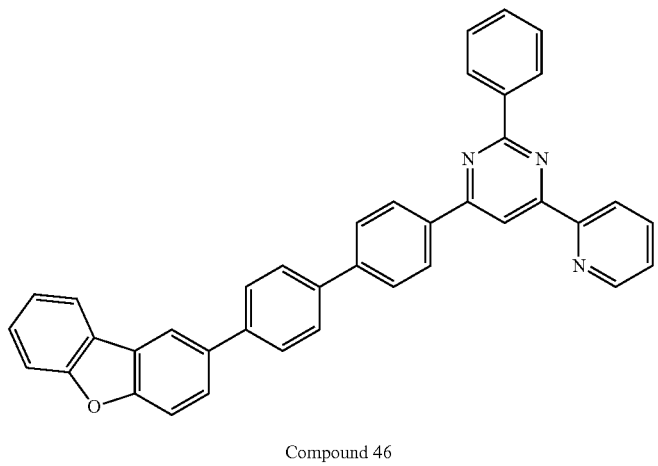
Compound 46

(13-1) Synthesis of Compound 44

Synthesis was made by the same method as in (1-1) synthesis of the compound 7, except for using a compound 43 (9.8 g, 81 mmol) in place of the compound 1 and the compound 19 (16 g, 85 mmol) in place of the compound 2, so that a compound 44 (9.5 g, a yield of 41%) in a form of a light-yellow solid was obtained.

(13-2) Synthesis of Compound 45

Synthesis was made by the same method as in (1-2) synthesis of the compound 7, except for using the compound 44 (9.5 g, 33 mmol) in place of the compound 3, so that a compound 45 (3.5 g, a yield of 27%) in a form of a white solid was obtained.

(13-3) Synthesis of Compound 46

Synthesis was made by the same method as in (1-3) synthesis of the compound 7, except for using the compound 45 (3.5 g, 9.0 mmol) in place of the compound 5 and the compound 23 (2.9 g, 9.9 mmol) in place of the compound 6, so that a compound 46 (2.9 g, a yield of 58%) in a form of a white solid was obtained. As a result of FD-MS (Field Desorption Mass Spectrometry) analysis, the reactant was identified as the compound 46.

Synthesis Example 14

Synthesis of Compound 50

A synthesis scheme of a compound 50 is shown below.

[Formula 160]

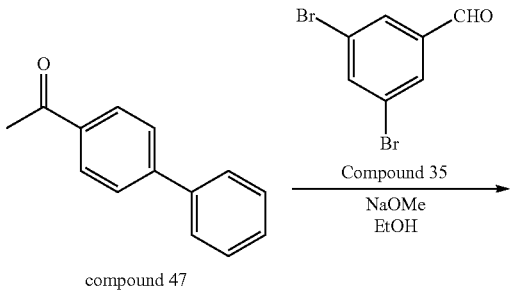

compound 47

-continued
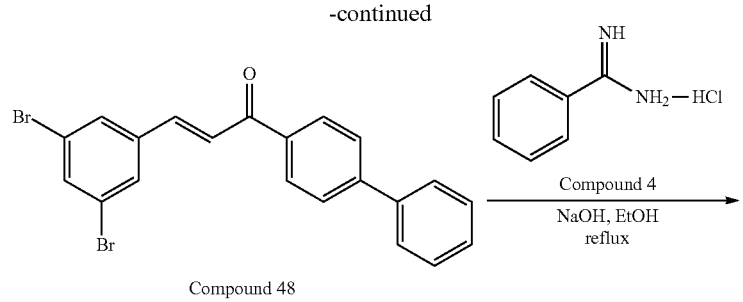
Compound 48
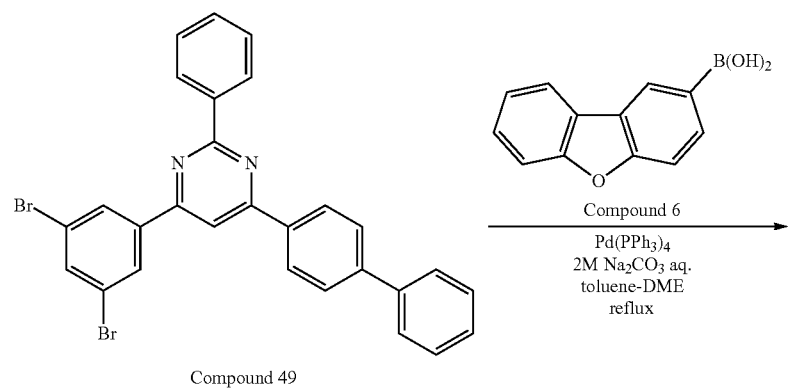
Compound 49
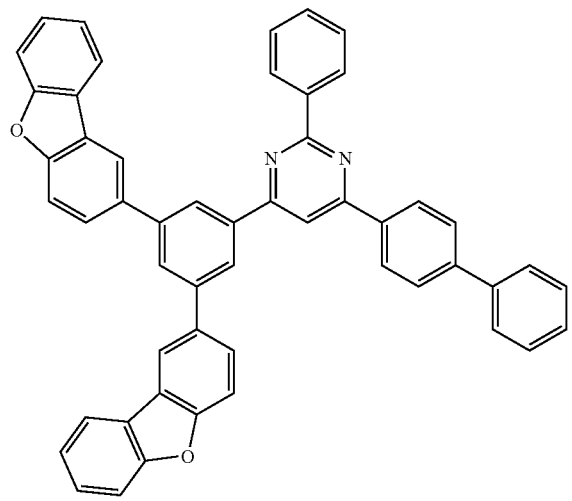
Compound 50

(14-1) Synthesis of Compound 48

Synthesis was made by the same method as in (1-1) synthesis of the compound 7, except for using a compound 47 (37 g, 191 mmol) in place of the compound 1 and using the compound 35 (50 g, 191 mmol) in place of the compound 2, so that a compound 48 (82 g, a yield of 98%) in a form of a yellow solid was obtained.

(14-2) Synthesis of Compound 49

Synthesis was made by the same method as in (1-2) synthesis of the compound 7, except for using the compound 48 (82 g, 186 mmol) in place of the compound 3, so that a compound 49 (40 g, a yield of 40%) in a form of a white solid was obtained.

(14-3) Synthesis of Compound 50

Synthesis was made by the same method as in (1-3) synthesis of the compound 7, except for using the compound 49 (6.0 g, 11 mmol) in place of the compound 5 and using 2.2 mol equivalent weight of the compound 6 relative to the compound 49, so that a compound 50 (4.2 g, a yield of 53%) in a form of a white solid was obtained. As a result of FD-MS (Field Desorption Mass Spectrometry) analysis, the reactant was identified as the compound 50.

Synthesis Example 15

Synthesis of Compound 51

A synthesis scheme of a compound 51 is shown below.

[Formula 161]

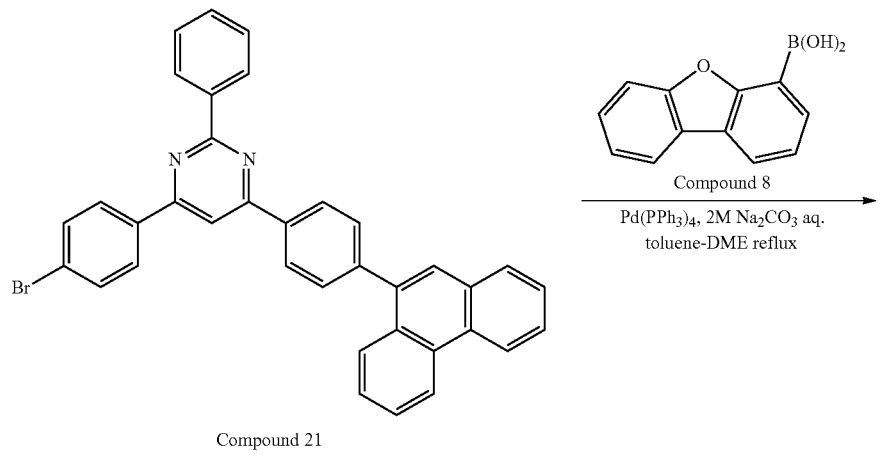

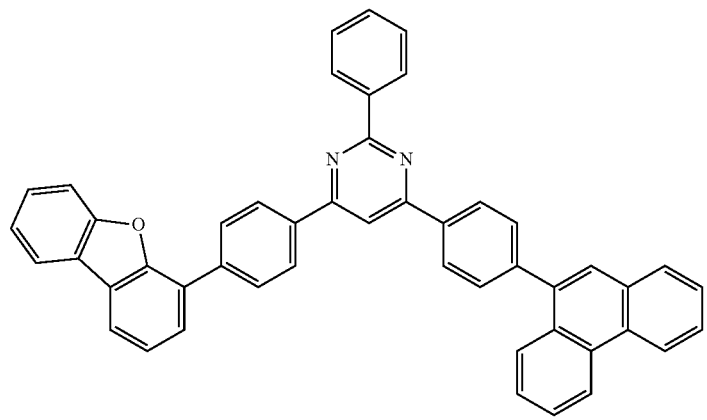

(15-1) Synthesis of Compound 51

Synthesis was made by the same method as in (1-3) synthesis of the compound 7, except for using the compound 21 (6.0 g, 11 mmol) in place of the compound 5 and using the compound 8 (2.7 g, 13 mmol) in place of the compound 6, so that a compound 51 (2.7 g, a yield of 39%) in a form of a white solid was obtained. As a result of FD-MS (Field Desorption Mass Spectrometry) analysis, the reactant was identified as the compound 51.

Synthesis Example 16

Synthesis of Compound 52

A synthesis scheme of a compound 52 is shown below.

[Formula 162]

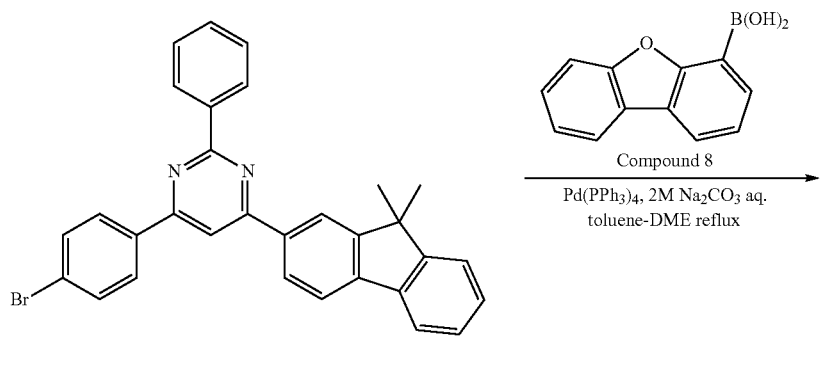

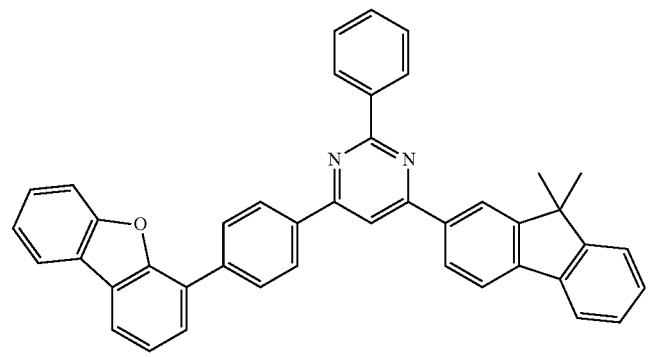

Compound 52

(16-1) Synthesis of Compound 52

Synthesis was made by the same method as in (1-3) synthesis of the compound 7, except for using the compound 27 (6.0 g, 12 mmol) in place of the compound 5 and the compound 8 (3.0 g, 14 mmol) in place of the compound 6, so that a compound 52 (5.6 g, a yield of 79%) in a form of a white solid was obtained. As a result of FD-MS (Field Desorption Mass Spectrometry) analysis, the reactant was identified as the compound 52.

Synthesis Example 17

Synthesis of Compound 53

A synthesis scheme of a compound 53 is shown below.

[Formula 163]

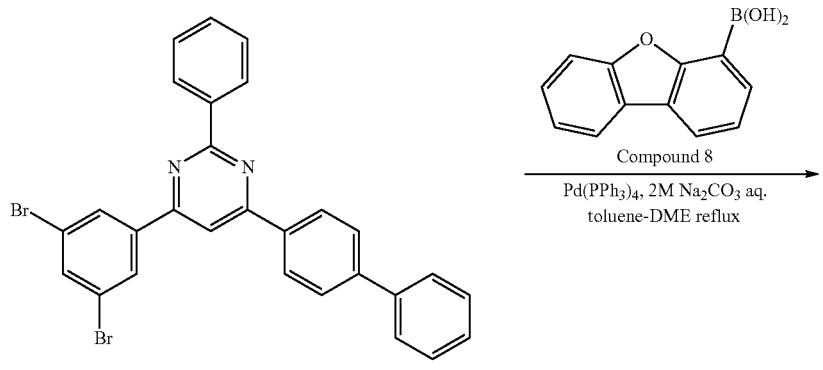

Compound 49

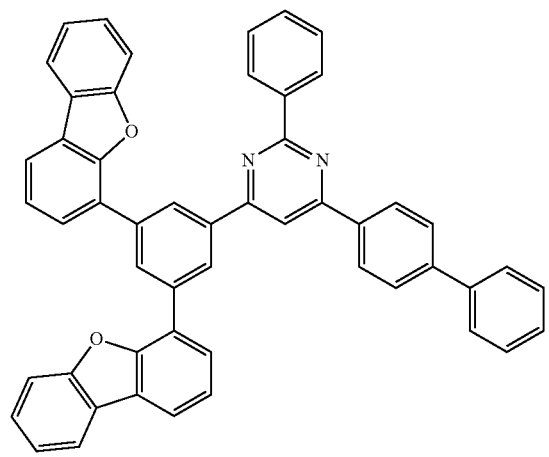

Compound 53

(17-1) Synthesis of Compound 53

Synthesis was made by the same method as in (1-3) synthesis of the compound 7, except for using the compound 49 (6.0 g, 11 mmol) in place of the compound 5 and using the compound 8 (5.2 g, 24 mmol) in place of the compound 6, so that a compound 53 (4.9 g, a yield of 61%) in a form of a white solid was obtained. As a result of FD-MS (Field Desorption Mass Spectrometry) analysis, the reactant was identified as the compound 53.

Synthesis Example 18

Synthesis of Compound 59

A synthesis scheme of a compound 59 is shown below.

[Formula 164]

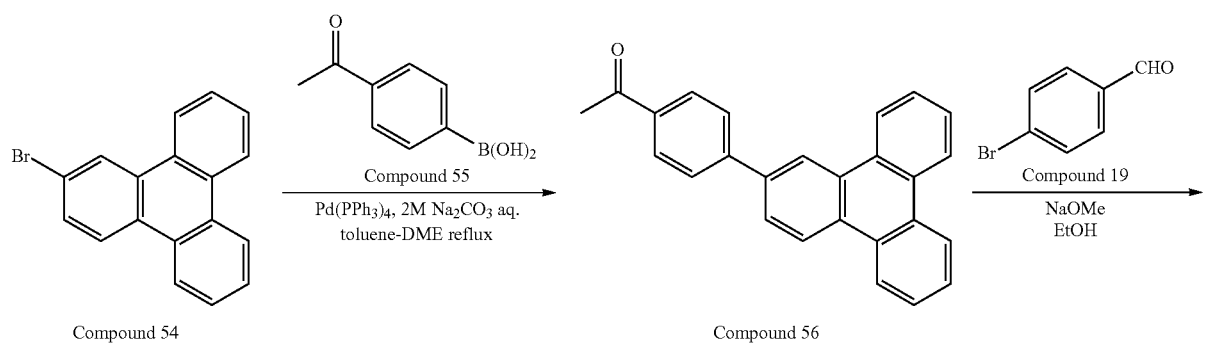

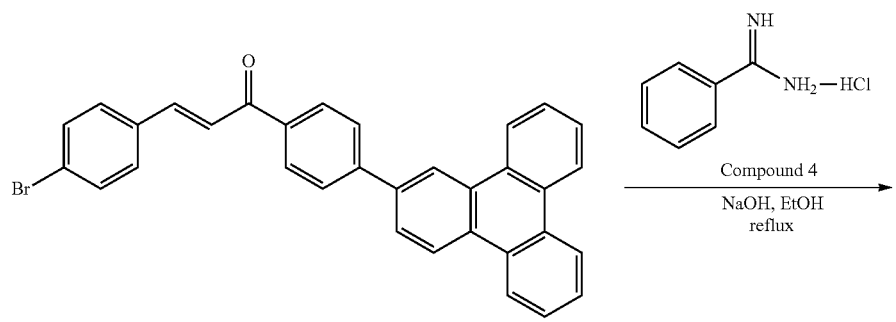

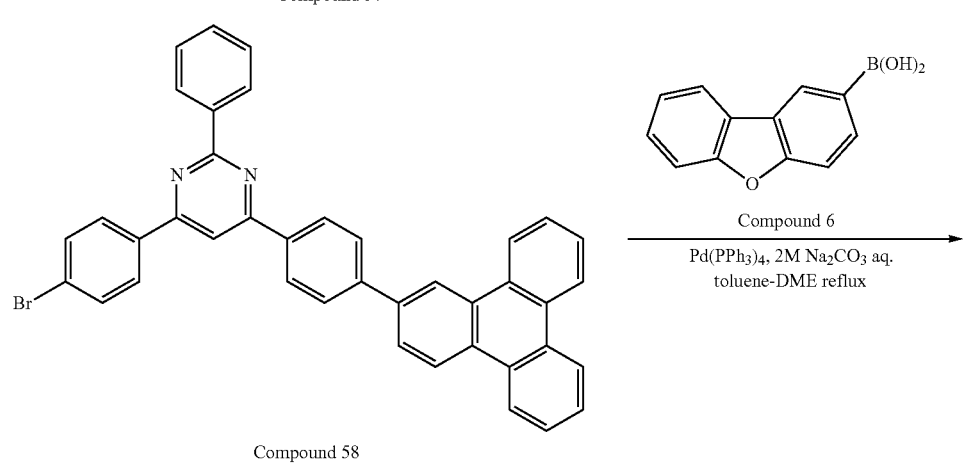

-continued

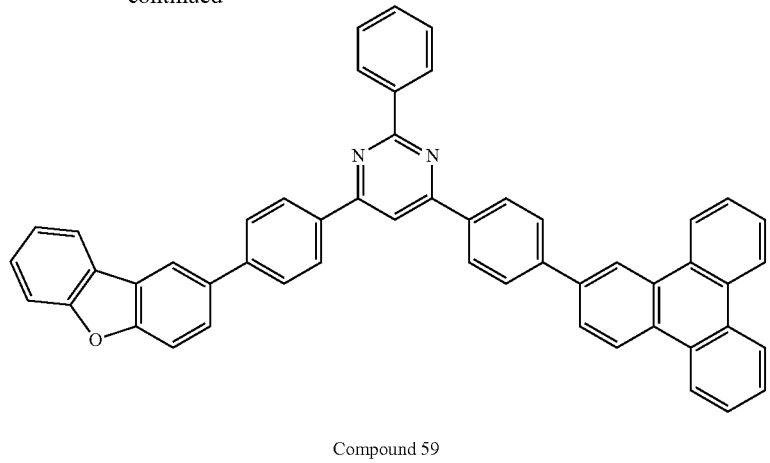

Compound 59

(18-1) Synthesis of Compound 56
Synthesis was made by the same method as in (1-3) synthesis of the compound 7, except for using the compound 54 (54 g, 176 mmol) in place of the compound 5 and using the compound 55 (32 g, 194 mmol) in place of the compound 6, so that a compound 56 (58 g, a yield of 95%) in a form of a white solid was obtained.

(18-2) Synthesis of Compound 57
Synthesis was made by the same method as in (1-1) synthesis of the compound 7, except for using the compound 56 (42 g, 122 mmol) in place of the compound 1 and using 4-bromobenzaldehyde (the compound 19) (24 g, 128 mmol) in place of the compound 2, so that a partially refined product (78 g) of a compound 57 in a form of a yellow solid was obtained. Without further refining the product, the subsequent reaction was performed.

(18-3) Synthesis of Compound 58
Synthesis was made by the same method as in (1-2) synthesis of the compound 7, except for using the partially refined product (78 g) of the compound 57 in place of the compound 3, so that a compound 58 (27 g, a yield of 36%) in a form of a white solid was obtained.

(18-4) Synthesis of Compound 59
Synthesis was made by the same method as in (1-3) synthesis of the compound 7, except for using the compound 58 (6.0 g, 9.8 mmol) in place of the compound 5, so that a compound 59 (3.2 g, a yield of 47%) in a form of a white solid was obtained. As a result of FD-MS (Field Desorption Mass Spectrometry) analysis, the reactant was identified as the compound 59.

Synthesis Example 19

Synthesis of Compound 64

A synthesis scheme of a compound 64 is shown below.

[Formula 165]

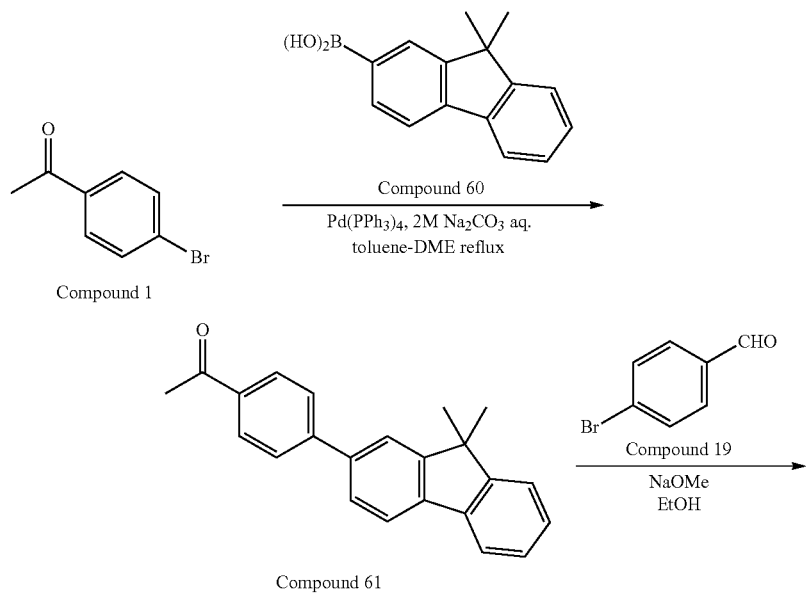

-continued

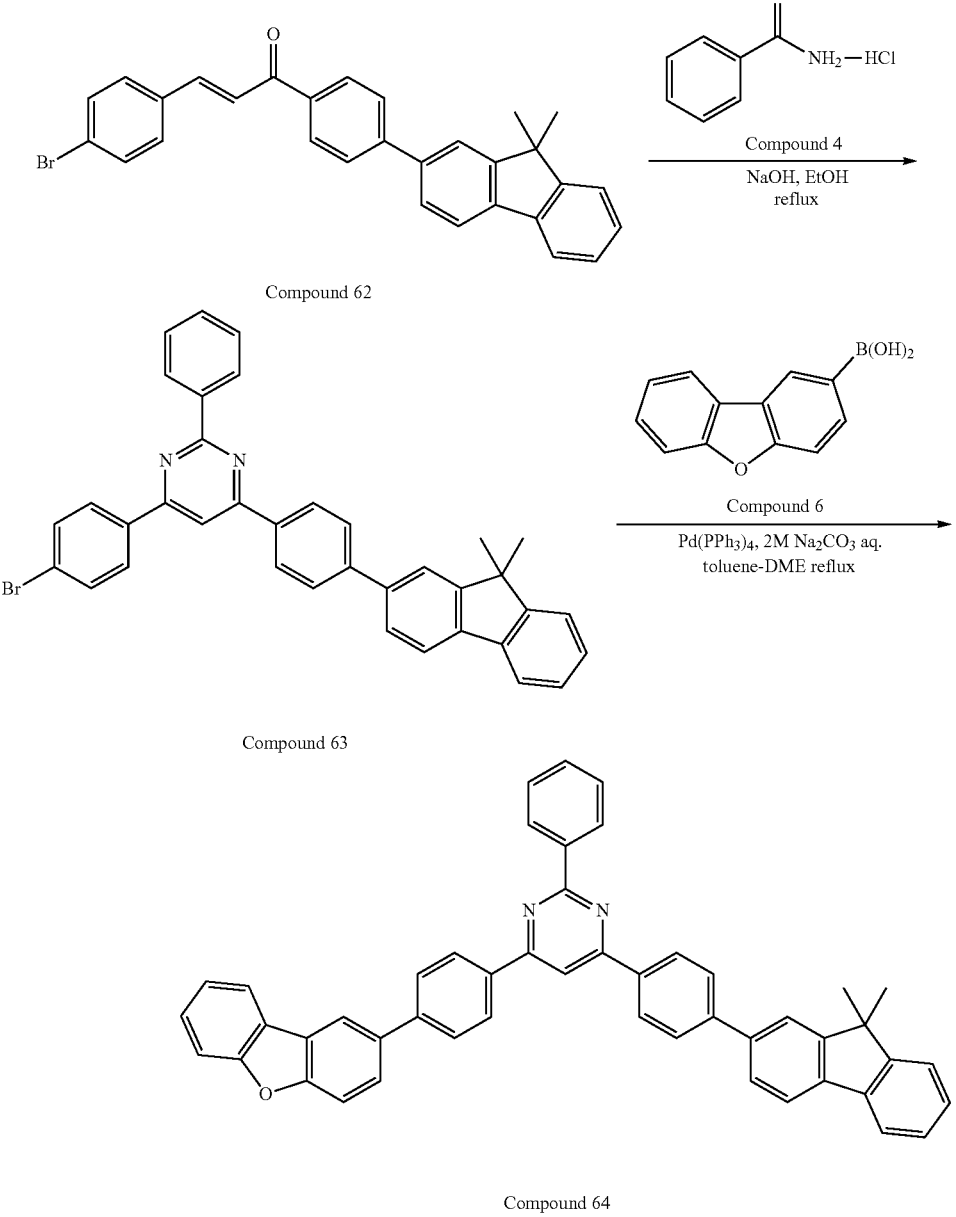

Compound 62

Compound 63

Compound 64

(19-1) Synthesis of Compound 61

Synthesis was made by the same method as in (1-3) synthesis of the compound 7, except for using the compound 1 (50 g, 251 mmol) in place of the compound 5 and using the compound 60 (66 g, 276 mmol) in place of the compound 6, so that a compound 61 (72 g, a yield of 92%) in a form of a white solid was obtained.

(19-2) Synthesis of Compound 62

Synthesis was made by the same method as in (1-1) synthesis of the compound 7, except for using the compound 61 (72 g, 230 mmol) in place of the compound 1 and using 4-bromobenzaldehyde (the compound 19) (43 g, 230 mmol) in place of the compound 2, so that a compound 62 (107 g, a yield of 97%) in a form of a white solid was obtained.

(19-3) Synthesis of Compound 63

Synthesis was made by the same method as in (1-2) synthesis of the compound 7, except for using the compound 62 (107 g, 223 mmol) in place of the compound 3, so that a compound 63 (47 g, a yield of 36%) in a form of a white solid was obtained.

(19-4) Synthesis of Compound 64

Synthesis was made by the same method as in (1-3) synthesis of the compound 7, except for using the compound 63 (7.0 g, 12 mmol) in place of the compound 5, so that a compound 64 (4.9 g, a yield of 61%) in a form of a white solid was obtained. As a result of FD-MS (Field Desorption Mass Spectrometry) analysis, the reactant was identified as the compound 64.

Synthesis Example 20

Synthesis of Compound 65

A synthesis scheme of a compound 65 is shown below.

[Formula 166]

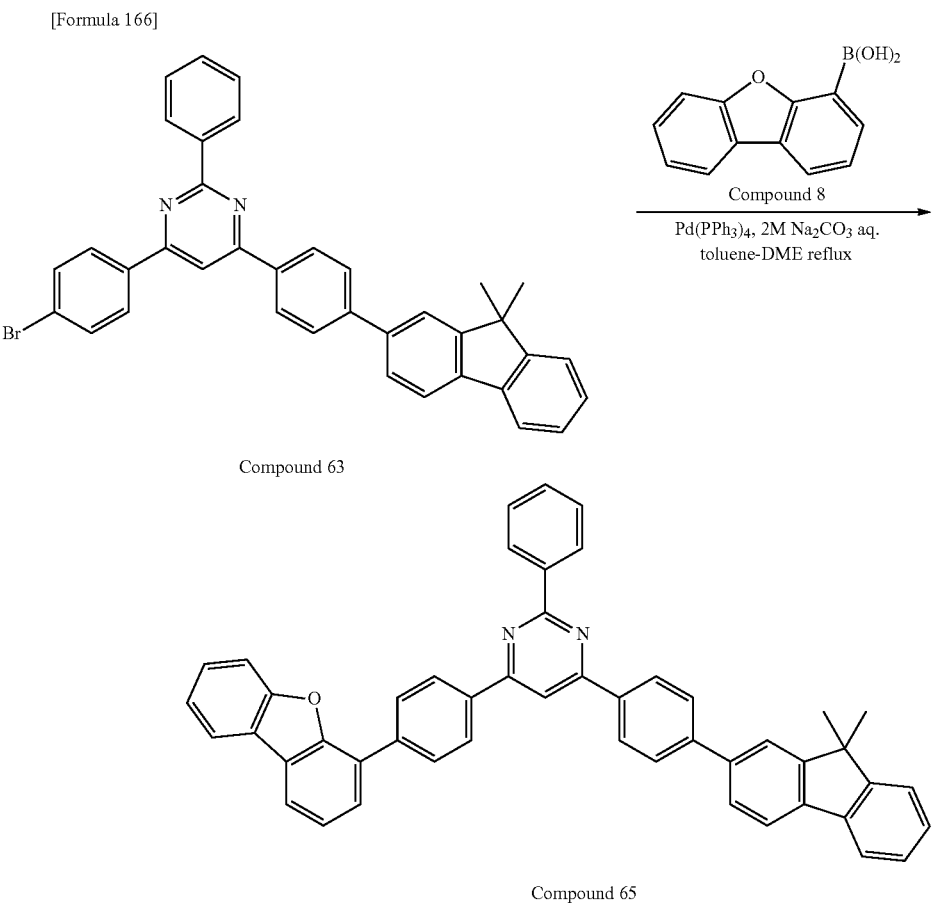

(20-1) Synthesis of Compound 65

Synthesis was made by the same method as in (1-3) synthesis of the compound 7, except for using the compound 63 (7.0 g, 12 mmol) in place of the compound 5 and the compound 8 (2.8 g, 13 mmol) in place of the compound 6, so that a compound 65 (4.3 g, a yield of 53%) in a form of a white solid was obtained. As a result of FD-MS (Field Desorption Mass Spectrometry) analysis, the reactant was identified as the compound 65.

Synthesis Example 21

Synthesis of Compound 69

A synthesis scheme of a compound 69 is shown below.

[Formula 167]

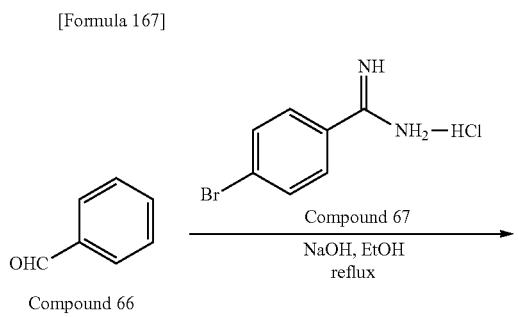

-continued

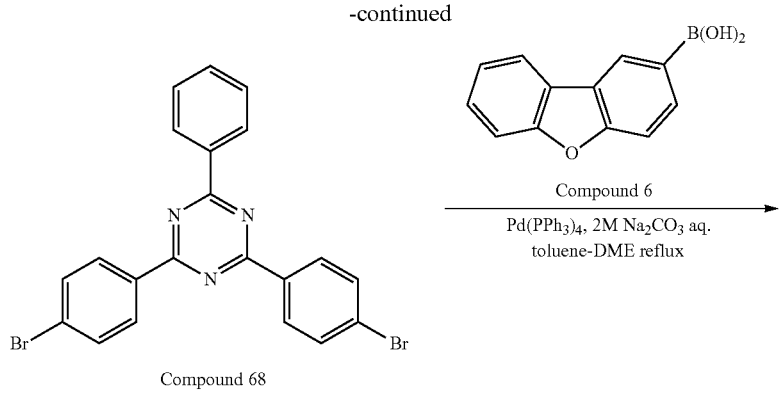

Compound 68

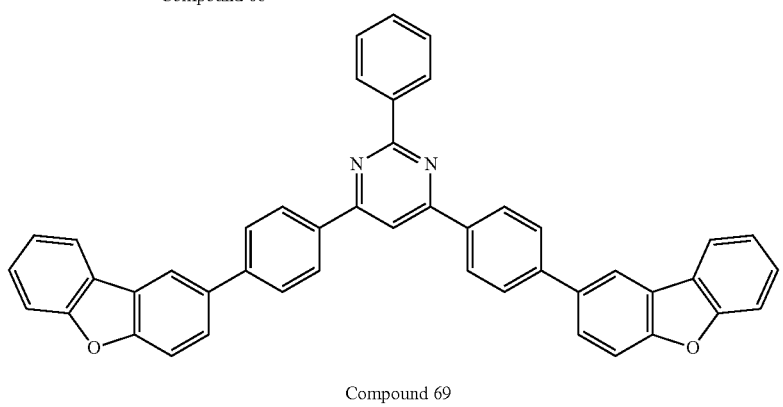

Compound 69

(21-1) Synthesis of Compound 68
Synthesis was made by the same method as in (1-2) synthesis of the compound 7, except for using a compound 66 (7.7 g, 72 mmol) in place of the compound 3 and using the compound 67 (34 g, 145 mmol) in place of the compound 4, so that a compound 68 (9.4 g, a yield of 32%) in a form of a white solid was obtained.

(21-2) Synthesis of Compound 69
Synthesis was made by the same method as in (1-3) synthesis of the compound 7, except for using the compound 68 (4.5 g, 9.6 mmol) in place of the compound 5 and using 2.2 mol equivalent weight of the compound 6 relative to the compound 68, so that a compound 69 (4.4 g, a yield of 71%) in a form of a white solid was obtained. As a result of FD-MS (Field Desorption Mass Spectrometry) analysis, the reactant was identified as the compound 69.

Synthesis Example 21

Synthesis of Compound 70

A synthesis scheme of a compound 70 is shown below.

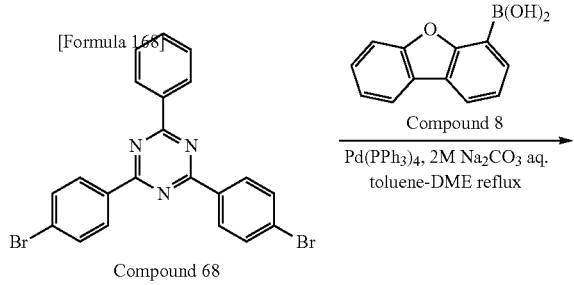

Compound 68

-continued

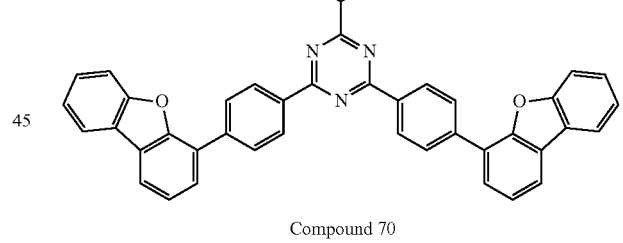

Compound 70

(22-1) Synthesis of Compound 70

Synthesis was made by the same method as in (1-3) synthesis of the compound 7, except for using the compound 68 (4.9 g, 10 mmol) in place of the compound 5 and using the compound 8 (4.9 g, 23 mmol) in place of the compound 6, so that a compound 70 (3.1 g, a yield of 46%) in a form of a white solid was obtained. As a result of FD-MS (Field Desorption Mass Spectrometry) analysis, the reactant was identified as the compound 70.

Synthesis Example 23

Synthesis of Compound 71

A synthesis scheme of a compound 71 is shown below.

[Formual 169]

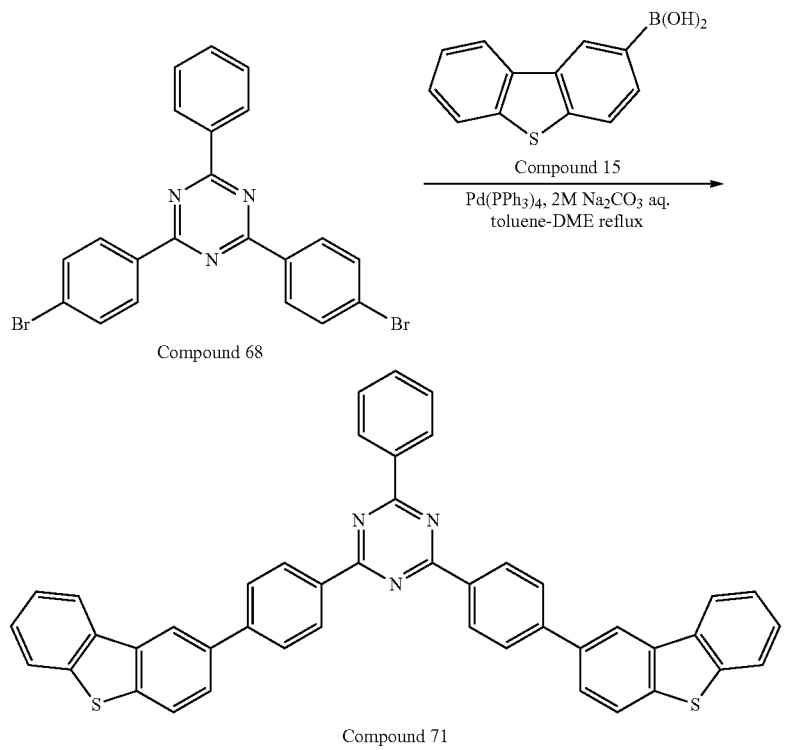

(23-1) Synthesis of Compound 71

Synthesis was made by the same method as in (1-3) synthesis of the compound 7, except for using the compound 68 (4.5 g, 9.6 mmol) in place of the compound 5 and using the compound 15 (4.8 g, 21 mmol) in place of the compound 6, so that a compound 71 (3.4 g, a yield of 53%) in a form of a white solid was obtained. As a result of FD-MS (Field Desorption Mass Spectrometry) analysis, the reactant was identified as the compound 71.

Synthesis Example 24

Synthesis of Compound 72

A synthesis scheme of a compound 72 is shown below.

[Formula 170]

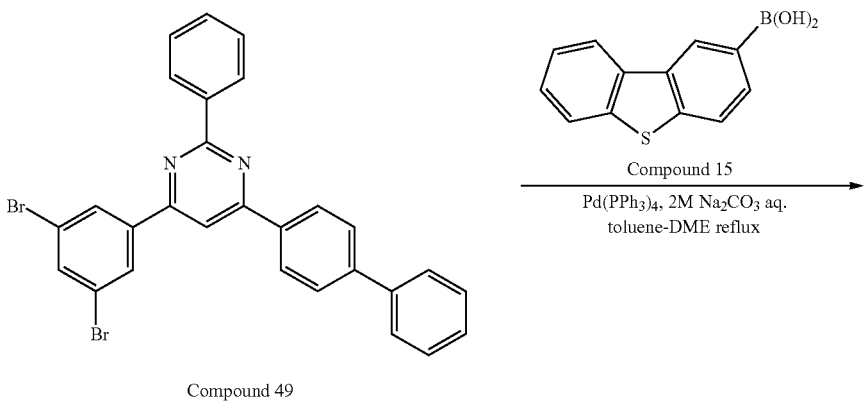

-continued

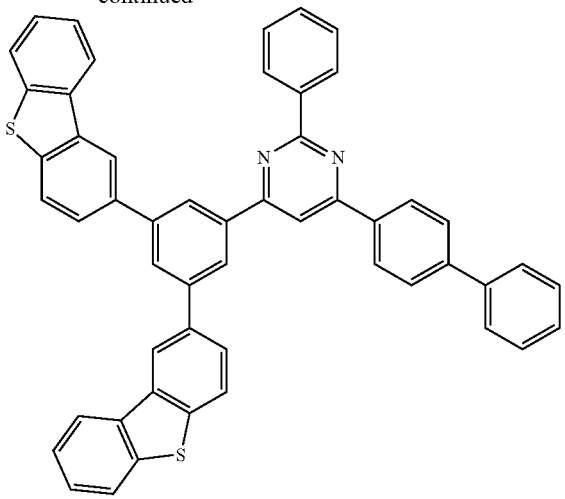

Compound 72

(24-1) Synthesis of Compound 72

Synthesis was made by the same method as in (1-3) synthesis of the compound 7, except for using the compound 49 (10 g, 18 mmol) in place of the compound 5 and using the compound 15 (9.3 g, 41 mmol) in place of the compound 6, so that a compound 72 (9.7 g, a yield of 70%) in a form of a white solid was obtained. As a result of FD-MS (Field Desorption Mass Spectrometry) analysis, the reactant was identified as the compound 72.

Synthesis Example 25

Synthesis of Compound 74

A synthesis scheme of a compound 74 is shown below.

[Formula 171]

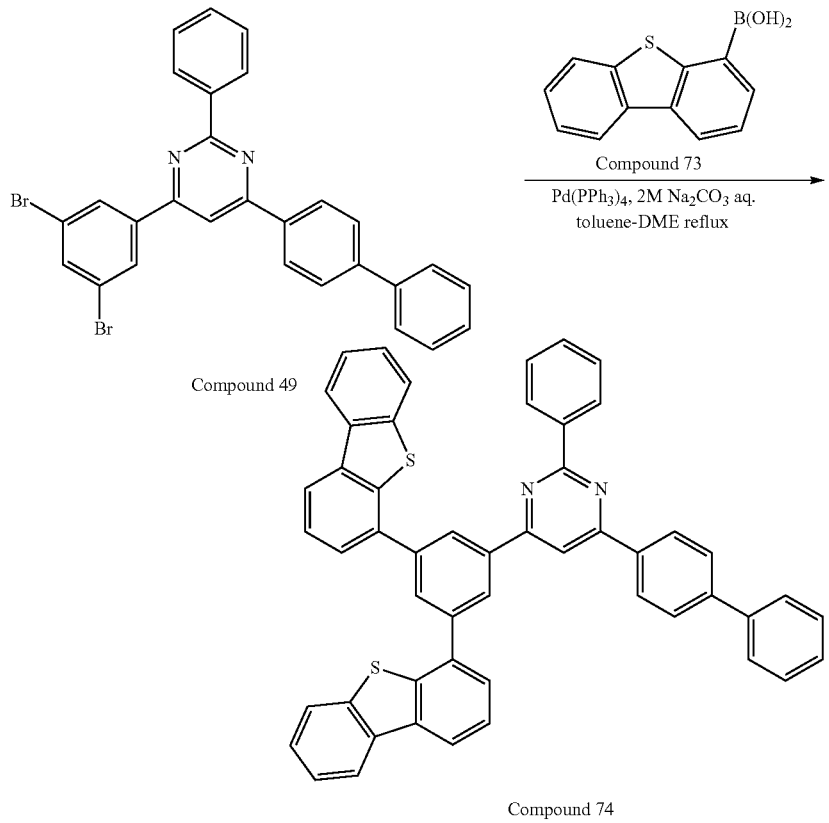

(25-1) Synthesis of Compound 74

Synthesis was made by the same method as in (1-3) synthesis of the compound 7, except for using the compound 49 (10 g, 18 mmol) in place of the compound 5 and using the compound 73 (9.3 g, 41 mmol) in place of the compound 6, so that a compound 74 (9.5 g, a yield of 68%) in a form of a white solid was obtained. As a result of FD-MS (Field Desorption Mass Spectrometry) analysis, the reactant was identified as the compound 74.

Synthesis Example 26

Synthesis of Compound 78

A synthesis scheme of a compound 78 is shown below.

[Formula 172]

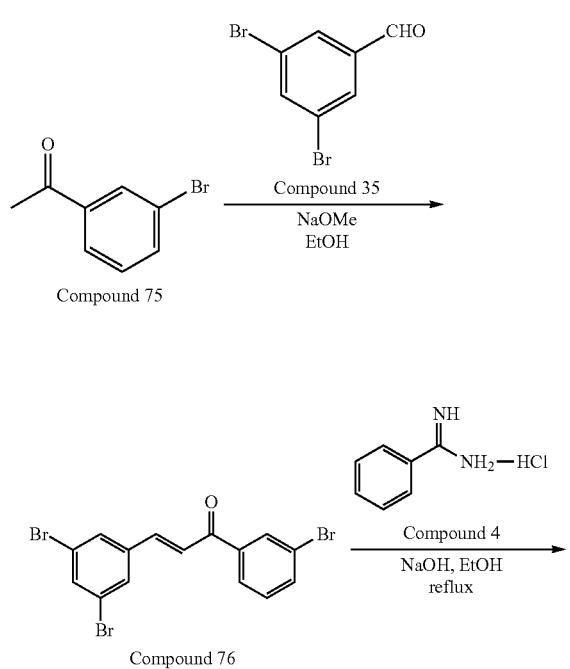

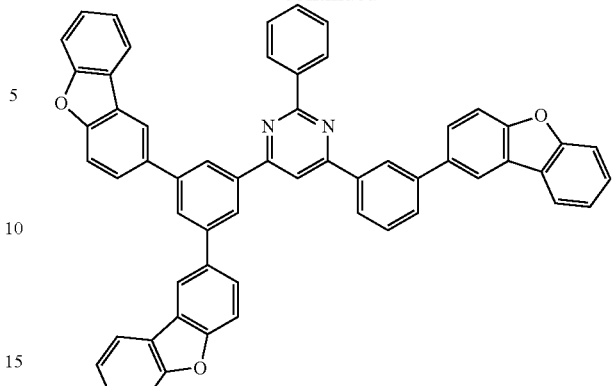

Compound 78

(26-1) Synthesis of Compound 76

Synthesis was made by the same method as in (1-1) synthesis of the compound 7, except for using the compound 75 (38 g, 193 mmol) in place of the compound 1 and the compound 35 (50 g, 189 mmol) in place of the compound 2, so that a compound 76 (75 g, a yield of 89%) in a form of a white solid was obtained.

(26-2) Synthesis of Compound 77

Synthesis was made by the same method as in (1-2) synthesis of the compound 7, except for using the compound 76 (71 g, 158 mmol) in place of the compound 3, so that a compound 77 (31 g, a yield of 33%) in a form of a white solid was obtained.

(26-3) Synthesis of Compound 78

Synthesis was made by the same method as in (1-3) synthesis of the compound 7, except for using the compound 77 (15 g, 28 mmol) in place of the compound 5 and using 3.5 equivalent weight of the compound 6 relative to the compound 77, so that a compound 78 (5.0 g, a yield of 23%) in a form of a white solid was obtained. As a result of FD-MS (Field Desorption Mass Spectrometry) analysis, the reactant was identified as the compound 78.

Synthesis Example 27

Synthesis of Compound 79

A synthesis scheme of a compound 79 is shown below.

[Formula 173]

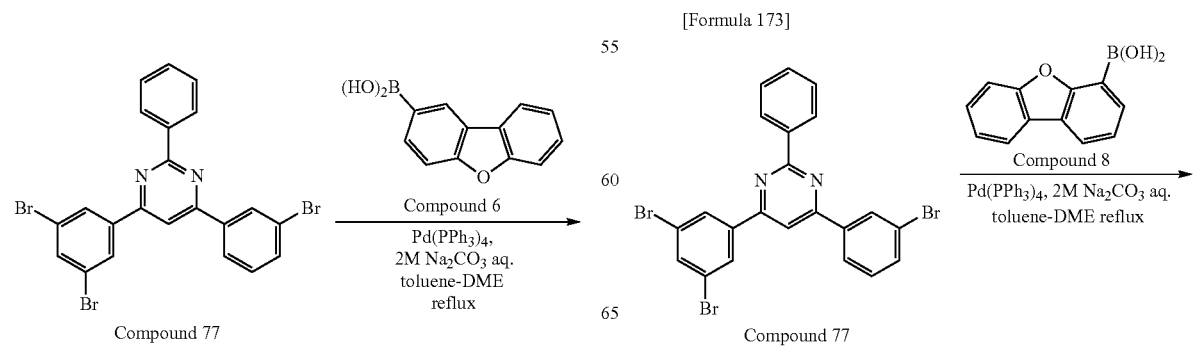

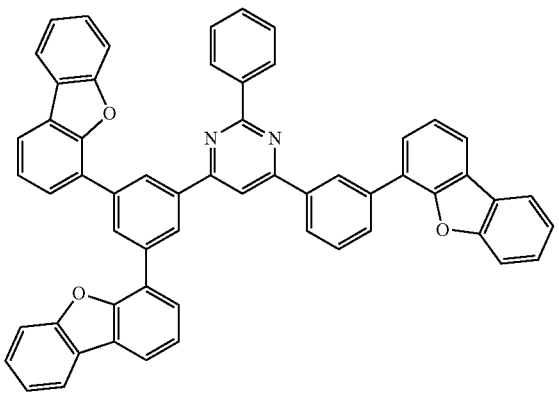

Compound 79

(27-1) Synthesis of Compound 79

Synthesis was made by the same method as in (1-3) synthesis of the compound 7, except for using the compound 77 (15 g, 28 mmol) in place of the compound 5 and using the compound 8 (20 g, 96 mmol) in place of the compound 6, so that a compound 79 (12 g, a yield of 52%) in a form of a white solid was obtained. As a result of FD-MS (Field Desorption Mass Spectrometry) analysis, the reactant was identified as the compound 79.

Synthesis Example 28

Synthesis of Compound 82

A synthesis scheme of a compound 82 is shown below.

[Formula 174]

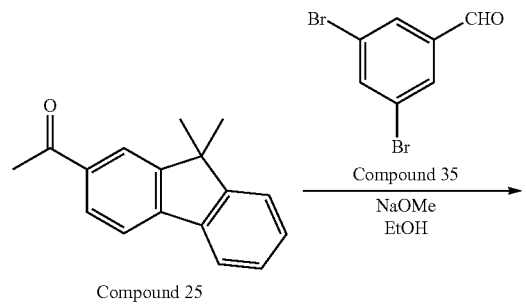

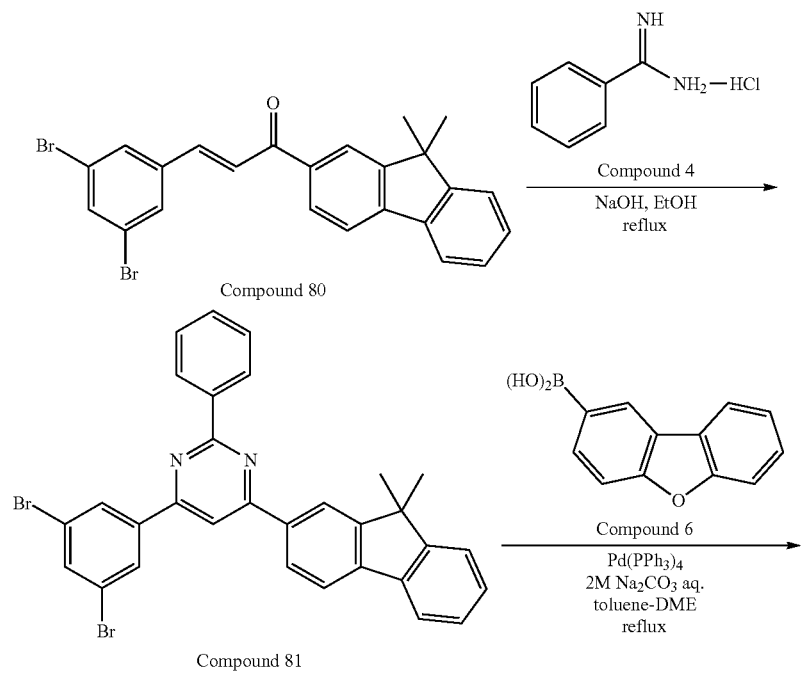

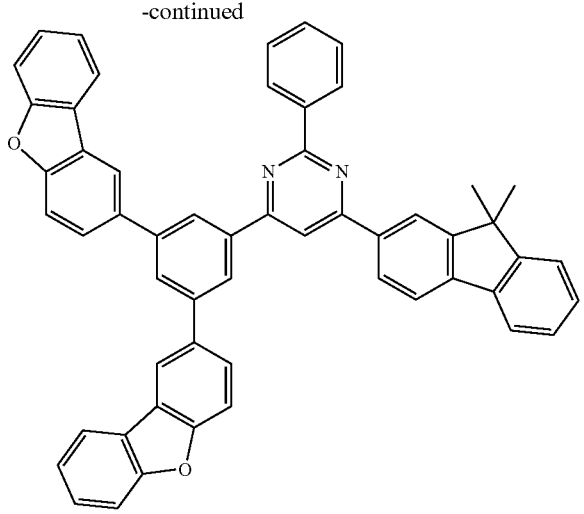

Compound 82

(28-1) Synthesis of Compound 80

Synthesis was made by the same method as in (1-1) synthesis of the compound 7, except for using the compound 25 (34 g, 144 mmol) in place of the compound 1 and using the compound 35 (42 g, 158 mmol) in place of the compound 2, so that a compound 80 (69 g, a yield of 100%) in a form of a light-brown solid was obtained.

(28-2) Synthesis of Compound 81

Synthesis was made by the same method as in (1-2) synthesis of the compound 7, except for using the compound 80 (69 g, 144 mmol) in place of the compound 3, so that a compound 81 (18 g, a yield of 22%) in a form of a light-yellow solid was obtained.

(28-3) Synthesis of Compound 82

Synthesis was made by the same method as in (1-3) synthesis of the compound 7, except for using the compound 81 (9.1 g, 16 mmol) in place of the compound 5 and using 2.2 mol equivalent weight of the compound 6 relative to the compound 81, so that a compound 82 (9.4 g, a yield of 79%) in a form of a light-yellow solid was obtained. As a result of FD-MS (Field Desorption Mass Spectrometry) analysis, the reactant was identified as the compound 82.

Synthesis Example 29

Synthesis of Compound 83

A synthesis scheme of a compound 83 is shown below.

[Formula 175]

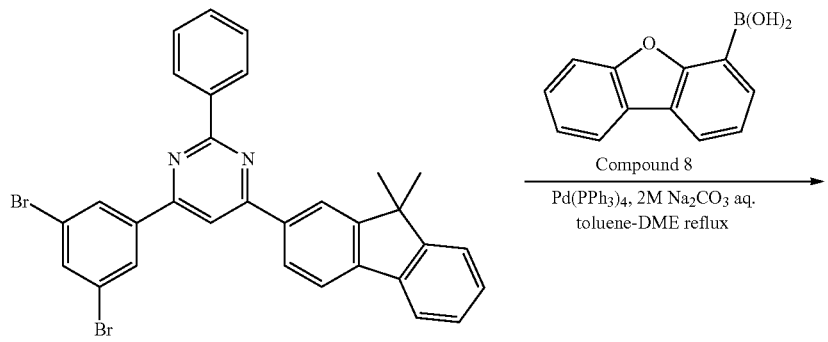

Compound 81

-continued

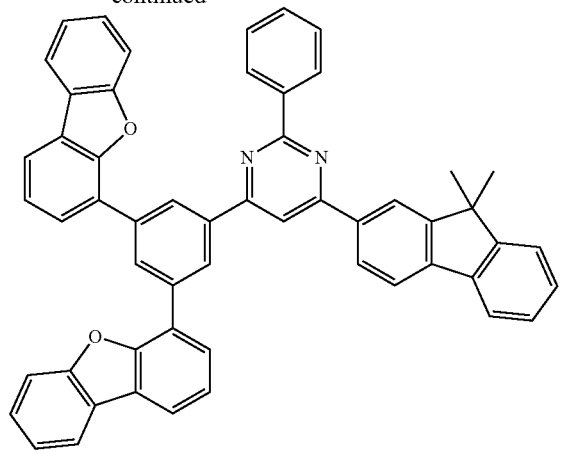
Compound 83

(29-1) Synthesis of Compound 83

Synthesis was made by the same method as in (1-3) synthesis of the compound 7, except for using the compound 81 (9.0 g, 15 mmol) in place of the compound 5 and using the compound 8 (7.2 g, 34 mmol) in place of the compound 6, so that a compound 83 (8.1 g, a yield of 69%) in a form of a light-yellow solid was obtained. As a result of FD-MS (Field Desorption Mass Spectrometry) analysis, the reactant was identified as the compound 83.

Synthesis Example 30

Synthesis of Compound 88

A synthesis scheme of a compound 88 is shown below.

[Formula 176]

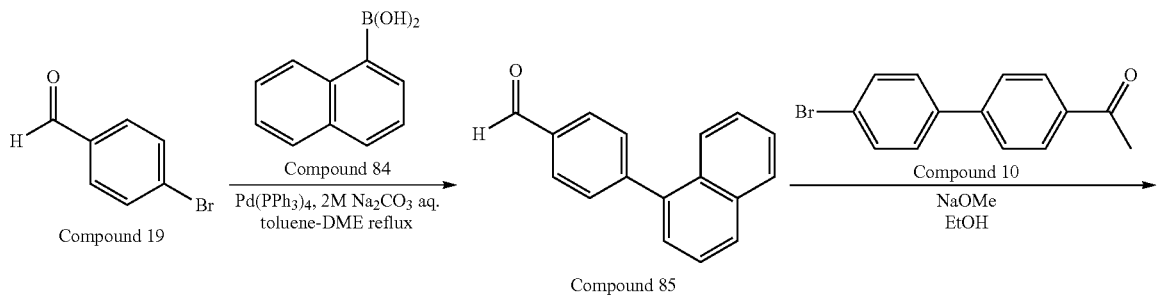

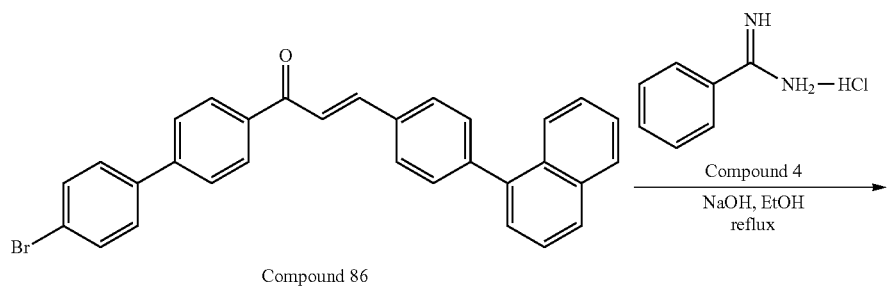

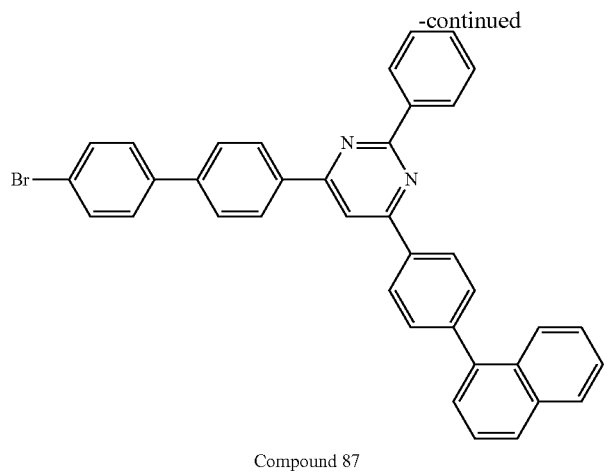
Compound 87

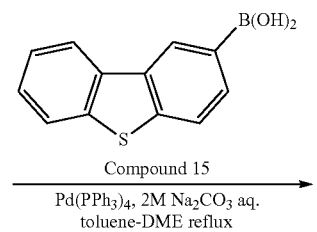
Compound 15

Pd(PPh₃)₄, 2M Na₂CO₃ aq.
toluene-DME reflux

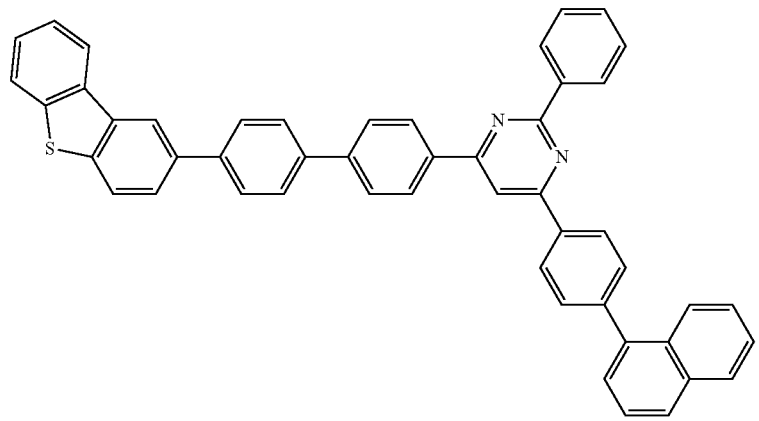
Compound 88

(30-1) Synthesis of Compound 85

Synthesis was made by the same method as in (1-3) synthesis of the compound 7, except for using the compound 19 (50 g, 270 mmol) in place of the compound 5 and using the compound 84 (56 g, 325 mmol) in place of the compound 6, so that a compound 85 (53 g, a yield of 85%) in a form of a white solid was obtained.

(30-2) Synthesis of Compound 86

Synthesis was made by the same method as in (1-1) synthesis of the compound 7, except for using the compound 10 (65 g, 235 mmol) in place of the compound 1 and using the compound 85 (53 g, 229 mmol) in place of the compound 2, so that a compound 86 (109 g) in a form of a light-yellow solid was obtained.

(30-3) Synthesis of Compound 87

Synthesis was made by the same method as in (1-2) synthesis of the compound 7, except for using the compound 86 (108 g, 221 mmol) in place of the compound 3, so that a compound 87 (44 g, a yield of 34%) in a form of a white solid was obtained.

(30-4) Synthesis of Compound 88

Synthesis was made by the same method as in (1-3) synthesis of the compound 7, except for using the compound 87 (6.0 g, 10 mmol) in place of the compound 5 and using the compound 15 (2.8 g, 12 mmol) in place of the compound 6, so that a compound 88 (5.9 g, a yield of 84%) in a form of a white solid was obtained. As a result of FD-MS (Field Desorption Mass Spectrometry) analysis, the reactant was identified as the compound 88.

Synthesis Example 31

Synthesis of Compound 89

A synthesis scheme of a compound 89 is shown below.

[Formula 177]

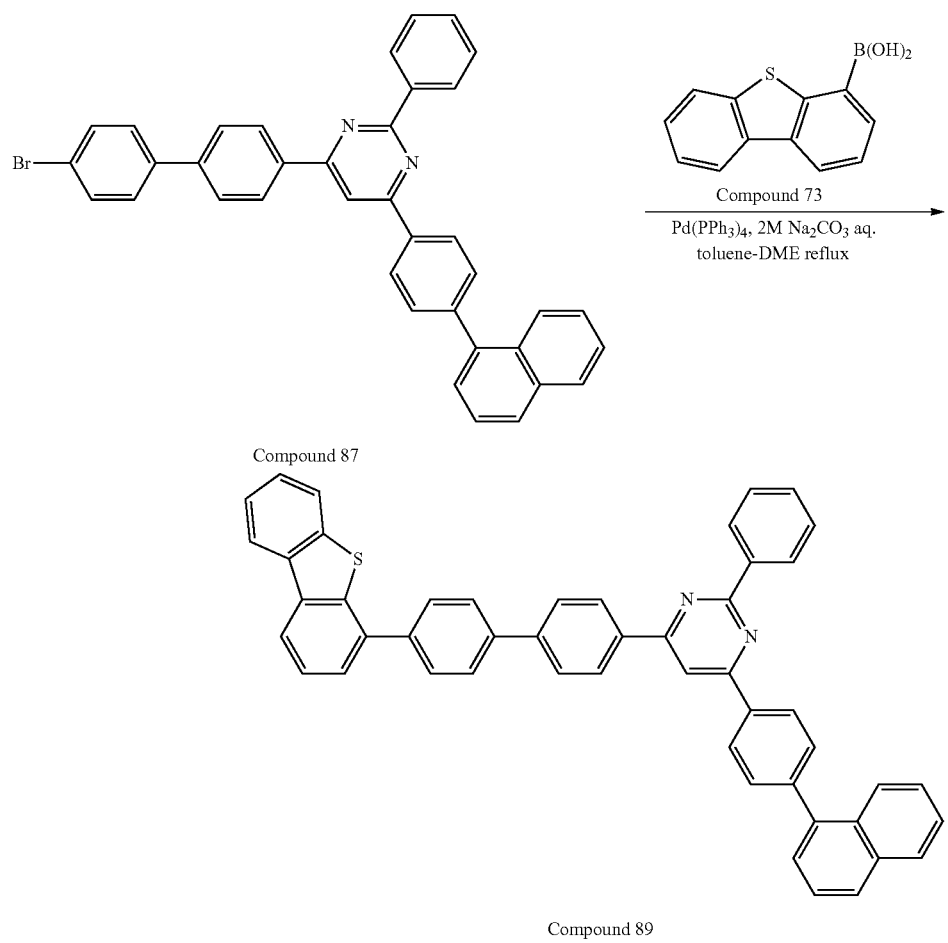

(31-1) Synthesis of Compound 89

Synthesis was made by the same method as in (1-3) synthesis of the compound 7, except for using the compound 87 (6.0 g, 10 mmol) in place of the compound 5 and using the compound 73 (2.8 g, 12 mmol) in place of the compound 6, so that a compound 89 (6.4 g, a yield of 91%) in a form of a white solid was obtained. As a result of FD-MS (Field Desorption Mass Spectrometry) analysis, the reactant was identified as the compound 89.

Manufacturing of Organic EL Device

For manufacturing the organic EL device, the following compounds were used in addition to the compounds synthesized in the above Synthesis Examples.

[Formula 178]

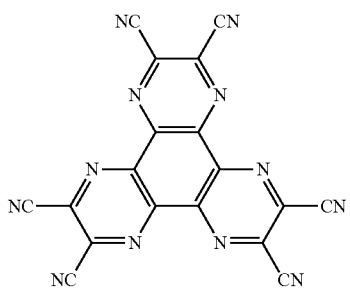

(HI-1)

(HT-1)

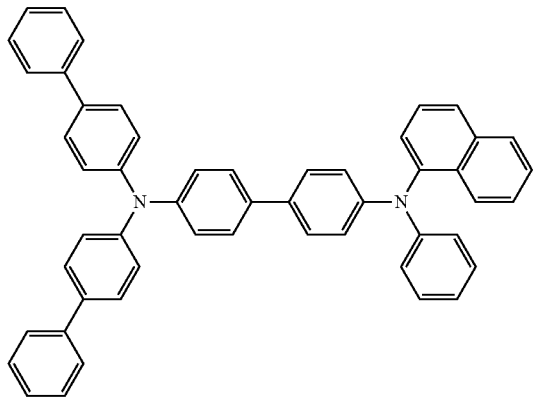

(HT-2)

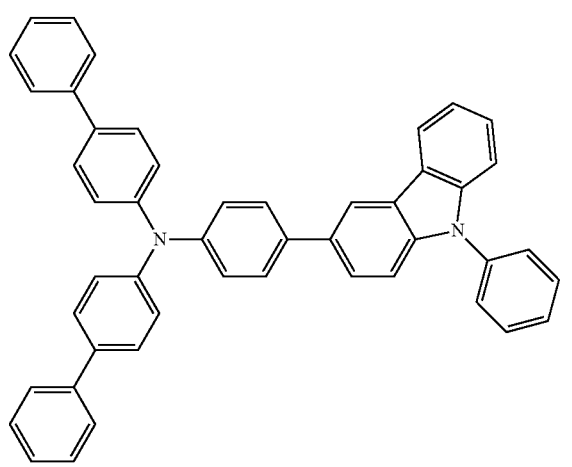

(BH-1)

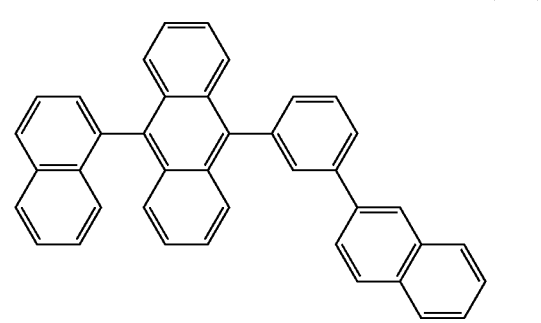

(BD-1)

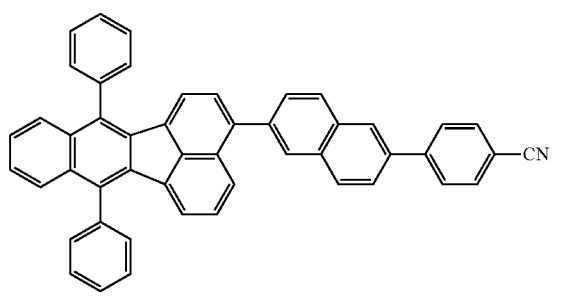

(ET-1)

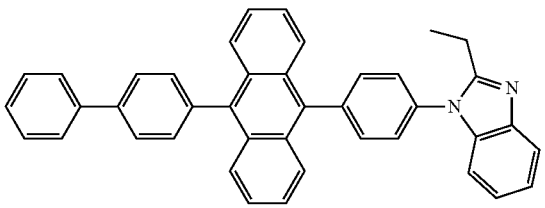

Example 1

A glass substrate (size: 25 mm×75 mm×0.7 mm thick, manufactured by Geomatec Co., Ltd.) having an ITO transparent electrode (anode) was ultrasonic-cleaned in isopropyl alcohol for five minutes, and then UV/ozone-cleaned for 30 minutes. After the glass substrate having the transparent electrode line was cleaned, the glass substrate was mounted on a substrate holder of a vacuum evaporation apparatus. Initially, a compound HI-1 was evaporated on a surface of the glass substrate where the transparent electrode line was provided in a manner to cover the transparent electrode, thereby forming a 5-nm thick HI-1 film. The HI-1 film serves as a hole injecting layer.

After the formation of the HT-1 film, a compound HT-1 was evaporated on the HT-1 film to form an 80-nm thick HT-1 film. The HT-1 film serves as a first hole transporting layer.

After the film formation of the HT-1 film, a compound HT-2 was evaporated on the HT-1 film to form a 15-nm thick HT-2 film on the HT-1 film. The HT-2 film serves as a second hole transporting layer.

A compound BH-1 (host material) and a compound BD-1 (dopant material) (mass ratio of BH-1 to BD-1 was 20:1) were co-evaporated on the HT-2 film to form a 25-nm thick emitting layer.

The compound 7 was evaporated on this emitting layer to form a 20-nm thick blocking layer.

A compound ET-1 (electron transporting material) was evaporated on the blocking layer to form a 5-nm thick electron injecting layer.

LiF was evaporated on the electron injecting layer to form a 1-nm thick LiF film.

A metal Al was evaporated on the LiF film to form an 80-nm thick metal cathode.

Thus, the organic EL device of Example 1 was manufactured.

Examples 2 to 19 and Comparative 1

Organic EL devices of Examples 2 to 19 and Comparative 1 were manufactured in the same manner as the organic EL device in the Example 1, except for using materials shown in Table 1 as a material for the blocking layer. BCP shown below was used as the material for the blocking layer of the organic EL device in Comparative 1.

[Formula 179]

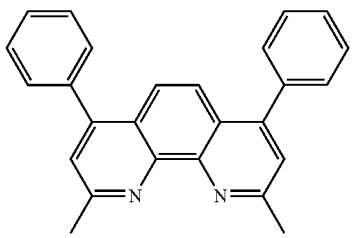

BCP

Evaluation of Device

The manufactured organic EL devices were evaluated as below. The results are shown in Table 1.

Initial Performance

Voltage was applied to the organic EL device so that a current density becomes 10 mA/cm², and a voltage value (V) at that time was measured. EL spectra were measured with a spectral radiance meter (CS-1000, manufactured by KONICA MINOLTA). Chromaticity $CIE_x$, $CIE_y$, current efficiency L/J(cd/A) and external quantum efficiency EQE (%) were calculated from the obtained spectral-radiance spectra.

Measurement of TTF Ratio

When the triplet energy of the host material, the dopant material and the blocking layer material satisfies a predetermined relation, the ratio of luminous intensity derived from TTF relative to the entire emission can be high, so that a fluorescent device can be highly efficient to the level unachievable by a typically known fluorescent device.

The ratio of luminous intensity derived from TTF is measurable by a transitional EL method. The transitional EL method is a method for measuring reduction behavior (transitional property) of EL emission after DC voltage applied on the device is removed. EL luminous intensity are classified into a luminescence component from singlet excitons generated in first recombination and a luminescence component from singlet excitons generated through TTF phenomenon. Since lifetime of the singlet excitons is very short at nanosecond order, EL emission is rapidly reduced after removal of DC voltage.

On the other hand, since the TTF phenomenon provides emission from singlet excitons generated through long-life triplet excitons, EL emission is gradually reduced. Thus, since there is a large difference in time between emission from the singlet excitons and emission from the triplet excitons, luminous intensity derived from TTF is obtainable. Specifically, the luminous intensity can be determined by the following method.

Figure 13:
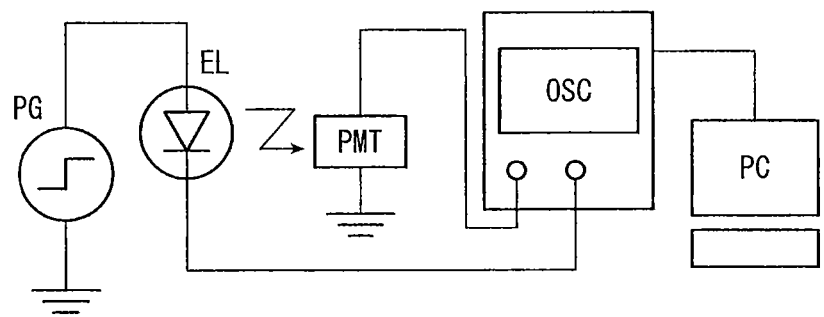
FIG. 13 is a view showing a measurement system of transitional EL waves.

Transitional EL waveform is measured as follows (see FIG. 13). Pulse voltage waveform output from a voltage pulse generator (PG) is applied on an EL device. The applied voltage waveform is loaded in an oscilloscope (OSC). When a pulse voltage is applied on the EL device, the EL device generates pulse emission. This emission is loaded in the oscilloscope (OSC) through a photomultiplier (PMT). The voltage waveform and the pulse emission are synchronized and loaded in a personal computer (PC).

The ratio of luminous intensity derived from TTF is determined as follows based on analysis of the transitional EL waveform.

A rate equation for reduction behavior of triplet excitons is resolved and the reduction behavior of luminous intensity based on TTF phenomenon is brought into modeling. Time-varying reduction of a density $n_T$ of triplet excitons within the emitting layer is represented by the following rate equation using a reduction speed a due to lifetime of the triplet excitons and a reduction speed γ due to collision of the triplet excitons.

$$\frac{dn_T}{dt} = -\alpha \cdot n_T - \gamma \cdot n_T^2 \quad \text{[Formula 1]}$$

When this differential formula is approximately resolved, the following formula is obtained. Herein, $I_{TTF}$ represents luminous intensity derived from TTF. A is a constant. Thus, when the transitional EL emission is based on TTF, a reciprocal number of the square root of intensity of the transitional EL emission is shown approximately in a linear line. The measured transitional EL waveform data is fit in the following approximate expression to obtain the constant A. At this time, luminous intensity $1/A^2$ at the time t=0 when DC voltage is removed is defined as the ratio of luminous intensity derived from TTF.

$$\frac{1}{\sqrt{I_{TTF}}} \propto A + \gamma \cdot t \quad \text{[Formula 2]}$$

Figure 14:
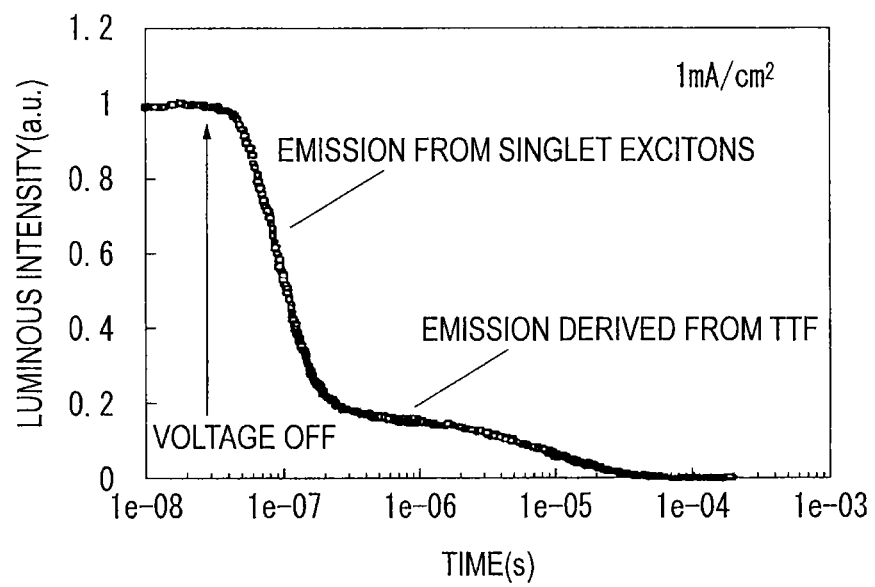
FIG. 14A is a view showing a measurement method of a ratio of luminous intensity derived from TTF and is a graph showing a change over time of luminous intensity of the EL device.
FIG. 14B is a view showing a measurement method of a ratio of the luminous intensity derived from TTF and is a graph showing a change over time of a reciprocal square root of the luminous intensity.
Figure 14:
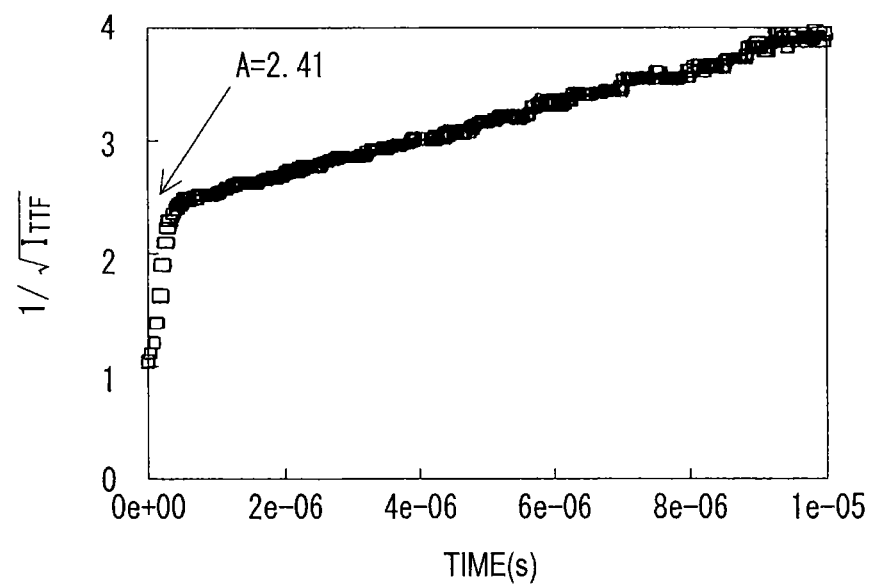

A graph of FIG. 14(A) shows a measurement example where a predetermined DC voltage is applied on the EL device and then the DC voltage is removed and shows time-varying luminous intensity of the EL device. The DC voltage was removed at the time of about $3 \times 10^{-8}$ seconds in the graph of FIG. 14(A). In the graph, the luminous intensity when voltage is removed is defined as 1. After rapid reduction before the elapse of about $2 \times 10^{-7}$, a gradual reduction component appears. In the graph of FIG. 14(B), the voltage removal time is a starting point and the reciprocal numbers of the square root of luminous intensity before the elapse of $10^{-5}$ seconds after voltage removal are plotted in an approximately linear line. A value at an intersection A of the ordinate axis and the linear line extended to the starting point is 2.41. Accordingly, the ratio of luminous intensity derived from TTF obtained from the transitional EL waveform is $1/2.41^2 = 0.17$, which means 17% of the entire luminous intensity is derived from TTF.

The luminous intensity is preferably fitted in a linear line by the method of least squares. In this case, the luminous intensity before the elapse of $10^{-5}$ seconds is preferably fitted.

Voltage pulse waveform (pulse width: 500 micro second, frequency: 20 Hz, voltage: equivalent to 0.1 to 100 mA/cm²) output from a pulse generator (8114A: manufactured by Agilent Technologies) was applied. EL emission was input in a photomultiplier (R928: manufactured by Hamamatsu Photonics K.K.). The pulse voltage waveform and the EL emission were synchronized and loaded in an oscilloscope (2440: Tektronix) to obtain a transitional EL waveform. The transitional EL waveform was analyzed to determine a TTF ratio.

Voltage was applied on the organic EL device of Example 1 at the room temperature. The pulse voltage was removed at the time of about $3 \times 10^{-8}$ seconds.

Based on the graph, where the voltage removal time was a starting point and the reciprocal numbers of the square root of luminous intensity before the elapse of $1.5 \times 10^{-5}$ seconds after voltage removal were plotted, the TTF ratio was obtained. The same measurement was performed in other Examples and Comparatives. The results are shown in Table 1.

TABLE 1

| | Blocking layer material | Voltage (V) | Chromaticity CIE x | Chromaticity CIE y | L/J (cd/A) | EQE (%) | TTF Ratio (%) |
|---|---|---|---|---|---|---|---|
| Example 1 | Compound 7 | 3.38 | 0.144 | 0.131 | 10.32 | 9.21 | 28 |
| Example 2 | Compound 9 | 3.51 | 0.142 | 0.137 | 10.39 | 9.06 | 32 |
| Example 3 | Compound 13 | 3.65 | 0.142 | 0.151 | 10.63 | 8.64 | 33 |
| Example 4 | Compound 14 | 3.52 | 0.145 | 0.131 | 9.84 | 8.76 | 29 |
| Example 5 | Compound 16 | 3.55 | 0.145 | 0.127 | 9.76 | 8.81 | 32 |
| Example 6 | Compound 22 | 3.61 | 0.143 | 0.137 | 11.09 | 9.65 | 32 |
| Example 7 | Compound 31 | 3.75 | 0.143 | 0.134 | 10.05 | 8.87 | 35 |
| Example 8 | Compound 50 | 4.08 | 0.144 | 0.128 | 9.76 | 8.87 | 29 |
| Example 9 | Compound 51 | 3.59 | 0.143 | 0.137 | 11.10 | 9.64 | 31 |
| Example 10 | Compound 52 | 3.81 | 0.143 | 0.132 | 11.17 | 9.96 | 33 |
| Example 11 | Compound 53 | 4.15 | 0.143 | 0.134 | 11.03 | 9.72 | 33 |
| Example 12 | Compound 24 | 3.71 | 0.143 | 0.131 | 10.53 | 9.42 | 30 |
| Example 13 | Compound 72 | 3.81 | 0.141 | 0.138 | 10.03 | 8.74 | 32 |
| Example 14 | Compound 74 | 3.64 | 0.143 | 0.135 | 11.34 | 9.96 | 30 |
| Example 15 | Compound 78 | 3.75 | 0.142 | 0.130 | 11.04 | 9.96 | 31 |
| Example 16 | Compound 79 | 4.02 | 0.142 | 0.132 | 10.50 | 9.40 | 34 |
| Example 17 | Compound 83 | 3.78 | 0.143 | 0.134 | 11.21 | 9.87 | 36 |
| Example 18 | Compound 88 | 3.58 | 0.142 | 0.136 | 11.05 | 9.69 | 31 |
| Example 19 | Compound 89 | 3.56 | 0.143 | 0.135 | 10.78 | 9.43 | 28 |
| Comp. 1 | BCP | 4.30 | 0.144 | 0.128 | 8.43 | 7.65 | 25 |

Since the aromatic heterocyclic compound of the invention was used for the blocking layer of the organic EL devices of Examples 1 to 19, the organic EL devices of Examples 1 to 19 exhibited a higher TTF ratio, a higher current efficiency and a higher external quantum efficiency than the organic EL device of Comparative 1. Moreover, a drive voltage of the organic EL devices of Examples 1 to 19 was also lower than that of the organic EL device of Comparative 1.

The invention claimed is:
1. An aromatic heterocyclic derivative of formula (4):

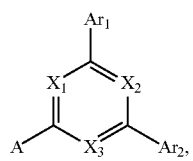

(4)

wherein $X_1$, $X_2$, and $X_3$ are each independently a nitrogen atom or $CR_1$, with a proviso that at least one of $X_1$, $X_2$, and $X_3$ is a nitrogen atom,
$R_1$ is a hydrogen atom, a halogen atom, a cyano group, a substituted or unsubstituted aryl group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted alkenyl group having 2 to 30 carbon atoms, a substituted or unsubstituted alkynyl group having 2 to 30 carbon atoms, a substituted or unsubstituted alkylsilyl group having 3 to 30 carbon atoms, a substituted or unsubstituted arylsilyl group having 6 to 30 ring carbon atoms, a substituted or unsubstituted alkoxy group having 1 to 30 carbon atoms, a substituted or unsubstituted aralkyl group having 6 to 30 ring carbon atoms, or a substituted or unsubstituted aryloxy group having 6 to 30 ring carbon atoms,
$Ar_1$ and $Ar_2$ are each a group of formula (5), and
A is a group of formula (5):

$(HAr)_a$-$L_1$-  (5), wherein
a is 1, and $L_1$ is a substituted or unsubstituted phenylene group, and
HAr is represented by formula (6):

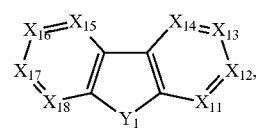

(6)

wherein $Y_1$ is an oxygen atom or a sulfur atom;
$X_{11}$, $X_{12}$, $X_{13}$, $X_{14}$, $X_{15}$, $X_{16}$, $X_{17}$, and $X_{18}$ are each independently a nitrogen atom or $CR_{13}$, with a proviso that $X_{13}$ or $X_{16}$ is a carbon atom bonded to $L_1$ by a single bond;
$R_{13}$ is a hydrogen atom, a halogen atom, a cyano group, a substituted or unsubstituted aryl group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted alkenyl group having 2 to 30 carbon atoms, a substituted or unsubstituted alkynyl group having 2 to 30 carbon atoms, a substituted or unsubstituted alkylsilyl group having 3 to 30 carbon atoms, a substituted or unsubstituted arylsilyl group having 6 to 30 ring carbon atoms, a substituted or unsubstituted alkoxy group having 1 to 30carbon atoms, a substituted or unsubstituted aralkyl group having 6 to 30 ring carbon atoms, or a substituted or unsubstituted aryloxy group having 6 to 30 ring carbon atoms,
a plurality of $R_{13}$ are mutually the same or different, and adjacent $R_{13}$ optionally bond to each other to form a ring.
2. An organic-electroluminescence-device material comprising the aromatic heterocyclic derivative according to claim 1.
3. An organic electroluminescence device comprising:
an anode;
an emitting layer;
an electron transporting zone; and
a cathode, in this sequence;

wherein:
the emitting layer comprises a host material and a fluorescent dopant material,
when a triplet energy of the host material is represented as $E^T_h$ and a triplet energy of the fluorescent dopant material is represented as $E^T_d$, a relationship of formula (2A) is satisfied:

$$E^T_h < E^T_d \qquad (2A)$$

the electron transporting zone comprises a blocking layer having a triplet energy represented as $E^T_b$ wherein the relationship of formula (3A) is satisfied:

$$E^T_b > E^T_h \qquad (3A)$$

and the blocking layer comprises an aromatic heterocyclic derivative of formula (1),

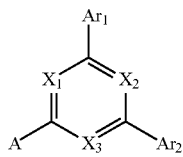
(1)

wherein:
$X_1$ to $X_3$ each are independently a nitrogen atom or $CR_1$, with a proviso that at least one of $X_1$ to $X_3$ is a nitrogen atom;
$R_1$ independently represents a hydrogen atom, a halogen atom, a cyano group, a substituted or unsubstituted aryl group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted alkenyl group having 2 to 30 carbon atoms, a substituted or unsubstituted alkynyl group having 2 to 30 carbon atoms, a substituted or unsubstituted alkylsilyl group having 3 to 30 carbon atoms, a substituted or unsubstituted arylsilyl group having 6 to 30 ring carbon atoms, a substituted or unsubstituted alkoxy group having 1 to 30 carbon atoms, a substituted or unsubstituted aralkyl group having 6 to 30 ring carbon atoms, or a substituted or unsubstituted aryloxy group having 6 to 30 ring carbon atoms;
A is represented by formula (2) below, $$(HAr)_a\text{-}L_1\text{-} \qquad (2)$$

wherein:
HAr is represented by formula (3) below;
a is an integer of 1 to 5;
when a is 1, $L_1$ is a single bond or a divalent linking group;
when a is in a range of 2 to 5, $L_1$ is a trivalent to hexavalent linking group and HAr is the same or different;
the linking group is a substituted or unsubstituted aryl group having 6 to 30 ring carbon atoms, a substituted or unsubstituted heterocyclic group having 5 to 30 ring atoms, or a divalent to hexavalent residue induced from any one of a group formed by mutually bonding two or three of the substituted or unsubstituted aryl group having 6 to 30 ring carbon atoms and the substituted or unsubstituted heterocyclic group having 5 to 30 ring atoms;
the mutually bonded groups are the same or different,

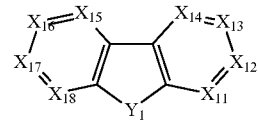
(3)

wherein:
$Y_1$ is an oxygen atom, a sulfur atom or $SiR_{11}R_{12}$;
$X_{11}$ to $X_{18}$ each are independently a nitrogen atom or $CR_{13}$, with a proviso that $X_{11}$, $X_{13}$, $X_{16}$ or $X_{18}$ is a carbon atom bonded to $L_1$ by a single bond;
$R_{11}$ and $R_{12}$ represent the same as $R_1$ in the formula (1);
$R_{11}$ and $R_{12}$ are the same or different;
$R_{13}$ independently represents a hydrogen atom, a halogen atom, a cyano group, a substituted or unsubstituted aryl group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted alkenyl group having 2 to 30 carbon atoms, a substituted or unsubstituted alkynyl group having 2 to 30 carbon atoms, a substituted or unsubstituted alkylsilyl group having 3 to 30 carbon atoms, a substituted or unsubstituted arylsilyl group having 6 to 30 ring carbon atoms, a substituted or unsubstituted alkoxy group having 1 to 30 carbon atoms, a substituted or unsubstituted aralkyl group having 6 to 30 ring carbon atoms, or a substituted or unsubstituted aryloxy group having 6 to 30 ring carbon atoms;
a plurality of $R_{13}$ are mutually the same or different;
adjacent $R_{13}$ optionally bond to each other to form a ring; and
in the above formula (1), $Ar_1$ and $Ar_2$ each are independently represented by the formula (2), or represent a substituted or unsubstituted aryl group having 6 to 30 ring carbon atoms or a substituted or unsubstituted heterocyclic group having 5 to 30 ring atoms.

4. The organic electroluminescence device according to claim 3, wherein, in the formula (2), a is an integer of 1 to 3.

5. The organic electroluminescence device according to claim 3, wherein, in the formula (2), a is 1 or 2.

6. The organic electroluminescence device according to claim 3, wherein, in the formula (2):
a is 1 and $L_1$ is a linking group; and
the linking group is a divalent residue of a substituted or unsubstituted aryl group having 6 to 30 ring carbon atoms, or a divalent residue of a substituted or unsubstituted heterocyclic group having 5 to 30 ring atoms.

7. The organic electroluminescence device according to claim 3, wherein:
a in the formula (2) is 2;
$L_1$ in the formula (2) is a linking group; and
the linking group is a trivalent residue of a substituted or unsubstituted aryl group having 6 to 30 ring carbon atoms, or a trivalent residue of a substituted or unsubstituted heterocyclic group having 5 to 30 ring atoms.

8. The organic electroluminescence device according to claim 3, wherein, in the formula (3), $Y_1$ is an oxygen atom or a sulfur atom.

9. The organic electroluminescence device according to claim 3, wherein, in the formula (3):

$Y_1$ is an oxygen atom or a sulfur atom;

$X_{12}, X_{14}, X_{15},$ and $X_{17}$ are $CR_{13}$; and one of $X_{11}, X_{13}, X_{16}$ and $X_{18}$ is a carbon atom bonded to $L_1$ by a single bond and the rest of $X_{11}, X_{13}, X_{16}$ and $X_{18}$ are $CR_{13}$.

10. The organic electroluminescence device according to claim 3, wherein, in the formula (1), two or three of $X_1$ to $X_3$ are a nitrogen atom.

11. The organic electroluminescence device according to claim 3, wherein, in the formula (2), $L_1$ is a divalent or trivalent residue induced from one of benzene, biphenyl, terphenyl, naphthalene, and phenanthrene.

12. The organic electroluminescence device according to claim 3, further comprising at least one of an electron injecting layer and an electron transporting layer between the blocking layer and the cathode, wherein:
at least one of the electron injecting layer and the electron transporting layer comprises at least one of an electron-donating dopant material and an organic metal complex.

13. The organic electroluminescence device according to claim 12, wherein:
the electron-donating dopant material is at least one material selected from the group consisting of an alkali metal, an alkaline-earth metal, a rare earth metal, an alkali metal oxide, an alkali metal halogenide, an alkaline-earth metal oxide, an alkaline-earth metal halogenide, a rare earth metal oxide, and a rare earth metal halogenide; and
the organic metal complex is at least one complex selected from the group consisting of an organic metal complex including an alkali metal, an organic metal complex including an alkaline-earth metal, and an organic metal complex including a rare-earth metal.

14. The organic electroluminescence device according to claim 3, wherein the emitting layer is in contact with the electron transporting zone comprising the aromatic heterocyclic derivative.

15. The organic electroluminescence device according to claim 3, wherein the emitting layer comprises an anthracene derivative represented by a formula (20D) below,

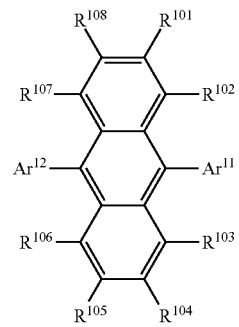

(20D)

wherein:
$Ar^{11}$ and $Ar^{12}$ each independently represent a substituted or unsubstituted monocyclic group having 5 to 30 ring atoms, a substituted or unsubstituted fused cyclic group having 10 to 30 ring atoms or a group formed by combining the monocyclic group and the fused cyclic group; and $R^{101}$ to $R^{108}$ each independently represent a hydrogen atom, a halogen atom, a cyano group, a substituted or unsubstituted monocyclic group having 5 to 30 ring atoms, a substituted or unsubstituted fused cyclic group having 10 to 30 ring atoms, a group formed by combining the monocyclic group and the fused cyclic group, a substituted or unsubstituted alkyl group having 1 to 30 carbon atoms, a substituted or unsubstituted cycloalkyl group having 3 to 30 ring carbon atoms, a substituted or unsubstituted alkylsilyl group having 3 to 30 carbon atoms, a substituted or unsubstituted arylsilyl group having 8 to 30 ring carbon atoms, a substituted or unsubstituted alkoxy group having 1 to 30 carbon atoms, a substituted or unsubstituted aralkyl group having 7 to 30 carbon atoms, a substituted or unsubstituted aryloxy group having 6 to 30 ring carbon atoms, or a substituted or unsubstituted silyl group.

16. The organic electroluminescence device according to claim 3, wherein a main peak wavelength of the fluorescent dopant material is 500 nm or less.

* * * * *